United States Patent
Yeung et al.

(10) Patent No.: US 12,122,827 B2
(45) Date of Patent: *Oct. 22, 2024

(54) IL-21 POLYPEPTIDES AND TARGETED CONSTRUCTS

(71) Applicant: Asher Biotherapeutics, Inc., South San Francisco, CA (US)

(72) Inventors: Yik Andy Yeung, South San Francisco, CA (US); Renee L. Greer, Pacifica, CA (US); Henry C. Nguyen, San Francisco, CA (US); David Liu, Pacifica, CA (US); Byong Kang, San Francisco, CA (US); Ivana Djuretic, Pacifica, CA (US)

(73) Assignee: ASHER BIOTHERAPEUTICS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/307,477

(22) Filed: Apr. 26, 2023

(65) Prior Publication Data

US 2023/0357343 A1 Nov. 9, 2023

Related U.S. Application Data

(63) Continuation of application No. PCT/US2022/026584, filed on Apr. 27, 2022, which is a continuation-in-part of application No. PCT/US2021/062485, filed on Dec. 8, 2021, and a continuation-in-part of application No. PCT/US2021/056312, filed on Oct. 22, 2021.

(60) Provisional application No. 63/297,631, filed on Jan. 7, 2022, provisional application No. 63/223,684, filed on Jul. 20, 2021, provisional application No. 63/190,669, filed on May 19, 2021.

(51) Int. Cl.
| | |
|---|---|
| *C07K 16/24* | (2006.01) |
| *A61K 38/00* | (2006.01) |
| *A61K 39/00* | (2006.01) |
| *A61P 35/00* | (2006.01) |
| *C07K 14/54* | (2006.01) |
| *C07K 16/28* | (2006.01) |
| *C07K 16/40* | (2006.01) |

(52) U.S. Cl.
CPC ............ *C07K 16/244* (2013.01); *A61P 35/00* (2018.01); *C07K 14/54* (2013.01); *C07K 16/2815* (2013.01); *C07K 16/40* (2013.01); *A61K 38/00* (2013.01); *A61K 2039/505* (2013.01); *C07K 2317/24* (2013.01); *C07K 2317/51* (2013.01); *C07K 2317/515* (2013.01); *C07K 2317/522* (2013.01); *C07K 2317/524* (2013.01); *C07K 2317/526* (2013.01); *C07K 2317/565* (2013.01); *C07K 2317/64* (2013.01); *C07K 2317/92* (2013.01); *C07K 2319/30* (2013.01); *C07K 2319/33* (2013.01); *C07K 2319/74* (2013.01)

(58) Field of Classification Search
CPC ..... A61P 35/00; C07K 14/54; C07K 16/2815; C07K 16/40; C07K 2317/24; A61K 38/00; A61K 2039/505
See application file for complete search history.

(56) References Cited

U.S. PATENT DOCUMENTS

| | | | |
|---|---|---|---|
| 6,940,003 B1 | 9/2005 | Kinney et al. | |
| 7,112,660 B1 * | 9/2006 | Domingues | A61P 37/08 424/85.2 |
| 7,186,805 B2 | 3/2007 | Presnell et al. | |
| 7,276,478 B2 | 10/2007 | Sivakumar et al. | |
| 7,695,936 B2 | 4/2010 | Carter et al. | |
| 8,034,326 B2 | 10/2011 | Hjorth et al. | |
| 8,211,420 B2 | 7/2012 | Bondensgaard et al. | |
| 8,383,367 B2 | 2/2013 | Hjorth et al. | |
| 8,822,653 B2 | 9/2014 | Sexton et al. | |
| 9,447,159 B2 | 9/2016 | Ast et al. | |
| 9,850,310 B2 | 12/2017 | Gaudet et al. | |
| 10,202,464 B2 | 2/2019 | Ast et al. | |
| 10,316,104 B2 | 6/2019 | Ast et al. | |
| 10,538,595 B2 | 1/2020 | Zhang | |
| 11,130,822 B2 | 9/2021 | Ast et al. | |
| 11,471,490 B2 | 10/2022 | Andresen et al. | |
| 11,518,808 B2 * | 12/2022 | Ali | C12N 15/85 |
| 11,541,103 B2 * | 1/2023 | Ali | C12N 15/63 |

(Continued)

FOREIGN PATENT DOCUMENTS

| | | |
|---|---|---|
| EP | 2970486 B1 | 5/2018 |
| EP | 3661954 B1 | 2/2022 |

(Continued)

OTHER PUBLICATIONS

Edelhoch et al., Structural Studies on Polypeptide Hormones, 1969, The Journal of Biological Chemistry, vol. 244, No. 14, pp. 3876-3883 (Year: 1969).*

(Continued)

*Primary Examiner* — Jeffrey Stucker
*Assistant Examiner* — Brittney E Donoghue
(74) *Attorney, Agent, or Firm* — WILSON SONSINI GOODRICH & ROSATI

(57) ABSTRACT

The present disclosure provides methods and compositions comprising IL-21 polypeptides, targeted cytokine construct that selectively activates target immune cells (e.g., CD8+ T cells) over other immune cell types. The cytokine of the present disclosure can further comprise mutations that alter its charge distribution to improve its half-life within the blood.

30 Claims, 42 Drawing Sheets

Specification includes a Sequence Listing.

(56) References Cited

U.S. PATENT DOCUMENTS

| | | | |
|---|---|---|---|
| 2003/0045474 A1* | 3/2003 | Sailer | A61K 38/1875 514/8.8 |
| 2009/0304659 A1 | 12/2009 | Banchereau et al. | |
| 2012/0107267 A1 | 5/2012 | Kang et al. | |
| 2012/0276125 A1 | 11/2012 | Ast et al. | |
| 2013/0336982 A1 | 12/2013 | Mader et al. | |
| 2014/0294759 A1 | 10/2014 | Chu et al. | |
| 2015/0191543 A1 | 7/2015 | Wu et al. | |
| 2015/0299324 A1 | 10/2015 | Hofer et al. | |
| 2018/0142027 A1 | 5/2018 | Igawa et al. | |
| 2019/0023790 A1 | 1/2019 | Giurleo et al. | |
| 2019/0046611 A1 | 2/2019 | Ali et al. | |
| 2019/0062448 A1 | 2/2019 | Soros et al. | |
| 2019/0085080 A1 | 3/2019 | Kaplan et al. | |
| 2019/0233517 A1 | 8/2019 | Wu | |
| 2019/0263877 A1 | 8/2019 | Yeung et al. | |
| 2019/0270817 A1 | 9/2019 | Ali et al. | |
| 2019/0315883 A1 | 10/2019 | Ast et al. | |
| 2019/0322763 A1 | 10/2019 | Ast et al. | |
| 2020/0078401 A1 | 3/2020 | Vijayanand et al. | |
| 2020/0317787 A1 | 10/2020 | Li et al. | |
| 2020/0330514 A1 | 10/2020 | Andresen et al. | |
| 2021/0017247 A1 | 1/2021 | Jones et al. | |
| 2021/0024631 A1 | 1/2021 | Kley et al. | |
| 2021/0163562 A1 | 6/2021 | Lu et al. | |
| 2022/0033455 A1 | 2/2022 | Wong | |
| 2022/0112288 A1 | 4/2022 | Ganesan et al. | |
| 2022/0162314 A1 | 5/2022 | Yeung et al. | |
| 2022/0251202 A1 | 8/2022 | Djuretic et al. | |
| 2023/0136331 A1 | 5/2023 | Ban et al. | |
| 2023/0340104 A1 | 10/2023 | Yeung et al. | |

FOREIGN PATENT DOCUMENTS

| | | | |
|---|---|---|---|
| WO | WO-2006106905 A1 | 10/2006 | |
| WO | WO-2006111524 A2 * | 10/2006 | A61P 31/12 |
| WO | WO-2007110205 A2 | 10/2007 | |
| WO | WO-2012107416 A2 | 8/2012 | |
| WO | WO-2012146628 A1 | 11/2012 | |
| WO | WO-2014023679 A1 | 2/2014 | |
| WO | WO-2014145907 A1 | 9/2014 | |
| WO | WO-2015164815 A1 | 10/2015 | |
| WO | WO-2016100375 A2 | 6/2016 | |
| WO | WO-2017027422 A1 | 2/2017 | |
| WO | WO-2017142928 A1 | 8/2017 | |
| WO | WO-2018119114 A1 | 6/2018 | |
| WO | WO-2018170096 A1 | 9/2018 | |
| WO | WO-2018176505 A1 | 10/2018 | |
| WO | WO-2018209115 A1 | 11/2018 | |
| WO | WO-2019010219 A1 | 1/2019 | |
| WO | WO-2019010224 A1 | 1/2019 | |
| WO | WO-2019033043 A2 | 2/2019 | |
| WO | WO-2019191519 A1 | 10/2019 | |
| WO | WO-2019196309 A1 | 10/2019 | |
| WO | WO-2019246392 A1 | 12/2019 | |
| WO | WO-2019246404 A1 | 12/2019 | |
| WO | WO-2020148554 A1 | 7/2020 | |
| WO | WO-2020247843 A2 | 12/2020 | |
| WO | WO-2021001289 A1 | 1/2021 | |
| WO | WO-2022006380 A2 | 1/2022 | |
| WO | WO-2022125711 A1 | 6/2022 | |
| WO | WO-2022135469 A1 | 6/2022 | |
| WO | WO-2022245500 A1 | 11/2022 | |
| WO | WO-2023048516 A1 | 3/2023 | |

OTHER PUBLICATIONS

Biopharma PEG, Things about Polypeptide Antibiotic You Need Know, 2019, Biopharma PEG, pp. 1-4, retrieved from: https://www.biochempeg.com/article/75.html (Year: 2019).*

Hicklin, Decoding the variety of human antibodies, 2019, NIH, p. 1, retrieved from: https://www.nih.gov/news-events/nihresearch-matters/decoding-variety-human-antibodies (Year: 2019).*

Fenton et al., Rheostat positions: A new classification of protein positions relevant to pharmacogenomics, 2020, Medicinal Chemistry Research, vol. 29, pp. 1133-1146 (Year: 2020).*

Guo et al., Protein tolerance to random amino acid change, 2004, PNAS, vol. 101, No. 25, pp. 9205-9210 (Year: 2004).*

Shen et al., Engineered IL-21 Cytokine Muteins Fused to Anti-PD-1-Antibodies Can Improve CD8+ T cell Function and Anti-Tumor Immunity, May 8, 2020, Frontiers in Immunology, vol. 11, Article 832, pp. 1-14 (Year: 2020).*

Hamming et al., Crystal Structure of Interleukin-21 Receptor (IL-21R) Bound to IL-21 Reveals That Sugar Chain Interacting with WSXWS Motif Is Integral Part of IL-21R, 2012, The Journal of Biological Chemistry, vol. 287, No. 12, pp. 9454-9460 (Year: 2012).*

Kussie et al., A Single Engineered Amino Acid Substitution Changes Antibody Fine Specificity, 1994, Journal of Immunology, pp. 146-152 (Year: 1994).*

Vajdos et al., Comprehensive Functional Maps of the Antigen binding Site of an Anti-ErbB2 Antibody Obtained with Shotgun Scanning Mutagenesis, 2002, Journal of Molecular Biology, vol. 320, pp. 415-428 (Year: 2002).*

Brown et al., Tolerance to Single, but not Multiple, Amino Acid Replacements in Antibody VH CDR2, 1996, Journal of Immunology, vol. 156, pp. 3285-3291 (Year: 1996).*

Devine et al., Location of the epitope for an anti-CD8α antibody 53.6.7 which enhances CD8α-MHC class I interaction indicates antibody stabilization of a higher affinity CD8 conformation, 2004, Immunology Letters, vol. 93, pp. 123-130 (Year: 2004).*

Ren et al., IL-21 in Homeostasis of Resident Memory and Exhausted CD8 T cells during Persistent Infection, 2020, International Journal of Molecular Sciences, vol. 21, Issue 6966, pp. 1-16 (Year: 2020).*

Asher Biotherapeutics. Asher Bio to Unveil Two New Immunotherapy Programs, a CD8+ T Cell Targeted IL-21 and a Cis-Targeted IL-2 for Cell Therapy Augmentation, at AACR Annual Meeting. pp. 1-3 (2022).

Atwell et al.: Stable heterodimers from remodeling the domain interface of a homodimer using a phage display library. J Mol Biol. 270:26-35 (1997).

Bosselut et al.: Role of CD8beta domains in CD8 coreceptor function: importance for MHC I binding. signaling. and positive selection of CD8+ T cells in the thymus. Immunity. 12(4):409-418 (2000).

Brinkmann et al.: The making of bispecific antibodies. Mabs. 9(2):182-212 (2017).

Carter: Bispecific human IgG by design. J Immunol Methods. 248:7-15 (2001).

Choi et al.: Crystal structures of immunoglobulin Fc heterodimers reveal the molecular basis for heterodimer formation. Mol Immunol. 65:377-83. Abstract Only. (2015).

Chothia et al.: Canonical structures for the hypervariable regions of immunoglobulins. J. Mol. Biol. 196:901-917 )1987).

Davis et al.: SEEDbodies: fusion proteins based on strand-exchange engineered domain (SEED) CH3 heterodimers in an Fc analogue platform for asymmetric binders or immunofusions and bispecific antibodies. Protein Eng Des Sel. 23:195-202 (2010).

De Nardis et al.: (2017). A new approach for generating bispecific antibodies based on a common light chain format and the stable architecture of human immunoglobulin G1. J Biol Chem. 292(35):14706-14717.

Dimitrov: Engineered CH2 domains (nanoantibodies). MaBS. 1:26-28 (2009).

Egelston et al.: Human breast tumor-infiltrating CD8 + T cells retain polyfunctionality despite PD-1 expression. Nat Commun. 9(1):4297 11 pages (2018).

Gao et al.: Optimization of the C-Terminus of an Autonomous Human IgG1 CH2 Domain for Stability and Aggregation Resistance. Mol Pharm. 16:3647-3656. Abstract Only. (2019).

Gebauer et al.: Engineered protein scaffolds as next-generation antibody therapeutics. Curr Opin Chem Biol. 13:245-255 (2009).

Gunasekaran et al.: Enhancing antibody Fc heterodimer formation through electrostatic steering effects: applications to bispecific molecules and monovalent IgG. J Biol Chem. 285:19637-19646 (2010).

(56) References Cited

OTHER PUBLICATIONS

Heeley et al.: Mutations flanking the polyglutamine repeat in the modulatory domain of rat glucocorticoid receptor lead to an increase in affinity for hormone. Endocr Res. 28(3):217-229. Abstract Only. (2002).

Heng et al.: Immunological Genome Project Consortium: networks of gene expression in immune cells. Nat Immunol. 9(10):1091-1094 (2008).

Jefferis et al.: (2002). Interaction sites on human IgG-Fc for FcgammaR: current models. Immunol Lett. 82:57-65.

Labrijn et al.: Controlled Fab-arm exchange for the generation of stable bispecific IgG1. Nat Protoc. 9:2450-63. Abstract Only. (2014).

Labrijn et al.: Efficient generation of stable bispecific IgG1 by controlled Fab-arm exchange. PNAS USA. 110(13):5145-5150 (2013).

Merchant et al.: An efficient route to human bispecific IgG. Nat Biotechnol. 16:677-681 (1998).

Ribas et al.: Cancer immunotherapy using checkpoint blockade. Science. 359(6382):1350-1355. 18 pages (2018).

Ridgway et al.: 'Knobs-into-holes' engineering of antibody CH3 domains for heavy chain heterodimerization. Prot Eng. 9:617-621 (1996).

Rothschilds et al.: Order of administration of combination cytokine therapies can decouple toxicity from efficacy in syngeneic mouse tumor models. Oncoimmunology. 8(5):e1558678. 16 pages (2019).

Skegro et al.: Immunoglobulin domain interface exchange as a platform technology for the generation of Fc heterodimers and bispecific antibodies. J Biol Chem. 292(23):9745-9759 (2017).

Wei et al.: Structural basis of a novel heterodimeric Fc for bispecific antibody production. Oncotarget. 8(31):51037-51049 (2017).

Bondensgaard K, et al. The existence of multiple conformers of interleukin-21 directs engineering of a superpotent analogue. J Biol Chem. Aug. 10, 2007;282(32):23326-36. Epub Jun. 12, 2007.

Kang L, et al. Rational design of interleukin-21 antagonist through selective elimination of the gammaC binding epitope. J Biol Chem. Apr. 16, 2010;285(16):12223-31. Epub Feb. 18, 2010.

PCT/US2022/026584 International Search Report and Written Opinion mailed Sep. 9, 2022.

Shen S, et al. Engineered IL-21 Cytokine Muteins Fused to Anti-PD-1 Antibodies Can Improve CD8+ T Cell Function and Anti-tumor Immunity. Front Immunol. May 8, 2020;11:832.

Young PA, et al. Antibody-cytokine fusion proteins for treatment of cancer: engineering cytokines for improved efficacy and safety. Semin Oncol. Oct. 2014;41(5):623-36. Epub Aug. 12, 2014.

Heeley et al., Mutations flanking the polyglutamine repeat in the modulaory domain of rat glucocorticoid receptor lead to an increase in affinity for hormone. Endocr. Res. 28:217-229 (2002).

Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines. Oncoimmunology 6(3):e1277306 (2017).

Clement et al. Anti-CD8 antibodies can trigger CD8+T cell effector function in the absence of TCR engagement and improve peptide-MHCI tetramer staining. J Immunol. 187(2):654-663 (2011).

De Pascalis, Roberto, et al., Grafting of "Abbreviated" Complementarity-Determining Regions Containing Specificity-Determining Residues Essential for Ligand Contact to Engineer a Less Immunogenic Humanized Monoclonal Antibody. The Journal of Immunology 169(6):3076-3084 (2002).

Goel, Manisha, et al., Plasticity within the Antigen-Combining Site May Manifest as Molecular Mimicry in the Humoral Immune Response. Journal of Immunology 173:7358-7367 (2004).

Khan, Tarique, et al., Adjustable Locks and Flexible Keys: Plasticity of Epitope-Paratope Interactions in Germline Antibodies. Journal of Immunology 192:5398-5405 (2014).

MacCallum, et al. Antibody-Antigen Interactions: Contact Analysis And Binding Site Topography. Journal of Molecular Biology 262(5):732-745 (1996).

Mariuzza, et al., The Structural Basis of Antigen-Antibody Recognition. Annual Review Biology Physics Chemistry 16:139-159 (1987).

Poosarla, Venkata, et al., Computational De Novo Design of Antibodies Binding to a Peptide With High Affinity. Biotechnology Bioengineering 114(6):1331-1342 (2017).

Sailer, Zachary, et al., Molecular Ensembles Make Evolution Unpredictable. PNAS USA 114(45):11938-11943 (2017).

Shore et al. The crystal structure of CD8 in complex with YTS156.7.7 Fab and interaction with other CD8 antibodies define the binding mode of CD8 alphabeta to MHC class I. J Mol Biol 384(5):1190-1202 (2008).

U.S. Appl. No. 18/308,338 Office Action dated Mar. 28, 2024.

Wooldridge, Linda et al. Anti-CD8 antibodies can inhibit or enhance peptide-MHC class I (pMHCI) multimer binding: this is paralleled by their effects on CTL activation and occurs in the absence of an interaction between pMHCI and CD8 on the cell surface. J Immunol 171(12):6650-6660 (2003).

* cited by examiner

FIG. 1A

Amino acid sequence of wild type IL-21
QGQDRHMIRMRQLIDIVDQLKNYVNDLVPEFLPAPEDVETNCEWSAFSCFQKAQLKSANTGNNERIINVSIKKLKRKPPSTNAGRRQ
KHRLTCPSCDSYEKKPPKEFLERFKSLLQKMIHQHLSSRTHGSEDS (SEQ ID NO: 1)

FIG. 1B

Amino acid sequence of IL-21R
CPDLVCYTDYLQTVICILEMWNLHPSTLTLTWQDQYEELKDEATSCSLHRSAHNATHATYTCHMDVFHFMADDIFSVNITDQSGNYS
QECGSFLLAESIKPAPPFNVTVTFSGQYNISWRSDYEDPAFYMLKGKLQYELQYRNRGDPWAVSPRRKLISVDSRSVSLLPLEFRKDSSY
ELQVRAGPMPGSSYQGTWSEWSDPVIFQTQSEELKEGWNPHLLLLLLLVIVFIPAFWSLKTHPLWRLWKKIWAVPSPERFFMPLYKG
CSGDFKKWVGAPFTGSSLELGPWSPEVPSTLEVYSCHPPRSPAKRLQLTELQEPAELVESDGVPKPSFWPTAQNSGGSAYSEERDRPY
GLVSIDTVTVLDAEGPCTWPCSCEDDGYPALDLDAGLEPSPGLEDPLLDAGTTVLSCGCVSAGSPGLGGPLGSLLDRLKPPLADGED
WAGGLPWGGRSPGGVSESEAGSPLAGLDMDTFDSGFVGSDCSSPVECDFTSPGDEGPPRSYLRQWVVIPPPLSSPGPQAS (SEQ
ID NO: 381)

FIG. 1C

Amino acid sequence of gamma common receptor
LNTTILTPNGNEDTTADFFLTTMPTDSLSVSTLPLPEVQCFVFNVEYMNCTWNSSSEPQPTNLTLHYWYKNSDNDKVQKCSHYLFSEE
ITSGCQLQKKEIHLYQTFVVQLQDPREPRRQATQMLKLQNLVIPWAPENLTLHKLSESQLELNWNNRFLNHCLEHLVQYRTDWDHS
WTEQSVDYRHKFSLPSVDGQKRYTFRVRSRFNPLCGSAQHWSEWSHPIHWGSNTSKENPFLFALEAVVISVGSMGLIISLLCVYFWL
ERTMPRIPTLKNLEDLVTEYHGNFSAWSGVSKGLAESLQPDYSERLCLVSEIPPKGGALGEGPGASPCNQHSPYWAPPCYTLKPET
(SEQ ID NO: 382)

FIG. 2

| Amino acid number | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Wild-type residue | Q | G | Q | D | R | H | M | I | R | M | R | Q | L | I | D | I | V | D | Q | L |
| Mutation position | | | | | | | | | | | | | | | | | | | | |

| Amino acid number | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|
| Wild-type residue | K | N | Y | V | N | D | L | V | P | E | F | L | P | A | P | E | D | V | E | T |
| Mutation position | | | | | | | | | | | | | | | | | | | | |

| Amino acid number | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|
| Wild-type residue | N | C | E | W | S | A | F | S | C | F | Q | K | A | Q | L | K | S | A | N | T |
| Mutation position | | | | | | | | | | | | | | | | x | | | | |

| Amino acid number | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|
| Wild-type residue | G | N | N | E | R | I | I | N | V | S | I | K | K | L | K | R | K | P | P | S |
| Mutation position | | | | | | | | | | | | | | | | | | | | x |

| Amino acid number | 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|---|
| Wild-type residue | T | N | A | G | R | R | Q | K | H | R | L | T | C | P | S | C | D | S | Y | E |
| Mutation position | x | x | x | x | x | x | x | x | x | x | x | x | | | | | | | | |

| Amino acid number | 101 | 102 | 103 | 104 | 105 | 106 | 107 | 108 | 109 | 110 | 111 | 112 | 113 | 114 | 115 | 116 | 117 | 118 | 119 | 120 |
|---|---|---|---|---|---|---|---|---|---|---|---|---|---|---|---|---|---|---|---|---|
| Wild-type residue | K | K | P | P | K | E | F | I | E | R | F | K | S | I | L | Q | K | M | I | H |
| Mutation position | | x | | | | | | | | | | | | | | | | | | |

| Amino acid number | 121 | 122 | 123 | 124 | 125 | 126 | 127 | 128 | 129 | 130 | 131 | 132 | 133 |
|---|---|---|---|---|---|---|---|---|---|---|---|---|---|
| Wild-type residue | Q | H | L | S | S | R | T | H | G | S | E | D | S |
| Mutation position | | | | | | | | | | | | | |

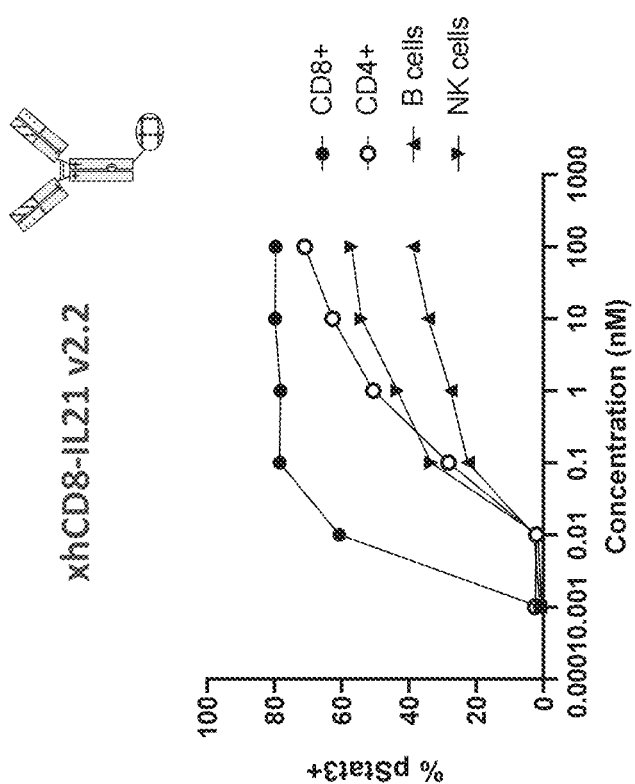
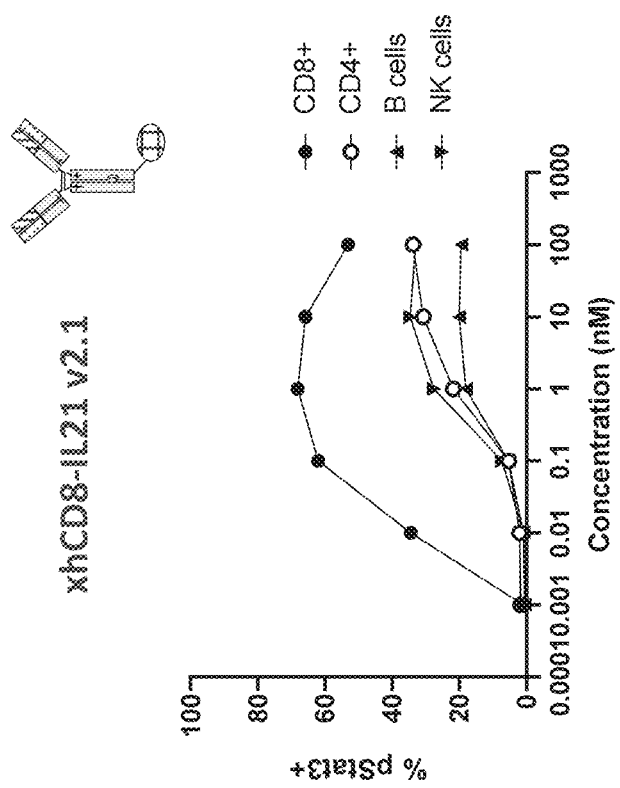
FIG. 8A xhCD8-IL21 v2.1
FIG. 8B xhCD8-IL21 v2.2 xhCD8-IL21 v2.4 xhCD8-IL21 v2.3

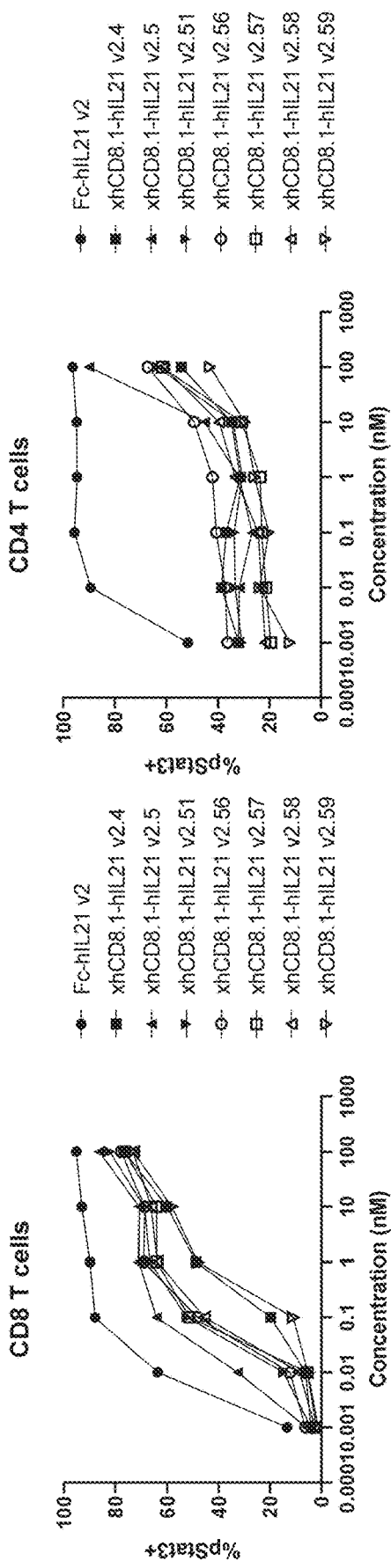

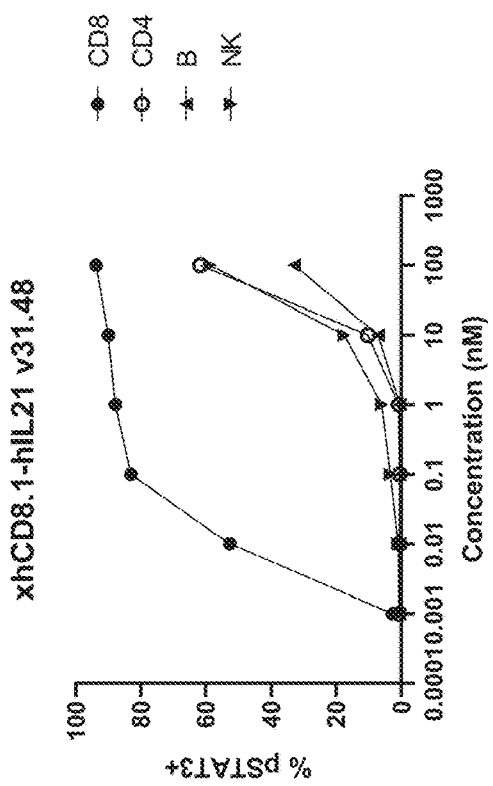
FIG. 14D
xhCD8.1-hIL21 v31.48
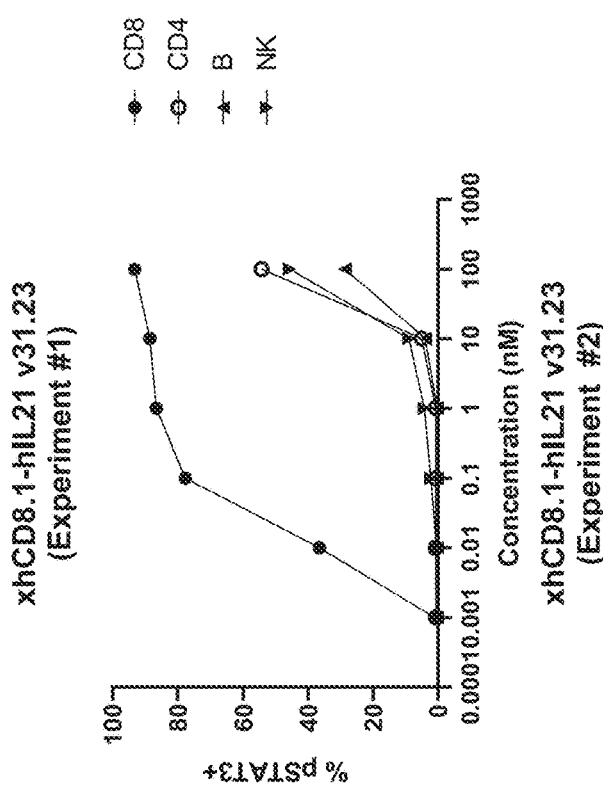
FIG. 14C
xhCD8.1-hIL21 v31.23
(Experiment #1)
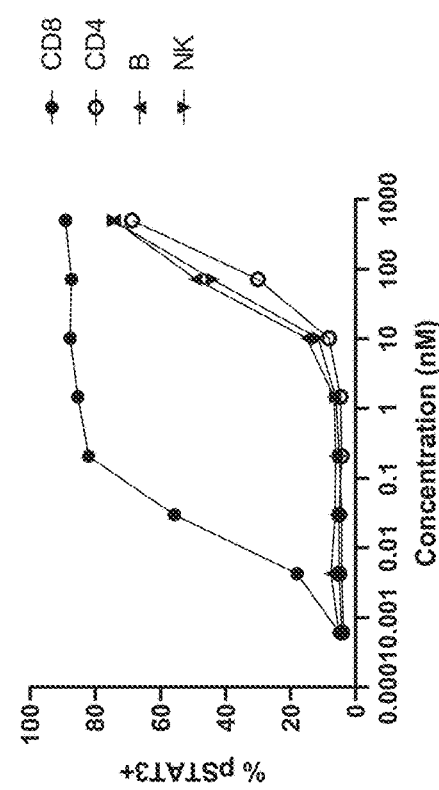
xhCD8.1-hIL21 v31.23
(Experiment #2)

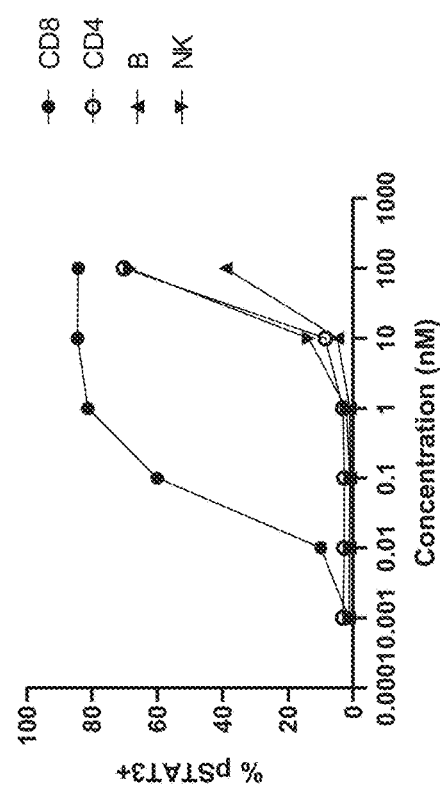
FIG. 15D
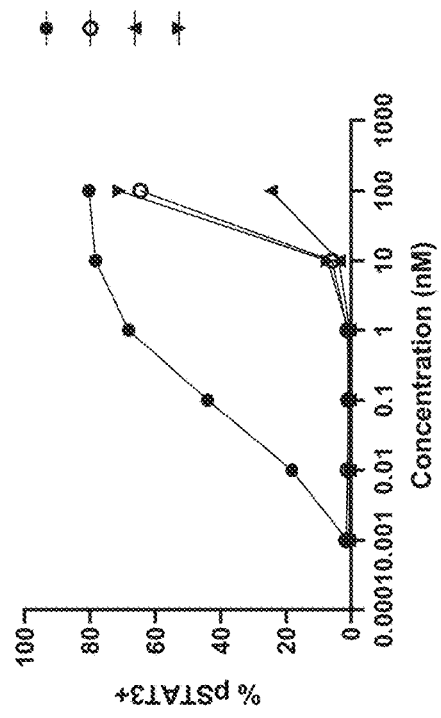
FIG. 15C
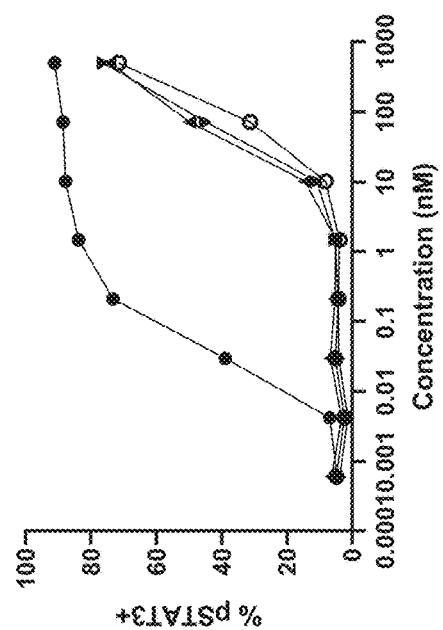

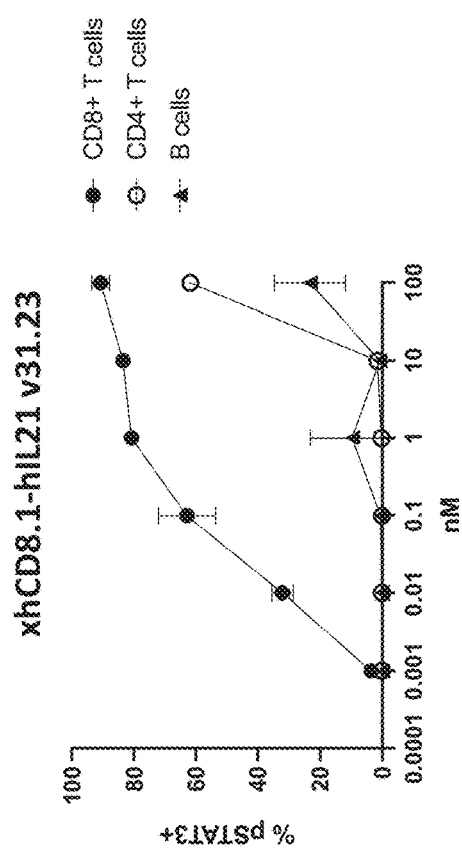
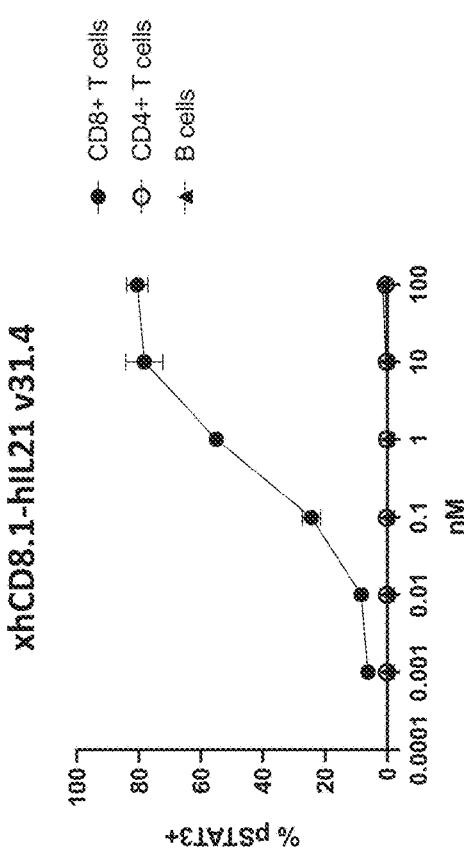
FIG. 23A
FIG. 23B

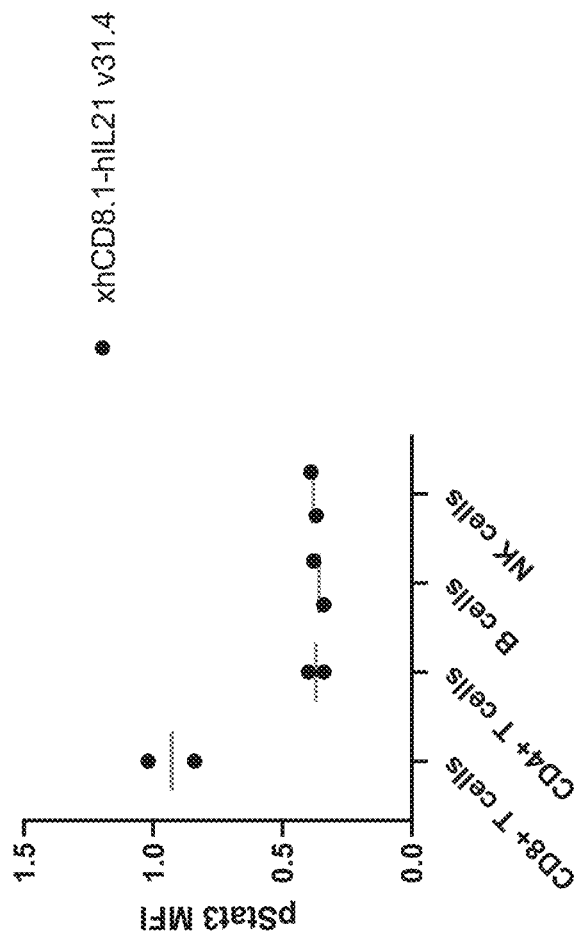

IL-21 POLYPEPTIDES AND TARGETED CONSTRUCTS

CROSS-REFERENCE TO RELATED APPLICATIONS

This application is a continuation of International Application No. PCT/US2022/026584, filed Apr. 27, 2022, which claims benefit to U.S. Provisional Application No. 63/297,631, filed Jan. 7, 2022, U.S. Provisional Application No. 63/223,684, filed Jul. 20, 2021, International Application No. PCT/US2021/062485, filed Dec. 8, 2021, International Application No. PCT/US2021/056312, filed Oct. 22, 2021, and U.S. Provisional Application No. 63/190,669, filed May 19, 2021. The entire contents of each application are incorporated herein by this reference.

SEQUENCE LISTING

The instant application contains a Sequence Listing which has been submitted electronically in XML format and is hereby incorporated by reference in its entirety. Said XML copy, created on May 5, 2023, is named 59820-705.301_Replacement_SL.xml and is 610,295 bytes in size.

BACKGROUND

Interleukin-21 (IL-21) is a T cell derived pleiotropic cytokine that regulates the activity of both innate and adaptive immune cells. IL-21 can augment T cell survival and effector function. Interleukin-21 is a type I cytokine and a member of the common cytokine receptor gamma-chain (γc) family that has emerged as a promising immune therapeutic for the treatment of cancer. In some cases, IL-21 that is produced by activated CD4+ T cells and natural killer T (NKT) cells signals via a heterodimeric receptor complex comprised of a discrete IL-21 receptor (IL-21R) subunit together with the γc. In some cases, activation of the IL-21R complex leads to the activation of the JAK/STAT signaling pathway. IL-21R is broadly expressed in hematopoietic cells including T and B lymphocytes, natural killer (NK) cells and myeloid cells. IL-21 is a potent mitogen and survival factor for both NK cells and activated T cells. IL-21 can support the differentiation of CD4+ T helper 17 (Th17) as well as follicular helper T cells (Tfh) and can antagonize regulatory T cell (Treg) differentiation. Additionally, IL-21 can augment the survival of CD8+ T cells resulting in a less activated but more persistent T cell phenotype that leads to enhanced tumor and viral control. A challenge of cytokine immunotherapy is that in some cases, while activating immune cells to potentiate immune responses, the same cytokine can also activate counter-regulatory pathways as exemplified by IL-2 and IFNγ. These counter-regulatory pathways can activate regulatory T cell responses and inhibitory pathways. Because it plays a key role in anti-tumor and anti-viral responses, in addition to exerting major effects on inflammatory responses that lead to the development of autoimmune diseases and inflammatory diseases, IL-21 has been an attractive target for several therapies.

There remains a need for treatment modalities utilizing IL-21, including modalities combining IL-21 moieties that direct IL-21 to specific cell types.

SUMMARY

Provided herein, in one embodiment of the disclosure is an IL-21 polypeptide or a functional fragment or a variant thereof comprising a polypeptide sequence having at least 80% sequence identity to SEQ ID NO: 1, wherein the IL-21 polypeptide has an isoelectric point that is at least about 0.6 units to about 5 units lower, compared to that of a wild-type IL-21 protein having a sequence of SEQ ID NO: 1. In some embodiments, the isoelectric point of SEQ ID NO: 1 is about 9.42. In some embodiments, the IL-21 polypeptide has an isoelectric point of about 7.12 to about 8.72. In some embodiments, the polypeptide provides an improved exposure compared to the wild-type IL-21 protein, as measured by at least about 1.5 times greater under the curve (AUC) for the polypeptide, relative to that of the wild-type IL-21, when administered to a subject, at equivalent concentrations. In some embodiments, the IL-21 polypeptide comprises at least one amino acid substitution that reduces the isoelectric point of the IL-21 polypeptide by about 0.6 units to about 5 units relative to the human IL-21 polypeptide without the amino acid substitution. In some embodiments, the IL-21 polypeptide comprises at least four amino acid substitutions that reduce the isoelectric point of the IL-21 polypeptide about 0.6 units to about 5 units relative to the human IL-21 polypeptide without the amino acid substitutions. In some embodiments, the IL-21 polypeptide comprises up to 10, 11, 12, 13, 14, 15, 16, 17, 18, 19 or 20 amino acid substitutions that reduce the isoelectric point.

In some embodiments, the disclosure provides an IL-21 polypeptide or a functional fragment or variant thereof, wherein relative to a region of a human IL-21 polypeptide that comprises about 2 to 20 positively charged amino acid residues, the IL-21 polypeptide comprises at least one amino acid substitution of the about 2 to 20 positively charged amino acid residues. In some embodiments, the region of the human IL-21 polypeptide does not include amino acid residues that bind a human IL-21 receptor. In some embodiments, the region of the human IL-21 polypeptide comprises amino acid residues S80 to T92 of the human IL-21 polypeptide comprising SEQ ID NO: 1. In some embodiments, the disclosure provides an IL-21 polypeptide or a functional fragment or variant thereof, wherein a human IL-21 polypeptide comprises at least one positively charged amino acid residue on the surface of the human IL-21 polypeptide in a three-dimensional structure of the human IL-21 polypeptide which does not directly interact with or bind a human IL-21 receptor, and wherein the IL-21 polypeptide comprises at least one amino acid substitution of the at least one positively charged amino acid residue. In some embodiments, the disclosure provides an IL-21 polypeptide that does not comprise an amino acid substitution at G84 of the human IL-21 polypeptide comprising SEQ ID NO: 1.

In some embodiments, the IL-21 polypeptide comprises a mutation at one or more positions selected from the group consisting of: K56, T81, N82, A83, G84, R85, R86, Q87, K88, H89, R90, L91, and T92 of SEQ ID NO: 1. In some embodiments, the IL-21 polypeptide comprises a mutation (e.g., an amino acid substitution) at one or more positions selected from the group consisting of: S80, T81, N82, A83, G84, R85, R86, Q87, K88, H89, R90, L91, and T92 of SEQ ID NO: 1. In some embodiments, the IL-21 polypeptide comprises 4, 5, 6, 7, 8, 9, 10, 11, or 12 amino acid substitutions at positions selected from S80, T81, N82, A83, R85, R86, Q87, K88, H89, R90, L91, or T92 of SEQ ID NO: 1. In some embodiments, the IL-21 polypeptide comprises 4, 5, 6, 7, 8, 9, 10, 11, or 12 amino acid substitutions selected from S80G, T81G, N82G, N82E, A82G, A83E, A83S, R85G, R85E, R85S, R86G, R86E, Q87G, Q87E, Q87S, K88G, H89G, H89S, R90G, R90S, R90E, R90A, L91G, L91S, T92G, T92S. In some embodiments, the IL-21 polypeptide comprises (a) R85G, R86G, K88G and R90E, or (b) S80G, T81G, N82E, A83G, R85G, R86G, Q87G, K88G, H89G, R90E, L91G, and T92G. In some embodiments, the disclosure provides an IL-21 polypeptide that does not comprise an amino acid substitution at G84 of the human IL-21 polypeptide comprising SEQ ID NO: 1.

In some embodiments, the disclosure provides an IL-21 polypeptide or functional fragment or variant thereof comprising the amino acid sequence: QGQDRHMIRMRQLIDI-VDQLKNYVNDLVPEFLPAPEDVETNCEWSAFSCFQ-KAQLKSANT GNNERIINVSIKKLKRKPPX$_1$X$_2$X$_3$X$_4$ GX$_5$X$_6$X$_7$X$_8$X$_9$X$_{10}$X$_{11}$X$_{12}$CPSCDSYEKKPPKEFLERFK-SL LQKMIHQHLSSRTHGSEDS (SEQ ID NO: 380), wherein X$_1$=G, S; X$_2$=G, T; X$_3$=G, E, N; X$_4$=G, S, E, A; X$_5$=G, E, S, R; X$_6$=G, E, R; X$_7$=S, G, E, Q; X$_8$=G, K; X$_9$=G, S, H; X$_{10}$=A, E, S, G, R; X$_{11}$=S, G, L; and X$_{12}$=G, S, T, provided at least one of X$_5$, X$_6$, X$_8$, X$_9$, and X$_{10}$ is not the amino acid residue at the identical position set forth in SEQ ID NO: 1, optionally wherein:
  (i) X$_5$=G, X$_6$=G, X$_8$=G, X$_{10}$=A;
  (ii) X$_5$=G, X$_6$=G, X$_8$=G, X$_{10}$=E;
  (iii) X$_1$=G, X$_2$=G, X$_3$=G, X$_4$=S, X$_5$=E, X$_6$=G, X$_7$=S, X$_8$=G, X$_9$=G, X$_{10}$=S;
  (iv) X$_1$=G, X$_2$=G, X$_3$=G, X$_4$=S, X$_5$=G, X$_6$=G, X$_7$=S, X$_8$=G, X$_9$=G, X$_{10}$=E;
  (v) X$_5$=G, X$_6$=G, X$_7$=S, X$_8$=G, X$_9$=G, X$_{10}$=E;
  (vi) X$_5$=G, X$_6$=G, X$_7$=S, X$_8$=G, X$_9$=G, X$_{10}$=S;
  (vii) X$_5$=G, X$_6$=G, X$_7$=G, X$_8$=G, X$_9$=G, X$_{10}$=E;
  (viii) X$_5$=G, X$_6$=G, X$_7$=G, X$_8$=G, X$_9$=G, X$_{10}$=G;
  (ix) X$_5$=G, X$_6$=G, X$_7$=E, X$_8$=G, X$_9$=G, X$_{10}$=G;
  (x) X$_1$=G, X$_2$=G, X$_3$=G, X$_4$=S, X$_5$=G, X$_6$=G, X$_7$=S, X$_8$=G, X$_9$=G, X$_{10}$=G, X$_{11}$=S, X$_{12}$=G;
  (xi) X$_1$=G, X$_2$=G, X$_3$=G, X$_4$=G, X$_5$=G, X$_6$=G, X$_7$=G, X$_8$=G, X$_9$=G, X$_{10}$=G, X$_{11}$=G, X$_{12}$=G;
  (xii) X$_1$=G, X$_2$=G, X$_3$=G, X$_4$=S, X$_5$=G, X$_6$=G, X$_7$=E, X$_8$=G, X$_9$=G, X$_{10}$=G, X$_{11}$=S, X$_{12}$=G;
  (xiii) X$_1$=G, X$_2$=G, X$_3$=G, X$_4$=E, X$_5$=G, X$_6$=G, X$_7$=E, X$_8$=G, X$_9$=G, X$_{10}$=G, X$_{11}$=S, X$_{12}$=G;
  (xiv) X$_3$=G, X$_4$=G, X$_5$=S, X$_6$=G, X$_7$=G, X$_8$=G, X$_9$=S, X$_{10}$=G, X$_{11}$=G, X$_{12}$=S;
  (xv) X$_3$=G, X$_4$=G, X$_5$=E, X$_6$=G, X$_7$=G, X$_8$=G, X$_9$=S, X$_{10}$=G, X$_{11}$=G, X$_{12}$=S;
  (xvi) X$_1$=G, X$_2$=G, X$_3$=G, X$_4$=G, X$_5$=E, X$_6$=G, X$_7$=G, X$_8$=G, X$_9$=G, X$_{10}$=G, X$_{11}$=G, X$_{12}$=G;
  (xvii) X$_1$=G, X$_2$=G, X$_3$=G, X$_4$=S, X$_5$=G, X$_6$=G, X$_7$=S, X$_8$=G, X$_9$=G, X$_{10}$=E, X$_{11}$=G, X$_{12}$=G;
  (xviii) X$_1$=G, X$_2$=G, X$_3$=G, X$_4$=G, X$_5$=G, X$_6$=G, X$_7$=G, X$_8$=G, X$_9$=G, X$_{10}$=E, X$_{11}$=G, X$_{12}$=G;
  (xix) X$_3$=G, X$_4$=G, X$_5$=S, X$_6$=G, X$_7$=G, X$_8$=G, X$_9$=S, X$_{10}$=E, X$_{11}$=G, X$_{12}$=S;
  (xx) X$_3$=G, X$_4$=G, X$_5$=G, X$_6$=G, X$_7$=G, X$_8$=G, X$_9$=G, X$_{10}$=E, X$_{11}$=G, X$_{12}$=G;
  (xxi) X$_5$=G, X$_6$=G, X$_7$=G, X$_8$=G, X$_9$=G, X$_{10}$=E, X$_{11}$=G;
  (xxii) X$_3$=G, X$_4$=G, X$_5$=G, X$_6$=G, X$_7$=G, X$_8$=G, X$_9$=G, X$_{10}$=E, X$_{11}$=G;
  (xxiii) X$_3$=G, X$_4$=G, X$_5$=G, X$_6$=E, X$_7$=G, X$_8$=G, X$_9$=G, X$_{10}$=E, X$_{11}$=G;
  (xxiv) X$_3$=G, X$_4$=G, X$_5$=E, X$_6$=G, X$_7$=G, X$_8$=G, X$_9$=G, X$_{10}$=E, X$_{11}$=G;
  (xxv) X$_1$=G, X$_2$=G, X$_3$=G, X$_4$=E, X$_5$=G, X$_6$=G, X$_7$=G, X$_8$=G, X$_9$=G, X$_{10}$=E, X$_{11}$=G, X$_{12}$=G; or
  (xxvi) X$_1$=G, X$_2$=G, X$_3$=E, X$_4$=G, X$_5$=G, X$_6$=G, X$_7$=G, X$_8$=G, X$_9$=G, X$_{10}$=E, X$_{11}$=G, X$_{12}$=G. In some embodiments, the disclosure provides an IL-21 polypeptide that does not comprise an amino acid substitution at G84 of the human IL-21 polypeptide comprising SEQ ID NO: 1.

In some embodiments, the disclosure provides an IL-21 polypeptide or functional fragment or variant thereof comprising an amino acid sequence at least 90%, about 95%, about 96%, about 97%, about 98%, or about 99% identical to an amino acid sequence selected from SEQ ID NOs: 2, 4-15, and 23-40. In some embodiments, the IL-21 polypeptide comprises an amino acid sequence selected from SEQ ID NOs: 2, 4-15, and 23-40. In some embodiments, the IL-21 polypeptide comprises the amino acid sequence of SEQ ID NO: 40.

In some embodiments, the disclosure provides an IL-21 polypeptide or functional fragment or variant thereof comprising at least one amino acid substitution that reduces binding to a human IL-21 receptor compared to binding by the human IL-21 polypeptide. In some embodiments, the at least one amino acid substitution is at one or more amino acid residues at positions R5, I8, R9, R11, L13, I14, I16, V17, D18, K72, K73, L74, K75, R76, K77, or K117, of SEQ ID NO: 1. In some embodiments, the at least one amino acid substitution is selected from: R5F, R5A, R5E, R5S, R5T, R5N, R5Q, R5V, R5I, R5L, R5Y, I8E, R9A, R9D, R9E, R9H, R9S, R9T, R9N, R9G, R9V, R9I, R9L, R9Y, R11D, R11E, L13F, L13R, I14D, I16A, I16S, I16R, V17I, V17A, D18A, K72A, K72E, K73A, K73E, K75A, K75E, L74I, L74F, L74M, L74V, R76E, R76F, R76A, R76N, R76D, R76S, R76T, R76Q, R76V, R76I, R76L, R76Y, R76M, K77A, K77E, and K117A. In some embodiments, the at least one amino acid substitution is R76E or R76Q. In some embodiments, the IL-21 polypeptide comprises a mutation at a position selected from the group consisting of: R5, I8, R9, R11, Q12, I14, D15, D18, Q19, Y23, R65, S70, K72, K73, K75, R76, K77, S80, Q116, and K117 of SEQ ID NO: 1. In some embodiments, the IL-21 polypeptide comprises an amino acid sequence that is at least about 85%, about 90%, about 95%, about 96%, about 97%, about 98%, about 99%, or about 100% identical to the sequence of SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15. In some embodiments, the IL-21 polypeptide comprises an amino acid sequence that is at least about 85%, about 90%, about 95%, about 96%, about 97%, about 98%, about 99%, or about 100% identical to the sequence of SEQ ID NO: 16, SEQ ID NO: 17, SEQ ID NO: 18, SEQ ID NO: 19, SEQ ID NO: 20, or SEQ ID NO: 21. In some embodiments, the IL-21 polypeptide comprises an amino acid sequence that is at least about 85%, about 90%, about 95%, about 96%, about 97%, about 98%, about 99%, or about 100% identical to a sequence selected from SEQ ID NOs: 2, 4-15, and 23-40. In some embodiments, the IL-21 polypeptide comprises an amino acid sequence that is at least about 85%, about 90%, about 95%, about 96%, about 97%, about 98%, about 99%, or about 100% identical to a sequence selected from SEQ ID NOs: 16-21, 41-98 and 374-379. In some embodiments, the IL-21 polypeptide comprises an amino acid sequence that is at least about 85%, about 90%, about 95%, about 96%, about 97%, about 98%, about 99%, or about 100% identical to a sequence selected from SEQ ID NOs: 16-21, 41-93 and 374-379. In some embodiments, the IL-21 polypeptide comprises an amino acid sequence that is at least about 85%, about 90%, about 95%, about 96%, about 97%, about 98%, about 99%, or about 100% identical to a sequence selected from SEQ ID NOs: 94-98.

Provided herein, in one embodiment of the disclosure, is a targeted cytokine construct comprising an IL-21 polypeptide or a functional fragment or a variant thereof according to the present disclosure and an antibody or an antigen binding fragment thereof. In some embodiments, the antibody or antigen binding fragment thereof specifically binds to a CD8+ T cell. In some embodiments, the antibody or antigen binding fragment thereof specifically binds to at least one of: CD8α, CD8αα, or CD8αβ. In some embodiments, the antibody or antigen binding fragment thereof specifically binds to CD8β.

Provided herein, in one embodiment of the disclosure, is a targeted cytokine construct comprising: a) an IL-21 polypeptide or a functional fragment or a variant thereof comprising an amino acid sequence that is at least 80% identical to SEQ ID NO: 1; and b) an antibody or an antigen binding fragment thereof that specifically binds to at least one of CD8α, CD8αα, or CD8αβ.

Provided herein, in one embodiment of the disclosure, is a targeted cytokine construct comprising: a) an IL-21 polypeptide or a functional fragment or a variant thereof comprising an amino acid sequence that is at least 80% identical to SEQ ID NO: 1; and b) an antibody or an antigen binding fragment thereof that specifically binds to CD8β.

In some embodiments, the IL-21 polypeptide comprises a mutation at one or more amino acid positions of SEQ ID NO: 1. In some embodiments, the IL-21 polypeptide comprises a mutation at one or more positions selected from the group consisting of: K56, T81, N82, A83, G84, R85, R86, Q87, K88, H89, R90, L91, and T92 of SEQ ID NO: 1. In some embodiments, the IL-21 polypeptide comprises mutation at a position selected from the group consisting of: R5, I8, R9, R11, Q12, I14, D15, D18, Q19, Y23, R65, S70, K72, K73, K75, R76, K77, S80, Q116, and K117 of SEQ ID NO: 1. In some embodiments, the IL-21 polypeptide or a functional fragment or a variant thereof comprises an amino acid sequence that is at least about 85%, about 90%, about 95%, about 96%, about 97%, about 98%, about 99%, or about 100% identical to the sequence of SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15.

In some embodiments, the IL-21 polypeptide or a functional fragment or a variant thereof comprises an amino acid sequence that is at least about 85%, about 90%, about 95%, about 96%, about 97%, about 98%, about 99%, or about 100% identical to the sequence of SEQ ID NO: 16, SEQ ID NO: 17, SEQ ID NO: 18, SEQ ID NO: 19, SEQ ID NO: 20, or SEQ ID NO: 21. In some embodiments, the construct activates CD8+ T cells with at least about 10-fold or greater potency as compared to activation of NK or CD4+ T cells. In some embodiments, the construct activates CD8+ T cells with a potency that is at least about 10-fold to about 100,000-fold greater as compared to activation of NK or CD4+ T cells. In some embodiments, the antibody or antigen binding fragment thereof comprises: i) a first polypeptide, arranged from N-to-C terminus, comprising: a variable light chain (VL) amino acid sequence, and a light chain constant region amino acid sequence (CL1); ii) a second polypeptide, arranged from N-to-C terminus, comprising: a variable heavy chain (VH) amino acid sequence, a heavy chain CH1 constant region amino acid sequence, a hinge region amino acid sequence, a heavy chain CH2 constant region amino acid sequence, and a heavy chain CH3 constant region amino acid sequence; iii) a third polypeptide, arranged from N-to-C terminus, comprising: a hinge region amino acid sequence, a heavy chain CH2 constant region amino acid sequence, and a heavy chain CH3 constant region amino acid sequence, wherein the CH2 and CH3 domains of each of the second and third polypeptides form an Fc domain. In some embodiments, the third polypeptide, arranged from N-to-C terminus, comprises: a variable heavy chain (VH) amino acid sequence, a heavy chain CH1 constant region amino acid sequence, a hinge region amino acid sequence, a heavy chain CH2 constant region amino acid sequence, a heavy chain CH3 constant region amino acid sequence, wherein the antibody or antigen binding fragment thereof further comprises: iv) a fourth polypeptide, arranged from N-to-C terminus, comprising: a variable light chain (VL) amino acid sequence, and a light chain constant amino acid sequence (CL1). In some embodiments, the IL-21 polypeptide or a functional fragment or a variant thereof and the antibody or antigen binding fragment thereof are operably linked to each other. In some embodiments, the IL-21 polypeptide or a functional fragment or a variant thereof is linked to the N-terminus or C-terminus of the antibody or antigen binding fragment thereof. In some embodiments, the IL-21 polypeptide or a functional fragment or variant thereof is conjugated to the C-terminus of the second or the third polypeptide. In some embodiments, the targeted cytokine construct comprises at least one molecule of the IL-21 polypeptide. In some embodiments, the Fc domain is a human IgG Fc domain. In some embodiments, the Fc domain is an IgG1, IgG2, IgG3, or IgG4 Fc domain. In some embodiments, the Fc domain comprises one or more modifications that promote heterodimerization. In some embodiments, the second polypeptide comprises a knob modification in the CH2 or the CH3 domain, and the third polypeptide comprises a hole modification in the CH2 or the CH3 domain; or wherein the third polypeptide comprises a knob modification in the CH2 or the CH3 domain and the second polypeptide comprises a hole modification in the CH2 or the CH3. In some embodiments, at least one of the second and the third polypeptide comprises the following mutations: L234A, L235A, and G237A, numbering according to the EU index.

Provided herein, in one embodiments of the disclosure, is a targeted cytokine construct comprising: a) an IL-21 polypeptide or a functional fragment or variant thereof comprising an amino acid sequence that is at least 80% identical to SEQ ID NO: 1; and b) an antibody or an antigen binding fragment thereof comprising a first antigen binding arm and a second antigen binding arm, wherein the first and the second antigen binding arms bind to two different antigens, wherein at least one of the first and the second antigen binding arm specifically binds to CD8α, CD8αα, CD8αβ.

Provided herein, in one embodiments of the disclosure, is a targeted cytokine construct comprising: a) an IL-21 polypeptide or a functional fragment or variant thereof comprising an amino acid sequence that is at least 80% identical to SEQ ID NO: 1; and b) an antibody or an antigen binding fragment thereof comprising a first antigen binding arm and a second antigen binding arm, wherein the first and the second antigen binding arms bind to two different antigens, wherein at least one of the first and the second antigen binding arm specifically binds to CD80β. In some embodiments, the targeted cytokine construct activates CD8+ T cells with at least about 10-fold or greater potency as compared to activation of NK cells or CD4+ T cells. In some embodiments, targeted cytokine construct activates CD8+ T cells a potency that is at least about 10-fold to about 100,000-fold greater as compared to activation of NK cells or CD4+ T cells. In some embodiments, the IL-21 polypeptide or a functional fragment thereof or a variant thereof comprises a mutation at a position selected from the group consisting of: K56, T81, N82, A83, R85, G84, R86, Q87, K88, H89, R90, L91, and T92 of SEQ ID NO: 1. In some embodiments, the IL-21 polypeptide or a functional fragment thereof or a variant thereof comprises a mutation at a position selected from the group consisting of: R5, I8, R9, R11, Q12, I14, D15, D18, Q19, Y23, R65, S70, K72, K73, K75, R76, K77, S80, Q116, and K117 of SEQ ID NO: 1. In some embodiments, the IL-21 polypeptide or a functional fragment or a variant thereof comprises an amino acid sequence that is at least about 85%, about 90%, about 95%, about 96%, about 97%, about 98%, about 99%, or about 100% identical to the sequence of SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15. In some embodiments, the IL-21 polypeptide or a functional fragment or a variant thereof comprises an amino acid sequence that is at least about 85%, about 90%, about 95%, about 96%, about 97%, about 98%, about 99%, or about 100% identical to the sequence of SEQ ID NO: 16, SEQ ID NO: 17, SEQ ID NO: 18, SEQ ID NO: 19, SEQ ID NO: 20, or SEQ ID NO: 21.

In some embodiments, the disclosure provides a fusion protein comprising:
a) an IL-21 polypeptide comprising (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide; and
b) an antibody or an antigen binding fragment thereof that specifically binds to CD8αβ or CD8β. In some embodiments, the IL-21 polypeptide does not comprise a G84 substitution. In some embodiments, the at least one amino acid substitution providing reduced binding is R76E or R76Q.

In some embodiments, the disclosure provides a fusion protein comprising:
a) an IL-21 polypeptide comprising (i) four or more amino acid substitutions providing a reduced isoelectric point relative to a human IL-21 polypeptide comprising SEQ ID NO: 1, wherein the four or more amino acid substitutions are within S80 to T92 of SEQ ID NO: 1, wherein at least four amino acid substitutions are at residues R85, R86, K88, H89, R90, or a combination thereof, and (ii) at least one amino acid substitution providing reduced binding to a human IL-21 receptor relative to binding by the human IL-21 polypeptide; and
b) an antibody or an antigen binding fragment thereof that specifically binds to CD8αβ or CD8β.

In some embodiments, the disclosure provides a fusion protein comprising:
a) an IL-21 polypeptide comprising (i) four or more amino acid substitutions providing a reduced isoelectric point relative to a human IL-21 polypeptide comprising SEQ ID NO: 1, wherein the four or more amino acid substitutions are within S80 to T92 of SEQ ID NO: 1, wherein at least four amino acid substitutions are at residues R85, R86, K88, H89, R90, or a combination thereof, and (ii) at least one amino acid substitution providing reduced binding to a human IL-21 receptor relative to binding by the human IL-21 polypeptide, wherein the at least one amino acid substitution is at a residue selected from R5, I8, R9, R11, L13, I14, I16, V17, D18, K72, K73, L74, K75, R76, K77, K117, and a combination thereof, and
b) an antibody or an antigen binding fragment thereof that specifically binds to CD8αβ or CD8β.

In some embodiments, the disclosure provides a fusion protein comprising:
a) an IL-21 polypeptide comprising (i) four or more amino acid substitutions providing a reduced isoelectric point relative to a human IL-21 polypeptide comprising SEQ ID NO: 1, wherein the four or more amino acid substitutions are within S80 to T92 of SEQ ID NO: 1, wherein at least four amino acid substitutions are at residues R85, R86, K88, H89, R90, or a combination thereof, and (ii) at least one amino acid substitution selected from: (a) R11D; (b) R11E; (c) I14D, D18A and K117A; (d) R76E; (e) R5F; (f) R76F; (g) I8E; (h) R5A; (i) R5E; (j) R5S; (k) R5T; (l) R5N; (m) R5Q; (n) R5V; (o) R5I; (p) R5L; (q) R5Y; (r) R76A; (s) R76N; (t) R76D; (u) R76S; (v) R76T; (w) R76Q; (x) R76V; (y) R76I; (z) R76L; (aa) R76Y; (bb) K77A; (cc) K77E; (dd) K72A; (ee) K72E; (ff) K75A; (gg) K75E; (hh) K73A; (ii) K73E; (jj) R5F and K77A; (kk) R5F and K77E; (ll) R5F and K72A; (mm) R5F and K72E; (nn) R5F and K76A; (oo) R5F and K76E; (pp) K73A and K76F; (qq) K73E and K76F; (rr) R9A; (ss) R9D; (tt) R9E; (uu) R9H; (vv) R9S; (ww) R9T; (xx) R9N; (zz) R9G; (aaa) R9V; (bbb) R9I; (ccc) R9L; (ddd) R9Y; (eee) K72A and R76F; (fff) K75A and R76F; (ggg) R76F and K77A; (hhh) K75E and R76F; (iii) V17I and L74I; (jjj) I16A and L74F; (kkk) I16S, V17I, and L74V; (lll) I16R, V17I, and L74I; (mmm) L13F, I16A, V17A and L74M; and (nnn) L13R, I16A, V17I and L74I; and b) an antibody or an antigen binding fragment thereof that specifically binds to CD8αβ or CD8β.

In some embodiments, the disclosure provides a fusion protein comprising:

a) an IL-21 polypeptide comprising (i) four or more amino acid substitutions providing a reduced isoelectric point relative to a human IL-21 polypeptide comprising SEQ ID NO: 1, wherein the four or more amino acid substitutions are at residues S80, T81, N82, A83, R85, R86, Q87, K88, H89, R90, L91, T92, or a combination thereof, and (ii) at least one amino acid substitution providing reduced binding to a human IL-21 receptor relative to binding by the human IL-21 polypeptide, wherein the at least one amino acid substitution is at a residue selected from R5, I8, R9, R11, L13, I14, I16, V17, D18, K72, K73, L74, K75, R76, K77, K117, and a combination thereof, and b) an antibody or an antigen binding fragment thereof that specifically binds to CD8αβ or CD8β.

In some embodiments, the disclosure provides a fusion protein comprising:

a) an IL-21 polypeptide comprising (i) four or more amino acid substitutions providing a reduced isoelectric point relative to a human IL-21 polypeptide comprising SEQ ID NO: 1, wherein the four or more amino acid substitutions are at residues S80, T81, N82, A83, R85, R86, Q87, K88, H89, R90, L91, T92, or a combination thereof, and (ii) at least one amino acid substitution providing reduced binding to a human IL-21 receptor relative to binding by the human IL-21 polypeptide, wherein the at least one amino acid substitution is at residue R76; and b) an antibody or an antigen binding fragment thereof that specifically binds to CD8αβ or CD8β.

In some embodiments, the disclosure provides a fusion protein comprising:
a) an IL-21 polypeptide comprising (i) an amino acid sequence selected from SEQ ID NOs: 2, 4-15 and 23-40, and (ii) at least one amino acid substitution providing reduced binding to a human IL-21 receptor relative to binding by the human IL-21 polypeptide; and
b) an antibody or an antigen binding fragment thereof that specifically binds to CD8αβ or CD8β.

In some embodiments, the disclosure provides a fusion protein comprising:
a) an IL-21 polypeptide comprising (i) an amino acid sequence selected from SEQ ID NOs: 2, 4-15 and 23-40, and (ii) at least one amino acid substitution providing reduced binding to a human IL-21 receptor relative to binding by the human IL-21 polypeptide, wherein the at least one amino acid substitution is at a residue selected from R5, I8, R9, R11, L13, I14, I16, V17, D18, K72, K73, L74, K75, R76, K77, K117, and a combination thereof; and
b) an antibody or an antigen binding fragment thereof that specifically binds to CD8αβ or CD8β.

In some embodiments, the disclosure provides a fusion protein comprising:
a) an IL-21 polypeptide comprising (i) an amino acid sequence selected from SEQ ID NOs: 2, 4-15 and 23-40, and (ii) at least one amino acid substitution providing reduced binding to a human IL-21 receptor relative to binding by the human IL-21 polypeptide, wherein the at least one amino acid substitution is at residue R76; and
b) an antibody or an antigen binding fragment thereof that specifically binds to CD8αβ or CD8β.

In some embodiments, the IL-21 polypeptide and the antibody or antigen binding fragment thereof are linked to each other via a linker. In some embodiments, the IL-21 polypeptide is linked to the N-terminus or C-terminus of the antibody or antigen binding fragment thereof. In some embodiments, the IL-21 polypeptide is linked to the C-terminus of the antibody or antigen binding fragment thereof.

In some embodiments, the disclosure provides a fusion protein comprising:
a) a first polypeptide comprising a VL chain and a CL1 chain;
b) a second polypeptide comprising a VH chain and a HC constant domain, wherein an IL-21 polypeptide is operably linked to the C-terminus of the HC constant domain, and wherein the HC constant domain comprises a knob modification;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the VH chains and VL chains comprise CDRs that specifically bind to CD8αβ or CD8β,
wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain;
b) a second polypeptide comprising a VH chain and a HC constant domain, wherein the HC constant domain comprises a knob modification;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the VH chains and VL chains comprise CDRs that specifically bind to CD8αβ or CD8β,
wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

Provided herein, in one embodiment of the disclosure, is a polynucleotide encoding an IL-21 polypeptide or a functional fragment or a variant thereof according to any one of claims 1-8.

Provided herein, in one embodiment of the disclosure, is a polynucleotide that codes for a targeted cytokine construct comprising an IL-21 polypeptide or a functional fragment or a variant thereof and an antibody or an antigen binding fragment thereof, according to the present disclosure, the polynucleotide comprising a coding sequence for the IL-21 polypeptide and a coding sequence for the antibody or an antigen binding fragment thereof.

Provided herein, in one embodiment of the disclosure, is a vector comprising the polynucleotide the present disclosure.

Provided herein, in one embodiment of the disclosure, is a host cell comprising the polynucleotide or the vector of the present disclosure.

Provided herein, in one embodiment of the disclosure, is a pharmaceutical composition comprising an IL-21 polypeptide or a functional fragment or variant thereof according to the present disclosure and a pharmaceutically acceptable carrier.

Provided herein, in one embodiment of the disclosure, is a pharmaceutical composition comprising a targeted cytokine construct according to the present disclosure and a pharmaceutically acceptable carrier.

Provided herein, in one embodiment of the disclosure, is a method for selective activation of CD8+ T cells, wherein the method comprises contacting a population of cells comprising CD8+ T cells, CD4+ T cells, and NK cells, with a targeted cytokine construct according to the present disclosure. In some embodiments, the selective activation comprises activation of CD8+ T cells with at least about 10-fold or greater potency, as compared to activation of NK cells or CD4+ T cells in the population of cells. In some embodiments, the selective activation comprises activation of CD8+ T cells with a potency that is at least about 10-fold to about 100,000-fold greater as compared to activation of NK cells or CD4+ T cells in the population of cells. In some embodiments, the selective activation of CD8+ T cells results in increased STAT3 phosphorylation of the CD8+ T cells compared to the STAT3 phosphorylation of the NK cells or CD4+ T cells in the population of cells.

Provided herein, in one embodiment of the disclosure, is a method of treating a disease in a subject, the method comprising administering an IL-21 polypeptide or a functional fragment or a variant thereof according to the present disclosure, a targeted cytokine construct described herein, or a pharmaceutical composition according to the present disclosure. In some embodiments, the method further comprises an additional therapeutic agent. In some embodiments, the disease comprises a cancer or a chronic infection. In some embodiments, the disease comprises the cancer and wherein the cancer is acute lymphoblastic leukemia (ALL) (including non T cell ALL), acute myeloid leukemia, B cell prolymphocytic leukemia, B cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammopathy of undetermined significance (MGUS), multiple myeloma, myelodysplasia and myelodysplastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, or Waldenstrom macroglobulinemia, Mantle cell lymphoma (MCL), Transformed follicular lymphoma (TFL), Primary mediastinal B cell lymphoma (PMBCL), Multiple myeloma, Hairy cell lymphoma/leukemia, lung cancer, small-cell lung cancer, non-small cell lung (NSCL) cancer, bronchioloalveolar cell lung cancer, squamous cell cancer, adenocarcinoma of the lung, squamous carcinoma of the lung, cancer of the peritoneum, head and neck cancer, bone cancer, pancreatic cancer, skin cancer, cancer of the head or neck, cutaneous or intraocular melanoma, thyroid cancer, uterine cancer, gastrointestinal cancer, ovarian cancer, rectal cancer, cancer of the anal region, stomach cancer, gastric cancer, colon cancer, breast cancer, endometrial carcinoma, uterine cancer, carcinoma of the fallopian tubes, carcinoma of the cervix, carcinoma of the vagina, vulval cancer, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, bladder cancer, liver cancer, hepatoma, hepatocellular cancer, cervical cancer, salivary gland carcinoma, biliary cancer, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenoma and Ewing's sarcoma, including refractory versions of any of the above cancers, or a combination of one or more of the above cancers.

In some embodiments, the antibody or antigen binding fragment comprises a heavy chain variable (VH) domain and a light chain variable (VL) domain; and wherein: (a) the VH domain comprises a CDR-H1 comprising the amino acid sequence of SEQ ID NO:137, a CDR-H2 comprising the amino acid sequence of SEQ ID NO:138, and a CDR-H3 comprising the amino acid sequence of SEQ ID NO:139; and wherein the VL domain comprises a CDR-L1 comprising the amino acid sequence of SEQ ID NO:140, a CDR-L2 comprising the amino acid sequence of SEQ ID NO:141, and a CDR-L3 comprising the amino acid sequence of SEQ ID NO:142; (b) the VH domain comprises a CDR-H1 comprising the amino acid sequence of SEQ ID NO:149, a CDR-H2 comprising the amino acid sequence of SEQ ID NO:150, and a CDR-H3 comprising the amino acid sequence of SEQ ID NO:151; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154; (c) the VH domain comprises a CDR-H1 comprising the amino acid sequence of SEQ ID NO:155, a CDR-H2 comprising the amino acid sequence of SEQ ID NO:156, and a CDR-H3 comprising the amino acid sequence of SEQ ID NO:157; and wherein the VL domain comprises a CDR-L1 comprising the amino acid sequence of SEQ ID NO:158, a CDR-L2 comprising the amino acid sequence of SEQ ID NO:159, and a CDR-L3 comprising the amino acid sequence of SEQ ID NO:160; (d) the VH domain comprises a CDR-H1 comprising the amino acid sequence of SEQ ID NO: 161, a CDR-H2 comprising the amino acid sequence of SEQ ID NO:162, and a CDR-H3 comprising the amino acid sequence of SEQ ID NO:163; and wherein the VL domain comprises a CDR-L1 comprising the amino acid sequence of SEQ ID NO:164, a CDR-L2 comprising the amino acid sequence of SEQ ID NO:165, and a CDR-L3 comprising the amino acid sequence of SEQ ID NO:166; (e) the VH domain comprises a CDR-H1 comprising the amino acid sequence of SEQ ID NO:167, a CDR-H2 comprising the amino acid sequence of SEQ ID NO:168, and a CDR-H3 comprising the amino acid sequence of SEQ ID NO:169; and wherein the VL domain comprises a CDR-L1 comprising the amino acid sequence of SEQ ID NO:170, a CDR-L2 comprising the amino acid sequence of SEQ ID NO:171, and a CDR-L3 comprising the amino acid sequence of SEQ ID NO:172; (f) the VH domain comprises a CDR-H1 comprising the amino acid sequence of SEQ ID NO:173, a CDR-H2 comprising the amino acid sequence of SEQ ID NO:174, and a CDR-H3 comprising the amino acid sequence of SEQ ID NO:175; and wherein the VL domain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178; (g) the VH domain comprises a CDR-H1 comprising the amino acid sequence of SEQ ID NO:179, a CDR-H2 comprising the amino acid sequence of SEQ ID NO:180, and a CDR-H3 comprising the amino acid sequence of SEQ ID NO:181; and wherein the VL domain comprises a CDR-L1 comprising the amino acid sequence of SEQ ID NO:182, a CDR-L2 comprising the amino acid sequence of SEQ ID NO:183, and a CDR-L3 comprising the amino acid sequence of SEQ ID NO:184; (h) the VH domain comprises a CDR-H1 comprising the amino acid sequence of SEQ ID NO:143, a CDR-H2 comprising the amino acid sequence of SEQ ID NO:144, and a CDR-H3 comprising the amino acid sequence of SEQ ID NO:145; and wherein the VL domain comprises a CDR-L1 comprising the amino acid sequence of SEQ ID NO:146, a CDR-L2 comprising the amino acid sequence of SEQ ID NO:147, and a CDR-L3 comprising the amino acid sequence of SEQ ID NO:148; (i) the VH domain comprises a CDR-H1 comprising the amino acid sequence of X1X2AIS, wherein X1 is S, K, G, N, R, D, T, or G, and wherein X2 is Y, L, H, or F (SEQ ID NO:185), a CDR-H2 comprising the amino acid sequence of X1X2X3PX4X5X6X7X8X9YX10QKFX11G, wherein X1 is G or H, X2 is I or F, X3 is I, N, or M, X4 is G, N, H, S, R, I, or A, X5 is A, N, H, S, T, F, or Y, X6 is A, D, or G, X7 is T, E, K, V, Q, or A, X8 is A or T, X9 is N or K, X10 is A or N, and X11 is Q or T (SEQ ID NO:186), and a CDR-H3 comprising the amino acid sequence of X1X2X3GX4X5LFX6X7, wherein X1 is D or A, X2 is A, G, E, R, Y, K, N, Q, L, or F, X3 is A, L, P, or Y, X4 is I or L, X5 is R, A, Q, or S, X6 is A or D, and X7 is D, E, A, or S (SEQ ID NO: 187); and wherein the VL domain comprises a CDR-L1 comprising the amino acid sequence of X1X2SX3X4IX5GX6LN, wherein X1 is R or G, X2 is A or T, X3 is Q or E, X4 is E, N, T, S, A, K, D, G, R, or Q, X5 is Y or S, and X6 is A or V (SEQ ID NO:188), a CDR-L2 comprising the amino acid sequence of GX1X2X3LX4X5, wherein X1 is A or S, X2 is T, S, E, Q, or D, X3 is N, R, A, E, or H, X4 is Q or A, and X5 is S or D (SEQ ID NO:189), and a CDR-L3 comprising the amino acid sequence of QX1X2X3X4X5PWT, wherein X1 is S, N, D, Q, A, or E, X2 is T, I, or S, X3 is Y, L, or F, X4 is D, G, T, E, Q, A, or Y, and X5 is A, T, R, S, K, or Y (SEQ ID NO:190); (j) the VH domain comprises a CDR-H1 comprising the amino acid sequence of SEQ ID NO:199, a CDR-H2 comprising the amino acid sequence of SEQ ID NO:200, and a CDR-H3 comprising the amino acid sequence of SEQ ID NO:201; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202; (k) the VH domain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and wherein the VL domain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207; (l) the VH domain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202; (m) the VH domain comprises a CDR-H1 comprising the amino acid sequence of X1YX2MS, wherein X1 is S, D, E, A, or Q and X2 is A, G, or T (SEQ ID NO:208), a CDR-H2 comprising the amino acid sequence of DIX1X2X3GX4X5TX6YADSVKG, wherein X1 is T, N, S, Q, E, H, R, or A, X2 is Y, W, F, or H, X3 is A, S, Q, E, or T, X4 is G or E, X5 is S or I, and X6 is A or G (SEQ ID NO:209), and a CDR-H3 comprising the amino acid sequence of X1X2X3YX4WX5X6AX7DX8, wherein X1 is S or A, X2 is N, H, A, D, L, Q, Y, or R, X3 is A, N, S, or G, X4 is A, V, R, E, or S, X5 is D or S, X6 is D, N, Q, E, S, T, or L, X7 is L, F, or M, and X8 is I, Y, or V (SEQ ID NO:210); and wherein the VL domain comprises a CDR-L1 comprising the amino acid sequence of RASQSVSSNLA (SEQ ID NO:176), a CDR-L2 comprising the amino acid sequence of GASSRAT (SEQ ID NO: 177), and a CDR-L3 comprising the amino acid sequence of QQYGSSPPVT (SEQ ID NO:178); (n) the VH domain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178); (o) the VH domain comprises a CDR-H1 comprising the amino acid sequence of SEQ ID NO:220, a CDR-H2 comprising the amino acid sequence of SEQ ID NO:260, and a CDR-H3 comprising the amino acid sequence of SEQ ID NO:222; and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178); or (p) the VH domain comprises a CDR-H1 comprising the amino acid sequence of SEQ ID NO:252, a CDR-H2 comprising the amino acid sequence of SEQ ID NO:253, and a CDR-H3 comprising the amino acid sequence of SEQ ID NO:254; and wherein the VL domain comprises a CDR-L1 comprising the amino acid sequence of SEQ ID NO:255, a CDR-L2 comprising the amino acid sequence of SEQ ID NO:256, and a CDR-L3 comprising the amino acid sequence of SEQ ID NO:257.

In some embodiments, the antibody or antigen binding fragment comprises a heavy chain variable (VH) domain and a light chain variable (VL) domain; and wherein: (a) the VH domain comprises a CDR-H1 comprising the amino acid sequence of SEQ ID NO:226, a CDR-H2 comprising the amino acid sequence of SEQ ID NO:227, and a CDR-H3 comprising the amino acid sequence of SEQ ID NO:151; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154; (b) the VH domain comprises a CDR-H1 comprising the amino acid sequence of SEQ ID NO:228, a CDR-H2 comprising the amino acid sequence of SEQ ID NO:227, and a CDR-H3 comprising the amino acid sequence of SEQ ID NO:157; and wherein the VL domain comprises a CDR-L1 comprising the amino acid sequence of SEQ ID NO:158, a CDR-L2 comprising the amino acid sequence of SEQ ID NO:159, and a CDR-L3 comprising the amino acid sequence of SEQ ID NO:160; (c) the VH domain comprises a CDR-H1 comprising the amino acid sequence of SEQ ID NO:223, a CDR-H2 comprising the amino acid sequence of SEQ ID NO:227, and a CDR-H3 comprising the amino acid sequence of SEQ ID NO:163; and wherein the VL domain comprises a CDR-L1 comprising the amino acid sequence of SEQ ID NO:164, a CDR-L2 comprising the amino acid sequence of SEQ ID NO:165, and a CDR-L3 comprising the amino acid sequence of SEQ ID NO:166; (d) the VH domain comprises a CDR-H1 comprising the amino acid sequence of SEQ ID NO:229, a CDR-H2 comprising the amino acid sequence of SEQ ID NO:227, and a CDR-H3 comprising the amino acid sequence of SEQ ID NO:169; and wherein the VL domain comprises a CDR-L1 comprising the amino acid sequence of SEQ ID NO:170, a CDR-L2 comprising the amino acid sequence of SEQ ID NO:171, and a CDR-L3 comprising the amino acid sequence of SEQ ID NO:172; (e) the VH domain comprises a CDR-H1 comprising the amino acid sequence of SEQ ID NO:230, a CDR-H2 comprising the amino acid sequence of SEQ ID NO:231, and a CDR-H3 comprising the amino acid sequence of SEQ ID NO:175; and wherein the VL domain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178; (f) the VH domain comprises a CDR-H1 comprising the amino acid sequence of SEQ ID NO:230, a CDR-H2 comprising the amino acid sequence of SEQ ID NO:232, and a CDR-H3 comprising the amino acid sequence of SEQ ID NO:181; and wherein the VL domain comprises a CDR-L1 comprising the amino acid sequence of SEQ ID NO:182, a CDR-L2 comprising the amino acid sequence of SEQ ID NO:183, and a CDR-L3 comprising the amino acid sequence of SEQ ID NO:184; (g) the VH domain comprises a CDR-H1 comprising the amino acid sequence of SEQ ID NO:223, a CDR-H2 comprising the amino acid sequence of SEQ ID NO:224, and a CDR-H3 comprising the amino acid sequence of SEQ ID NO:225; and wherein the VL domain comprises a CDR-L1 comprising the amino acid sequence of SEQ ID NO:140, a CDR-L2 comprising the amino acid sequence of SEQ ID NO:141, and a CDR-L3 comprising the amino acid sequence of SEQ ID NO:142; (h) the VH domain comprises a CDR-H1 comprising the amino acid sequence of SEQ ID NO:233, a CDR-H2 comprising the amino acid sequence of SEQ ID NO:234, and a CDR-H3 comprising the amino acid sequence of SEQ ID NO:145; and wherein the VL domain comprises a CDR-L1 comprising the amino acid sequence of SEQ ID NO:146, a CDR-L2 comprising the amino acid sequence of SEQ ID NO:147, and a CDR-L3 comprising the amino acid sequence of SEQ ID NO:148; (i) the VH domain comprises a CDR-H1 comprising the amino acid sequence of GX1X2FX3X4X5, wherein X1 is G, Y, S, or A, X2 is T, S, G, R, N, or H, X3 is S, T, R, H, Y, G, or P, X4 is S, K, G, N, R, D, T, or G, and X5 is Y, L, H, or F (SEQ ID NO:235), a CDR-H2 comprising the amino acid sequence of X1PX2X3X4X5, wherein X1 is I, N, or M, X2 is G, N, H, S, R, I, or A, X3 is A, N, H, S, T, F, or Y, X4 is A, D, or G, and X5 is T, E, K, V, Q, or A (SEQ ID NO:236), and a CDR-H3 comprising the amino acid sequence of X1X2X3GX4X5LFX6X7, wherein X1 is D or A, X2 is A, G, E, R, Y, K, N, Q, L, or F, X3 is A, L, P, or Y, X4 is I or L, X5 is R, A, Q, or S, X6 is A or D, and X7 is D, E, A, or S (SEQ ID NO:237); and wherein the VL domain comprises a CDR-L1 comprising the amino acid sequence of X1X2SX3X4IX5GX6LN, wherein X1 is R or G, X2 is A or T, X3 is Q or E, X4 is E, N, T, S, A, K, D, G, R, or Q, X5 is Y or S, and X6 is A or V (SEQ ID NO:188), a CDR-L2 comprising the amino acid sequence of GX1X2X3LX4X5, wherein X1 is A or S, X2 is T, S, E, Q, or D, X3 is N, R, A, E, or H, X4 is Q or A, and X5 is S or D (SEQ ID NO:189), and a CDR-L3 comprising the amino acid sequence of QX1X2X3X4X5PWT, wherein X1 is S, N, D, Q, A, or E, X2 is T, I, or S, X3 is Y, L, or F, X4 is D, G, T, E, Q, A, or Y, and X5 is A, T, R, S, K, or Y (SEQ ID NO: 190); (j) the VH domain comprises a CDR-H1 comprising the amino acid sequence of SEQ ID NO:241, a CDR-H2 comprising the amino acid sequence of SEQ ID NO:242, and a CDR-H3 comprising the amino acid sequence of SEQ ID NO:204; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202; (k) the VH domain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and wherein the VL domain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207; (l) the VH domain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202; (m) the VH domain comprises a CDR-H1 comprising the amino acid sequence of GFTFX1X2Y, wherein X1 is S, D, E, Q, S, or A and X2 is S, D, E, A, or Q (SEQ ID NO:244), a CDR-H2 comprising the amino acid sequence of X1X2X3GX4X5, wherein X1 is T, N, S, Q, E, H, R or A, X2 is Y, W, F, or H, X3 is A, S, Q, E, or T, X4 is G or E, and X5 is S or I (SEQ ID NO:245), and a CDR-H3 comprising the amino acid sequence of X1X2X3YX4WX5X6AX7DX8, wherein X1 is S or A, X2 is N, H, A, D, L, Q, Y, or R, X3 is A, N, S, or G, X4 is A, V, R, E, or S, X5 is D or S, X6 is D, N, Q, E, S, T, or L, X7 is L, F, or M, and X8 is I, Y, or V (SEQ ID NO:246); and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178); (n) the VH domain comprises a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288; and wherein the VL domain comprises a CDR-L1 comprising the amino acid sequence of RASQSVSSNLA (SEQ ID NO:176), a CDR-L2 comprising the amino acid sequence of GASSRAT (SEQ ID NO: 177), and a CDR-L3 comprising the amino acid sequence of QQYGSSPPVT (SEQ ID NO:178); (o) the VH domain comprises a CDR-H1 comprising the amino acid sequence of SEQ ID NO:250, a CDR-H2 comprising the amino acid sequence of SEQ ID NO:261, and a CDR-H3 comprising the amino acid sequence of SEQ ID NO:288; and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO: 178); or (p) the VH domain comprises a CDR-H1 comprising the amino acid sequence of SEQ ID NO:223, a CDR-H2 comprising the amino acid sequence of SEQ ID NO:224, and a CDR-H3 comprising the amino acid sequence of SEQ ID NO:284;

and wherein the VL domain comprises a CDR-L1 comprising the amino acid sequence of SEQ ID NO:285, a CDR-L2 comprising the amino acid sequence of SEQ ID NO:286, and a CDR-L3 comprising the amino acid sequence of SEQ ID NO:287.

In some embodiments, (a) the VH domain comprises an amino acid sequence that is at least 90%, at least 95%, at least 99%, or 100% identical to the sequence of SEQ ID NO:109, and wherein the VL domain comprises an amino acid sequence that is at least 90%, at least 95%, at least 99%, or 100% identical to the sequence of SEQ ID NO:110; (b) the VH domain comprises an amino acid sequence that is at least 90%, at least 95%, at least 99%, or 100% identical to the sequence of SEQ ID NO:111, and wherein the VL domain comprises an amino acid sequence that is at least 90%, at least 95%, at least 99%, or 100% identical to the sequence of SEQ ID NO:112; (c) the VH domain comprises an amino acid sequence that is at least 90%, at least 95%, at least 99%, or 100% identical to the sequence of SEQ ID NO:113, and wherein the VL domain comprises an amino acid sequence that is at least 90%, at least 95%, at least 99%, or 100% identical to the sequence of SEQ ID NO:114; (d) the VH domain comprises an amino acid sequence that is at least 90%, at least 95%, at least 99%, or 100% identical to the sequence of SEQ ID NO:115, and wherein the VL domain comprises an amino acid sequence that is at least 90%, at least 95%, at least 99%, or 100% identical to the sequence of SEQ ID NO: 116; (e) the VH domain comprises an amino acid sequence that is at least 90%, at least 95%, at least 99%, or 100% identical to the sequence of SEQ ID NO: 117, and wherein the VL domain comprises an amino acid sequence that is at least 90%, at least 95%, at least 99%, or 100% identical to the sequence of SEQ ID NO: 118; (f) the VH domain comprises an amino acid sequence that is at least 90%, at least 95%, at least 99%, or 100% identical to the sequence of SEQ ID NO:119, and wherein the VL domain comprises an amino acid sequence that is at least 90%, at least 95%, at least 99%, or 100% identical to the sequence of SEQ ID NO:120; (g) the VH domain comprises an amino acid sequence that is at least 90%, at least 95%, at least 99%, or 100% identical to the sequence of SEQ ID NO:123; and wherein the VL domain comprises an amino acid sequence that is at least 90%, at least 95%, at least 99%, or 100% identical to the sequence of SEQ ID NO:124; (h) the VH domain comprises an amino acid sequence that is at least 90%, at least 95%, at least 99%, or 100% identical to the sequence of SEQ ID NO:129, and wherein the VL domain comprises an amino acid sequence that is at least 90%, at least 95%, at least 99%, or 100% identical to the sequence of SEQ ID NO:130; (i) the VH domain comprises an amino acid sequence that is at least 90%, at least 95%, at least 99%, or 100% identical to the sequence of SEQ ID NO:131; and wherein the VL domain comprises an amino acid sequence that is at least 90%, at least 95%, at least 99%, or 100% identical to the sequence of SEQ ID NO:132; (j) the VH domain comprises an amino acid sequence that is at least 90%, at least 95%, at least 99%, or 100% identical to the sequence of SEQ ID NO:125; and wherein the VL domain comprises an amino acid sequence that is at least 90%, at least 95%, at least 99%, or 100% identical to the sequence of SEQ ID NO:126; (k) the VH domain comprises an amino acid sequence that is at least 90%, at least 95%, at least 99%, or 100% identical to the sequence of SEQ ID NO:127, and wherein the VL domain comprises an amino acid sequence that is at least 90%, at least 95%, at least 99%, or 100% identical to the sequence of SEQ ID NO:128; (l) the VH domain comprises an amino acid sequence that is at least 90%, at least 95%, at least 99%, or 100% identical to the sequence of SEQ ID NO:133; and wherein the VL domain comprises an amino acid sequence that is at least 90%, at least 95%, at least 99%, or 100% identical to the sequence of SEQ ID NO:134; (m) the VH domain comprises an amino acid sequence that is at least 90%, at least 95%, at least 99%, or 100% identical to the sequence of SEQ ID NO:135; and wherein the VL domain comprises an amino acid sequence that is at least 90%, at least 95%, at least 99%, or 100% identical to the sequence of SEQ ID NO:136; (n) the VH domain comprises an amino acid sequence that is at least 90%, at least 95%, at least 99%, or 100% identical to the sequence of SEQ ID NO:107; and wherein the VL domain comprises an amino acid sequence that is at least 90%, at least 95%, at least 99%, or 100% identical to the sequence of SEQ ID NO:108; (o) the VH domain comprises an amino acid sequence that is at least 90%, at least 95%, at least 99%, or 100% identical to the sequence of SEQ ID NO:121; and wherein the VL domain comprises an amino acid sequence that is at least 90%, at least 95%, at least 99%, or 100% identical to the sequence of SEQ ID NO:122; or (p) the VH domain comprises an amino acid sequence that is at least 90%, at least 95%, at least 99%, or 100% identical to the sequence of SEQ ID NO:258; and wherein the VL domain comprises an amino acid sequence that is at least 90%, at least 95%, at least 99%, or 100% identical to the sequence of SEQ ID NO:259.

In some embodiments, (a) the VH domain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and wherein the VL domain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(b) the VH domain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and wherein the VL domain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(c) the VH domain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and wherein the VL domain comprises a CDR-L1 comprising the amino acid sequence of SEQ ID NO: 176, a CDR-L2 comprising the amino acid sequence of SEQ ID NO:177, and a CDR-L3 comprising the amino acid sequence of SEQ ID NO:178; or (d) the VH domain comprises a CDR-H1 comprising the amino acid sequence of SEQ ID NO:250, a CDR-H2 comprising the amino acid sequence of SEQ ID NO: 251, and a CDR-H3 comprising the amino acid sequence of SEQ ID NO:288; and wherein the VL domain comprises a CDR-L1 comprising the amino acid sequence of SEQ ID NO: 176, a CDR-L2 comprising the amino acid sequence of SEQ ID NO:177, and a CDR-L3 comprising the amino acid sequence of SEQ ID NO:178.

In some embodiments, (a) the VH domain comprises an amino acid sequence that is at least 90%, at least 95%, at least 99%, or 100% identical to the sequence of SEQ ID NO:129, and wherein the VL domain comprises an amino acid sequence that is at least 90%, at least 95%, at least 99%, or 100% identical to the sequence of SEQ ID NO:130; or (b) the VH domain comprises an amino acid sequence that is at least 90%, at least 95%, at least 99%, or 100% identical to the sequence of SEQ ID NO:127, and wherein the VL domain comprises an amino acid sequence that is at least 90%, at least 95%, at least 99%, or 100% identical to the sequence of SEQ ID NO:128.

In some embodiments, the disclosure provides a fusion protein comprising:
a) an IL-21 polypeptide comprising (i) four or more amino acid substitutions providing a reduced isoelectric point relative to a human IL-21 polypeptide comprising SEQ ID NO: 1, wherein the four or more amino acid substitutions are within S80 to T92 of SEQ ID NO: 1, wherein at least four amino acid substitutions are at residues R85, R86, K88, H89, R90, or a combination thereof, and (ii) at least one amino acid substitution providing reduced binding to a human IL-21 receptor relative to binding by the human IL-21 polypeptide; and
b) an antibody or an antigen binding fragment thereof that specifically binds to CD8αβ or CD8β, wherein the antibody or antigen binding fragment thereof comprises:
  (i) a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
  (ii) a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and a VL domain comprising comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
  (iii) a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and a VL domain comprising a CDR-L1 comprising the amino acid sequence of SEQ ID NO: 176, a CDR-L2 comprising the amino acid sequence of SEQ ID NO:177, and a CDR-L3 comprising the amino acid sequence of SEQ ID NO:178; or
  (iv) a VH domain comprising a CDR-H1 comprising the amino acid sequence of SEQ ID NO:250, a CDR-H2 comprising the amino acid sequence of SEQ ID NO: 251, and a CDR-H3 comprising the amino acid sequence of SEQ ID NO:288; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178.

In some embodiments, the disclosure provides a fusion protein comprising:
a) an IL-21 polypeptide comprising (i) four or more amino acid substitutions providing a reduced isoelectric point relative to a human IL-21 polypeptide comprising SEQ ID NO: 1, wherein the four or more amino acid substitutions are within S80 to T92 of SEQ ID NO: 1, wherein at least four amino acid substitutions are at residues R85, R86, K88, H89, R90, or a combination thereof, and (ii) at least one amino acid substitution providing reduced binding to a human IL-21 receptor relative to binding by the human IL-21 polypeptide, wherein the at least one amino acid substitution is at a residue selected from R5, I8, R9, R11, L13, I14, I16, V17, D18, K72, K73, L74, K75, R76, K77, K117, and a combination thereof; and
b) an antibody or an antigen binding fragment thereof that specifically binds to CD8αβ or CD8β, wherein the antibody or antigen binding fragment thereof comprises:
  (i) a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
  (ii) a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and a VL domain comprising comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
  (iii) a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and a VL domain comprising a CDR-L1 comprising the amino acid sequence of SEQ ID NO: 176, a CDR-L2 comprising the amino acid sequence of SEQ ID NO:177, and a CDR-L3 comprising the amino acid sequence of SEQ ID NO:178; or
  (iv) a VH domain comprising a CDR-H1 comprising the amino acid sequence of SEQ ID NO:250, a CDR-H2 comprising the amino acid sequence of SEQ ID NO: 251, and a CDR-H3 comprising the amino acid sequence of SEQ ID NO:288; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178.

In some embodiments, the disclosure provides a fusion protein comprising:
a) an IL-21 polypeptide comprising (i) four or more amino acid substitutions providing a reduced isoelectric point relative to a human IL-21 polypeptide comprising SEQ ID NO: 1, wherein the four or more amino acid substitutions are within S80 to T92 of SEQ ID NO: 1, wherein at least four amino acid substitutions are at residues R85, R86, K88, H89, R90, or a combination thereof, and (ii) at least one amino acid substitution selected from: (a) R11D; (b) R11E; (c) I14D, D18A and K117A; (d) R76E; (e) R5F; (f) R76F; (g) I8E; (h) R5A; (i) R5E; (j) R5S; (k) R5T; (l) R5N; (m) R5Q; (n) R5V; (o) R5I; (p) R5L; (q) R5Y; (r) R76A; (s) R76N; (t) R76D; (u) R76S; (v) R76T; (w) R76Q; (x) R76V; (y) R76I; (z) R76L; (aa) R76Y; (bb) K77A; (cc) K77E; (dd) K72A; (ee) K72E; (ff) K75A; (gg) K75E; (hh) K73A; (ii) K73E; (jj) R5F and K77A; (kk) R5F and K77E; (ll) R5F and K72A; (mm) R5F and K72E; (nn) R5F and K76A; (oo) R5F and K76E; (pp) K73A and K76F; (qq) K73E and K76F; (rr) R9A; (ss) R9D; (tt) R9E; (uu) R9H; (vv) R9S; (ww) R9T; (xx) R9N; (zz) R9G; (aaa) R9V; (bbb) R9I; (ccc) R9L; (ddd) R9Y; (eee) K72A and R76F; (fff) K75A and R76F; (ggg) R76F and K77A; (hhh) K75E and R76F; (iii) V17I and L74I; (jjj) I16A and L74F; (kkk) I16S, V17I, and L74V; (lll) I16R, V17I, and L74I; (mmm) L13F, I16A, V17A and L74M; and (nnn) L13R, I16A, V17I and L74I; and
b) an antibody or an antigen binding fragment thereof that specifically binds to CD8αβ or CD8β, wherein the antibody or antigen binding fragment thereof comprises:
   (i) a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
   (ii) a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and a VL domain comprising comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
   (iii) a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178; or
   (iv) a VH domain comprising a CDR-H1 comprising the amino acid sequence of SEQ ID NO:250, a CDR-H2 comprising the amino acid sequence of SEQ ID NO: 251, and a CDR-H3 comprising the amino acid sequence of SEQ ID NO:288; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178.

In some embodiments, the disclosure provides a fusion protein comprising:
a) an IL-21 polypeptide comprising (i) four or more amino acid substitutions providing a reduced isoelectric point relative to a human IL-21 polypeptide comprising SEQ ID NO: 1, wherein the four or more amino acid substitutions are at residues S80, T81, N82, A83, R85, R86, Q87, K88, H89, R90, L91, T92, or a combination thereof, and (ii) at least one amino acid substitution providing reduced binding to a human IL-21 receptor relative to binding by the human IL-21 polypeptide, wherein the at least one amino acid substitution is at a residue selected from R5, I8, R9, R11, L13, I14, I16, V17, D18, K72, K73, L74, K75, R76, K77, K117, and a combination thereof, and b) an antibody or an antigen binding fragment thereof that specifically binds to CD8αβ or CD8β, wherein the antibody or antigen binding fragment thereof comprises:
   (i) a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
   (ii) a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and a VL domain comprising comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
   (iii) a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178; or
   (iv) a VH domain comprising a CDR-H1 comprising the amino acid sequence of SEQ ID NO:250, a CDR-H2 comprising the amino acid sequence of SEQ ID NO: 251, and a CDR-H3 comprising the amino acid sequence of SEQ ID NO:288; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178.

In some embodiments, the disclosure provides a fusion protein comprising:

a) an IL-21 polypeptide comprising (i) four or more amino acid substitutions providing a reduced isoelectric point relative to a human IL-21 polypeptide comprising SEQ ID NO: 1, wherein the four or more amino acid substitutions are at residues S80, T81, N82, A83, R85, R86, Q87, K88, H89, R90, L91, T92, or a combination thereof, and (ii) at least one amino acid substitution providing reduced binding to a human IL-21 receptor relative to binding by the human IL-21 polypeptide, wherein the at least one amino acid substitution is at residue R76; and b) an antibody or an antigen binding fragment thereof that specifically binds to CD8αβ or CD8β.

In some embodiments, the disclosure provides a fusion protein comprising:

a) an IL-21 polypeptide comprising (i) an amino acid sequence selected from SEQ ID NOs: 2, 4-15 and 23-40, and (ii) at least one amino acid substitution providing reduced binding to a human IL-21 receptor relative to binding by the human IL-21 polypeptide; and b) an antibody or an antigen binding fragment thereof that specifically binds to CD8αβ or CD8β, wherein the antibody or antigen binding fragment thereof comprises:

(i) a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(ii) a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and a VL domain comprising comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(iii) a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178; or (iv) a VH domain comprising a CDR-H1 comprising the amino acid sequence of SEQ ID NO:250, a CDR-H2 comprising the amino acid sequence of SEQ ID NO: 251, and a CDR-H3 comprising the amino acid sequence of SEQ ID NO:288; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178.

In some embodiments, the disclosure provides a fusion protein comprising:

a) an IL-21 polypeptide comprising (i) an amino acid sequence selected from SEQ ID NOs: 2, 4-15 and 23-40, and (ii) at least one amino acid substitution providing reduced binding to a human IL-21 receptor relative to binding by the human IL-21 polypeptide, wherein the at least one amino acid substitution is at a residue selected from R5, I8, R9, R11, L13, I14, I16, V17, D18, K72, K73, L74, K75, R76, K77, K117, and a combination thereof; and b) an antibody or an antigen binding fragment thereof that specifically binds to CD8αβ or CD8β, wherein the antibody or antigen binding fragment thereof comprises:

(i) a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO: 204; and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(ii) a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and a VL domain comprising comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(iii) a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178; or (iv) a VH domain comprising a CDR-H1 comprising the amino acid sequence of SEQ ID NO:250, a CDR-H2 comprising the amino acid sequence of SEQ ID NO: 251, and a CDR-H3 comprising the amino acid sequence of SEQ ID NO:288; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178.

In some embodiments, the disclosure provides a fusion protein comprising:

a) an IL-21 polypeptide comprising (i) an amino acid sequence selected from SEQ ID NOs: 2, 4-15 and 23-40, and (ii) at least one amino acid substitution providing reduced binding to a human IL-21 receptor relative to binding by the human IL-21 polypeptide, wherein the at least one amino acid substitution is at residue R76; and b) an antibody or an antigen binding fragment thereof that specifically binds to CD8αβ or CD8β, wherein the antibody or antigen binding fragment thereof comprises:

(i) a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(ii) a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and a VL domain comprising comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(iii) a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178; or (iv) a VH domain comprising a CDR-H1 comprising the amino acid sequence of SEQ ID NO:250, a CDR-H2 comprising the amino acid sequence of SEQ ID NO: 251, and a CDR-H3 comprising the amino acid sequence of SEQ ID NO:288; and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
b) a second polypeptide comprising a VH chain and a HC constant domain, wherein the HC constant domain comprises a knob modification, and wherein the VH chain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:
- a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
- b) a second polypeptide comprising a VH chain and a HC constant domain, wherein the HC constant domain comprises a knob modification, and wherein the VH chain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222;
- c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
- d) a fourth polypeptide comprising a VL chain and a CL1 chain, wherein the VL chain of the first polypeptide and the fourth polypeptide are the same, and wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:
- a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
- b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204;
- c) a third polypeptide comprising a VH chain and a HC constant domain, wherein the HC constant domain comprises a hole modification, and wherein the VH chain of the second polypeptide and the third polypeptide are the same; and
- d) a fourth polypeptide comprising a VL chain and a CL1 chain, wherein the VL chain of the first polypeptide and the fourth polypeptide are the same, and wherein the IL-21 polypeptide comprises an amino acid sequence selected from SEQ ID NOs: 2, 4-15 and 23-40, and at least one amino acid substitution providing reduced binding to a human IL-21 receptor relative to binding by the human IL-21 polypeptide.

In some embodiments, the disclosure provides a fusion protein comprising:
- a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
- b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204;
- c) a third polypeptide comprising a VH chain and a HC constant domain, wherein the HC constant domain comprises a hole modification, and wherein the VH chain of the second polypeptide and the third polypeptide are the same; and
- d) a fourth polypeptide comprising a VL chain and a CL1 chain, wherein the VL chain of the first polypeptide and the fourth polypeptide are the same, and wherein the IL-21 polypeptide comprises an amino acid sequence selected from SEQ ID NOs: 2, 4-15 and 23-40, and at least one amino acid substitution providing reduced binding to a human IL-21 receptor relative to binding by the human IL-21 polypeptide.

In some embodiments, the disclosure provides a fusion protein comprising:
- a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
- b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222;
- c) a third polypeptide comprising a VH chain and a HC constant domain, wherein the HC constant domain comprises a hole modification, and wherein the VH chain of the second polypeptide and the third polypeptide are the same; and d) a fourth polypeptide comprising a VL chain and a CL1 chain, wherein the VL chain of the first polypeptide and the fourth polypeptide are the same, and wherein the IL-21 polypeptide comprises an amino acid sequence selected from SEQ ID NOs: 2, 4-15 and 23-40, and at least one amino acid substitution providing reduced binding to a human IL-21 receptor relative to binding by the human IL-21 polypeptide.

In some embodiments, the disclosure provides a fusion protein comprising:

a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;

b) a second polypeptide comprising a VH chain and a HC constant domain, wherein the HC constant domain comprises a knob modification, and wherein the VH chain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222;

c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and d) a fourth polypeptide comprising a VL chain and a CL1 chain, wherein the VL chain of the first polypeptide and the fourth polypeptide are the same, and wherein the IL-21 polypeptide comprises an amino acid sequence selected from SEQ ID NOs: 2, 4-15 and 23-40, and at least one amino acid substitution providing reduced binding to a human IL-21 receptor relative to binding by the human IL-21 polypeptide.

In some embodiments, the disclosure provides a fusion protein comprising:

a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204;

c) a third polypeptide comprising a VH chain and a HC constant domain, wherein the HC constant domain comprises a hole modification, and wherein the VH chain of the second polypeptide and the third polypeptide are the same; and d) a fourth polypeptide comprising a VL chain and a CL1 chain, wherein the VL chain of the first polypeptide and the fourth polypeptide are the same, and wherein the IL-21 polypeptide comprises an amino acid sequence selected from SEQ ID NOs: 16-21, 41-98, and 374-379.

In some embodiments, the disclosure provides a fusion protein comprising:

a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

b) a second polypeptide comprising a VH chain and a HC constant domain, wherein the HC constant domain comprises a knob modification, and wherein the VH chain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204;

c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and d) a fourth polypeptide comprising a VL chain and a CL1 chain, wherein the VL chain of the first polypeptide and the fourth polypeptide are the same, and wherein the IL-21 polypeptide comprises an amino acid sequence selected from SEQ ID NOs: 16-21, 41-98, and 374-379.

In some embodiments, the disclosure provides a fusion protein comprising:

a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;

b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222;

c) a third polypeptide comprising a VH chain and a HC constant domain, wherein the HC constant domain comprises a hole modification, and wherein the VH chain of the second polypeptide and the third polypeptide are the same; and d) a fourth polypeptide comprising a VL chain and a CL1 chain, wherein the VL chain of the first polypeptide and the fourth polypeptide are the same, and wherein the IL-21 polypeptide comprises an amino acid sequence selected from SEQ ID NOs: 16-21, 41-98, and 374-379.

In some embodiments, the disclosure provides a fusion protein comprising:

a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
b) a second polypeptide comprising a VH chain and a HC constant domain, wherein the HC constant domain comprises a knob modification, and wherein the VH chain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises an amino acid sequence selected from SEQ ID NOs: 16-21, 41-98, and 374-379.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

b) a second polypeptide comprising a VH chain and a HC constant domain, wherein the HC constant domain comprises a knob modification, and wherein the VH chain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:

a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
b) a second polypeptide comprising a VH chain and a HC constant domain, wherein the HC constant domain comprises a knob modification, and wherein the VH chain comprises a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises (i) one or more amino acid substitutions providing a reduced isoelectric point relative to a human IL-21 polypeptide comprising SEQ ID NO: 1, wherein the one or more amino acid substitutions are within S80 to T92 of SEQ ID NO: 1, wherein at least one amino acid substitution is at residue R85, R86, K88, H89, R90, or a combination thereof, and (ii) at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises an amino acid sequence selected from SEQ ID NOs: 2, 4-15 and 23-40, and at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
b) a second polypeptide comprising a VH chain and a HC constant domain, wherein the HC constant domain comprises a knob modification, and wherein the VH chain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises an amino acid sequence selected from SEQ ID NOs: 2, 4-15 and 23-40, and at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises an amino acid sequence selected from SEQ ID NOs: 2, 4-15 and 23-40, and at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
b) a second polypeptide comprising a VH chain and a HC constant domain, wherein the HC constant domain comprises a knob modification, and wherein the VH chain comprises a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises an amino acid sequence selected from SEQ ID NOs: 2, 4-15 and 23-40, and at least one amino acid substitution providing reduced binding to a human IL-21 receptor relative to binding by the human IL-21 polypeptide.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises an amino acid sequence selected from SEQ ID NOs: 16-21, 41-98, and 374-379.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
b) a second polypeptide comprising a VH chain and a HC constant domain, wherein the HC constant domain comprises a knob modification, and wherein the VH chain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and wherein the VH chains and VL chains comprise CDRs that specifically bind to CD8αβ or CD8β,
wherein the IL-21 polypeptide comprises an amino acid sequence selected from SEQ ID NOs: 16-21, 41-98, and 374-379.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
b) a second polypeptide comprising a VH chain and a HC constant domain, wherein an IL-21 polypeptide is operably linked to the C-terminus of the HC constant domain, wherein the HC constant domain comprises a knob modification, and wherein the VH chain comprises a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288;
c) a third polypeptide comprising a VH chain and a HC constant domain, wherein the HC constant domain comprises a hole modification, and wherein the VH chain of the second polypeptide and the third polypeptide are the same; and
d) a fourth polypeptide comprising a VL chain and a CL1 chain, wherein the VL chain of the first polypeptide and the fourth polypeptide are the same, and
wherein the IL-21 polypeptide comprises an amino acid sequence selected from SEQ ID NOs: 16-21, 41-98, and 374-379.

In some embodiments, the disclosure provides a fusion protein comprising:
a) a first polypeptide comprising a VL chain and a CL1 chain, wherein the VL chain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;
b) a second polypeptide comprising a VH chain and a HC constant domain, wherein the HC constant domain comprises a knob modification, and wherein the VH chain comprises a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288;
c) a third polypeptide comprising a VH chain and a HC constant domain, wherein an IL-21 polypeptide is operably linked to the C-terminus of the HC constant domain, wherein the HC constant domain comprises a hole modification, and wherein the VH chain of the second polypeptide and the third polypeptide are the same; and d) a fourth polypeptide comprising a VL chain and a CL1 chain, wherein the VL chain of the first polypeptide and the fourth polypeptide are the same, and wherein the IL-21 polypeptide comprises an amino acid sequence selected from SEQ ID NOs: 16-21, 41-98, and 374-379.

In some embodiments, the fusion protein comprises four polypeptide chains, wherein:

the first polypeptide chain comprises the amino acid sequence of SEQ ID NO:262, the second polypeptide chain comprises the amino acid sequence of SEQ ID NO:263, the third polypeptide chain comprises the amino acid sequence of SEQ ID NO:264, and the fourth polypeptide chain comprises the amino acid sequence of SEQ ID NO:262;

the first polypeptide chain comprises the amino acid sequence of SEQ ID NO:266, the second polypeptide chain comprises the amino acid sequence of SEQ ID NO:267, the third polypeptide chain comprises the amino acid sequence of SEQ ID NO:268, and the fourth polypeptide chain comprises the amino acid sequence of SEQ ID NO:266;

the first polypeptide chain comprises the amino acid sequence of SEQ ID NO:270, the second polypeptide chain comprises the amino acid sequence of SEQ ID NO:271, the third polypeptide chain comprises the amino acid sequence of SEQ ID NO:272, and the fourth polypeptide chain comprises the amino acid sequence of SEQ ID NO: 270;

the first polypeptide chain comprises the amino acid sequence of SEQ ID NO: 274, the second polypeptide chain comprises the amino acid sequence of SEQ ID NO:275, the third polypeptide chain comprises the amino acid sequence of SEQ ID NO:276, and the fourth polypeptide chain comprises the amino acid sequence of SEQ ID NO: 274; or the first polypeptide chain comprises the amino acid sequence of SEQ ID NO:278, the second polypeptide chain comprises the amino acid sequence of SEQ ID NO:279, the third polypeptide chain comprises the amino acid sequence of SEQ ID NO:280, and the fourth polypeptide chain comprises the amino acid sequence of SEQ ID NO: 278.

In some embodiments, the fusion protein comprises four polypeptide chains, wherein:

the first polypeptide chain comprises the amino acid sequence of SEQ ID NO:262, the second polypeptide chain comprises the amino acid sequence of SEQ ID NO:263, the third polypeptide chain comprises the amino acid sequence of SEQ ID NO:265, and the fourth polypeptide chain comprises the amino acid sequence of SEQ ID NO:262;

the first polypeptide chain comprises the amino acid sequence of SEQ ID NO:266, the second polypeptide chain comprises the amino acid sequence of SEQ ID NO:267, the third polypeptide chain comprises the amino acid sequence of SEQ ID NO:269, and the fourth polypeptide chain comprises the amino acid sequence of SEQ ID NO:266;

the first polypeptide chain comprises the amino acid sequence of SEQ ID NO:270, the second polypeptide chain comprises the amino acid sequence of SEQ ID NO:271, the third polypeptide chain comprises the amino acid sequence of SEQ ID NO:273, and the fourth polypeptide chain comprises the amino acid sequence of SEQ ID NO: 270;

the first polypeptide chain comprises the amino acid sequence of SEQ ID NO: 274, the second polypeptide chain comprises the amino acid sequence of SEQ ID NO:275, the third polypeptide chain comprises the amino acid sequence of SEQ ID NO:277, and the fourth polypeptide chain comprises the amino acid sequence of SEQ ID NO: 274; or the first polypeptide chain comprises the amino acid sequence of SEQ ID NO:278, the second polypeptide chain comprises the amino acid sequence of SEQ ID NO:279, the third polypeptide chain comprises the amino acid sequence of SEQ ID NO:281, and the fourth polypeptide chain comprises the amino acid sequence of SEQ ID NO: 278.

In some embodiments, the fusion protein comprises four polypeptide chains, wherein:

(a) the first polypeptide chain comprises the amino acid sequence of SEQ ID NO:297, the second polypeptide chain comprises the amino acid sequence of SEQ ID NO:298, the third polypeptide chain comprises the amino acid sequence of SEQ ID NO:299, and the fourth polypeptide chain comprises the amino acid sequence of SEQ ID NO:297;

(b) the first polypeptide chain comprises the amino acid sequence of SEQ ID NO:301, the second polypeptide chain comprises the amino acid sequence of SEQ ID NO:302, the third polypeptide chain comprises the amino acid sequence of SEQ ID NO: 303 and the fourth polypeptide chain comprises the amino acid sequence of SEQ ID NO:301;

(c) the first polypeptide chain comprises the amino acid sequence of SEQ ID NO:305, the second polypeptide chain comprises the amino acid sequence of SEQ ID NO:306, the third polypeptide chain comprises the amino acid sequence of SEQ ID NO:307, and the fourth polypeptide chain comprises the amino acid sequence of SEQ ID NO: 305; or (d) the first polypeptide chain comprises the amino acid sequence of SEQ ID NO: 309, the second polypeptide chain comprises the amino acid sequence of SEQ ID NO:310, the third polypeptide chain comprises the amino acid sequence of SEQ ID NO: 311, and the fourth polypeptide chain comprises the amino acid sequence of SEQ ID NO: 309.

In some embodiments, the fusion protein comprises four polypeptide chains, wherein:

(a) the first polypeptide chain comprises the amino acid sequence of SEQ ID NO:297, the second polypeptide chain comprises the amino acid sequence of SEQ ID NO:298, the third polypeptide chain comprises the amino acid sequence of SEQ ID NO:300, and the fourth polypeptide chain comprises the amino acid sequence of SEQ ID NO:297;

(b) the first polypeptide chain comprises the amino acid sequence of SEQ ID NO:301, the second polypeptide chain comprises the amino acid sequence of SEQ ID NO:302, the third polypeptide chain comprises the amino acid sequence of SEQ ID NO:304 and the fourth polypeptide chain comprises the amino acid sequence of SEQ ID NO:301;

(c) the first polypeptide chain comprises the amino acid sequence of SEQ ID NO:305, the second polypeptide chain comprises the amino acid sequence of SEQ ID NO:306, the third polypeptide chain comprises the amino acid sequence of SEQ ID NO:308, and the fourth polypeptide chain comprises the amino acid sequence of SEQ ID NO: 305; or (d) the first polypeptide chain comprises the amino acid sequence of SEQ ID NO: 309, the second polypeptide chain comprises the amino acid sequence of SEQ ID NO:310, the third polypeptide chain comprises the amino acid sequence of SEQ ID NO: 312, and the fourth polypeptide chain comprises the amino acid sequence of SEQ ID NO: 309.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1C show the amino acid sequences of the following polypeptides: mature IL-21 (SEQ ID NO: 1) (FIG. 1A), IL-21R (SEQ ID NO: 381) (FIG. 1B), and the common gamma chain (SEQ ID NO: 382) (FIG. 1C).

FIG. 2 shows the amino acid sequences of the mature wild-type IL-21 polypeptide (SEQ ID NO: 1) and the modifications to generate charge variants. "X" denotes the amino acid position substituted in the sequence of wild-type IL-21 polypeptide to generate charge variants.

FIGS. 8A-8F show activation of STAT3 in human PBMCs by fusion proteins of an anti-human CD8 antibody, xhCD8, with various attenuated versions of IL-21 v2. STAT3 activation is shown for CD8+ T cells, CD4+ T cells, NK cells and B cells. Fusion proteins of xhCD8 with exemplary IL-21 polypeptides comprising attenuation mutations, IL-21 v2.1 (FIG. 8A), IL-21 v2.2 (FIG. 8B), IL-21 v2.3 (FIG. 8C), IL-21 v2.4 (FIG. 8D), IL-21 v2.5 (FIG. 8E) and IL-21 v2.6 (FIG. 8F), all show preferential STAT3 activation of CD8+ T cells over NK, B and CD4+ T cells, as measured by $EC_{50}$ as well as maximal STAT3 activation.

FIGS. 9A-9H show activation of STAT3 in human PBMCs by fusion proteins of an anti-human CD8 antibody, xhCD8.1, with additional attenuated versions of IL-21 v2 or untargeted Fc fusion to IL-21 v2 as a control. STAT3 activation is shown in CD8+ T cells in FIGS. 9A, 9C, 9E and 9G, and in CD4+ T cells in FIGS. 9B, 9D, 9F, and 9H.

FIG. 13A shows the dosing scheme for FTY720 and xmCD8-mIL21 v1.1, and tumor growth curves for 0.1 mpk (FIG. 13B), 0.3 mpk (FIG. 13C), or 1 mpk (FIG. 13D) xmCD8-mIL21 v1.1. Plotted values are the mean tumor volume and error bars show the standard error of the mean, with each group comprising 8 animals.

FIGS. 14A-14F show activation of STAT3 in human whole blood from additional donors by fusion proteins of an anti-human CD8 antibody, xhCD8.1, with various attenuated versions of IL-21 v31. STAT3 activation is shown for CD8+ T cells, CD4+ T cells, NK cells, and B cells. Fusion proteins of xhCD8.1 with exemplary IL-21 polypeptides comprising attenuation mutations, IL-21 v31.4 (FIG. 14A), IL-21 v31.6 (FIG. 14B), IL-21 v31.23 (FIG. 14C), IL-21 v31.48 (FIG. 14D), and IL-21 v31.51 (FIG. 14E), all show preferential STAT3 activation of CD8+ T cells over NK, B and CD4+ T cells, as measured by $EC_{50}$. In the case of xhCD8.1-hIL21 v31.4 and xhCD8.1-hIL21 v31.23, data from two different donors analyzed in two separate experiments are shown (FIGS. 14A & 14C). Untargeted, unattenuated Fc-hIL21 v31 is shown in FIG. 14F, with activation observed in all cell types shown.

FIGS. 15A-15D show activation of STAT3 in human whole blood by fusion proteins of an anti-human CD8 antibody, xhCD8v11, with various attenuated versions of IL-21 v31. STAT3 activation is shown for CD8+ T cells, CD4+ T cells, NK cells, and B cells. Fusion proteins of xhCD8v 11 with exemplary IL-21 polypeptides comprising attenuation mutations, IL-21 v31.4 (FIG. 15A), IL-21 v31.6 (FIG. 15B), IL-21 v31.23 (FIG. 15C), and IL-21 v31.51 (FIG. 15D), all show preferential STAT3 activation of CD8+ T cells over NK, B and CD4+ T cells, as measured by $EC_{50}$. In the case of xhCD8v11-hIL21 v31.23, data from two different donors analyzed in two separate experiments are shown (FIG. 15C).

FIG. 21A indicates residues P78 and P79 (Pro-Pro), and C93 and P94 (Cys-Pro) surrounding the flexible loop. FIG. 21B shows the charge of wild-type IL-21 indicating the flexible loop is highly charged.

FIGS. 23A-23D show in vitro activation of STAT3 in cynomolgus monkey whole blood by fusion proteins of anti-human CD8 antibodies, xhCD8.1 or xhCD8v11, with various attenuated versions of IL-21 v31. STAT3 activation is shown for CD8+ T cells, CD4+ T cells, and B cells. CD8+ T cell targeted fusion proteins, xhCD8.1-IL-21 v31.4 (FIG. 23A), xhCD8.1-IL-21 v31.23 (FIG. 23B) and xhCD8v11-IL-21 v31.23 (FIG. 23C), all show preferential STAT3 activation of CD8+ T cells over B and CD4+ T cells, as measured by $EC_{50}$. Untargeted, unattenuated Fc-hIL21 v31 is shown in FIG. 23D, with activation observed in all cell types shown.

FIG. 24 shows in vivo activation of STAT3 in cynomolgus monkey by xhCD8.1-IL-21 v31.4. STAT3 activation levels in CD8+ T cells, CD4+ T cells, NK cells and B cells were assessed 20 min post-dose. Results show that xhCD8.1-IL-21 v31.4 preferentially activates STAT3 in CD8+ T cells over CD4+ T cells, NK cells and B cells, as measured by STAT3 MFI.

DETAILED DESCRIPTION OF THE INVENTION

This disclosure, in some embodiments, provides IL-21 polypeptides or functional fragments or variants thereof that comprise improved properties relative to a wild-type IL-21 (SEQ ID NO: 1). Examples of improved properties include, but are not limited to: (i) improved systemic exposure (e.g., as measured by an increased area under the curve (AUC) upon administering the IL-21 polypeptide or a functional fragment or variant thereof to a subject, relative to that following administration of a wild-type IL-21 protein); (ii) attenuated binding to IL-21 receptor; (iii) reduced cytotoxicity, or any combination thereof.

Figure 21A:
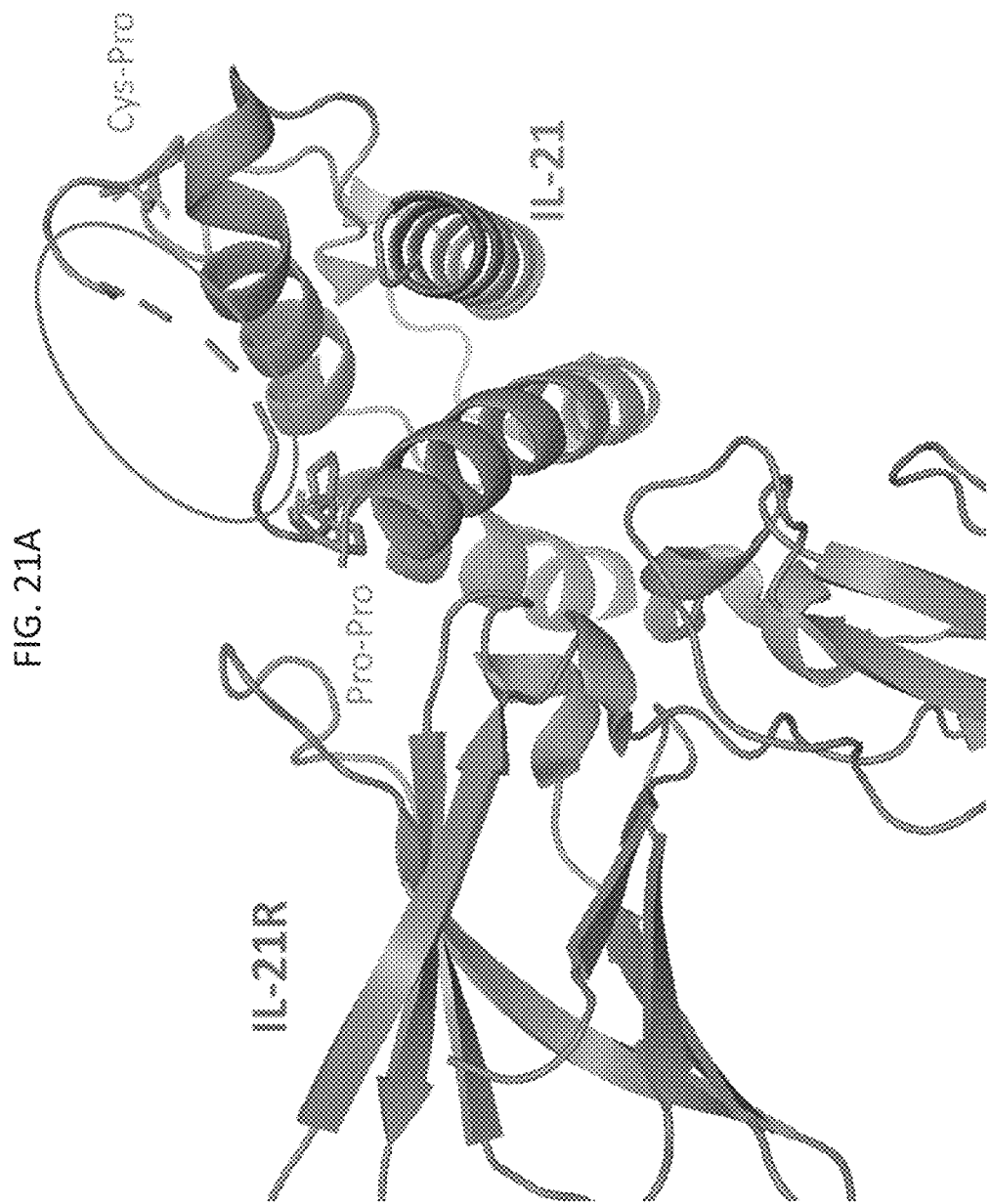
FIGS. 21A and 21B each provide a structural schematic showing the interaction between wild-type IL-21 (SEQ ID NO: 1) and IL-21R (SEQ ID NO: 381). Residues S80-T92 of SEQ ID NO: 1 form a largely unstructured, flexible loop (circled).
Figure 21B:
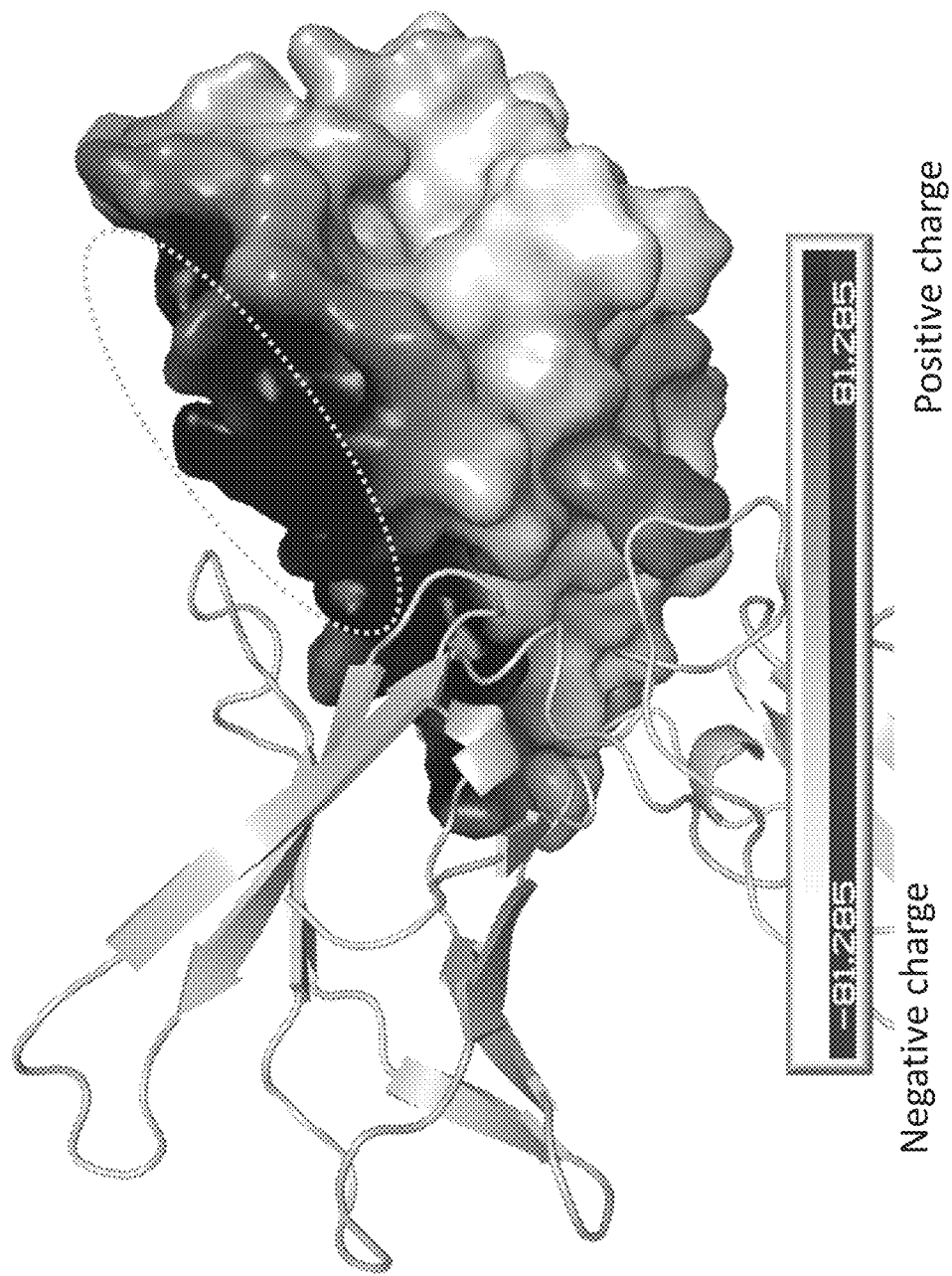

As described herein, the present disclosure provides IL-21 polypeptides or functional fragments or variants thereof with reduced charge (i.e., isoelectric point) and reduced binding affinity to human IL-21 receptor relative to a human IL-21 polypeptide (SEQ ID NO: 1). In particular, the disclosure provides IL-21 polypeptides with one or more amino acid substitutions in a positively charged region of located within residues S80-T92 of human IL-21. As shown in FIG. 21B, residues within S80-T92 of human IL-21 form a flexible loop that does not directly interact with the human IL-21 receptor. Without wishing to be bound by theory, it is believed that residues P78, P79, C93 and P94 of human IL-21 provide structural rigidity surrounding the loop. The present disclosure provides IL-21 polypeptides having one or more amino acid substitutions within the flexible loop with a reduced isoelectric point and improved bioavailability and biological activity. As described herein, the IL-21 polypeptides of the disclosure having reduced isoelectric points relative to the human IL-21 polypeptide demonstrate increased circulatory half-life and reduced polyreactivity (e.g., with positively charged proteins abundant in circulation). As shown in FIGS. 4A-4D, fusion proteins with IL-21 polypeptides having reduced isoelectric points relative to human IL-21 have improved half-life. The disclosure further provides fusion proteins of IL-21 polypeptides to anti-CD8 antibodies which selectively activate CD8+ T cells over CD4+ T cells, NK cells and B cells, including in vivo in non-human primates (see FIG. 24). Without being bound by theory, fusion proteins of the IL-21 polypeptides with antigen binding domains that specifically bind CD8ab or CD8b selectively activate CD8+ T cells relative to NK cells which express CD8aa. In addition, the IL-21 polypeptides with reduced isoelectric points have lower binding affinities to proteins abundant in circulation, such as heparin and hemoglobin (see Table 5). Further, without being bound by theory, IL-21 polypeptides of disclosure having glycine and/or serine substitutions in the flexible loop may have reduced immunogenicity relative to unmodified human IL-21 following administration to a subject.

The disclosure also provides IL-21 polypeptides having reduced binding to human IL-21 receptors. As shown herein, attenuated binding of the IL-21 polypeptide of the disclosure to its receptor reduces IL-21 mediated suppressive effects on alloreactive T cells and dendritic cells (see FIG. 22). Without wishing to be bound by theory, attenuated binding of the IL-21 polypeptide of the disclosure to its receptor is expected to avoid the sink effect of binding to B cells and NK cells. Also demonstrated herein is the therapeutic efficacy of fusion proteins comprising the IL-21 polypeptides of the disclosure and anti-CD8 targeting antibodies. Without being bound by theory, linking of the IL-21 polypeptide with attenuated binding to an anti-CD8 targeting antibody provides selective restoration of the attenuated IL-21 polypeptide. Specifically, FIG. 12 shows such fusion proteins provide anti-tumor efficacy in vivo. This efficacy results, at least in part, from peripheral activation of CD8+ T cells as blocking lymphocyte trafficking reduces the curative response (see FIGS. 13A-13D). Without being bound by theory, T cells in the tumor microenvironment may be dysfunctional and express inhibitory molecules, and thus peripheral activation of CD8+ T cells by the fusion protein provides the anti-tumor immune response. Accordingly, the present disclosure provides novel IL-21 polypeptides and fusion proteins comprising the IL-21 polypeptides having improved biological properties, as well as methods of using such polypeptides to treat diseases in subjects.

Various embodiments of the present disclosure provide methods and compositions involving the use of cytokines (e.g., interleukin 21 (IL-21) or IL-21 polypeptides or functional fragments or variants thereof comprising one or more mutated amino acid residues relative to a wild-type IL-21 polypeptide sequence) that are directed or targeted to activate specific cell subsets (e.g., CD8+ T cells), hereby referred to as targeted cytokine constructs. Without wishing to be bound by a certain theory, it is contemplated that being able to selectively activate certain cell types may enable a more robust response as well as the ability to limit the activation of other cell types that would be counter-productive to a successful immune response. In some cases, the methods and compositions disclosed herein allow for targeted delivery of IL-21 polypeptides to desired cell types and for administration of IL-21 at relatively low concentrations to elicit selective activation of CD8+ T cells. In some cases, use of targeted cytokine constructs disclosed herein provide more selective cell (such as a CD8+ T cells) activation compared to activation of other cell types, such as natural killer (NK) cells, CD4+ T cells or B cells.

Definitions

Unless otherwise defined herein, scientific and technical terms used in connection with this disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As used in the specification and claims, the singular forms "a," "an," and "the" include plural references unless the context clearly dictates otherwise. For example, the term "a chimeric transmembrane receptor polypeptide" includes a plurality of chimeric transmembrane receptor polypeptides.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

As used herein, "area under the curve" or "AUC" is a pharmacokinetic parameter that refers to the area under the plot of plasma concentration of a drug (e.g., IL-21 polypeptide or fusion protein described herein) versus time after dosage. In some embodiments, the AUC measures a patient's exposure to a drug and depends on dose, bioavailability, and clearance. Methods for determining the AUC are known to those of skill in the art and include, but is not limited to, the Rectangle Method, the Trapezoidal Rule, and Simpson's Rule.

A "cytokine" is a form of immunomodulatory polypeptide that can mediate cross-talk between initiating/primary cells and target/effector cells. It can function as a soluble form or cell-surface associated to bind the "cytokine receptor" on target immune cells to activate signaling. "Cytokine receptor" as used here is the polypeptide on the cell surface that activates intracellular signaling upon binding the cytokine on the extracellular cell surface. Cytokines can include, but are not limited to, chemokines, interferons, interleukins, lymphokines, and tumor necrosis factors. Cytokines are produced by a wide range of cells, including immune cells, endothelial cells, fibroblasts, and stromal cells. A given cytokine may be produced by more than one cell type. Cytokines are pleiotropic; since the receptors are expressed on multiple immune cell subsets, one cytokine can activate the signaling pathway in multiple cells. However, depending on the cell type, the signaling events for a cytokine can result in different downstream cellular events such as activation, proliferation, survival, apoptosis, effector function and secretion of other immunomodulatory proteins. A given cytokine, in some embodiments, is a wild-type cytokine polypeptide, a fragment thereof, or a variant thereof, such as a mutated cytokine polypeptide (also referred to herein as a mutein cytokine, e.g., a mutein IL-21 or an IL-21 mutein).

The term "antigen," as used herein, refers to a molecule or a fragment thereof capable of being bound by a selective binding agent. As an example, an antigen can be a ligand that can be bound by a selective binding agent such as a receptor. As another example, an antigen can be an antigenic molecule that can be bound by a selective binding agent such as an immunological protein (e.g., an antibody). An antigen can also refer to a molecule or fragment thereof capable of being used in an animal to produce antibodies capable of binding to that antigen.

The term "antibody", as used herein, means any antigen-binding molecule comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the disclosure, the FRs of an antibody (or antigen-binding portion thereof) may be identical to the human germline sequences, or may be naturally or artificially modified. An amino acid consensus sequence may be defined based on a side-by-side analysis of two or more CDRs.

The term "intact antibody" refers to an antibody comprising four polypeptide chains, two heavy (H) chains and two light (L) chains inter-connected by disulfide bonds. In one embodiment, the antibody is an intact antibody. In one embodiment, the intact antibody is an intact human IgG1, IgG2 or IgG4 isotype. In certain embodiments, the antibody, or antigen-binding fragment thereof, is a human IgG1, IgG2, or IgG4 isotype.

The terms "antigen-binding portion" of an antibody, "antigen-binding fragment," or "antibody-fragment," of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from intact antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide.

The term "variable region" or "variable domain" of an antibody, or fragment thereof, as used herein refers to the portions of the light and heavy chains of antibody molecules that include amino acid sequences of complementarity determining regions (CDRs; i.e., CDR-1, CDR-2, and CDR-3), and framework regions (FRs). VH refers to the variable domain of the heavy chain. VL refers to the variable domain of the light chain. According to the methods used in this disclosure, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

The term "complementarity determining regions" or "CDRs" as used herein refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia et al., J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262 (5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

The term "framework regions" (hereinafter FR) as used herein refers to those variable domain residues other than the CDR residues. Each variable domain typically has four FRs identified as FR1, FR2, FR3 and FR4. Common structural features among the variable regions of antibodies, or functional fragments thereof, are well known in the art. The DNA sequence encoding a particular antibody can generally be found following well known methods such as those described in Kabat, et al. 1987 Sequence of Proteins of Immunological Interest, U.S. Department of Health and Human Services, Bethesda MD, which is incorporated herein as a reference. In addition, a general method for cloning functional variable regions from antibodies can be found in Chaudhary, V. K., et al., 1990 Proc. Natl. Acad. Sci. USA 87:1066, which is incorporated herein as a reference.

A "variant Fc region" comprises an amino acid sequence which differs from that of a native sequence Fc region by virtue of at least one "amino acid modification" as herein defined. A variant Fc region has at least one amino acid substitution compared to a native sequence Fc region or to the Fc region of a parent polypeptide, e.g., from about one to about ten amino acid substitutions, from about one to about five amino acid substitutions in a native sequence Fc region or in the Fc region of the parent polypeptide. In one embodiment, a variant Fc region herein can have a sequence that has at least about 80% identity, at least about 85% identity, at least about 90% identity, at least about 95% identity or at least about 99% identity with a native sequence Fc region. According to another embodiment, the variant Fc region herein can have a sequence that has at least about 80% identity, at least about 85% identity, at least about 90% identity, at least about 95% identity or at least about 99% identity with an Fc region of a parent polypeptide.

The terms "Fc receptor" or "FcR," as used herein, generally refers to a receptor, or any derivative, variant or fragment thereof, that can bind to the Fc region of an antibody. In certain embodiments, the FcR is one which binds an IgG antibody (a gamma receptor, Fcgamma R) and includes receptors of the Fcgamma RI (CD64), Fcgamma RII (CD32), and Fcgamma RIII (CD16) subclasses, including allelic variants and alternatively spliced forms of these receptors. Fcgamma RII receptors include Fcgamma RIIA (an "activating receptor") and Fcgamma RIIB (an "inhibiting receptor"), which have similar amino acid sequences that differ primarily in the cytoplasmic domains thereof. The term "FcR" also includes the neonatal receptor, FcRn, which is responsible for the transfer of maternal IgGs to the fetus.

By "effector function" as used herein is meant a biochemical event that results from the interaction of an antibody Fc region with an Fc receptor or ligand, which vary with the antibody isotype. Effector functions include but are not limited to antibody-dependent cell-mediated cytotoxicity (ADCC), antibody-dependent cell-mediated phagocytosis (ADCP), complement-dependent cytotoxicity (CDC), cytokine secretion, immune complex-mediated antigen uptake by antigen presenting cells, down regulation of cell surface receptors (e.g. B cell receptor), and B cell activation. "Antibody-dependent cell-mediated cytotoxicity" or "ADCC" refers to a cell-mediated reaction in which nonspecific cytotoxic cells that express FcRs (such as Natural Killer (NK) cells, neutrophils, and macrophages) recognize bound antibody on a target cell and subsequently cause lysis of the target cell. ADCC is correlated with binding to FcγRIIIa; increased binding to FcγRIIIa leads to an increase in ADCC activity. To assess ADCC activity of a molecule of interest, an in vitro ADCC assay such as that described in U.S. Pat. No. 5,500,362 or 5,821,337 may be performed. "ADCP" or antibody dependent cell-mediated phagocytosis as used herein is meant the cell-mediated reaction wherein nonspecific cytotoxic cells that express FcγRs recognize bound antibody on a target cell and subsequently cause phagocytosis of the target cell.

"Fc null" and "Fc null variant" are used interchangeably and used herein to describe a modified Fc which have reduced or abolished effector functions. Such Fc null or Fc null variant have reduced or abolished to FcγRs and/or complement receptors. Preferably, such Fc null or Fc null variant has abolished effector functions. Exemplary methods for the modification include but not limited to chemical alteration, amino acid residue substitution, insertion and deletions. Exemplary amino acid positions on Fc molecules where one or more modifications were introduced to decrease effector function of the resulting variant (numbering based on the EU numbering scheme) at position i) IgG1: C220, C226, C229, E233, L234, L235, G237, P238, S239 D265, S267, N297, L328, P331, K322, A327 and P329, ii) IgG2: V234, G237, D265, H268, N297, V309, A330, A331, K322 and iii) IgG4: L235, G237, D265 and E318. Exemplary Fc molecules having decreased effector function include those having one or more of the following substitutions: i) IgG1: N297A, N297Q, D265A/N297A, D265A/N297Q, C220S/C226S/C229S/P238S, S267E/L328F, C226S/C229S/E233P/L234V/L235A, L234F/L235E/P331S, L234A/L235A, L234A/L235A/G237A, L234A/L235A/G237A/K322A, L234A/L235A/G237A/A330S/A331S, L234A/L235A/P329G, E233P/L234V/L235A/G236del/S239K, E233P/L234V/L235A/G236del/S267K, E233P/L234V/L235A/G236del/S239K/A327G, E233P/L234V/L235A/G236del/S267K/A327G and E233P/L234V/L235A/G236del, L234A/L235A/G237 deleted; ii) IgG2:

A330S/A331S, V234A/G237A, V234A/G237A/D265A, D265A/A330S/A331S, V234A/G237A/D265A/A330S/A331S, and H268Q/V309L/A330S/A331S; iii) IgG4: L235A/G237A/E318A, D265A, L235A/G237A/D265A and L235A/G237A/D265A/E318A.

"Epitope" as used herein refers to a determinant capable of specific binding to the variable region of an antibody molecule known as a paratope. Epitopes are groupings of molecules such as amino acids or sugar side chains and usually have specific structural characteristics, as well as specific charge characteristics. A single antigen may have more than one epitope. The epitope may comprise amino acid residues directly involved in the binding and other amino acid residues, which are not directly involved in the binding, such as amino acid residues which are effectively blocked by the antigen binding peptide (in other words, the amino acid residue is within the footprint of the antigen binding peptide). Epitopes may be either conformational or linear. An epitope typically includes at least 3, and more usually, at least 5 or 8-10 amino acids. Antibodies that recognize the same epitope can be verified in a simple immunoassay showing the ability of one antibody to block the binding of another antibody to a target antigen, for example "binning".

"Linker" as used herein refers to a molecule that connect two polypeptide chains. Linker can be a polypeptide linker or a synthetic chemical linker (for example, see disclosed in Protein Engineering, 9(3), 299-305, 1996). The length and sequence of the polypeptide linkers is not particularly limited and can be selected according to the purpose by those skilled in the art. Polypeptide linker comprises one or more amino acids. Preferably, polypeptide linker is a peptide with a length of at least 5 amino acids, preferably with a length of 5 to 100, more preferably of 10 to 50 amino acids. In one embodiment, said peptide linker is G, S, GS, SG, SGG, GGS, and GSG (with G=glycine and S=serine). In another embodiment, said peptide linker is $(GGGS)_xG_n$ (SEQ ID NO: 294) or $(GGGGS)_xG_n$ (SEQ ID NO: 295), $(GGGGGS)_xG_n$ (SEQ ID NO: 296), S(GGGS)xGn (SEQ ID NO:289), S(GGGGS)xGn (SEQ ID NO:290), or S(GGGGGS)xGn (SEQ ID NO:291), with x=1, 2, 3, 4, 5, 6, 7, 8, 9, 10, 11, or 12 and n=0, 1, 2 or 3. In some embodiments, the linker is $(GGGGS)_xG_n$ with x=2, 3, or 4 and n=0 (SEQ ID NO: 372); in some embodiments the linker is $(GGGGS)_xG_n$ with x=3 and n=0 (SEQ ID NO: 373). In some embodiments, the linker comprises the sequence SGGGGSGGGGSGGGGS (SEQ ID NO:292), or SGGGGSGGGGSGGGG (SEQ ID NO:293). Synthetic chemical linkers include crosslinking agents that are routinely used to crosslink peptides, for example, N-hydroxy succinimide (NHS), disuccinimidyl suberate (DSS), bis(succinimidyl) suberate (BS3), dithiobis(succinimidyl propionate) (DSP), dithiobis(succinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl] sulfone (BSOCOES), and bis[2-(succinimidoxycarbonyloxy)ethyl] sulfone (sulfo-BSOCOES).

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g., deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein, in some examples, refers to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides can include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif, FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three-dimensional structure, and can perform any function, known or unknown. A polynucleotide can comprise one or more analogs (e.g., altered backbone, sugar, or nucleobase). If present, modifications to the nucleotide structure can be imparted before or after assembly of the polymer.

Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components.

The term "gene," as used herein, refers to a nucleic acid (e.g., DNA such as genomic DNA and cDNA) and its corresponding nucleotide sequence that is involved in encoding an RNA transcript. The term as used herein with reference to genomic DNA includes intervening, non-coding regions as well as regulatory regions and can include 5' and 3' ends. In some uses, the term encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some cases, genes do not encode a polypeptide, for example, ribosomal RNA genes (rRNA) and transfer RNA (tRNA) genes. In some cases, the term "gene" includes not only the transcribed sequences, but in addition, also includes non-transcribed regions including upstream and downstream regulatory regions, enhancers and promoters. A gene, in some cases, refers to an "endogenous gene" or a native gene in its natural location in the genome of an organism. A gene, in some cases, refers to an "exogenous gene" or a non-native gene. A non-native gene, in some cases, refers to a gene not normally found in the host organism but which is introduced into the host organism by gene transfer. A non-native gene, in some cases, refers to a gene not in its natural location in the genome of an organism. A non-native gene, in some cases, also refers to a naturally occurring nucleic acid or polypeptide sequence that comprises mutations, insertions and/or deletions (e.g., non-native sequence).

The term "regulating" with reference to expression or activity, as used herein, refers to altering the level of expression or activity. Regulation can occur at the transcription level and/or translation level.

The terms "peptide," "polypeptide," and "protein" are used interchangeably herein to refer to a polymer of at least two amino acid residues joined by peptide bond(s). This term does not connote a specific length of polymer, nor is it intended to imply or distinguish whether the peptide is produced using recombinant techniques, chemical or enzymatic synthesis, or is naturally occurring. The terms apply to naturally occurring amino acid polymers as well as amino acid polymers comprising at least one modified amino acid. In some cases, the polymer can be interrupted by non-amino acids. The terms include amino acid chains of any length, including full length proteins, and proteins with or without secondary and/or tertiary structure (e.g., domains). The terms also encompass an amino acid polymer that has been modified, for example, by disulfide bond formation, glycosylation, lipidation, acetylation, phosphorylation, oxidation, and any other manipulation such as conjugation with a labeling component. The terms "amino acid" and "amino acids," as used herein, generally refer to natural and non-natural amino acids, including, but not limited to, modified amino acids and amino acid analogues. Modified amino acids can include natural amino acids and non-natural amino acids, which have been chemically modified to include a group or a chemical moiety not naturally present on the amino acid. Amino acid analogues can refer to amino acid derivatives. The term "amino acid" includes both D-amino acids and L-amino acids.

The terms "derivative," "variant," and "fragment," when used herein with reference to a polypeptide, refers to a polypeptide related to a wild type polypeptide, for example either by amino acid sequence, structure (e.g., secondary and/or tertiary), activity (e.g., enzymatic activity) and/or function. Derivatives, variants and fragments of a polypeptide can comprise one or more amino acid variations (e.g., mutations, insertions, and deletions), truncations, modifications, or combinations thereof compared to a wild type polypeptide.

The term "residue" as used herein means a position in a protein and its associated amino acid identity. For example, Leu 234 (also referred to as Leu234 or L234) is a residue at position 234 in the human antibody IgG1.

The term "wild-type" as used herein means an amino acid sequence or a nucleotide sequence that is found in nature, including allelic variations. A wild-type protein has an amino acid sequence or a nucleotide sequence that has not been intentionally modified.

The terms "substitution" or "mutation" refers to a change to the polypeptide backbone wherein an amino acid occurring naturally in the wild-type sequence of a polypeptide is substituted to another amino acid not naturally occurring at the same position in the said polypeptide. In some cases, a mutation or mutations is introduced to modify a polypeptide's affinity to its receptor thereby altering its activity such that it becomes different from the affinity and activity of the wild-type cognate polypeptide. Mutations can also improve a polypeptide's biophysical properties. Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

The terms "affinity" or "binding affinity" refer to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity can generally be represented by the dissociation constant ($K_D$), which is the ratio of dissociation and association rate constants (koff and kon, respectively). Thus, equivalent affinities may comprise different rate constants, as long as the ratio of the rate constants remains the same. Affinity can be measured by common methods known in the art, such as enzyme-linked immunosorbent assay (ELISA), surface plasmon resonance (SPR) technologies (e.g., BIAcore), BioLayer Interferometry (BLI) technologies (e.g. Octet) and other traditional binding assays (Heeley, Endocr Res 28, 217-229 (2002). In some examples, binding affinity is determined by Scatchard analysis, which comprises generating a Scatchard plot, which is a plot of the ratio of concentrations of bound ligand to unbound ligand versus the bound ligand concentration.

The terms "binding" or "specific binding" as used here, can refer to the ability of a polypeptide or an antigen binding domain to selectively interact with the receptor for the polypeptide or target antigen, respectively, and this specific interaction can be distinguished from non-targeted or undesired or non-specific interactions. Examples of specific binding can include but are not limited to IL-21 cytokine binding to its specific receptors (e.g., IL-21R and common gamma chain) and an antigen binding domain binding to a specific antigen (e.g., CD8 or PD-1).

The terms "subject," "individual," and "patient" are used interchangeably herein to refer to a vertebrate, preferably a mammal such as a human. Mammals include, but are not limited to, murines, simians, humans, farm animals, sport animals, and pets. Tissues, cells and their progeny of a biological entity obtained in vivo or cultured in vitro are also encompassed.

The terms "treatment" and "treating," as used herein, refer to an approach for obtaining beneficial or desired results including but not limited to a therapeutic benefit and/or a prophylactic benefit. For example, a treatment can comprise administering a system or cell population disclosed herein. By therapeutic benefit is meant any therapeutically relevant improvement in or effect on one or more diseases, conditions, or symptoms under treatment. For prophylactic benefit, a composition can be administered to a subject at risk of developing a particular disease, condition, or symptom, or to a subject reporting one or more of the physiological symptoms of a disease, even though the disease, condition, or symptom may not have yet been manifested.

The terms "effective amount," or "therapeutically effective amount," or "effective dose," or "effective dosage," refer to the quantity of a composition, for example a composition comprising immune cells such as lymphocytes (e.g., T lymphocytes and/or NK cells), which can be combined with a targeted cytokine construct of the present disclosure, that is sufficient to result in a desired activity upon administration to a subject in need thereof. Within the context of the present disclosure, the term "therapeutically effective" refers to that quantity of a composition that is sufficient to delay the manifestation, arrest the progression, relieve or alleviate at least one symptom of a disorder treated by the methods of the present disclosure.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Alignment for purposes of determining percent amino acid sequence identity can for example be achieved using publicly available sequence comparison computer program ALIGN-2. The source code for the ALIGN-2 sequence comparison computer program is available with user documentation in the U.S. Copyright Office, Washington D.C., 20559, where it is registered under U.S. Copyright Registration No. TXU510087. The ALIGN-2 program can be compiled for use on a UNIX operating system, such as a digital UNIX V4.0D. All sequence comparison parameters are set by the ALIGN-2 program and do not vary.

For all amino acid positions discussed in the present disclosure, in the context of antibodies or antigen binding fragments thereof, numbering is according to the EU index. The "EU index" or "EU index as in Kabat et al." or "EU numbering scheme" refers to the numbering of the EU antibody (See Edelman et al., 1969; Kabat et al., 1991).

Interleukin-21 Polypeptides

Interleukin-21 (IL-21) is a cytokine that can be expressed by T cells, B cells, NK cells and myeloid cells, and regulates the activity of both innate and adaptive immune cells and improves T cell survival and effector function. Several Phase I and II clinical trials include IL-21 as the investigational product for the treatment of cancers, inflammatory diseases, and autoimmune diseases, including, melanoma, renal cell carcinoma, acute myeloid leukemia, non-Hodgkin's lymphoma, ovarian cancer, colorectal cancer, systemic lupus erythematosus, Crohn's disease and rheumatoid arthritis.

IL-21 has a four-helix bundle structure and exists as a monomer. In humans, two isoforms of IL-21 are known, each of which are derived from a precursor molecule. The first IL-21 isoform comprises 162 amino acids (aa), the first 29 of which make up the signal peptide; and the second IL-21 isoform comprises 153 aa, the first 29 of which make up the signal peptide as in the first isoform.

IL-21 binds to the heterodimeric IL-21 receptor complex, comprising of an IL-21 receptor (IL-21R) and common gamma chain (γc). IL-21 receptor complex is expressed on the surface of T, B, and NK cells. IL-21 receptor complex is similar in structure to the IL-2 receptor complex, in that each of these cytokine receptor complex comprises a γc.

When IL-21 binds to IL-21 receptor complex, the JAK/STAT signaling pathway is activated to activate target genes. While IL-21-induced signaling may be therapeutically desirable, careful consideration of the timing and the location of the signaling is needed, given IL-21's broad expression profile and due to the fact that IL-21 has the ability to potentiate CD8+ T cell responses as well as to suppress antigen presentation and T cell priming.

The present disclosure provides, in some embodiments, IL-21 polypeptides or functional fragments or variants thereof, comprising at least one amino acid substitution, relative to the wild-type IL-21 amino acid sequence, which is provided herein as SEQ ID NO: 1. Unless noted otherwise, the terms "wild-type IL-21," "wild-type IL-21 polypeptide," "human IL-21," and "human IL-21 polypeptide" are used interchangeably and can refer to the amino acid sequence of SEQ ID NO: 1. Such IL-21 polypeptides comprising at least one amino acid substitution relative to SEQ ID NO: 1 are also referred to herein as IL-21 muteins. In exemplary aspects, an IL-21 polypeptide or functional fragment or variant thereof, as described herein, comprises at least one and not more than X amino acid substitutions, wherein X is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or greater. In some embodiments, an IL-21 polypeptide or functional fragment or variant thereof, as described herein, comprises at least 35 amino acid substitutions compared to SEQ ID NO: 1. In exemplary embodiments, an IL-21 polypeptide or functional fragment or variant thereof, as described herein, comprises an amino acid sequence which differs from the amino acid sequence of human IL-21 (SEQ ID NO: 1) by 10 amino acids, 15 amino acids, 20 amino acids, or 25 amino acids. In some embodiments, an IL-21 polypeptide or functional fragment or variant thereof, as described herein, comprises an amino acid sequence which differs from the amino acid sequence of human IL-21 (SEQ ID NO: 1) by no more than 16 amino acids. In some embodiments, an IL-21 polypeptide or functional fragment or variant thereof, as described herein, comprises an amino acid sequence which differs from the amino acid sequence of human IL-21 (SEQ ID NO: 1) by 4, 5, 6, 7, 8, 9, 10, 11, 12, 13, 14, 15 or 16 amino acids. In exemplary embodiments, an IL-21 polypeptide or functional fragment or variant thereof, as described herein, comprises an amino acid sequence which differs from the amino acid sequence of human IL-21 (SEQ ID NO: 1) by no more than 7 amino acids or no more than 5 amino acids. In some embodiments, an IL-21 polypeptide or functional fragment or variant thereof, as described herein, comprises an amino acid sequence which differs from the amino acid sequence of human IL-21 (SEQ ID NO: 1) by 10, 11, 12, 13, 14, 15 or 16 amino acids. In exemplary embodiments, an IL-21 polypeptide or functional fragment or variant thereof, as described herein, comprises an amino acid sequence which differs from the amino acid sequence of human IL-21 (SEQ ID NO: 1) by 3, 4, 5, or 6 amino acids. In some embodiments, an IL-21 polypeptide or functional fragment or variant thereof, as described herein, comprises an amino acid sequence which differs from the amino acid sequence of human IL-21 (SEQ ID NO: 1) by 5 to 16. In exemplary embodiments, an IL-21 polypeptide or functional fragment or variant thereof, as described herein, comprises an amino acid sequence which differs from the amino acid sequence of human IL-21 (SEQ ID NO: 1) by 3 to 6 amino acids or 1 to 5 amino acids. In exemplary embodiments, an IL-21 polypeptide or functional fragment or variant thereof, as described herein, comprises an amino acid sequence which differs from the amino acid sequence of human IL-21 (SEQ ID NO: 1) by one or two amino acids.

Altered Isoelectric Point or Charge Distribution

In some embodiments, an IL-21 polypeptide or a functional fragment or a variant thereof comprises at least one mutation that alters the isoelectric point with or without affecting its binding to IL-21R. In some embodiments, an IL-21 polypeptide or a functional fragment or a variant therefor comprises at least one mutation that alters the isoelectric point without affecting binding to IL-21R. An altered isoelectric point of a protein can change the surface charge distribution, thereby affecting protein yield, non-specific binding, and the blood or circulatory half-life for a given protein. In some embodiments, the mutations in the IL-21 polypeptide or a functional fragment or a variant thereof decreases the theoretical isoelectric point by a given unit measured by a publicly available database ProtParam (SwissProt), which is hereby incorporated by reference.

In some embodiments, the IL-21 polypeptide or a functional fragment or a variant thereof has an isoelectric point difference of about 0.6 to about 5.0 units compared to the isoelectric point of SEQ ID NO: 1, which has an isoelectric point of about 9.42. In some embodiments, the IL-21 polypeptide or a functional fragment or a variant thereof has an isoelectric point of about 6.0 to about 9.0. In some embodiments, the IL-21 polypeptide or a functional fragment or a variant thereof comprises a theoretical isoelectric point of about 6 to about 9. In some embodiments, the IL-21 polypeptide or a functional fragment or a variant thereof comprises a theoretical isoelectric point of at least about 6. In some embodiments, the IL-21 polypeptide or a functional fragment or a variant thereof comprises a theoretical isoelectric point of at most about 9. In some embodiments, the IL-21 polypeptide or a functional fragment or a variant thereof comprises a theoretical isoelectric point of about 9 to about 8.9, about 9 to about 8.8, about 9 to about 8.7, about 9 to about 8.5, about 9 to about 8.3, about 9 to about 8.1, about 9 to about 7.9, about 9 to about 7.7, about 9 to about 7.5, about 9 to about 7.3, about 9 to about 7, about 9 to about 6.5, about 9 to about 6.0, about 8.9 to about 8.8, about 8.9 to about 8.7, about 8.9 to about 8.5, about 8.9 to about 8.3, about 8.9 to about 8.1, about 8.9 to about 7.9, about 8.9 to about 7.7, about 8.9 to about 7.5, about 8.9 to about 7.3, about 8.9 to about 7, about 8.9 to about 6.5, about 8.9 to about 6.0, about 8.8 to about 8.7, about 8.8 to about 8.5, about 8.8 to about 8.3, about 8.8 to about 8.1, about 8.8 to about 7.9, about 8.8 to about 7.7, about 8.8 to about 7.5, about 8.8 to about 7.3, about 8.8 to about 7, about 8.8 to about 6.5, about 8.8 to about 6.0, about 8.7 to about 8.6, about 8.7 to about 8.5, about 8.7 to about 8.3, about 8.7 to about 8.1, about 8.7 to about 7.9, about 8.7 to about 7.7, about 8.7 to about 7.5, about 8.7 to about 7.3, about 8.7 to about 7, about 8.7 to about 6.5, about 8.7 to about 6.0, about 8.5 to about 8.3, about 8.5 to about 8.4, about 8.5 to about 8.39, about 8.5 to about 8.1, about 8.5 to about 7.9, about 8.5 to about 7.7, about 8.5 to about 7.5, about 8.5 to about 7.3, about 8.5 to about 7, about 8.5 to about 6.5, about 8.5 to about 6.0, about 8.39, about 8.3 to about 8.1, about 8.3 to about 7.9, about 8.3 to about 7.7, about 8.3 to about 7.5, about 8.3 to about 7.3, about 8.3 to about 7, about 8.3 to about 6.5, about 8.3 to about 6.0, about 8.1 to about 7.9, about 8.1 to about 7.7, about 8.1 to about 7.5, about 8.1 to about 7.3, about 8.1 to about 7, about 8.1 to about 6.5, about 8.1 to about 6.0, about 7.9 to about 7.7, about 7.9 to about 7.5, about 7.9 to about 7.3, about 7.9 to about 7, about 7.9 to about 6.5, about 7.9 to about 6.0, about 7.7 to about 7.5, about 7.7 to about 7.3, about 7.7 to about 7, about 7.5 to about 7.3, about 7.5 to about 7, or about 7.3 to about 7, about 7.3 to about 6.5, about 7.3 to about 6.0, about 7.0 to about 6.5, about 7.0 to about 6.0, or about 6.5 to about 6.0. In some embodiments, the IL-21 polypeptide or a functional fragment or a variant thereof comprises a theoretical isoelectric point of about 9, about 8.9, about 8.8, about 8.79, about 8.7, about 8.5, about 8.39, about 8.3, about 8.1, about 7.9, about 7.7, about 7.5, about 7.3, about 7, about 6.5 or about 6.0. In some embodiments, the IL-21 polypeptide or a functional fragment or a variant thereof has a theoretical isoelectric point of less than 9.0. In some embodiments, the IL-21 polypeptide or a functional fragment or a variant thereof has a theoretical isoelectric point of less than 8.9, less than 8.8, less than 8.7, less than 8.5, less than 8.3, less than 8.1, less than 7.9, less than 7.7, less than 7.5, less than 7.3, less than 7.2, less than 7.0, less than 6.5 or less than 6.2.

In some instances, an altered isoelectric point can increase the protein yield of IL-21 polypeptide or a functional fragment or a variant thereof during the purification compared to wild-type IL-21. In some embodiments, the increased protein yield is at least 5% greater than wild-type IL-21. In some embodiments, the increased protein yield is at least 5%, 10%, 15%, 20%, 25%, 50%, 75%, 100%, 125%, 150%, 175%, 200%, 225%, 250%, 275%, or 300% greater than wild-type IL-21. In some embodiments, the increased protein yield is at least 5%, 10%, 15%, 20%, 25%, 50%, 75%, 100%, 125%, 150%, 175%, 200%, 225%, 250%, 275%, or 300% greater than wild-type IL-21. In some embodiments, the increased protein yield is 5% to 10%, 5% to 15%, 5% to 20%, 5% to 25%, 5% to 50%, 5% to 75%, 5% to 100%, 5% to 125%, 5% to 150%, 5% to 175%, 5% to 200%, 5% to 225%, 5% to 250%, 5% to 275%, 5% to 300%, 10% to 15%, 10% to 20%, 10% to 25%, 10% to 50%, 10% to 75%, 10% to 100%, 10% to 125%, 10% to 150%, 10% to 175%, 10% to 200%, 10% to 225%, 10% to 250%, 10% to 275%, 10% to 300%, 15% to 20%, 15% to 25%, 15% to 50%, 15% to 75%, 15% to 100%, 15% to 125%, 15% to 150%, 15% to 175%, 15% to 200%, 15% to 225%, 15% to 250%, 15% to 275%, 15% to 300%, 20% to 25%, 20% to 50%, 20% to 75%, 20% to 100%, 20% to 125%, 20% to 150%, 20% to 175%, 20% to 200%, 20% to 225%, 20% to 250%, 20% to 275%, 20% to 300%, 25% to 50%, 25% to 75%, 25% to 100%, 25% to 125%, 25% to 150%, 25% to 175%, 25% to 200%, 25% to 225%, 25% to 250%, 25% to 275%, 25% to 300%, 50% to 75%, 50% to 100%, 50% to 125%, 50% to 150%, 50% to 175%, 50% to 200%, 75% to 100%, 75% to 125%, 75% to 150%, 75% to 175%, 75% to 200%, 75% to 225%, 75% to 250%, 75% to 275%, 75% to 300%, 100% to 125%, 100% to 150%, 100% to 175%, 100% to 200%, 100% to 225%, 100% to 250%, 100% to 275%, 100% to 300%, 125% to 150%, 125% to 175%, 125% to 200%, 125% to 225%, 125% to 250%, 125% to 275%, 125% to 300, 150% to 175%, 150% to 200%, 175% to 200%, 175% to 225%, 175% to 250%, 175% to 275%, 175% to 300%, 200% to 225%, 200% to 250%, 200% to 275%, 200% to 300%, 225% to 250%, 225% to 275%, 225% to 300%, 250% to 275%, 250% to 300%, or 275% to 300%. In some embodiments, the increased protein yield is about 5%, 10%, 15%, 20%, 25%, 50%, 75%, 100%, 125%, 150%, 175%, 200%, 225%, 250%, 275%, or 300%.

In some embodiments, relative to a region of wild-type IL-21 polypeptide that comprises one or more positively charged amino acid residues, the IL-21 polypeptide or a functional fragment or a variant thereof comprises at least one amino acid substitution of the one or more positively charged amino acid residues. In some cases, the region of wild-type IL-21 comprises 2-20 positively charged amino acid residues. In some embodiments, the region in wild-type IL-21 comprises 2-3, 2-4, 2-5, 2-7. 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 3-18, 14-19, 14-20, 15-16, 15-17, 15-18, 15-19, 15-20, 16-17, 16-18, 16-19, 16-20, 17-18, 17-19, 17-20 18-19, 18-20, or 19-20 amino acid residues with at least 2, 3, 4, 5, 6, 7, 8, 9, 10, 11, 12, 13, 14, 15, 16, 17, 18, 19 or 20 positively charged amino acid residues. In some embodiments, the region of wild-type IL-21 comprises 12 amino acid residues, of which 2, 3, 4, 5, 6, 7, 8, 9, 10, 11 or 12 amino acid residues are positively charged. In some embodiments, the region of wild-type IL-21 comprises 12 amino acid residues, of which 2, 3, 4, 5, or 6 amino acid residues are positively charged.

In some embodiments, amino acids within the region of wild-type IL-21 do not bind a human IL-21 receptor. In some embodiments, the region of wild-type IL-21 comprises amino acid residues S80-T92 of SEQ ID NO: 1. In some embodiments, the region of wild-type IL-21 comprises positively charged amino acid residues R85, R86, K88, H89, and R90. In some embodiments, the IL-21 polypeptide or a functional fragment or a variant thereof comprises at least one amino acid substitution in the region of wild-type IL-21. In some embodiments, the IL-21 polypeptide or a functional fragment or a variant thereof comprises at least one amino acid substitution of S80-T92. In some embodiments, the IL-21 polypeptide or a functional fragment or a variant thereof comprises at least four amino acid substitutions of S80-T92. In some embodiments, the IL-21 polypeptide or a functional fragment or a variant thereof comprises at least four amino acid substitutions of S80-T92, provided G84 is not substituted. In some embodiments, the IL-21 polypeptide or a functional fragment or a variant thereof comprises at least one amino acid substitution at R85, R86, K88, H89 or R90. In some embodiments, the IL-21 polypeptide or a functional fragment or a variant thereof comprises an amino acid substitution at one or more of S80, T81, N82, A83, R85, R86, Q87, K88, H89, R90, L91 and T92. In some embodiments, the IL-21 polypeptide or a functional fragment or a variant thereof comprises amino acid substitutions at S80, T81, N82, A83, R85, R86, Q87, K88, H89, R90, L91 and T92.

In some embodiments, the IL-21 polypeptide or a functional fragment or a variant thereof that comprises an altered isoelectric point relative to wild-type IL-21 (SEQ ID NO: 1) comprises a mutation in a position selected from the group consisting of K56, S80, T81, N82, A83, G84, R85, R86, Q87, K88, H89, R90, L91, and T92 of SEQ ID NO: 1. In some embodiments, the IL-21 polypeptide or a functional fragment or a variant thereof that comprises an altered isoelectric point relative to wild-type IL-21 (SEQ ID NO: 1) comprises a mutation in a position selected from the group consisting of K56, T81, N82, A83, G84, R85, R86, Q87, K88, H89, R90, L91, and T92 of SEQ ID NO: 1. In some embodiments, the IL-21 polypeptide or a functional fragment or a variant thereof that comprises an altered isoelectric point relative to wild-type IL-21 (SEQ ID NO: 1)

comprises a mutation in a position selected from the group consisting of S80, T81, N82, A83, G84, R85, R86, Q87, K88, H89, R90, L91, and T92 of SEQ ID NO: 1. In some embodiments, the IL-21 polypeptide or a functional fragment or a variant thereof that comprises an altered isoelectric point relative to wild-type IL-21 (SEQ ID NO: 1) comprises a mutation in a position selected from the group consisting of S80, T81, N82, A83, R85, R86, Q87, K88, H89, R90, L91, and T92 of SEQ ID NO: 1.

In some embodiments, the IL-21 polypeptide or a functional fragment or a variant thereof comprises a mutation at position K56 of SEQ ID NO: 1. In some instances, the mutation comprises K56G, K56S, K56E, K56D, or K56A. In some embodiments, the IL-21 polypeptide or a functional fragment or a variant thereof comprises a mutation at position S80. In some embodiments, the mutation comprises S80G, S80A, S80D or S80E. In some embodiments, the IL-21 polypeptide or a functional fragment or a variant thereof comprises a mutation at position T81 of SEQ ID NO: 1. In some instances, the mutation comprises T81G, T81S, T81E, T81D, or T81A. In some embodiments, the IL-21 polypeptide or a functional fragment or a variant thereof comprises a mutation at position N82 of SEQ ID NO: 1. In some instances, the mutation comprises N82G, N82S, N82E, N82D, or N82A. In some embodiments, the IL-21 polypeptide or a functional fragment or a variant thereof comprises a mutation at position A83 of SEQ ID NO: 1. In some instances, the mutation comprises A83G, A83S, A83E, or A83D. In some embodiments, the IL-21 polypeptide or a functional fragment or a variant thereof comprises a mutation at position G84 of SEQ ID NO: 1. In some instances, the mutation comprises G84A, G84S, G84E, or G84D. In some embodiments, G84 is not mutated. In some embodiments, the IL-21 polypeptide or a functional fragment or a variant thereof comprises a mutation at position R85 of SEQ ID NO: 1. In some instances, the mutation comprises R85G, R85S, R85E, R85D, or R85A. In some embodiments, the IL-21 polypeptide or a functional fragment or a variant thereof comprises a mutation at position R86 of SEQ ID NO: 1. In some instances, the mutation comprises R86G, R86S, R86E, R86D, or R86A. In some embodiments, the IL-21 polypeptide or a functional fragment or a variant thereof comprises a mutation at position Q87 of SEQ ID NO: 1. In some instances, the mutation comprises Q87G, Q87S, Q87E, Q87D, or Q87A. In some embodiments, the IL-21 polypeptide or a functional fragment or a variant thereof comprises a mutation at position K88 of SEQ ID NO: 1. In some instances, the mutation comprises K88G, K88S, K88E, K88D, or K88A. In some embodiments, the IL-21 polypeptide or a functional fragment or a variant thereof comprises a mutation at position H89 of SEQ ID NO: 1. In some instances, the mutation comprises H89G, H89S, H89E, H89D, or H89A. In some embodiments, the IL-21 polypeptide or a functional fragment or a variant thereof comprises a mutation at position R90 of SEQ ID NO: 1. In some instances, the mutation comprises R90G, R90S, R90E, R90D, or R90A. In some embodiments, the IL-21 polypeptide or a functional fragment or a variant thereof comprises a mutation at position L91 of SEQ ID NO: 1. In some instances, the mutation comprises L91G, L91S, L91E, L91D, or L91A. In some embodiments, the IL-21 polypeptide or a functional fragment or a variant thereof comprises a mutation at position T92 of SEQ ID NO: 1. In some instances, the mutation comprises T92G, T92S, T92E, T92D, or T92A.

In some embodiments, an IL-21 polypeptide or a functional fragment or a variant thereof that has an altered isoelectric point relative to the IL-21 of SEQ ID NO: 1 comprises an amino acid sequence that is at least 75% identical to the sequence of SEQ ID NO: 1 and comprises a mutation in at least one position selected from the group consisting of positions K56 and R90 of SEQ ID NO: 1. In some embodiments, an IL-21 polypeptide or a functional fragment or a variant thereof that has an altered isoelectric point relative to the IL-21 of SEQ ID NO: 1 comprises an amino acid sequence that is at least 80%, 85%, 90%, 95%, 97%, 98%, 99%, or 100% identical to the sequence of SEQ ID NO: 1 and comprises a mutation in at least one position selected from the group consisting of positions K56 and R90 of SEQ ID NO: 1. The mutation at position K56, in some instances, is K56G, K56S, K56E, K56D, or K56A; the mutation at position R90, in some instances, is R90G, R90S, R90E, R90D, or R90A. The altered isoelectric point, in some examples, is a reduced isoelectric point compared to the IL-21 of SEQ ID NO: 1 (which is about 9.42), e.g., reduced by at least about 0.6 units.

In some embodiments, an IL-21 polypeptide comprises at least 80% sequence identity to SEQ ID NO: 1 and comprises amino acids selected from the group consisting of G85, G86, G88, and A90; G85, G86, G88, and E90; A56, A75, G85, G86, G88, and E90; A56, E75, G85, G86, G88, and A90; E56, A75, G85, G86, G88, and A90; G80, G81, G82, S83, E85, G86, S87, G88, G89, and S90; G80, G81, G82, S83, G85, G86, S87, G88, G89, S90; G85, G86, S87, G88, G89, and E90; G85, G86, S87, G88, G89, and S90; G85, G86, G87, G88, G89, and E90; G85, G86, G87, G88, G89, and G90; or G85, G86, E87, G88, G89, and G90, wherein the position numbers correspond to SEQ ID NO: 1.

In some embodiments, an IL-21 polypeptide comprises at least 80% sequence identity to SEQ ID NO: 1 and comprises amino acids G85, G86, G88, and A90. In some embodiments, an IL-21 polypeptide comprises at least 85%, 90%, 95%, 96%, 97%, 98%, 99% or 100% sequence identity to SEQ ID NO: 1 and comprises amino acids G85, G86, G88, and A90. In some embodiments, an IL-21 polypeptide comprises at least 80% sequence identity to SEQ ID NO: 1 and comprises amino acids G85, G86, G88, and E90. In some embodiments, an IL-21 polypeptide comprises at least 85%, 90%, 95%, 96%, 97%, 98%, 99% or 100% sequence identity to SEQ ID NO: 1 and comprises amino acids G85, G86, G88, and E90. In some embodiments, an IL-21 polypeptide comprises at least 80% sequence identity to SEQ ID NO: 1 and comprises amino acids A56, A75, G85, G86, G88, and E90. In some embodiments, an IL-21 polypeptide comprises at least 85%, 90%, 95%, 96%, 97%, 98%, 99% or 100% sequence identity to SEQ ID NO: 1 and comprises amino acids A56, A75, G85, G86, G88, and E90. In some embodiments, an IL-21 polypeptide comprises at least 80% sequence identity to SEQ ID NO: 1 and comprises amino acids: A56, E75, G85, G86, G88, and A90. In some embodiments, an IL-21 polypeptide comprises at least 85%, 90%, 95%, 96%, 97%, 98%, 99% or 100% sequence identity to SEQ ID NO: 1 and comprises amino acids A56, E75, G85, G86, G88, and A90. In some embodiments, an IL-21 polypeptide comprises at least 80% sequence identity to SEQ ID NO: 1 and comprises amino acids: A56, A75, G85, G86, G88, and A90. In some embodiments, an IL-21 polypeptide comprises at least 85%, 90%, 95%, 96%, 97%, 98%, 99% or 100% sequence identity to SEQ ID NO: 1 and comprises amino acids A56, A75, G85, G86, G88, and A90. In some embodiments, an IL-21 polypeptide comprises at least 80% sequence identity to SEQ ID NO: 1 and comprises amino acids: E56, A75, G85, G86, G88, and A90. In some embodiments, an IL-21 polypeptide comprises at least 85%, 90%, 95%, 96%, 97%, 98%, 99% or 100% sequence identity to SEQ ID NO: 1 and comprises amino acids E56, A75, G85, G86, G88, and A90. In some embodiments, an IL-21 polypeptide comprises at least 80% sequence identity to SEQ ID NO: 1 and comprises amino acids: G80, G81, G82, S83, E85, G86, S87, G88, G89, and S90. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, S83, E85, G86, S87, G88, G89, and S90. In some embodiments, an IL-21 polypeptide comprises at least 80% sequence identity to SEQ ID NO: 1 and comprises amino acids: G80, G81, G82, S83, G85, G86, S87, G88, G89, and S90. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, S83, G85, G86, S87, G88, G89, and S90. In some embodiments, an IL-21 polypeptide comprises at least 80% sequence identity to SEQ ID NO: 1 and comprises amino acids: G80, G81, G82, S83, G85, G86, S87, G88, G89, and E90. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, S83, G85, G86, S87, G88, G89, and E90. In some embodiments, an IL-21 polypeptide comprises at least 80% sequence identity to SEQ ID NO: 1 and comprises amino acids: G85, G86, S87, G88, G89, and E90. In some embodiments, an IL-21 polypeptide comprises at least 85%, 90%, 95%, 96%, 97%, 98%, 99% or 100% sequence identity to SEQ ID NO: 1 and comprises amino acids G85, G86, S87, G88, G89, and E90. In some embodiments, an IL-21 polypeptide comprises at least 80% sequence identity to SEQ ID NO: 1 and comprises amino acids: G85, G86, S87, G88, G89, and S90. In some embodiments, an IL-21 polypeptide comprises at least 85%, 90%, 95%, 96%, 97%, 98%, 99% or 100% sequence identity to SEQ ID NO: 1 and comprises amino acids G85, G86, S87, G88, G89, and S90. In some embodiments, an IL-21 polypeptide comprises at least 80% sequence identity to SEQ ID NO: 1 and comprises amino acids: G85, G86, G87, G88, G89, and E90. In some embodiments, an IL-21 polypeptide comprises at least 85%, 90%, 95%, 96%, 97%, 98%, 99% or 100% sequence identity to SEQ ID NO: 1 and comprises amino acids G85, G86, G87, G88, G89, and E90. In some embodiments, an IL-21 polypeptide comprises at least 80% sequence identity to SEQ ID NO: 1 and comprises amino acids: G85, G86, G87, G88, G89, and G90. In some embodiments, an IL-21 polypeptide comprises at least 85%, 90%, 95%, 96%, 97%, 98%, 99% or 100% sequence identity to SEQ ID NO: 1 and comprises amino acids G85, G86, G87, G88, G89, and G90. In some embodiments, an IL-21 polypeptide comprises at least 80% sequence identity to SEQ ID NO: 1 and comprises amino acids: G85, G86, E87, G88, G89, and G90. In some embodiments, an IL-21 polypeptide comprises at least 85%, 90%, 95%, 96%, 97%, 98%, 99% or 100% sequence identity to SEQ ID NO: 1 and comprises amino acids G85, G86, E87, G88, G89, and G90. Provided in some embodiments are charge variant IL-21 polypeptides or functional fragments or variants thereof that comprise a sequence that is at least 90%, 91%, 92%, 93%, 94%, 95%, 96%, 97%, 98%, 99%, or 100% identical to a sequence selected from the group consisting of SEQ ID NOs: 2, 4, 5, 6, 7, 8, 9, 10, 11, 12, 13, 14 and 15.

In some embodiments, an IL-21 polypeptide comprises at least 80% sequence identity to SEQ ID NO: 1 and comprises amino acids: G80, G81, G82, S83, G85, G86, S87, G88, G89, G90, S91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, S83, G85, G86, S87, G88, G89, G90, S91 and G92. In some embodiments, an IL-21 polypeptide comprises at least 80% sequence identity to SEQ ID NO: 1 and comprises amino acids: G80, G81, G82, G83, G85, G86, G87, G88, G89, G90, G91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, G83, G85, G86, G87, G88, G89, G90, G91 and G92. In some embodiments, an IL-21 polypeptide comprises at least 80% sequence identity to SEQ ID NO: 1 and comprises amino acids: G80, G81, G82, S83, G85, G86, E87, G88, G89, G90, S91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, S83, G85, G86, E87, G88, G89, G90, S91 and G92. In some embodiments, an IL-21 polypeptide comprises at least 80% sequence identity to SEQ ID NO: 1 and comprises amino acids: G80, G81, G82, E83, G85, G86, E87, G88, G89, G90, S91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, E83, G85, G86, E87, G88, G89, G90, S91 and G92. In some embodiments, an IL-21 polypeptide comprises at least 80% sequence identity to SEQ ID NO: 1 and comprises amino acids: G82, G83, S85, G86, G87, G88, S89, G90, G91 and S92. In some embodiments, an IL-21 polypeptide comprises at least 85%, 90%, 95%, 96%, 97%, 98%, 99% or 100% sequence identity to SEQ ID NO: 1 and comprises amino acids G82, G83, S85, G86, G87, G88, S89, G90, G91 and S92. In some embodiments, an IL-21 polypeptide comprises at least 80% sequence identity to SEQ ID NO: 1 and comprises amino acids: G82, G83, E85, G86, G87, G88, S89, G90, G91 and S92. In some embodiments, an IL-21 polypeptide comprises at least 85%, 90%, 95%, 96%, 97%, 98%, 99% or 100% sequence identity to SEQ ID NO: 1 and comprises amino acids G82, G83, E85, G86, G87, G88, S89, G90, G91 and S92. In some embodiments, an IL-21 polypeptide comprises at least 80% sequence identity to SEQ ID NO: 1 and comprises amino acids: G80, G81, G82, G83, E85, G86, G87, G88, G89, G90, G91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, G83, E85, G86, G87, G88, G89, G90, G91 and G92. In some embodiments, an IL-21 polypeptide comprises at least 80% sequence identity to SEQ ID NO: 1 and comprises amino acids: G80, G81, G82, S83, G85, G86, S87, G88, G89, E90, G91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, S83, G85, G86, S87, G88, G89, E90, G91 and G92. In some embodiments, an IL-21 polypeptide comprises at least 80% sequence identity to SEQ ID NO: 1 and comprises amino acids: G80, G81, G82, G83, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, G83, G85, G86, G87, G88, G89, E90, G91 and G92. In some embodiments, an IL-21 polypeptide comprises at least 80% sequence identity to SEQ ID NO: 1 and comprises amino acids: G82, G83, S85, G86, G87, G88, S89, E90, G91 and S92. In some embodiments, an IL-21 polypeptide comprises at least 85%, 90%, 95%, 96%, 97%, 98%, 99% or 100% sequence identity to SEQ ID NO: 1 and comprises amino acids G82, G83, S85, G86, G87, G88, S89, E90, G91 and S92. In some embodiments, an IL-21 polypeptide comprises at least 80% sequence identity to SEQ ID NO: 1 and comprises amino acids: G82, G83, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 1 and comprises amino acids G82, G83, G85, G86, G87, G88, G89, E90, G91 and G92. In some embodiments, an IL-21 polypeptide comprises at least 80% sequence identity to SEQ ID NO: 1 and comprises amino acids: G85, G86, G87, G88, G89, E90, and G91. In some embodiments, an IL-21 polypeptide comprises at least 85%, 90%, 95%, 96%, 97%, 98%, 99% or 100% sequence identity to SEQ ID NO: 1 and comprises amino acids G85, G86, G87, G88, G89, E90, and G91. In some embodiments, an IL-21 polypeptide comprises at least 80% sequence identity to SEQ ID NO: 1 and comprises amino acids: G82, G83, G85, G86, G87, G88, G89, E90, and G91. In some embodiments, an IL-21 polypeptide comprises at least 85%, 90%, 95%, 96%, 97%, 98%, 99% or 100% sequence identity to SEQ ID NO: 1 and comprises amino acids G82, G83, G85, G86, G87, G88, G89, E90, and G91. In some embodiments, an IL-21 polypeptide comprises at least 80% sequence identity to SEQ ID NO: 1 and comprises amino acids: G82, G83, G85, E86, G87, G88, G89, E90, and G91. In some embodiments, an IL-21 polypeptide comprises at least 85%, 90%, 95%, 96%, 97%, 98%, 99% or 100% sequence identity to SEQ ID NO: 1 and comprises amino acids G82, G83, G85, E86, G87, G88, G89, E90, and G91. In some embodiments, an IL-21 polypeptide comprises at least 80% sequence identity to SEQ ID NO: 1 and comprises amino acids: G82, G83, E85, G86, G87, G88, G89, E90, and G91. In some embodiments, an IL-21 polypeptide comprises at least 85%, 90%, 95%, 96%, 97%, 98%, 99% or 100% sequence identity to SEQ ID NO: 1 and comprises amino acids G82, G83, E85, G86, G87, G88, G89, E90, and G91. In some embodiments, an IL-21 polypeptide comprises at least 80% sequence identity to SEQ ID NO: 1 and comprises amino acids: G80, G81, G82, G83, E84, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, G83, E84, G85, G86, G87, G88, G89, E90, G91 and G92. In some embodiments, an IL-21 polypeptide comprises at least 80% sequence identity to SEQ ID NO: 1 and comprises amino acids: G80, G81, G82, E83, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, G82, E83, G85, G86, G87, G88, G89, E90, G91 and G92. In some embodiments, an IL-21 polypeptide comprises at least 80% sequence identity to SEQ ID NO: 1 and comprises amino acids: G80, G81, E82, G83, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 1 and comprises amino acids G80, G81, E82, G83, G85, G86, G87, G88, G89, E90, G91 and G92. Provided in some embodiments are charge variant IL-21 polypeptides or functional fragments or variants thereof that comprise a sequence that is at least 90%, 91%, 92%, 93%, 94%, 95%, 96%, 97%, 98%, 99%, or 100% identical to a sequence selected from the group consisting of SEQ ID NOs. 23-40. Provided in some embodiments are charge variant IL-21 polypeptides or functional fragments or variants thereof that comprise a sequence that is at least 90%, 91%, 92%, 93%, 94%, 95%, 96%, 97%, 98%, 99%, or 100% identical to a sequence selected from the group consisting of SEQ ID NOs. 2, 4, 5, 6, 7, 8, 9, 10, 11, 12, 13, 14 15, 23, 24, 25, 26, 27, 28, 29, 30, 31, 32, 33, 34, 35, 36, 37, 38, 39 and 40.

In some embodiments, an IL-21 polypeptide comprises about 75% sequence identity to about 100% sequence identity to a sequence selected from the group consisting of SEQ ID NOs. 2, 4, 5, 6, 7, 8, 9, 10, 11, 12, 13, 14 and 15. In some embodiments, an IL-21 polypeptide comprises at least about 75% sequence identity to a sequence selected from the group consisting of SEQ ID NOs. 2, 4, 5, 6, 7, 8, 9, 10, 11, 12, 13, 14 and 15. In some embodiments, an IL-21 polypeptide comprises at most about 100% sequence identity to a sequence selected from the group consisting of SEQ ID NOs. 2, 4, 5, 6, 7, 8, 9, 10, 11, 12, 13, 14 and 15. In some embodiments, an IL-21 polypeptide comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity to a sequence selected from the group consisting of SEQ ID NOs. 2, 4, 5, 6, 7, 8, 9, 10, 11, 12, 13, 14 and 15. In some embodiments, an IL-21 polypeptide comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to a sequence selected from the group consisting of SEQ ID NOs. 2, 4, 5, 6, 7, 8, 9, 10, 11, 12, 13, 14 and 15.

In some embodiments, an IL-21 polypeptide comprises about 75% sequence identity to about 100% sequence identity to a sequence selected from the group consisting of SEQ ID NOs. 23-40. In some embodiments, an IL-21 polypeptide comprises at least about 75% sequence identity to a sequence selected from the group consisting of SEQ ID NOs. 23-40. In some embodiments, an IL-21 polypeptide comprises at most about 100% sequence identity to a sequence selected from the group consisting of SEQ ID NOs. 23-40. In some embodiments, an IL-21 polypeptide comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity to a sequence selected from the group consisting of SEQ ID NOs. 23-40. In some embodiments, an IL-21 polypeptide comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to a sequence selected from the group consisting of SEQ ID NOs. 23-40.

In some embodiments, an IL-21 polypeptide comprises about 75% sequence identity to about 100% sequence identity to a sequence selected from the group consisting of SEQ ID NOs. 2, 4, 5, 6, 7, 8, 9, 10, 11, 12, 13, 14 15, 23, 24, 25, 26, 27, 28, 29, 30, 31, 32, 33, 34, 35, 36, 37, 38, 39 and 40. In some embodiments, an IL-21 polypeptide comprises at least about 75% sequence identity to a sequence selected from the group consisting of SEQ ID NOs. 2, 4, 5, 6, 7, 8, 9, 10, 11, 12, 13, 14 15, 23, 24, 25, 26, 27, 28, 29, 30, 31, 32, 33, 34, 35, 36, 37, 38, 39 and 40. In some embodiments, an IL-21 polypeptide comprises at most about 100% sequence identity to a sequence selected from the group consisting of SEQ ID NOs. 2, 4, 5, 6, 7, 8, 9, 10, 11, 12, 13, 14 15, 23, 24, 25, 26, 27, 28, 29, 30, 31, 32, 33, 34, 35, 36, 37, 38, 39 and 40. In some embodiments, an IL-21 polypeptide comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity to a sequence selected from the group consisting of SEQ ID NOs. 2, 4, 5, 6, 7, 8, 9, 10, 11, 12, 13, 14 15, 23, 24, 25, 26, 27, 28, 29, 30, 31, 32, 33, 34, 35, 36, 37, 38, 39 and 40. In some embodiments, an IL-21 polypeptide comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to a sequence selected from the group consisting of SEQ ID NOs. 2, 4, 5, 6, 7, 8, 9, 10, 11, 12, 13, 14 15, 23, 24, 25, 26, 27, 28, 29, 30, 31, 32, 33, 34, 35, 36, 37, 38, 39 and 40.

In some embodiments, an IL-21 polypeptide or a functional fragment or a variant thereof comprises at least 80% sequence identity to SEQ ID NO: 4 and comprises amino acids G85, G86, G88, and A90. In some embodiments, an IL-21 polypeptide or a functional fragment or a variant thereof comprises at least 85%, 90%, 95%, 96%, 97%, 98%, 99% or 100% sequence identity to SEQ ID NO: 4 and comprises amino acids G85, G86, G88, and A90. In some embodiments, an IL-21 polypeptide or a functional fragment or a variant thereof comprises at least 80% sequence identity to SEQ ID NO: 2 and comprises amino acids G85, G86, G88, and E90. In some embodiments, an IL-21 polypeptide or a functional fragment or a variant thereof comprises at least 85%, 90%, 95%, 96%, 97%, 98%, 99% or 100% sequence identity to SEQ ID NO: 2 and comprises amino acids G85, G86, G88, and E90. In some embodiments, an IL-21 polypeptide or a functional fragment or a variant thereof comprises at least 80% sequence identity to SEQ ID NO: 5 and comprises amino acids A56, A75, G85, G86, G88, and E90. In some embodiments, an IL-21 polypeptide or a functional fragment or a variant thereof comprises at least 85%, 90%, 95%, 96%, 97%, 98%, 99% or 100% sequence identity to SEQ ID NO: 5 and comprises amino acids A56, A75, G85, G86, G88, and E90. In some embodiments, an IL-21 polypeptide or a functional fragment or a variant thereof comprises at least 80% sequence identity to SEQ ID NO: 6 and comprises amino acids: A56, E75, G85, G86, G88, and A90. In some embodiments, an IL-21 polypeptide or a functional fragment or a variant thereof comprises at least 85%, 90%, 95%, 96%, 97%, 98%, 99% or 100% sequence identity to SEQ ID NO: 6 and comprises amino acids A56, E75, G85, G86, G88, and A90. In some embodiments, an IL-21 polypeptide or a functional fragment or a variant thereof comprises at least 80% sequence identity to SEQ ID NO: 7 and comprises amino acids: A56, A75, G85, G86, G88, and A90. In some embodiments, an IL-21 polypeptide or a functional fragment or a variant thereof comprises at least 85%, 90%, 95%, 96%, 97%, 98%, 99% or 100% sequence identity to SEQ ID NO: 7 and comprises amino acids A56, A75, G85, G86, G88, and A90. In some embodiments, an IL-21 polypeptide or a functional fragment or a variant thereof comprises at least 80% sequence identity to SEQ ID NO: 8 and comprises amino acids: E56, A75, G85, G86, G88, and A90. In some embodiments, an IL-21 polypeptide or a functional fragment or a variant thereof comprises at least 85%, 90%, 95%, 96%, 97%, 98%, 99% or 100% sequence identity to SEQ ID NO: 8 and comprises amino acids E56, A75, G85, G86, G88, and A90. In some embodiments, an IL-21 polypeptide or a functional fragment or a variant thereof comprises at least 80% sequence identity to SEQ ID NO: 9 and comprises amino acids: G80, G81, G82, S83, E85, G86, S87, G88, G89, and S90. In some embodiments, an IL-21 polypeptide or a functional fragment or a variant thereof comprises at least 85%, 90%, 95%, 96%, 97%, 98%, 99% or 100% sequence identity to SEQ ID NO: 9 and comprises amino acids G80, G81, G82, S83, E85, G86, S87, G88, G89, and S90. In some embodiments, an IL-21 polypeptide or a functional fragment or a variant thereof comprises at least 80% sequence identity to SEQ ID NO: 10 and comprises amino acids: G80, G81, G82, S83, G85, G86, S87, G88, G89, S90. In some embodiments, an IL-21 polypeptide or a functional fragment or a variant thereof comprises at least 85%, 90%, 95%, 96%, 97%, 98%, 99% or 100% sequence identity to SEQ ID NO: 10 and comprises amino acids G80, G81, G82, S83, G85, G86, S87, G88, G89, S90. In some embodiments, an IL-21 polypeptide or a functional fragment or a variant thereof comprises at least 80% sequence identity to SEQ ID NO: 10 and comprises amino acids: G80, G81, G82, S83, G85, G86, S87, G88, G89, E90. In some embodiments, an IL-21 polypeptide or a functional fragment or a variant thereof comprises at least 85%, 90%, 95%, 96%, 97%, 98%, 99% or 100% sequence identity to SEQ ID NO: 10 and comprises amino acids G80, G81, G82, S83, G85, G86, S87, G88, G89, E90. In some embodiments, an IL-21 polypeptide or a functional fragment or a variant thereof comprises at least 80% sequence identity to SEQ ID NO: 11 and comprises amino acids: G85, G86, S87, G88, G89, and E90. In some embodiments, an IL-21 polypeptide or a functional fragment or a variant thereof comprises at least 85%, 90%, 95%, 96%, 97%, 98%, 99% or 100% sequence identity to SEQ ID NO: 11 and comprises amino acids G85, G86, S87, G88, G89, and E90. In some embodiments, an IL-21 polypeptide or a functional fragment or a variant thereof comprises at least 80% sequence identity to SEQ ID NO: 12 and comprises amino acids: G85, G86, S87, G88, G89, and S90. In some embodiments, an IL-21 polypeptide or a functional fragment or a variant thereof comprises at least 85%, 90%, 95%, 96%, 97%, 98%, 99% or 100% sequence identity to SEQ ID NO: 12 and comprises amino acids G85, G86, S87, G88, G89, and S90. In some embodiments, an IL-21 polypeptide or a functional fragment or a variant thereof comprises at least 80% sequence identity to SEQ ID NO: 13 and comprises amino acids: G85, G86, G87, G88, G89, and E90. In some embodiments, an IL-21 polypeptide or a functional fragment or a variant thereof comprises at least 85%, 90%, 95%, 96%, 97%, 98%, 99% or 100% sequence identity to SEQ ID NO: 13 and comprises amino acids G85, G86, G87, G88, G89, and E90. In some embodiments, an IL-21 polypeptide or a functional fragment or a variant thereof comprises at least 80% sequence identity to SEQ ID NO: 14 and comprises amino acids: G85, G86, G87, G88, G89, and G90. In some embodiments, an IL-21 polypeptide or a functional fragment or a variant thereof comprises at least 85%, 90%, 95%, 96%, 97%, 98%, 99% or 100% sequence identity to SEQ ID NO: 14 and comprises amino acids G85, G86, G87, G88, G89, and G90. In some embodiments, an IL-21 polypeptide or a functional fragment or a variant thereof comprises at least 80% sequence identity to SEQ ID NO: 15 and comprises amino acids: G85, G86, E87, G88, G89, and G90. In some embodiments, an IL-21 polypeptide or a functional fragment or a variant thereof comprises at least 85%, 90%, 95%, 96%, 97%, 98%, 99% or 100% sequence identity to SEQ ID NO: 15 and comprises amino acids G85, G86, E87, G88, G89, and G90.

In some embodiments, an IL-21 polypeptide comprises at least 80% sequence identity to SEQ ID NO: 23 and comprises amino acids: G80, G81, G82, S83, G85, G86, S87, G88, G89, G90, S91 and G92. In some embodiments, an IL-21 polypeptide comprises at least 85%, 90%, 95%, 96%, 97%, 98%, 99% or 100% sequence identity to SEQ ID NO: 23 and comprises amino acids G80, G81, G82, S83, G85, G86, S87, G88, G89, G90, S91 and G92. In some embodiments, an IL-21 polypeptide comprises at least 80% sequence identity to SEQ ID NO: 24 and comprises amino acids: G80, G81, G82, G83, G85, G86, G87, G88, G89, G90, G91 and G92. In some embodiments, an IL-21 polypeptide comprises at least 85%, 90%, 95%, 96%, 97%, 98%, 99% or 100% sequence identity to SEQ ID NO: 24 and comprises amino acids G80, G81, G82, G83, G85, G86, G87, G88, G89, G90, G91 and G92. In some embodiments, an IL-21 polypeptide comprises at least 80% sequence identity to SEQ ID NO: 25 and comprises amino acids: G80, G81, G82, S83, G85, G86, E87, G88, G89, G90, S91 and G92. In some embodiments, an IL-21 polypeptide comprises at least 85%, 90%, 95%, 96%, 97%, 98%, 99% or 100% sequence identity to SEQ ID NO: 25 and comprises amino acids G80, G81, G82, S83, G85, G86, E87, G88, G89, G90, S91 and G92. In some embodiments, an IL-21 polypeptide comprises at least 80% sequence identity to SEQ ID NO: 26 and comprises amino acids: G80, G81, G82, E83, G85, G86, E87, G88, G89, G90, S91 and G92. In some embodiments, an IL-21 polypeptide comprises at least 85%, 90%, 95%, 96%, 97%, 98%, 99% or 100% sequence identity to SEQ ID NO: 26 and comprises amino acids G80, G81, G82, E83, G85, G86, E87, G88, G89, G90, S91 and G92. In some embodiments, an IL-21 polypeptide comprises at least 80% sequence identity to SEQ ID NO: 27 and comprises amino acids: G82, G83, S85, G86, G87, G88, S89, G90, G91 and S92. In some embodiments, an IL-21 polypeptide comprises at least 85%, 90%, 95%, 96%, 97%, 98%, 99% or 100% sequence identity to SEQ ID NO: 27 and comprises amino acids G82, G83, S85, G86, G87, G88, S89, G90, G91 and S92. In some embodiments, an IL-21 polypeptide comprises at least 80% sequence identity to SEQ ID NO: 28 and comprises amino acids: G82, G83, E85, G86, G87, G88, S89, G90, G91 and S92. In some embodiments, an IL-21 polypeptide comprises at least 85%, 90%, 95%, 96%, 97%, 98%, 99% or 100% sequence identity to SEQ ID NO: 28 and comprises amino acids G82, G83, E85, G86, G87, G88, S89, G90, G91 and S92. In some embodiments, an IL-21 polypeptide comprises at least 80% sequence identity to SEQ ID NO: 29 and comprises amino acids: G80, G81, G82, G83, E85, G86, G87, G88, G89, G90, G91 and G92. In some embodiments, an IL-21 polypeptide comprises at least 85%, 90%, 95%, 96%, 97%, 98%, 99% or 100% sequence identity to SEQ ID NO: 29 and comprises amino acids G80, G81, G82, G83, E85, G86, G87, G88, G89, G90, G91 and G92. In some embodiments, an IL-21 polypeptide comprises at least 80% sequence identity to SEQ ID NO: 30 and comprises amino acids: G80, G81, G82, S83, G85, G86, S87, G88, G89, E90, G91 and G92. In some embodiments, an IL-21 polypeptide comprises at least 85%, 90%, 95%, 96%, 97%, 98%, 99% or 100% sequence identity to SEQ ID NO: 30 and comprises amino acids G80, G81, G82, S83, G85, G86, S87, G88, G89, E90, G91 and G92. In some embodiments, an IL-21 polypeptide comprises at least 80% sequence identity to SEQ ID NO: 31 and comprises amino acids: G80, G81, G82, G83, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 31 and comprises amino acids G80, G81, G82, G83, G85, G86, G87, G88, G89, E90, G91 and G92. In some embodiments, an IL-21 polypeptide comprises at least 80% sequence identity to SEQ ID NO: 32 and comprises amino acids: G82, G83, S85, G86, G87, G88, S89, E90, G91 and S92. In some embodiments, an IL-21 polypeptide comprises at least 85%, 90%, 95%, 96%, 97%, 98%, 99% or 100% sequence identity to SEQ ID NO: 32 and comprises amino acids G82, G83, S85, G86, G87, G88, S89, E90, G91 and S92. In some embodiments, an IL-21 polypeptide comprises at least 80% sequence identity to SEQ ID NO: 33 and comprises amino acids: G82, G83, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 33 and comprises amino acids G82, G83, G85, G86, G87, G88, G89, E90, G91 and G92. In some embodiments, an IL-21 polypeptide comprises at least 80% sequence identity to SEQ ID NO: 34 and comprises amino acids: G85, G86, G87, G88, G89, E90, and G91. In some embodiments, an IL-21 polypeptide comprises at least 85%, 90%, 95%, 96%, 97%, 98%, 99% or 100% sequence identity to SEQ ID NO: 34 and comprises amino acids G85, G86, G87, G88, G89, E90, and G91. In some embodiments, an IL-21 polypeptide comprises at least 80% sequence identity to SEQ ID NO: 35 and comprises amino acids: G82, G83, G85, G86, G87, G88, G89, E90, and G91. In some embodiments, an IL-21 polypeptide comprises at least 85%, 90%, 95%, 96%, 97%, 98%, 99% or 100% sequence identity to SEQ ID NO: 35 and comprises amino acids G82, G83, G85, G86, G87, G88, G89, E90, and G91. In some embodiments, an IL-21 polypeptide comprises at least 80% sequence identity to SEQ ID NO: 36 and comprises amino acids: G82, G83, G85, E86, G87, G88, G89, E90, and G91. In some embodiments, an IL-21 polypeptide comprises at least 85%, 90%, 95%, 96%, 97%, 98%, 99% or 100% sequence identity to SEQ ID NO: 36 and comprises amino acids G82, G83, G85, E86, G87, G88, G89, E90, and G91. In some embodiments, an IL-21 polypeptide comprises at least 80% sequence identity to SEQ ID NO: 37 and comprises amino acids: G82, G83, E85, G86, G87, G88, G89, E90, and G91. In some embodiments, an IL-21 polypeptide comprises at least 85%, 90%, 95%, 96%, 97%, 98%, 99% or 100% sequence identity to SEQ ID NO: 37 and comprises amino acids G82, G83, E85, G86, G87, G88, G89, E90, and G91. In some embodiments, an IL-21 polypeptide comprises at least 80% sequence identity to SEQ ID NO: 38 and comprises amino acids: G80, G81, G82, G83, E84, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 38 and comprises amino acids G80, G81, G82, G83, E84, G85, G86, G87, G88, G89, E90, G91 and G92. In some embodiments, an IL-21 polypeptide comprises at least 80% sequence identity to SEQ ID NO: 39 and comprises amino acids: G80, G81, G82, E83, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 39 and comprises amino acids G80, G81, G82, E83, G85, G86, G87, G88, G89, E90, G91 and G92. In some embodiments, an IL-21 polypeptide comprises at least 80% sequence identity to SEQ ID NO: 40 and comprises amino acids: G80, G81, E82, G83, G85, G86, G87, G88, G89, E90, G91 and G92. In some embodiments, an IL-21 polypeptide comprises at least 85%, 90%, 95%, 96%, 97%, 98%, 99% or 100% sequence identity to SEQ ID NO: 40 and comprises amino acids G80, G81, E82, G83, G85, G86, G87, G88, G89, E90, G91 and G92.

In some embodiments, an IL-21 polypeptide comprises QGQDRHMIRMRQLIDIVDQLKNYVNDLVPEFLPAP-EDVETNCEWSAFSCFQKAQLX$_1$SAN TGNNERIINV-SIKKLX$_2$RKPPX$_3$X$_4$X$_5$X$_6$X$_7$X$_8$X$_9$X$_{10}$X$_{11}$X$_{12}$X$_{13}$X$_{14}$X$_{15}$CPSCDSYEKKPPKEFLER FKSLLQKMIHQHLSSR-THGSEDS (SEQ ID NO: 383), wherein X$_1$=A, E, K; X$_2$=A, E, K; X$_3$=G, S; X$_4$=G, T; X$_5$=G, E, N; X$_6$=G, S, E, A; X$_7$=E, G; X$_8$=G, E, S, R; X$_9$=G, E, R; X$_{10}$=S, G, E, Q; X$_{11}$=G, K; X$_{12}$=G, S, H; X$_{13}$=A, E, S, G, R; X$_{14}$=S, G, L; X$_{15}$=G, S, T; and wherein at least one amino acid residue is not the amino acid residue at the identical position set forth in SEQ ID NO: 1. In some embodiments, at least one of X$_8$, X$_9$, X$_{11}$, X$_{12}$, and X$_{13}$ is not the amino acid residue at the identical position set forth in SEQ ID NO: 1.

In some embodiments, the IL-21 polypeptide comprises the amino acid sequence: QGQDRHMIRMRQLIDI-VDQLKNYVNDLVPEFLPAPEDVETNCEWSAFSCF-QKAQLKSANT GNNERIINVSIKKLKRKPPX$_1$X$_2$X$_3$X$_4$GX$_5$X$_6$X$_7$X$_8$X$_9$X$_{10}$X$_{11}$X$_{12}$CPSCDSYEKKPPKEFLER-FKSL LQKMIHQHLSSRTHGSEDS (SEQ ID NO: 380), wherein X$_1$=G, S; X$_2$=G, T; X$_3$=G, E, N; X$_4$=G, S, E, A; X$_5$=G, E, S, R; X$_6$=G, E, R; X$_7$=S, G, E, Q; X$_8$=G, K; X$_9$=G, S, H; X$_{10}$=A, E, S, G, R; X$_{11}$=S, G, L; and X$_{12}$=G, S, T, provided at least one of X$_5$, X$_6$, X$_8$, X$_9$, and X$_{10}$ is not the amino acid residue at the identical position set forth in SEQ ID NO: 1. In some embodiments, X$_5$=G, X$_6$=G, X$_8$=G, X$_{10}$=A. In some embodiments, X$_5$=G, X$_6$=G, X$_8$=G, X$_{10}$=E. In some embodiments, X$_1$=G, X$_2$=G, X$_3$=G, X$_4$=S, X$_5$=E, X$_6$=G, X$_7$=S, X$_8$=G, X$_9$=G, X$_{10}$=S. In some embodiments, X$_1$=G, X$_2$=G, X$_3$=G, X$_4$=S, X$_5$=G, X$_6$=G, X$_7$=S, X$_8$=G, X$_9$=G, X$_{10}$=E. In some embodiments, X$_5$=G, X$_6$=G, X$_7$=S, X$_8$=G, X$_9$=G, X$_{10}$=E. In some embodiments, X$_5$=G, X$_6$=G, X$_7$=S, X$_8$=G, X$_9$=G, X$_{10}$=S. In some embodiments, X$_5$=G, X$_6$=G, X$_7$=G, X$_8$=G, X$_9$=G, X$_{10}$=E. In some embodiments, X$_5$=G, X$_6$=G, X$_7$=G, X$_8$=G, X$_9$=G, X$_{10}$=G. In some embodiments, X$_5$=G, X$_6$=G, X$_7$=E, X$_8$=G, X$_9$=G, X$_{10}$=G. In some embodiments, X$_1$=G, X$_2$=G, X$_3$=G, X$_4$=S, X$_5$G, X$_6$G, X$_7$=S, X$_8$=G, X$_9$=G, X$_{10}$=G, X$_{11}$=S, X$_{12}$=G. In some embodiments, X$_1$=G, X$_2$=G, X$_3$=G, X$_4$=G, X$_5$=G, X$_6$=G, X$_7$=G, X$_8$=G, X$_9$=G, X$_{10}$=G, X$_{11}$=G, X$_{12}$=G. In some embodiments, X$_1$=G, X$_2$=G, X$_3$=G, X$_4$=S, X$_5$=G, X$_6$=G, X$_7$=E, X$_8$=G, X$_9$=G, X$_{10}$=G, X$_{11}$=S, X$_{12}$=G. In some embodiments, X$_1$=G, X$_2$=G, X$_3$=G, X$_4$=E, X$_5$=G, X$_6$=G, X$_7$=E, X$_8$=G, X$_9$=G, X$_{10}$=G, X$_{11}$=S, X$_{12}$=G. In some embodiments, X$_3$=G, X$_4$=G, X$_5$=S, X$_6$=G, X$_7$=G, X$_8$=G, X$_9$=S, X$_{10}$=G, X$_{11}$=G, X$_{12}$=S. In some embodiments, X$_3$=G, X$_4$=G, X$_5$=E, X$_6$=G, X$_7$=G, X$_8$=G, X$_9$=S, X$_{10}$=G, X$_{11}$=G, X$_{12}$=S. In some embodiments, X$_1$=G, X$_2$=G, X$_3$=G, X$_4$=G, X$_5$=E, X$_6$=G, X$_7$=G, X$_8$=G, X$_9$=G, X$_{10}$=G, X$_{11}$=G, X$_{12}$=G. In some embodiments, X$_1$=G, X$_2$=G, X$_3$=G, X$_4$=S, X$_5$=G, X$_6$=G, X$_7$=S, X$_8$=G, X$_9$=G, X$_{10}$=E, X$_{11}$=G, X$_{12}$=G. In some embodiments, X$_1$=G, X$_2$=G, X$_3$=G, X$_4$=G, X$_5$=G, X$_6$=G, X$_7$=G, X$_8$=G, X$_9$=G, X$_{10}$=E, X$_{11}$=G, X$_{12}$=G. In some embodiments, X$_3$=G, X$_4$=G, X$_5$=S, X$_6$=G, X$_7$=G, X$_8$=G, X$_9$=S, X$_{10}$=E, X$_{11}$=G, X$_{12}$=S. In some embodiments, X$_3$=G, X$_4$=G, X$_5$=G, X$_6$=G, X$_7$=G, X$_8$=G, X$_9$=G, X$_{10}$=E, X$_{11}$=G, X$_{12}$=G. In some embodiments, X$_5$=G, X$_6$=G, X$_7$=G, X$_8$=G, X$_9$=G, X$_{10}$=E, X$_{11}$=G. In some embodiments, X$_3$=G, X$_4$=G, X$_5$=G, X$_6$=G, X$_7$=G, X$_8$=G, X$_9$=G, X$_{10}$=E, X$_{11}$=G. In some embodiments, X$_3$=G, X$_4$=G, X$_5$=G, X$_6$=E, X$_7$=G, X$_8$=G, X$_9$=G, X$_{10}$=E, X$_{11}$=G. In some embodiments, X$_3$=G, X$_4$=G, X$_5$=E, X$_6$=G, X$_7$=G, X$_8$=G, X$_9$=G, X$_{10}$=E, X$_{11}$=G. In some embodiments, X$_1$=G, X$_2$=G, X$_3$=G, X$_4$=E, X$_5$=G, X$_6$=G, X$_7$=G, X$_8$=G, X$_9$=G, X$_{10}$=E, X$_{11}$=G, X$_{12}$=G. In some embodiments, X$_1$=G, X$_2$=G, X$_3$=E, X$_4$=G, X$_5$=G, X$_6$=G, X$_7$=G, X$_8$=G, X$_9$=G, X$_{10}$=E, X$_{11}$=G, X$_{12}$=G.

In some embodiments, the IL-21 polypeptide comprises an amino acid sequence starting at position 78 as defined by SEQ ID NO: 1, wherein the amino acid sequence is PPX$_1$X$_2$X$_3$X$_4$GX$_5$X$_6$X$_7$X$_8$X$_9$X$_{10}$X$_{11}$X$_{12}$CP (SEQ ID NO: 386), wherein X$_1$=G, S; X$_2$=G, T; X$_3$=G, E, N; X$_4$=G, S, E, A; X$_5$=G, E, S, R; X$_6$=G, E, R; X$_7$=S, G, E, Q; X$_8$=G, K; X$_9$=G, S, H; X$_{10}$=A, E, S, G, R; X$_{11}$=S, G, L; and X$_{12}$=G, S, T, provided at least one of X$_5$, X$_6$, X$_8$, X$_9$, and X$_{10}$ is not the amino acid residue at the identical position set forth in SEQ ID NO: 1.

In some embodiments, the IL-21 polypeptide comprises an amino acid sequence starting at position 80 as defined by SEQ ID NO: 1, wherein the amino acid sequence is X$_1$X$_2$X$_3$X$_4$GX$_5$X$_6$X$_7$X$_8$X$_9$X$_{10}$X$_{11}$X$_{12}$, wherein X$_1$=G, S; X$_2$=G, T; X$_3$=G, E, N; X$_4$=G, S, E, A; X$_5$=G, E, S, R; X$_6$=G, E, R; X$_7$=S, G, E, Q; X$_8$=G, K; X$_9$=G, S, H; X$_{10}$=A, E, S, G, R; X$_{11}$=S, G, L; and X$_{12}$=G, S, T, provided at least one of X$_5$, X$_6$, X$_8$, X$_9$, and X$_{10}$ is not the amino acid residue at the identical position set forth in SEQ ID NO: 1.

Reduced IL-21R Binding

In some embodiments, the disclosure provides an IL-21 polypeptide or a functional fragment or a variant thereof with reduced binding affinity to IL-21R. In some embodiments, an IL-21 polypeptide or a functional fragment or a variant thereof comprises at least one mutation that reduces its binding affinity to IL-21R. Such mutations are in some embodiments in one or more positions selected from the group consisting of: R5, I8, R9, R11, Q12, I14, D15, D18, Q19, Y23, R65, S70, K72, K73, K75, R76, K77, S80, Q116, and K117, wherein the position numbering is number according to the amino acid sequence of SEQ ID NO: 1. In some embodiments, such mutations are in one or more positions selected from the group consisting of: R5, I8, R9, R11, L13, I14, I16, V17, D18, K72, K73, L74, K75, R76, K77, and K117, wherein the position numbering is number according to the amino acid sequence of SEQ ID NO: 1. In some embodiments, the mutation at position R5 comprises an amino acid substitution selected from the group consisting of A, D, E, S, T, N, Q, V, I, L, Y, or F. In some embodiments, the mutation at position 18 comprises an amino acid substitution selected from the group consisting of Q, H, E. In some embodiments, the mutation at position R9 comprises an amino acid substitution selected from the group consisting of A, D, E, S, T, N, Q, V, I, L, Y, or F. In some embodiments, the mutation at position R11 comprises an amino acid substitution selected from the group consisting of D or E. In some embodiments, the mutation at position Q12 comprises an amino acid substitution selected from the group consisting of L, I, or Y. In some embodiments, the mutation at position L13 comprises an amino acid substitution selected from the group consisting of F or R. In some embodiments, the mutation at position I14 comprises an amino acid substitution selected from the group consisting of D or E. In some embodiments, the mutation at position D15 comprises an amino acid substitution selected from the group consisting of R, K, H, L, Y, or F. In some embodiments, the mutation at position I16 comprises an amino acid substitution selected from the group consisting of A, S or R. In some embodiments, the mutation at position V17 comprises an amino acid substitution selected from the group consisting of I or A. In some embodiments, the mutation at position D18 comprises an amino acid substitution selected from the group consisting of A, K, or R. In some embodiments, the mutation at position Q19 comprises an amino acid substitution selected from the group consisting of L, or Y. In some embodiments, the mutation at position Y23 comprises an amino acid substitution of E. In some embodiments, the mutation at position R65 comprises an amino acid substitution selected from the group consisting of G, S, E, D or A. In some embodiments, the mutation at position S70 comprises an amino acid substitution selected from the group consisting of H, Y, L, V or F. In some embodiments, the mutation at position K72 comprises an amino acid substitution selected from the group consisting of G, S, E, D or A. In some embodiments, the mutation at position K73 comprises an amino acid substitution selected from the group consisting of A, Y, L, F, G, S, T, E, or D. In some embodiments, the mutation at position L74 comprises an amino acid substitution selected from the group consisting of I, F, V, or M. In some embodiments, the mutation at position K75 comprises an amino acid substitution selected from the group consisting of G, S, E, D or A. In some embodiments, the mutation at position R76 comprises an amino acid substitution selected from the group consisting of A, D, E, S, T, N, Q, V, I, L, Y, or F. In some embodiments, the mutation at position K77 comprises an amino acid substitution selected from the group consisting of G, S, E, D or A. In some embodiments, the mutation at position S80 comprises an amino acid substitution of H, A, G, E, or D. In some embodiments, the mutation at position Q116 comprises an amino acid substitution is Y. In some embodiments, the mutation at position K117 comprises an amino acid substitution selected from the group consisting of A, D, or E.

In some cases, an IL-21 polypeptide or a functional fragment or a variant thereof comprises at least one amino acid substitution selected from: R5F, R5A, R5E, R5S, R5T, R5N, R5Q, R5V, R5I, R5L, R5Y, I8E, R9A, R9D, R9E, R9H, R9S, R9T, R9N, R9G, R9V, R9I, R9L, R9Y, R11D, R11E, L13F, L13R, I14D, I16A, I16S, I16R, V17I, V17A, D18A, K72A, K72E, K73A, K73E, K75A, K75E, L74I, L74F, L74M, L74V, R76E, R76F, R76A, R76N, R76D, R76S, R76T, R76Q, R76V, R76I, R76L, R76Y, R76M, K77A, K77E, and K117A. In some cases, an IL-21 polypeptide or a functional fragment or a variant thereof comprises amino acid substitution is R76E or R76Q.

An example sequence for an IL-21 polypeptide or a functional fragment or a variant thereof of this disclosure is provided as follows: QGQDX$_1$HMX$_2$X$_3$MX$_4$X$_5$LX$_6$X$_7$IVX$_8$X$_9$LKNX$_{10}$VNDLVPEFLPAPEDVETNC-EWSAFSCFQKA QLKSANTGNNEX$_{11}$IINVX$_{12}$IX$_{13}$X$_{14}$LX15X$_{16}$X$_{17}$PPX$_{18}$TNAGRRQKHRLTCPSCD-SYEKKPPKE FLERFKSLLX$_{19}$X$_{20}$MIHQHLSSR-THGSEDS (SEQ ID NO: 22). In some embodiments, X$_1$=R, A, D, E, S, T, N, Q, V, I, L, Y, or F. In some embodiments, X$_2$=I, Q, H, E. In some embodiments, X$_3$=R, A, D, E, S, T, N, Q, V, I, L, Y, or F. In some embodiments, X$_4$=R, D or E. In some embodiments, X$_5$=Q, L, I, or Y. In some embodiments, X$_6$=I, D or E. In some embodiments, X$_7$=D, R, K, H, L, Y, or F. In some embodiments, X$_8$=D, A, K, or R. In some embodiments, X$_9$=Q, L, or Y. In some embodiments, X$_{10}$=Y or E. In some embodiments, X$_{11}$=R, G, S, E, D, or A. In some embodiments, X$_{12}$=S, H, Y, L, V, or F. In some embodiments, X$_{13}$=K, G, S, E, D, or A. In some embodiments, X$_{14}$=K, A, Y, L, F, G, S, T, E, A, or D. In some embodiments, X$_{15}$=K, G, S, E, D, or A. In some embodiments, X$_{16}$=R, A, D, E, S, T, N, Q, V, I, L, Y, or F. In some embodiments, X$_{17}$=K, G, S, E, D, or A. In some embodiments, X$_{18}$=S, H, A, G, E, or D. In some embodiments, X$_{19}$=Q or Y. In some embodiments, X$_{20}$=K, A, D, or E.

In some embodiments, an IL-21 polypeptide or a functional fragment or a variant thereof with reduced binding to IL-21R comprises the sequence: QGQDX$_1$HMX$_2$X$_3$MX$_4$QX5X$_6$DX$_7$X$_8$X$_9$QLKNYVNDLVPEFLPA-PEDVETNCEWSAFSCFQKA QLKSANTGNNERII-NVSIX$_{10}$X$_{11}$X$_{12}$X$_{13}$X$_{14}$X$_{15}$PPSTNAGRRQKHRLTCPS-CDSYEKKPPKEFLE RFKSLLQ X$_{16}$MIHQHLSSR-THGSEDS (SEQ ID NO: 384), wherein X$_1$=F, A, E, S, T, N, Q, V, I, L, Y, R; X$_2$=E, I; X$_3$=A, D, E, H, S, T, N, G, V, I, L, Y, R; X$_4$=D, E, R; X$_5$=F, R, L; X$_6$=D, I; X$_7$=A, S, R, I; X$_8$=I, A, V; X$_9$=A, D; X$_{10}$=A, E, K; X$_{11}$=A, E, K; X$_{12}$=I, F, M, L; X$_{13}$=A, K, E; X$_{14}$=E, F, A, N, D, S, T, Q, V, I, L, Y, M, R; X$_{15}$=A, E, K; X$_{16}$=A, K; provided at least one of X$_1$-X$_{16}$ is not the amino acid residue at the identical position set forth in SEQ ID NO: 1.

In some embodiments, the disclosure provides an IL-21 polypeptide comprising an amino acid sequence at least 80%, 85%, 90%, 91%, 92%, 93%, 94%, 95%, 96%, 97%, 98% or 99% identical to an amino acid sequence selected from SEQ ID NOs: 313-371. In some embodiments, the disclosure provides an IL-21 polypeptide comprising an amino acid sequence selected from SEQ ID NOs: 313-371.

Combination of Mutations

An IL-21 polypeptide or a functional fragment of a variant thereof, as described herein, comprises, in some embodiments, a combination of (a) mutations that alter its isoelectric point relative to a wild-type IL-21 (SEQ ID NO: 1) and (b) mutations that attenuate its binding to IL-21R, relative to the wild-type IL-21. In some embodiments, a mutation in group (a) is at a position selected from positions: K56, T81, N82, A83, G84, R85, R86, Q87, K88, H89, R90, L91, and T92; and a mutation in group (b) is at a position selected from the group consisting of: R5, I8, R9, R11, Q12, I14, D15, D18, Q19, Y23, R65, S70, K72, K73, K75, R76, K77, S80, Q116, and K117, wherein the position numbering is according to the amino acid sequence of SEQ ID NO: 1. In some embodiments, a mutation in group (a) is at a position selected from positions: S80, T81, N82, A83, G84, R85, R86, Q87, K88, H89, R90, L91, and T92; and a mutation in group (b) is at a position selected from the group consisting of: R5, I8, R9, R11, L13, I14, I16, V17, D18, K72, K73, L74, K75, R76, K77, and K117, wherein the position numbering is according to the amino acid sequence of SEQ ID NO: 1. In some embodiments, a mutation in group (a) is at a position selected from positions: S80, T81, N82, A83, R85, R86, Q87, K88, H89, R90, L91, and T92; and a mutation in group (b) is at a position selected from the group consisting of: R5, I8, R9, R11, L13, I14, I16, V17, D18, K72, K73, L74, K75, R76, K77, and K117, wherein the position numbering is according to the amino acid sequence of SEQ ID NO: 1. In some embodiments, a mutation in group (a) is at a position selected from positions: S80, T81, N82, A83, G84, R85, R86, Q87, K88, H89, R90, L91, and T92; and a mutation in group (b) is at position R76, wherein the position numbering is according to the amino acid sequence of SEQ ID NO: 1.

In some embodiments, an IL-21 polypeptide comprises a consensus sequence as follows: QGQDX$_1$HMX$_2$X$_3$MX$_4$X$_5$LX$_6$X$_7$IVX$_8$X$_9$LKNX$_{10}$VNDLVPEFLPAPED-VETNCEWSAFSCFQKAQLX$_{11}$SANTGNNEX$_{12}$IINVX$_{13}$IX$_{14}$X$_{15}$X$_{16}$X$_{17}$X$_{18}$PPX$_{19}$X$_{20}$X$_{21}$X$_{22}$X$_{23}$X$_{24}$X$_{25}$X$_{26}$X$_{27}$X$_{2}$X$_{29}$X$_{30}$X$_{31}$CPSCDSYEKKPPKEFLERFKSL-LX$_{32}$X$_{33}$MIHQHLSSRTHGSEDS (SEQ ID NO: 3). In some embodiments, X$_1$=R, A, D, E, S, T, N, Q, V, I, L, Y, or F. In some embodiments, X$_2$=I, Q, H, E. In some embodiments, $X_3$=R, A, D, E, S, T, N, Q, V, I, L, Y, or F. In some embodiments, $X_4$=R, D or E. In some embodiments, $X_5$=Q, L, I, or Y. In some embodiments, $X_6$=I or D or E. In some embodiments, $X_7$=D, R, K, H, L, Y, or F. In some embodiments, $X_8$=D, A, K, or R. In some embodiments, $X_9$=Q, L, or Y. In some embodiments, $X_{10}$=Y or E. $X_{11}$=G, S, E, D, or A. In some embodiments, $X_{12}$=R, G, S, E, D, or A. In some embodiments, $X_{13}$=S, H, Y, L, V, or F. In some embodiments, $X_{14}$=K, G, S, E, D, or A. In some embodiments, $X_{15}$=K, A, Y, L, F, G, S, T, E, A, or D. In some embodiments, $X_{16}$=K, G, S, E, D, or A. In some embodiments, $X_{17}$=R, A, D, E, S, T, N, Q, V, I, L, Y, or F. In some embodiments, $X_{18}$=K, G, S, E, D, or A. In some embodiments, $X_{19}$=S, H, A, G, E, or D. In some embodiments, $X_{20}$=G, S, E, D, or A. In some embodiments, $X_{21}$=G, S, E, D, or A. In some embodiments, $X_{22}$=G, S, E, or D. In some embodiments, $X_{23}$=A, S, E, or D. In some embodiments, $X_{24}$=G, S, E, D, or A. In some embodiments, $X_{25}$=G, S, E, D, or A. In some embodiments, $X_{26}$=G, S, E, D, or A. In some embodiments, $X_{27}$=G, S, E, D, or A. In some embodiments, $X_{28}$=G, S, E, D, or A. In some embodiments, $X_{29}$=G, S, E, D, or A. In some embodiments, $X_{30}$=G, S, E, D, or A. In some embodiments, $X_{31}$=G, S, E, D, or A. In some embodiments, $X_{32}$=Y. In some embodiments, $X_{33}$=A, D, or E.

In some embodiments, an IL-21 polypeptide comprises a consensus sequence as follows: QGQDX$_1$HMX$_2$X$_3$MX$_4$QX$_5$X$_6$DX$_7$X$_8$X$_9$QLKNYVNDLVPEFLPAPEDVET-NCEWSAFSCFQKA QLX$_{10}$SANTGNNERIINVSIX$_{11}$X$_{12}$X$_{13}$X$_{14}$X$_{15}$X$_{16}$PPX$_{17}$X$_{18}$X$_{19}$X$_{20}$X$_{21}$X$_{22}$X$_{23}$X$_{24}$X$_{25}$X$_{26}$X$_{27}$X$_{28}$X$_{29}$C PSCDSYEKKPPKEFLERFKSLLQ X$_{30}$MIHQHLSSRTHGSEDS (SEQ ID NO: 385), wherein $X_1$=F, A, E, S, T, N, Q, V, I, L, Y, R; $X_2$=E, I; $X_3$=A, D, E, H, S, T, N, G, V, I, L, Y, R; $X_4$=D, E, R; $X_5$=F, R, L; $X_6$=D, I; $X_7$=A, S, R, I; $X_8$=I, A, V; $X_9$=A, D; $X_{10}$=A, E, K; $X_{11}$=A, E, K; $X_{12}$=A, E, K; $X_{13}$=I, F, M, L; $X_{14}$=A, K, E; $X_{15}$=E, F, A, N, D, S, T, Q, V, I, L, Y, M, R; $X_{16}$=A, E, K; $X_{17}$=G, S; $X_{18}$=G, T; $X_{19}$=G, E, N; $X_{20}$=G, S, E, A; $X_{21}$=E, G; $X_{22}$=G, E, S, R; $X_{23}$=G, E, R; $X_{24}$=S, G, E, Q; $X_{25}$=G, K; $X_{26}$=G, S, H; $X_{27}$=A, E, S, G, R; $X_{28}$=S, G, L; $X_{29}$=G, S, T; $X_{30}$=A, K, provided at least one of $X_1$-$X_9$ $X_{11}$-$X_{16}$ and $X_{30}$ is not the amino acid residue at the identical position set forth in SEQ ID NO: 1 and reduces binding to IL-21R, and provided at least one of $X_{10}$ and $X_{17}$-$X_{29}$ is not the amino acid residue at the identical position set forth in SEQ ID NO: 1 and reduces the isoelectric point relative to human IL-21 (SEQ ID NO: 1).

In some embodiments, an IL-21 polypeptide or a functional fragment or a variant thereof comprising a combination of mutations comprises at least one mutation in a position of SEQ ID NO: 2. In some embodiments, an IL-21 polypeptide or a functional fragment or a variant thereof comprising a combination of mutations comprises at least one mutation in a position selected from the group consisting of positions: R5, I8, R9, R11, Q12, I14, D15, D18, Q19, Y23, R65, S70, K72, K73, K75, R76, K77, S80, Q116, and K117, wherein the position numbering is according to SEQ ID NO: 2. In some embodiments, an IL-21 polypeptide or a functional fragment or a variant thereof comprising a combination of mutations comprises at least one mutation in a position selected from the group consisting of positions: R5, I8, R9, R1, L13, I14, I16, V17, D18, K72, K73, L74, K75, R76, K77, and K117, wherein the position numbering is according to SEQ ID NO: 2.

In some embodiments, an IL-21 polypeptide or a functional fragment or a variant thereof comprising a combination of mutations comprises at least one mutation in a position of SEQ ID NO: 40. In some embodiments, an IL-21 polypeptide or a functional fragment or a variant thereof comprising a combination of mutations comprises at least one mutation in a position selected from the group consisting of positions: R5, I8, R9, R11, Q12, I14, D15, D18, Q19, Y23, R65, S70, K72, K73, K75, R76, K77, S80, Q116, and K117, wherein the position numbering is according to SEQ ID NO: 40. In some embodiments, an IL-21 polypeptide or a functional fragment or a variant thereof comprising a combination of mutations comprises at least one mutation in a position selected from the group consisting of positions: R5, I8, R9, R11, L13, I14, I16, V17, D18, K72, K73, L74, K75, R76, K77, and K117, wherein the position numbering is according to SEQ ID NO: 40.

In some embodiments, an IL-21 polypeptide or a functional fragment or a variant thereof comprises (i) four or more amino acid substitutions providing a reduced isoelectric point relative to a human IL-21 polypeptide comprising SEQ ID NO: 1, wherein the four or more amino acid substitutions are within S80 to T92 of SEQ ID NO: 1, wherein at least four amino acid substitutions are at residues R85, R86, K88, H89, R90, or a combination thereof, and (ii) at least one amino acid substitution selected from (a) R11D; (b) R11E; (c) I14D, D18A and K117A; (d) R76E; (e) R5F; (f) R76F; (g) I8E; (h) R5A; (i) R5E; (j) R5S; (k) R5T; (l) R5N; (m) R5Q; (n) R5V; (o) R5I; (p) R5L; (q) R5Y; (r) R76A; (s) R76N; (t) R76D; (u) R76S; (v) R76T; (w) R76Q; (x) R76V; (y) R76I; (z) R76L; (aa) R76Y; (bb) K77A; (cc) K77E; (dd) K72A; (ee) K72E; (ff) K75A; (gg) K75E; (hh) K73A; (ii) K73E; (jj) R5F and K77A; (kk) R5F and K77E; (ll) R5F and K72A; (mm) R5F and K72E; (nn) R5F and K76A; (oo) R5F and K76E; (pp) K73A and K76F; (qq) K73E and K76F; (rr) R9A; (ss) R9D; (tt) R9E; (uu) R9H; (vv) R9S; (ww) R9T; (xx) R9N; (zz) R9G; (aaa) R9V; (bbb) R9I; (ccc) R9L; (ddd) R9Y; (eee) K72A and R76F; (fff) K75A and R76F; (ggg) R76F and K77A; (hhh) K75E and R76F; (iii) V17I and L74I; (jjj) I16A and L74F; (kkk) I16S, V17I, and L74V; (lll) I16R, V17I, and L74I; (mmm) L13F, I16A, V17A and L74M; and (nnn) L13R, I16A, V17A and L74I.

In some embodiments, an IL-21 polypeptide or a functional fragment or a variant thereof comprises (i) an amino acid sequence selected from SEQ ID Nos: 2, 4-15 and 23-40, and (ii) at least one amino acid substitution selected from (a) R11D; (b) R11E; (c) I14D, D18A and K117A; (d) R76E; (e) R5F; (f) R76F; (g) I8E; (h) R5A; (i) R5E; (j) R5S; (k) R5T; (l) R5N; (m) R5Q; (n) R5V; (o) R5I; (p) R5L; (q) R5Y; (r) R76A; (s) R76N; (t) R76D; (u) R76S; (v) R76T; (w) R76Q; (x) R76V; (y) R76I; (z) R76L; (aa) R76Y; (bb) K77A; (cc) K77E; (dd) K72A; (ee) K72E; (ff) K75A; (gg) K75E; (hh) K73A; (ii) K73E; (jj) R5F and K77A; (kk) R5F and K77E; (ll) R5F and K72A; (mm) R5F and K72E; (nn) R5F and K76A; (oo) R5F and K76E; (pp) K73A and K76F; (qq) K73E and K76F; (rr) R9A; (ss) R9D; (tt) R9E; (uu) R9H; (vv) R9S; (ww) R9T; (xx) R9N; (zz) R9G; (aaa) R9V; (bbb) R9I; (ccc) R9L; (ddd) R9Y; (eee) K72A and R76F; (fff) K75A and R76F; (ggg) R76F and K77A; (hhh) K75E and R76F; (iii) V17I and L74I; (jjj) I16A and L74F; (kkk) I16S, V17I, and L74V; (lll) I16R, V17I, and L74I; (mmm) L13F, I16A, V17A and L74M; and (nnn) L13R, I16A, V17A and L74I.

In some embodiments, an IL-21 polypeptide or a functional fragment or a variant thereof comprises a R11D mutation and comprises about 75% sequence identity to about 100% sequence identity to SEQ ID NO: 16. In some embodiments, an IL-21 polypeptide or a functional fragment or a variant thereof comprises a R11D mutation and comprises at least about 75% sequence identity SEQ ID NO: 16. In some embodiments, an IL-21 polypeptide or a functional fragment or a variant thereof comprises a R11D mutation and comprises at most about 100% sequence identity SEQ ID NO: 16. In some embodiments, an IL-21 polypeptide or a functional fragment or a variant thereof comprises a R11D mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 16. In some embodiments, an IL-21 polypeptide or a functional fragment or a variant thereof comprises a R11D mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 16.

In some embodiments, an IL-21 polypeptide or a functional fragment or a variant thereof comprises a R11E mutation and comprises about 75% sequence identity to about 100% sequence identity to SEQ ID NO: 17. In some embodiments, an IL-21 polypeptide or a functional fragment or a variant thereof comprises a R11E mutation and comprises at least about 75% sequence identity SEQ ID NO: 17. In some embodiments, an IL-21 polypeptide or a functional fragment or a variant thereof comprises a R11E mutation and comprises at most about 100% sequence identity SEQ ID NO: 17. In some embodiments, an IL-21 polypeptide or a functional fragment or a variant thereof comprises a R11E mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 17. In some embodiments, an IL-21 polypeptide or a functional fragment or a variant thereof comprises a R11E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 17.

In some embodiments, an IL-21 polypeptide or a functional fragment or a variant thereof or a functional fragment or a variant thereof comprises a I14D, D18A and K117A mutation and comprises about 75% sequence identity to about 100% sequence identity to SEQ ID NO: 18. In some embodiments, an IL-21 polypeptide or a functional fragment or a variant thereof or a functional fragment or a variant thereof comprises a I14D, D18A and K117A mutation and comprises at least about 75% sequence identity SEQ ID NO: 18. In some embodiments, an IL-21 polypeptide or a functional fragment or a variant thereof or a functional fragment or a variant thereof comprises a I14D, D18A and K117A mutation and comprises at most about 100% sequence identity SEQ ID NO: 18. In some embodiments, an IL-21 polypeptide or a functional fragment or a variant thereof or a functional fragment or a variant thereof comprises a I14D, D18A and K117A mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity to SEQ ID NO: 18. In some embodiments, an IL-21 polypeptide or a functional fragment or a variant thereof comprises a I14D, D18A and K117A mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 18.

In some embodiments, an IL-21 polypeptide or a functional fragment or a variant thereof comprises a R76E mutation and comprises about 75% sequence identity to about 100% sequence identity to SEQ ID NO: 19. In some embodiments, an IL-21 polypeptide or a functional fragment or a variant thereof comprises a R76E mutation and comprises at least about 75% sequence identity SEQ ID NO: 19. In some embodiments, an IL-21 polypeptide or a functional fragment or a variant thereof comprises a R76E mutation and comprises at most about 100% sequence identity SEQ ID NO: 19. In some embodiments, an IL-21 polypeptide or a functional fragment or a variant thereof comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 19. In some embodiments, an IL-21 polypeptide or a functional fragment or a variant thereof comprises a R76E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 19.

In some embodiments, an IL-21 polypeptide or a functional fragment or a variant thereof comprises a R5F mutation and comprises about 75% sequence identity to about 100% sequence identity to SEQ ID NO: 20. In some embodiments, an IL-21 polypeptide or a functional fragment or a variant thereof comprises a R5F mutation and comprises at least about 75% sequence identity SEQ ID NO: 20. In some embodiments, an IL-21 polypeptide or a functional fragment or a variant thereof comprises at most about 100% sequence identity SEQ ID NO: 20. In some embodiments, an IL-21 polypeptide or a functional fragment or a variant thereof comprises a R5F mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 29. In some embodiments, an IL-21 polypeptide or a functional fragment or a variant thereof comprises a R5F mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 20.

In some embodiments, an IL-21 polypeptide or a functional fragment or a variant thereof comprises a R76F mutation and comprises about 75% sequence identity to about 100% sequence identity to SEQ ID NO: 21. In some embodiments, an IL-21 polypeptide or a functional fragment or a variant thereof comprises a R76F mutation and comprises at least about 75% sequence identity SEQ ID NO: 21. In some embodiments, an IL-21 polypeptide or a functional fragment or a variant thereof comprises a R76F mutation and comprises at most about 100% sequence identity SEQ ID NO: 21. In some embodiments, an IL-21 polypeptide or a functional fragment or a variant thereof comprises a R76F mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity to SEQ ID NO: 21. In some embodiments, an IL-21 polypeptide or a functional fragment or a variant thereof comprises a R76F mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 21.

In some embodiments, an IL-21 polypeptide or a functional fragment or a variant thereof comprises an I8E mutation and comprises about 75% sequence identity to about 100% sequence identity to SEQ ID NO: 41. In some embodiments, an IL-21 polypeptide or a functional fragment or a variant thereof comprises an I8E mutation and comprises at least about 75% sequence identity SEQ ID NO: 41. In some embodiments, an IL-21 polypeptide or a functional fragment or a variant thereof comprises an I8E mutation and comprises at most about 100% sequence identity SEQ ID NO: 41. In some embodiments, an IL-21 polypeptide or a functional fragment or a variant thereof comprises an I8E mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 41. In some embodiments, an IL-21 polypeptide or a functional fragment or a variant thereof comprises an I8E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 41.

In some embodiments, an IL-21 polypeptide or a functional fragment or a variant thereof comprises an R5A mutation and comprises about 75% sequence identity to about 100% sequence identity to SEQ ID NO: 42. In some embodiments, an IL-21 polypeptide or a functional fragment or a variant thereof comprises an R5A mutation and comprises at least about 75% sequence identity SEQ ID NO: 42. In some embodiments, an IL-21 polypeptide or a functional fragment or a variant thereof comprises an R5A mutation and comprises at most about 100% sequence identity SEQ ID NO: 42. In some embodiments, an IL-21 polypeptide or a functional fragment or a variant thereof comprises an R5A mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 42. In some embodiments, an IL-21 polypeptide or a functional fragment or a variant thereof comprises an R5A mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 42.

In some embodiments, an IL-21 polypeptide or a functional fragment or a variant thereof comprises an R5E mutation and comprises about 75% sequence identity to about 100% sequence identity to SEQ ID NO: 43. In some embodiments, an IL-21 polypeptide or a functional fragment or a variant thereof comprises an R5E mutation and comprises at least about 75% sequence identity SEQ ID NO: 43. In some embodiments, an IL-21 polypeptide or a functional fragment or a variant thereof comprises an R5E mutation and comprises at most about 100% sequence identity SEQ ID NO: 43. In some embodiments, an IL-21 polypeptide or a functional fragment or a variant thereof comprises an R5E mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 43. In some embodiments, an IL-21 polypeptide or a functional fragment or a variant thereof comprises an R5E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 43.

In some embodiments, an IL-21 polypeptide or a functional fragment or a variant thereof comprises an R5S mutation and comprises about 75% sequence identity to about 100% sequence identity to SEQ ID NO: 44. In some embodiments, an IL-21 polypeptide or a functional fragment or a variant thereof comprises an R5S mutation and comprises at least about 75% sequence identity SEQ ID NO: 44. In some embodiments, an IL-21 polypeptide or a functional fragment or a variant thereof comprises an R5S mutation and comprises at most about 100% sequence identity SEQ ID NO: 44. In some embodiments, an IL-21 polypeptide or a functional fragment or a variant thereof comprises an R5S mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 44. In some embodiments, an IL-21 polypeptide or a functional fragment or a variant thereof comprises an R5S mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 44.

In some embodiments, an IL-21 polypeptide or a functional fragment or a variant thereof comprises an R5T mutation and comprises about 75% sequence identity to about 100% sequence identity to SEQ ID NO: 45. In some embodiments, an IL-21 polypeptide or a functional fragment or a variant thereof comprises an R5T mutation and comprises at least about 75% sequence identity SEQ ID NO: 45. In some embodiments, an IL-21 polypeptide or a functional fragment or a variant thereof comprises an R5T mutation and comprises at most about 100% sequence identity SEQ ID NO: 45. In some embodiments, an IL-21 polypeptide or a functional fragment or a variant thereof comprises an R5T mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 45. In some embodiments, an IL-21 polypeptide or a functional fragment or a variant thereof comprises an R5T mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 45.

In some embodiments, an IL-21 polypeptide or a functional fragment or a variant thereof comprises an R5N mutation and comprises about 75% sequence identity to about 100% sequence identity to SEQ ID NO: 46. In some embodiments, an IL-21 polypeptide or a functional fragment or a variant thereof comprises an R5N mutation and comprises at least about 75% sequence identity SEQ ID NO: 46. In some embodiments, an IL-21 polypeptide or a functional fragment or a variant thereof comprises an R5N mutation and comprises at most about 100% sequence identity SEQ ID NO: 46. In some embodiments, an IL-21 polypeptide or a functional fragment or a variant thereof comprises an R5N mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 46. In some embodiments, an IL-21 polypeptide or a functional fragment or a variant thereof comprises an R5N mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 46.

In some embodiments, an IL-21 polypeptide or a functional fragment or a variant thereof comprises an R5Q mutation and comprises about 75% sequence identity to about 100% sequence identity to SEQ ID NO: 47. In some embodiments, an IL-21 polypeptide or a functional fragment or a variant thereof comprises an R5Q mutation and comprises at least about 75% sequence identity SEQ ID NO: 47. In some embodiments, an IL-21 polypeptide or a functional fragment or a variant thereof comprises an R5Q mutation and comprises at most about 100% sequence identity SEQ ID NO: 47. In some embodiments, an IL-21 polypeptide or a functional fragment or a variant thereof comprises an R5Q mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 47. In some embodiments, an IL-21 polypeptide or a functional fragment or a variant thereof comprises an R5Q mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 47.

In some embodiments, an IL-21 polypeptide or a functional fragment or a variant thereof comprises an R5V mutation and comprises about 75% sequence identity to about 100% sequence identity to SEQ ID NO: 48. In some embodiments, an IL-21 polypeptide or a functional fragment or a variant thereof comprises an R5V mutation and comprises at least about 75% sequence identity SEQ ID NO: 48. In some embodiments, an IL-21 polypeptide or a functional fragment or a variant thereof comprises an R5V mutation and comprises at most about 100% sequence identity SEQ ID NO: 48. In some embodiments, an IL-21 polypeptide or a functional fragment or a variant thereof comprises an R5V mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 48. In some embodiments, an IL-21 polypeptide or a functional fragment or a variant thereof comprises an R5V mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 48.

In some embodiments, an IL-21 polypeptide or a functional fragment or a variant thereof comprises an R5I mutation and comprises about 75% sequence identity to about 100% sequence identity to SEQ ID NO: 49. In some embodiments, an IL-21 polypeptide or a functional fragment or a variant thereof comprises an R5I mutation and comprises at least about 75% sequence identity SEQ ID NO: 49. In some embodiments, an IL-21 polypeptide or a functional fragment or a variant thereof comprises an R5I mutation and comprises at most about 100% sequence identity SEQ ID NO: 49. In some embodiments, an IL-21 polypeptide or a functional fragment or a variant thereof comprises an R5I mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 49. In some embodiments, an IL-21 polypeptide or a functional fragment or a variant thereof comprises an R5I mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 49.

In some embodiments, an IL-21 polypeptide or a functional fragment or a variant thereof comprises an R5L mutation and comprises about 75% sequence identity to about 100% sequence identity to SEQ ID NO: 50. In some embodiments, an IL-21 polypeptide or a functional fragment or a variant thereof comprises an R5L mutation and comprises at least about 75% sequence identity SEQ ID NO: 50. In some embodiments, an IL-21 polypeptide or a functional fragment or a variant thereof comprises an R5L mutation and comprises at most about 100% sequence identity SEQ ID NO: 50. In some embodiments, an IL-21 polypeptide or a functional fragment or a variant thereof comprises an R5L mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 50. In some embodiments, an IL-21 polypeptide or a functional fragment or a variant thereof comprises an R5L mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 50.

In some embodiments, an IL-21 polypeptide or a functional fragment or a variant thereof comprises an R5Y mutation and comprises about 75% sequence identity to about 100% sequence identity to SEQ ID NO: 51. In some embodiments, an IL-21 polypeptide or a functional fragment or a variant thereof comprises an R5Y mutation and comprises at least about 75% sequence identity SEQ ID NO: 51. In some embodiments, an IL-21 polypeptide or a functional fragment or a variant thereof comprises an R5Y mutation and comprises at most about 100% sequence identity SEQ ID NO: 51. In some embodiments, an IL-21 polypeptide or a functional fragment or a variant thereof comprises an R5Y mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 51. In some embodiments, an IL-21 polypeptide or a functional fragment or a variant thereof comprises an R5Y mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 51.

In some embodiments, an IL-21 polypeptide or a functional fragment or a variant thereof comprises an R76A mutation and comprises about 75% sequence identity to about 100% sequence identity to SEQ ID NO: 52. In some embodiments, an IL-21 polypeptide or a functional fragment or a variant thereof comprises an R76A mutation and comprises at least about 75% sequence identity SEQ ID NO: 52. In some embodiments, an IL-21 polypeptide or a functional fragment or a variant thereof comprises an R76A mutation and comprises at most about 100% sequence identity SEQ ID NO: 52. In some embodiments, an IL-21 polypeptide or a functional fragment or a variant thereof comprises an R76A mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 52. In some embodiments, an IL-21 polypeptide or a functional fragment or a variant thereof comprises an R76A mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 52.

In some embodiments, an IL-21 polypeptide or a functional fragment or a variant thereof comprises an R76N mutation and comprises about 75% sequence identity to about 100% sequence identity to SEQ ID NO: 53. In some embodiments, an IL-21 polypeptide or a functional fragment or a variant thereof comprises an R76N mutation and comprises at least about 75% sequence identity SEQ ID NO: 53. In some embodiments, an IL-21 polypeptide or a functional fragment or a variant thereof comprises an R76N mutation and comprises at most about 100% sequence identity SEQ ID NO: 53. In some embodiments, an IL-21 polypeptide or a functional fragment or a variant thereof comprises an R76N mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 53. In some embodiments, an IL-21 polypeptide or a functional fragment or a variant thereof comprises an R76N mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 53.

In some embodiments, an IL-21 polypeptide or a functional fragment or a variant thereof comprises an R76D mutation and comprises about 75% sequence identity to about 100% sequence identity to SEQ ID NO: 54. In some embodiments, an IL-21 polypeptide or a functional fragment or a variant thereof comprises an R76D mutation and comprises at least about 75% sequence identity SEQ ID NO: 54. In some embodiments, an IL-21 polypeptide or a functional fragment or a variant thereof comprises an R76D mutation and comprises at most about 100% sequence identity SEQ ID NO: 54. In some embodiments, an IL-21 polypeptide or a functional fragment or a variant thereof comprises an R76D mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 54. In some embodiments, an IL-21 polypeptide or a functional fragment or a variant thereof comprises an R76D mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 54.

In some embodiments, an IL-21 polypeptide or a functional fragment or a variant thereof comprises an R76S mutation and comprises about 75% sequence identity to about 100% sequence identity to SEQ ID NO: 55. In some embodiments, an IL-21 polypeptide or a functional fragment or a variant thereof comprises an R76S mutation and comprises at least about 75% sequence identity SEQ ID NO: 55. In some embodiments, an IL-21 polypeptide or a functional fragment or a variant thereof comprises an R76S mutation and comprises at most about 100% sequence identity SEQ ID NO: 55. In some embodiments, an IL-21 polypeptide or a functional fragment or a variant thereof comprises an R76S mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 55. In some embodiments, an IL-21 polypeptide or a functional fragment or a variant thereof comprises an R76S mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 55.

In some embodiments, an IL-21 polypeptide or a functional fragment or a variant thereof comprises an R76T mutation and comprises about 75% sequence identity to about 100% sequence identity to SEQ ID NO: 56. In some embodiments, an IL-21 polypeptide or a functional fragment or a variant thereof comprises an R76T mutation and comprises at least about 75% sequence identity SEQ ID NO: 56. In some embodiments, an IL-21 polypeptide or a functional fragment or a variant thereof comprises an R76T mutation and comprises at most about 100% sequence identity SEQ ID NO: 56. In some embodiments, an IL-21 polypeptide or a functional fragment or a variant thereof comprises an R76T mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 6 In some embodiments, an IL-21 polypeptide or a functional fragment or a variant thereof comprises an R76T mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 56.

In some embodiments, an IL-21 polypeptide or a functional fragment or a variant thereof comprises an R76Q mutation and comprises about 75% sequence identity to about 100% sequence identity to SEQ ID NO: 57. In some embodiments, an IL-21 polypeptide or a functional fragment or a variant thereof comprises an R76Q mutation and comprises at least about 75% sequence identity SEQ ID NO: 57. In some embodiments, an IL-21 polypeptide or a functional fragment or a variant thereof comprises an R76Q mutation and comprises at most about 100% sequence identity SEQ ID NO: 57. In some embodiments, an IL-21 polypeptide or a functional fragment or a variant thereof comprises an R76Q mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 57. In some embodiments, an IL-21 polypeptide or a functional fragment or a variant thereof comprises an R76Q mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 57.

In some embodiments, an IL-21 polypeptide or a functional fragment or a variant thereof comprises an R76V mutation and comprises about 75% sequence identity to about 100% sequence identity to SEQ ID NO: 58. In some embodiments, an IL-21 polypeptide or a functional fragment or a variant thereof comprises an R76V mutation and comprises at least about 75% sequence identity SEQ ID NO: 58. In some embodiments, an IL-21 polypeptide or a functional fragment or a variant thereof comprises an R76V mutation and comprises at most about 100% sequence identity SEQ ID NO: 58. In some embodiments, an IL-21 polypeptide or a functional fragment or a variant thereof comprises an R76V mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 58. In some embodiments, an IL-21 polypeptide or a functional fragment or a variant thereof comprises an R76V mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 58.

In some embodiments, an IL-21 polypeptide or a functional fragment or a variant thereof comprises an R76I mutation and comprises about 75% sequence identity to about 100% sequence identity to SEQ ID NO: 59. In some embodiments, an IL-21 polypeptide or a functional fragment or a variant thereof comprises an R76I mutation and comprises at least about 75% sequence identity SEQ ID NO: 59. In some embodiments, an IL-21 polypeptide or a functional fragment or a variant thereof comprises an R76I mutation and comprises at most about 100% sequence identity SEQ ID NO: 59. In some embodiments, an IL-21 polypeptide or a functional fragment or a variant thereof comprises an R76I mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 59. In some embodiments, an IL-21 polypeptide or a functional fragment or a variant thereof comprises an R76I mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 59.

In some embodiments, an IL-21 polypeptide or a functional fragment or a variant thereof comprises an R76L mutation and comprises about 75% sequence identity to about 100% sequence identity to SEQ ID NO: 60. In some embodiments, an IL-21 polypeptide or a functional fragment or a variant thereof comprises an R76L mutation and comprises at least about 75% sequence identity SEQ ID NO: 60. In some embodiments, an IL-21 polypeptide or a functional fragment or a variant thereof comprises an R76L mutation and comprises at most about 100% sequence identity SEQ ID NO: 60. In some embodiments, an IL-21 polypeptide or a functional fragment or a variant thereof comprises an R76L mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 60. In some embodiments, an IL-21 polypeptide or a functional fragment or a variant thereof comprises an R76L mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 60.

In some embodiments, an IL-21 polypeptide or a functional fragment or a variant thereof comprises an R76Y mutation and comprises about 75% sequence identity to about 100% sequence identity to SEQ ID NO: 61. In some embodiments, an IL-21 polypeptide or a functional fragment or a variant thereof comprises an R76Y mutation and comprises at least about 75% sequence identity SEQ ID NO: 61. In some embodiments, an IL-21 polypeptide or a functional fragment or a variant thereof comprises an R76Y mutation and comprises at most about 100% sequence identity SEQ ID NO: 61. In some embodiments, an IL-21 polypeptide or a functional fragment or a variant thereof comprises an R76Y mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 61. In some embodiments, an IL-21 polypeptide or a functional fragment or a variant thereof comprises an R76Y mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 61.

In some embodiments, an IL-21 polypeptide or a functional fragment or a variant thereof comprises a K77A mutation and comprises about 75% sequence identity to about 100% sequence identity to SEQ ID NO: 62. In some embodiments, an IL-21 polypeptide or a functional fragment or a variant thereof comprises a K77A mutation and comprises at least about 75% sequence identity SEQ ID NO: 62. In some embodiments, an IL-21 polypeptide or a functional fragment or a variant thereof comprises a K77A mutation and comprises at most about 100% sequence identity SEQ ID NO: 62. In some embodiments, an IL-21 polypeptide or a functional fragment or a variant thereof comprises a K77A mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 62. In some embodiments, an IL-21 polypeptide or a functional fragment or a variant thereof comprises a K77A mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 62.

In some embodiments, an IL-21 polypeptide or a functional fragment or a variant thereof comprises a K77E mutation and comprises about 75% sequence identity to about 100% sequence identity to SEQ ID NO: 63. In some embodiments, an IL-21 polypeptide or a functional fragment or a variant thereof comprises a K77E mutation and comprises at least about 75% sequence identity SEQ ID NO: 63. In some embodiments, an IL-21 polypeptide or a functional fragment or a variant thereof comprises a K77E mutation and comprises at most about 100% sequence identity SEQ ID NO: 63. In some embodiments, an IL-21 polypeptide or a functional fragment or a variant thereof comprises a K77E mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 63. In some embodiments, an IL-21 polypeptide or a functional fragment or a variant thereof comprises a K77E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 63.

In some embodiments, an IL-21 polypeptide or a functional fragment or a variant thereof comprises a K72A mutation and comprises about 75% sequence identity to about 100% sequence identity to SEQ ID NO: 64. In some embodiments, an IL-21 polypeptide or a functional fragment or a variant thereof comprises a K72A mutation and comprises at least about 75% sequence identity SEQ ID NO: 64. In some embodiments, an IL-21 polypeptide or a functional fragment or a variant thereof comprises a K72A mutation and comprises at most about 100% sequence identity SEQ ID NO: 64. In some embodiments, an IL-21 polypeptide or a functional fragment or a variant thereof comprises a K72A mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 64. In some embodiments, an IL-21 polypeptide or a functional fragment or a variant thereof comprises a K72A mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 64.

In some embodiments, an IL-21 polypeptide or a functional fragment or a variant thereof comprises a K72E mutation and comprises about 75% sequence identity to about 100% sequence identity to SEQ ID NO: 65. In some embodiments, an IL-21 polypeptide or a functional fragment or a variant thereof comprises a K72E mutation and comprises at least about 75% sequence identity SEQ ID NO: 65. In some embodiments, an IL-21 polypeptide or a functional fragment or a variant thereof comprises a K72E mutation and comprises at most about 100% sequence identity SEQ ID NO: 65. In some embodiments, an IL-21 polypeptide or a functional fragment or a variant thereof comprises a K72E mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 65. In some embodiments, an IL-21 polypeptide or a functional fragment or a variant thereof comprises a K72E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 65.

In some embodiments, an IL-21 polypeptide or a functional fragment or a variant thereof comprises a K75A mutation and comprises about 75% sequence identity to about 100% sequence identity to SEQ ID NO: 66. In some embodiments, an IL-21 polypeptide or a functional fragment or a variant thereof comprises a K75A mutation and comprises at least about 75% sequence identity SEQ ID NO: 66. In some embodiments, an IL-21 polypeptide or a functional fragment or a variant thereof comprises a K75A mutation and comprises at most about 100% sequence identity SEQ ID NO: 66. In some embodiments, an IL-21 polypeptide or a functional fragment or a variant thereof comprises a K75A mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 66. In some embodiments, an IL-21 polypeptide or a functional fragment or a variant thereof comprises a K75A mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 66.

In some embodiments, an IL-21 polypeptide or a functional fragment or a variant thereof comprises a K75E mutation and comprises about 75% sequence identity to about 100% sequence identity to SEQ ID NO: 67. In some embodiments, an IL-21 polypeptide or a functional fragment or a variant thereof comprises a K75E mutation and comprises at least about 75% sequence identity SEQ ID NO: 67. In some embodiments, an IL-21 polypeptide or a functional fragment or a variant thereof comprises a K75E mutation and comprises at most about 100% sequence identity SEQ ID NO: 67. In some embodiments, an IL-21 polypeptide or a functional fragment or a variant thereof comprises a K75E mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 67. In some embodiments, an IL-21 polypeptide or a functional fragment or a variant thereof comprises a K75E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 67.

In some embodiments, an IL-21 polypeptide or a functional fragment or a variant thereof comprises a K73A mutation and comprises about 75% sequence identity to about 100% sequence identity to SEQ ID NO: 68. In some embodiments, an IL-21 polypeptide or a functional fragment or a variant thereof comprises a K73A mutation and comprises at least about 75% sequence identity SEQ ID NO: 68. In some embodiments, an IL-21 polypeptide or a functional fragment or a variant thereof comprises a K73A mutation and comprises at most about 100% sequence identity SEQ ID NO: 68. In some embodiments, an IL-21 polypeptide or a functional fragment or a variant thereof comprises a K73A mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 68. In some embodiments, an IL-21 polypeptide or a functional fragment or a variant thereof comprises a K73A mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 68.

In some embodiments, an IL-21 polypeptide or a functional fragment or a variant thereof comprises a K73E mutation and comprises about 75% sequence identity to about 100% sequence identity to SEQ ID NO: 69. In some embodiments, an IL-21 polypeptide or a functional fragment or a variant thereof comprises a K73E mutation and comprises at least about 75% sequence identity SEQ ID NO: 69. In some embodiments, an IL-21 polypeptide or a functional fragment or a variant thereof comprises a K73E mutation and comprises at most about 100% sequence identity SEQ ID NO: 69. In some embodiments, an IL-21 polypeptide or a functional fragment or a variant thereof comprises a K73E mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 69. In some embodiments, an IL-21 polypeptide or a functional fragment or a variant thereof comprises a K73E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 69.

In some embodiments, an IL-21 polypeptide or a functional fragment or a variant thereof comprises R5F and K77A mutations and comprises about 75% sequence identity to about 100% sequence identity to SEQ ID NO: 70. In some embodiments, an IL-21 polypeptide or a functional fragment or a variant thereof comprises R5F and K77A mutations and comprises at least about 75% sequence identity SEQ ID NO: 70. In some embodiments, an IL-21 polypeptide or a functional fragment or a variant thereof comprises R5F and K77A mutations and comprises at most about 100% sequence identity SEQ ID NO: 70. In some embodiments, an IL-21 polypeptide or a functional fragment or a variant thereof comprises R5F and K77A mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 70. In some embodiments, an IL-21 polypeptide or a functional fragment or a variant thereof comprises R5F and K77A mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 70.

In some embodiments, an IL-21 polypeptide or a functional fragment or a variant thereof comprises R5F and K77E mutations and comprises about 75% sequence identity to about 100% sequence identity to SEQ ID NO: 71. In some embodiments, an IL-21 polypeptide or a functional fragment or a variant thereof comprises R5F and K77E mutations and comprises at least about 75% sequence identity SEQ ID NO: 71. In some embodiments, an IL-21 polypeptide or a functional fragment or a variant thereof comprises R5F and K77E mutations and comprises at most about 100% sequence identity SEQ ID NO: 71. In some embodiments, an IL-21 polypeptide or a functional fragment or a variant thereof comprises R5F and K77E mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 71. In some embodiments, an IL-21 polypeptide or a functional fragment or a variant thereof comprises R5F and K77E mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 71.

In some embodiments, an IL-21 polypeptide or a functional fragment or a variant thereof comprises R5F and K72A mutations and comprises about 75% sequence identity to about 100% sequence identity to SEQ ID NO: 72. In some embodiments, an IL-21 polypeptide or a functional fragment or a variant thereof comprises R5F and K72A mutations and comprises at least about 75% sequence identity SEQ ID NO: 72. In some embodiments, an IL-21 polypeptide or a functional fragment or a variant thereof comprises R5F and K72A mutations and comprises at most about 100% sequence identity SEQ ID NO: 72. In some embodiments, an IL-21 polypeptide or a functional fragment or a variant thereof comprises R5F and K72A mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 72. In some embodiments, an IL-21 polypeptide or a functional fragment or a variant thereof comprises R5F and K72A mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 72.

In some embodiments, an IL-21 polypeptide or a functional fragment or a variant thereof comprises R5F and K72E mutations and comprises about 75% sequence identity to about 100% sequence identity to SEQ ID NO: 73. In some embodiments, an IL-21 polypeptide or a functional fragment or a variant thereof comprises R5F and K72E mutations and comprises at least about 75% sequence identity SEQ ID NO: 73. In some embodiments, an IL-21 polypeptide or a functional fragment or a variant thereof comprises R5F and K72E mutations and comprises at most about 100% sequence identity SEQ ID NO: 73. In some embodiments, an IL-21 polypeptide or a functional fragment or a variant thereof comprises R5F and K72E mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 73. In some embodiments, an IL-21 polypeptide or a functional fragment or a variant thereof comprises R5F and K72E mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 73.

In some embodiments, an IL-21 polypeptide or a functional fragment or a variant thereof comprises R5F and K76A mutations and comprises about 75% sequence identity to about 100% sequence identity to SEQ ID NO: 74. In some embodiments, an IL-21 polypeptide or a functional fragment or a variant thereof comprises R5F and K76A mutations and comprises at least about 75% sequence identity SEQ ID NO: 74. In some embodiments, an IL-21 polypeptide or a functional fragment or a variant thereof comprises R5F and K76A mutations and comprises at most about 100% sequence identity SEQ ID NO: 74. In some embodiments, an IL-21 polypeptide or a functional fragment or a variant thereof comprises R5F and K76A mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 74. In some embodiments, an IL-21 polypeptide or a functional fragment or a variant thereof comprises R5F and K76A mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 74.

In some embodiments, an IL-21 polypeptide or a functional fragment or a variant thereof comprises R5F and K76E mutations and comprises about 75% sequence identity to about 100% sequence identity to SEQ ID NO: 75. In some embodiments, an IL-21 polypeptide or a functional fragment or a variant thereof comprises R5F and K76E mutations and comprises at least about 75% sequence identity SEQ ID NO: 75. In some embodiments, an IL-21 polypeptide or a functional fragment or a variant thereof comprises R5F and K76E mutations and comprises at most about 100% sequence identity SEQ ID NO: 75. In some embodiments, an IL-21 polypeptide or a functional fragment or a variant thereof comprises R5F and K76E mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 75. In some embodiments, an IL-21 polypeptide or a functional fragment or a variant thereof comprises R5F and K76E mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 75.

In some embodiments, an IL-21 polypeptide or a functional fragment or a variant thereof comprises K73A and K76F mutations and comprises about 75% sequence identity to about 100% sequence identity to SEQ ID NO: 76. In some embodiments, an IL-21 polypeptide or a functional fragment or a variant thereof comprises K73A and K76F mutations and comprises at least about 75% sequence identity SEQ ID NO: 76. In some embodiments, an IL-21 polypeptide or a functional fragment or a variant thereof comprises K73A and K76F mutations and comprises at most about 100% sequence identity SEQ ID NO: 76. In some embodiments, an IL-21 polypeptide or a functional fragment or a variant thereof comprises K73A and K76F mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 76. In some embodiments, an IL-21 polypeptide or a functional fragment or a variant thereof comprises K73A and K76F mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 76.

In some embodiments, an IL-21 polypeptide or a functional fragment or a variant thereof comprises K73E and K76F mutations and comprises about 75% sequence identity to about 100% sequence identity to SEQ ID NO: 77. In some embodiments, an IL-21 polypeptide or a functional fragment or a variant thereof comprises K73E and K76F mutations and comprises at least about 75% sequence identity SEQ ID NO: 77. In some embodiments, an IL-21 polypeptide or a functional fragment or a variant thereof comprises K73E and K76F mutations and comprises at most about 100% sequence identity SEQ ID NO: 77. In some embodiments, an IL-21 polypeptide or a functional fragment or a variant thereof comprises K73E and K76F mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 77. In some embodiments, an IL-21 polypeptide or a functional fragment or a variant thereof comprises K73E and K76F mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 77.

In some embodiments, an IL-21 polypeptide or a functional fragment or a variant thereof comprises an R9A mutation and comprises about 75% sequence identity to about 100% sequence identity to SEQ ID NO: 78. In some embodiments, an IL-21 polypeptide or a functional fragment or a variant thereof comprises an R9A mutation and comprises at least about 75% sequence identity SEQ ID NO: 78. In some embodiments, an IL-21 polypeptide or a functional fragment or a variant thereof comprises an R9A mutation and comprises at most about 100% sequence identity SEQ ID NO: 78. In some embodiments, an IL-21 polypeptide or a functional fragment or a variant thereof comprises an R9A mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 78. In some embodiments, an IL-21 polypeptide or a functional fragment or a variant thereof comprises an R9A mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 78.

In some embodiments, an IL-21 polypeptide or a functional fragment or a variant thereof comprises an R9D mutation and comprises about 75% sequence identity to about 100% sequence identity to SEQ ID NO: 79. In some embodiments, an IL-21 polypeptide or a functional fragment or a variant thereof comprises an R9D mutation and comprises at least about 75% sequence identity SEQ ID NO: 79. In some embodiments, an IL-21 polypeptide or a functional fragment or a variant thereof comprises an R9D mutation and comprises at most about 100% sequence identity SEQ ID NO: 79. In some embodiments, an IL-21 polypeptide or a functional fragment or a variant thereof comprises an R9D mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 79. In some embodiments, an IL-21 polypeptide or a functional fragment or a variant thereof comprises an R9D mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 79.

In some embodiments, an IL-21 polypeptide or a functional fragment or a variant thereof comprises an R9E mutation and comprises about 75% sequence identity to about 100% sequence identity to SEQ ID NO: 80. In some embodiments, an IL-21 polypeptide or a functional fragment or a variant thereof comprises an R9E mutation and comprises at least about 75% sequence identity SEQ ID NO: 80. In some embodiments, an IL-21 polypeptide or a functional fragment or a variant thereof comprises an R9E mutation and comprises at most about 100% sequence identity SEQ ID NO: 80. In some embodiments, an IL-21 polypeptide or a functional fragment or a variant thereof comprises an R9E mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 80. In some embodiments, an IL-21 polypeptide or a functional fragment or a variant thereof comprises an R9E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 80.

In some embodiments, an IL-21 polypeptide or a functional fragment or a variant thereof comprises an R9H mutation and comprises about 75% sequence identity to about 100% sequence identity to SEQ ID NO: 81. In some embodiments, an IL-21 polypeptide or a functional fragment or a variant thereof comprises an R9H mutation and comprises at least about 75% sequence identity SEQ ID NO: 81. In some embodiments, an IL-21 polypeptide or a functional fragment or a variant thereof comprises an R9HE mutation and comprises at most about 100% sequence identity SEQ ID NO: 81. In some embodiments, an IL-21 polypeptide or a functional fragment or a variant thereof comprises an R9H mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 81. In some embodiments, an IL-21 polypeptide or a functional fragment or a variant thereof comprises an R9H mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 81.

In some embodiments, an IL-21 polypeptide or a functional fragment or a variant thereof comprises an R9S mutation and comprises about 75% sequence identity to about 100% sequence identity to SEQ ID NO: 82. In some embodiments, an IL-21 polypeptide or a functional fragment or a variant thereof comprises an R9S mutation and comprises at least about 75% sequence identity SEQ ID NO: 82. In some embodiments, an IL-21 polypeptide or a functional fragment or a variant thereof comprises an R9S mutation and comprises at most about 100% sequence identity SEQ ID NO: 82. In some embodiments, an IL-21 polypeptide or a functional fragment or a variant thereof comprises an R9S mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 82. In some embodiments, an IL-21 polypeptide or a functional fragment or a variant thereof comprises an R9S mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 82.

In some embodiments, an IL-21 polypeptide or a functional fragment or a variant thereof comprises an R9T mutation and comprises about 75% sequence identity to about 100% sequence identity to SEQ ID NO: 83. In some embodiments, an IL-21 polypeptide or a functional fragment or a variant thereof comprises an R9T mutation and comprises at least about 75% sequence identity SEQ ID NO: 83. In some embodiments, an IL-21 polypeptide or a functional fragment or a variant thereof comprises an R9T mutation and comprises at most about 100% sequence identity SEQ ID NO: 83. In some embodiments, an IL-21 polypeptide or a functional fragment or a variant thereof comprises an R9T mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 83. In some embodiments, an IL-21 polypeptide or a functional fragment or a variant thereof comprises an R9T mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 83.

In some embodiments, an IL-21 polypeptide or a functional fragment or a variant thereof comprises an R9N mutation and comprises about 75% sequence identity to about 100% sequence identity to SEQ ID NO: 84. In some embodiments, an IL-21 polypeptide or a functional fragment or a variant thereof comprises an R9N mutation and comprises at least about 75% sequence identity SEQ ID NO: 84.

In some embodiments, an IL-21 polypeptide or a functional fragment or a variant thereof comprises an R9N mutation and comprises at most about 100% sequence identity SEQ ID NO: 84. In some embodiments, an IL-21 polypeptide or a functional fragment or a variant thereof comprises an R9N mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 84. In some embodiments, an IL-21 polypeptide or a functional fragment or a variant thereof comprises an R9N mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 84.

In some embodiments, an IL-21 polypeptide or a functional fragment or a variant thereof comprises an R9G mutation and comprises about 75% sequence identity to about 100% sequence identity to SEQ ID NO: 85. In some embodiments, an IL-21 polypeptide or a functional fragment or a variant thereof comprises an R9G mutation and comprises at least about 75% sequence identity SEQ ID NO: 85. In some embodiments, an IL-21 polypeptide or a functional fragment or a variant thereof comprises an R9G mutation and comprises at most about 100% sequence identity SEQ ID NO: 85. In some embodiments, an IL-21 polypeptide or a functional fragment or a variant thereof comprises an R9G mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 85. In some embodiments, an IL-21 polypeptide or a functional fragment or a variant thereof comprises an R9G mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 85.

In some embodiments, an IL-21 polypeptide or a functional fragment or a variant thereof comprises an R9V mutation and comprises about 75% sequence identity to about 100% sequence identity to SEQ ID NO: 86. In some embodiments, an IL-21 polypeptide or a functional fragment or a variant thereof comprises an R9V mutation and comprises at least about 75% sequence identity SEQ ID NO: 86. In some embodiments, an IL-21 polypeptide or a functional fragment or a variant thereof comprises an R9V mutation and comprises at most about 100% sequence identity SEQ ID NO: 86. In some embodiments, an IL-21 polypeptide or a functional fragment or a variant thereof comprises an R9V mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 86. In some embodiments, an IL-21 polypeptide or a functional fragment or a variant thereof comprises an R9V mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 86.

In some embodiments, an IL-21 polypeptide or a functional fragment or a variant thereof comprises an R9I mutation and comprises about 75% sequence identity to about 100% sequence identity to SEQ ID NO: 87. In some embodiments, an IL-21 polypeptide or a functional fragment or a variant thereof comprises an R9I mutation and comprises at least about 75% sequence identity SEQ ID NO: 87. In some embodiments, an IL-21 polypeptide or a functional fragment or a variant thereof comprises an R9I mutation and comprises at most about 100% sequence identity SEQ ID NO: 87. In some embodiments, an IL-21 polypeptide or a functional fragment or a variant thereof comprises an R9I mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 87. In some embodiments, an IL-21 polypeptide or a functional fragment or a variant thereof comprises an R9I mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 87.

In some embodiments, an IL-21 polypeptide or a functional fragment or a variant thereof comprises an R9L mutation and comprises about 75% sequence identity to about 100% sequence identity to SEQ ID NO: 88. In some embodiments, an IL-21 polypeptide or a functional fragment or a variant thereof comprises an R9L mutation and comprises at least about 75% sequence identity SEQ ID NO: 88. In some embodiments, an IL-21 polypeptide or a functional fragment or a variant thereof comprises an R9L mutation and comprises at most about 100% sequence identity SEQ ID NO: 88. In some embodiments, an IL-21 polypeptide or a functional fragment or a variant thereof comprises an R9L mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 88. In some embodiments, an IL-21 polypeptide or a functional fragment or a variant thereof comprises an R9L mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 88.

In some embodiments, an IL-21 polypeptide or a functional fragment or a variant thereof comprises an R9Y mutation and comprises about 75% sequence identity to about 100% sequence identity to SEQ ID NO: 89. In some embodiments, an IL-21 polypeptide or a functional fragment or a variant thereof comprises an R9Y mutation and comprises at least about 75% sequence identity SEQ ID NO: 89. In some embodiments, an IL-21 polypeptide or a functional fragment or a variant thereof comprises an R9Y mutation and comprises at most about 100% sequence identity SEQ ID NO: 89. In some embodiments, an IL-21 polypeptide or a functional fragment or a variant thereof comprises an R9Y mutation and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 89. In some embodiments, an IL-21 polypeptide or a functional fragment or a variant thereof comprises an R9Y mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 89.

In some embodiments, an IL-21 polypeptide or a functional fragment or a variant thereof comprises K72A and R76F mutations and comprises about 75% sequence identity to about 100% sequence identity to SEQ ID NO: 90. In some embodiments, an IL-21 polypeptide or a functional fragment or a variant thereof comprises K72A and R76F mutations and comprises at least about 75% sequence identity SEQ ID NO:90. In some embodiments, an IL-21 polypeptide or a functional fragment or a variant thereof comprises K72A and R76F mutations and comprises at most about 100% sequence identity SEQ ID NO: 90. In some embodiments, an IL-21 polypeptide or a functional fragment or a variant thereof comprises K72A and R76F mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 90. In some embodiments, an IL-21 polypeptide or a functional fragment or a variant thereof comprises K72A and R76F mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 90.

In some embodiments, an IL-21 polypeptide or a functional fragment or a variant thereof comprises K75A and R76F mutations and comprises about 75% sequence identity to about 100% sequence identity to SEQ ID NO: 91. In some embodiments, an IL-21 polypeptide or a functional fragment or a variant thereof comprises K75A and R76F mutations and comprises at least about 75% sequence identity SEQ ID NO:91. In some embodiments, an IL-21 polypeptide or a functional fragment or a variant thereof comprises K75A and R76F mutations and comprises at most about 100% sequence identity SEQ ID NO: 91. In some embodiments, an IL-21 polypeptide or a functional fragment or a variant thereof comprises K75A and R76F mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 91. In some embodiments, an IL-21 polypeptide or a functional fragment or a variant thereof comprises K75A and R76F mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 91.

In some embodiments, an IL-21 polypeptide or a functional fragment or a variant thereof comprises R76F and K77A mutations and comprises about 75% sequence identity to about 100% sequence identity to SEQ ID NO: 92. In some embodiments, an IL-21 polypeptide or a functional fragment or a variant thereof comprises R76F and K77A mutations and comprises at least about 75% sequence identity SEQ ID NO:92. In some embodiments, an IL-21 polypeptide or a functional fragment or a variant thereof comprises R76F and K77A mutations and comprises at most about 100% sequence identity SEQ ID NO: 92. In some embodiments, an IL-21 polypeptide or a functional fragment or a variant thereof comprises R76F and K77A mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 92. In some embodiments, an IL-21 polypeptide or a functional fragment or a variant thereof comprises R76F and K77A mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 92.

In some embodiments, an IL-21 polypeptide or a functional fragment or a variant thereof comprises K75E and R76F mutations and comprises about 75% sequence identity to about 100% sequence identity to SEQ ID NO: 93. In some embodiments, an IL-21 polypeptide or a functional fragment or a variant thereof comprises K75E and R76F mutations and comprises at least about 75% sequence identity SEQ ID NO:93. In some embodiments, an IL-21 polypeptide or a functional fragment or a variant thereof comprises K75E and R76F mutations and comprises at most about 100% sequence identity SEQ ID NO: 93. In some embodiments, an IL-21 polypeptide or a functional fragment or a variant thereof comprises K75E and R76F mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 93. In some embodiments, an IL-21 polypeptide or a functional fragment or a variant thereof comprises K75E and R76F mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 93.

In some embodiments, an IL-21 polypeptide or a functional fragment or a variant thereof comprises V17I and L74I mutations and comprises about 75% sequence identity to about 100% sequence identity to SEQ ID NO: 374. In some embodiments, an IL-21 polypeptide or a functional fragment or a variant thereof comprises V17I and L74I mutations and comprises at least about 75% sequence identity SEQ ID NO:374. In some embodiments, an IL-21 polypeptide or a functional fragment or a variant thereof comprises V17I and L74I mutations and comprises at most about 100% sequence identity SEQ ID NO: 374. In some embodiments, an IL-21 polypeptide or a functional fragment or a variant thereof comprises V17I and L74I mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 374. In some embodiments, an IL-21 polypeptide or a functional fragment or a variant thereof comprises V17I and L74I mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 374.

In some embodiments, an IL-21 polypeptide or a functional fragment or a variant thereof comprises I16A and L74F mutations and comprises about 75% sequence identity to about 100% sequence identity to SEQ ID NO: 375. In some embodiments, an IL-21 polypeptide or a functional fragment or a variant thereof comprises I16A and L74F mutations and comprises at least about 75% sequence identity SEQ ID NO:375. In some embodiments, an IL-21 polypeptide or a functional fragment or a variant thereof comprises I16A and L74F mutations and comprises at most about 100% sequence identity SEQ ID NO: 375. In some embodiments, an IL-21 polypeptide or a functional fragment or a variant thereof comprises I16A and L74F mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 375. In some embodiments, an IL-21 polypeptide or a functional fragment or a variant thereof comprises I16A and L74F mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 375.

In some embodiments, an IL-21 polypeptide or a functional fragment or a variant thereof comprises I16S, V17I, and L74V mutations and comprises about 75% sequence identity to about 100% sequence identity to SEQ ID NO: 376. In some embodiments, an IL-21 polypeptide or a functional fragment or a variant thereof comprises I16S, V17I, and L74V mutations and comprises at least about 75% sequence identity SEQ ID NO:376. In some embodiments, an IL-21 polypeptide or a functional fragment or a variant thereof comprises I16S, V17I, and L74V mutations and comprises at most about 100% sequence identity SEQ ID NO: 376. In some embodiments, an IL-21 polypeptide or a functional fragment or a variant thereof comprises I16S, V17I, and L74V mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 376. In some embodiments, an IL-21 polypeptide or a functional fragment or a variant thereof comprises I16S, V17I, and L74V mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 376.

In some embodiments, an IL-21 polypeptide or a functional fragment or a variant thereof comprises I16R, V17I, and L74I mutations and comprises about 75% sequence identity to about 100% sequence identity to SEQ ID NO: 377. In some embodiments, an IL-21 polypeptide or a functional fragment or a variant thereof comprises I16R, V17I, and L74I mutations and comprises at least about 75% sequence identity SEQ ID NO:377. In some embodiments, an IL-21 polypeptide or a functional fragment or a variant thereof comprises I16R, V17I, and L74I mutations and comprises at most about 100% sequence identity SEQ ID NO: 377. In some embodiments, an IL-21 polypeptide or a functional fragment or a variant thereof comprises I16R, V17I, and L74I mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 377. In some embodiments, an IL-21 polypeptide or a functional fragment or a variant thereof comprises I16R, V17I, and L74I mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 377.

In some embodiments, an IL-21 polypeptide or a functional fragment or a variant thereof comprises L13F, I16A, V17A and L74M mutations and comprises about 75% sequence identity to about 100% sequence identity to SEQ ID NO: 378. In some embodiments, an IL-21 polypeptide or a functional fragment or a variant thereof comprises L13F, I16A, V17A and L74M mutations and comprises at least about 75% sequence identity SEQ ID NO:378. In some embodiments, an IL-21 polypeptide or a functional fragment or a variant thereof comprises L13F, I16A, V17A and L74M mutations and comprises at most about 100% sequence identity SEQ ID NO: 378. In some embodiments, an IL-21 polypeptide or a functional fragment or a variant thereof comprises L13F, I16A, V17A and L74M mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 378. In some embodiments, an IL-21 polypeptide or a functional fragment or a variant thereof comprises L13F, I16A, V17A and L74M mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 378.

In some embodiments, an IL-21 polypeptide or a functional fragment or a variant thereof comprises L13R, I16A, V17I and L74I mutations and comprises about 75% sequence identity to about 100% sequence identity to SEQ ID NO: 379. In some embodiments, an IL-21 polypeptide or a functional fragment or a variant thereof comprises L13R, I16A, V17I and L74I mutations and comprises at least about 75% sequence identity SEQ ID NO:379. In some embodiments, an IL-21 polypeptide or a functional fragment or a variant thereof comprises L13R, I16A, V17I and L74I mutations and comprises at most about 100% sequence identity SEQ ID NO: 379. In some embodiments, an IL-21 polypeptide or a functional fragment or a variant thereof comprises L13R, I16A, V17I and L74I mutations and comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 379. In some embodiments, an IL-21 polypeptide or a functional fragment or a variant thereof comprises L13R, I16A, V17I and L74I mutations and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 379.

In some embodiments, an IL-21 polypeptide or a functional fragment or a variant thereof comprises a R76E mutation and comprises about 75% sequence identity to about 100% sequence identity to SEQ ID NO: 94. In some embodiments, an IL-21 polypeptide or a functional fragment or a variant thereof comprises a R76E mutation and comprises at least about 75% sequence identity SEQ ID NO: 94. In some embodiments, an IL-21 polypeptide or a functional fragment or a variant thereof comprises a R76E mutation and comprises at most about 100% sequence identity SEQ ID NO: 94. In some embodiments, an IL-21 polypeptide or a functional fragment or a variant thereof comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 94. In some embodiments, an IL-21 polypeptide or a functional fragment or a variant thereof comprises a R76E mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 94.

In some embodiments, an IL-21 polypeptide or a functional fragment or a variant thereof comprises a R76F mutation and comprises about 75% sequence identity to about 100% sequence identity to SEQ ID NO: 95. In some embodiments, an IL-21 polypeptide or a functional fragment or a variant thereof comprises a R76F mutation and comprises at least about 75% sequence identity SEQ ID NO: 95. In some embodiments, an IL-21 polypeptide or a functional fragment or a variant thereof comprises a R76F mutation and comprises at most about 100% sequence identity SEQ ID NO: 95. In some embodiments, an IL-21 polypeptide or a functional fragment or a variant thereof comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 95. In some embodiments, an IL-21 polypeptide or a functional fragment or a variant thereof comprises a R76F mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 95.

In some embodiments, an IL-21 polypeptide or a functional fragment or a variant thereof comprises a R76Q mutation and comprises about 75% sequence identity to about 100% sequence identity to SEQ ID NO: 96. In some embodiments, an IL-21 polypeptide or a functional fragment or a variant thereof comprises a R76Q mutation and comprises at least about 75% sequence identity SEQ ID NO: 96. In some embodiments, an IL-21 polypeptide or a functional fragment or a variant thereof comprises a R76Q mutation and comprises at most about 100% sequence identity SEQ ID NO: 96. In some embodiments, an IL-21 polypeptide or a functional fragment or a variant thereof comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 96. In some embodiments, an IL-21 polypeptide or a functional fragment or a variant thereof comprises a R76Q mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 96.

In some embodiments, an IL-21 polypeptide or a functional fragment or a variant thereof comprises an R9S mutation and comprises about 75% sequence identity to about 100% sequence identity to SEQ ID NO: 97. In some embodiments, an IL-21 polypeptide or a functional fragment or a variant thereof comprises an R9S mutation and comprises at least about 75% sequence identity SEQ ID NO: 97. In some embodiments, an IL-21 polypeptide or a functional fragment or a variant thereof comprises an R9S mutation and comprises at most about 100% sequence identity SEQ ID NO: 97. In some embodiments, an IL-21 polypeptide or a functional fragment or a variant thereof comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 97. In some embodiments, an IL-21 polypeptide or a functional fragment or a variant thereof comprises an R9S mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 97.

In some embodiments, an IL-21 polypeptide or a functional fragment or a variant thereof comprises an R9G mutation and comprises about 75% sequence identity to about 100% sequence identity to SEQ ID NO: 98. In some embodiments, an IL-21 polypeptide or a functional fragment or a variant thereof comprises an R9G mutation and comprises at least about 75% sequence identity SEQ ID NO: 98. In some embodiments, an IL-21 polypeptide or a functional fragment or a variant thereof comprises an R9G mutation and comprises at most about 100% sequence identity SEQ ID NO: 98. In some embodiments, an IL-21 polypeptide or a functional fragment or a variant thereof comprises about 75% sequence identity to about 80% sequence identity, about 75% sequence identity to about 85% sequence identity, about 75% sequence identity to about 90% sequence identity, about 75% sequence identity to about 95% sequence identity, about 75% sequence identity to about 96% sequence identity, about 75% sequence identity to about 97% sequence identity, about 75% sequence identity to about 98% sequence identity, about 75% sequence identity to about 99% sequence identity, about 75% sequence identity to about 100% sequence identity, about 80% sequence identity to about 85% sequence identity, about 80% sequence identity to about 90% sequence identity, about 80% sequence identity to about 95% sequence identity, about 80% sequence identity to about 96% sequence identity, about 80% sequence identity to about 97% sequence identity, about 80% sequence identity to about 98% sequence identity, about 80% sequence identity to about 99% sequence identity, about 80% sequence identity to about 100% sequence identity, about 85% sequence identity to about 90% sequence identity, about 85% sequence identity to about 95% sequence identity, about 85% sequence identity to about 96% sequence identity, about 85% sequence identity to about 97% sequence identity, about 85% sequence identity to about 98% sequence identity, about 85% sequence identity to about 99% sequence identity, about 85% sequence identity to about 100% sequence identity, about 90% sequence identity to about 95% sequence identity, about 90% sequence identity to about 96% sequence identity, about 90% sequence identity to about 97% sequence identity, about 90% sequence identity to about 98% sequence identity, about 90% sequence identity to about 99% sequence identity, about 90% sequence identity to about 100% sequence identity, about 95% sequence identity to about 96% sequence identity, about 95% sequence identity to about 97% sequence identity, about 95% sequence identity to about 98% sequence identity, about 95% sequence identity to about 99% sequence identity, about 95% sequence identity to about 100% sequence identity, about 96% sequence identity to about 97% sequence identity, about 96% sequence identity to about 98% sequence identity, about 96% sequence identity to about 99% sequence identity, about 96% sequence identity to about 100% sequence identity, about 97% sequence identity to about 98% sequence identity, about 97% sequence identity to about 99% sequence identity, about 97% sequence identity to about 100% sequence identity, about 98% sequence identity to about 99% sequence identity, about 98% sequence identity to about 100% sequence identity, or about 99% sequence identity to about 100% sequence identity, to SEQ ID NO: 98. In some embodiments, an IL-21 polypeptide or a functional fragment or a variant thereof comprises an R9G mutation and comprises about 75% sequence identity, about 80% sequence identity, about 85% sequence identity, about 90% sequence identity, about 95% sequence identity, about 96% sequence identity, about 97% sequence identity, about 98% sequence identity, about 99% sequence identity, or about 100% sequence identity to SEQ ID NO: 98.

In some embodiments, an IL-21 polypeptide or a functional fragment or a variant thereof comprises at least 75% sequence identity to SEQ ID NOs: 16-21. In some embodiments, an IL-21 polypeptide comprises at least 80%, at least 85%, at least 90%, at least 95%, at least 96%, at least 97%, at least 98%, at least 99%, or 100% sequence identity to SEQ ID NOs: 16-21. In some embodiments, an IL-21 polypeptide comprises 75-80%, 80-85%, 85-90%, 90-95%, 95-99% sequence identity to SEQ ID NOs: 16-21. In some embodiments, an IL-21 polypeptide comprises a sequence selected from the group consisting of: SEQ ID NOs: 16-21.

In some embodiments, an IL-21 polypeptide or a functional fragment or a variant thereof comprises at least 75% sequence identity to SEQ ID NOs: 16-21, 41-93, and 374-379. In some embodiments, an IL-21 polypeptide comprises at least 80%, at least 85%, at least 90%, at least 95%, at least 96%, at least 97%, at least 98%, at least 99%, or 100% sequence identity to SEQ ID NOs: 16-21, 41-93, and 374-379. In some embodiments, an IL-21 polypeptide comprises 75-80%, 80-85%, 85-90%, 90-95%, 95-99% sequence identity to SEQ ID NOs: 16-21, 41-93, and 374-379. In some embodiments, an IL-21 polypeptide comprises a sequence selected from the group consisting of: SEQ ID NOs: 16-21, 41-93, and 374-379.

In some embodiments, an IL-21 polypeptide or a functional fragment or a variant thereof comprises at least 75% sequence identity to SEQ ID NOs: 94-98. In some embodiments, an IL-21 polypeptide comprises at least 80%, at least 85%, at least 90%, at least 95%, at least 96%, at least 97%, at least 98%, at least 99%, or 100% sequence identity to SEQ ID NOs: 94-98. In some embodiments, an IL-21 polypeptide comprises 75-80%, 80-85%, 85-90%, 90-95%, 95-99% sequence identity to SEQ ID NOs: 94-98. In some embodiments, an IL-21 polypeptide comprises a sequence selected from the group consisting of: SEQ ID NOs: 97-98.

In some embodiments, an IL-21 polypeptide or a functional fragment or a variant thereof comprises at least 75% sequence identity to SEQ ID NOs: 16-21, 41-98, and 374-379. In some embodiments, an IL-21 polypeptide comprises at least 80%, at least 85%, at least 90%, at least 95%, at least 96%, at least 97%, at least 98%, at least 99%, or 100% sequence identity to SEQ ID NOs: 16-21, 41-98, and 374-379. In some embodiments, an IL-21 polypeptide comprises 75-80%, 80-85%, 85-90%, 90-95%, 95-99% sequence identity to SEQ ID NOs: 16-21, 41-98, and 374-379. In some embodiments, an IL-21 polypeptide comprises a sequence selected from the group consisting of: SEQ ID NOs: 16-21, 41-98, and 374-379.

In some embodiments, an IL-21 polypeptide or a functional fragment or a variant thereof comprises at least 75% sequence identity to SEQ ID NO: 16 In some embodiments, an IL-21 polypeptide comprises at least 80%, at least 85%, at least 90%, at least 95%, at least 96%, at least 97%, at least 98%, at least 99%, or 100% sequence identity to SEQ ID NO: 16. In some embodiments, an IL-21 polypeptide comprises 75-80%, 80-85%, 85-90%, 90-95%, 95-99% sequence identity to SEQ ID NO: 16. In some embodiments, an IL-21 polypeptide comprises SEQ ID NO: 16.

In some embodiments, an IL-21 polypeptide or a functional fragment or a variant thereof comprises at least 75% sequence identity to SEQ ID NO: 17. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 17. In some embodiments, an IL-21 polypeptide comprises 75-80%, 80-85%, 85-90%, 90-95%, 95-99% sequence identity to SEQ ID NO: 17. In some embodiments, an IL-21 polypeptide comprises SEQ ID NO: 17.

In some embodiments, an IL-21 polypeptide or a functional fragment or a variant thereof comprises at least 75% sequence identity to SEQ ID NO: 18. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 18. In some embodiments, an IL-21 polypeptide comprises 75-80%, 80-85%, 85-90%, 90-95%, 95-99% sequence identity to SEQ ID NO: 18. In some embodiments, an IL-21 polypeptide comprises SEQ ID NO: 18.

In some embodiments, an IL-21 polypeptide or a functional fragment or a variant thereof comprises at least 75% sequence identity to SEQ ID NO: 19. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 19. In some embodiments, an IL-21 polypeptide comprises 75-80%, 80-85%, 85-90%, 90-95%, 95-99% sequence identity to SEQ ID NO: 19. In some embodiments, an IL-21 polypeptide comprises SEQ ID NO: 19.

In some embodiments, an IL-21 polypeptide or a functional fragment or a variant thereof comprises at least 75% sequence identity to SEQ ID NO: 20. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 20. In some embodiments, an IL-21 polypeptide comprises 75-80%, 80-85%, 85-90%, 90-95%, 95-99% sequence identity to SEQ ID NO: 20. In some embodiments, an IL-21 polypeptide comprises SEQ ID NO: 20.

In some embodiments, an IL-21 polypeptide or a functional fragment or a variant thereof comprises at least 75% sequence identity to SEQ ID NO: 21. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 21. In some embodiments, an IL-21 polypeptide comprises 75-80%, 80-85%, 85-90%, 90-95%, 95-99% sequence identity to SEQ ID NO: 21. In some embodiments, an IL-21 polypeptide SEQ ID NO: 21.

In some embodiments, an IL-21 polypeptide or a functional fragment or a variant thereof comprises at least 75% sequence identity to SEQ ID NO: 41. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 41. In some embodiments, an IL-21 polypeptide comprises 75-80%, 80-85%, 85-90%, 90-95%, 95-99% sequence identity to SEQ ID NO: 41. In some embodiments, an IL-21 polypeptide SEQ ID NO: 41.

In some embodiments, an IL-21 polypeptide or a functional fragment or a variant thereof comprises at least 75% sequence identity to SEQ ID NO: 42. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 42. In some embodiments, an IL-21 polypeptide comprises 75-80%, 80-85%, 85-90%, 90-95%, 95-99% sequence identity to SEQ ID NO: 42. In some embodiments, an IL-21 polypeptide SEQ ID NO: 42.

In some embodiments, an IL-21 polypeptide or a functional fragment or a variant thereof comprises at least 75% sequence identity to SEQ ID NO: 43. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 43. In some embodiments, an IL-21 polypeptide comprises 75-80%, 80-85%, 85-90%, 90-95%, 95-99% sequence identity to SEQ ID NO: 43. In some embodiments, an IL-21 polypeptide SEQ ID NO: 43.

In some embodiments, an IL-21 polypeptide or a functional fragment or a variant thereof comprises at least 75% sequence identity to SEQ ID NO: 44. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 44. In some embodiments, an IL-21 polypeptide comprises 75-80%, 80-85%, 85-90%, 90-95%, 95-99% sequence identity to SEQ ID NO: 44. In some embodiments, an IL-21 polypeptide SEQ ID NO: 44.

In some embodiments, an IL-21 polypeptide or a functional fragment or a variant thereof comprises at least 75% sequence identity to SEQ ID NO: 45. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 45. In some embodiments, an IL-21 polypeptide comprises 75-80%, 80-85%, 85-90%, 90-95%, 95-99% sequence identity to SEQ ID NO: 45. In some embodiments, an IL-21 polypeptide SEQ ID NO: 45.

In some embodiments, an IL-21 polypeptide or a functional fragment or a variant thereof comprises at least 75% sequence identity to SEQ ID NO: 46 In some embodiments, an IL-21 polypeptide comprises at least 80%, at least 85%, at least 90%, at least 95%, at least 96%, at least 97%, at least 98%, at least 99%, or 100% sequence identity to SEQ ID NO: 46. In some embodiments, an IL-21 polypeptide comprises 75-80%, 80-85%, 85-90%, 90-95%, 95-99% sequence identity to SEQ ID NO: 46. In some embodiments, an IL-21 polypeptide SEQ ID NO: 46.

In some embodiments, an IL-21 polypeptide or a functional fragment or a variant thereof comprises at least 75% sequence identity to SEQ ID NO: 47. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 47. In some embodiments, an IL-21 polypeptide comprises 75-80%, 80-85%, 85-90%, 90-95%, 95-99% sequence identity to SEQ ID NO: 47. In some embodiments, an IL-21 polypeptide SEQ ID NO: 47.

In some embodiments, an IL-21 polypeptide or a functional fragment or a variant thereof comprises at least 75% sequence identity to SEQ ID NO: 48. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 48. In some embodiments, an IL-21 polypeptide comprises 75-80%, 80-85%, 85-90%, 90-95%, 95-99% sequence identity to SEQ ID NO: 48. In some embodiments, an IL-21 polypeptide SEQ ID NO: 48.

In some embodiments, an IL-21 polypeptide or a functional fragment or a variant thereof comprises at least 75% sequence identity to SEQ ID NO: 49. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 49. In some embodiments, an IL-21 polypeptide comprises 75-80%, 80-85%, 85-90%, 90-95%, 95-99% sequence identity to SEQ ID NO: 49. In some embodiments, an IL-21 polypeptide SEQ ID NO: 49.

In some embodiments, an IL-21 polypeptide or a functional fragment or a variant thereof comprises at least 75% sequence identity to SEQ ID NO: 50. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 50. In some embodiments, an IL-21 polypeptide comprises 75-80%, 80-85%, 85-90%, 90-95%, 95-99% sequence identity to SEQ ID NO: 50. In some embodiments, an IL-21 polypeptide SEQ ID NO: 50.

In some embodiments, an IL-21 polypeptide or a functional fragment or a variant thereof comprises at least 75% sequence identity to SEQ ID NO: 51. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 51. In some embodiments, an IL-21 polypeptide comprises 75-80%, 80-85%, 85-90%, 90-95%, 95-99% sequence identity to SEQ ID NO:5. In some embodiments, an IL-21 polypeptide SEQ ID NO: 51.

In some embodiments, an IL-21 polypeptide or a functional fragment or a variant thereof comprises at least 75% sequence identity to SEQ ID NO: 52. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 52. In some embodiments, an IL-21 polypeptide comprises 75-80%, 80-85%, 85-90%, 90-95%, 95-99% sequence identity to SEQ ID NO: 52. In some embodiments, an IL-21 polypeptide SEQ ID NO: 52.

In some embodiments, an IL-21 polypeptide or a functional fragment or a variant thereof comprises at least 75% sequence identity to SEQ ID NO: 53. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 53. In some embodiments, an IL-21 polypeptide comprises 75-80%, 80-85%, 85-90%, 90-95%, 95-99% sequence identity to SEQ ID NO: 53. In some embodiments, an IL-21 polypeptide SEQ ID NO: 53.

In some embodiments, an IL-21 polypeptide or a functional fragment or a variant thereof comprises at least 75% sequence identity to SEQ ID NO: 54. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 54. In some embodiments, an IL-21 polypeptide comprises 75-80%, 80-85%, 85-90%, 90-95%, 95-99% sequence identity to SEQ ID NO: 54. In some embodiments, an IL-21 polypeptide SEQ ID NO: 54.

In some embodiments, an IL-21 polypeptide or a functional fragment or a variant thereof comprises at least 75% sequence identity to SEQ ID NO: 55. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 55. In some embodiments, an IL-21 polypeptide comprises 75-80%, 80-85%, 85-90%, 90-95%, 95-99% sequence identity to SEQ ID NO: 55. In some embodiments, an IL-21 polypeptide SEQ ID NO: 55.

In some embodiments, an IL-21 polypeptide or a functional fragment or a variant thereof comprises at least 75% sequence identity to SEQ ID NO: 56. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 56. In some embodiments, an IL-21 polypeptide comprises 75-80%, 80-85%, 85-90%, 90-95%, 95-99% sequence identity to SEQ ID NO: 56. In some embodiments, an IL-21 polypeptide SEQ ID NO: 56.

In some embodiments, an IL-21 polypeptide or a functional fragment or a variant thereof comprises at least 75% sequence identity to SEQ ID NO: 57. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 57. In some embodiments, an IL-21 polypeptide comprises 75-80%, 80-85%, 85-90%, 90-95%, 95-99% sequence identity to SEQ ID NO: 57. In some embodiments, an IL-21 polypeptide SEQ ID NO: 57.

In some embodiments, an IL-21 polypeptide or a functional fragment or a variant thereof comprises at least 75% sequence identity to SEQ ID NO: 58. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 58. In some embodiments, an IL-21 polypeptide comprises 75-80%, 80-85%, 85-90%, 90-95%, 95-99% sequence identity to SEQ ID NO: 58. In some embodiments, an IL-21 polypeptide SEQ ID NO: 58.

In some embodiments, an IL-21 polypeptide or a functional fragment or a variant thereof comprises at least 75% sequence identity to SEQ ID NO: 59. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 59. In some embodiments, an IL-21 polypeptide comprises 75-80%, 80-85%, 85-90%, 90-95%, 95-99% sequence identity to SEQ ID NO: 59. In some embodiments, an IL-21 polypeptide SEQ ID NO: 59.

In some embodiments, an IL-21 polypeptide or a functional fragment or a variant thereof comprises at least 75% sequence identity to SEQ ID NO: 60. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 60. In some embodiments, an IL-21 polypeptide comprises 75-80%, 80-85%, 85-90%, 90-95%, 95-99% sequence identity to SEQ ID NO: 60. In some embodiments, an IL-21 polypeptide SEQ ID NO: 60.

In some embodiments, an IL-21 polypeptide or a functional fragment or a variant thereof comprises at least 75% sequence identity to SEQ ID NO: 61. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 61. In some embodiments, an IL-21 polypeptide comprises 75-80%, 80-85%, 85-90%, 90-95%, 95-99% sequence identity to SEQ ID NO: 61. In some embodiments, an IL-21 polypeptide SEQ ID NO: 61.

In some embodiments, an IL-21 polypeptide or a functional fragment or a variant thereof comprises at least 75% sequence identity to SEQ ID NO: 62. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 62. In some embodiments, an IL-21 polypeptide comprises 75-80%, 80-85%, 85-90%, 90-95%, 95-99% sequence identity to SEQ ID NO: 62. In some embodiments, an IL-21 polypeptide SEQ ID NO: 62.

In some embodiments, an IL-21 polypeptide or a functional fragment or a variant thereof comprises at least 75% sequence identity to SEQ ID NO: 63. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 63. In some embodiments, an IL-21 polypeptide comprises 75-80%, 80-85%, 85-90%, 90-95%, 95-99% sequence identity to SEQ ID NO: 63. In some embodiments, an IL-21 polypeptide SEQ ID NO: 63.

In some embodiments, an IL-21 polypeptide or a functional fragment or a variant thereof comprises at least 75% sequence identity to SEQ ID NO: 64. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 64. In some embodiments, an IL-21 polypeptide comprises 75-80%, 80-85%, 85-90%, 90-95%, 95-99% sequence identity to SEQ ID NO: 64. In some embodiments, an IL-21 polypeptide SEQ ID NO: 64.

In some embodiments, an IL-21 polypeptide or a functional fragment or a variant thereof comprises at least 75% sequence identity to SEQ ID NO: 65. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 65. In some embodiments, an IL-21 polypeptide comprises 75-80%, 80-85%, 85-90%, 90-95%, 95-99% sequence identity to SEQ ID NO: 65. In some embodiments, an IL-21 polypeptide SEQ ID NO: 65.

In some embodiments, an IL-21 polypeptide or a functional fragment or a variant thereof comprises at least 75% sequence identity to SEQ ID NO: 66. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 66. In some embodiments, an IL-21 polypeptide comprises 75-80%, 80-85%, 85-90%, 90-95%, 95-99% sequence identity to SEQ ID NO: 66. In some embodiments, an IL-21 polypeptide SEQ ID NO: 66.

In some embodiments, an IL-21 polypeptide or a functional fragment or a variant thereof comprises at least 75% sequence identity to SEQ ID NO: 67. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 67. In some embodiments, an IL-21 polypeptide comprises 75-80%, 80-85%, 85-90%, 90-95%, 95-99% sequence identity to SEQ ID NO: 67. In some embodiments, an IL-21 polypeptide SEQ ID NO: 67.

In some embodiments, an IL-21 polypeptide or a functional fragment or a variant thereof comprises at least 75% sequence identity to SEQ ID NO: 68. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 68. In some embodiments, an IL-21 polypeptide comprises 75-80%, 80-85%, 85-90%, 90-95%, 95-99% sequence identity to SEQ ID NO: 68. In some embodiments, an IL-21 polypeptide SEQ ID NO: 68.

In some embodiments, an IL-21 polypeptide or a functional fragment or a variant thereof comprises at least 75% sequence identity to SEQ ID NO: 69. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 69. In some embodiments, an IL-21 polypeptide comprises 75-80%, 80-85%, 85-90%, 90-95%, 95-99% sequence identity to SEQ ID NO: 69. In some embodiments, an IL-21 polypeptide SEQ ID NO: 69.

In some embodiments, an IL-21 polypeptide or a functional fragment or a variant thereof comprises at least 75% sequence identity to SEQ ID NO: 70. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 70. In some embodiments, an IL-21 polypeptide comprises 75-80%, 80-85%, 85-90%, 90-95%, 95-99% sequence identity to SEQ ID NO: 70. In some embodiments, an IL-21 polypeptide SEQ ID NO: 70.

In some embodiments, an IL-21 polypeptide or a functional fragment or a variant thereof comprises at least 75% sequence identity to SEQ ID NO: 71. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 71. In some embodiments, an IL-21 polypeptide comprises 75-80%, 80-85%, 85-90%, 90-95%, 95-99% sequence identity to SEQ ID NO: 71. In some embodiments, an IL-21 polypeptide SEQ ID NO: 71.

In some embodiments, an IL-21 polypeptide or a functional fragment or a variant thereof comprises at least 75% sequence identity to SEQ ID NO: 72. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 72. In some embodiments, an IL-21 polypeptide comprises 75-80%, 80-85%, 85-90%, 90-95%, 95-99% sequence identity to SEQ ID NO: 72. In some embodiments, an IL-21 polypeptide SEQ ID NO: 72.

In some embodiments, an IL-21 polypeptide or a functional fragment or a variant thereof comprises at least 75% sequence identity to SEQ ID NO: 73. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 73. In some embodiments, an IL-21 polypeptide comprises 75-80%, 80-85%, 85-90%, 90-95%, 95-99% sequence identity to SEQ ID NO: 73. In some embodiments, an IL-21 polypeptide SEQ ID NO: 73.

In some embodiments, an IL-21 polypeptide or a functional fragment or a variant thereof comprises at least 75% sequence identity to SEQ ID NO: 74. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 74. In some embodiments, an IL-21 polypeptide comprises 75-80%, 80-85%, 85-90%, 90-95%, 95-99% sequence identity to SEQ ID NO: 74. In some embodiments, an IL-21 polypeptide SEQ ID NO: 74.

In some embodiments, an IL-21 polypeptide or a functional fragment or a variant thereof comprises at least 75% sequence identity to SEQ ID NO: 75. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 75. In some embodiments, an IL-21 polypeptide comprises 75-80%, 80-85%, 85-90%, 90-95%, 95-99% sequence identity to SEQ ID NO: 75. In some embodiments, an IL-21 polypeptide SEQ ID NO: 75.

In some embodiments, an IL-21 polypeptide or a functional fragment or a variant thereof comprises at least 75% sequence identity to SEQ ID NO: 76. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 76. In some embodiments, an IL-21 polypeptide comprises 75-80%, 80-85%, 85-90%, 90-95%, 95-99% sequence identity to SEQ ID NO: 76. In some embodiments, an IL-21 polypeptide SEQ ID NO: 76.

In some embodiments, an IL-21 polypeptide or a functional fragment or a variant thereof comprises at least 75% sequence identity to SEQ ID NO: 77. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 77. In some embodiments, an IL-21 polypeptide comprises 75-80%, 80-85%, 85-90%, 90-95%, 95-99% sequence identity to SEQ ID NO: 77. In some embodiments, an IL-21 polypeptide SEQ ID NO: 77.

In some embodiments, an IL-21 polypeptide or a functional fragment or a variant thereof comprises at least 75% sequence identity to SEQ ID NO: 78. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 78. In some embodiments, an IL-21 polypeptide comprises 75-80%, 80-85%, 85-90%, 90-95%, 95-99% sequence identity to SEQ ID NO: 78. In some embodiments, an IL-21 polypeptide SEQ ID NO: 78.

In some embodiments, an IL-21 polypeptide or a functional fragment or a variant thereof comprises at least 75% sequence identity to SEQ ID NO: 79. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 79. In some embodiments, an IL-21 polypeptide comprises 75-80%, 80-85%, 85-90%, 90-95%, 95-99% sequence identity to SEQ ID NO: 79. In some embodiments, an IL-21 polypeptide SEQ ID NO: 79.

In some embodiments, an IL-21 polypeptide or a functional fragment or a variant thereof comprises at least 75% sequence identity to SEQ ID NO: 80. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 80. In some embodiments, an IL-21 polypeptide comprises 75-80%, 80-85%, 85-90%, 90-95%, 95-99% sequence identity to SEQ ID NO: 80. In some embodiments, an IL-21 polypeptide SEQ ID NO: 80.

In some embodiments, an IL-21 polypeptide or a functional fragment or a variant thereof comprises at least 75% sequence identity to SEQ ID NO: 81. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 81. In some embodiments, an IL-21 polypeptide comprises 75-80%, 80-85%, 85-90%, 90-95%, 95-99% sequence identity to SEQ ID NO: 81. In some embodiments, an IL-21 polypeptide SEQ ID NO: 81.

In some embodiments, an IL-21 polypeptide or a functional fragment or a variant thereof comprises at least 75% sequence identity to SEQ ID NO: 82. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 82. In some embodiments, an IL-21 polypeptide comprises 75-80%, 80-85%, 85-90%, 90-95%, 95-99% sequence identity to SEQ ID NO: 82. In some embodiments, an IL-21 polypeptide SEQ ID NO: 82.

In some embodiments, an IL-21 polypeptide or a functional fragment or a variant thereof comprises at least 75% sequence identity to SEQ ID NO: 83. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 83. In some embodiments, an IL-21 polypeptide comprises 75-80%, 80-85%, 85-90%, 90-95%, 95-99% sequence identity to SEQ ID NO: 83. In some embodiments, an IL-21 polypeptide SEQ ID NO: 83.

In some embodiments, an IL-21 polypeptide or a functional fragment or a variant thereof comprises at least 75% sequence identity to SEQ ID NO: 84. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 84. In some embodiments, an IL-21 polypeptide comprises 75-80%, 80-85%, 85-90%, 90-95%, 95-99% sequence identity to SEQ ID NO: 84. In some embodiments, an IL-21 polypeptide SEQ ID NO: 84.

In some embodiments, an IL-21 polypeptide or a functional fragment or a variant thereof comprises at least 75% sequence identity to SEQ ID NO: 85. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 85. In some embodiments, an IL-21 polypeptide comprises 75-80%, 80-85%, 85-90%, 90-95%, 95-99% sequence identity to SEQ ID NO: 85. In some embodiments, an IL-21 polypeptide SEQ ID NO: 85.

In some embodiments, an IL-21 polypeptide or a functional fragment or a variant thereof comprises at least 75% sequence identity to SEQ ID NO: 86. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 86. In some embodiments, an IL-21 polypeptide comprises 75-80%, 80-85%, 85-90%, 90-95%, 95-99% sequence identity to SEQ ID NO: 86. In some embodiments, an IL-21 polypeptide SEQ ID NO: 86.

In some embodiments, an IL-21 polypeptide or a functional fragment or a variant thereof comprises at least 75% sequence identity to SEQ ID NO: 87. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 87. In some embodiments, an IL-21 polypeptide comprises 75-80%, 80-85%, 85-90%, 90-95%, 95-99% sequence identity to SEQ ID NO: 87. In some embodiments, an IL-21 polypeptide SEQ ID NO: 87.

In some embodiments, an IL-21 polypeptide or a functional fragment or a variant thereof comprises at least 75% sequence identity to SEQ ID NO: 88. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 88. In some embodiments, an IL-21 polypeptide comprises 75-80%, 80-85%, 85-90%, 90-95%, 95-99% sequence identity to SEQ ID NO: 88. In some embodiments, an IL-21 polypeptide SEQ ID NO: 88.

In some embodiments, an IL-21 polypeptide or a functional fragment or a variant thereof comprises at least 75% sequence identity to SEQ ID NO: 89. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 89. In some embodiments, an IL-21 polypeptide comprises 75-80%, 80-85%, 85-90%, 90-95%, 95-99% sequence identity to SEQ ID NO: 89. In some embodiments, an IL-21 polypeptide SEQ ID NO: 89.

In some embodiments, an IL-21 polypeptide or a functional fragment or a variant thereof comprises at least 75% sequence identity to SEQ ID NO: 90. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 90. In some embodiments, an IL-21 polypeptide comprises 75-80%, 80-85%, 85-90%, 90-95%, 95-99% sequence identity to SEQ ID NO: 90. In some embodiments, an IL-21 polypeptide SEQ ID NO: 90.

In some embodiments, an IL-21 polypeptide or a functional fragment or a variant thereof comprises at least 75% sequence identity to SEQ ID NO: 91. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 91. In some embodiments, an IL-21 polypeptide comprises 75-80%, 80-85%, 85-90%, 90-95%, 95-99% sequence identity to SEQ ID NO: 91. In some embodiments, an IL-21 polypeptide SEQ ID NO: 91.

In some embodiments, an IL-21 polypeptide or a functional fragment or a variant thereof comprises at least 75% sequence identity to SEQ ID NO: 92. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 92. In some embodiments, an IL-21 polypeptide comprises 75-80%, 80-85%, 85-90%, 90-95%, 95-99% sequence identity to SEQ ID NO: 92. In some embodiments, an IL-21 polypeptide SEQ ID NO: 92.

In some embodiments, an IL-21 polypeptide or a functional fragment or a variant thereof comprises at least 75% sequence identity to SEQ ID NO: 93. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 93. In some embodiments, an IL-21 polypeptide comprises 75-80%, 80-85%, 85-90%, 90-95%, 95-99% sequence identity to SEQ ID NO: 93. In some embodiments, an IL-21 polypeptide SEQ ID NO: 93.

In some embodiments, an IL-21 polypeptide or a functional fragment or a variant thereof comprises at least 75% sequence identity to SEQ ID NO: 94. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 94. In some embodiments, an IL-21 polypeptide comprises 75-80%, 80-85%, 85-90%, 90-95%, 95-99% sequence identity to SEQ ID NO: 94. In some embodiments, an IL-21 polypeptide SEQ ID NO: 94.

In some embodiments, an IL-21 polypeptide or a functional fragment or a variant thereof comprises at least 75% sequence identity to SEQ ID NO: 95. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 95. In some embodiments, an IL-21 polypeptide comprises 75-80%, 80-85%, 85-90%, 90-95%, 95-99% sequence identity to SEQ ID NO: 95. In some embodiments, an IL-21 polypeptide SEQ ID NO: 95.

In some embodiments, an IL-21 polypeptide or a functional fragment or a variant thereof comprises at least 75% sequence identity to SEQ ID NO: 96. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 96. In some embodiments, an IL-21 polypeptide comprises 75-80%, 80-85%, 85-90%, 90-95%, 95-99% sequence identity to SEQ ID NO: 96. In some embodiments, an IL-21 polypeptide SEQ ID NO: 96.

In some embodiments, an IL-21 polypeptide or a functional fragment or a variant thereof comprises at least 75% sequence identity to SEQ ID NO: 97. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 97. In some embodiments, an IL-21 polypeptide comprises 75-80%, 80-85%, 85-90%, 90-95%, 95-99% sequence identity to SEQ ID NO: 97. In some embodiments, an IL-21 polypeptide SEQ ID NO: 97.

In some embodiments, an IL-21 polypeptide or a functional fragment or a variant thereof comprises at least 75% sequence identity to SEQ ID NO: 98. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 98. In some embodiments, an IL-21 polypeptide comprises 75-80%, 80-85%, 85-90%, 90-95%, 95-99% sequence identity to SEQ ID NO: 98. In some embodiments, an IL-21 polypeptide SEQ ID NO: 98.

In some embodiments, an IL-21 polypeptide or a functional fragment or a variant thereof comprises at least 75% sequence identity to SEQ ID NO: 374. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 374. In some embodiments, an IL-21 polypeptide comprises 75-80%, 80-85%, 85-90%, 90-95%, 95-99% sequence identity to SEQ ID NO: 374. In some embodiments, an IL-21 polypeptide SEQ ID NO: 374.

In some embodiments, an IL-21 polypeptide or a functional fragment or a variant thereof comprises at least 75% sequence identity to SEQ ID NO: 375. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 375. In some embodiments, an IL-21 polypeptide comprises 75-80%, 80-85%, 85-90%, 90-95%, 95-99% sequence identity to SEQ ID NO: 375. In some embodiments, an IL-21 polypeptide SEQ ID NO: 375.

In some embodiments, an IL-21 polypeptide or a functional fragment or a variant thereof comprises at least 75% sequence identity to SEQ ID NO: 376. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 376. In some embodiments, an IL-21 polypeptide comprises 75-80%, 80-85%, 85-90%, 90-95%, 95-99% sequence identity to SEQ ID NO: 376. In some embodiments, an IL-21 polypeptide SEQ ID NO: 376.

In some embodiments, an IL-21 polypeptide or a functional fragment or a variant thereof comprises at least 75% sequence identity to SEQ ID NO: 377. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 377. In some embodiments, an IL-21 polypeptide comprises 75-80%, 80-85%, 85-90%, 90-95%, 95-99% sequence identity to SEQ ID NO: 377. In some embodiments, an IL-21 polypeptide SEQ ID NO: 377.

In some embodiments, an IL-21 polypeptide or a functional fragment or a variant thereof comprises at least 75% sequence identity to SEQ ID NO: 378. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 378. In some embodiments, an IL-21 polypeptide comprises 75-80%, 80-85%, 85-90%, 90-95%, 95-99% sequence identity to SEQ ID NO: 378. In some embodiments, an IL-21 polypeptide SEQ ID NO: 378.

In some embodiments, an IL-21 polypeptide or a functional fragment or a variant thereof comprises at least 75% sequence identity to SEQ ID NO: 379. In some embodiments, an IL-21 polypeptide comprises at least 80%, at least 85%, at least 90%, at least 95%, at least 96%, at least 97%, at least 98%, at least 99%, or 100% sequence identity to SEQ ID NO: 379. In some embodiments, an IL-21 polypeptide comprises 75-80%, 80-85%, 85-90%, 90-95%, 95-99% sequence identity to SEQ ID NO: 379. In some embodiments, an IL-21 polypeptide SEQ ID NO: 379.

Antigen Binding Protein or Functional Fragments Thereof

Some embodiments of this disclosure provides a targeted cytokine construct comprising an antigen binding protein (e.g., an antibody or an antigen binding fragment thereof) as a targeting protein and an IL-21 polypeptide as disclosed herein. The antigen binding protein or a functional fragment thereof can, in some embodiments, specifically bind to CD8+ T cells and comprise specificity to at least one antigen selected from the group consisting of CD8-alpha (CD8α or CD8a), CD8-beta (CD8-β), CD8-αα, or CD8-αβ. As provided herein, the term "CD8-alpha" can be used interchangeably with "CD8α" or "CD8a". As provided herein, the term "CD8-beta" can be used interchangeably with the terms "CD8-β" or "CD8b". As provided herein the term "CD8-αα" can be used interchangeably with "CD8aa". As provided herein the term "CD8-αβ" can be used interchangeably with "CD8ab". In some embodiments, the antibody or antigen binding fragment thereof may specifically bind to a different antigen, such as an immune checkpoint protein.

In some embodiments, the antigen binding protein or functional fragment thereof comprises an antigen binding domain selected from the group consisting of an scFv, a single domain antibody, VHH, VNAR, sdAbs, nanobody, or a functional fragment thereof.

In some embodiments, the antigen binding protein or a functional fragment thereof comprises a full-length intact antibody. The full-length intact antibody can comprise: a first polypeptide, arranged from N-to-C terminus, comprising: variable light chain (VL) amino acid sequence, and a light chain constant region amino acid sequence (CL1); a second polypeptide, arranged from N-to-C terminus, comprising: a variable heavy chain (VH) amino acid sequence, a heavy chain CH1 constant region amino acid sequence, a hinge region amino acid sequence, a heavy chain CH2 constant region amino acid sequence, and a heavy chain CH3 constant region amino acid sequence; a third polypeptide, arranged from N-to-C terminus, comprising: a variable heavy chain (VH) amino acid sequence, a heavy chain CH1 constant region amino acid sequence, a hinge region amino acid sequence, a heavy chain CH2 constant region amino acid sequence, and a heavy chain CH3 constant region amino acid sequence; and a fourth polypeptide, arranged from N-to-C terminus, comprising: a variable light chain (VL) amino acid sequence, and a light chain constant amino acid sequence (CL1), wherein the CH2 and CH3 domains of each of the second and third polypeptides form an Fc domain.

In some embodiments, the antigen binding protein or a functional fragment thereof comprises: i) a first polypeptide, arranged from N-to-C terminus, comprising: a variable light chain (VL) amino acid sequence; and a light chain constant region amino acid sequence (CL1) domain; ii) a second polypeptide, arranged from N-to-C terminus, comprising: a variable heavy chain (VH) amino acid sequence, a heavy chain CH1 constant region amino acid sequence, a hinge region amino acid sequence, a heavy chain CH2 constant region amino acid sequence, and a heavy chain CH3 constant region amino acid sequence; and iii) a third polypeptide, arranged from N-to-C terminus, comprising: a hinge region amino acid sequence, a heavy chain CH2 constant region amino acid sequence, and a heavy chain CH3 constant region amino acid sequence, wherein the CH2 and CH3 domains of each of the second and third polypeptides form an Fc domain.

In some embodiments, the Fe domain is a human IgG Fe domain. In some embodiments, the Fe domain is an IgG1, IgG2, IgG3, or IgG4 Fe domain. In some embodiments, the Fe domain comprises one or more modifications that promote heterodimerization. In some embodiments, the second polypeptide comprises a knob modification in the CH2 or the CH3 domain, and the third polypeptide comprises a hole modification in the CH2 or the CH3 domain; or wherein the third polypeptide comprises a knob modification in the CH2 or the CH3 domain and the second polypeptide comprises a hole modification in the CH2 or the CH3 domain. In some embodiments, the second polypeptide comprises a knob modification in the CH3 domain, and the third polypeptide comprises a hole modification in the CH3 domain; or wherein the third polypeptide comprises a knob modification in the CH3 domain and the second polypeptide comprises a hole modification in the CH3 domain.

In some embodiments, the antigen binding protein or functional fragment thereof is a monovalent or bivalent antibody. In some embodiments, the bivalent antibody is monospecific or bispecific. In some embodiments, the antigen binding protein or functional fragment thereof is a humanized antibody or a functional fragment thereof.

A bispecific antibody can comprise two antigen binding arms, wherein the two antigen binding arms recognize different antigens. In some embodiments, the first or the second antigen binding arm independently binds to an immune checkpoint protein. In some embodiments, the immune checkpoint protein is selected from the group consisting of PD-1, CD28, CTLA-4, ICOS, TMIGD2, 4-1BB, BTLA, CD160, LIGHT, LAG3, OX40, CD27, CD39, CD73, CD40L, GITR, DNAM-1, TIGIT, CD96, 2B4, TIM-3, CEACAM1, SIRPα, DC-SIGN, CD200R, DR3, PD-L1, PD-L2, CD80, CD86, ICOS ligand, B7-H3, B7-H4, VISTA, B7-H7(HHLA2), 4-1BBL, HVEM, OX40L, CD70, CD40, GITRL, CD155, CD48, Galectin-9, Adenosine, IDO, TDO, CD47, BTN2A1, CD200, LAYN, LAIR1, CD276, VTCN1, KIR, A2AR, MHC class I, MHC class II, GALS, TGFR, TREM1, TREM2, HLA-G, CCR4, CCR8, CSF1R, MICA/B, LILRB4, SIGLEC-15, arginase and TL1A. In some embodiments, the first antigen binding arm binds to PD-1. In some embodiments, the first or the second antigen binding arm independently binds to CD8α, CD8αα, CD8αβ or CD8β.

In some embodiments, the antigen binding molecules of the present disclosure bind to an epitope on CD8a wherein the binding of the antigen binding molecule to CD8a does not block the interaction of CD8aa or CD8ab with MHC class I molecules on target cells or antigen presenting cells. In some embodiments, the antigen binding molecule of the present disclosure binds to an epitope on CD8b wherein the binding of the antigen binding molecule to CD8b does not block the interaction of CD8ab with MHC class I molecules on target cells or antigen presenting cells.

In some embodiments, the fusion protein binds human CD8, and the binding of the fusion protein to CD8 does not block the interaction of CD8 with MHC class I. In some embodiments, the antigen binding molecule of the present disclosure binds to an epitope on CD8ab wherein the binding of the antigen binding molecule to CD8ab does not block the interaction of CD8aa or CD8ab with MHC class I molecules on target cells or antigen presenting cells. In some embodiments, the antigen binding molecule of the present disclosure binds to an epitope on CD8a wherein the binding of the antigen binding molecule to CD8a does not block the interaction of CD8ab with MHC class I molecules on target cells or antigen presenting cells.

In some embodiments, the fusion protein binds human CD8, and the binding of the fusion protein to CD8 does not block the interaction of CD8 with MHC class I. In some embodiments, the antigen binding molecule of the present disclosure binds to an epitope on CD8α wherein the binding of the antigen binding molecule to CD8α does not block the interaction of CD8αα or CD8αβ with MHC class I molecules on target cells or antigen presenting cells. In some embodiments, the antigen binding molecule of the present disclosure binds to an epitope on CD8β wherein the binding of the antigen binding molecule to CD8β does not block the interaction of CD8αβ with MHC class I molecules on target cells or antigen presenting cells. In some embodiments, whether an anti-CD8 antibody or fusion protein of the present disclosure blocks the interaction of CD8 with MHC class I can be assayed, e.g., by assaying activation status of CD8+ T cells (e.g., upon antigen stimulation) in the presence or absence of the anti-CD8 antibody or fusion protein.

In some embodiments, an anti-CD8 antibody or fusion protein of the present disclosure comprises a VH domain comprising the sequence of EVQLVESGG-GLVQPGRSLKLSCAASGFTFSNYYMAWVRQAPTK-GLEWVAYINTGGGTTY YRDSVKGRFTISRDDAKST-LYLQMDSLRSEDTATYYCTTAIGYYFDYWGQGVM-VTVSS (SEQ ID NO:99) and a VL domain comprising the sequence of DIQLTQSPASLSASLGETVSIECLASEDIY-SYLAWYQQKPGKSPQVLIYAANRLQDGVPSRF SGSGSGTQYSLKISGMQPEDEGDYFCLQGSKFPY-TFGAGTKLELK (SEQ ID NO:100). In some embodiments, an anti-CD8 antibody or fusion protein of the present disclosure comprises a VH domain comprising the sequence of EVKLQESGPSLVQPSQTLSLTCSVSGFSLIS-DSVHWVRQPPGKGLEWMGGIWADGSTDYNS ALKSRLSISRDTSKSQGFLKMNSLQTDDTAIYFCTSN-RESYYFDYWGQGTMVTVSS (SEQ ID NO:101) and a VL domain comprising the sequence of DIQMTQSPASL-SASLGDKVTITCQASQNIDKYIAWYQQKPGKAPRQ-LIHYTSTLVSGTPSRF SGSGSGRDYSFSISSVESEDI-ASYYCLQYDTLYTFGAGTKLELK (SEQ ID NO:102). In some embodiments, an anti-CD8 antibody or fusion protein of the present disclosure comprises a VH domain comprising the sequence of EVKLQESGPSLVQP-SQTLSLTCSVSGFSLISDSVHWVRQPPGKGLEWMG-GIWADGSTDYNS ALKSRLSISRDTSKSQGFLKMNS-LQTDDTAIYFCTSARESYYFDYWGQGTMVTVSS (SEQ ID NO:103) and a VL domain comprising the sequence of DIQMTQSPASLSASLGDKVTI-TCQASQNIDKYIAWYQQKPGKAPRQLIHYTSTLVSG-TPSRF SGSGSGRDYSFSISSVESEDIASYYCLQYAT-LYTFGAGTKLELK (SEQ ID NO:104). In some embodiments, an anti-CD8 antibody or fusion protein of the present disclosure comprises a VH domain comprising the sequence of EVQLVESGGALVQPGRSLKLSCAASGLTFSDCY-MAWVRQTPTKGLEWVSYISSDGGSTYY GDSVKG-RFTISRDNAKSTLYLQMNSLRSEDMATYYCACATD-LSSYWSFDFWGPGTMVTV SS (SEQ ID NO:105) and a VL domain comprising the sequence of DIQMTQSPSSLPVSLGERVTISCRASQGISNNLNW-YQQKPDGTIKPLIYHTSNLQSGVPSRFS GSGSGT-DYSLTISSLEPEDFAMYYCQQDATFPLTFGSGTKLEIK (SEQ ID NO:106).

In some embodiments, an anti-CD8 antibody or fusion protein of the present disclosure comprises a VH domain comprising the sequence of SEQ ID NO:107 and a VL domain comprising the sequence of SEQ ID NO:108. In some embodiments, an anti-CD8 antibody or fusion protein of the present disclosure comprises a VH domain comprising the sequence of SEQ ID NO:109 and a VL domain comprising the sequence of SEQ ID NO:110. In some embodiments, an anti-CD8 antibody or fusion protein of the present disclosure comprises a VH domain comprising the sequence of SEQ ID NO:111 and a VL domain comprising the sequence of SEQ ID NO:112. In some embodiments, an anti-CD8 antibody or fusion protein of the present disclosure comprises a VH domain comprising the sequence of SEQ ID NO:113 and a VL domain comprising the sequence of SEQ ID NO:114. In some embodiments, an anti-CD8 antibody or fusion protein of the present disclosure comprises a VH domain comprising the sequence of SEQ ID NO:115 and a VL domain comprising the sequence of SEQ ID NO:116. In some embodiments, an anti-CD8 antibody or fusion protein of the present disclosure comprises a VH domain comprising the sequence of SEQ ID NO:117 and a VL domain comprising the sequence of SEQ ID NO:118. In some embodiments, an anti-CD8 antibody or fusion protein of the present disclosure comprises a VH domain comprising the sequence of SEQ ID NO:119 and a VL domain comprising the sequence of SEQ ID NO:120. In some embodiments, an anti-CD8 antibody or fusion protein of the present disclosure comprises a VH domain comprising the sequence of SEQ ID NO:121 and a VL domain comprising the sequence of SEQ ID NO:122. In some embodiments, an anti-CD8 antibody or fusion protein of the present disclosure comprises a VH domain comprising the sequence of SEQ ID NO:123 and a VL domain comprising the sequence of SEQ ID NO:124. In some embodiments, an anti-CD8 antibody or fusion protein of the present disclosure comprises a VH domain comprising the sequence of SEQ ID NO:125 and a VL domain comprising the sequence of SEQ ID NO:126. In some embodiments, an anti-CD8 antibody or fusion protein of the present disclosure comprises a VH domain comprising the sequence of SEQ ID NO:127 and a VL domain comprising the sequence of SEQ ID NO:128. In some embodiments, an anti-CD8 antibody or fusion protein of the present disclosure comprises a VH domain comprising the sequence of SEQ ID NO:129 and a VL domain comprising the sequence of SEQ ID NO:130. In some embodiments, an anti-CD8 antibody or fusion protein of the present disclosure comprises a VH domain comprising the sequence of SEQ ID NO:131 and a VL domain comprising the sequence of SEQ ID NO:132. In some embodiments, an anti-CD8 antibody or fusion protein of the present disclosure comprises a VH domain comprising the sequence of SEQ ID NO:133 and a VL domain comprising the sequence of SEQ ID NO:134. In some embodiments, an anti-CD8 antibody or fusion protein of the present disclosure comprises a VH domain comprising the sequence of SEQ ID NO:135 and a VL domain comprising the sequence of SEQ ID NO:136. In some embodiments, an anti-CD8 antibody or fusion protein of the present disclosure comprises a VH domain comprising the sequence of SEQ ID NO:258 and a VL domain comprising the sequence of SEQ ID NO:259.

In some embodiments, the antigen binding molecules (and fusion proteins) of the present disclosure specifically bind human CD8b and/or human CD8ab.

In some embodiments, the anti-CD8 antibody of the present disclosure is a human antibody or antibody fragment. In some embodiments, the anti-CD8 antibody of the present disclosure is a humanized antibody or antibody fragment.

In some embodiments, the anti-CD8 antibody of the present disclosure specifically binds human CD8b and/or human CD8ab with at least 10-fold, at least 20-fold, at least 30-fold, at least 40-fold, at least 50-fold, at least 60-fold, at least 70-fold, at least 80-fold, at least 90-fold, at least 100-fold, or at least 200-fold higher affinity than its binding to human CD8a and/or human CD8aa, e.g., as expressed on natural killer (NK) cells (e.g., human NK cells). In some embodiments, the anti-CD8 antibody of the present disclosure specifically binds human CD8b and/or human CD8ab with at least 10-fold higher affinity than its binding to human CD8a and/or human CD8aa, e.g., as expressed on natural killer (NK) cells. In some embodiments, the human CD8b and/or human CD8ab are expressed on the surface of a human cell, e.g., a human T cell.

In some embodiments, the anti-CD8 antibody of the present disclosure specifically binds to a cell expressing a human CD8ab heterodimer on its surface (e.g., a human T cell) with an EC50 that is less than 1000 nM. In some embodiments, the anti-CD8 antibody of the present disclosure specifically binds to human CD8+ T cells.

In some embodiments, an anti-CD8 antibody of the present disclosure comprises a VH domain comprising a CDR-H1 comprising the amino acid sequence of SEQ ID NO:137, a CDR-H2 comprising the amino acid sequence of SEQ ID NO:138, and a CDR-H3 comprising the amino acid sequence of SEQ ID NO:139 and a VL domain comprising a CDR-L1 comprising the amino acid sequence of SEQ ID NO:140, a CDR-L2 comprising the amino acid sequence of SEQ ID NO:141, and a CDR-L3 comprising the amino acid sequence of SEQ ID NO:142. In some embodiments, an anti-CD8 antibody of the present disclosure comprises 1, 2, or 3 heavy chain CDRs of antibody xhCD8 (e.g., as shown in Tables 10-12) and/or 1, 2, or 3 light chain CDRs of antibody xhCD8 (e.g., as shown in Tables 10-12). In some embodiments, the antibody is humanized.

In some embodiments, an anti-CD8 antibody of the present disclosure comprises a VH domain comprising a CDR-H1 comprising the amino acid sequence of SEQ ID NO:143, a CDR-H2 comprising the amino acid sequence of SEQ ID NO:144, and a CDR-H3 comprising the amino acid sequence of SEQ ID NO: 145 and a VL domain comprising a CDR-L1 comprising the amino acid sequence of SEQ ID NO:146, a CDR-L2 comprising the amino acid sequence of SEQ ID NO:147, and a CDR-L3 comprising the amino acid sequence of SEQ ID NO:148. In some embodiments, an anti-CD8 antibody of the present disclosure comprises 1, 2, or 3 heavy chain CDRs of antibody xhCD8v8 (e.g., as shown in Tables 10-12) and/or 1, 2, or 3 light chain CDRs of antibody xhCD8v8 (e.g., as shown in Tables 10-12). In some embodiments, the antibody is humanized.

In some embodiments, an anti-CD8 antibody of the present disclosure comprises a VH domain comprising a CDR-H1 comprising the amino acid sequence of SEQ ID NO:252, a CDR-H2 comprising the amino acid sequence of SEQ ID NO:253, and a CDR-H3 comprising the amino acid sequence of SEQ ID NO:254 and a VL domain comprising a CDR-L1 comprising the amino acid sequence of SEQ ID NO:255, a CDR-L2 comprising the amino acid sequence of SEQ ID NO:256, and a CDR-L3 comprising the amino acid sequence of SEQ ID NO:257. In some embodiments, the VH domain comprises an amino acid sequence that is at least 90%, at least 95%, at least 99%, or 100% identical to the sequence of SEQ ID NO:258 and/or the VL domain comprises an amino acid sequence that is at least 90%, at least 95%, at least 99%, or 100% identical to the sequence of SEQ ID NO:259. In some embodiments, an anti-CD8 antibody of the present disclosure comprises 1, 2, or 3 heavy chain CDRs of antibody xhCD8v1 (e.g., as shown in Tables 10-12) and/or 1, 2, or 3 light chain CDRs of antibody xhCD8v1 (e.g., as shown in Tables 10-12). In some embodiments, the antibody is humanized.

In some embodiments, an anti-CD8 antibody of the present disclosure comprises a VH domain comprising a CDR-H1 comprising the amino acid sequence of SEQ ID NO:149, a CDR-H2 comprising the amino acid sequence of SEQ ID NO:150, and a CDR-H3 comprising the amino acid sequence of SEQ ID NO: 151 and a VL domain comprising a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154. In some embodiments, the VH domain comprises an amino acid sequence that is at least 90%, at least 95%, at least 99%, or 100% identical to the sequence of SEQ ID NO:109 and/or the VL domain comprises an amino acid sequence that is at least 90%, at least 95%, at least 99%, or 100% identical to the sequence of SEQ ID NO:110. In some embodiments, an anti-CD8 antibody of the present disclosure comprises 1, 2, or 3 heavy chain CDRs of antibody xhCD8v2 (e.g., as shown in Tables 10-12) and/or 1, 2, or 3 light chain CDRs of antibody xhCD8v2 (e.g., as shown in Tables 10-12). In some embodiments, the antibody is humanized.

In some embodiments, an anti-CD8 antibody of the present disclosure comprises a VH domain comprising a CDR-H1 comprising the amino acid sequence of SEQ ID NO:155, a CDR-H2 comprising the amino acid sequence of SEQ ID NO:156, and a CDR-H3 comprising the amino acid sequence of SEQ ID NO:157 and a VL domain comprising a CDR-L1 comprising the amino acid sequence of SEQ ID NO:158, a CDR-L2 comprising the amino acid sequence of SEQ ID NO:159, and a CDR-L3 comprising the amino acid sequence of SEQ ID NO:160. In some embodiments, the VH domain comprises an amino acid sequence that is at least 90%, at least 95%, at least 99%, or 100% identical to the sequence of SEQ ID NO:111 and/or the VL domain comprises an amino acid sequence that is at least 90%, at least 95%, at least 99%, or 100% identical to the sequence of SEQ ID NO:112. In some embodiments, an anti-CD8 antibody of the present disclosure comprises 1, 2, or 3 heavy chain CDRs of antibody xhCD8v3 (e.g., as shown in Tables 10-12) and/or 1, 2, or 3 light chain CDRs of antibody xhCD8v3 (e.g., as shown in Tables 10-12). In some embodiments, the antibody is humanized.

In some embodiments, an anti-CD8 antibody of the present disclosure comprises a VH domain comprising a CDR-H1 comprising the amino acid sequence of SEQ ID NO:161, a CDR-H2 comprising the amino acid sequence of SEQ ID NO:162, and a CDR-H3 comprising the amino acid sequence of SEQ ID NO: 163 and a VL domain comprising a CDR-L1 comprising the amino acid sequence of SEQ ID NO:164, a CDR-L2 comprising the amino acid sequence of SEQ ID NO:165, and a CDR-L3 comprising the amino acid sequence of SEQ ID NO:166. In some embodiments, the VH domain comprises an amino acid sequence that is at least 90%, at least 95%, at least 99%, or 100% identical to the sequence of SEQ ID NO:113 and/or the VL domain comprises an amino acid sequence that is at least 90%, at least 95%, at least 99%, or 100% identical to the sequence of SEQ ID NO:114. In some embodiments, an anti-CD8 antibody of the present disclosure comprises 1, 2, or 3 heavy chain CDRs of antibody xhCD8v4 (e.g., as shown in Tables 10-12) and/or 1, 2, or 3 light chain CDRs of antibody xhCD8v4 (e.g., as shown in Tables 10-12). In some embodiments, the antibody is humanized.

In some embodiments, an anti-CD8 antibody of the present disclosure comprises a VH domain comprising a CDR-H1 comprising the amino acid sequence of SEQ ID NO: 167, a CDR-H2 comprising the amino acid sequence of SEQ ID NO:168, and a CDR-H3 comprising the amino acid sequence of SEQ ID NO: 169 and a VL domain comprising a CDR-L1 comprising the amino acid sequence of SEQ ID NO:170, a CDR-L2 comprising the amino acid sequence of SEQ ID NO:171, and a CDR-L3 comprising the amino acid sequence of SEQ ID NO:172. In some embodiments, the VH domain comprises an amino acid sequence that is at least 90%, at least 95%, at least 99%, or 100% identical to the sequence of SEQ ID NO:115 and/or the VL domain comprises an amino acid sequence that is at least 90%, at least 95%, at least 99%, or 100% identical to the sequence of SEQ ID NO:116. In some embodiments, an anti-CD8 antibody of the present disclosure comprises 1, 2, or 3 heavy chain CDRs of antibody xhCD8v5 (e.g., as shown in Tables 10-12) and/or 1, 2, or 3 light chain CDRs of antibody xhCD8v5 (e.g., as shown in Tables 10-12). In some embodiments, the antibody is humanized.

In some embodiments, an anti-CD8 antibody of the present disclosure comprises a VH domain comprising a CDR-H1 comprising the amino acid sequence of SEQ ID NO:173, a CDR-H2 comprising the amino acid sequence of SEQ ID NO:174, and a CDR-H3 comprising the amino acid sequence of SEQ ID NO: 175 and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178. In some embodiments, the VH domain comprises an amino acid sequence that is at least 90%, at least 95%, at least 99%, or 100% identical to the sequence of SEQ ID NO:117 and/or the VL domain comprises an amino acid sequence that is at least 90%, at least 95%, at least 99%, or 100% identical to the sequence of SEQ ID NO:118. In some embodiments, an anti-CD8 antibody of the present disclosure comprises 1, 2, or 3 heavy chain CDRs of antibody xhCD8v6 (e.g., as shown in Tables 10-12) and/or 1, 2, or 3 light chain CDRs of antibody xhCD8v6 (e.g., as shown in Tables 10-12). In some embodiments, the antibody is human.

In some embodiments, an anti-CD8 antibody of the present disclosure comprises a VH domain comprising a CDR-H1 comprising the amino acid sequence of SEQ ID NO:179, a CDR-H2 comprising the amino acid sequence of SEQ ID NO:180, and a CDR-H3 comprising the amino acid sequence of SEQ ID NO: 181 and a VL domain comprising a CDR-L1 comprising the amino acid sequence of SEQ ID NO:182, a CDR-L2 comprising the amino acid sequence of SEQ ID NO:183, and a CDR-L3 comprising the amino acid sequence of SEQ ID NO:184. In some embodiments, the VH domain comprises an amino acid sequence that is at least 90%, at least 95%, at least 99%, or 100% identical to the sequence of SEQ ID NO:119 and/or the VL domain comprises an amino acid sequence that is at least 90%, at least 95%, at least 99%, or 100% identical to the sequence of SEQ ID NO:120. In some embodiments, an anti-CD8 antibody of the present disclosure comprises 1, 2, or 3 heavy chain CDRs of antibody xhCD8v7 (e.g., as shown in Tables 10-12) and/or 1, 2, or 3 light chain CDRs of antibody xhCD8v7 (e.g., as shown in Tables 10-12). In some embodiments, the antibody is human.

In some embodiments, an anti-CD8 antibody of the present disclosure comprises a VH domain comprising a CDR-H1 comprising the amino acid sequence of $X_1X_2AIS$, wherein $X_1$ is S, K, G, N, R, D, T, or G, and wherein $X_2$ is Y, L, H, or F (SEQ ID NO:185), a CDR-H2 comprising the amino acid sequence of $X_1X_2X_3PX_4X_5X_6X_7X_8X_9YX_{10}QKFX_{11}G$, wherein $X_1$ is G or H, $X_2$ is I or F, $X_3$ is I, N, or M, $X_4$ is G, N, H, S, R, I, or A, $X_5$ is A, N, H, S, T, F, or Y, $X_6$ is A, D, or G, $X_7$ is T, E, K, V, Q, or A, $X_8$ is A or T, $X_9$ is N or K, $X_{10}$ is A or N, and $X_{11}$ is Q or T (SEQ ID NO:186), and a CDR-H3 comprising the amino acid sequence of $X_1X_2X_3GX_4X_5LFX_6X_7$, wherein $X_1$ is D or A, $X_2$ is A, G, E, R, Y, K, N, Q, L, or F, $X_3$ is A, L, P, or Y, $X_4$ is I or L, $X_5$ is R, A, Q, or S, $X_6$ is A or D, and $X_7$ is D, E, A, or S (SEQ ID NO: 187) and a VL domain comprising a CDR-L1 comprising the amino acid sequence of $X_1X_2SX_3X_4IX_5GX_6LN$, wherein $X_1$ is R or G, $X_2$ is A or T, $X_3$ is Q or E, $X_4$ is E, N, T, S, A, K, D, G, R, or Q, $X_5$ is Y or S, and $X_6$ is A or V (SEQ ID NO:188), a CDR-L2 comprising the amino acid sequence of $GX_1X_2X_3LX_4X_5$, wherein $X_1$ is A or S, $X_2$ is T, S, E, Q, or D, $X_3$ is N, R, A, E, or H, $X_4$ is Q or A, and $X_5$ is S or D (SEQ ID NO:189), and a CDR-L3 comprising the amino acid sequence of $QX_1X_2X_3X_4X_5PWT$, wherein $X_1$ is S, N, D, Q, A, or E, $X_2$ is T, I, or S, $X_3$ is Y, L, or F, $X_4$ is D, G, T, E, Q, A, or Y, and $X_5$ is A, T, R, S, K, or Y (SEQ ID NO:190). In some embodiments, the VH domain further comprises a FW-1 comprising the sequence QVQLVQSGAEVKKPGSSVKVSCKASGGTFS (SEQ ID NO:191), a FW-2 comprising the sequence WVRQAPGQGLEWMG (SEQ ID NO:192), a FW-3 comprising the sequence RVTITADESTSTAYMELSSLRSEDTAVYYCAR (SEQ ID NO:193), and/or a FW-4 comprising the sequence WGQGTLVTVSS (SEQ ID NO:194). In some embodiments, the VL domain further comprises a FW-1 comprising the sequence DIQMTQSPSSLSASVGDRVTITC (SEQ ID NO:195), a FW-2 comprising the sequence WYQQKPGKAPKLLIY (SEQ ID NO:196), a FW-3 comprising the sequence GVPSRFSGSGSGTDFTLTISSLQPEDFATYYC (SEQ ID NO:197), and/or a FW-4 comprising the sequence FGGGTKVEIK (SEQ ID NO:198).

In some embodiments, an anti-CD8 antibody of the present disclosure comprises a VH domain comprising a CDR-H1 comprising the amino acid sequence of SEQ ID NO:199, a CDR-H2 comprising the amino acid sequence of SEQ ID NO:200, and a CDR-H3 comprising the amino acid sequence of SEQ ID NO:201 and a VL domain comprising a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202. In some embodiments, the VH domain comprises an amino acid sequence that is at least 90%, at least 95%, at least 99%, or 100% identical to the sequence of SEQ ID NO:123 and/or the VL domain comprises an amino acid sequence that is at least 90%, at least 95%, at least 99%, or 100% identical to the sequence of SEQ ID NO:124. In some embodiments, an anti-CD8 antibody of the present disclosure comprises 1, 2, or 3 heavy chain CDRs of antibody xhCD8v9 (e.g., as shown in Tables 10-12) and/or 1, 2, or 3 light chain CDRs of antibody xhCD8v9 (e.g., as shown in Tables 10-12). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:123 and a VL domain comprising a CDR-L1, CDR-L2, and CDR-L3 from the sequence of SEQ ID NO:124. In some embodiments, the VH domain further comprises a FW-1 comprising the sequence QVQLVQSGAEVKKPGSSVKVSCKASGGTFS (SEQ ID NO:191), a FW-2 comprising the sequence WVRQAPGQGLEWMG (SEQ ID NO:192), a FW-3 comprising the sequence RVTITADESTSTAYMELSSLRSEDTAVYYCAR (SEQ ID NO:193), and/or a FW-4 comprising the sequence WGQGTLVTVSS (SEQ ID NO:194). In some embodiments, the VL domain further comprises a FW-1 comprising the sequence DIQMTQSPSSLSASVGDRVTITC (SEQ ID NO:195), a FW-2 comprising the sequence WYQQKPGKAPKLLIY (SEQ ID NO:196), a FW-3 comprising the sequence GVPSRFSGSGSGTDFTLTISSLQPEDFATYYC (SEQ ID NO:197), and/or a FW-4 comprising the sequence FGGGTKVEIK (SEQ ID NO: 198).

In some embodiments, an anti-CD8 antibody of the present disclosure comprises a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204 and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207. In some embodiments, the VH domain comprises an amino acid sequence that is at least 90%, at least 95%, at least 99%, or 100% identical to the sequence of SEQ ID NO:129 and/or the VL domain comprises an amino acid sequence that is at least 90%, at least 95%, at least 99%, or 100% identical to the sequence of SEQ ID NO:130. In some embodiments, the VH domain comprises the amino acid sequence of SEQ ID NO:129; and the VL domain comprises the amino acid sequence of SEQ ID NO:130. In some embodiments, an anti-CD8 antibody of the present disclosure comprises 1, 2, or 3 heavy chain CDRs of antibody xhCD8v12 (xhCD8.1) (e.g., as shown in Tables 10-12) and/or 1, 2, or 3 light chain CDRs of antibody xhCD8v12 (xhCD8.1) (e.g., as shown in Tables 10-12). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:129 and a VL domain comprising a CDR-L1, CDR-L2, and CDR-L3 from the sequence of SEQ ID NO:130. In some embodiments, the VH domain further comprises a FW-1 comprising the sequence QVQLVQSGAEVKKPGSSVKVSCKASGGTFS (SEQ ID NO:191), a FW-2 comprising the sequence WVRQAPGQGLEWMG (SEQ ID NO:192), a FW-3 comprising the sequence RVTITADESTSTAYMELSSLRSEDTAVYYCAR (SEQ ID NO:193), and/or a FW-4 comprising the sequence WGQGTLVTVSS (SEQ ID NO:194). In some embodiments, the VL domain further comprises a FW-1 comprising the sequence DIQMTQSPSSLSASVGDRVTITC (SEQ ID NO:195), a FW-2 comprising the sequence WYQQKPGKAPKLLIY (SEQ ID NO:196), a FW-3 comprising the sequence GVPSRFSGSGSGTDFTLTISSLQPEDFATYYC (SEQ ID NO:197), and/or a FW-4 comprising the sequence FGGGTKVEIK (SEQ ID NO:198).

In some embodiments, an anti-CD8 antibody of the present disclosure comprises a VH domain comprising a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204 and a VL domain comprising a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202. In some embodiments, the VH domain comprises an amino acid sequence that is at least 90%, at least 95%, at least 99%, or 100% identical to the sequence of SEQ ID NO:131 and/or the VL domain comprises an amino acid sequence that is at least 90%, at least 95%, at least 99%, or 100% identical to the sequence of SEQ ID NO:132. In some embodiments, an anti-CD8 antibody of the present disclosure comprises 1, 2, or 3 heavy chain CDRs of antibody xhCD8v13 (e.g., as shown in Tables 10-12) and/or 1, 2, or 3 light chain CDRs of antibody xhCD8v13 (e.g., as shown in Tables 10-12). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:131 and a VL domain comprising a CDR-L1, CDR-L2, and CDR-L3 from the sequence of SEQ ID NO:132. In some embodiments, the VH domain further comprises a FW-1 comprising the sequence QVQLVQSGAEVKKPGSSVKVSCKASGGTFS (SEQ ID NO:191), a FW-2 comprising the sequence WVRQAPGQGLEWMG (SEQ ID NO:192), a FW-3 comprising the sequence RVTITADESTSTAYMELSSLRSEDTAVYYCAR (SEQ ID NO:193), and/or a FW-4 comprising the sequence WGQGTLVTVSS (SEQ ID NO:194). In some embodiments, the VL domain further comprises a FW-1 comprising the sequence DIQMTQSPSSLSASVGDRVTITC (SEQ ID NO:195), a FW-2 comprising the sequence WYQQKPGKAPKLLIY (SEQ ID NO:196), a FW-3 comprising the sequence GVPSRFSGSGSGTDFTLTISSLQPEDFATYYC (SEQ ID NO:197), and/or a FW-4 comprising the sequence FGGGTKVEIK (SEQ ID NO:198).

In some embodiments, an anti-CD8 antibody of the present disclosure comprises a VH domain comprising a CDR-H1 comprising the amino acid sequence of $X_1YX_2MS$, wherein $X_1$ is S, D, E, A, or Q and $X_2$ is A, G, or T (SEQ ID NO:208), a CDR-H2 comprising the amino acid sequence of $DIX_1X_2X_3GX_4X_5TX_6YADSVKG$, wherein $X_1$ is T, N, S, Q, E, H, R, or A, $X_2$ is Y, W, F, or H, $X_3$ is A, S, Q, E, or T, $X_4$ is G or E, $X_5$ is S or I, and $X_6$ is A or G (SEQ ID NO:209), and a CDR-H3 comprising the amino acid sequence of $X_1X_2X_3YX_4WX_5X_6AX_7DX_8$, wherein $X_1$ is S or A, $X_2$ is N, H, A, D, L, Q, Y, or R, $X_3$ is A, N, S, or G, $X_4$ is A, V, R, E, or S, $X_5$ is D or S, $X_6$ is D, N, Q, E, S, T, or L, $X_7$ is L, F, or M, and $X_8$ is I, Y, or V (SEQ ID NO:210) and a VL domain comprising a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178). In some embodiments, the VH domain further comprises a FW-1 comprising the sequence EVQLVESGGGLVQPGGSLRLSCAASGFTFS (SEQ ID NO:211), a FW-2 comprising the sequence WVRQAPGKGLEWVS (SEQ ID NO:212), a FW-3 comprising the sequence RFTISRDNAKNSLYLQMNSLRAEDTAVYYCAR (SEQ ID NO:213), and/or a FW-4 comprising the sequence WGQGTMVTVSS (SEQ ID NO:214) or WGQGTLVTVSS (SEQ ID NO:215). In some embodiments, the VL domain further comprises a FW-1 comprising the sequence EIVLTQSPGTLSLSPGERATLSC (SEQ ID NO:216), a FW-2 comprising the sequence WYQQKPGQAPRLLIY (SEQ ID NO:217), a FW-3 comprising the sequence GIPDRFSGSGSGTDFTLTISRLEPEDFAVYYC (SEQ ID NO:218), and/or a FW-4 comprising the sequence FGQGTKVEIK (SEQ ID NO:219).

In some embodiments, an anti-CD8 antibody of the present disclosure comprises a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222 and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178. In some embodiments, the VH domain comprises an amino acid sequence that is at least 90%, at least 95%, at least 99%, or 100% identical to the sequence of SEQ ID NO:125 and/or the VL domain comprises an amino acid sequence that is at least 90%, at least 95%, at least 99%, or 100% identical to the sequence of SEQ ID NO:126. In some embodiments, an anti-CD8 antibody of the present disclosure comprises 1, 2, or 3 heavy chain CDRs of antibody xhCD8v10 (e.g., as shown in Tables 10-12) and/or 1, 2, or 3 light chain CDRs of antibody xhCD8v10 (e.g., as shown in Tables 10-12). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:125 and a VL domain comprising a CDR-L1, CDR-L2, and CDR-L3 from the sequence of SEQ ID NO:126. In some embodiments, the VH domain further comprises a FW-1 comprising the sequence EVQLVESGGGLVQPGGSLRLSCAASGFTFS (SEQ ID NO:211), a FW-2 comprising the sequence WVRQAPGKGLEWVS (SEQ ID NO:212), a FW-3 comprising the sequence RFTISRDNAKNSLYLQMNSLRAEDTAVYYCAR (SEQ ID NO:213), and/or a FW-4 comprising the sequence WGQGTMVTVSS (SEQ ID NO:214) or WGQGTLVTVSS (SEQ ID NO:215). In some embodiments, the VL domain further comprises a FW-1 comprising the sequence EIVLTQSPGTLSLSPGERATLSC (SEQ ID NO:216), a FW-2 comprising the sequence WYQQKPGQAPRLLIY (SEQ ID NO:217), a FW-3 comprising the sequence GIPDRFSGSGSGTDFTLTISRLEPEDFAVYYC (SEQ ID NO:218), and/or a FW-4 comprising the sequence FGQGTKVEIK (SEQ ID NO:219).

In some embodiments, an anti-CD8 antibody of the present disclosure comprises a VH domain comprising a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222 and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178. In some embodiments, the VH domain comprises an amino acid sequence that is at least 90%, at least 95%, at least 99%, or 100% identical to the sequence of SEQ ID NO:127 and/or the VL domain comprises an amino acid sequence that is at least 90%, at least 95%, at least 99%, or 100% identical to the sequence of SEQ ID NO: 128. In some embodiments, the VH domain comprises the amino acid sequence of SEQ ID NO: 127; and the VL domain comprises the amino acid sequence of SEQ ID NO:128. In some embodiments, an anti-CD8 antibody of the present disclosure comprises 1, 2, or 3 heavy chain CDRs of antibody xhCD8v11 (e.g., as shown in Tables 10-12) and/or 1, 2, or 3 light chain CDRs of antibody xhCD8v11 (e.g., as shown in Tables 10-12). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:127 and a VL domain comprising a CDR-L1, CDR-L2, and CDR-L3 from the sequence of SEQ ID NO:128. In some embodiments, the VH domain further comprises a FW-1 comprising the sequence EVQLVESGGGLVQPGGSLRLSCAASGFTFS (SEQ ID NO:211), a FW-2 comprising the sequence WVRQAPGKGLEWVS (SEQ ID NO:212), a FW-3 comprising the sequence RFTISRDNAKNSLYLQMNSLRAEDTAVYYCAR (SEQ ID NO:213), and/or a FW-4 comprising the sequence WGQGTMVTVSS (SEQ ID NO:214) or WGQGTLVTVSS (SEQ ID NO:215). In some embodiments, the VL domain further comprises a FW-1 comprising the sequence EIVLTQSPGTLSLSPGERATLSC (SEQ ID NO:216), a FW-2 comprising the sequence WYQQKPGQAPRLLIY (SEQ ID NO:217), a FW-3 comprising the sequence GIPDRFSGSGSGTDFTLTISRLEPEDFAVYYC (SEQ ID NO:218), and/or a FW-4 comprising the sequence FGQGTKVEIK (SEQ ID NO:219).

In some embodiments, an anti-CD8 antibody of the present disclosure comprises a VH domain comprising a CDR-H1 comprising the amino acid sequence of SEQ ID NO:220, a CDR-H2 comprising the amino acid sequence of SEQ ID NO:260, and a CDR-H3 comprising the amino acid sequence of SEQ ID NO:222 and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178. In some embodiments, the VH domain comprises an amino acid sequence that is at least 90%, at least 95%, at least 99%, or 100% identical to the sequence of SEQ ID NO:133 and/or the VL domain comprises an amino acid sequence that is at least 90%, at least 95%, at least 99%, or 100% identical to the sequence of SEQ ID NO:134. In some embodiments, an anti-CD8 antibody of the present disclosure comprises 1, 2, or 3 heavy chain CDRs of antibody xhCD8v14 (e.g., as shown in Tables 10-12) and/or 1, 2, or 3 light chain CDRs of antibody xhCD8v14 (e.g., as shown in Tables 10-12). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:133 and a VL domain comprising a CDR-L1, CDR-L2, and CDR-L3 from the sequence of SEQ ID NO:134. In some embodiments, the VH domain further comprises a FW-1 comprising the sequence EVQLVESGGGLVQPGGSLRLSCAASGFTFS (SEQ ID NO:211), a FW-2 comprising the sequence WVRQAPGKGLEWVS (SEQ ID NO:212), a FW-3 comprising the sequence RFTISRDNAKNSLYLQMNSLRAEDTAVYYCAR (SEQ ID NO:213), and/or a FW-4 comprising the sequence WGQGTMVTVSS (SEQ ID NO:214) or WGQGTLVTVSS (SEQ ID NO:215). In some embodiments, the VL domain further comprises a FW-1 comprising the sequence EIVLTQSPGTLSLSPGERATLSC (SEQ ID NO:216), a FW-2 comprising the sequence WYQQKPGQAPRLLIY (SEQ ID NO:217), a FW-3 comprising the sequence GIPDRFSGSGSGTDFTLTISRLEPEDFAVYYC (SEQ ID NO:218), and/or a FW-4 comprising the sequence FGQGTKVEIK (SEQ ID NO:219).

In some embodiments, an anti-CD8 antibody of the present disclosure comprises a VH domain comprising a CDR-H1 comprising the amino acid sequence of SEQ ID NO:220, a CDR-H2 comprising the amino acid sequence of SEQ ID NO:260, and a CDR-H3 comprising the amino acid sequence of SEQ ID NO:222 and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178. In some embodiments, the VH domain comprises an amino acid sequence that is at least 90%, at least 95%, at least 99%, or 100% identical to the sequence of SEQ ID NO:135 and/or the VL domain comprises an amino acid sequence that is at least 90%, at least 95%, at least 99%, or 100% identical to the sequence of SEQ ID NO:136. In some embodiments, an anti-CD8 antibody of the present disclosure comprises 1, 2, or 3 heavy chain CDRs of antibody xhCD8v15 (e.g., as shown in Tables 10-12) and/or 1, 2, or 3 light chain CDRs of antibody xhCD8v15 (e.g., as shown in Tables 10-12). In some embodiments, the antibody is humanized. In some embodiments, an anti-CD8 antibody of the present disclosure comprises a VH domain comprising a CDR-H1, CDR-H2, and CDR-H3 from the sequence of SEQ ID NO:135 and a VL domain comprising a CDR-L1, CDR-L2, and CDR-L3 from the sequence of SEQ ID NO:136. In some embodiments, the VH domain further comprises a FW-1 comprising the sequence EVQLVESGGGLVQPGGSLRLSCAASGFTFS (SEQ ID NO:211), a FW-2 comprising the sequence WVRQAPGKGLEWVS (SEQ ID NO:212), a FW-3 comprising the sequence RFTISRDNAKNSLYLQMNSLRAEDTAVYYCAR (SEQ ID NO:213), and/or a FW-4 comprising the sequence WGQGTMVTVSS (SEQ ID NO:214) or WGQGTLVTVSS (SEQ ID NO:215). In some embodiments, the VL domain further comprises a FW-1 comprising the sequence EIVLTQSPGTLSLSPGERATLSC (SEQ ID NO:216), a FW-2 comprising the sequence WYQQKPGQAPRLLIY (SEQ ID NO:217), a FW-3 comprising the sequence GIPDRFSGSGSGTDFTLTISRLEPEDFAVYYC (SEQ ID NO:218), and/or a FW-4 comprising the sequence FGQGTKVEIK (SEQ ID NO:219).

Multiple definitions for the CDR sequences of antibody variable domains are known in the art. Unless otherwise specified, CDR sequences are described herein according to the definition of Kabat (see, e.g., Kabat et al., *Sequences of Proteins of Immunological Interest*, Fifth Edition, NIH Publication 91-3242, Bethesda MD (1991), vols. 1-3). However, other definitions are known and contemplated for use. For example, in some embodiments, CDR sequences can be described by the definition of Chothia (see, e.g., Chothia and Lesk, *J. Mol. Biol.* 196:901-917 (1987).

In some embodiments, an anti-CD8 antibody of the present disclosure comprises a VH domain comprising a CDR-H1 comprising the amino acid sequence of SEQ ID NO:223, a CDR-H2 comprising the amino acid sequence of SEQ ID NO:224, and a CDR-H3 comprising the amino acid sequence of SEQ ID NO:225 and a VL domain comprising a CDR-L1 comprising the amino acid sequence of SEQ ID NO:140, a CDR-L2 comprising the amino acid sequence of SEQ ID NO:141, and a CDR-L3 comprising the amino acid sequence of SEQ ID NO:142. In some embodiments, an anti-CD8 antibody of the present disclosure comprises a VH domain comprising a CDR-H1 comprising the amino acid sequence of SEQ ID NO:226, a CDR-H2 comprising the amino acid sequence of SEQ ID NO:227, and a CDR-H3 comprising the amino acid sequence of SEQ ID NO:151 and a VL domain comprising a CDR-L1 comprising the amino acid sequence of SEQ ID NO:152, a CDR-L2 comprising the amino acid sequence of SEQ ID NO: 153, and a CDR-L3 comprising the amino acid sequence of SEQ ID NO:154. In some embodiments, an anti-CD8 antibody of the present disclosure comprises a VH domain comprising a CDR-H1 comprising the amino acid sequence of SEQ ID NO:228, a CDR-H2 comprising the amino acid sequence of SEQ ID NO:227, and a CDR-H3 comprising the amino acid sequence of SEQ ID NO:157 and a VL domain comprising a CDR-L1 comprising the amino acid sequence of SEQ ID NO:158, a CDR-L2 comprising the amino acid sequence of SEQ ID NO:159, and a CDR-L3 comprising the amino acid sequence of SEQ ID NO:160. In some embodiments, an anti-CD8 antibody of the present disclosure comprises a VH domain comprising a CDR-H1 comprising the amino acid sequence of SEQ ID NO:223, a CDR-H2 comprising the amino acid sequence of SEQ ID NO:227, and a CDR-H3 comprising the amino acid sequence of SEQ ID NO:163 and a VL domain comprising a CDR-L1 comprising the amino acid sequence of SEQ ID NO:164, a CDR-L2 comprising the amino acid sequence of SEQ ID NO:165, and a CDR-L3 comprising the amino acid sequence of SEQ ID NO:166. In some embodiments, an anti-CD8 antibody of the present disclosure comprises a VH domain comprising a CDR-H1 comprising the amino acid sequence of SEQ ID NO:229, a CDR-H2 comprising the amino acid sequence of SEQ ID NO:227, and a CDR-H3 comprising the amino acid sequence of SEQ ID NO:169 and a VL domain comprising a CDR-L1 comprising the amino acid sequence of SEQ ID NO:170, a CDR-L2 comprising the amino acid sequence of SEQ ID NO:171, and a CDR-L3 comprising the amino acid sequence of SEQ ID NO:172. In some embodiments, an anti-CD8 antibody of the present disclosure comprises a VH domain comprising a CDR-H1 comprising the amino acid sequence of SEQ ID NO:230, a CDR-H2 comprising the amino acid sequence of SEQ ID NO:231, and a CDR-H3 comprising the amino acid sequence of SEQ ID NO:175 and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178. In some embodiments, an anti-CD8 antibody of the present disclosure comprises a VH domain comprising a CDR-H1 comprising the amino acid sequence of SEQ ID NO:230, a CDR-H2 comprising the amino acid sequence of SEQ ID NO:232, and a CDR-H3 comprising the amino acid sequence of SEQ ID NO:181 and a VL domain comprising a CDR-L1 comprising the amino acid sequence of SEQ ID NO:182, a CDR-L2 comprising the amino acid sequence of SEQ ID NO:183, and a CDR-L3 comprising the amino acid sequence of SEQ ID NO:184. In some embodiments, an anti-CD8 antibody of the present disclosure comprises a VH domain comprising a CDR-H1 comprising the amino acid sequence of SEQ ID NO:233, a CDR-H2 comprising the amino acid sequence of SEQ ID NO:234, and a CDR-H3 comprising the amino acid sequence of SEQ ID NO:145 and a VL domain comprising a CDR-L1 comprising the amino acid sequence of SEQ ID NO:146, a CDR-L2 comprising the amino acid sequence of SEQ ID NO:147, and a CDR-L3 comprising the amino acid sequence of SEQ ID NO:148.

In some embodiments, an anti-CD8 antibody of the present disclosure comprises a VH domain comprising a CDR-H1 comprising the amino acid sequence of $GX_1X_2FX_3X_4X_5$, wherein $X_1$ is G, Y, S, or A, $X_2$ is T, S, G, R, N, or H, $X_3$ is S, T, R, H, Y, G, or P, $X_4$ is S, K, G, N, R, D, T, or G, and $X_5$ is Y, L, H, or F (SEQ ID NO:235), a CDR-H2 comprising the amino acid sequence of $X_1PX_2X_3X_4X_5$, wherein $X_1$ is I, N, or M, $X_2$ is G, N, H, S, R, I, or A, $X_3$ is A, N, H, S, T, F, or Y, $X_4$ is A, D, or G, and $X_5$ is T, E, K, V, Q, or A (SEQ ID NO:236), and a CDR-H3 comprising the amino acid sequence of $X_1X_2X_3GX_4X_5LFX_6X_7$, wherein $X_1$ is D or A, $X_2$ is A, G, E, R, Y, K, N, Q, L, or F, $X_3$ is A, L, P, or Y, $X_4$ is I or L, $X_5$ is R, A, Q, or S, $X_6$ is A or D, and $X_7$ is D, E, A, or S (SEQ ID NO:237) and a VL domain comprising a CDR-L1 comprising the amino acid sequence of $X_1X_2SX_3X_4IX_5GX_6LN$, wherein $X_1$ is R or G, $X_2$ is A or T, $X_3$ is Q or E, $X_4$ is E, N, T, S, A, K, D, G, R, or Q, $X_5$ is Y or S, and $X_6$ is A or V (SEQ ID NO:188), a CDR-L2 comprising the amino acid sequence of $GX_1X_2X_3LX_4X_5$, wherein $X_1$ is A or S, $X_2$ is T, S, E, Q, or D, $X_3$ is N, R, A, E, or H, $X_4$ is Q or A, and $X_5$ is S or D (SEQ ID NO:189), and a CDR-L3 comprising the amino acid sequence of $QX_1X_2X_3X_4X_5PWT$, wherein $X_1$ is S, N, D, Q, A, or E, $X_2$ is T, I, or S, $X_3$ is Y, L, or F, $X_4$ is D, G, T, E, Q, A, or Y, and $X_5$ is A, T, R, S, K, or Y (SEQ ID NO:190). In some embodiments, the VH domain further comprises a FW-1 comprising the sequence QVQLVQS-GAEVKKPGSSVKVSCKAS (SEQ ID NO:238), a FW-2 comprising the sequence AISWVRQAPGQGLEWMGGI (SEQ ID NO:239), a FW-3 comprising the sequence ANY-AQKFQGRVTITADESTSTAYMELSSLRSEDTAVYY-CAR (SEQ ID NO:240), and/or a FW-4 comprising the sequence WGQGTLVTVSS (SEQ ID NO:194). In some embodiments, the VL domain further comprises a FW-1 comprising the sequence DIQMTQSPSSL-SASVGDRVTITC (SEQ ID NO:195), a FW-2 comprising the sequence WYQQKPGKAPKLLIY (SEQ ID NO:196), a FW-3 comprising the sequence GVPSRFSGSGSGTDFTLTISSLQPEDFATYYC (SEQ ID NO:197), and/or a FW-4 comprising the sequence FGGGTKVEIK (SEQ ID NO:198).

In some embodiments, an anti-CD8 antibody of the present disclosure comprises a VH domain comprising a CDR-H1 comprising the amino acid sequence of SEQ ID NO:241, a CDR-H2 comprising the amino acid sequence of SEQ ID NO:242, and a CDR-H3 comprising the amino acid sequence of SEQ ID NO:204 and a VL domain comprising a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202. In some embodiments, the VH domain further comprises a FW-1 comprising the sequence QVQLVQSGAEVKKPGSSVKVSCKAS (SEQ ID NO:238), a FW-2 comprising the sequence AISWVRQAPGQGLEWMGGI (SEQ ID NO:239), a FW-3 comprising the sequence ANYAQKFQGRVTITADEST-STAYMELSSLRSEDTAVYYCAR (SEQ ID NO:240), and/ or a FW-4 comprising the sequence WGQGTLVTVSS (SEQ ID NO: 194). In some embodiments, the VL domain further comprises a FW-1 comprising the sequence DIQMTQSPSSLSASVGDRVTITC (SEQ ID NO:195), a FW-2 comprising the sequence WYQQKPGKAPKLLIY (SEQ ID NO:196), a FW-3 comprising the sequence GVPSRFSGSGSGTDFTLTISSLQPEDFATYYC (SEQ ID NO:197), and/or a FW-4 comprising the sequence FGGGTKVEIK (SEQ ID NO:198).

In some embodiments, an anti-CD8 antibody of the present disclosure comprises a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204 and a VL domain comprising a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207. In some embodiments, the VH domain further comprises a FW-1 comprising the sequence QVQLVQSGAEVKKPGSSVKVSCKAS (SEQ ID NO:238), a FW-2 comprising the sequence AISWVRQAPGQGLEWMGGI (SEQ ID NO:239), a FW-3 comprising the sequence ANYAQKFQGRVTITADEST-STAYMELSSLRSEDTAVYYCAR (SEQ ID NO:240), and/or a FW-4 comprising the sequence WGQGTLVTVSS (SEQ ID NO: 194). In some embodiments, the VL domain further comprises a FW-1 comprising the sequence DIQMTQSPSSLSASVGDRVTITC (SEQ ID NO:195), a FW-2 comprising the sequence WYQQKPGKAPKLLIY (SEQ ID NO:196), a FW-3 comprising the sequence GVPSRFSGSGSGTDFTLTISSLQPEDFATYYC (SEQ ID NO:197), and/or a FW-4 comprising the sequence FGGGTKVEIK (SEQ ID NO:198).

In some embodiments, an anti-CD8 antibody of the present disclosure comprises a VH domain comprising a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204 and a VL domain comprising a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202. In some embodiments, the VH domain further comprises a FW-1 comprising the sequence QVQLVQSGAEVKKPGSSVKVSCKAS (SEQ ID NO:238), a FW-2 comprising the sequence AISWVRQAPGQGLEWMGGI (SEQ ID NO:239), a FW-3 comprising the sequence ANYAQKFQGRVTITADEST-STAYMELSSLRSEDTAVYYCAR (SEQ ID NO:240), and/or a FW-4 comprising the sequence WGQGTLVTVSS (SEQ ID NO: 194). In some embodiments, the VL domain further comprises a FW-1 comprising the sequence DIQMTQSPSSLSASVGDRVTITC (SEQ ID NO:195), a FW-2 comprising the sequence WYQQKPGKAPKLLIY (SEQ ID NO:196), a FW-3 comprising the sequence GVPSRFSGSGSGTDFTLTISSLQPEDFATYYC (SEQ ID NO:197), and/or a FW-4 comprising the sequence FGGGTKVEIK (SEQ ID NO:198).

In some embodiments, an anti-CD8 antibody of the present disclosure comprises a VH domain comprising a CDR-H1 comprising the amino acid sequence of GFTFX$_1$X$_2$Y, wherein X$_1$ is S, D, E, Q, S, or A and X$_2$ is S, D, E, A, or Q (SEQ ID NO:244), a CDR-H2 comprising the amino acid sequence of X$_1$X$_2$X$_3$GX$_4$X$_5$, wherein X$_1$ is T, N, S, Q, E, H, R or A, X$_2$ is Y, W, F, or H, X$_3$ is A, S, Q, E, or T, X$_4$ is G or E, and X$_5$ is S or I (SEQ ID NO:245), and a CDR-H3 comprising the amino acid sequence of X$_1$X$_2$X$_3$YX$_4$WX$_5$X$_6$AX$_7$DX$_8$, wherein X$_1$ is S or A, X$_2$ is N, H, A, D, L, Q, Y, or R, X$_3$ is A, N, S, or G, X$_4$ is A, V, R, E, or S, X$_5$ is D or S, X$_6$ is D, N, Q, E, S, T, or L, X$_7$ is L, F, or M, and X$_8$ is I, Y, or V (SEQ ID NO:246) and a VL domain comprising a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178). In some embodiments, the VH domain further comprises a FW-1 comprising the sequence EVQLVESGGGLVQPGGSLRLS-CAAS (SEQ ID NO:247), a FW-2 comprising the sequence AMSWVRQAPGKGLEWVSDI (SEQ ID NO:248), a FW-3 comprising the sequence TAYADSVKGRFTISRDNAKNS-LYLQMNSLRAEDTAVYYCAR (SEQ ID NO:249), and/or a FW-4 comprising the sequence WGQGTMVTVSS (SEQ ID NO:214) or WGQGTLVTVSS (SEQ ID NO:215). In some embodiments, the VL domain further comprises a FW-1 comprising the sequence EIVLTQSPGTLSLSPGER-ATLSC (SEQ ID NO:216), a FW-2 comprising the sequence WYQQKPGQAPRLLIY (SEQ ID NO:217), a FW-3 comprising the sequence GIPDRFSGSGSGTDFTLTISR-LEPEDFAVYYC (SEQ ID NO:218), and/or a FW-4 comprising the sequence FGQGTKVEIK (SEQ ID NO:219).

In some embodiments, an anti-CD8 antibody of the present disclosure comprises a VH domain comprising a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288 and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178. In some embodiments, the VH domain further comprises a FW-1 comprising the sequence EVQLVESGGGLVQPGGSLRLSCAAS (SEQ ID NO:247), a FW-2 comprising the sequence AMSWVRQAPGK-GLEWVSDI (SEQ ID NO:248), a FW-3 comprising the sequence TAYADSVKGRFTISRDNAKNSLYLQMNSL-RAEDTAVYYCAR (SEQ ID NO:249), and/or a FW-4 comprising the sequence WGQGTMVTVSS (SEQ ID NO:214) or WGQGTLVTVSS (SEQ ID NO:215). In some embodiments, the VL domain further comprises a FW-1 comprising the sequence EIVLTQSPGTLSLSPGERATLSC (SEQ ID NO:216), a FW-2 comprising the sequence WYQQKPGQAPRLLIY (SEQ ID NO:217), a FW-3 comprising the sequence GIPDRFSGSGSGTDFTLTISR-LEPEDFAVYYC (SEQ ID NO:218), and/or a FW-4 comprising the sequence FGQGTKVEIK (SEQ ID NO:219).

In some embodiments, an anti-CD8 antibody of the present disclosure comprises a VH domain comprising a CDR-H1 comprising the amino acid sequence of SEQ ID NO:250, a CDR-H2 comprising the amino acid sequence of SEQ ID NO:261, and a CDR-H3 comprising the amino acid sequence of SEQ ID NO:288 and a VL domain comprising a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178. In some embodiments, the VH domain further comprises a FW-1 comprising the sequence EVQLVESGGGLVQPGGSLRLSCAAS (SEQ ID NO:247), a FW-2 comprising the sequence AMSWVRQAPGK-GLEWVSDI (SEQ ID NO:248), a FW-3 comprising the sequence TAYADSVKGRFTISRDNAKNSLYLQMNSL-RAEDTAVYYCAR (SEQ ID NO:249), and/or a FW-4 comprising the sequence WGQGTMVTVSS (SEQ ID NO:214) or WGQGTLVTVSS (SEQ ID NO:215). In some embodiments, the VL domain further comprises a FW-1 comprising the sequence EIVLTQSPGTLSLSPGERATLSC (SEQ ID NO:216), a FW-2 comprising the sequence WYQQKPGQAPRLLIY (SEQ ID NO:217), a FW-3 comprising the sequence GIPDRFSGSGSGTDFTLTISRLEPEDFAVYYC (SEQ ID NO:218), and/or a FW-4 comprising the sequence FGQGTKVEIK (SEQ ID NO:219). In some embodiments, the present disclosure provides an anti-CD8 antibody comprising a VH domain comprising CDR-H1, CDR-H2, and CDR-H3 sequences of a single antibody listed in Table 10 and a VL domain comprising CDR-L1, CDR-L2, and CDR-L3 sequences of the single antibody listed in Table 10. For example, the anti-CD8 antibody comprises the six CDRs of antibody xhCD8, xhCD8v1, xhCD8v2, xhCD8v3, xhCD8v4, xhCD8v5, xhCD8v6, xhCD8v7, xhCD8v8, xhCD8v9, xhCD8v10, xhCD8v11, xhCD8v12 (xhCD8.1), xhCD8v13, xhCD8v14, xhCD8v15, V9 family, or V11 family shown in Table 10. In some embodiments, the present disclosure provides an anti-CD8 antibody comprising a VH domain comprising CDR-H1, CDR-H2, and CDR-H3 sequences of a single antibody listed in Table 10 and a VL domain comprising CDR-L1, CDR-L2, and CDR-L3 sequences of the single antibody listed in Table 10. For example, the anti-CD8 antibody comprises the six CDRs of antibody xhCD8, xhCD8v1, xhCD8v2, xhCD8v3, xhCD8v4, xhCD8v5, xhCD8v6, xhCD8v7, xhCD8v8, xhCD8v9, xhCD8v10, xhCD8v11, xhCD8v12 (xhCD8.1), xhCD8v13, xhCD8v14, xhCD8v15, V9 family, or V11 family shown in Table 10. In some embodiments, the present disclosure provides a fusion protein comprising an anti-CD8 antibody comprising a VH domain comprising CDR-H1, CDR-H2, and CDR-H3 sequences of the single antibody listed in Table 10 and a VL domain comprising CDR-L1, CDR-L2, and CDR-L3 sequences of a single antibody listed in Table 10. For example, the anti-CD8 antibody of the fusion protein comprises the six CDRs of antibody xhCD8, xhCD8v1, xhCD8v2, xhCD8v3, xhCD8v4, xhCD8v5, xhCD8v6, xhCD8v7, xhCD8v8, xhCD8v9, xhCD8v10, xhCD8v11, xhCD8v12 (xhCD8.1), xhCD8v13, xhCD8v14, xhCD8v15, V9 family, or V11 family shown in Table 10. In some embodiments, the present disclosure provides a fusion protein comprising an anti-CD8 antibody comprising a VH domain comprising CDR-H1, CDR-H2, and CDR-H3 sequences of a single antibody listed in Table 11 and a VL domain comprising CDR-L1, CDR-L2, and CDR-L3 sequences of the single antibody listed in Table 11. For example, the anti-CD8 antibody of the fusion protein comprises the six CDRs of antibody xhCD8, xhCD8v1, xhCD8v2, xhCD8v3, xhCD8v4, xhCD8v5, xhCD8v6, xhCD8v7, xhCD8v8, xhCD8v9, xhCD8v10, xhCD8v11, xhCD8v12 (xhCD8.1), xhCD8v13, xhCD8v14, xhCD8v15, V9 family, or VII family shown in Table 11. In some embodiments, the present disclosure provides an anti-CD8 antibody comprising a VH domain comprising CDR-H1, CDR-H2, and CDR-H3 sequences of a VH domain listed in Table 12 and a VL domain comprising CDR-L1, CDR-L2, and CDR-L3 sequences of a VL domain listed in Table 12 (in some embodiments, the VH and VL domains are from the same single antibody listed in Table 12). For example, the anti-CD8 antibody comprises the VH and VL of antibody xhCD8, xhCD8v1, xhCD8v2, xhCD8v3, xhCD8v4, xhCD8v5, xhCD8v6, xhCD8v7, xhCD8v8, xhCD8v9, xhCD8v10, xhCD8v11, xhCD8v12 (xhCD8.1), xhCD8v13, xhCD8v14, or xhCD8v15 shown in Table 12. In some embodiments, the present disclosure provides a fusion protein comprising an anti-CD8 antibody comprising a VH domain comprising CDR-H1, CDR-H2, and CDR-H3 sequences of a VH domain listed in Table 12 and a VL domain comprising CDR-L1, CDR-L2, and CDR-L3 sequences of a VL domain listed in Table 12 (in some embodiments, the VH and VL domains are from the same single antibody listed in Table 12). In some embodiments, the present disclosure provides an anti-CD8 antibody comprising a VH domain sequence and a VL domain sequence for a single antibody as listed in Table 12. In some embodiments, the present disclosure provides a fusion protein comprising an anti-CD8 antibody comprising a VH domain sequence and a VL domain sequence for a single antibody as listed in Table 12. For example, the anti-CD8 antibody of the fusion protein comprises the VH and VL of antibody xhCD8, xhCD8v1, xhCD8v2, xhCD8v3, xhCD8v4, xhCD8v5, xhCD8v6, xhCD8v7, xhCD8v8, xhCD8v9, xhCD8v10, xhCD8v11, xhCD8v12 (xhCD8.1), xhCD8v13, xhCD8v14, or xhCD8v15 shown in Table 12.

Linkers

In some embodiments, the targeted cytokine construct comprises a linker between the antigen binding protein or a functional fragment thereof (e.g., an antibody or an antigen binding fragment thereof as described above) and the IL-21 polypeptide or a functional fragment or a variant thereof. Many different linker polypeptides are known in the art and may be used in the context of an targeted cytokine construct. In some embodiments, the targeted cytokine construct comprises one or more copies of a peptide comprising the sequence of: GGGGS (SEQ ID NO:387), GGNGT (SEQ ID NO: 388), or YGNGT (SEQ ID NO: 389) between the antigen binding protein and the IL-21 polypeptide or a functional fragment or a variant thereof. In some embodiments, the polypeptide region between the antigen binding protein and the IL-21 polypeptide or a functional fragment or a variant thereof comprises a single copy of GGGGS (SEQ ID NO: 387), GGNGT (SEQ ID NO: 388), or YGNGT (SEQ ID NO: 389).

Targeted Cytokine Protein

The present disclosure provides in some embodiments a fusion protein comprising an antigen binding protein or a functional fragment and an IL-21 polypeptide or a functional fragment or a variant thereof. In some embodiments, the fusion protein can comprise the antigen binding protein or a functional fragment that is operably linked to an IL-21 polypeptide or a functional fragment or a variant thereof. In some embodiments, the antigen binding protein or functional fragment thereof binds a receptor on a T cell. In some embodiments, the T cell is a CD8+ T cell. In some embodiments, the T cell is not a Treg cell (e.g., T cell expressing FoxP3). In some embodiments, the antigen binding protein or functional fragment thereof is an anti-CD8 antibody or antigen binding fragment thereof as described herein.

In some embodiments, the targeted cytokine construct comprises an antibody or antigen binding fragment having the structure: i) a first polypeptide, arranged from N-to-C terminus, comprising: a variable light chain (VL) amino acid sequence, and a light chain constant region amino acid sequence (CL1); ii) a second polypeptide, arranged from N-to-C terminus, comprising: a variable heavy chain (VH) amino acid sequence, a heavy chain CH1 constant region amino acid sequence, a hinge region amino acid sequence, a heavy chain CH2 constant region amino acid sequence, and a heavy chain CH3 constant region amino acid sequence; iii) a third polypeptide, arranged from N-to-C terminus, comprising: a hinge region amino acid sequence, a heavy chain CH2 constant region amino acid sequence, and a heavy chain CH3 constant region amino acid sequence, wherein the CH2 and CH3 domains of each of the second and third polypeptides form an Fc domain.

In some embodiments, iii) the third polypeptide comprises, arranged from N-to-C terminus, comprising: a variable heavy chain (VH) amino acid sequence, a heavy chain CH1 constant region amino acid sequence, a hinge region amino acid sequence, a heavy chain CH2 constant region amino acid sequence, and a heavy chain CH3 constant region amino acid sequence; wherein the antibody or antigen binding fragment thereof further comprises: iv) a fourth polypeptide, arranged from N-to-C terminus, comprising: a variable light chain (VL) amino acid sequence, and a light chain constant amino acid sequence (CL1).

In some embodiments, the IL-21 polypeptide or a functional fragment or a variant thereof and the antibody or antigen binding fragment thereof are operably linked to each other. In some embodiments, the IL-21 polypeptide or a functional fragment or a variant thereof is linked to the N-terminus or C-terminus of the antibody or antigen binding fragment thereof. In some embodiments, the IL-21 polypeptide or a functional fragment or a variant thereof is conjugated to the C-terminus of the first, second, or third polypeptide. In some embodiments, the IL-21 polypeptide or a functional fragment or a variant thereof is conjugated to the N-terminus of the first, second, or third polypeptide. In some embodiments, the IL-21 polypeptide or a functional fragment or a variant thereof is conjugated to the C-terminus of the first, second, third, or fourth polypeptide. In some embodiments, the IL-21 polypeptide or a functional fragment or a variant thereof is conjugated to the hinge region of the second or third polypeptide. In some embodiments, the targeted cytokine construct comprises at least one molecule of the IL-21 polypeptide or a functional fragment or a variant thereof. In some embodiments, the targeted cytokine construct comprises at least 1, 2, 3, 4, or 5 molecules of the IL-21 polypeptide, such from 1 to 2, 1 to 3, 1 to 4, 1 to 5, 2 to 3, 2 to 4, 2 to 5, 3 to 4, 3 to 5, or 4 to 5 molecules of the IL-21 polypeptide or a functional fragment or a variant thereof.

In some embodiments, the Fc domain comprises a human IgG Fc domain, such as IgG1, IgG2, IgG3, or IgG4 Fc domain. In some embodiments, the Fc domain comprises one or more modifications that promote heterodimerization. In some embodiments, the second polypeptide comprises a knob modification in the CH2 or the CH3 domain, and the third polypeptide comprises a hole modification in the CH2 or the CH3 domain; or wherein the third polypeptide comprises a knob modification in the CH2 or the CH3 domain and the second polypeptide comprises a hole modification in the CH2 or the CH3. For example, an IgG Fc domain of the targeted cytokine construct can comprise a knob-into-hole modification in the CH3 domains. The "hole" heavy chain may be connected to an IL-21 polypeptide and carry the S354C, T366S, L368A and Y407V mutations in the CH3 domain, whereas the unfused "knob" heavy chain can carry the Y349C and T366W mutations in the CH3 domain (EU numbering). Alternately, the "hole" heavy chain may be unfused and carry the S354C, T366S, L368A and Y407V mutations in the CH3 domain, whereas the "knob" heavy chain may be connected to the IL-21 polypeptide and can carry the Y349C and T366W mutations in the CH3 domain (EU numbering). In some embodiments, at least one of said first and second Fc domains comprise the following Fc mutations according to EU numbering: L234A, L235A, and G237A.

In some embodiments, an IL-21 polypeptide or a functional fragment or a variant thereof is conjugated to at least one of: the N-terminus and the C-terminus of the second or the third polypeptide. In some embodiments, an IL-21 polypeptide or a functional fragment or a variant thereof is conjugated to the C-terminus of the second or the third polypeptide. In some embodiments, an IL-21 polypeptide or a functional fragment or a variant thereof is conjugated to at least one of: the N-terminus or the C-terminus of the second or the third polypeptide. In some embodiments, an IL-21 polypeptide or a functional fragment or a variant thereof is conjugated to the N-terminus or the C-terminus of first or the fourth polypeptide. In some embodiments, an IL-21 polypeptide is conjugated to at least one of: the hinge region of the second or the third polypeptide.

In some embodiments, a fusion protein of the present disclosure displays one or more of the following: binds human CD8 and does not block an interaction of CD8 with MHC class I; and activates CD8+ T cells with at least 10-fold, 25-fold, 50-fold, 100-fold, 250-fold, 500-fold, or 1000-fold greater potency, e.g., as compared to activation of NK cells, CD4+ T cells or B cells. In some embodiments, whether an anti-CD8 antibody or fusion protein of the present disclosure blocks the interaction of CD8 with MHC class I can be assayed, e.g., by assaying activation status of CD8+ T cells (e.g., upon antigen stimulation) in the presence or absence of the anti-CD8 antibody or fusion protein. In some embodiments, activation of CD8+ T cells, CD4+ T cells, and/or NK cells can be measured, e.g., by assaying STAT3 phosphorylation. For an exemplary assay and conditions, see, e.g., Example 3.

A targeted cytokine construct comprising and IL-21 polypeptide or a functional fragment or a variant thereof of the disclosure, in certain embodiments, the IL-21 polypeptide binds to IL-21R with $K_D$ that is greater than about 1 nM. In some embodiments, the IL-21 polypeptide binds to IL-21R with $K_D$ that is greater than about 10 nM. In some embodiments, the IL-21 polypeptide binds to IL-21R with $K_D$ that is greater than about 100 nM. In some embodiments, the IL-21 polypeptide binds to IL-21R with $K_D$ that is greater than about 1 μM. In some embodiments, the IL-21 polypeptide binds to IL-21R with $K_D$ that is greater than about 10 μM. In some embodiments, the IL-21 polypeptide binds to IL-21R with $K_D$ that is greater than about 100 μM. In some embodiments, the IL-21 polypeptide binds to In some embodiments the IL-21 polypeptide or functional fragment thereof has a $K_D$ of about 1 nM, about 5 nM, about 10 nM, about 20 nM, about 25 nM, about 50 nM, about 100 nM, about 200 nM, about 300 nM, about 400 nM, about 500 nM, about 600 nM, about 700 nM, about 800 nM, about 900 nM, about 1.0 μM, about 1.5 μM, about 2.0 μM, about 2.5 μM, about 3.0 μM, about 3.5 μM, about 4.0 μM, about 4.5 μM, about 5.0 μM about 10.0 μM, about 20.0 μM, about 30.0 μM, about 40.0 μM, about 50.0 μM, about 100 μM or about 1000 μM. In some embodiments, the IL-21 polypeptide has a $K_D$ of about 1 nM to about 5 nM, about 1 nM to about 10 nM, about 1 nM to about 20 nM, about 1 nM to about 25 nM, about 1 nM to about 50 nM, about 1 nM to about 100 nM, about 1 nM to about 200 nM, about 1 nM to about 300 nM, about 1 nM to about 400 nM, about 1 nM to about 500 nM, about 1 nM to about 600 nM, about 1 nM to about 700 nM, about 1 nM to about 800 nM, about 1 nM to about 900 nM, about 1 nM to about 1.0 μM, about 1 nM to about 1.5 μM, about 1 nM to about 2.0 μM, about 1 nM to about 2.5 μM, about 1 nM to about 3.0 μM, about 1 nM to about 3.5 μM, about 1 nM to about 4.0 μM, about 1 nM to about 4.5 μM, about 1 nM to about 5.0 μM, about 5 nM to about 10 nM, about 5 nM to about 20 nM, about 5 nM to about 25 nM, about 5 nM to about 50 nM, about 5 nM to about 100 nM, about 5 nM to about 200 nM, about 5 nM to about 300 nM, about 5 nM to about 400 nM, about 5 nM to about 500 nM, about 5 nM to about 600 nM, about 5 nM to about 700 nM, about 5 nM to about 800 nM, about 5 nM to about 900 nM, about 5 nM to about 1.0 µM, about 5 nM to about 1.5 µM, about 5 nM to about 2.0 µM, about 5 nM to about 2.5 µM, about 5 nM to about 3.0 µM, about 5 nM to about 3.5 µM, about 5 nM to about 4.0 µM, about 5 nM to about 4.5 µM, about 5 nM to about 5.0 µM, 10 nM to about 20 nM, about 10 nM to about 25 nM, about 10 nM to about 50 nM, about 10 nM to about 100 nM, about 10 nM to about 200 nM, about 10 nM to about 300 nM, about 10 nM to about 400 nM, about 10 nM to about 500 nM, about 10 nM to about 600 nM, about 10 nM to about 700 nM, about 10 nM to about 800 nM, about 10 nM to about 900 nM, about 10 nM to about 1.0 µM, about 10 nM to about 1.5 µM, about 10 nM to about 2.0 µM, about 10 nM to about 2.5 µM, about 10 nM to about 3.0 µM, about 10 nM to about 3.5 µM, about 10 nM to about 4.0 µM, about 10 nM to about 4.5 µM, about 10 nM to about 5.0 µM, about 20 nM to about 25 nM, about 20 nM to about 50 nM, about 20 nM to about 100 nM, about 20 nM to about 200 nM, about 20 nM to about 300 nM, about 20 nM to about 400 nM, about 20 nM to about 500 nM, about 20 nM to about 600 nM, about 20 nM to about 700 nM, about 20 nM to about 800 nM, about 20 nM to about 900 nM, about 20 nM to about 1.0 µM, about 20 nM to about 1.5 µM, about 20 nM to about 2.0 µM, about 20 nM to about 2.5 µM, about 20 nM to about 3.0 µM, about 20 nM to about 3.5 µM, about 20 nM to about 4.0 µM, about 20 nM to about 4.5 µM, about 20 nM to about 5.0 µM, about 25 nM to about 50 nM, about 25 nM to about 100 nM, about 25 nM to about 200 nM, about 25 nM to about 300 nM, about 25 nM to about 400 nM, about 25 nM to about 500 nM, about 25 nM to about 600 nM, about 25 nM to about 700 nM, about 25 nM to about 800 nM, about 25 nM to about 900 nM, about 25 nM to about 1.0 µM, about 25 nM to about 1.5 µM, about 25 nM to about 2.0 µM, about 25 nM to about 2.5 µM, about 25 nM to about 3.0 µM, about 25 nM to about 3.5 µM, about 25 nM to about 4.0 µM, about 25 nM to about 4.5 µM, about 25 nM to about 5.0 µM, about 50 nM to about 100 nM, about 50 nM to about 200 nM, about 50 nM to about 300 nM, about 50 nM to about 400 nM, about 50 nM to about 500 nM, about 50 nM to about 600 nM, about 50 nM to about 700 nM, about 50 nM to about 800 nM, about 50 nM to about 900 nM, about 50 nM to about 1.0 µM, about 50 nM to about 1.5 µM, about 50 nM to about 2.0 µM, about 50 nM to about 2.5 µM, about 50 nM to about 3.0 µM, about 50 nM to about 3.5 µM, about 50 nM to about 4.0 µM, about 50 nM to about 4.5 µM, about 50 nM to about 5.0 µM, about 100 nM to about 200 nM, about 100 nM to about 300 nM, about 100 nM to about 400 nM, about 100 nM to about 500 nM, about 100 nM to about 600 nM, about 100 nM to about 700 nM, about 100 nM to about 800 nM, about 100 nM to about 900 nM, about 100 nM to about 1.0 µM, about 100 nM to about 1.5 µM, about 100 nM to about 2.0 µM, about 100 nM to about 2.5 µM, about 100 nM to about 3.0 µM, about 100 nM to about 3.5 µM, about 100 nM to about 4.0 µM, about 100 nM to about 4.5 µM, about 100 nM to about 5.0 µM, about 200 nM to about 300 nM, about 200 nM to about 400 nM, about 200 nM to about 500 nM, about 200 nM to about 600 nM, about 200 nM to about 700 nM, about 200 nM to about 800 nM, about 200 nM to about 900 nM, about 200 nM to about 1.0 µM, about 200 nM to about 1.5 µM, about 200 nM to about 2.0 µM, about 200 nM to about 2.5 µM, about 200 nM to about 3.0 µM, about 200 nM to about 3.5 µM, about 200 nM to about 4.0 µM, about 200 nM to about 4.5 µM, about 200 nM to about 5.0 µM, about 300 nM to about 400 nM, about 300 nM to about 500 nM, about 300 nM to about 600 nM, about 300 nM to about 700 nM, about 300 nM to about 800 nM, about 300 nM to about 900 nM, about 300 nM to about 1.0 µM, about 300 nM to about 1.5 µM, about 300 nM to about 2.0 µM, about 300 nM to about 2.5 µM, about 300 nM to about 3.0 µM, about 300 nM to about 3.5 µM, about 300 nM to about 4.0 µM, about 300 nM to about 4.5 µM, about 300 nM to about 5.0 µM, about 400 nM to about 500 nM, about 400 nM to about 600 nM, about 400 nM to about 700 nM, about 400 nM to about 800 nM, about 400 nM to about 900 nM, about 400 nM to about 1.0 µM, about 400 nM to about 1.5 µM, about 400 nM to about 2.0 µM, about 400 nM to about 2.5 µM, about 400 nM to about 3.0 µM, about 400 nM to about 3.5 µM, about 400 nM to about 4.0 µM, about 400 nM to about 4.5 µM, about 400 nM to about 5.0 µM, about 500 nM to about 600 nM, about 500 nM to about 700 nM, about 500 nM to about 800 nM, about 500 nM to about 900 nM, about 500 nM to about 1.0 µM, about 500 nM to about 1.5 µM, about 500 nM to about 2.0 µM, about 500 nM to about 2.5 µM, about 500 nM to about 3.0 µM, about 500 nM to about 3.5 µM, about 500 nM to about 4.0 µM, about 500 nM to about 4.5 µM, about 500 nM to about 5.0 µM, about 600 nM to about 700 nM, about 600 nM to about 800 nM, about 600 nM to about 900 nM, about 600 nM to about 1.0 µM, about 600 nM to about 1.5 µM, about 600 nM to about 2.0 µM, about 600 nM to about 2.5 µM, about 600 nM to about 3.0 µM, about 600 nM to about 3.5 µM, about 600 nM to about 4.0 µM, about 600 nM to about 4.5 µM, about 600 nM to about 5.0 µM, about 700 nM to about 800 nM, about 700 nM to about 900 nM, about 700 nM to about 1.0 µM, about 700 nM to about 1.5 µM, about 700 nM to about 2.0 µM, about 700 nM to about 2.5 µM, about 700 nM to about 3.0 µM, about 700 nM to about 3.5 µM, about 700 nM to about 4.0 µM, about 700 nM to about 4.5 µM, about 700 nM to about 5.0 µM, about 800 nM to about 900 nM, about 800 nM to about 1.0 µM, about 800 nM to about 1.5 µM, about 800 nM to about 2.0 µM, about 800 nM to about 2.5 µM, about 800 nM to about 3.0 µM, about 800 nM to about 3.5 µM, about 800 nM to about 4.0 µM, about 800 nM to about 4.5 µM, about 800 nM to about 5.0 µM, about 900 nM to about 1.0 µM, about 900 nM to about 1.5 µM, about 900 nM to about 2.0 µM, about 900 nM to about 2.5 µM, about 900 nM to about 3.0 µM, about 900 nM to about 3.5 µM, about 900 nM to about 4.0 µM, about 900 nM to about 4.5 µM, about 900 nM to about 5.0 µM, about 1.0 µM to about 1.5 µM, about 1.0 µM to about 2.0 µM, about 1.0 µM to about 2.5 µM, about 1.0 µM to about 3.0 µM, about 1.0 µM to about 3.5 µM, about 1.0 µM to about 4.0 µM, about 1.0 µM to about 4.5 µM, about 1.0 µM to about 5.0 µM, about 1.5 µM to about 2.0 µM, about 1.5 µM to about 2.5 µM, about 1.5 µM to about 3.0 µM, about 1.5 µM to about 3.5 µM, about 1.5 µM to about 4.0 µM, about 1.5 µM to about 4.5 µM, about 1.5 µM to about 5.0 µM, about 2.0 µM to about 2.5 µM, about 2.0 µM to about 3.0 µM, about 2.0 µM to about 3.5 µM, about 2.0 µM to about 4.0 µM, about 2.0 µM to about 4.5 µM, about 2.0 µM to about 5.0 µM, about 2.5 µM to about 3.0 µM, about 2.5 µM to about 3.5 µM, about 2.5 µM to about 4.0 µM, about 2.5 µM to about 4.5 µM, about 2.5 µM to about 5.0 µM, about 3.0 µM to about 3.5 µM, about 3.0 µM to about 4.0 µM, about 3.0 µM to about 4.5 µM, about 3.0 µM to about 5.0 µM, about 3.5 µM to about 4.0 µM, about 3.5 µM to about 4.5 µM, about 3.5 µM to about 5.0 µM, about 4.0 µM to about 4.5 µM, about 4.0 µM to about 5.0 µM, about 4.5 µM to about 5.0 µM, about 10 µM to about 100 µM, or about 100 μM to about 1000 μM. In some embodiments, the $K_D$ is determined by surface plasmon resonance or using a BIAcore instrument.

In some embodiments, the disclosure provides a fusion protein comprising: a first polypeptide chain comprises the amino acid sequence of SEQ ID NO:262, a second polypeptide chain comprises the amino acid sequence of SEQ ID NO:263, a third polypeptide chain comprises the amino acid sequence of SEQ ID NO:264, and a fourth polypeptide chain comprises the amino acid sequence of SEQ ID NO:262.

In some embodiments, the disclosure provides a fusion protein comprising: a first polypeptide chain comprises the amino acid sequence of SEQ ID NO:266, a second polypeptide chain comprises the amino acid sequence of SEQ ID NO:267, a third polypeptide chain comprises the amino acid sequence of SEQ ID NO:268, and a fourth polypeptide chain comprises the amino acid sequence of SEQ ID NO:266.

In some embodiments, the disclosure provides a fusion protein comprising: a first polypeptide chain comprises the amino acid sequence of SEQ ID NO:270, a second polypeptide chain comprises the amino acid sequence of SEQ ID NO:271, a third polypeptide chain comprises the amino acid sequence of SEQ ID NO:272, and a fourth polypeptide chain comprises the amino acid sequence of SEQ ID NO: 270.

In some embodiments, the disclosure provides a fusion protein comprising: a first polypeptide chain comprises the amino acid sequence of SEQ ID NO: 274, a second polypeptide chain comprises the amino acid sequence of SEQ ID NO:275, a third polypeptide chain comprises the amino acid sequence of SEQ ID NO:276, and a fourth polypeptide chain comprises the amino acid sequence of SEQ ID NO: 274.

In some embodiments, the disclosure provides a fusion protein comprising: a first polypeptide chain comprises the amino acid sequence of SEQ ID NO:278, a second polypeptide chain comprises the amino acid sequence of SEQ ID NO:279, a third polypeptide chain comprises the amino acid sequence of SEQ ID NO:280, and a fourth polypeptide chain comprises the amino acid sequence of SEQ ID NO: 278.

In some embodiments, the disclosure provides a fusion protein comprising: a first polypeptide chain comprises the amino acid sequence of SEQ ID NO:262, a second polypeptide chain comprises the amino acid sequence of SEQ ID NO:263, a third polypeptide chain comprises the amino acid sequence of SEQ ID NO:265, and a fourth polypeptide chain comprises the amino acid sequence of SEQ ID NO:262.

In some embodiments, the disclosure provides a fusion protein comprising: a first polypeptide chain comprises the amino acid sequence of SEQ ID NO:266, a second polypeptide chain comprises the amino acid sequence of SEQ ID NO:267, a third polypeptide chain comprises the amino acid sequence of SEQ ID NO:269, and a fourth polypeptide chain comprises the amino acid sequence of SEQ ID NO:266.

In some embodiments, the disclosure provides a fusion protein comprising: a first polypeptide chain comprises the amino acid sequence of SEQ ID NO:270, a second polypeptide chain comprises the amino acid sequence of SEQ ID NO:271, a third polypeptide chain comprises the amino acid sequence of SEQ ID NO:273, and a fourth polypeptide chain comprises the amino acid sequence of SEQ ID NO: 270.

In some embodiments, the disclosure provides a fusion protein comprising: a first polypeptide chain comprises the amino acid sequence of SEQ ID NO: 274, a second polypeptide chain comprises the amino acid sequence of SEQ ID NO:275, a third polypeptide chain comprises the amino acid sequence of SEQ ID NO:277, and a fourth polypeptide chain comprises the amino acid sequence of SEQ ID NO: 274.

In some embodiments, the disclosure provides a fusion protein comprising: a first polypeptide chain comprises the amino acid sequence of SEQ ID NO:278, a second polypeptide chain comprises the amino acid sequence of SEQ ID NO:279, a third polypeptide chain comprises the amino acid sequence of SEQ ID NO:281, and a fourth polypeptide chain comprises the amino acid sequence of SEQ ID NO: 278.

In some embodiments, the disclosure provides a fusion protein comprising: a first polypeptide chain comprises the amino acid sequence of SEQ ID NO:297, a second polypeptide chain comprises the amino acid sequence of SEQ ID NO:298, a third polypeptide chain comprises the amino acid sequence of SEQ ID NO:299, and a fourth polypeptide chain comprises the amino acid sequence of SEQ ID NO:297.

In some embodiments, the disclosure provides a fusion protein comprising: a first polypeptide chain comprises the amino acid sequence of SEQ ID NO:301, a second polypeptide chain comprises the amino acid sequence of SEQ ID NO:302, a third polypeptide chain comprises the amino acid sequence of SEQ ID NO:303 and a fourth polypeptide chain comprises the amino acid sequence of SEQ ID NO:301.

In some embodiments, the disclosure provides a fusion protein comprising: a first polypeptide chain comprises the amino acid sequence of SEQ ID NO:305, a second polypeptide chain comprises the amino acid sequence of SEQ ID NO:306, a third polypeptide chain comprises the amino acid sequence of SEQ ID NO:307, and a fourth polypeptide chain comprises the amino acid sequence of SEQ ID NO: 305.

In some embodiments, the disclosure provides a fusion protein comprising: a first polypeptide chain comprises the amino acid sequence of SEQ ID NO: 309, a second polypeptide chain comprises the amino acid sequence of SEQ ID NO:310, a third polypeptide chain comprises the amino acid sequence of SEQ ID NO:311, and a fourth polypeptide chain comprises the amino acid sequence of SEQ ID NO: 309.

In some embodiments, the disclosure provides a fusion protein comprising: a first polypeptide chain comprises the amino acid sequence of SEQ ID NO:297, a second polypeptide chain comprises the amino acid sequence of SEQ ID NO:298, a third polypeptide chain comprises the amino acid sequence of SEQ ID NO:300, and a fourth polypeptide chain comprises the amino acid sequence of SEQ ID NO:297.

In some embodiments, the disclosure provides a fusion protein comprising: a first polypeptide chain comprises the amino acid sequence of SEQ ID NO:301, a second polypeptide chain comprises the amino acid sequence of SEQ ID NO:302, a third polypeptide chain comprises the amino acid sequence of SEQ ID NO:304 and a fourth polypeptide chain comprises the amino acid sequence of SEQ ID NO:301.

In some embodiments, the disclosure provides a fusion protein comprising: a first polypeptide chain comprises the amino acid sequence of SEQ ID NO:305, a second polypeptide chain comprises the amino acid sequence of SEQ ID NO:306, a third polypeptide chain comprises the amino acid sequence of SEQ ID NO:308, and a fourth polypeptide chain comprises the amino acid sequence of SEQ ID NO: 305.

In some embodiments, the disclosure provides a fusion protein comprising: a first polypeptide chain comprises the amino acid sequence of SEQ ID NO: 309, a second polypeptide chain comprises the amino acid sequence of SEQ ID NO:310, a third polypeptide chain comprises the amino acid sequence of SEQ ID NO:312, and a fourth polypeptide chain comprises the amino acid sequence of SEQ ID NO: 309.

Also provided, in some embodiments, are at least one polynucleotide encoding a targeted cytokine construct, antibody or functional fragment thereof, or a cytokine or functional fragment thereof. In some embodiments, the polynucleotide molecules are provided as a DNA construct. In other embodiments, the polynucleotide molecules are provided as a messenger RNA transcript.

In some embodiments are provided nucleic acid sequences that are codon optimized for expression in a host cell, e.g., a bacterium, such as E. coli, or a eukaryotic cell, such as a CHO cell. In some examples, the nucleic acid sequences are codon optimized for expression in CHO cells.

The polynucleotide molecules are constructed by known methods such as by incorporating the genes encoding the binding proteins into a genetic construct linked to a suitable promoter, and optionally a suitable transcription terminator, and expressing it in bacteria or other appropriate expression system such as, for example CHO cells. Depending on the vector system and host utilized, any number of suitable transcription and translation elements, including constitutive and inducible promoters, may be used. The promoter is selected such that it drives the expression of the polynucleotide in the respective host cell.

In some embodiments, a polynucleotide as described herein is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described herein. Examples of expression vectors for expression in E. coli are pSKK (Le Gall et al., J Immunol Methods. (2004) 285(1):111-27) or pcDNA5 (Invitrogen) for expression in mammalian cells.

Thus, the targeted cytokine constructs as described herein, in some embodiments, are produced by introducing at least one vector encoding the protein as described above into a host cell and culturing said host cell under conditions whereby the protein domains are expressed, may be isolated and, optionally, further purified.

Method of Use

The disclosure further provides a method for selectively activating CD8+ T cells over other cells present in PBMC populations. These other cells can include, but are not limited to, CD4+, NK cells, B cells, dendritic cells, and innate lymphoid cells. In certain embodiments, the method of the disclosure can also be used to for the treatment of cancers, infectious diseases, chronic infections.

In some embodiments the disease or disorder can be selected for the group consisting of an autoimmune disease, inflammation, autoimmune disease, atopic diseases, paraneoplastic autoimmune diseases, cartilage inflammation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, vasculitis, myelitis, polymyositis, dermatomyositis, polyarteritis nodosa, Wegener's granulomatosis, arteritis, esophagitis rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple sclerosis (MS), asthma, COPD, rhinosinusitis, rhinosinusitis with polyps, eosinophilic esophagitis, eosinophilic bronchitis, Guillain-Barre disease, Type I diabetes mellitus, thyroiditis (e.g., Graves' disease), Addison's disease, Raynaud's phenomenon, autoimmune hepatitis, GVHD, transplantation rejection, kidney damage, hepatitis C-induced vasculitis, or spontaneous loss of pregnancy.

In some embodiments, the disease is the cancer. In some embodiments, the cancer is acute lymphoblastic leukemia (ALL) (including non T cell ALL), acute myeloid leukemia, B cell prolymphocytic leukemia, B cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammopathy of undetermined significance (MGUS), multiple myeloma, myelodysplasia and myelodysplastic syndrome, non-Hodgkin's lymphoma (NHL), plasma cell proliferative disorder (including asymptomatic myeloma, smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, or Waldenstrom macroglobulinemia, Mantle cell lymphoma (MCL), Transformed follicular lymphoma (TFL), Primary mediastinal B cell lymphoma (PMBCL), Multiple myeloma, Hairy cell lymphoma/leukemia, lung cancer, small-cell lung cancer, non-small cell lung (NSCL) cancer, bronchioloalveolar cell lung cancer, squamous cell cancer, adenocarcinoma of the lung, squamous carcinoma of the lung, cancer of the peritoneum, head and neck cancer, bone cancer, pancreatic cancer, skin cancer, cancer of the head or neck, cutaneous or intraocular melanoma, thyroid cancer, uterine cancer, gastrointestinal cancer, ovarian cancer, rectal cancer, cancer of the anal region, stomach cancer, gastric cancer, colon cancer, breast cancer, endometrial carcinoma, uterine cancer, carcinoma of the fallopian tubes, carcinoma of the cervix, carcinoma of the vagina, vulval cancer, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, bladder cancer, liver cancer, hepatoma, hepatocellular cancer, cervical cancer, salivary gland carcinoma, biliary cancer, neoplasms of the central nervous system (CNS), spinal axis tumors, brain stem glioma, glioblastoma multiforme, astrocytoma, schwannomas, ependymomas, medulloblastomas, meningiomas, squamous cell carcinomas, pituitary adenoma and Ewing's sarcoma, including refractory versions of any of the above cancers, or a combination of one or more of the above cancers.

In some embodiments, the disclosure provides a method of enhancing and/or restoring T cell activity in an aging subject, comprising administering to the subject a composition described herein. In some embodiments, the disclosure provides a method of enhancing efficacy of a vaccine in an aging subject, comprising administering to the subject a composition described herein prior to receiving the vaccine. In some embodiments, the disclosure provides a method of treating a disease, disorder, or condition, associated with aging of immune cells, comprising administering to the subject a composition described herein.

The targeted cytokine of the present disclosure provides selective activation of T cells, e.g., CD8+ T cells, over other non-CD8+ cell types, such as CD4+ T cells or NK cells. IL-21 generally acts on a broad class of cells, such as regulatory T cells. Stimulation and subsequent activation of cells via IL-21 can be measured by phosphorylation of STAT3. Cellular activation by IL-21 can be reported as an EC50 of STAT3 phosphorylation (pSTAT3). In some embodiments, the contacting results in a selective increase in cytotoxic function of CD8+ T cells in the culture of cells, as compared to the cytotoxic function of the CD8+ T cells, upon contacting the culture of cells with a reference construct that comprises the same IL-21 polypeptide or a functional fragment or variant thereof but does not comprise the antigen binding protein or functional fragment thereof.

In some embodiments, potency of activation of CD8+ T cell and other cell types is measured by EC50 of cell activation as assessed by STAT3 phosphorylation. In some embodiments, the targeted cytokine construct has an EC50 of STAT3 phosphorylation for CD8+ T cells lower than other cell types. In some embodiments, the other cells are non-CD8+ cells. The non-CD8+ cells can be, but are not limited to B cells, CD4+ T cells, or NK cells. In some embodiments, the selective activation of CD8+ T cells is measured by an increase in STAT3 phosphorylation of the CD8+ T cells compared to the STAT3 phosphorylation of non-CD8+ cells in the culture of cells. In some embodiments, the increase in STAT3 phosphorylation is at least 5×, at least 10× or at least 100× more for the CD8+ T cells compared to the STAT3 phosphorylation of non-CD8+ cells in the culture of cells. In some embodiments, the targeted cytokine construct has a lower EC50 of STAT3 phosphorylation for CD8+ T cells than other cell types by at least 5×, at least 10×, at least 50×, at least 100×, at least 1,000×, at least 10,000×, or at least 100,000×.

In some embodiments, the targeted cytokine construct activates CD8+ T cells with at least about 10-fold or greater potency as compared to activation of NK cells. In some embodiments, the construct activates CD8+ T cells a potency that is at least about 10-fold to about 50-fold greater as compared to activation of NK cells. In some embodiments, the construct activates CD8+ T cells a potency that is at least about 10-fold to about 15-fold, 15-fold to about 20-fold, 20-fold to about 25-fold, 25-fold to about 30-fold, 30-fold to about 35-fold, 35-fold to about 40-fold, 40-fold to about 45-fold, 45-fold to about 50-fold, 50-fold to about 100-fold, 100-fold to about 1,000-fold, 1,000-fold to about 10,000-fold, 10,000-fold to about 100,000-fold, about 10-fold, 15-fold, 20-fold, 25-fold, 30-fold, 35-fold, 40-fold, 45-fold, 50-fold, 100-fold, 1,000-fold, 10,000-fold or about 100,000-fold greater as compared to activation of NK cells.

In some embodiments, the targeted cytokine construct activates CD8+ T cells with at least about 10-fold or greater potency as compared to activation of CD4+ T cells. In some embodiments, the construct activates CD8+ T cells a potency that is at least about 10-fold to about 50-fold greater as compared to activation of CD4+ cells. In some embodiments, the construct activates CD4+ T cells a potency that is at least about 10-fold to about 15-fold, 15-fold to about 20-fold, 20-fold to about 25-fold, 25-fold to about 30-fold, 30-fold to about 35-fold, 35-fold to about 40-fold, 40-fold to about 45-fold, 45-fold to about 50-fold, 50-fold to about 100-fold, 100-fold to about 1,000-fold, 1,000-fold to about 10,000-fold, 10,000-fold to about 100,000-fold, about 10-fold, 15-fold, 20-fold, 25-fold, 30-fold, 35-fold, 40-fold, 45-fold, 50-fold, 100-fold, 1,000-fold, 10,000-fold or about 100,000-fold greater as compared to activation of CD4+ T cells.

Host Cells

Provided herein are host cells comprising a nucleic acid or vector of the present disclosure. As used herein, the term "host cell" refers to any type of cell that can contain the presently disclosed vector and is capable of producing an expression product encoded by the nucleic acid (e.g., mRNA, protein). The host cell in some aspects is an adherent cell or a suspended cell, i.e., a cell that grows in suspension. The host cell in exemplary aspects is a cultured cell or a primary cell which is isolated directly from an organism, e.g., a human. The host cell can be of any cell type, can originate from any type of tissue, and can be of any developmental stage.

In exemplary aspects, the cell is a eukaryotic cell, including, but not limited to, a yeast cell, filamentous fungi cell, protozoa cell, algae cell, insect cell, or mammalian cell. Such host cells are described in the art. See, e.g., Frenzel, et al., Front Immunol 4: 217 (2013). In exemplary aspects, the eukaryotic cells are mammalian cells. In exemplary aspects, the mammalian cells are non-human mammalian cells. In some aspects, the cells are Chinese Hamster Ovary (CHO) cells and derivatives thereof (e.g., CHO-KI, CHO pro-3, CS9), mouse myeloma cells (e.g., NS0, GS-NS0, Sp2/0), cells engineered to be deficient in dihydrofolate reductase (DHFR) activity (e.g., DUKX-X11, DG44), human embryonic kidney 293 (HEK293) cells or derivatives thereof (e.g., HEK293T, HEK293-EBNA), green African monkey kidney cells (e.g., COS cells, VERO cells), human cervical cancer cells (e.g., HeLa), human bone osteosarcoma epithelial cells U2-OS, adenocarcinomic human alveolar basal epithelial cells A549, human fibrosarcoma cells HT1080, mouse brain tumor cells CAD, embryonic carcinoma cells P19, mouse embryo fibroblast cells NIH 3T3, mouse fibroblast cells L929, mouse neuroblastoma cells N2a, human breast cancer cells MCF-7, retinoblastoma cells Y79, human retinoblastoma cells SO—Rb50, human liver cancer cells Hep G2, mouse B myeloma cells J558L, or baby hamster kidney (BHK) cells (Gaillet et al. 2007; Khan, Adv Pharm Bull 3(2): 257-263 (2013)). In a particular embodiment, the host cell is CS9 (a CHO cell line).

For purposes of amplifying or replicating the vector, the host cell is in some aspects is a prokaryotic cell, e.g., a bacterial cell.

Also provided by the present disclosure is a population of cells comprising at least one host cell described herein. The population of cells in some aspects is a heterogeneous population comprising the host cell comprising vectors described, in addition to at least one other cell, which does not comprise any of the vectors. Alternatively, in some aspects, the population of cells is a substantially homogeneous population, in which the population comprises mainly host cells (e.g., consisting essentially of) comprising the vector. The population in some aspects is a clonal population of cells, in which all cells of the population are clones of a single host cell comprising a vector, such that all cells of the population comprise the vector. In exemplary embodiments of the present disclosure, the population of cells is a clonal population comprising host cells comprising a vector as described herein.

Pharmaceutical Compositions

Compositions comprising an IL-21 polypeptide, a conjugate comprising the IL-21 polypeptide, a fusion protein comprising the IL-21 polypeptide and an antigen-binding protein, a conjugate comprising the antigen-binding protein, a fusion protein comprising the antigen-binding protein of the disclosure, a nucleic acid, vector, or host cell, of the present disclosure, or a combination thereof, are provided herein. The compositions in some aspects comprise an IL-21 polypeptide, an antigen-binding protein, a conjugate, fusion protein, nucleic acid, vector, or host cell of the present disclosure, or a combination thereof, in isolated and/or purified form. In some aspects, the composition comprises a single type (e.g., structure/combination of mutations relative to wild-type IL-21 polypeptide) of an IL-21 polypeptide, antigen-binding protein, a conjugate, fusion protein, nucleic acid, vector, or host cell of the present disclosure, or comprises a combination of two or more different types of IL-21 polypeptides, antigen-binding proteins, conjugates, fusion proteins, nucleic acids, vectors or host cells of the present disclosure.

In some embodiments, the composition comprises agents which enhance the chemico-physico features of an IL-21 polypeptide, antigen-binding protein, a conjugate, fusion protein, nucleic acid, vector, or host cell, e.g., via stabilizing, for example, the IL-21 polypeptide or fusion protein at certain temperatures (e.g., room temperature), increasing shelf life, reducing degradation, e.g., oxidation protease mediated degradation, increasing half-life of, for example, the IL-21 mutein or fusion protein, etc. In some embodiments, the composition comprises any of the agents disclosed herein as a heterologous moiety or conjugate moiety, optionally, in admixture with an IL-21 polypeptide, conjugates, fusion proteins, nucleic acids, vectors, or host cells of the present disclosure.

In some embodiments, the composition additionally comprises a pharmaceutically acceptable carrier, diluents, or excipient. In some embodiments, an IL-21 polypeptides, antigen-binding proteins, conjugates, fusion proteins, nucleic acids, vectors, or host cells as presently disclosed (hereinafter referred to as "active agents"), or combinations thereof, are formulated into a pharmaceutical composition comprising the active agent, along with a pharmaceutically acceptable carrier, diluent, or excipient. In this regard, the present disclosure further provides pharmaceutical compositions comprising an active agent (any of the IL-21 polypeptides, antigen-binding proteins, conjugates, fusion proteins, nucleic acids, vectors, or host cells of the present disclosure), which pharmaceutical composition is suitable for administration to a subject, e.g., a mammal.

In some embodiments, the active agent is present in the pharmaceutical composition at a purity level suitable for administration to a subject. In some embodiments, the active agent has a purity level of at least about 90%, about 91%, about 92%, about 93%, about 94%, about 95%, about 96%, about 97%, about 98% or about 99%, and a pharmaceutically acceptable diluent, carrier or excipient. In some embodiments, the compositions contain an active agent at a concentration of about 0.001 to about 200.0 mg/ml.

In exemplary aspects, the pharmaceutical compositions comprise a pharmaceutically acceptable carrier. As used herein, the term "pharmaceutically acceptable carriers" include but are not limited to any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The pharmaceutical composition can comprise any pharmaceutically acceptable ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesive, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the Handbook of Pharmaceutical Excipients, Third Edition, A. H. Kibbe (Pharmaceutical Press, London, U K, 2000), which is incorporated by reference in its entirety. Remington's Pharmaceutical Sciences, Sixteenth Edition, E. W. Martin (Mack Publishing Co., Easton, Pa., 1980), which is incorporated by reference in its entirety.

In some embodiments, the pharmaceutical composition comprises formulation materials that are nontoxic to recipients at the dosages and concentrations employed. In specific embodiments, pharmaceutical compositions comprising an active agent and one or more pharmaceutically acceptable salts; polyols; surfactants; osmotic balancing agents; tonicity agents; anti-oxidants; antibiotics; antimycotics; bulking agents; lyoprotectants; anti-foaming agents; chelating agents; preservatives; colorants; analgesics; or additional pharmaceutical agents. In exemplary aspects, the pharmaceutical composition comprises one or more polyols and/or one or more surfactants, optionally, in addition to one or more excipients, including but not limited to, pharmaceutically acceptable salts; osmotic balancing agents (tonicity agents); anti-oxidants; antibiotics; antimycotics; bulking agents; cytoprotectants; anti-foaming agents; chelating agents; preservatives; colorants; and analgesics.

In some embodiments, the pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetra acetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

The pharmaceutical compositions can be formulated to achieve a physiologically compatible pH. In some embodiments, the pH of the pharmaceutical composition can be for example between about 4 or about 5 and about 8.0 or about 4.5 and about 7.5 or about 5.0 to about 7.5. In exemplary embodiments, the pH of the pharmaceutical composition is between 5.5 and 7.5.

Routes of Administration

With regard to the present disclosure, the active agent, or pharmaceutical composition comprising the same, can be administered to the subject via any suitable route of administration. For example, the active agent can be administered to a subject via parenteral, nasal, oral, pulmonary, topical, vaginal, or rectal administration. The following discussion on routes of administration is merely provided to illustrate exemplary embodiments and should not be construed as limiting the scope in any way.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The active agent of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethyl sulfoxide, glycerol, ketals such as 2,2-dimethyl-153-dioxolane-4-methanol, ethers, poly(ethylene glycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropyl methylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and I mixtures thereof.

The parenteral formulations in some embodiments contain from about 0.5% to about 25% by weight of the active agent of the present disclosure in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with the present disclosure. The requirements for effective pharmaceutical carriers for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)).

Dosages

The active agents of the disclosure are believed to be useful in methods more specifically activating CD8+ T cells through IL-21 signaling, as described herein, and are thus believed to be useful in methods of treating or preventing one or more diseases, e.g., cancer. For purposes of the disclosure, the amount or dose of the active agent administered should be sufficient to effect, e.g., a therapeutic or prophylactic response, in the subject or animal over a reasonable time frame. For example, the dose of the active agent of the present disclosure should be sufficient to treat cancer as described herein in a period of from about 1 to 4 minutes, 1 to 4 hours or 1 to 4 weeks or longer, e.g., 5 to 20 or more weeks, from the time of administration. In certain embodiments, the time period could be even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing the extent to which cancer is treated upon administration of a given dose of the active agent of the present disclosure to a mammal among a set of mammals, each set of which is given a different dose of the active agent, could be used to determine a starting dose to be administered to a mammal. The extent to which cancer is treated upon administration of a certain dose can be represented by, for example, the cytotoxicity of the active agent or the extent of tumor regression achieved with the active agent in a mouse xenograft model. Methods of measuring cytotoxicity of the fusion proteins and methods of assaying tumor regression are known in the art.

The dose of the active agent of the present disclosure also will be determined by the existence, nature and extent of any adverse side effects that might accompany the administration of a particular active agent of the present disclosure. Typically, the attending physician will decide the dosage of the active agent of the present disclosure with which to treat each individual patient, taking into consideration a variety of factors, such as age, body weight, general health, diet, sex, active agent of the present disclosure to be administered, route of administration, and the severity of the condition being treated. By way of example and not intending to limit the present disclosure, the dose of the active agent of the present disclosure can be about 0.000001 to about 1 g/kg body weight of the subject being treated/day, from about 0.000001 to about 0.001 g/kg body weight/day, or about 0.01 mg to about 1 g/kg body weight/day.

Controlled Release Formulations

In some embodiments, the active agents described herein can be modified into a depot form, such that the manner in which the active agent of the present disclosure is released into the body to which it is administered is controlled with respect to time and location within the body (see, for example, U.S. Pat. No. 4,450,150). Depot forms of active agents of the present disclosure can be, for example, an implantable composition comprising the active agents and a porous or non-porous material, such as a polymer, wherein the active agent is encapsulated by or diffused throughout the material and/or degradation of the non-porous material. The depot is then implanted into the desired location within the body of the subject and the active agent is released from the implant at a predetermined rate.

The pharmaceutical composition comprising the active agent in certain aspects is modified to have any type of in vivo release profile. In some aspects, the pharmaceutical composition is an immediate release, controlled release, sustained release, extended release, delayed release, or bi-phasic release formulation. Methods of formulating peptides for controlled release are known in the art. See, for example, Qian et al., J Pharm 374: 46-52 (2009) and International Patent Application Publication Nos. WO 2008/130158, WO2004/033036; WO2000/032218; and WO 1999/040942.

The instant compositions can further comprise, for example, micelles or liposomes, or some other encapsulated form, or can be administered in an extended release form to provide a prolonged storage and/or delivery effect.

Combinations

In some embodiments, the IL-21 polypeptide or a targeted cytokine construct composition is administered in combination with a cell therapy (e.g., an adoptive cell therapy, a T-cell therapy, such as a CAR-T cell therapy, a TCR-T cell therapy, a tumor infiltrating lymphocyte (TIL) therapy), cancer vaccine, anti-angiogenesis agent, antibody drug conjugate, chemotherapeutic agent, immune stimulating agent (e.g. IL-2), immune priming agent (e.g. IL-2) or immune checkpoint inhibitor (ICI). In some embodiments, the chemotherapeutic agent is a kinase inhibitor, antimetabolite, cytotoxin or cytostatic agent, anti-hormonal agent, platinum-based chemotherapeutic agent, methyltransferase inhibitor, antibody, or anti-cancer peptide.

In some cases, the IL-21 polypeptide disclosed herein is used to treat, or enhance the efficacy of treatment associated with tumor types not responsive to a therapy using IL-2 (e.g., a therapy that promotes IL-2 signaling in one or more cells of the subject). In some cases, the IL-21 polypeptide enhances the efficacy of treatment associated with tumor types not responsive to a therapy that targets PD-1 (e.g., a therapy that inhibits PD-1 signaling in one or more cells of the subject). In some cases, the IL-21 polypeptide enhances the efficacy of treatment associated with tumor types not responsive to both a therapy comprising IL-2 and a therapy that targets PD-1. For example, PD-1 resistant tumor are associated with reduced memory T cell numbers and increased exhausted T cell numbers, suggesting use of the IL-21 polypeptide of the present disclosure can improve the outcome of the treatment of these tumors.

In some embodiments, the immune checkpoint inhibitor targets PD-L1, PD-1, CTLA-4, CEACAM, LAIR1, CD160, 2B4, CD80, CD86, CD276, VTCN1, HVEM, KIR, A2AR, MHC class I, MHC class II, GALS, adenosine, TGFR, OX40, CD137, CD40, CD47, TREM1, TREM2, HLA-G, CCR4, CCR8, CD39, CD73, IDO, CSF1R, TIM-3, BTLA, VISTA, LAG-3, TIGIT, IDO, MICA/B, LILRB4, SIGLEC-15, or arginase, including without limitation an inhibitor of PD-1 (e.g., an anti-PD-1 antibody), PD-L1 (e.g., an anti-PD-L1 antibody), or CTLA-4 (e.g., an anti-CTLA-4 antibody).

Examples of anti-PD-1 antibodies include, without limitation, pembrolizumab, nivolumab, cemiplimab, zimberelimab (Arcus), sasanlimab (Pfizer), JTX-4014, spartalizumab (PDR001; Novartis), camrelizumab (SHR1210; Jiangsu HengRui Medicine), sintilimab (1B1308; Innovent and Eli Lilly), tislelizumab (BGB-A317), toripalimab (JS 001), dostarlimab (TSR-042, WBP-285), INCMGA00012 (MGA012), AMP-224, and AMP-514 (MEDI0680). Examples of anti-PD-L1 antibodies include, without limitation, atezolizumab, avelumab, durvalumab, KN035, and CK-301 (Checkpoint Therapeutics). Examples of PD-L1 inhibitors (non-antibody based) include, without limitation, AUNP12, CA-170, and BMS-986189. Examples of anti-CTLA-4 antibodies include, without limitation, ipilimumab, tremelimumab, BMS-986218, BMS-986249, BMS-986288, HBM4003, ONC-392, KN044, ADG116, ADU-1604, AGEN1181, AGEN1884, MK-1308, and REGN4659.

In some embodiments, an IL-21 polypeptide or fusion protein thereof is administered in combination with a tumor targeting antibody. In some embodiments, a tumor targeting antibody is specific for a cancer antigen or a tumor antigen. In some embodiments, the tumor targeting antibody is Rituxan or cetuximab.

The IL-21 polypeptide of the present disclosure can be administered in combination with another cytokine therapy. In some embodiments, the cytokine therapy comprises IL-2 or any functional variant thereof, or a target IL-2 construct comprising IL-2 or functional variant thereof (for example, such as those described in international patent application nos. PCT/US20/36454 and PCT/US21/56312, each of which is hereby incorporated by reference in its entirety). In some embodiments, the IL-21 polypeptide or target cytokine construct composition is administered in combination with IL-2 or functional variant thereof, a target IL-2 construct comprising IL-2 or functional variant thereof, such as those described in international patent application nos. PCT/US20/36454 and PCT/US21/56312.

Kits

The present disclosure additionally provides kits comprising an IL-21 polypeptide or functional fragment or variant thereof, an antigen-binding protein, a conjugate, fusion protein, nucleic acid, vector, or host cell of the present disclosure, or a combination thereof. The kit in exemplary aspects comprises at least one IL-21 polypeptide or a functional fragment or a variant thereof, antigen-binding protein, a conjugate, fusion protein, nucleic acid, vector, or host cell of the present disclosure, or a combination thereof, in a container. In exemplary aspects, the at least one IL-21 polypeptide or a functional fragment or a variant thereof, antigen-binding protein, a conjugate, fusion protein, nucleic acid, vector, or host cell of the present disclosure, is provided in the kit as a unit dose. For purposes herein "unit dose" refers to a discrete amount dispersed in a suitable carrier. In exemplary aspects, the unit dose is the amount sufficient to provide a subject with a desired effect, e.g., treatment of cancer. In exemplary aspects, the kit comprises several unit doses, e.g., a week or month supply of unit doses, optionally, each of which is individually packaged or otherwise separated from other unit doses. In some embodiments, the components of the kit/unit dose are packaged with instructions for administration to a patient. In some embodiments, the kit comprises one or more devices for administration to a patient, e.g., a needle and syringe, and the like. In some aspects, the at least one IL-21 polypeptide or a functional fragment or a variant thereof, antigen-binding protein, a conjugate, fusion protein, nucleic acid, vector, or host cell of the present disclosure, or a combination thereof, is/are pre-packaged in a ready to use form, e.g., a syringe, an intravenous bag, etc. In exemplary aspects, the ready to use form is for a single use. In exemplary aspects, the kit comprises multiple single use, ready to use forms of the at least one IL-21 polypeptide or a functional fragment or a variant thereof, antigen-binding protein, a conjugate, fusion protein, nucleic acid, vector, or host cell of the present disclosure. In some aspects, the kit further comprises other therapeutic or diagnostic agents or pharmaceutically acceptable carriers (e.g., solvents, buffers, diluents, etc.), including any of those described herein.

Methods of Manufacture

The IL-21 polypeptide or functional fragment or variant thereof, as described herein, may be obtained by methods known in the art. Suitable methods of de novo synthesizing polypeptides are described in, for example, Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; and U.S. Pat. No. 5,449,752. Additional exemplary methods of making the peptides of the invention are set forth herein.

In some embodiments, the IL-21 polypeptide or functional fragment or variant thereof, as described herein, can be commercially synthesized by companies, such as Synpep (Dublin, Calif), Peptide Technologies Corp. (Gaithersburg, Md.), Multiple Peptide Systems (San Diego, Calif.), Peptide 2.0 Inc. (Chantilly, Va.), and American Peptide Co. (Sunnyvale, Calif.). In this respect, the IL-21 muteins can be synthetic, recombinant, isolated, and/or purified.

Also, in some aspects, an IL-21 polypeptide or functional fragment or variant thereof, as described herein, can be recombinantly produced using a nucleic acid encoding the amino acid sequence of the peptide using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994.

Methods of making an IL-21 polypeptide or functional fragment or variant thereof, as described herein, or a targeted cytokine construct comprising an IL-21 polypeptide or functional fragment or variant thereof, as described herein, are provided herein. The method, in exemplary embodiments, comprises culturing a host cell of the present disclosure to express the IL-21 polypeptide or functional fragment or variant thereof, as described herein, or a targeted cytokine construct, and harvesting the expressed IL-21 polypeptide or functional fragment or variant thereof.

Methods of making fusion protein comprising an IL-21 polypeptide or a functional fragment or a variant thereof or a targeted cytokine construct as described herein are also provided herein. The method, in exemplary embodiments, comprises culturing a host cell of the present disclosure to express the fusion protein and harvesting the expressed fusion protein.

In exemplary embodiments, the method comprises culturing a host cell comprising a nucleic acid encoding the IL-21 polypeptide or a functional fragment or a variant thereof or fusion protein as described herein so as to express the IL-21 polypeptide or a functional fragment or a variant thereof or fusion protein. The host cell can be any of the host cells described herein. In exemplary aspects, the host cell is selected from the group consisting of CHO cells, NS0 cells, COS cells, VERO cells, and BHK cells. In exemplary aspects, the step of culturing a host cell comprises culturing the host cell in a growth medium to support the growth and expansion of the host cell. In exemplary aspects, the growth medium increases cell density, culture viability and productivity in a timely manner. In exemplary aspects, the growth medium comprises amino acids, vitamins, inorganic salts, glucose, and serum as a source of growth factors, hormones, and attachment factors. In exemplary aspects, the growth medium is a fully chemically defined media consisting of amino acids, vitamins, trace elements, inorganic salts, lipids and insulin or insulin-like growth factors. In addition to nutrients, the growth medium also helps maintain pH and osmolality. Several growth media are commercially available and are described in the art. See, e.g., Arora, "Cell Culture Media: A Review" MATER METHODS 3:175 (2013).

In exemplary aspects, the method of making an IL-21 polypeptide or a functional fragment or a variant thereof or fusion protein of the present disclosure comprises culturing the host cell in a feed medium. In exemplary aspects, the method comprises culturing in a feed medium in a fed-batch mode. Methods of recombinant protein production are known in the art. See, e.g., Li et al., "Cell culture processes for monoclonal antibody production" MAbs 2(5): 466-477 (2010).

The method making an IL-21 polypeptide or a functional fragment or a variant thereof or fusion protein can comprise one or more steps for purifying the polypeptide from a cell culture or the supernatant thereof and preferably recovering the purified protein. In exemplary aspects, the method comprises one or more chromatography steps, e.g., affinity chromatography (e.g., protein A affinity chromatography), ion exchange chromatography, hydrophobic interaction chromatography. In exemplary aspects, the method comprises purifying the protein using a Protein A affinity chromatography resin.

In exemplary embodiments, the method further comprises steps for formulating the purified protein, etc., thereby obtaining a formulation comprising the purified protein. Such steps are described in Formulation and Process Development Strategies for Manufacturing, eds. Jameel and Hershenson, John Wiley & Sons, Inc. (Hoboken, N.J.), 2010.

OTHER EMBODIMENTS

The disclosure relates to the following embodiments. Throughout this section, the term "embodiment" is abbreviated as "E" followed by an ordinal. For example, "E1" is equivalent to Embodiment 1.

E1. An IL-21 polypeptide or a functional fragment or a variant thereof comprising a polypeptide sequence having at least 80% sequence identity to SEQ ID NO: 1, wherein the IL-21 polypeptide has an isoelectric point that is at least about 0.6 units to about 5 units lower, compared to that of a wild-type IL-21 protein having a sequence of SEQ ID NO: 1.

E2. The IL-21 polypeptide of embodiment 1, wherein the isoelectric point of SEQ ID NO: 1 is about 9.42.

E3. The IL-21 polypeptide of embodiment 1 or 2, wherein the IL-21 polypeptide has an isoelectric point of about 7.12 to about 8.72.

E4. The IL-21 polypeptide of any one of embodiments 1-3, wherein the polypeptide provides an improved exposure compared to the wild-type IL-21 protein, as measured by at least about 1.5 times greater under the curve (AUC) for the polypeptide, relative to that of the wild-type IL-21, when administered to a subject, at equivalent concentrations.

E5. The IL-21 polypeptide of any one of embodiments 1-4, wherein the IL-21 polypeptide comprises a mutation at one or more positions selected from the group consisting of: K56, T81, N82, A83, G84, R85, R86, Q87, K88, H89, R90, L91, and T92 of SEQ ID NO: 1.

E6. The IL-21 polypeptide of embodiment 5, comprising a mutation at a position selected from the group consisting of: R5, I8, R9, R11, Q12, I14, D15, D18, Q19, Y23, R65, S70, K72, K73, K75, R76, K77, S80, Q116, and K117 of SEQ ID NO: 1.

E7. The IL-21 polypeptide of any one of embodiments 1-6, comprising an amino acid sequence that is at least about 85%, about 90%, about 95%, about 96%, about 97%, about 98%, about 99%, or about 100% identical to a sequence selected from the group consisting of SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 23-SEQ ID NO: 40.

E8. The IL-21 polypeptide of any one of embodiments 1-7, comprising an amino acid sequence that is at least about 85%, about 90%, about 95%, about 96%, about 97%, about 98%, about 99%, or about 100% identical to a sequence selected from the group consisting of SEQ ID NO: 16, SEQ ID NO: 17, SEQ ID NO: 18, SEQ ID NO: 19, SEQ ID NO: 20, SEQ ID NO: 21, and SEQ ID NO: 41-SEQ ID NO: 93.

E9. A targeted cytokine construct comprising an IL-21 polypeptide or a functional fragment or a variant thereof according to any one of embodiments 1-8 and an antibody or an antigen binding fragment thereof.

E10. The targeted cytokine construct of embodiment 9, wherein the antibody or antigen binding fragment thereof specifically binds to a CD8+ T cell.

E11. The targeted cytokine construct of embodiment 9 or 10, wherein the antibody or antigen binding fragment thereof specifically binds to at least one of: CD8α, CD8αα, or CD8αβ.

E12. The targeted cytokine construct of embodiment 9 or 10, wherein the antibody or antigen binding fragment thereof specifically binds to CD8β.

E13. A targeted cytokine construct comprising:
a) an IL-21 polypeptide or a functional fragment or a variant thereof comprising an amino acid sequence that is at least 80% identical to SEQ ID NO: 1; and
b) an antibody or an antigen binding fragment thereof that specifically binds to at least one of CD8α, CD8αα, or CD8αβ.

E14. A targeted cytokine construct comprising:
a) an IL-21 polypeptide or a functional fragment or a variant thereof comprising an amino acid sequence that is at least 80% identical to SEQ ID NO: 1; and
b) an antibody or an antigen binding fragment thereof that specifically binds to CD8β.

E15. The targeted cytokine construct of embodiment 13 or 14, wherein the IL-21 polypeptide comprises a mutation at one or more amino acid positions of SEQ ID NO: 1.

E16. The targeted cytokine construct of any one of embodiments 13-15, wherein the IL-21 polypeptide comprises a mutation at one or more positions selected from the group consisting of: K56, T81, N82, A83, G84, R85, R86, Q87, K88, H89, R90, L91, and T92 of SEQ ID NO: 1.

E17. The targeted cytokine construct of any one of embodiments 13-16, wherein the IL-21 polypeptide comprises mutation at a position selected from the group consisting of: R5, I8, R9, R11, Q12, I14, D15, D18, Q19, Y23, R65, S70, K72, K73, K75, R76, K77, S80, Q116, and K117 of SEQ ID NO: 1.

E18. The targeted cytokine construct of any one of embodiments 13-17, wherein the IL-21 polypeptide or a functional fragment or a variant thereof comprises an amino acid sequence that is at least about 85%, about 90%, about 95%, about 96%, about 97%, about 98%, about 99%, or about 100% identical to a sequence selected from the group consisting of SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15, and SEQ ID NO: 23-SEQ ID NO: 40.

E19. The targeted cytokine construct of any one of embodiments 13-18, wherein the IL-21 polypeptide or a functional fragment or a variant thereof comprises an amino acid sequence that is at least about 85%, about 90%, about 95%, about 96%, about 97%, about 98%, about 99%, or about 100% identical to a sequence selected from the group consisting of SEQ ID NO: 16, SEQ ID NO: 17, SEQ ID NO: 18, SEQ ID NO: 19, SEQ ID NO: 20, SEQ ID NO: 21, and SEQ ID NO: 41-SEQ ID NO: 93.

E20. The targeted cytokine construct of any one of embodiments 13-19, wherein the construct activates CD8+ T cells with at least about 10-fold or greater potency as compared to activation of NK or CD4+ T cells.

E21. The targeted cytokine construct of any one of embodiments 13-20, wherein the construct activates CD8+ T cells with a potency that is at least about 10-fold to about 100,000-fold greater as compared to activation of NK or CD4+ T cells.

E22. The targeted cytokine construct of any one of embodiments 13-21, wherein the antibody or antigen binding fragment thereof comprises:
  i) a first polypeptide, arranged from N-to-C terminus, comprising:
    a variable light chain (VL) amino acid sequence, and
    a) a light chain constant region amino acid sequence (CL1);
  ii) a second polypeptide, arranged from N-to-C terminus, comprising:
    a) a variable heavy chain (VH) amino acid sequence,
    b) a heavy chain CH1 constant region amino acid sequence,
    c) a hinge region amino acid sequence,
    d) a heavy chain CH2 constant region amino acid sequence, and
    e) a heavy chain CH3 constant region amino acid sequence; and
  iii) a third polypeptide, arranged from N-to-C terminus, comprising:
    a) a hinge region amino acid sequence,
    b) a heavy chain CH2 constant region amino acid sequence, and
    c) a heavy chain CH3 constant region amino acid sequence,
wherein the CH2 and CH3 domains of each of the second and third polypeptides form an Fc domain.

E23. The targeted cytokine construct of embodiment 22, wherein the third polypeptide, arranged from N-to-C terminus, comprises:
  a) a variable heavy chain (VH) amino acid sequence,
  b) a heavy chain CH1 constant region amino acid sequence,
  c) a hinge region amino acid sequence,
  d) a heavy chain CH2 constant region amino acid sequence,
  e) a heavy chain CH3 constant region amino acid sequence,
wherein the antibody or antigen binding fragment thereof further comprises:
  iv) a fourth polypeptide, arranged from N-to-C terminus, comprising:
    a) a variable light chain (VL) amino acid sequence, and
    b) a light chain constant amino acid sequence (CL1).

E24. The targeted cytokine construct of embodiment 22 or 23, wherein the IL-21 polypeptide or a functional fragment or a variant thereof and the antibody or antigen binding fragment thereof are operably linked to each other.

E25. The targeted cytokine construct of embodiment 24, wherein the IL-21 polypeptide or a functional fragment or a variant thereof is linked to the N-terminus or C-terminus of the antibody or antigen binding fragment thereof.

E26. The targeted cytokine construct of any one of embodiments 22-25, wherein the IL-21 polypeptide or a functional fragment or variant thereof is conjugated to the C-terminus of the second or the third polypeptide.

E27. The targeted cytokine construct of any one of embodiments 9-26, comprising at least one molecule of the IL-21 polypeptide.

E28. The targeted cytokine construct of any one of embodiments 22-27, wherein the Fc domain is a human IgG Fc domain.

E29. The targeted cytokine construct of any one of embodiments 22-28, wherein the Fc domain is an IgG1, IgG2, IgG3, or IgG4 Fc domain.

E30. The targeted cytokine construct of embodiment 28 or 29, wherein the Fc domain comprises one or more modifications that promote heterodimerization.

E31. The targeted cytokine construct of any one of embodiments 22-30, wherein the second polypeptide comprises a knob modification in the CH2 or the CH3 domain, and the third polypeptide comprises a hole modification in the CH2 or the CH3 domain; or wherein the third polypeptide comprises a knob modification in the CH2 or the CH3 domain and the second polypeptide comprises a hole modification in the CH2 or the CH3.

E32. The fusion protein of any one of embodiments 22-31, wherein at least one of the second and the third polypeptide comprises the following mutations: L234A, L235A, and G237A, numbering according to the EU index.

E33. A targeted cytokine construct comprising:
  a) an IL-21 polypeptide or a functional fragment or variant thereof comprising an amino acid sequence that is at least 80% identical to SEQ ID NO: 1; and
  b) an antibody or an antigen binding fragment thereof comprising a first antigen binding arm and a second antigen binding arm, wherein the first and the second antigen binding arms bind to two different antigens, wherein at least one of the first and the second antigen binding arm specifically binds to CD8α, CD8αα, CD8αβ.

E34. A targeted cytokine construct comprising:
  a) an IL-21 polypeptide or a functional fragment or variant thereof comprising an amino acid sequence that is at least 80% identical to SEQ ID NO: 1; and
  b) an antibody or an antigen binding fragment thereof comprising a first antigen binding arm and a second antigen binding arm, wherein the first and the second antigen binding arms bind to two different antigens, wherein at least one of the first and the second antigen binding arm specifically binds to CD8β.

E35. The targeted cytokine construct of embodiment 33 or 34, wherein the construct activates CD8+ T cells with at least about 10-fold or greater potency as compared to activation of NK cells or CD4+ T cells.

E36. The targeted cytokine construct of embodiment 34 or 35, wherein the construct activates CD8+ T cells a potency that is at least about 10-fold to about 100,000-fold greater as compared to activation of NK cells or CD4+ T cells.

E37. The targeted cytokine construct of any one of embodiments 34-36, wherein the IL-21 polypeptide or a functional fragment thereof or a variant thereof comprises a mutation at a position selected from the group consisting of: K56, T81, N82, A83, R85, G84, R86, Q87, K88, H89, R90, L91, and T92 of SEQ ID NO: 1.

E38. The targeted cytokine construct of any one of embodiments 34-37, wherein the IL-21 polypeptide or a functional fragment thereof or a variant thereof comprises a mutation at a position selected from the group consisting of: R5, I8, R9, R11, Q12, I14, D15, D18, Q19, Y23, R65, S70, K72, K73, K75, R76, K77, S80, Q116, and K117 of SEQ ID NO: 1.

E39. The targeted cytokine construct of any one of embodiments 34-38, wherein the IL-21 polypeptide or a functional fragment or a variant thereof comprises an amino acid sequence that is at least about 85%, about 90%, about 95%, about 96%, about 97%, about 98%, about 99%, or about 100% identical to a sequence selected from the group consisting of SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 23-SEQ ID NO: 40.

E40. The targeted cytokine construct of any one of embodiments 34-39, wherein the IL-21 polypeptide or a functional fragment or a variant thereof comprises an amino acid sequence that is at least about 85%, about 90%, about 95%, about 96%, about 97%, about 98%, about 99%, or about 100% identical to a sequence selected from the group consisting of SEQ ID NO: 16, SEQ ID NO: 17, SEQ ID NO: 18, SEQ ID NO: 19, SEQ ID NO: 20, SEQ ID NO: 21, and SEQ ID NO: 41-SEQ ID NO:93.

E41. A polynucleotide encoding an IL-21 polypeptide or a functional fragment or a variant thereof according to any one of embodiments 1-8.

E42. A polynucleotide that codes for a targeted cytokine construct comprising an IL-21 polypeptide or a functional fragment or a variant thereof and an antibody or an antigen binding fragment thereof, according to any one of embodiments 9-40, the polynucleotide comprising a coding sequence for the IL-21 polypeptide and a coding sequence for the antibody or an antigen binding fragment thereof.

E43. A vector comprising the polynucleotide of embodiment 41 or 42

E44. A host cell comprising the polynucleotide of embodiment 41 or 42 or the vector of embodiment 43.

E45. A pharmaceutical composition comprising an IL-21 polypeptide or a functional fragment or variant thereof according to any one of embodiments 1-8 and a pharmaceutically acceptable carrier.

E46. A pharmaceutical composition comprising a targeted cytokine construct according to any one of embodiments 9-40 and a pharmaceutically acceptable carrier.

E47. A method for selective activation of CD8+ T cells, wherein the method comprises contacting a population of cells comprising CD8+ T cells, CD4+ T cells, and NK cells, with a targeted cytokine construct according to any one of embodiments 9-40.

E48. The method of embodiment 47, wherein selective activation comprises activation of CD8+ T cells with at least about 10-fold or greater potency, as compared to activation of NK cells or CD4+ T cells in the population of cells.

E49. The method of embodiment 47 or 48, wherein selective activation comprises activation of CD8+ T cells with a potency that is at least about 10-fold to about 100,000-fold greater as compared to activation of NK cells or CD4+ T cells in the population of cells.

E50. The method of any one of embodiments 47-49, wherein the selective activation of CD8+ T cells results in increased STAT3 phosphorylation of the CD8+ T cells compared to the STAT3 phosphorylation of the NK cells or CD4+ T cells in the population of cells.

E51. A method of treating a disease in a subject, the method comprising administering an IL-21 polypeptide or a functional fragment or a variant thereof according to any one of embodiments 1-8, a targeted cytokine construct according to any one of embodiments 9-40, or a pharmaceutical composition according to embodiment 45 or 46.

E52. The method of embodiment 51, further comprising an additional therapeutic agent.

E53. The method of embodiment 51 or 52, wherein the disease comprises a cancer or a chronic infection.

E54. The method of any one of embodiments 51-53, wherein the disease comprises the cancer and wherein the cancer is acute lymphoblastic leukemia (ALL) (including non T cell ALL), acute myeloid leukemia, B cell prolymphocytic leukemia, B cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammopathy of undetermined significance (MGUS), multiple myeloma, myelodysplasia and myelodysplastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma, solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, or Waldenstrom macroglobulinemia, Mantle cell lymphoma (MCL), Transformed follicular lymphoma (TFL), Primary mediastinal B cell lymphoma (PMBCL), Multiple myeloma, H-airy, cell lymphoma/leukemia, lung cancer, small-cell lung cancer, non-small cell lung (NSCL) cancer, bronchioloalveolar cell lung cancer, squamous cell cancer, adenocarcinoma of the lung, squamous carcinoma of the lung, cancer of the peritoneum, head and neck cancer, bone cancer, pancreatic cancer, skin cancer, cancer of the head or neck, cutaneous or intraocular melanoma, thyroid cancer, uterine cancer, gastrointestinal cancer, ovarian cancer, rectal cancer, cancer of the anal region, stomach cancer, gastric cancer, colon cancer, breast cancer, endometrial carcinoma, uterine cancer, carcinoma of the fallopian tubes, carcinoma of the cervix, carcinoma of the vagina, vulval cancer, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, bladder cancer, liver cancer, hepatoma, hepatocellular cancer, cervical cancer, salivary gland carcinoma, biliary cancer, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenoma and Ewing's sarcoma, including refractory versions of any of the above cancers, or a combination of one or more of the above cancers.

E55. The targeted cytokine construct of any one of embodiments 13-40, wherein the antibody or antigen binding fragment comprises a heavy chain variable (VH) domain and a light chain variable (VL) domain; and wherein:
   (a) the VH domain comprises a CDR-H1 comprising the amino acid sequence of SEQ ID NO:137, a CDR-H2 comprising the amino acid sequence of SEQ ID NO:138, and a CDR-H3 comprising the amino acid sequence of SEQ ID NO: 139; and wherein the VL domain comprises a CDR-L1 comprising the amino acid sequence of SEQ ID NO: 140, a CDR-L2 comprising the amino acid sequence of SEQ ID NO:141, and a CDR-L3 comprising the amino acid sequence of SEQ ID NO:142;

(b) the VH domain comprises a CDR-H1 comprising the amino acid sequence of SEQ ID NO:149, a CDR-H2 comprising the amino acid sequence of SEQ ID NO:150, and a CDR-H3 comprising the amino acid sequence of SEQ ID NO:151; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154;

(c) the VH domain comprises a CDR-H1 comprising the amino acid sequence of SEQ ID NO:155, a CDR-H2 comprising the amino acid sequence of SEQ ID NO:156, and a CDR-H3 comprising the amino acid sequence of SEQ ID NO:157; and wherein the VL domain comprises a CDR-L1 comprising the amino acid sequence of SEQ ID NO:158, a CDR-L2 comprising the amino acid sequence of SEQ ID NO:159, and a CDR-L3 comprising the amino acid sequence of SEQ ID NO:160;

(d) the VH domain comprises a CDR-H1 comprising the amino acid sequence of SEQ ID NO:161, a CDR-H2 comprising the amino acid sequence of SEQ ID NO:162, and a CDR-H3 comprising the amino acid sequence of SEQ ID NO:163; and wherein the VL domain comprises a CDR-L1 comprising the amino acid sequence of SEQ ID NO:164, a CDR-L2 comprising the amino acid sequence of SEQ ID NO:165, and a CDR-L3 comprising the amino acid sequence of SEQ ID NO:166;

(e) the VH domain comprises a CDR-H1 comprising the amino acid sequence of SEQ ID NO:167, a CDR-H2 comprising the amino acid sequence of SEQ ID NO:168, and a CDR-H3 comprising the amino acid sequence of SEQ ID NO:169; and wherein the VL domain comprises a CDR-L1 comprising the amino acid sequence of SEQ ID NO: 170, a CDR-L2 comprising the amino acid sequence of SEQ ID NO:171, and a CDR-L3 comprising the amino acid sequence of SEQ ID NO:172;

(f) the VH domain comprises a CDR-H1 comprising the amino acid sequence of SEQ ID NO:173, a CDR-H2 comprising the amino acid sequence of SEQ ID NO:174, and a CDR-H3 comprising the amino acid sequence of SEQ ID NO:175; and wherein the VL domain comprises a CDR-L1 comprising the amino acid sequence of SEQ ID NO:176, a CDR-L2 comprising the amino acid sequence of SEQ ID NO:177, and a CDR-L3 comprising the amino acid sequence of SEQ ID NO:178;

(g) the VH domain comprises a CDR-H1 comprising the amino acid sequence of SEQ ID NO:179, a CDR-H2 comprising the amino acid sequence of SEQ ID NO: 180, and a CDR-H3 comprising the amino acid sequence of SEQ ID NO:181; and wherein the VL domain comprises a CDR-L1 comprising the amino acid sequence of SEQ ID NO: 182, a CDR-L2 comprising the amino acid sequence of SEQ ID NO: 183, and a CDR-L3 comprising the amino acid sequence of SEQ ID NO:184;

(h) the VH domain comprises a CDR-H1 comprising the amino acid sequence of SEQ ID NO:143, a CDR-H2 comprising the amino acid sequence of SEQ ID NO:144, and a CDR-H3 comprising the amino acid sequence of SEQ ID NO:145; and wherein the VL domain comprises a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO:148;

(i) the VH domain comprises a CDR-H1 comprising the amino acid sequence of $X_1X_2AIS$, wherein $X_1$ is S, K, G, N, R, D, T, or G, and wherein $X_2$ is Y, L, H, or F (SEQ ID NO:185), a CDR-H2 comprising the amino acid sequence of $X_1X_2X_3PX_4X_5X_6X_7X_8X_9YX_{10}QKFX_{11}G$, wherein $X_1$ is G or H, $X_2$ is I or F, $X_3$ is I, N, or M, $X_4$ is G, N, H, S, R, I, or A, $X_5$ is A, N, H, S, T, F, or Y, $X_6$ is A, D, or G, $X_7$ is T, E, K, V, Q, or A, $X_8$ is A or T, $X_9$ is N or K, $X_{10}$ is A or N, and $X_{11}$ is Q or T (SEQ ID NO:186), and a CDR-H3 comprising the amino acid sequence of $X_1X_2X_3GX_4X_5LFX_6X_7$, wherein $X_1$ is D or A, $X_2$ is A, G, E, R, Y, K, N, Q, L, or F, $X_3$ is A, L, P, or Y, $X_4$ is I or L, $X_5$ is R, A, Q, or S, $X_6$ is A or D, and $X_7$ is D, E, A, or S (SEQ ID NO:187); and wherein the VL domain comprises a CDR-L1 comprising the amino acid sequence of $X_1X_2SX_3X_4IX_5GX_6LN$, wherein $X_1$ is R or G, $X_2$ is A or T, $X_3$ is Q or E, $X_4$ is E, N, T, S, A, K, D, G, R, or Q, $X_5$ is Y or S, and $X_6$ is A or V (SEQ ID NO:188), a CDR-L2 comprising the amino acid sequence of $GX_1X_2X_3LX_4X_5$, wherein $X_1$ is A or S, $X_2$ is T, S, E, Q, or D, $X_3$ is N, R, A, E, or H, $X_4$ is Q or A, and $X_5$ is S or D (SEQ ID NO:189), and a CDR-L3 comprising the amino acid sequence of $QX_1X_2X_3X_4X_5PWT$, wherein $X_1$ is S, N, D, Q, A, or E, $X_2$ is T, I, or S, $X_3$ is Y, L, or F, $X_4$ is D, G, T, E, Q, A, or Y, and $X_5$ is A, T, R, S, K, or Y (SEQ ID NO:190);

j) the VH domain comprises a CDR-H1 comprising the amino acid sequence of SEQ ID NO:199, a CDR-H2 comprising the amino acid sequence of SEQ ID NO:200, and a CDR-H3 comprising the amino acid sequence of SEQ ID NO:201; and wherein the VL domain comprises a CDR-L1 comprising the amino acid sequence of SEQ ID NO: 152, a CDR-L2 comprising the amino acid sequence of SEQ ID NO: 153, and a CDR-L3 comprising the amino acid sequence of SEQ ID NO:202;

(k) the VH domain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and wherein the VL domain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;

(l) the VH domain comprises a CDR-H1 comprising the amino acid sequence of SEQ ID NO:199, a CDR-H2 comprising the amino acid sequence of SEQ ID NO:203, and a CDR-H3 comprising the amino acid sequence of SEQ ID NO:204; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:202;

(m) the VH domain comprises a CDR-H1 comprising the amino acid sequence of $X_1YX_2MS$, wherein $X_1$ is S, D, E, A, or Q and $X_2$ is A, G, or T (SEQ ID NO:208), a CDR-H2 comprising the amino acid sequence of DIX$_1$X$_2$X$_3$GX$_4$X$_5$TX$_6$YADSVKG, wherein X$_1$ is T, N, S, Q, E, H, R, or A, X$_2$ is Y, W, F, or H, X$_3$ is A, S, Q, E, or T, X$_4$ is G or E, X$_5$ is S or I, and X$_6$ is A or G (SEQ ID NO:209), and a CDR-H3 comprising the amino acid sequence of X$_1$X$_2$X$_3$YX$_4$WX$_5$X$_6$AX$_7$DX$_8$, wherein X$_1$ is S or A, X$_2$ is N, H, A, D, L, Q, Y, or R, X$_3$ is A, N, S, or G, X$_4$ is A, V, R, E, or S, X$_5$ is D or S, X$_6$ is D, N, Q, E, S, T, or L, X$_7$ is L, F, or M, and X$_8$ is I, Y, or V (SEQ ID NO:210); and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178);

(n) the VH domain comprises a CDR-H1 comprising the amino acid sequence of SEQ ID NO:220, a CDR-H2 comprising the amino acid sequence of SEQ ID NO:221, and a CDR-H3 comprising the amino acid sequence of SEQ ID NO:222; and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178);

(o) the VH domain comprises a CDR-H1 comprising the amino acid sequence of SEQ ID NO:220, a CDR-H2 comprising the amino acid sequence of SEQ ID NO:260, and a CDR-H3 comprising the amino acid sequence of SEQ ID NO:222; and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178); or (p) the VH domain comprises a CDR-H1 comprising the amino acid sequence of SEQ ID NO:252, a CDR-H2 comprising the amino acid sequence of SEQ ID NO:253, and a CDR-H3 comprising the amino acid sequence of SEQ ID NO:254; and wherein the VL domain comprises a CDR-L1 comprising the amino acid sequence of SEQ ID NO:255, a CDR-L2 comprising the amino acid sequence of SEQ ID NO:256, and a CDR-L3 comprising the amino acid sequence of SEQ ID NO:257.

E56. The targeted cytokine construct of any one of embodiments 13-40, wherein the antibody or antigen binding fragment comprises a heavy chain variable (VH) domain and a light chain variable (VL) domain; and wherein:

(a) the VH domain comprises a CDR-H1 comprising the amino acid sequence of SEQ ID NO:226, a CDR-H2 comprising the amino acid sequence of SEQ ID NO:227, and a CDR-H3 comprising the amino acid sequence of SEQ ID NO:151; and wherein the VL domain comprises a CDR-L1 comprising the amino acid sequence of SEQ ID NO:152, a CDR-L2 comprising the amino acid sequence of SEQ ID NO:153, and a CDR-L3 comprising the amino acid sequence of SEQ ID NO:154;

(b) the VH domain comprises a CDR-H1 comprising the amino acid sequence of SEQ ID NO:228, a CDR-H2 comprising the amino acid sequence of SEQ ID NO:227, and a CDR-H3 comprising the amino acid sequence of SEQ ID NO:157; and wherein the VL domain comprises a CDR-L1 comprising the amino acid sequence of SEQ ID NO:158, a CDR-L2 comprising the amino acid sequence of SEQ ID NO:159, and a CDR-L3 comprising the amino acid sequence of SEQ ID NO:160;

(c) the VH domain comprises a CDR-H1 comprising the amino acid sequence of SEQ ID NO:223, a CDR-H2 comprising the amino acid sequence of SEQ ID NO:227, and a CDR-H3 comprising the amino acid sequence of SEQ ID NO:163; and wherein the VL domain comprises a CDR-L1 comprising the amino acid sequence of SEQ ID NO: 164, a CDR-L2 comprising the amino acid sequence of SEQ ID NO:165, and a CDR-L3 comprising the amino acid sequence of SEQ ID NO:166;

(d) the VH domain comprises a CDR-H1 comprising the amino acid sequence of SEQ ID NO:229, a CDR-H2 comprising the amino acid sequence of SEQ ID NO:227, and a CDR-H3 comprising the amino acid sequence of SEQ ID NO:169; and wherein the VL domain comprises a CDR-L1 comprising the amino acid sequence of SEQ ID NO: 170, a CDR-L2 comprising the amino acid sequence of SEQ ID NO:171, and a CDR-L3 comprising the amino acid sequence of SEQ ID NO:172;

(e) the VH domain comprises a CDR-H1 comprising the amino acid sequence of SEQ ID NO:230, a CDR-H2 comprising the amino acid sequence of SEQ ID NO:231, and a CDR-H3 comprising the amino acid sequence of SEQ ID NO:175; and wherein the VL domain comprises a CDR-L1 comprising the amino acid sequence of SEQ ID NO: 176, a CDR-L2 comprising the amino acid sequence of SEQ ID NO: 177, and a CDR-L3 comprising the amino acid sequence of SEQ ID NO:178;

(f) the VH domain comprises a CDR-H1 comprising the amino acid sequence of SEQ ID NO:230, a CDR-H2 comprising the amino acid sequence of SEQ ID NO:232, and a CDR-H3 comprising the amino acid sequence of SEQ ID NO:181; and wherein the VL domain comprises a CDR-L1 comprising the amino acid sequence of SEQ ID NO: 182, a CDR-L2 comprising the amino acid sequence of SEQ ID NO: 183, and a CDR-L3 comprising the amino acid sequence of SEQ ID NO:184;

(g) the VH domain comprises a CDR-H1 comprising the amino acid sequence of SEQ ID NO:223, a CDR-H2 comprising the amino acid sequence of SEQ ID NO:224, and a CDR-H3 comprising the amino acid sequence of SEQ ID NO:225; and wherein the VL domain comprises a CDR-L1 comprising the amino acid sequence of SEQ ID NO: 140, a CDR-L2 comprising the amino acid sequence of SEQ ID NO:141, and a CDR-L3 comprising the amino acid sequence of SEQ ID NO:142;

(h) the VH domain comprises a CDR-H1 comprising the amino acid sequence of SEQ ID NO:233, a CDR-H2 comprising the amino acid sequence of SEQ ID NO:234, and a CDR-H3 comprising the amino acid sequence of SEQ ID NO:145; and wherein the VL domain comprises a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO:148;

(i) the VH domain comprises a CDR-H1 comprising the amino acid sequence of GX$_1$X$_2$FX$_3$X$_4$X$_5$, wherein X$_1$ is G, Y, S, or A, X$_2$ is T, S, G, R, N, or H, X$_3$ is S, T, R, H, Y, G, or P, $X_4$ is S, K, G, N, R, D, T, or G, and $X_5$ is Y, L, H, or F (SEQ ID NO:235), a CDR-H2 comprising the amino acid sequence of $X_1PX_2X_3X_4X_5$, wherein $X_1$ is I, N, or M, $X_2$ is G, N, H, S, R, I, or A, $X_3$ is A, N, H, S, T, F, or Y, $X_4$ is A, D, or G, and $X_5$ is T, E, K, V, Q, or A (SEQ ID NO:236), and a CDR-H3 comprising the amino acid sequence of $X_1X_2X_3GX_4X_5LFX_6X_7$, wherein $X_1$ is D or A, $X_2$ is A, G, E, R, Y, K, N, Q, L, or F, $X_3$ is A, L, P, or Y, $X_4$ is I or L, $X_5$ is R, A, Q, or S, $X_6$ is A or D, and $X_7$ is D, E, A, or S (SEQ ID NO:237); and wherein the VL domain comprises a CDR-L1 comprising the amino acid sequence of $X_1X_2SX_3X_4IX_5GX_6LN$, wherein $X_1$ is R or G, $X_2$ is A or T, $X_3$ is Q or E, $X_4$ is E, N, T, S, A, K, D, G, R, or Q, $X_5$ is Y or S, and $X_6$ is A or V (SEQ ID NO:188), a CDR-L2 comprising the amino acid sequence of $GX_1X_2X_3LX_4X_5$, wherein $X_1$ is A or S, $X_2$ is T, S, E, Q, or D, $X_3$ is N, R, A, E, or H, $X_4$ is Q or A, and $X_5$ is S or D (SEQ ID NO: 189), and a CDR-L3 comprising the amino acid sequence of $QX_1X_2X_3X_4X_5PWT$, wherein $X_1$ is S, N, D, Q, A, or E, $X_2$ is T, I, or S, $X_3$ is Y, L, or F, $X_4$ is D, G, T, E, Q, A, or Y, and $X_5$ is A, T, R, S, K, or Y (SEQ ID NO:190);
(j) the VH domain comprises a CDR-H1 comprising the amino acid sequence of SEQ ID NO:241, a CDR-H2 comprising the amino acid sequence of SEQ ID NO:242, and a CDR-H3 comprising the amino acid sequence of SEQ ID NO:204; and wherein the VL domain comprises a CDR-L1 comprising the amino acid sequence of SEQ ID NO: 152, a CDR-L2 comprising the amino acid sequence of SEQ ID NO:153, and a CDR-L3 comprising the amino acid sequence of SEQ ID NO:202;
(k) the VH domain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and wherein the VL domain comprises a CDR-L1 comprising the amino acid sequence of SEQ ID NO:205, a CDR-L2 comprising the amino acid sequence of SEQ ID NO:206, and a CDR-L3 comprising the amino acid sequence of SEQ ID NO:207;
(l) the VH domain comprises a CDR-H1 comprising the amino acid sequence of SEQ ID NO:241, a CDR-H2 comprising the amino acid sequence of SEQ ID NO:243, and a CDR-H3 comprising the amino acid sequence of SEQ ID NO:204; and wherein the VL domain comprises a CDR-L1 comprising the amino acid sequence of SEQ ID NO: 152, a CDR-L2 comprising the amino acid sequence of SEQ ID NO: 153, and a CDR-L3 comprising the amino acid sequence of SEQ ID NO:202;
(m) the VH domain comprises a CDR-H1 comprising the amino acid sequence of $GFTFX_1X_2Y$, wherein $X_1$ is S, D, E, Q, S, or A and $X_2$ is S, D, E, A, or Q (SEQ ID NO:244), a CDR-H2 comprising the amino acid sequence of $X_1X_2X_3GX_4X_5$, wherein $X_1$ is T, N, S, Q, E, H, R or A, $X_2$ is Y, W, F, or H, $X_3$ is A, S, Q, E, or T, $X_4$ is G or E, and $X_5$ is S or I (SEQ ID NO:245), and a CDR-H3 comprising the amino acid sequence of $X_1X_2X_3YX_4WX_5X_6AX_7DX_8$, wherein $X_1$ is S or A, $X_2$ is N, H, A, D, L, Q, Y, or R, $X_3$ is A, N, S, or G, $X_4$ is A, V, R, E, or S, $X_5$ is D or S, $X_6$ is D, N, Q, E, S, T, or L, $X_7$ is L, F, or M, and $X_8$ is I, Y, or V (SEQ ID NO:246); and wherein the VL domain comprises a CDR-L1 comprising the amino acid sequence of RASQSVSSNLA (SEQ ID NO:176), a CDR-L2 comprising the amino acid sequence of GASSRAT (SEQ ID NO: 177), and a CDR-L3 comprising the amino acid sequence of QQYGSSPPVT (SEQ ID NO: 178);
(n) the VH domain comprises a CDR-H1 comprising the amino acid sequence of SEQ ID NO:250, a CDR-H2 comprising the amino acid sequence of SEQ ID NO:251, and a CDR-H3 comprising the amino acid sequence of SEQ ID NO:288; and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178);
(o) the VH domain comprises a CDR-H1 comprising the amino acid sequence of SEQ ID NO:250, a CDR-H2 comprising the amino acid sequence of SEQ ID NO:261, and a CDR-H3 comprising the amino acid sequence of SEQ ID NO:288; and wherein the VL domain comprises a CDR-L1 comprising the amino acid sequence of RASQSVSSNLA (SEQ ID NO:176), a CDR-L2 comprising the amino acid sequence of GASSRAT (SEQ ID NO:177), and a CDR-L3 comprising the amino acid sequence of QQYGSSPPVT (SEQ ID NO:178); or
(p) the VH domain comprises a CDR-H1 comprising the amino acid sequence of SEQ ID NO:223, a CDR-H2 comprising the amino acid sequence of SEQ ID NO:224, and a CDR-H3 comprising the amino acid sequence of SEQ ID NO:284; and wherein the VL domain comprises a CDR-L1 comprising the amino acid sequence of SEQ ID NO:285, a CDR-L2 comprising the amino acid sequence of SEQ ID NO:286, and a CDR-L3 comprising the amino acid sequence of SEQ ID NO:287.

E57. The targeted cytokine construct of embodiment 55 or embodiment 56, wherein:
(a) the VH domain comprises an amino acid sequence that is at least 90%, at least 95%, at least 99%, or 100% identical to the sequence of SEQ ID NO: 109, and wherein the VL domain comprises an amino acid sequence that is at least 90%, at least 95%, at least 99%, or 100% identical to the sequence of SEQ ID NO:110;
(b) the VH domain comprises an amino acid sequence that is at least 90%, at least 95%, at least 99%, or 100% identical to the sequence of SEQ ID NO:111, and wherein the VL domain comprises an amino acid sequence that is at least 90%, at least 95%, at least 99%, or 100% identical to the sequence of SEQ ID NO:112;
(c) the VH domain comprises an amino acid sequence that is at least 90%, at least 95%, at least 99%, or 100% identical to the sequence of SEQ ID NO: 113, and wherein the VL domain comprises an amino acid sequence that is at least 90%, at least 95%, at least 99%, or 100% identical to the sequence of SEQ ID NO:114;
(d) the VH domain comprises an amino acid sequence that is at least 90%, at least 95%, at least 99%, or 100% identical to the sequence of SEQ ID NO:115, and wherein the VL domain comprises an amino acid sequence that is at least 90%, at least 95%, at least 99%, or 100% identical to the sequence of SEQ ID NO:116;
(e) the VH domain comprises an amino acid sequence that is at least 90%, at least 95%, at least 99%, or 100% identical to the sequence of SEQ ID NO:117, and wherein the VL domain comprises an amino acid sequence that is at least 90%, at least 95%, at least 99%, or 100% identical to the sequence of SEQ ID NO:118;

(f) the VH domain comprises an amino acid sequence that is at least 90%, at least 95%, at least 99%, or 100% identical to the sequence of SEQ ID NO:119, and wherein the VL domain comprises an amino acid sequence that is at least 90%, at least 95%, at least 99%, or 100% identical to the sequence of SEQ ID NO:120;

(g) the VH domain comprises an amino acid sequence that is at least 90%, at least 95%, at least 99%, or 100% identical to the sequence of SEQ ID NO:123; and wherein the VL domain comprises an amino acid sequence that is at least 90%, at least 95%, at least 99%, or 100% identical to the sequence of SEQ ID NO:124;

(h) the VH domain comprises an amino acid sequence that is at least 90%, at least 95%, at least 99%, or 100% identical to the sequence of SEQ ID NO:129, and wherein the VL domain comprises an amino acid sequence that is at least 90%, at least 95%, at least 99%, or 100% identical to the sequence of SEQ ID NO:130;

(i) the VH domain comprises an amino acid sequence that is at least 90%, at least 95%, at least 99%, or 100% identical to the sequence of SEQ ID NO:131; and wherein the VL domain comprises an amino acid sequence that is at least 90%, at least 95%, at least 99%, or 100% identical to the sequence of SEQ ID NO:132;

(j) the VH domain comprises an amino acid sequence that is at least 90%, at least 95%, at least 99%, or 100% identical to the sequence of SEQ ID NO:125; and wherein the VL domain comprises an amino acid sequence that is at least 90%, at least 95%, at least 99%, or 100% identical to the sequence of SEQ ID NO:126;

(k) the VH domain comprises an amino acid sequence that is at least 90%, at least 95%, at least 99%, or 100% identical to the sequence of SEQ ID NO:127, and wherein the VL domain comprises an amino acid sequence that is at least 90%, at least 95%, at least 99%, or 100% identical to the sequence of SEQ ID NO:128;

(l) the VH domain comprises an amino acid sequence that is at least 90%, at least 95%, at least 99%, or 100% identical to the sequence of SEQ ID NO:133; and wherein the VL domain comprises an amino acid sequence that is at least 90%, at least 95%, at least 99%, or 100% identical to the sequence of SEQ ID NO:134;

(m) the VH domain comprises an amino acid sequence that is at least 90%, at least 95%, at least 99%, or 100% identical to the sequence of SEQ ID NO:135; and wherein the VL domain comprises an amino acid sequence that is at least 90%, at least 95%, at least 99%, or 100% identical to the sequence of SEQ ID NO:136;

(n) the VH domain comprises an amino acid sequence that is at least 90%, at least 95%, at least 99%, or 100% identical to the sequence of SEQ ID NO:107; and wherein the VL domain comprises an amino acid sequence that is at least 90%, at least 95%, at least 99%, or 100% identical to the sequence of SEQ ID NO:108; or (o) the VH domain comprises an amino acid sequence that is at least 90%, at least 95%, at least 99%, or 100% identical to the sequence of SEQ ID NO:121; and wherein the VL domain comprises an amino acid sequence that is at least 90%, at least 95%, at least 99%, or 100% identical to the sequence of SEQ ID NO:122; or (p) the VH domain comprises an amino acid sequence that is at least 90%, at least 95%, at least 99%, or 100% identical to the sequence of SEQ ID NO:258; and wherein the VL domain comprises an amino acid sequence that is at least 90%, at least 95%, at least 99%, or 100% identical to the sequence of SEQ ID NO:259.

E58. The targeted cytokine construct of any one of embodiments 13-40, and 55-57, wherein the targeted cytokine construct comprises four polypeptide chains, wherein:
the first polypeptide chain comprises the amino acid sequence of SEQ ID NO:262, the second polypeptide chain comprises the amino acid sequence of SEQ ID NO:263, the third polypeptide chain comprises the amino acid sequence of SEQ ID NO:264, and the fourth polypeptide chain comprises the amino acid sequence of SEQ ID NO:262;
the first polypeptide chain comprises the amino acid sequence of SEQ ID NO:266, the second polypeptide chain comprises the amino acid sequence of SEQ ID NO:267, the third polypeptide chain comprises the amino acid sequence of SEQ ID NO:268, and the fourth polypeptide chain comprises the amino acid sequence of SEQ ID NO:266;
the first polypeptide chain comprises the amino acid sequence of SEQ ID NO:270, the second polypeptide chain comprises the amino acid sequence of SEQ ID NO:271, the third polypeptide chain comprises the amino acid sequence of SEQ ID NO:272, and the fourth polypeptide chain comprises the amino acid sequence of SEQ ID NO: 270;
the first polypeptide chain comprises the amino acid sequence of SEQ ID NO: 274, the second polypeptide chain comprises the amino acid sequence of SEQ ID NO:275, the third polypeptide chain comprises the amino acid sequence of SEQ ID NO:276, and the fourth polypeptide chain comprises the amino acid sequence of SEQ ID NO: 274; or
the first polypeptide chain comprises the amino acid sequence of SEQ ID NO:278, the second polypeptide chain comprises the amino acid sequence of SEQ ID NO:279, the third polypeptide chain comprises the amino acid sequence of SEQ ID NO:280, and the fourth polypeptide chain comprises the amino acid sequence of SEQ ID NO: 278.

E59. The targeted cytokine construct of any one of embodiments 13-40, and 55-57, wherein the targeted cytokine construct comprises four polypeptide chains, wherein:
the first polypeptide chain comprises the amino acid sequence of SEQ ID NO:262, the second polypeptide chain comprises the amino acid sequence of SEQ ID NO:263, the third polypeptide chain comprises the amino acid sequence of SEQ ID NO:265, and the fourth polypeptide chain comprises the amino acid sequence of SEQ ID NO:262;
the first polypeptide chain comprises the amino acid sequence of SEQ ID NO:266, the second polypeptide chain comprises the amino acid sequence of SEQ ID NO:267, the third polypeptide chain comprises the amino acid sequence of SEQ ID NO:269, and the fourth polypeptide chain comprises the amino acid sequence of SEQ ID NO:266;
the first polypeptide chain comprises the amino acid sequence of SEQ ID NO:270, the second polypeptide chain comprises the amino acid sequence of SEQ ID NO:271, the third polypeptide chain comprises the amino acid sequence of SEQ ID NO:273, and the fourth polypeptide chain comprises the amino acid sequence of SEQ ID NO: 270;
the first polypeptide chain comprises the amino acid sequence of SEQ ID NO: 274, the second polypeptide chain comprises the amino acid sequence of SEQ ID NO:275, the third polypeptide chain comprises the amino acid sequence of SEQ ID NO:277, and the fourth polypeptide chain comprises the amino acid sequence of SEQ ID NO: 274; or the first polypeptide chain comprises the amino acid sequence of SEQ ID NO:278, the second polypeptide chain comprises the amino acid sequence of SEQ ID NO:279, the third polypeptide chain comprises the amino acid sequence of SEQ ID NO:281, and the fourth polypeptide chain comprises the amino acid sequence of SEQ ID NO: 278.

EXAMPLES

Example 1: Design and Biophysical Characterization of Exemplary IL-21 Polypeptides and Fusion Proteins Comprising the Same Materials and Methods Recombinant DNA Techniques Techniques involving recombinant DNA manipulation, used for this study, were previously described in Sambrook et al., Molecular cloning: A laboratory manual; Cold Spring Harbor Laboratory Press, Cold Spring Harbor, N.Y., 1989. All reagents were used according to the manufacturer's instructions. DNA sequences were determined by double strand sequencing.

Gene Synthesis

Desired gene segments were either generated by PCR using appropriate templates or synthesized at Genewiz (South Plainfield, NJ), Integrated DNA Technologies (Coralville, IA) or 0 (Piscataway, NJ) from synthetic oligonucleotides. The gene segments were cloned into the expression vectors using either Gibson Assembly® method or using restriction digest followed by ligation. DNA was purified from transformed bacteria and concentration was determined by UV visible spectroscopy. DNA sequencing was used to confirm the DNA sequences of the subcloned gene fragments.

Isolation of Antibody Genes

Antibodies binding to CD8 antigens were generated using either humanization of mouse antibodies or in vitro phage display system.

For humanization, complementarity-determining regions (CDRs) of mouse residues were grafted into selected human framework(s) which exhibit close sequence similarity to the parental mouse framework and good stability. The resulting CDR-grafted antibodies were further humanized to remove any unnecessary non-human mutations.

For the in vitro display method, a non-immune human single chain Fv phage library generated from naïve B cells was panned for 5 to 6 rounds to isolate antibodies against the CD8 antigens. After the panning, individual phage clones that exhibited specific binding to target antigen over non-specific antigens in ELISA were identified. DNA fragments of heavy and light chain V-domain of the specific binders were subsequently cloned and sequenced.

Cloning of Antibody Constructs

General information regarding the nucleotide sequences of human immunoglobulins light and heavy chains can be found in: IMGT® (the international ImMunoGeneTics information System®) from Lefranc et al. IMGT®, the international ImMunoGeneTics information System® 25 years on. Nucleic Acids Res. 2015 January; 43. The DNA fragments of heavy and light chain V-domains were inserted in frame into the human IgG1 and Kappa light chain containing mammalian expression vector.

Cloning of Fusion Constructs

The IL-21 portions of the constructs were cloned in frame with the heavy chain using a $(G_4S)_3$ 15-mer linker (SEQ ID NO: 390) between the C-terminus of the IgG heavy chain and the N-terminus of IL-21. The C-terminal lysine residue of the IgG heavy chain was eliminated after fusing the IL-21 portion. To generate the constructs with asymmetric geometry, knob-into-hole modification was introduced into the CH3 domains of the Fc region to facilitate heterodimerization. Specifically, the "hole" domain carried the S354C, T366S, L368A and Y407V mutations in the CH3 domain, whereas the "knob" domain carried the Y349C and T366W mutations in the CH3 domain (EU numbering). To abolish FcγR binding/effector function and prevent FcR co-activation, mutations L234A/L235A/G237A (EU numbering) were introduced into the CH2 domain of each of the IgG heavy chains or the Fc region. The expression of the antibody-IL-21 fusion constructs was driven by an CMV promoter and transcription terminated by a synthetic polyA signal sequence located downstream of the coding sequence.

Purification of Fusion Proteins with IL-21 Polypeptides

Constructs encoding fusion proteins with IL-21 polypeptides as used in the examples were produced by co-transfecting exponentially growing Expi293 cells with the mammalian expression vectors using polyethylenimine (PEI). Supernatants were collected after 5 days of culture. IL-21 fusion constructs were first purified by affinity chromatography using a protein A matrix. The protein A column was equilibrated and washed in phosphate-buffered saline (PBS). The fusion constructs were eluted with 100 mM sodium citrate, pH 3.6 directly into 1 M Tris-HCl, pH 9 neutralization buffer. The eluted fractions were pooled and diluted into 20 mM MES, 25 mM sodium chloride pH 5.5 for further purification by ion-exchange chromatography (Mono-S, Cytiva) to separate heterodimers from homodimers. After loading the protein, the column was washed with 20 mM MES, pH 5.5. The protein was then eluted with a gradient of sodium chloride from 25 mM NaCl to 500 mM NaCl in 20 mM MES, pH 5.5 buffer. The major eluent peak corresponding to the heterodimer was collected and analyzed by analytical size exclusion chromatography (Superdex 200 Increase 5/150 GL, Cytiva). For in vitro studies, the protein was dialyzed into PBS if the % monomer was ≥98%. Otherwise, and for all in vivo studies, the ion exchange eluent peak was polished by size exclusion chromatography (HiLoad Superdex 200 pg 16/600 or 26/600, Cytiva) in PBS.

The protein concentration of purified IL-21 fusion constructs was determined by measuring the optical density (OD) at 280 nm, using the molar extinction coefficient calculated on the basis of the amino acid sequence. Purity, integrity and monomeric state of the fusion constructs were analyzed by SDS-PAGE in the presence and absence of a reducing agent (5 mM 1,4-dithiothreitol) and stained with Coomassie blue (SimpleBlue™ SafeStain, Invitrogen). The NuPAGE® Pre-Cast gel system (Invitrogen) was used according to the manufacturer's instructions (4-20% Tris-glycine gels or 3-12% Bis-Tris). The aggregate content of immunoconjugate samples was analyzed using a Superdex 200 5/150 GL analytical size-exclusion column (Cytiva).

Binding Affinity Determination by Surface Plasmon Resonance (SPR) for IL-21 Fusion Proteins with Human IL-21R Kinetic rate constants ($k_a$ and $k_d$) as well as affinity ($K_D$) of unattenuated IL-21 fusion proteins with human IL-21R were measured by surface plasmon resonance (SPR) using a BIAcore® T200 (Cytiva) at 37° C. Briefly, to determine the affinities, IL-21 fusion proteins were diluted to 10 μg/mL and captured at 10 μL/min via their Fc onto a CM4 sensor chip by a covalently immobilized anti-human Fc antibody (Southern Biotech, Catalog No. 2014-01). Protein was not captured on flow cell 1 to serve as a reference surface. Human IL-21R (Biolegend, Catalog No. 773104), diluted in HBS-P+ buffer supplemented with 1 g/L BSA, at concentrations of 0.12, 0.37, 1.1, 3.3 and 10 nM, or buffer was flowed over the surface-captured fusion protein for 2 minutes at 30 μL/min. Dissociation was monitored for 10 minutes, and the anti-hIgG-Fc surface was regenerated with three 60-seconds injections of 75 mM phosphoric acid before recapturing fusion protein in each subsequent cycle. All interactions were measured in triplicate. Binding data were double-referenced and analyzed by Biacore® Evaluation Software version 3.2 using a 1:1 Langmuir with mass transport model to determine $k_a$, $k_d$ and $K_D$ using Biacore Evaluation Software.

Binding affinity ($K_D$) of attenuated IL-21 fusion proteins with human IL-21R were measured by surface plasmon resonance (SPR) using a BIAcore® T200 (Cytiva) at 37° C. Recombinant human IL-21R was generated in house. Briefly, recombinant human IL-21R, comprised of the extracellular domain of IL-21R fused to 8×Histidine tag (SEQ ID NO: 391), were expressed in secreted form from HEK293 cells and purified by IMAC and size exclusion column chromatography. To determine the affinities, IL-21 fusion proteins were diluted to 10 μg/mL and captured at 10 μL/min via their Fc onto a CM4 sensor chip by a covalently immobilized anti-human Fc antibody (Southern Biotech). Protein was not captured on flow cell 1 to serve as a reference surface. A serial dilution was generated for human IL-21R, in HBS-P+ buffer supplemented with 1 g/L BSA, starting at nominal concentrations between 20-5 μM, followed by six to seven 5-fold serial dilutions, and flowed over the surface-captured fusion protein for 2 minutes at 30 μL/min. Buffer was also flowed over the surface to serve as a blank subtraction. Dissociation was monitored for 5-10 minutes, and the anti-hIgG-Fc surface was regenerated with three 30 to 60-seconds injections of 75 mM phosphoric acid before recapturing fusion protein in each subsequent binding cycle. Binding data were double-referenced and analyzed by Biacore® Evaluation Software version 3.2 using steady-state affinity for very weak interactions, or when possible, a 1:1 Langmuir with mass transport model to determine kinetic rate constants ($k_a$, $k_d$) and $K_D$.

Polyreactivity Assessment by ELISA

In order to measure polyreactivity of candidate fusion proteins, an ELISA assay was used to check for binding to a panel of irrelevant antigens. The following were used as antigens and purchased from Sigma: keyhole limpet hemocyanin, hemoglobin, and heparin biotin sodium salt.

Antigens were diluted in PBS to a concentration of 5 μg/mL and coated onto a 384-well Nunc MaxiSorp plate (Thermo Fisher Scientific) at a volume of 25 μL per well. The plates were incubated overnight at 4° C. The antigens were removed, and the plate was washed with milli-Q water (Millipore). Wells were filled with PBS supplemented with 0.05% Tween and 1 mM EDTA (assay buffer) and then incubated at room temperature for 1 hour. The assay buffer was removed, and the wells washed with milli-Q water. 25 μL of 10 μg/mL of assay buffer only (negative control), bococizumab (positive control for polyreactivity), or fusion proteins, diluted in assay buffer were added and incubated at room temperature for 1 hour. Samples were removed and the plate was washed with milli-Q water. 25 μl of the detection antibody, 1:25000 diluted horseradish peroxidase conjugated goat anti-human IgG (Jackson ImmunoResearch), was added and allowed to incubate for 1 hour at room temperature. The reagent was removed, and wells were washed with milli-Q water. Wells were developed using 25 μL of KPL SureBlue TMB Microwell Substrate (SeraCare) for 5-7 mins and quenched with 25 μL of 0.1 M HCl. The absorbance at 450 nm was recorded on a SpectraMax iD5 plate reader (Molecular Devices) and normalized against the assay buffer only control wells.

Results

Design of IL-21 Charge Variant Polypeptides

Design of various exemplary IL-21 polypeptides is depicted in FIG. 2, which shows the amino acid sequence of wild-type IL-21 with "X" denoting the amino acid substituted in the sequence of wild-type IL-21 for another amino acid to generate an exemplary IL-21 polypeptide as described herein. The IL-21 polypeptides were charge variants with altered (e.g., reduced) isoelectric point) relative to that of wild-type IL-21.

Increased surface charge or pI in protein-based molecules have been shown to correlate with increased systemic clearance, and decreased subcutaneous bioavailability (Boswell, C A et al. Bioconjug Chem. 21: 2153-2163, 2010; Herve, F et al. AAPS J. 10: 455-472, 2008; Zheng Y. MAbs 4: 243-255, 2012). Additionally, positive surface charge has been shown to correlate with decreased soluble expression and increased aggregation (Niwa, T, et al. PNAS, 106: 4201, 2009; Chan, P et al. Sci Reports, 3: 3333, 2013; Dudgeon K. et al, PNAS 109: 10879-84, 2012). In order to evaluate the impact of reducing positive surface charge on wild type IL-21, which has a theoretical pI of about 9.42, several exemplary charge variants were designed to remove positively charged surface residues at several locations predicted not to interfere with binding to the IL-21 receptor or common gamma chain. Specifically, several exemplary charge variant designs were made (Exemplary IL-21 polypeptide 1 to 31, also referred to as IL-21 v1 through IL-21 v31), amino acid substitutions to either glycine, serine, aspartic acid, alanine or glutamic acid, with sequences shown in Table 2. Theoretical pI values of the modified cytokine variants are also listed, as calculated by the ExPASy ProtParam tool.

Expression of IL-21 Charge Variant Polypeptides as Antibody Fusions

Figure 3A:
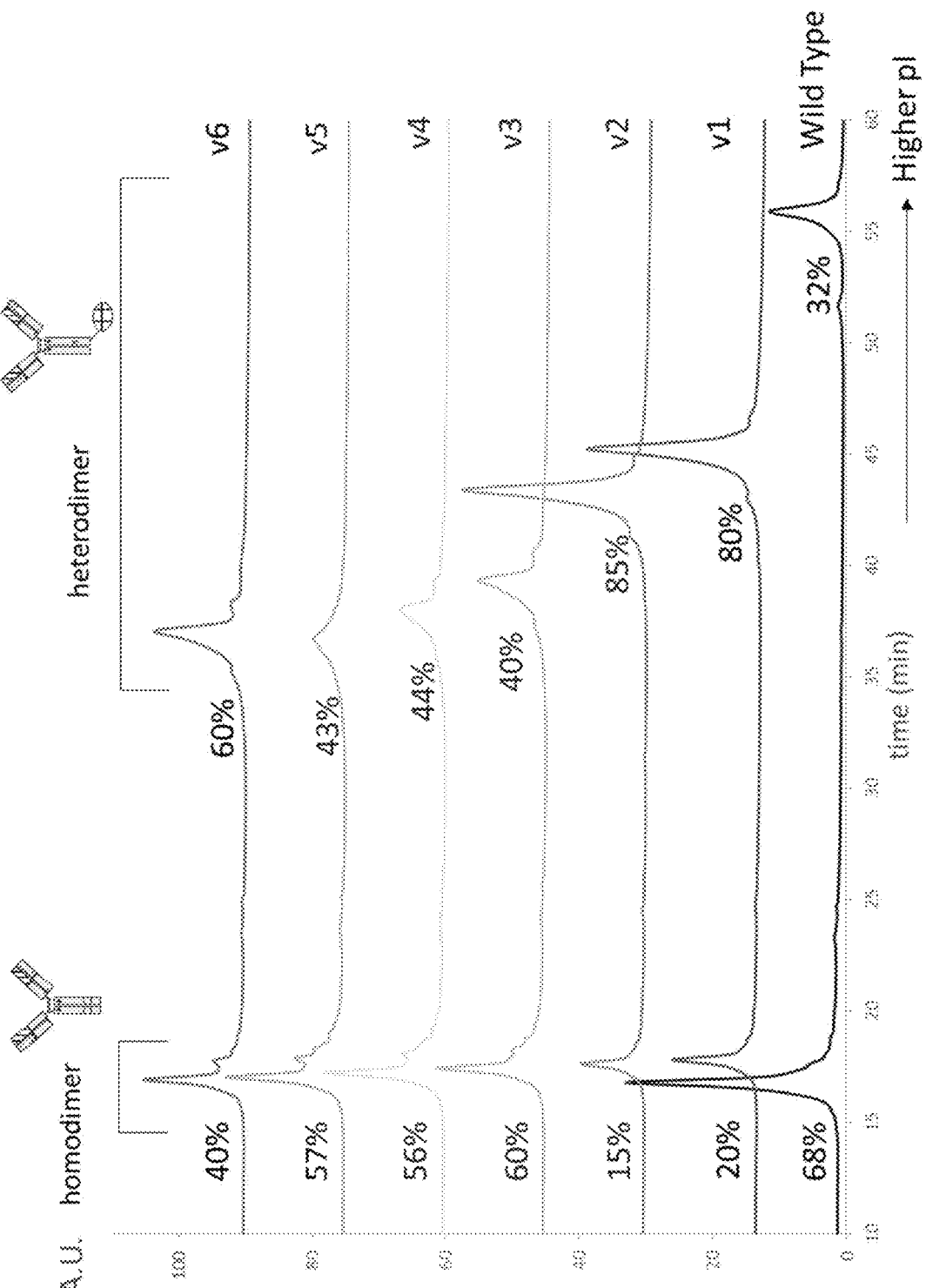
FIGS. 3A-3F show ion exchange chromatography traces of fusion proteins of anti-CD8 antibodies and either wild type IL-21 or IL-21 charge variants after Protein A purification. Fusion proteins of xhCD8 and either wild type IL-21 or exemplary IL-21 charge variants v1 through v6 are shown in FIG. 3A, as measured by HPLC. Fusion proteins of xhCD8.1 and exemplary IL-21 charge variants v2, or variants v7 through v31 are shown in FIGS. 3B through 3E, and fusion protein of xhCD8.1 and wild type IL-21 is shown in FIG. 3F, as measured by FPLC. In all cases, the peak(s) on the left are undesired products, primarily homodimer, whereas the peak on the right is the desired heterodimer fusion protein, and the percentages of total of each denoted region are shown.
Figure 3C:
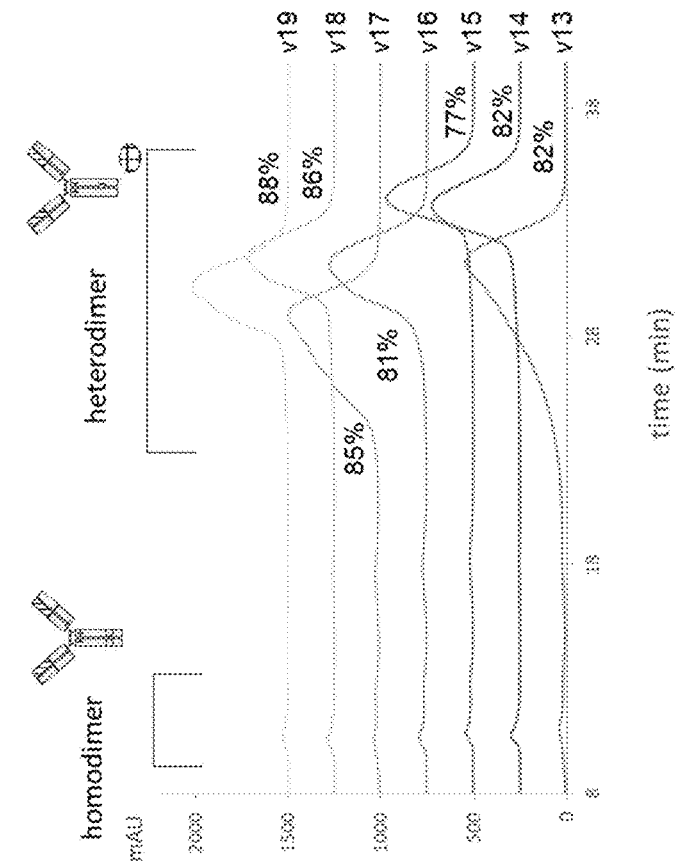
Figure 3B:
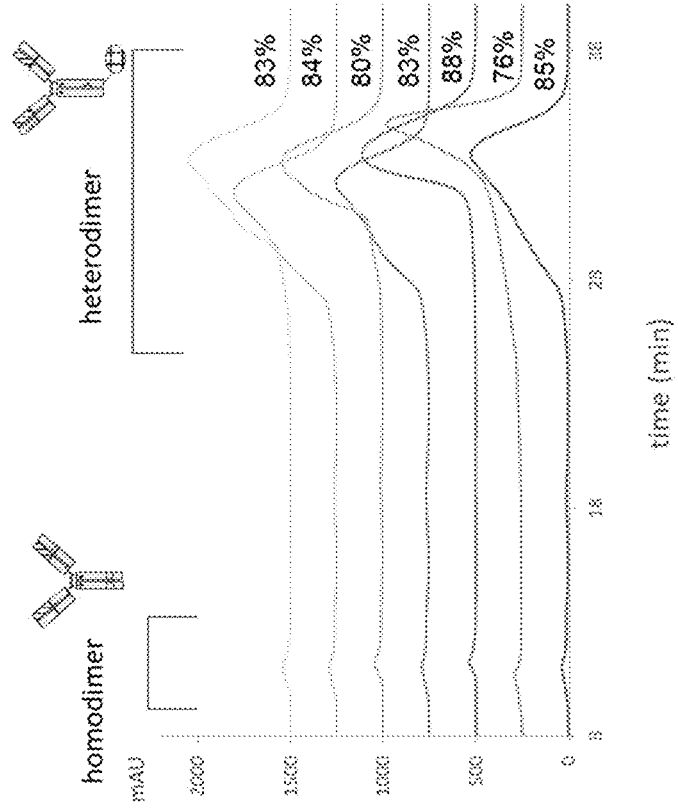
Figures 3D, 3E:
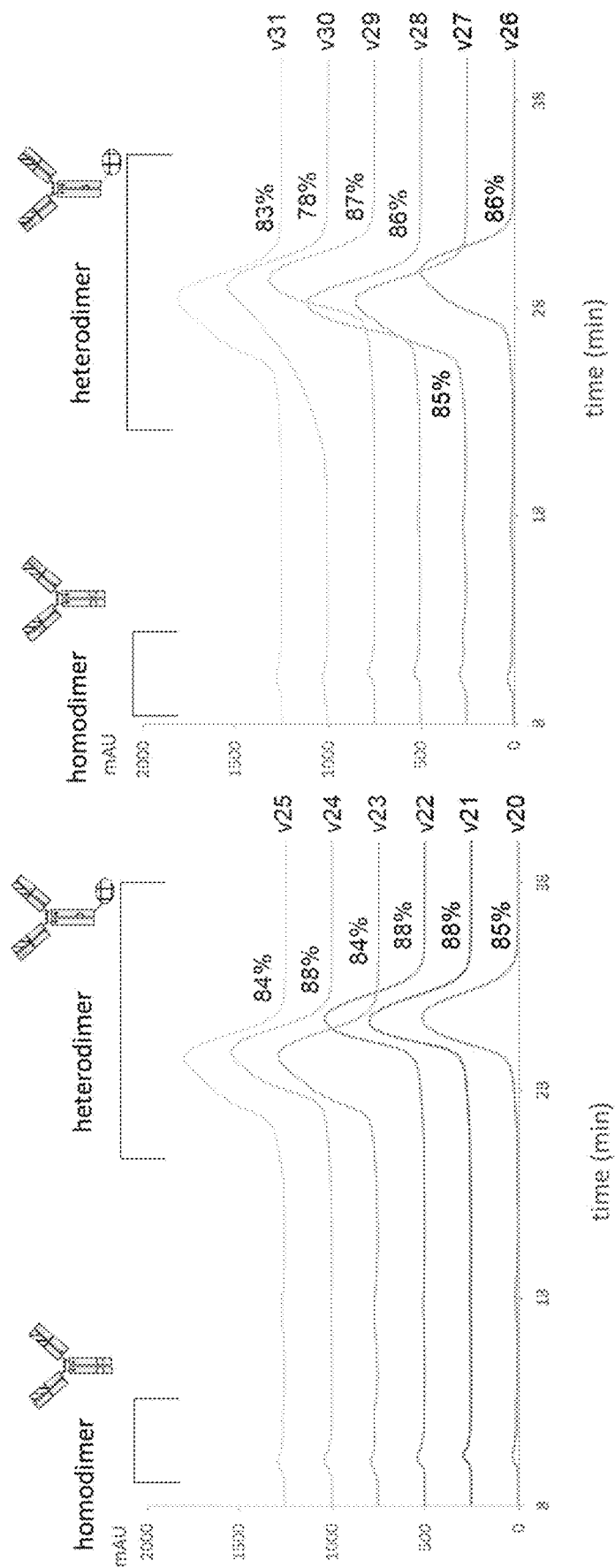
Figure 3F:
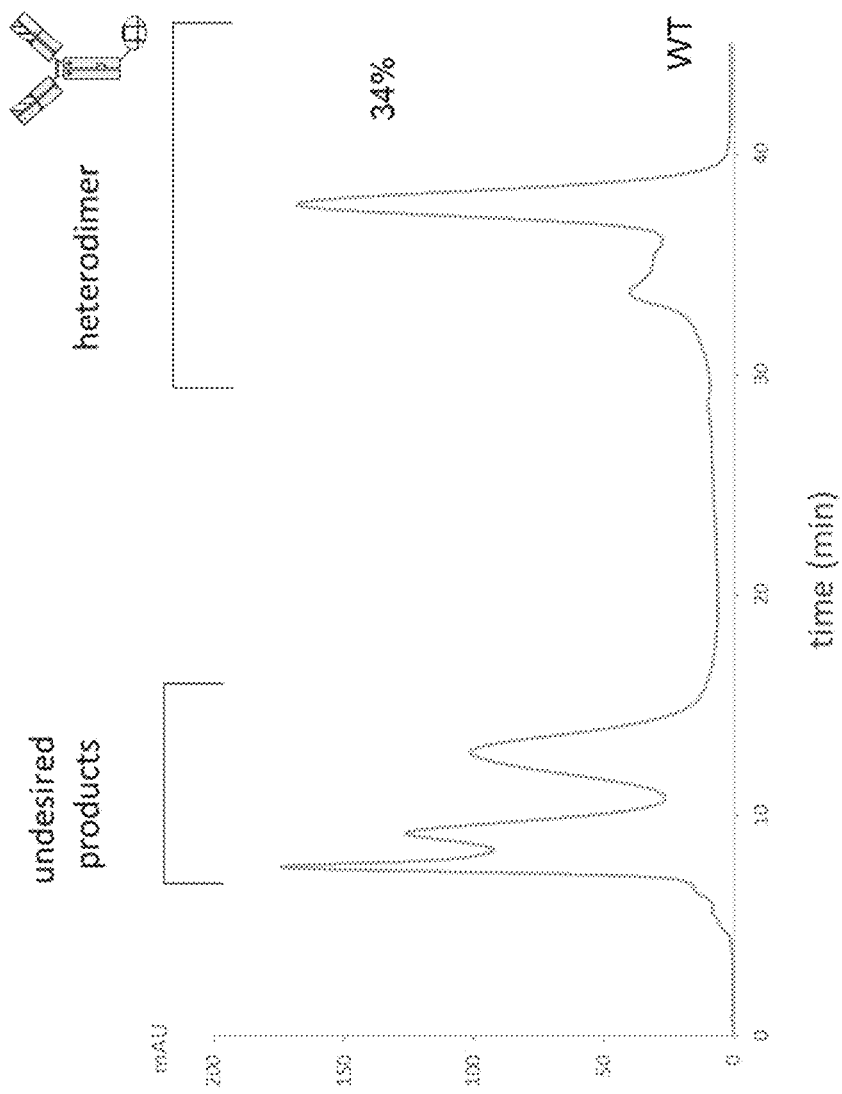
Figure 4A:
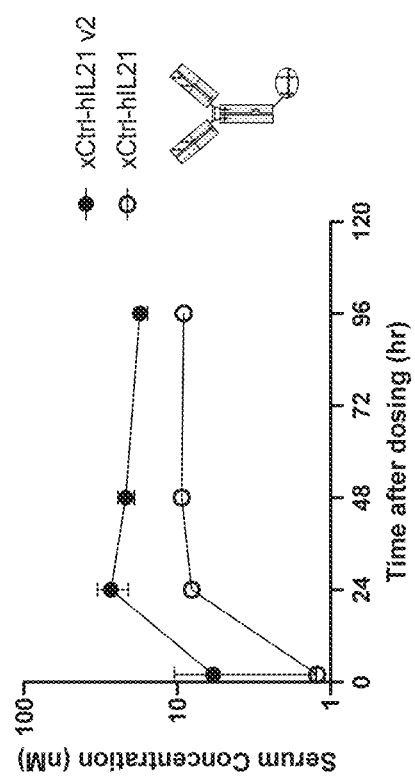
FIGS. 4A-4D show mouse pharmacokinetic data for fusion proteins. Serum concentrations are shown for 1 mg/kg of a control antibody (xCtrl) with either the wild-type IL-21 or exemplary charge variant IL-21 polypeptide IL-21 v2 dosed either intravenously (FIG. 4A) or subcutaneously (FIG. 4B). In a separate experiment, serum concentrations are additionally shown for 1 mg/kg wild type IL-21, or exemplary charge variant IL-21 polypeptides, IL-21 v2 or IL-21 v31 dosed subcutaneously (FIG. 4C) or intravenously (FIG. 4D).
Figure 4B:
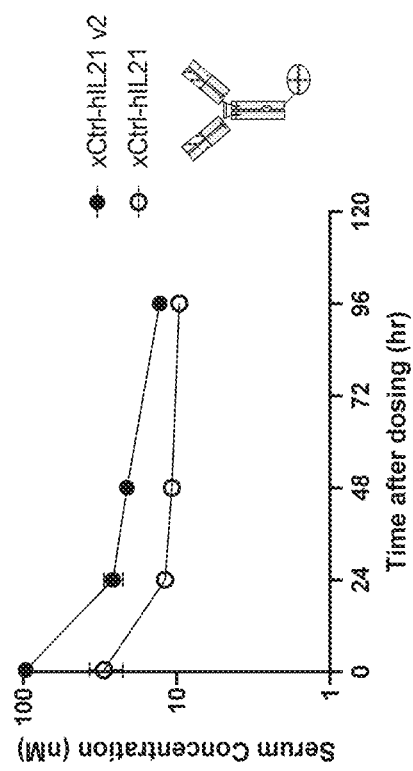
Figure 4D:
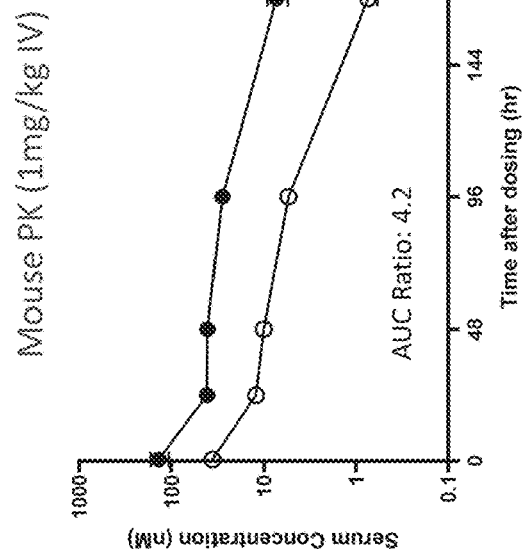
Figure 4C:
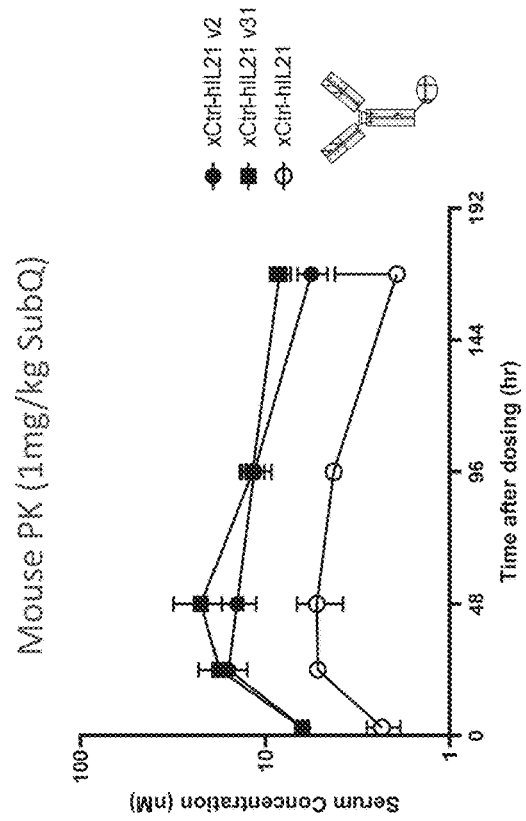

Protein expression characteristics of fusion proteins of an exemplary anti-CD8 antibody, either xhCD8 or xhCD8.1, with the exemplary IL-21 charge variant polypeptides, exemplary IL-21 polypeptide 1 to 6, were compared to fusion proteins with wild type IL-21, and the results are summarized in Table 3. Yields are reported after an intermediate step, after Protein A, as well as after two-steps of purification, Protein A and ion exchange chromatography, for selected protein fusions. In the case of fusion proteins with exemplary IL-21 polypeptide 1, exemplary IL-21 polypeptide 2, and exemplary IL-21 polypeptides 6 through 31, yields were higher than for fusion proteins with wild type IL-21 at both the Protein A intermediate stage, as well as the fully purified stage, after Protein A and ion exchange chromatography.

Ion exchange chromatography traces also show improvements for fusion proteins of all charge variants, exemplary IL-21 polypeptide, compared to fusion proteins of wild type IL-21, as shown in FIG. 3A-3E. In all traces, two peaks were observed, one representing a homodimer, an undesired product comprising the antibody only without cytokine, and one representing a heterodimer, the desired antibody-cytokine fusion product. The elution of the heterodimer peak was observed to be earlier for all exemplary charge variant fusion proteins compared to the wild type IL-21 fusion protein, consistent with a decrease in isoelectric point and surface charge. FIG. 3A shows ion exchange chromatography traces for fusion proteins of xhCD8 and either wild type IL-21 or exemplary IL-21 polypeptides 1 through 6. Here, the portion of total protein that was the desired product was about 32% in the case of the wild type IL-21 fusion protein, and higher for fusion proteins of all IL-21 charge variants, ranging from about 40% to about 85%. In FIGS. 3B through 3E, ion exchange chromatography traces are shown for fusion proteins of xhCD8.1 and exemplary IL-21 polypeptides 2 or 7 through 31. Here, the portion of total protein that was the desired product ranged from 77% to 88% for the charge-modified exemplary IL-21 polypeptides, which is higher than the portion of total protein of about 34% in the case of the fusion protein of xhCD8.1 and wild type IL-21 (FIG. 3F).

Kinetics Characterization of Wild Type IL-21 Compared to Selected Charge Variants Binding kinetics to IL-21R at 37° C. were compared for wild type IL-21 (Fc-hIL21 WT) and selected charge variants exemplary IL-21 polypeptide 1 (xhCD8-hIL21 v1), exemplary IL-21 polypeptide 2 (xhCD8-Fc-hIL21 v2), and exemplary IL-21 polypeptide 6 (xhCD8-hIL21 v6) and exemplary IL-21 polypeptide 27 through 31 (xhCD8.1-hIL21 v27-31). For wild type IL-21, a fusion protein to the human Fc was used, whereas, for the charge variants, a fusion protein to an anti-CD8 antibody was used. Kinetic and affinity parameters derived from averaging data from 3 replicate experiments are shown in Table 4. The IL-21R binding affinities of exemplary IL-21 polypeptide 1, exemplary IL-21 polypeptide 2, exemplary IL-21 polypeptide 27 through 31, are within 2-fold of that of wild type IL-21, indicating that there was no effect on IL-21R affinity by the charge modifications in exemplary IL-21 polypeptide. In the case of exemplary IL-21 polypeptide 6, there was approximately a 3-fold change in affinity.

Polyreactivity of Fusion Proteins with Wild Type IL-21 Versus Charge Variants

The results of a polyreactivity ELISA assay that measures binding of IL-21 fusion proteins to a panel of irrelevant proteins are shown in Table 5. Bococizumab, which has been shown to be polyreactive, is also included as a positive control. The polyreactivity of fusion protein with wild type IL-21, xhCD8.1-hIL21, was compared to that of fusion proteins comprising the same antibody, xhCD8.1, and IL-21 charge variants. Notably, binding to irrelevant antigens was reduced for all fusion proteins with the IL-21 charge variants compared to xhCD8.1-hIL21, indicating an improvement in polyreactivity for the charge variants.

Example 2: Pharmacokinetics of Exemplary IL-21 Charge Variant Polypeptide Containing Fusion Proteins in Mice Materials and Methods Mouse Pharmacokinetics Evaluation Female C57BL/6 mice at 8 weeks of age were used for pharmacokinetic evaluation of fusion proteins containing exemplary IL-21 polypeptide 2 (xCtrl-hIL21 v2) or wild-type IL-21 (xCtrl-hIL21) polypeptide. The fusion proteins were: xCtrl-hIL21 and xCtrl-hIL21 v2, fusion proteins of a control (Ctrl) antibody that is non-binding to mouse proteins, with either wild type IL-21 or exemplary IL-21 polypeptide 2, respectively. The control antibody was xhCD8.1 which does not bind mouse CD8b. All animals were housed and handled in accordance with the Institutional Animal Care and Use Committee of Explora BioLabs. Proteins were administered either intravenously or subcutaneously at a dose of 1 mg/kg in groups of 2 mice. Tail vein bleeds were performed at 30 minutes, 1, 2 5, and optionally 7 days post-dose for the mice dosed intravenously, and at 2 hours, 1, 2 and 4 days post-dose for the mice dosed subcutaneously. At each time point, approximately 25 μL blood and serum was collected. Serum was stored at −20° C. until they were used for analysis.

ELISA Evaluation of Serum Samples

Mouse serum concentration of the test molecules was measured by ELISA, using a standard curve generated by the proteins used for treatment. Briefly, 100 μL per well of 2 μg/mL of AffiniPure F(ab')$_2$ Fragment Donkey Anti-Human IgG, Fcγ fragment specific (Jackson ImmunoResearch) in PBS was coated onto a 96-well Nunc MaxiSorp plate (Thermo Fisher Scientific) overnight at 4° C. Coating solution was removed, and the plates were blocked with 250 μL per well of PBS+5% skim milk for 2 hours at room temperature. Plates were washed with PBS+0.05% Tween-20, and either protein standard or diluted serum was added. For the protein standard, a serial dilution was generated starting at 0.03 μg/mL, followed by seven 3-fold serial dilutions. Serum samples were diluted between 100-fold and 5000-fold, in order to keep the final readout within the range of the standard curve. All dilutions were in PBS+0.5% BSA+0.05% Tween-20, and 100 μL was used per/well. Serum samples and the protein standard were incubated at room temperature for 1-2 hours, followed by washing with PBS+0.05% Tween-20. Next, 100 μL per well of detection antibody (Peroxidase AffiniPure F'ab')$_2$ Fragment Goat Anti-Human IgG, Fcγ fragment specific) at 1:3000 dilution in PBS+0.5% BSA+0.05% Tween-20, and the plates were incubated at room temperature for 45 minutes. The plates were developed using 100 μL of 1-step Ultra TMB-ELISA substrate solution (Thermo Fisher Scientific) for 1-3 minutes, and stopped with 100 μL of 2 M sulfuric acid. The absorbance at 450 nm was read on a SpectraMax iD5 plate reader (Molecular Devices). A nonlinear regression was used to fit the standard curve, and absorbance at 450 nm of diluted serum samples were interpolated to the standard curve using Prism software (GraphPad). All serum concentrations were then converted to nanomolar concentration.

Results

The pharmacokinetics results are shown in FIGS. 4A-4D. With both the intravenous dosing and the subcutaneous dosing, the fusion protein comprising the charge variant exemplary IL-21 polypeptide sequence exhibited greater exposure than fusion protein comprising the wild type IL-21 sequence. Based on area under the curve (AUC) calculations using the trapezoidal rule, there is about 2.5-fold improvement in AUC by IV dosing and 2.3 to 2.8-fold improvement in AUC by subcutaneous dosing for the IL-21 charge variant exemplary polypeptide 2 (xCtrl-hIL21 v2) over wild type IL-21 (xCtrl-hIL21). Additionally, there is about 3.5-fold improvement in AUC by subcutaneous dosing for the IL-21 charge variant exemplary polypeptide 31 (xCtrl-hIL21 v31) over wild type IL-21 (xCtrl-hIL21). When comparing the intravenously-dosed exposure of xCtrl-hIL21 v31 and xCtrl-hIL21, there is an AUC ratio of 4.2 (FIG. 4D), indicating a large improvement of the hIL21 v31 charge modifications over wild type hIL21.

Based on the kinetics reported in Example 1, there is negligible difference in the binding kinetics of wild-type IL-21 and either exemplary IL-21 polypeptide 2 or exemplary IL-21 polypeptide 31 to IL-21R. Therefore, the observed differences in exposure cannot be attributed to any differences in target-mediated drug disposition of fusion proteins comprising exemplary IL-21 polypeptide 2 or exemplary IL-21 polypeptide 31 and wild type IL-21. Additionally, the targeting (Ctrl) antibody in the two fusion proteins described in each of FIGS. 4A-4D is the same and does not bind any mouse protein. The data suggest that the reduction in positive surface charge in exemplary IL-21 polypeptide 2 or exemplary IL-21 polypeptide 31 is responsible for the observed improvements in exposure over wild type IL-21.

Example 3: Evaluation of STAT3 Activation by IL-21 and Fusion Proteins

Materials and Methods

Evaluation of STAT3 Activation in Human Primary Cells

The ability of IL-21 to activate various immune cell subsets was determined in an assay measuring the phosphorylation of STAT3 by flow cytometry in either human PBMCs or human whole blood.

PBMCs were isolated from blood of healthy donors using Ficoll-Paque Plus (Cytiva) and red blood cells were lysed using ACK lysis buffer. PBMCs were resuspended in serum-free RPMI1640 media at 40×10$^6$ cells/mL and aliquoted into 96-well U-bottom plates (50 µL per well). IL-21 fusion proteins and control proteins including recombinant IL-21 and control fusion proteins, were diluted to desired concentrations and added to wells (50 µL added as 2× stimulus). Incubation was typically performed for 10-20 min at 37° C. Antibodies that could not be applied following methanol permeabilization—CD8a (SK1, Biolegend), CD4 (RPA-T4, Biolegend), CD62L (DREG-56, Biolegend), and CD19 (HIB19, Biolegend)—were added directly to the wells immediately following stimulation and incubated on ice for 10 min. Staining was stopped with 100 µL ice cold 8% PFA (4% final) for 10 min on ice. Cells were washed 2× with wash buffer (2% FBS in PBS). Cells were permeabilized in 100 µL pre-chilled Phosflow Perm buffer III (BD Biosciences) for 45 minutes on ice. Cells were washed 2× with wash buffer and stained for 30-45 min at 4° C. with antibodies against: CD3 (UCHT1, BD Biosciences), CD45RO (UCHL1, Biolegend), HLA-DR (L243, Biolegend), perforin (dG9, BD Biosciences), and pSTAT3 pY705 (4/P-STAT3, BD Biosciences) diluted in permeabilization buffer (eBiosciences). Cells were then analyzed on a flow cytometer. Cell populations were defined as follows: CD8+ T cells: CD3+CD8+, CD4+ T cells: CD3+CD4+, B cells: CD19+, NK cells: CD3-CD19-HLA-DR-Perforin+. Data were expressed as percent pSTAT3 positive, and in some cases as pSTAT3 mean fluorescence intensity (MFI), and imported into GraphPad Prism.

For assays in human whole blood, 90 µL human blood was used per well in a 1 mL 96 well deep plate well and prewarmed for 10 minutes at 37° C. IL-21 fusion proteins and control proteins, such as wild-type IL-21, and control fusion proteins were prepared and pre-warmed to 37° C. at 10× strength. 10 µL of prewarmed 10× stimuli was added to each well, creating 100 µL total volume at 1× stimuli concentration. Incubation was typically performed for 25 min at 37° C. The stimulation was quenched by adding pre-fix antibody staining cocktail, vortexing briefly and incubating on ice for 10 minutes in the dark. The pre-fix staining cocktail contained TruStain FcX (Biolegend) and antibodies against: CD4 (RPA-T4, Biolegend), CD19 (HIB19, BD), CD56 (NCAM16.2, BD), CD16 (3G8, Biolegend), and CD8 (SK1, Biolegend). 900 µL pre-warmed Lyse Fix (BD) was added to the sample wells and incubated at 37° C. for 10 minutes. Cells were washed in pre-chilled wash buffer containing PBS+0.5% bovine serum albumin and 2 mM EDTA. Pre-chilled Perm Buffer III (BD) was added and incubated for 60 minutes at −20° C., followed by two washes in wash buffer and one wash in TFP Perm/Wash (BD). Cells were resuspended in 25 µL "post-methanol" staining cocktail prepared in TFP Perm/Wash containing antibodies against: CD3 (UCHT1, BD), CD14 (MΦP9, BD), CD11c (B-ly6, BD), HLA-DR (L243, Biolegend), and pSTAT3 pY705 (4/P-STAT3, BD Biosciences). Cells were incubated for 30 min at 4° C. in the dark, then washed in TFP Perm/Wash buffer, followed by fixation in 100 µL 4% PFA for 10 minutes at room temperature. Cells were washed in wash buffer and analyzed on a flow cytometer. Data were expressed as percent pSTAT3 positive and imported into GraphPad Prism. Cell populations were defined as follows: CD8+ T cells: CD3+CD8+, CD4+ T cells: CD3+CD4+, B cells: CD19+, NK cells: CD3−CD19−CD16+CD56dim, myeloid cells: CD11c+ HLA-DR+.

Results

Evaluation of STAT3 Activation by Wild Type IL-21

Figure 5A:
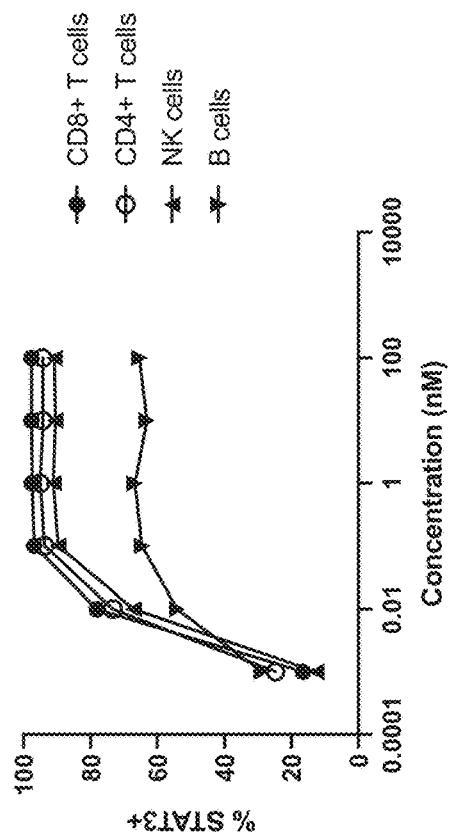
FIGS. 5A-5B show the activation of STAT3 by wild-type IL-21 in CD8+ T cells, CD4+ T cells, NK cells and B cells from human peripheral blood mononuclear cells (PBMCs) (FIG. 5A) or from whole blood (FIG. 5B). STAT3 activation was measured by flow cytometry, and all cell types were potently activated by wild-type IL-21.
Figure 5B:
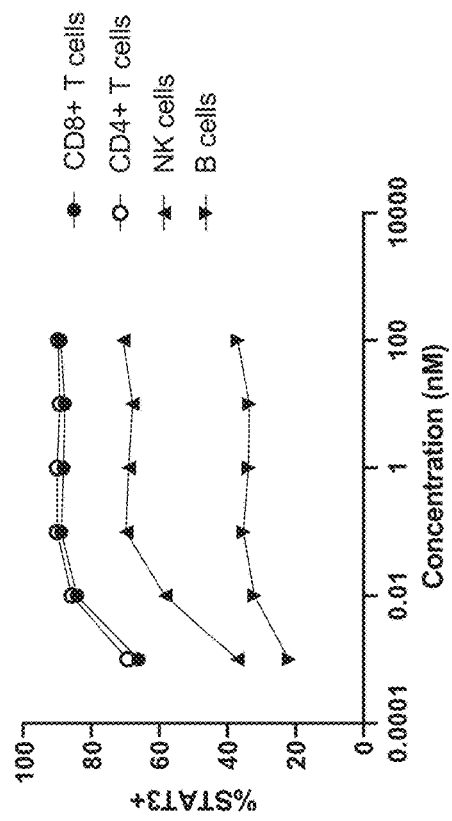

STAT3 activation profiles for different cell types in human PBMCs or whole blood by recombinant wild type human IL-21 are shown in FIGS. 5A-5B, respectively. CD8+ T cells, CD4+ T cells, NK and B cells are potently activated by recombinant IL-21 with similar $EC_{50S}$ in the pM range and high maximal STAT3 activation.

Selective Activation of CD8+ T Cells by CD8-Targeted IL-21 Charge Variants

Figure 6:
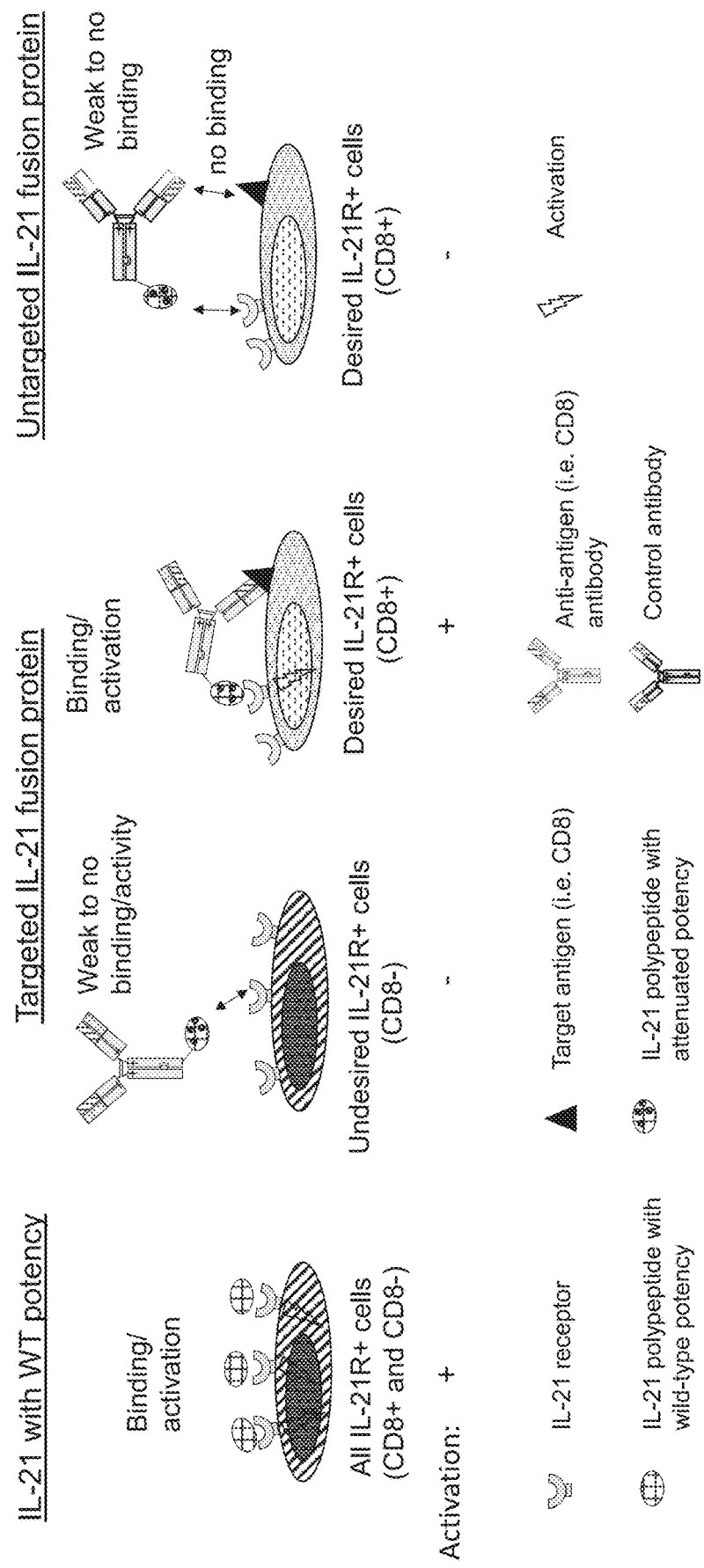
FIG. 6 is a schematic showing the general mechanism for how targeted fusions of mutant IL-21 polypeptides with CD8 antigen binding molecules and untargeted fusions with mutant IL-21 polypeptides work to stimulate cells expressing or not expressing CD8 antigens.

The concept of cis-targeting for selective activation of CD8+ T cells with CD8-targeted attenuated IL-21 is shown FIG. 6. Affinity attenuation of an IL-21 charge variant reduces activity on all cells expressing IL-21R. CD8-targeting enables the binding of the targeted fusion to CD8+ T cells and restores the IL-21 activity specifically on CD8+ T cells. In contrast, untargeted IL-21 mutein fusion showed weak to no activity on all IL-21R+ cell types, including CD8+ T cells.

Figure 7:
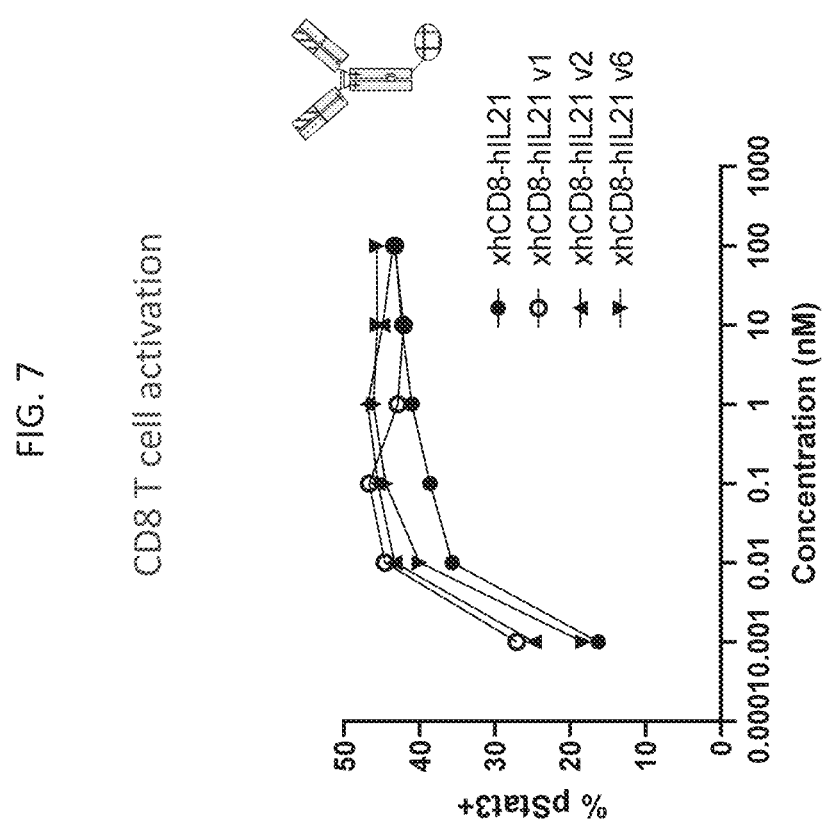
FIG. 7 shows activation of STAT3 in human CD8+ T cells by fusion proteins of anti CD8 antibody with either wild-type IL-21, exemplary IL-21 polypeptide charge variants IL-21 v1, IL-21 v2 or IL-21 v6.

STAT3 activation by fusion proteins comprising anti-CD8 antibody and either wild type IL-21 or exemplary IL-21 charge variant polypeptides were evaluated on CD8+ T cells. Data are shown in FIG. 7. Fusion proteins comprising anti-CD8 antibody and exemplary IL-21 polypeptide 1 (xhCD8-hIL21 v1), exemplary IL-21 polypeptide 2 (xhCD8-hIL21 v2) or exemplary IL-21 polypeptide 6 (xhCD8-hIL21 v6) was seen to mediate STAT3 activation with equivalent potency to that of fusion protein comprising anti-CD8 antibody and wild type IL-21 (xhCD8-hIL21).

Figure 8D:
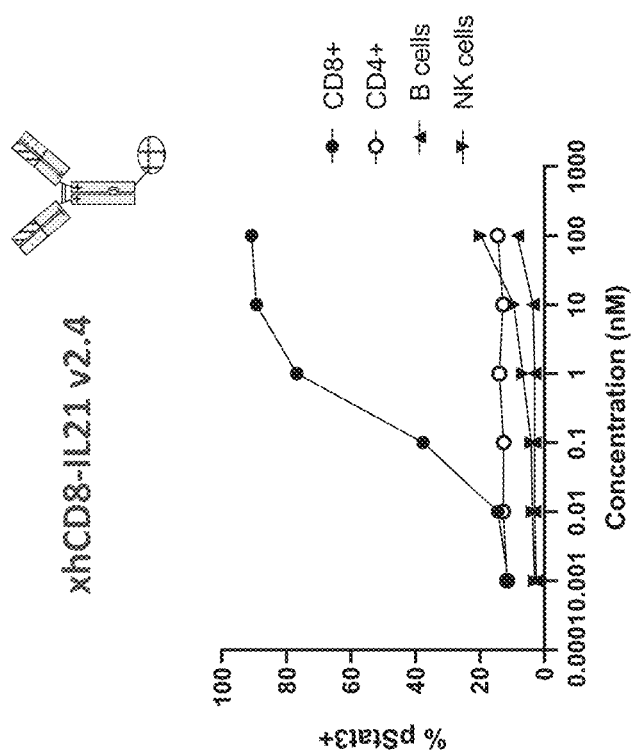
Figure 8C:
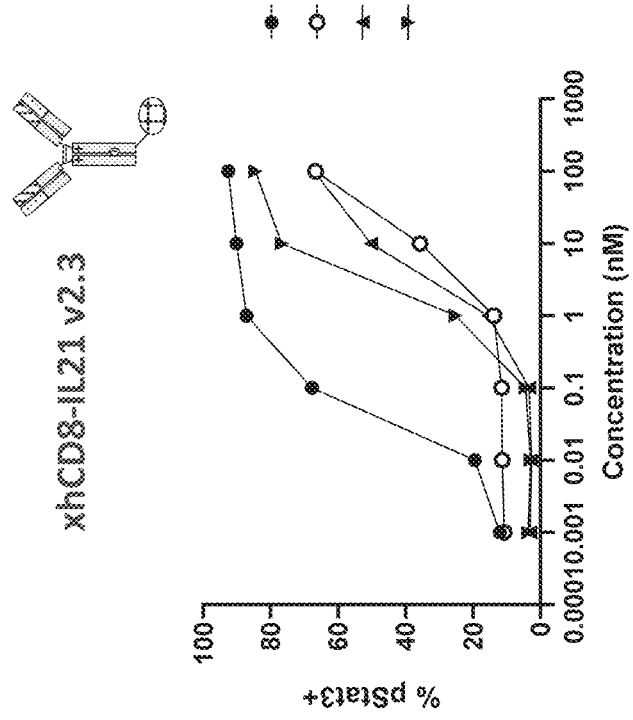
Figure 8F:
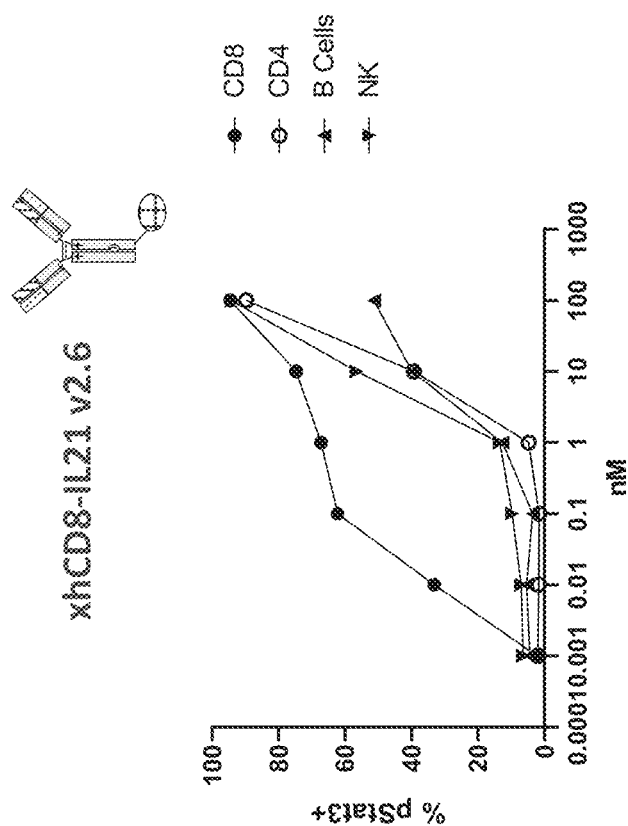
Figure 8E:
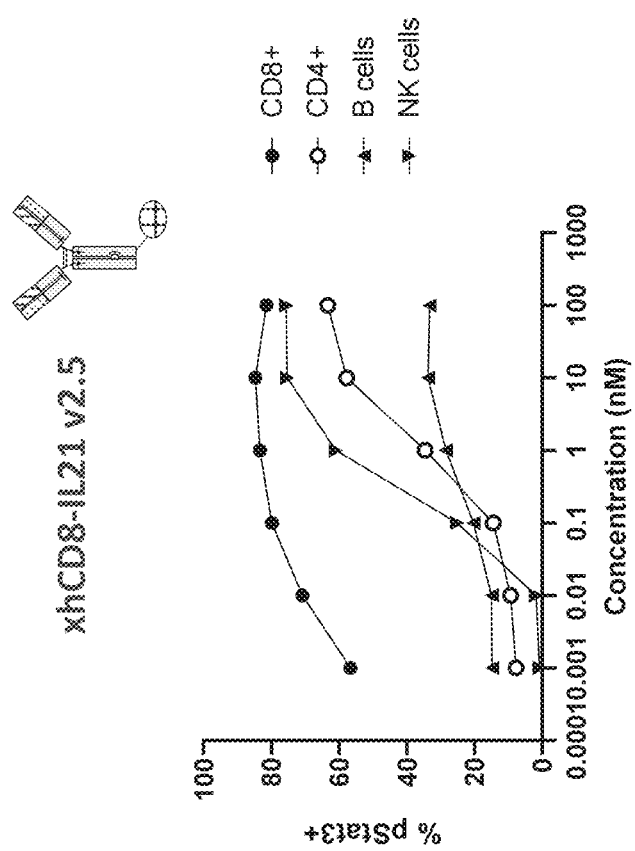
Figure 9B:
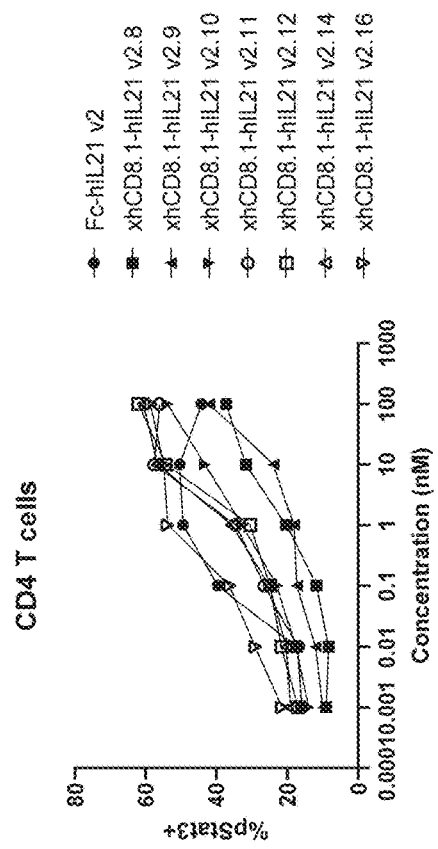
Figure 9A:
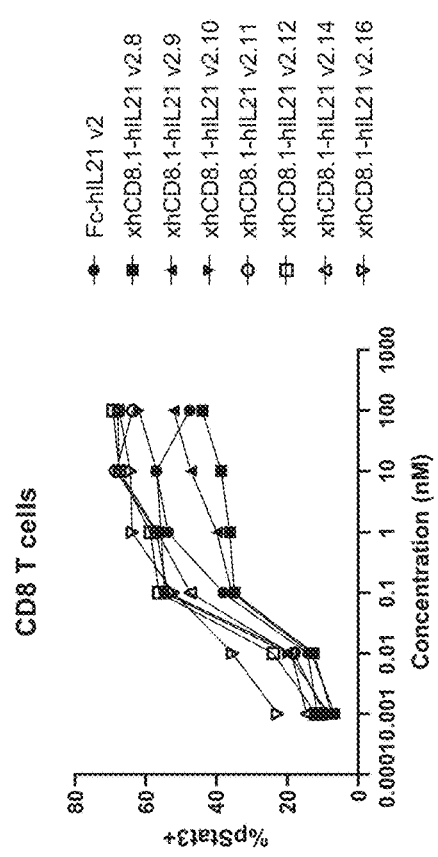
Figure 9C:
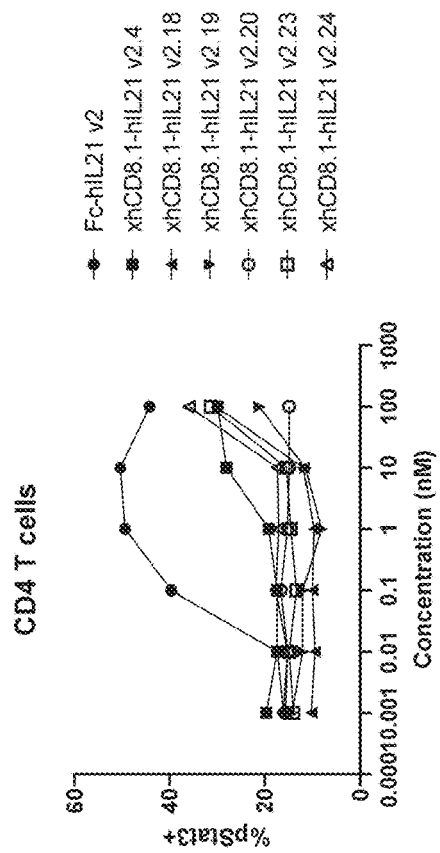
Figure 9D:
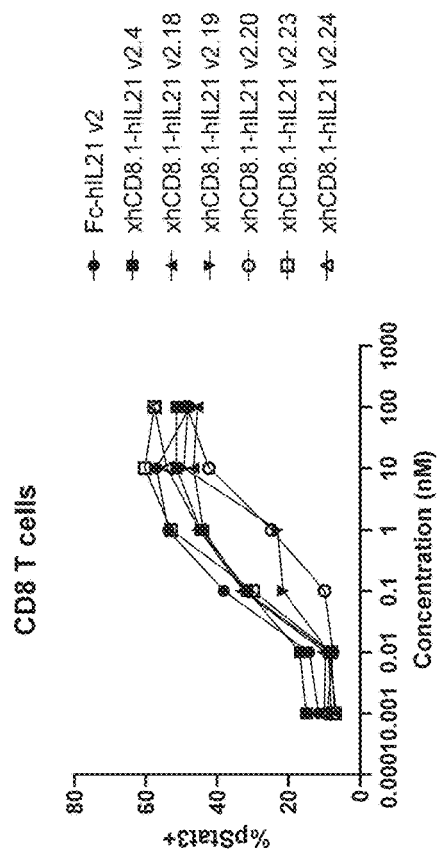
Figure 9F:
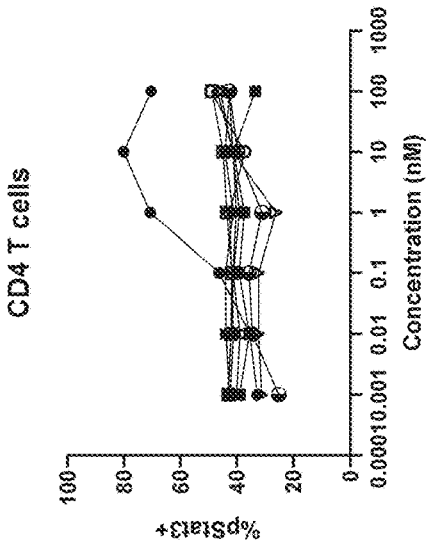
Figure 9E:
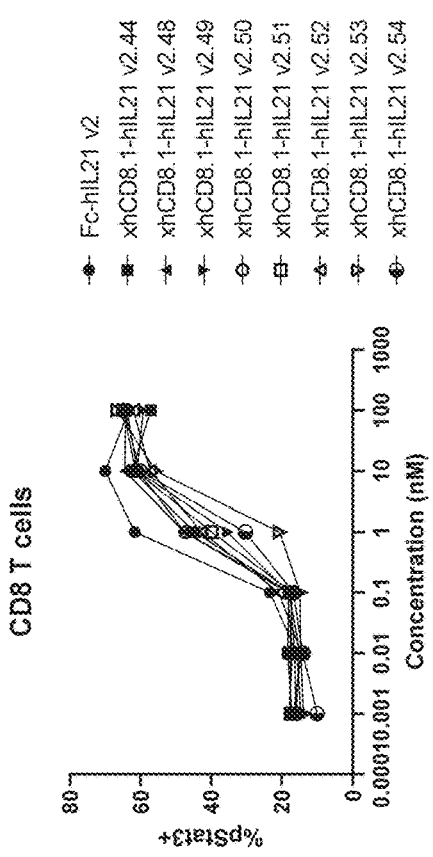
Figures 10A, 10B:
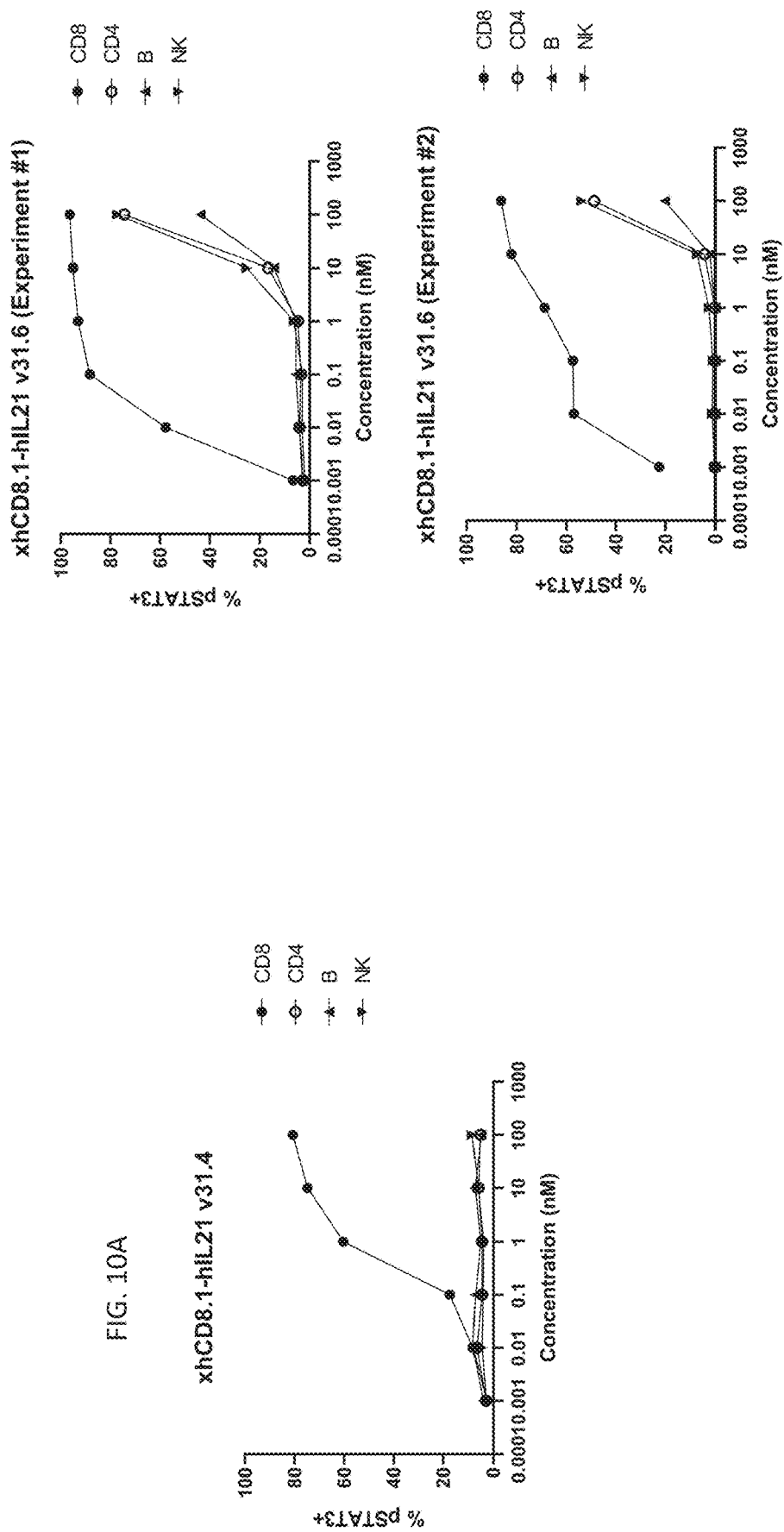
FIGS. 10A-10F show activation of STAT3 in human whole blood by fusion proteins of an anti-human CD8 antibody, xhCD8.1, with various attenuated versions of IL-21 v31. STAT3 activation is shown for CD8+ T cells, CD4+ T cells, NK cells, B cells and myeloid cells. Fusion proteins of xhCD8.1 with exemplary IL-21 polypeptides comprising attenuation mutations, IL-21 v31.4 (FIG. 10A), IL-21 v31.6 (FIG. 10B), IL-21 v31.23 (FIG. 10C), IL-21 v31.48 (FIG. 10D), and IL-21 v31.51 (FIG. 10E), all show preferential STAT3 activation of CD8+ T cells over NK, B and CD4+ T cells, as measured by $EC_{50}$ as well as maximal STAT3 activation. In the case of xhCD8.1-hIL21 v31.6, data from two separate experiments are shown (FIG. 10B). Untargeted, unattenuated Fc-hIL21 v2 is shown in FIG. 10F, with activation observed in all cell types shown.
Figure 10D:
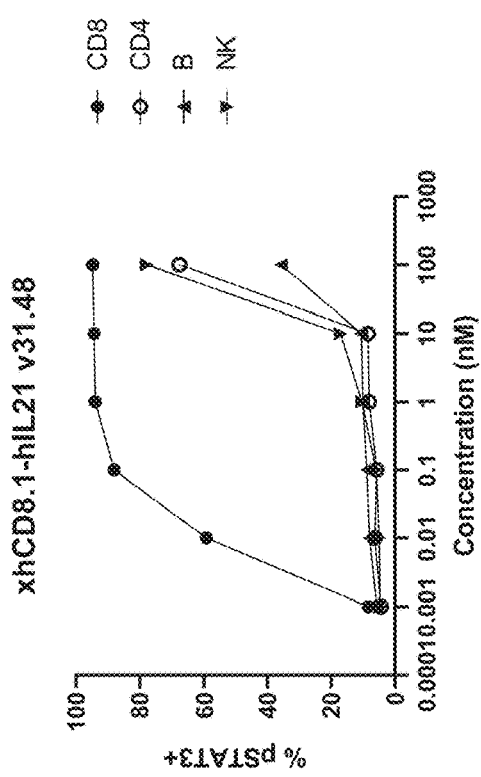
Figure 10C:
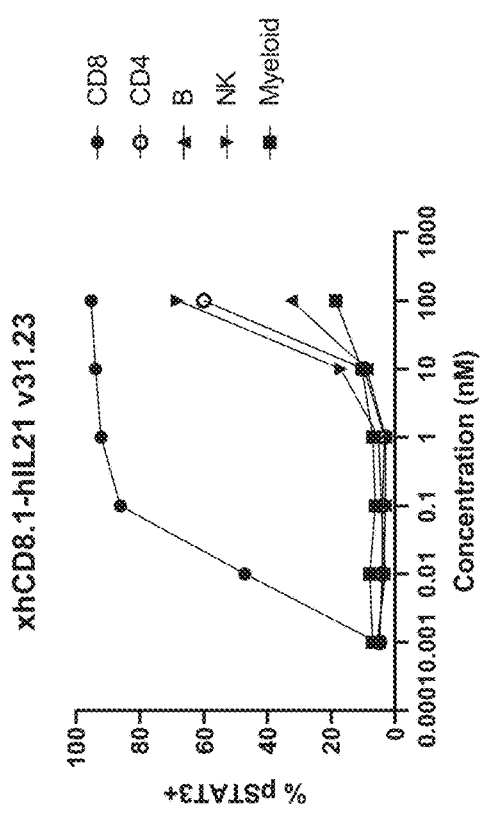
Figure 10F:
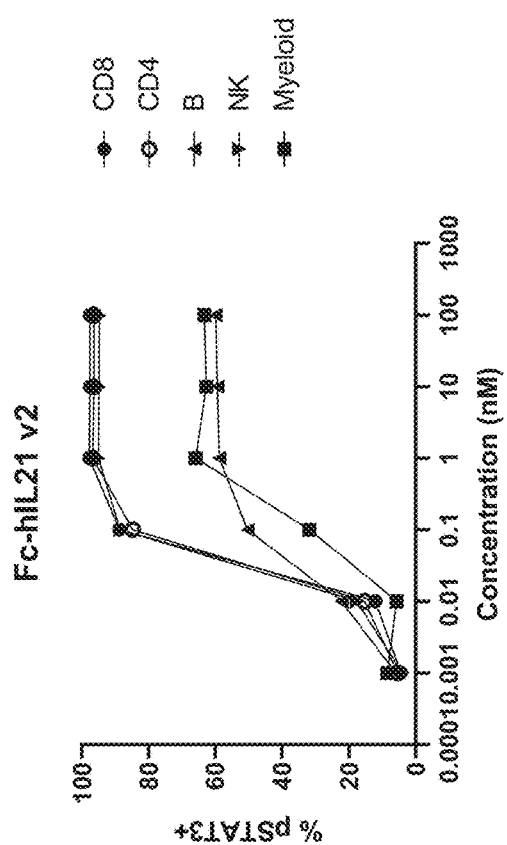
Figure 10E:
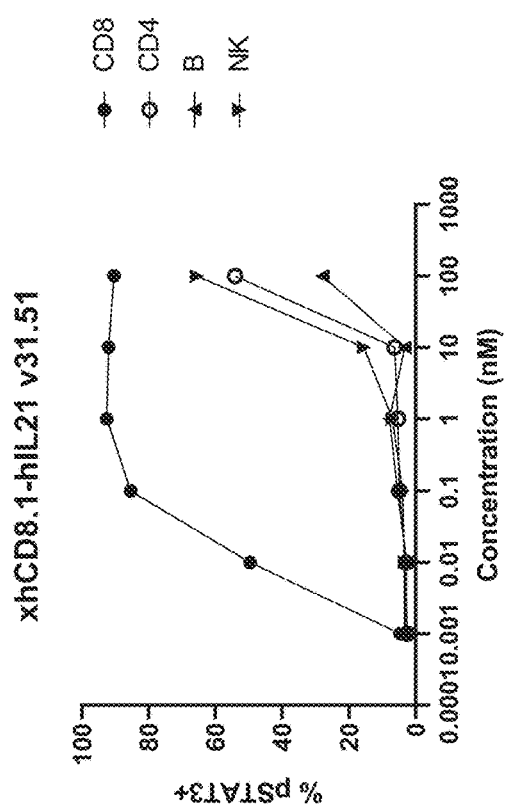
Figure 11A:
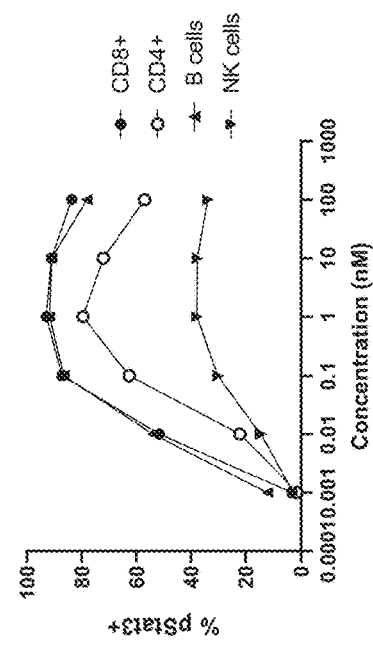
FIGS. 11A-11C show activation of STAT3 in mouse splenocytes. STAT3 activation is shown for CD8+ T cells, CD4+ T cells, NK cells and B cells. Activation profiles are shown for recombinant wild type mouse IL-21 (FIG. 11A); fusion protein of untargeted control antibody, xCtrl, and mouse IL-21 charge variant work mIL-21 v1 (FIG. 11B); and fusion protein of anti-mouse CD8 antibody, xmCD8, and attenuated mouse IL-21 charge variant, mIL21 v1.1 (FIG. 11C). For both recombinant wild type mouse IL-21 and xCtrl-mIL21 v1, all cell types are activated, whereas for xmCD8-mIL21 v1.1, there is preferential STAT3 activation of CD8+ T cells over NK, B, and CD4+ T cells, as measured by as measured by $EC_{50}$ as well as maximal STAT3 activation.
Figure 11C:
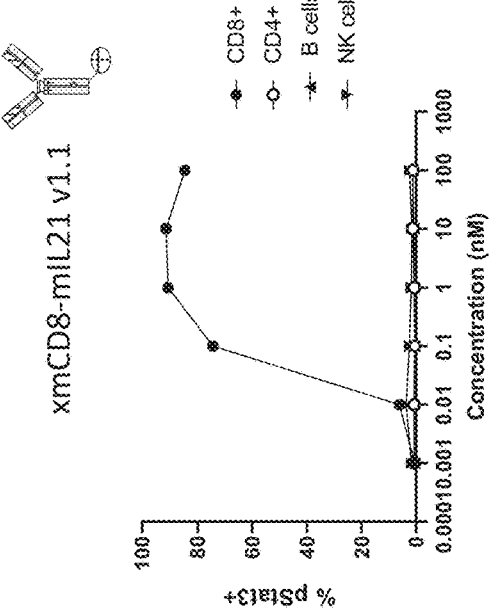
Figure 11B:
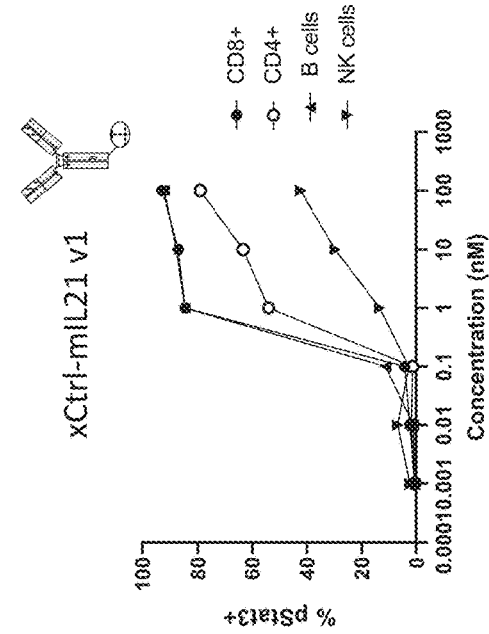

An initial round of IL-21 muteins were first generated on the exemplary IL-21 polypeptide sequence 2 (SEQ ID NO: 2) as a background and tested for STAT3 activation in human PBMCs. Table 6 summarizes the sequences of these muteins, along with the measured affinity constants using the methods described in Example 1. STAT3 activation profiles are shown for fusion proteins comprising anti-CD8 antibody, xhCD8, and IL-21 v2.1 (FIG. 8A), IL-21 v2.2 (FIG. 8B), IL-21 v2.3 (FIG. 8C), IL-21 v2.4 (FIG. 8D), IL-21 v2.5 (FIG. 8E), and IL-21 v2.6 (FIG. 8F). For all muteins, preferential STAT3 activation of CD8+ T cells was observed, as measured by $EC_{50}$ as well as maximal STAT3 activation.

Additional mutations that attenuate binding IL-21R were designed on the background of exemplary IL-21 polypeptide sequence 2, resulting in IL-21 muteins, IL-21 v2.7 through IL-21 v2.59. These were constructed as fusion proteins with an alternate anti-CD8 antibody, xhCD8.1, which shares the same epitope as xhCD8. Sequence information and binding affinities of the muteins are described in Table 6. STAT3 activation profiles are shown for CD8 T cells in FIGS. 9A, 9C, 9E, and 9G, and for CD4 T cells in FIGS. 9B, 9D, 9F, and 9H.

Selected IL-21 muteins that attenuate IL-21R binding were then generated on the exemplary IL-21 polypeptide sequence 31 (SEQ ID NO:94-SEQ ID NO:98) as a background and tested for STAT3 activation in whole human blood. Table 7 summarizes the sequences of these IL-21 muteins, while Table 8 summarizes example sequences for full length antibody-cytokine fusion proteins. STAT3 activation profiles in whole blood are shown for fusion proteins comprising anti-CD8 antibody, xhCD8.1, and IL-21 v31.4 (FIG. 10A), IL-21 v31.6 (FIG. 10B), IL-21 v31.23 (FIG. 10C), IL-21 v31.48 (FIG. 10D), IL-21 v31.51 (FIG. 10E). As a positive control, STAT3 activation of untargeted, unattenuated IL-21 fusion, Fc-IL-21v2 is shown in FIG. 10F. Additional data from whole blood of separate donors are shown in FIGS. 14A-14F, and reveals a consistent pattern of pSTAT3 activation across multiple donors.

Fusion proteins of exemplary IL-21 polypeptide sequences with an alternate anti-CD8 antibody, xhCD8v11, were constructed and evaluated in a whole human blood STAT3 activation assay. The results of these are shown in FIGS. 15A-15D, and reveals that all xhCD8v11 fusions selectively activate pSTAT3 signaling in CD8 T cells over other cell types.

Example 4: Construction and In Vitro Characterization of Mouse Surrogates of Cis-Targeted IL-21

Materials and Methods

Cloning of Murine Fusion Constructs

Murine IL-21 portions of the constructs were cloned in frame with the heavy chain using a $(G4S)_3$ 15-mer linker (SEQ ID NO: 390) between the C-terminus of the mouse IgG2a heavy chain and the N-terminus of IL-21. The C-terminal lysine residue of the IgG heavy chain was eliminated after fusing the IL-21 portion. To generate the constructs with asymmetric geometry, electrostatic modifications were introduced into the CH3 domains of the Fc region to facilitate heterodimerization. Specifically, the positively charged modifications carried the E356K and D399K mutations in the CH3 domain, whereas the negatively charged modifications carried the K409E and K439D mutations in the CH3 domain (EU numbering). To abolish FcγR binding/effector function and prevent FcR co-activation, mutations L234A/L235A/P329G (EU numbering) were introduced into the CH2 domain of each of the IgG heavy chains or the Fc region. The expression of the antibody-IL-21 fusion constructs was driven by an CMV promoter and transcription terminated by a synthetic polyA signal sequence located downstream of the coding sequence.

Evaluation of STAT3 Activation in Mouse Splenocytes

The ability of IL-21 to activate various immune cell subsets was determined in an assay measuring the phosphorylation of STAT3 by flow cytometry in mouse splenocytes Mouse spleens were mechanically dissociated in RPMI-1640 containing 10% FBS using the OctoMACS dissociation system (Miltenyi Biotech). Splenocytes were resuspended at 1-5×$10^6$ cells/ml in plain RPMI and rested for 1 hour at 37° C. with gentle agitation. Following rest, cells were resuspended in serum-free RPMI1640 media at 40×$10^6$ cells/mL and aliquoted into 96-well U-bottom plates (50 μL per well). IL-21 fusion proteins and control proteins including recombinant IL-21 (Biolegend) and control fusion proteins, were diluted to desired concentrations and added to wells (50 μL added as 2× stimulus) and incubated for 15 min at 37° C. Antibodies that could not be applied following methanol permeabilization—Nkp46 (29A1.4, Biolegend), B220 (RA3-6B2, Biolegend)—were added directly to the wells immediately following stimulation and incubated on ice for 10 min. Cells were washed 3× in pre-chilled wash buffer containing PBS+0.5% bovine serum albumin and 2 mM EDTA and fixed with 100 uL BD Fix/Perm buffer for 30 minutes at 4 C in the dark. Cells were washed 3× in pre-chilled wash buffer and resuspended in 100 μL pre-chilled Phosflow Perm buffer III (BD Biosciences) for 60 minutes at −20° C. Cells were washed 2× with wash buffer and 1× with TFP permeabilization buffer (BD Biosciences) and stained for 30-45 min at 4° C. with antibodies against: CD4 (RM4-5, BD Biosciences), CD3 (17A2, Biolegend), CD8 (53-6.7, Biolegend), CD11b (M1/70, Biolegend), CD11c (N418, Biolegend) and pSTAT3 pY705 (4/P-STAT3, BD Biosciences) diluted in TFP permeabilization buffer. Cell populations were defined as follows: CD8+ T cells: CD3+CD8+, CD4+ T cells: CD3+CD4+, B cells: B220+, NK cells: CD3−Nkp4.6+. Data were expressed as percent pSTAT3 positive, and in some cases as pSTAT3 mean fluorescence intensity (MFI), and imported into GraphPad Prism.

Results

Design of Engineered Murine IL-21 Muteins

Using the methods described in Example 1, initial attempts to express and purify fusion proteins with wild type murine IL-21 resulted in yields that were too low to generate usable material, less than 0.05 mg/L. Using the same design principles as for human IL-21, charge variants of murine IL-21 were designed to eliminate or reverse positive charge on a region of murine IL-21 that is expected to not affect binding to IL-21R or the gamma common chain. A fusion protein of xCtrl, a control antibody that does not bind any mouse proteins, and mIL-21 v1, a charge variant of murine IL-21 with sequence shown in Table 9, was successfully expressed and purified with final yield of approximately 8.6 mg/L after Protein A and ion exchange chromatography.

In order to create a CD8 cis-targeted murine surrogate, the same design principles were used as described in Example 3 and FIG. 6. Mutations that attenuated binding affinity to mouse IL-21R were introduced to mIL-21v1, resulting in the murine IL-21 mutein, mIL-21 v1.1, with sequence shown in Table 9. The fusion protein of xmCD8, a mouse CD8 specific antibody, and mIL-21 v1.1 was expressed and purified with final yield of 36.9 mg/L after Protein A and ion exchange chromatography.

Selective Activation of CD8+ T Cells by Murine CD8-Targeted IL-21 Charge Variants STAT3 activation profiles in mouse splenocytes are shown for wild type murine IL-21 (Biolegend) (FIG. 11A), xCtrl-mIL21 v1 (FIG. 11B), and xmCD8-mIL21 v1.1 (FIG. 11C). Wild type murine IL-21 and xCtrl-mIL21 v1 exhibit negligible selectivity of CD8+ T cell activation, whereas xmCD8-mIL21 v1.1 shows potent activation and >1000-fold selectivity on CD8+ T cells.

Example 5: In Vivo Efficacy of Murine Surrogates of Cis-Targeted IL-21

Materials and Methods

MC38 Mouse Tumor Model

C57BL6 female mice (Jackson Labs) at 8-10 weeks of age were housed and acclimated at the vivarium facility. Cultured MC38 cells were harvested and resuspended in serum free media (Ix DMEM, Sigma D6429) at $1.5\times10^7$ cells/mL for implantation. Mice were shaved and $1.5\times10^6$ cells (100 μL) are implanted subcutaneously above rear hind leg. Tumors were measured until tumor volume of 60-120 mm3 was reached at approximately 8 days post implantation (TV=width*width*length*0.5). Mice were then randomized into groups by tumor volume. Where indicated, 1 mg/kg FTY720 (Sigma) was dosed intraperitoneally 3× weekly beginning at 6 days post-implantation (~2 days prior to therapeutic agent dosing). Following randomization, each mouse was weighed and dosed subcutaneously with therapeutic agents under the scruff of the neck. Tumor volumes and body weights were measured every 3-4 days until either end of study (30-40 days post initial dose) or max tumor volume (2000 mm$^3$) was reached. At end of study mice were euthanized by $CO_2$ with appropriate secondary euthanasia.

Results

Figure 12:
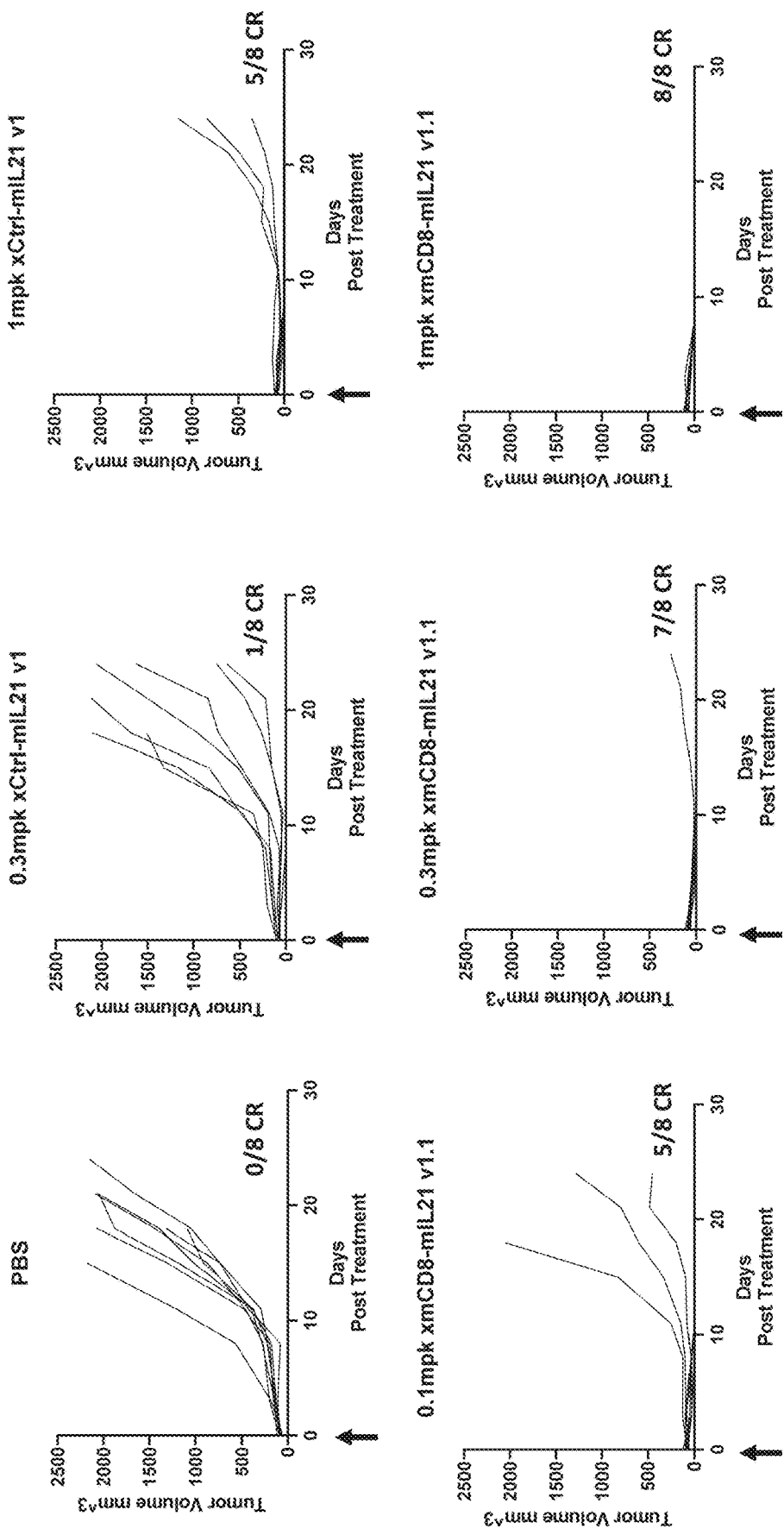
FIG. 12 shows tumor growth curves in an MC38 syngeneic tumor model treated with a single dose of either PBS; 0.3 or 1 mg/kg (mpk) of xCtrl-mIL21 v1, a fusion protein of untargeted control antibody, xCtrl, and unattenuated mouse IL-21 charge variant, IL-21 v1; or 0.1, 0.3 or 1mpk of xmCD8-mIL21 v1.1, a fusion protein of anti-mouse CD8 antibody, xmCD8, and attenuated mouse IL-21 charge variant, IL21 v1.1. Each subpanel shows tumor growth curves from each individual animal, the fraction showing complete responses (CR), and an arrow denoting the treatment time.

To the best of our knowledge, there has not been any reported single-agent efficacy of systemically administered untargeted mouse IL-21 in an MC38 mouse model. For example, three doses of approximately 10 mg/kg mouse IL-21 yielded 0/10 complete responses (CRs) in a previously reported study (Lewis et al. Oncoimmunology, Vol 7(1): 2018). Extension of cytokine half-life by fusion to an untargeted antibody also failed to control MC38 tumor growth with 0/5 CRs observed from three doses of approximately 2 mg/kg antibody-IL-21 fusion (Deng et al. J Clin Invest Insight, Vol 5(7): 2020). FIG. 12 shows potent efficacy with xCtrl-mIL21 v1, with 1/8 CRs and 5/8 CRs observed with a single dose of 0.3 mg/kg or 1 mg/kg, respectively. xCtrl-mIL21 v1 is differentiated from the construct used by Deng et al in that it is charge optimized. Based on the trends observed with human IL-21 charge variants in Example 2, it is speculated that xCtrl-mIL21 v1 would have improved bioavailability and exposure compared to the Deng et al construct, and these improved properties may be responsible for the observed efficacy in the MC38 tumor model.

CD8-targeted IL-21, xmCD8-mIL21 v1.1, also shows potent efficacy with 5/8 CRs, 7/8 CRs, and 8/8 CRs observed with single doses of 0.1, 0.3 and 1 mg/kg, respectively. When comparing efficacy in groups treated with dose-matched xCtrl-mIL21 v1, it is observed that xmCD8-IL21 v1.1 outperforms xmCtrl-mIL21 v1 in terms of the frequency of CRs as well as the degree of tumor growth inhibition. This suggests that there is an efficacy benefit to specifically targeting CD8+ T cells, and that pleiotropic IL-21 activation of cells other than CD8+ T cells by untargeted xCtrl-mIL21 v1 may inhibit the anti-tumor efficacy from IL-21 activity on CD8+ T cells.

Figure 13A:
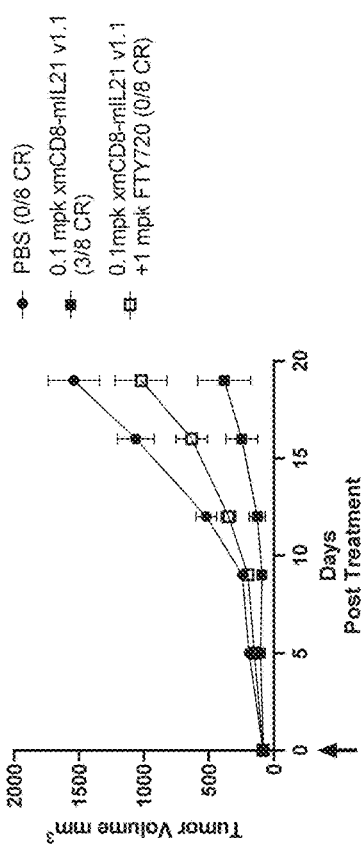
FIGS. 13A-13D show the impact of FTY720 on the anti-tumor potency of xmCD8-mIL21 v1.1 in an MC38 tumor model.
Figure 13B:
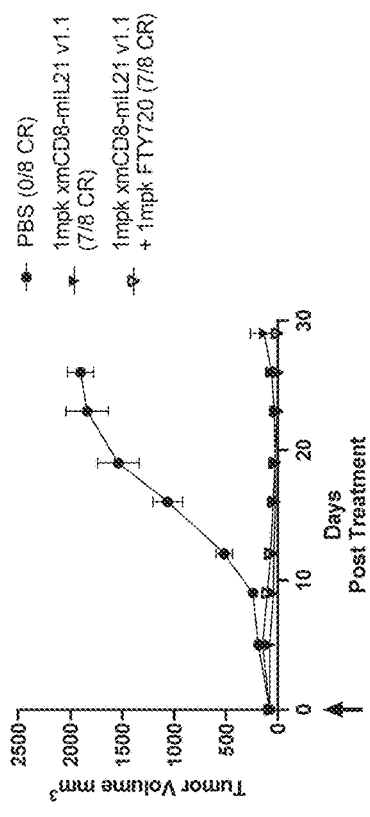
Figure 13C:
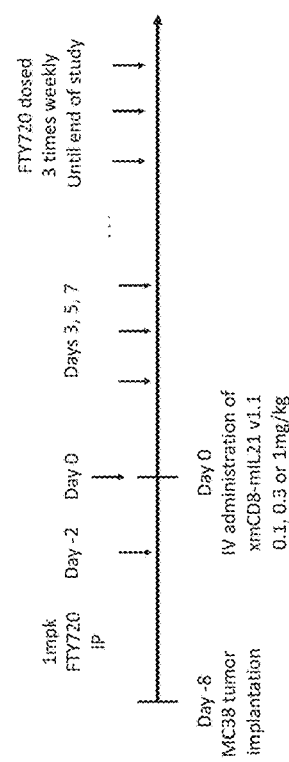
Figure 13D:
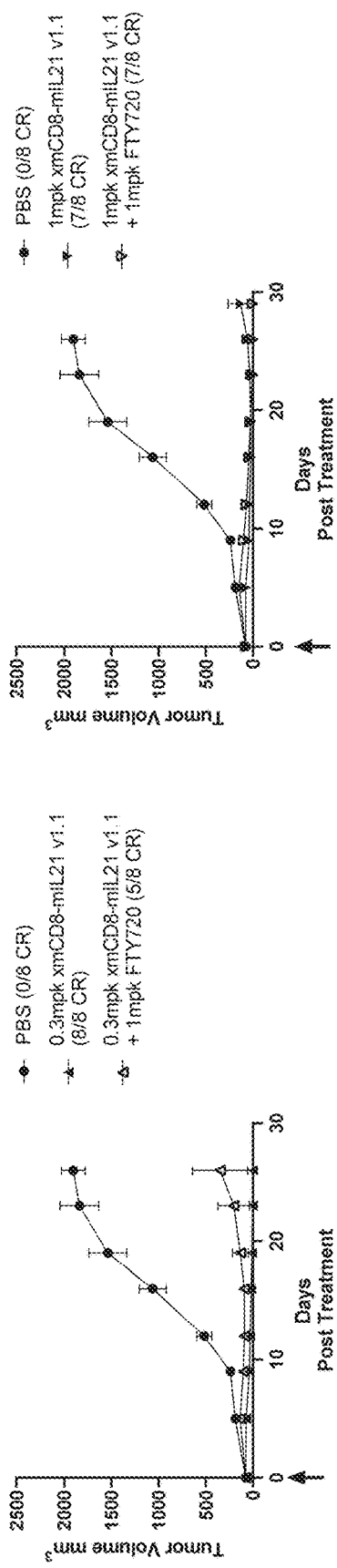
Figure 14B:
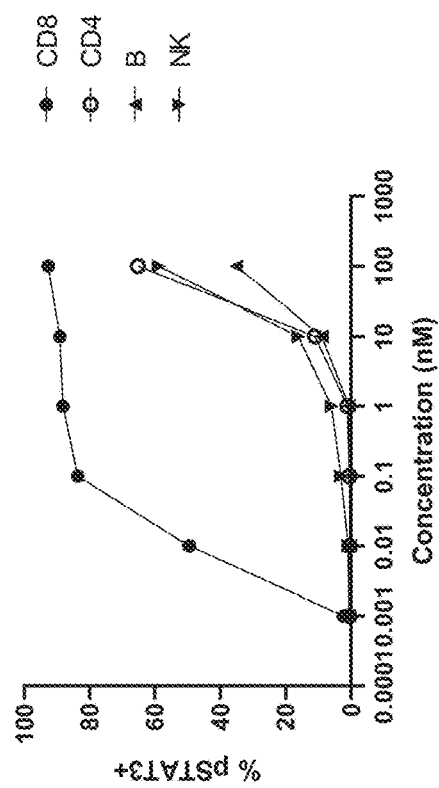
Figure 14A:
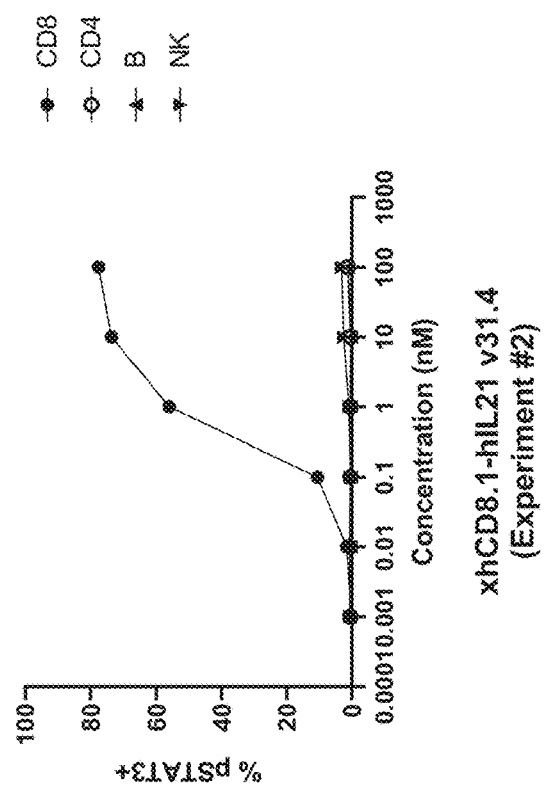
Figure 14E:
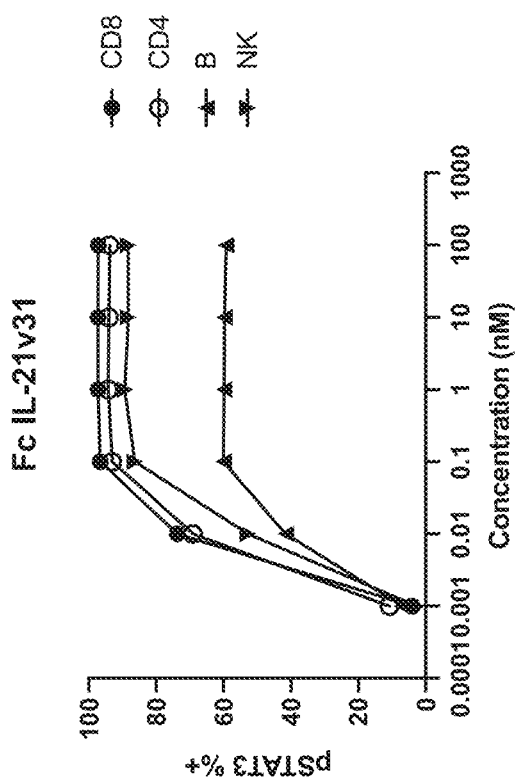
Figure 14F:
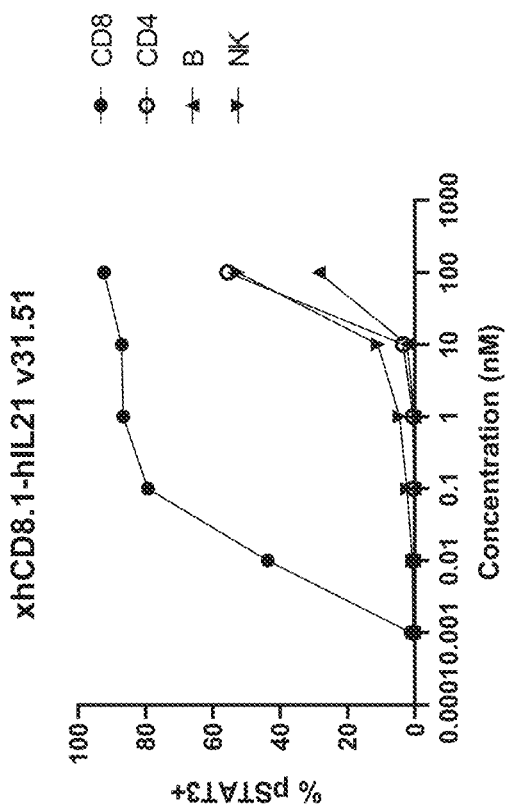

FTY720 is a potent small molecule agonist of sphingosine 1-phosphate receptor molecule that blocks lymphocyte trafficking (Brinkmann et al Nat Rev Drug Disc, 2010). The effect of FTY720 on the efficacy of a single dose of xmCD8-mIL21 v1.1 was evaluated in the MC38 tumor model, with dosing schedule described in FIG. 13A. The tumor growth curves of 0.1, 0.3 or 1 mg/kg of xmCD8-mIL21 v1.1 with and without FTY720 treatment are shown in FIGS. 13B, 13C and 13D, respectively. At the 0.1 mg/kg xmCD8-mIL21 v1.1 dose, less tumor growth inhibition and fewer CRs are observed when lymphocyte trafficking is blocked by FTY720 (FIG. 13B), indicating that the curative response of 0.1 mg/kg xmCD8-mIL21 v1.1 is contributed by peripheral activation of CD8+ T cells.

Example 6: Evaluation of CD8-Targeted IL-21 in PD1-Resistant Tumors and/or in Combination with CD8-Targeted IL2

The efficacy of CD8-targeted IL21 is evaluated in additional syngeneic mouse tumor models, using the methods previously described in Example 5.

In order to evaluate the efficacy of CD8-targeted IL-21 in tumor models that are PD-1 treatment resistant, efficacy is tested in a panel of syngeneic tumor models that are resistant to anti PD-1 treatment. Some examples of tumor models that are PD-1 resistant include B16F10, 4T1 and Pan02. CD8-targeted IL21 is administered either intravenously or subcutaneously with a single dose ranging from 0.01 to 5 mg/kg and tumor growth will be measured.

In order to evaluate the efficacy of CD8-targeted IL-21 in combination with CD8-targeted IL2 (as described in international patent application nos. PCT/US20/36454 and PCT/US21/56312, each of which is hereby incorporated by reference in its entirety), efficacy is tested in panels of tumor models where CD8-targeted IL2 as an single agent is both efficacious and not efficacious. In tumor models where CD8-targeted IL2 is efficacious, the dose of CD8-targeted IL2 is reduced to suboptimal doses to give moderate to low single-agent efficacy. Combinations of the suboptimal doses of CD8-targeted IL2 are combined with various doses of CD8-targeted IL21 ranging from 0.01 to 5 mg/kg, and tumor growth is measured. In tumor models where CD8-targeted IL2 is not efficacious as a single agent, a moderate to high dose of CD8-targeted IL2 (e.g., 0.1-5 mg/kg) is used in combination with various doses of CD8-targeted IL21 ranging from 0.1 to 5 mg/kg. Control groups with PBS-treatment as well as single agent dosing is used for comparison. Simultaneous and staggered dosing schemes for CD8-targeted IL2 and CD8-targeted IL21 are also evaluated.

Example 7: Construction and Evaluation of Additional IL-21 Variants with Attenuated Binding to IL-21R Materials and Methods Library Construction and Selection Based on the published crystal structure of IL-21 cytokine in complex with IL-21R, amino acid residues on IL-21 were identified that do not make direct contacts with IL-21R but that may affect the structure of IL-21 in a manner that would attenuate binding affinity to IL-21R. Four different combinations of four residues were selected for diversification using NNK degenerate codons to generate four independent libraries. Diversification was incorporated onto the IL-21 v2 background at the following sites: library 1 contained NNK diversity at positions V17, L20, L55, and L74; library 2 contained NNK diversity at positions I16, L20, L55 and L74; library 3 contained NNK diversity at positions I16, V17, L20 and L74; and library 4 contained NNK diversity at positions L13, I16, V17, and L74.

Using the IL-21 v2 sequence as a template, NNK-diversified libraries were constructed using PCR with primers containing degenerate nucleotides (Integrated DNA Technologies). PCR fragments were designed with flanking regions that match a linearized yeast display plasmid. Libraries were constructed according to published protocols for selection by yeast display (for example, Chao, G et al. Nat Protocols. 1: 755-768, 2006).

The four NNK libraries were displayed on yeast and sorted to isolate clones with desired affinity to IL21R. Controls hIL-21 v2.4 and hIL-21 v2.6 were also expressed clonally in a yeast display format. Overnight-induced yeast cells were labeled with mouse anti-human IL-21 (R&D Systems) and a recombinant human Fc fusion of heterodimeric IL-21R and common gamma chain (IL-21R-gc-Fc). After washing, cells were labeled with anti-mouse IgG Alexa488 and anti-human IgG Fc DyLight650 conjugates (Thermo). Two rounds of sorting were performed to enrich yeast populations with binding to IL-21R-gc-Fc between that of hIL-21 v2.4 and hIL-21 v2.6. After two rounds of sorting, plasmids were recovered from yeast by miniprep and transformed into E. coli to sequence individual clones.
Results
Characterization of Additional IL-21 Variants Nine sequences of interest were identified and expressed as fusion proteins to xhCD8.1. IL-21 variant sequences are listed in Table 6 as IL-21 v2.60 through IL-21 v2.65. The $K_D$'s of binding to IL-21R of these variants were measured as described in Example 1 and are listed in Table 6. Results shows that IL-21v2.61, IL-21v2.62, IL-21v2.63, IL-21v2.64, and IL-21v2.65, exhibit at least 50-fold reduction in binding to IL-21 receptors. The data here also shows that affinity attenuation to IL-21 receptors can be achieved by modifying non-contact residues. As described in Example 3, variants with IL-21R affinity attenuation exhibit reduced activity on cells expressing IL-21R, whereas fusing the variants to a CD8-targeting domain enables preferential binding of the targeted fusions to CD8+ T cells and thereby restores the IL-21 activity specifically on CD8+ T cells. STAT3 activation in human whole blood was measured for selected fusion proteins of xhCD8.1 to additional IL-21 variants, hIL21 v2.63 (FIG. 16A), hIL21 v2.64 (FIG. 16B), and hIL21 v2.65 (FIG. 16C). In all cases shown, STAT3 is activated on CD8+ T cells with >100-fold selectively over non-CD8 T cells.

Example 8: Characterization of Selected hIL-21 Fusion Proteins

Several hIL-21 fusion proteins were selected for additional characterization, namely xhCD8.1-hIL21 v31.4, xhCD8.1-hIL-21 v31.23, and xhCD8v11-hIL21 v31.23.

The yields of selected fusion proteins are shown in Table 13 after ProA and after ProA+IEX purification. These yields are mostly higher than the charge-modified unattenuated fusion proteins reported in Table 3, which shows increased yield over the fusion with wild-type IL-21. Ion-exchange chromatography traces are shown in FIGS. 17A-17C with percentage of total signal specified that represents the desired heterodimer product. These results indicate that combination of IL-21R attenuation modifications and the charge variant modifications, v31, along with different targeting arms, xhCD8v11 or xhCD8.1, can maintain good expression properties with a high percentage of material being the correctly formed heterodimer.

Polyreactivity data for selected fusion proteins are shown in Table 15 and reveal that these fusions exhibit favorable polyreactivity profiles as compared to positive control Bococizumab.

Example 9: Comparison of IL-21R Attenuation Muteins on Wild Type or v31 Charge Variant Background As shown in Example 2, the modification of charge in IL-21 reduces polyreactivity and improves bioavailability and exposure in mouse. Additionally, selected charge variants that were tested and reported in Table 4 do not affect binding affinity to IL-21R. However, some of the mutations used for IL-21R attenuation either eliminates or reverses a positively charged residue. The effect of the charge reduction from an exemplary IL-21R attenuation mutein was evaluated by comparing the IL-21R attenuation mutein on either the wild type IL21 background, or the IL21 v31 charge variant background. Specifically, fusion proteins of hIL-21 v31.4 were compared to hIL-21 v0.4, which contains the same arginine to glutamic acid mutation for IL-21R attenuation as hIL-21 v31.4 but on the wild type IL-21 background. The sequence of hIL-21 v0.4 can be found in Table 14.

Fusion proteins of xhCD8.1 with either hIL-21 v0.4 or hIL-21 v31.4 were evaluated for polyreactivity. As shown in Table 15 and Table 5, xhCD8.1-hIL21 v0.4 exhibits an improved polyreactivity profile compared to xhCD8.1-hIL21 (wild type IL-21 fusion), but the polyreactivity profile of xhCD8.1-hIL21 v31.4 is further improved with the incorporation of charge modifications (v31).

Highly polyreactive proteins exhibit reduced in vivo exposure due to non-specific interaction with cellular components. A pharmacokinetic study in mouse was set up to evaluate the impact of polyreactivity on the in vivo exposures of targeted fusions with and without v31 charge modification. Targeted fusions were generated using antibodies targeting human CD8, such as xhCD8.1 and xhCD8v11, which do not cross react with mouse CD8, therefore any observed exposure difference is primarily driven by the cytokine part of the fusion. Results in FIG. 18 shows that xhCD8.1-hIL21 v31.4 exhibits 1.9-fold increase in area-under-the-curve over xhCD8.1-hIL21 v0.4, which lacks v31 charge modification and exhibit higher polyreactivity profile (Table 15). Such results suggest that charge modification such as v31 can reduce polyreactivity and in turn enhance the in vivo exposure of IL-21 variants. Similarly, charge-modified xhCD8.1-hIL-21 v31.23, and xhCD8v11-hIL21 v31.23 show extended exposure in vivo over xhCD8.1-hIL21 v0.4, demonstrating the importance of the v31 charge modification for improved bioavailability and exposure.

Example 10: Characterization of Recombinant (Non-Fusion) hIL-21 and hIL-21 Variants

Materials and Methods

Expression and Purification of Non-Fusion Polypeptides

Recombinant (non-fusion) hIL-21 and hIL-21 variants were cloned into expression vectors and expressed as described in Example 1. A Gly-Gly-Ala-Ser linker (SEQ ID NO: 392), followed by 8His-tag (SEQ ID NO: 391) was inserted downstream of the cytokine molecule for purification. Supernatants were collected after 5 days of expression in Expi293 cells (Thermo Fisher), and were used either directly for a Biacore assay or subjected to purification. IL-21 polypeptides were first purified by affinity chromatography using Ni Sepharose resin (Cytiva). The column was equilibrated and washed with PBS supplemented with 0.5 M NaCl. Proteins were eluted with PBS supplemented with 0.5 M NaCl and 0.25 M imidazole. The eluted fractions were polished by size exclusion chromatography (HiLoad Superdex 200 pg 16/600, Cytiva) in PBS.

Polyreactivity Assessment of Non-Fusion Polypeptides

For polyreactivity measurements of recombinant (non-fusion) hIL-21 and hIL-21 variants, an ELISA assay was performed as described in Example 1 with the exception that detection was performed with 1:1000 diluted horseradish peroxidase conjugated mouse anti-His tag antibody (BioLegend).

Biacore Analysis of Non-Fusion IL-21 Variants

Kinetic rate constants (ka and kd) as well as binding affinity (KD) of non-fusion IL-21 muteins with human IL-21R were measured by surface plasmon resonance (SPR) using a BIAcore® 8K (Cytiva) at 25° C. To determine the affinities, a human IL-21 antibody (R&D Systems, Catalog No. MAB15001) diluted to 10 μg/mL was first captured at 10 μL/min for 2 minutes on flow cell 1 and 2 onto a CM5 sensor chip that was covalently immobilized with anti-mouse Fc antibody (Cytiva, Catalog No. BR100838). Next, IL-21 WT muteins supernatants were captured for 2 minutes at 10 μL/min on flow cell 2 with the human IL-21 antibody. No protein was captured on flow cell 1 to serve as a reference surface. A serial dilution was generated for the recombinant human IL-21R, that was generated in house as described earlier, in HBS-P+ buffer supplemented with 1 g/L BSA, starting at nominal concentrations of 20 μM, followed by five 5-fold serial dilutions, and flowed over the surface for 2 minutes at 30 μL/min to measure association. Buffer was also flowed over the surface to serve as a blank subtraction. Dissociation was monitored for 5 minutes, and the anti-mouse IgG-Fc surface was regenerated with 180 seconds injections of 10 mM glycine-HCl pH 1.7 before recapturing human IL-21 antibody/hIL-21 WT mutein protein in each subsequent binding cycle. Binding data were double-referenced and analyzed by Biacore® Insight Evaluation Software version 4.0.8 using steady-state affinity for very weak interactions, or when possible, a 1:1 Langmuir with mass transport model to determine kinetic rate constants (ka, kd) and KD.

Results

IL-21R attenuating mutations were incorporated on either the wild type hIL-21 or hIL-21 v31 background. The sequence of the cytokine portion, not inclusive of the downstream linker and 8His-tag (SEQ ID NO: 391), are shown in Table 14 with affinities reported as well where measured.

Selected IL-21R muteins were selected for full purification. After preparative SEC, the fully-purified materials were re-analyzed by SDS-PAGE (FIG. 19A) and analytical SEC (FIG. 19B). Based on SDS-PAGE analysis of the fully-purified protein, all non-fusion hIL-21 and hIL-21 variants appear to be monomeric and pure, with no contaminating bands observed. Analytical SEC reveals an increase in peak width and retention time for all wild-type hIL-21 based constructs (hIL-21, hIL-21 v0.4, hIL-21 v0.23 & hIL-21 v0.51) compared to the hIL-21 v31 based constructs (hIL-21 v31.4, hIL-21 v31.23 & hIL-21 v31.51). This indicates that wild-type hIL-21 based constructs have more column interactions than hIL-21 v31 based constructs, and that the hIL-21 v31 based constructs possess better developability properties (Kohli et al., MAbs, 7(4): 752-758, 2015).

Polyreactivity was also measured for these fully purified constructs. The results are shown in Table 16. Overall, there was less polyreactivity observed with hIL-21 v31 compared to any of the hIL-21 wild-type (v0) based variants, which suggests that the v31 charge modification alone improves polyreactivity more than any IL-21R attenuating mutation on the wild-type background.

Example 11: Exposure of Recombinant (Non-Fusion) hIL-21 and hIL-21 Variants

Materials and Methods

ELISA Evaluation of Serum Samples

Mouse serum concentration of the test molecules was measured by ELISA, using a standard curve generated using known concentrations of test molecules. Briefly, 100 μL per well of 2 pg/mL of anti-human IL-21 antibody (R&D Systems, Catalog No. AF15001) in PBS was coated onto a 96-well Nunc MaxiSorp plate (Thermo Fisher Scientific) overnight at 4° C. Coating solution was removed, and the plates were blocked with 250 μL per well of Blocker Casein in PBS (ThermoFisher Scientific) for 2 hours at room temperature. Plates were washed with PBS+0.1% Tween-20, and either protein standard or diluted serum was added. For the protein standard, a serial dilution was generated starting at 0.00333 μg/mL, followed by four 3-fold serial dilutions. Serum samples were diluted between 50-fold and 2000-fold, in order to keep the final readout within the range of the standard curve. All dilutions were in PBS+0.5% BSA+0.05% Tween-20, and 100 μL was used per/well. Serum samples and the protein standard were incubated at room temperature for 1-2 hours, followed by washing with PBS+0.1% Tween-20. Next, 100 μL per well of His Tag Biotinylated Antibody (R&D Systems, Catalog No. BAM050) at 10 nM was added and the plates were incubated at room temperature for 1 hour. Plates were washed with PBS+0.1% Tween-20. Then, 100 μL per well of Peroxidase Streptavidin (Jackson ImmunoResearch, Laboratories Inc., Catalog no. 016-030-084) at 1:2000 dilution in PBS+0.5% BSA+0.05% Tween-20 was added, and the plates were incubated at room temperature for 45 minutes. The plates were developed using 100 μL of 1-step Ultra TMB-ELISA substrate solution (Thermo Fisher Scientific) for 1-3 minutes and stopped with 100 μL of 2 M sulfuric acid. The absorbance at 450 nm was read on a SpectraMax iD5 plate reader (Molecular Devices). A nonlinear regression was used to fit the standard curve, and absorbance at 450 nm of diluted serum samples were converted to concentrations by interpolating the standard curve.

Results

The exposure of human recombinant (non-fusion) wild-type IL-21 and IL-21 charge variant, v31, were evaluated in mouse. Due to the lack of significant difference in molecular weight between the two IL-21 molecules (~16 kDa), renal filtration mediated clearance is not expected to contribute to any meaningful difference in exposure. Instead, the major difference in exposures between wildtype IL-21 and IL-21v31 is mediated by the non-specific clearance, as v31 modification do not alter the IL-21R affinities (Table 14). Results in FIG. 20 shows that v31 modification improves exposure compared to wild type IL-21, and a 4.3× increase in AUC ratio is observed. Overall, charge modification increases the bioavailability of recombinant IL-21 in non-fusion format, and this is consistent with the improvement observed in antibody fusion format (FIG. 4D).

Example 12: Measurement of Suppression of T Cell Activation

Materials and Methods

Activation of Allogeneic T Cells Assay

Immature human dendritic cells (DCs) were purchased (HemaCare—Charles River Laboratories) and activated for 3 days in GM-CSF, IL-4, and TNFa according to kit protocol (R&D Systems). Total T cells were isolated and enriched by a negative selection magnetic bead kit (Miltenyi Biotech). Activated DCs were harvested and plated at a ratio of 1:10 with T cells from mis-matched donors in the presence or absence of IL-21 molecules for 3 days. Molecules tested include two CD8+ T cell targeted fusions, xhCD8.1-hIL21 v31.4 and xhCD8.1-hIL21 v31.23, and an untargeted, unattenuated Fc-hIL21 v31. All three IL-21 molecules were tested at respective concentrations that give $EC_{95}$ response in CD8 T cells in an in vitro pSTAT3 assay. Following completion of co-culture, supernatants were harvested and assessed for IL-2 secretion by ELISA following the manufacturing protocol (IL-2 instant ELISA, ThermoFisher Scientific).

Results

Figure 22:
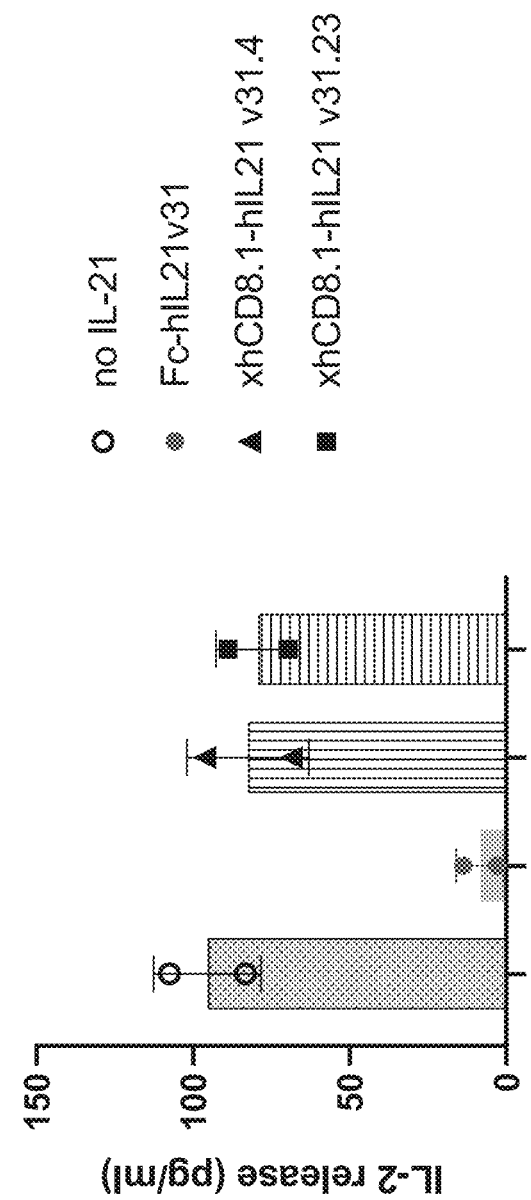
FIG. 22 shows the activities of IL-21 fusion molecules in cultures of alloreactive T cells and activated dendritic cells isolated from two different human PBMC donors. Molecules tested include two CD8+ T cell targeted fusions, xhCD8.1-hIL21 v31.4 and xhCD8.1-hIL21 v31.23, and an untargeted, unattenuated Fc-hIL21 v31. IL-2 release in culture was measured to determine the level of alloreactive T cell activation. In summary, Fc-hIL21 v31 suppressed activation of alloreactive T cells, while the CD8+ T cell targeted fusions did not.

IL-21 can mediate suppressive effects on dendritic cells (DCs), inhibiting their maturation and inducing apoptosis of conventional DCs. Additionally, IL-21 can inhibit T cell priming in mixed lymphocyte cultures (Wan et al, Immunity, (2013) 38:514-27). The ability of CD8+ T cell targeted fusions to avoid the IL-21 mediated suppressive effect on dendritic cells was evaluated in co-cultures of DCs and T cells from mismatched human donors. In the absence of IL-21, incubation of alloreactive T cells and DCs induces the release of IL-2 in culture. FIG. 22 shows that unattenuated Fc-hIL21 v31 inhibits IL-2 release, and therefore suppresses T cell activation. In contrast, both CD8+ T cell targeted fusions, xhCD8.1-hIL21 v31.4 and xhCD8.1-hIL21 v31.23, maintain similar level of IL-2 release as control, supporting that CD8+ T cell targeted IL-21 fusions do not interfere with the all response of mismatched T cells and dendritic cells.

Example 13: Evaluation of CD8-Targeted IL-21 Fusions in Cynomolgus Monkeys

Materials and Methods

Evaluation of In Vitro STAT3 Activation in Cynomolgus Monkey Blood Cells

The activation of STAT3 in cynomolgus monkey whole blood by IL-21 molecules was similarly performed as described in Example 3, with the exception that cynomolgus monkey specific antibodies were used to stain various cell types in blood. Specifically, antibodies used were CD3 (SP34.2, BD), CD4 (L200, BD), CD8a (SK1, Biolegend), CD14 (M5E2, Biolegend), CD20 (2H7, Biolegend), HLA-DR (L243, Biolegend), NKG2A (REA110, Miltenyi) and pStat3 pY705 (4/P-STAT3, BD). Cell populations were defined as follows: CD8+ T cells: CD3+CD8+, CD4+ T cells: CD3+CD4+, B cells: CD20+, NK cells: CD3−CD19−NKG2A+.

Evaluation of In Vivo STAT3 Activation in Cynomolgus Monkey

Two naïve cynomolgus non-human primates (*Macaca fascicularis*) were dosed intravenously of xhCD8.1-IL-21 v31.4. Blood samples were collected 20 min post dose. STAT3 activation in various blood cell types was determined following the STAT3 protocol described in Example 3. The following set of antibodies were used to stain various cell types and phosphorylated STAT3: CD3 (SP34.2, BD), CD4 (L200, BD), CD8a (SK1, Biolegend), CD14 (M5E2, Biolegend), CD20 (2H7, Biolegend), HLA-DR (L243, Biolegend), NKG2A (REA110, Miltenyi) and pStat3 pY705 (4/P-STAT3, BD).

Results

Figure 15B:
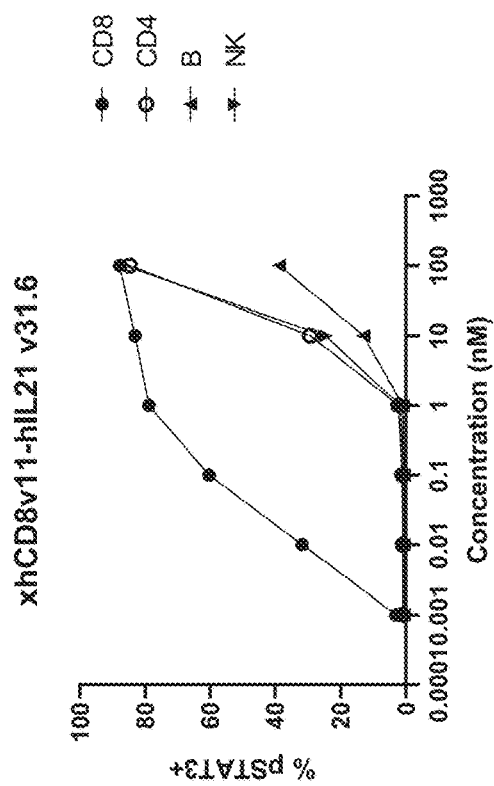
Figure 15A:
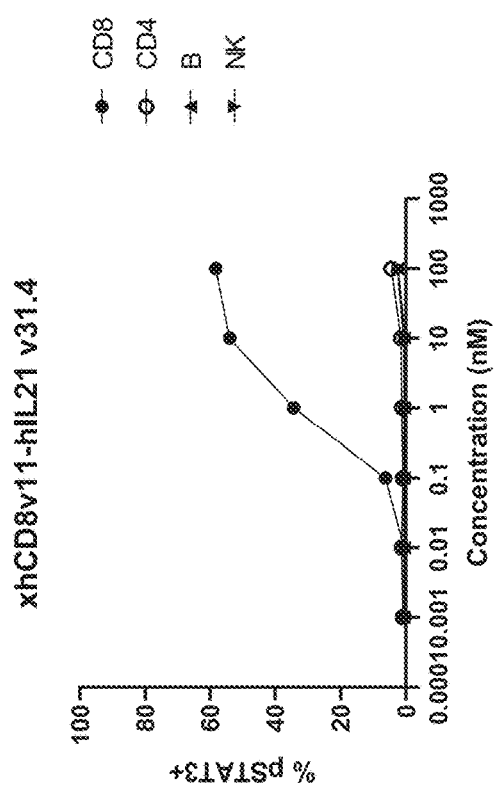
Figure 16B:
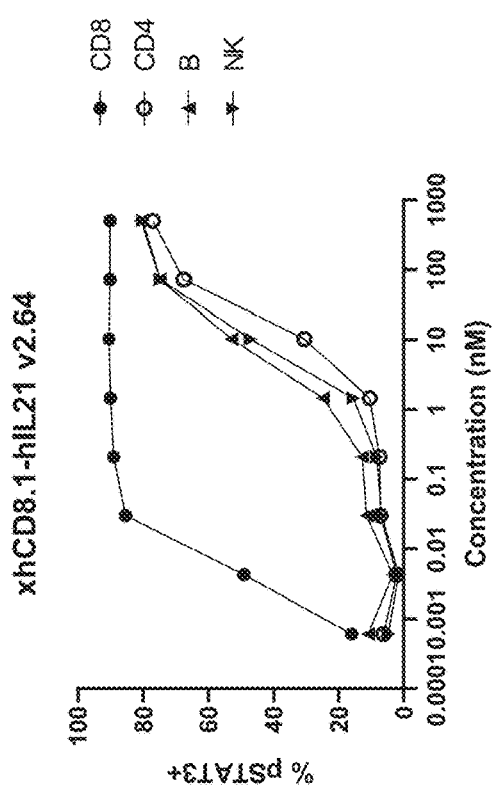
FIGS. 16A-16C show activation of STAT3 in human whole blood by fusion proteins of an anti-human CD8 antibody, xhCD8.1, with various versions of IL-21 v2 charge variant that also contained additional mutations. STAT3 activation is shown for CD8+ T cells, CD4+ T cells, NK cells, and B cells. Fusion proteins of xhCD8v.1 with exemplary IL-21 polypeptides comprising attenuation mutations, IL-21 v2.63 (FIG. 16A), IL-21 v2.64 (FIG. 16B), and IL-21 v2.65 (FIG. 16C) all show preferential STAT3 activation of CD8+ T cells over NK, B and CD4+ T cells, as measured by $EC_{50}$.
Figure 16A:
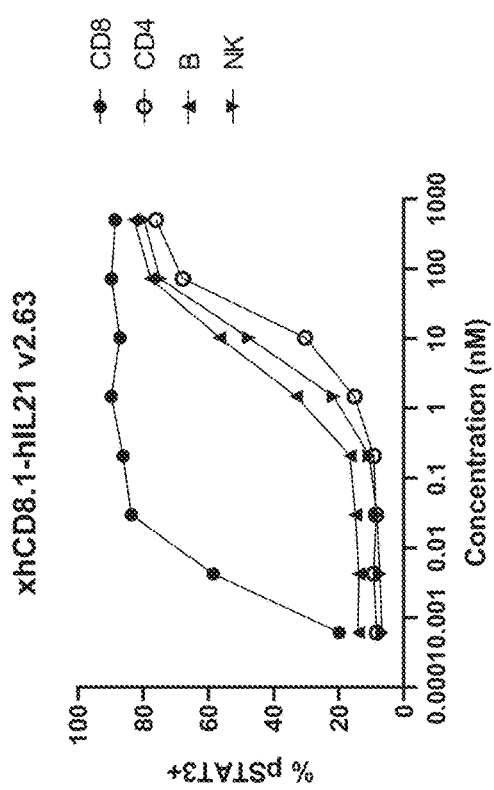
Figure 16C:
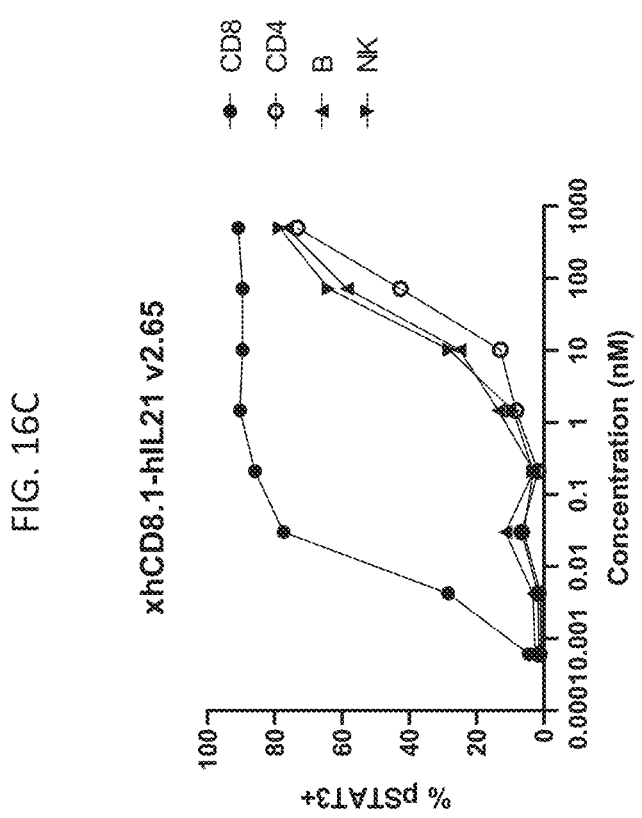
Figure 17A:
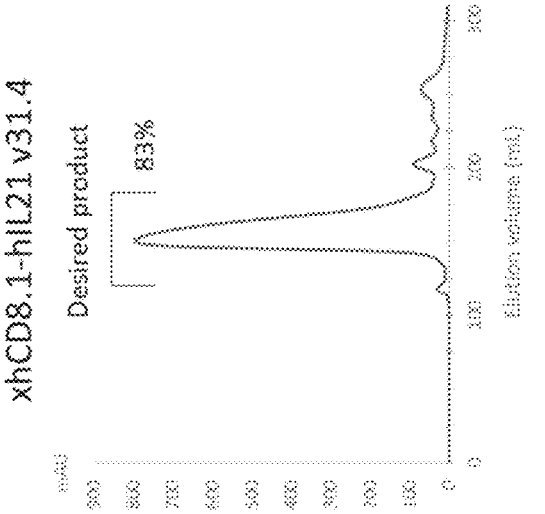
FIGS. 17A-17C show ion exchange chromatography traces of fusion proteins of anti-CD8 antibodies and IL-21R attenuated IL-21 charge variants after Protein A purification. Traces are shown for xhCD8v11-hIL21 v31.23 (FIG. 17A), xhCD8.1-hIL21 v31.23 (FIG. 17B), and xhCD8.1-hIL21 v31.4 (FIG. 17C), as measured by FPLC. In all cases, the peak(s) to the left of the major peak are undesired products, primarily homodimer, whereas the major peak in the middle is the desired heterodimer fusion protein, and the percentages of total of the desired peak are shown.
Figure 17B:
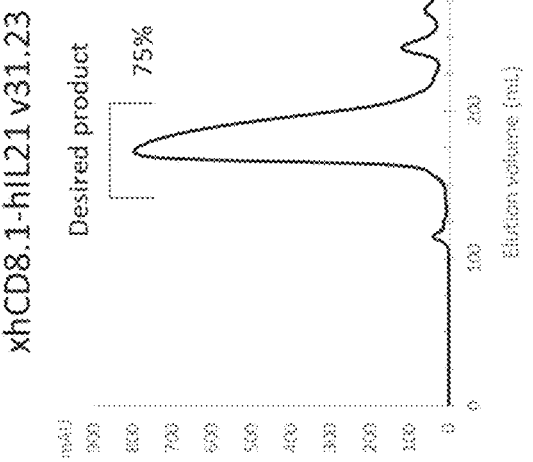
Figure 17C:
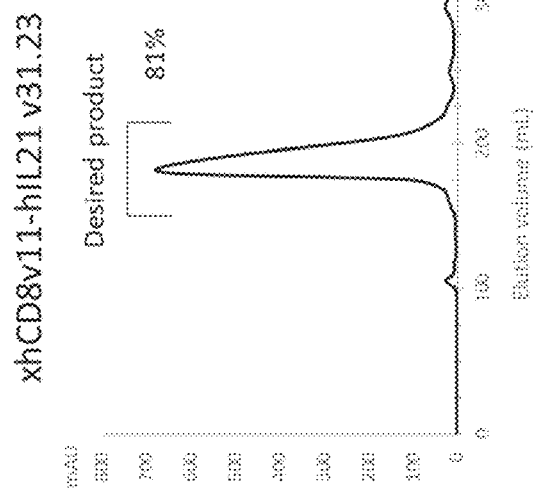
Figure 18:
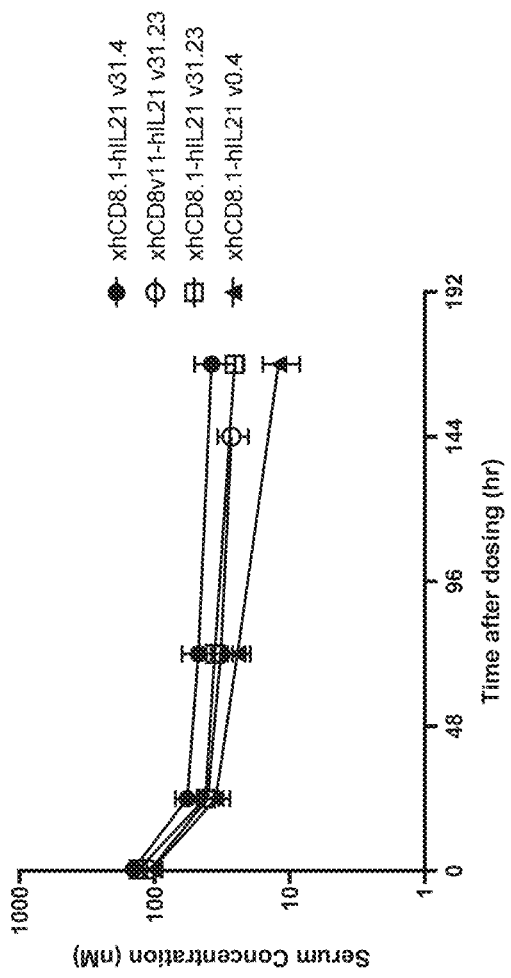
FIG. 18 shows the pharmacokinetic data for fusion proteins in wild-type C57BL6 mice. Serum concentrations are shown for fusion proteins of anti-human CD8 antibodies, xhCD8.1 or xhCD8v11, with either hIL-21 v31.4, hIL-21 v31.23, or hIL-21 v0.4 dosed intravenously. The anti-human CD8 antibodies, xhCD8.1 and xhCD8v11 are not cross reactive to mouse CD8. Exposures are shown for xhCD8.1-hIL21 v31.4, xhCD8v11-hIL21 v31.23, xhCD8.1-hIL21 v31.23 and xhCD8.1-hIL21 v0.4.
Figure 19A:
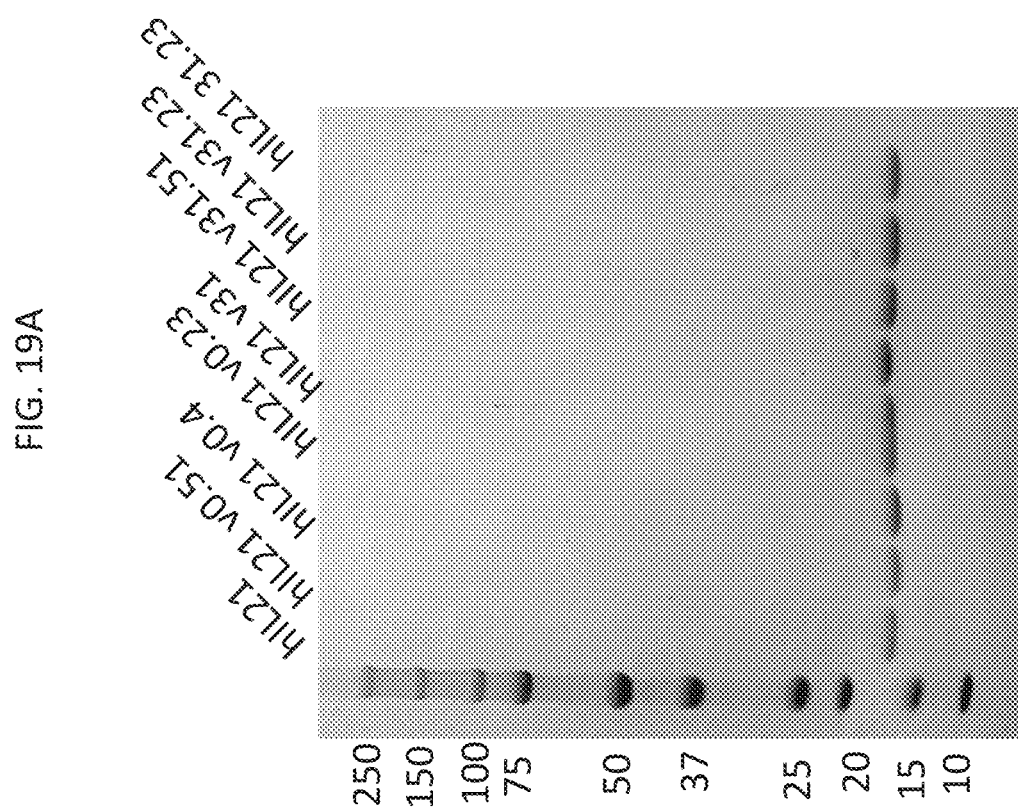
FIGS. 19A & 19B show the characterization data of recombinant cytokine variants based on wild-type IL-21 or the IL-21 v31 charge variant. SDS-PAGE of material purified by IMAC followed by preparative SEC is shown in FIG. 19A. Analytical SEC of material purified by IMAC followed by preparative SEC is shown in FIG. 19B. Retention times and peak widths are also reported to evaluate column interactions. In summary, recombinant cytokine variants based on the IL-21 v31 charge variant have lower retention times and narrower peak widths compared to variants based on wild-type IL-21, suggesting fewer column interactions and more favorable biophysical properties with IL-21 v31 based constructs.
Figure 19B:
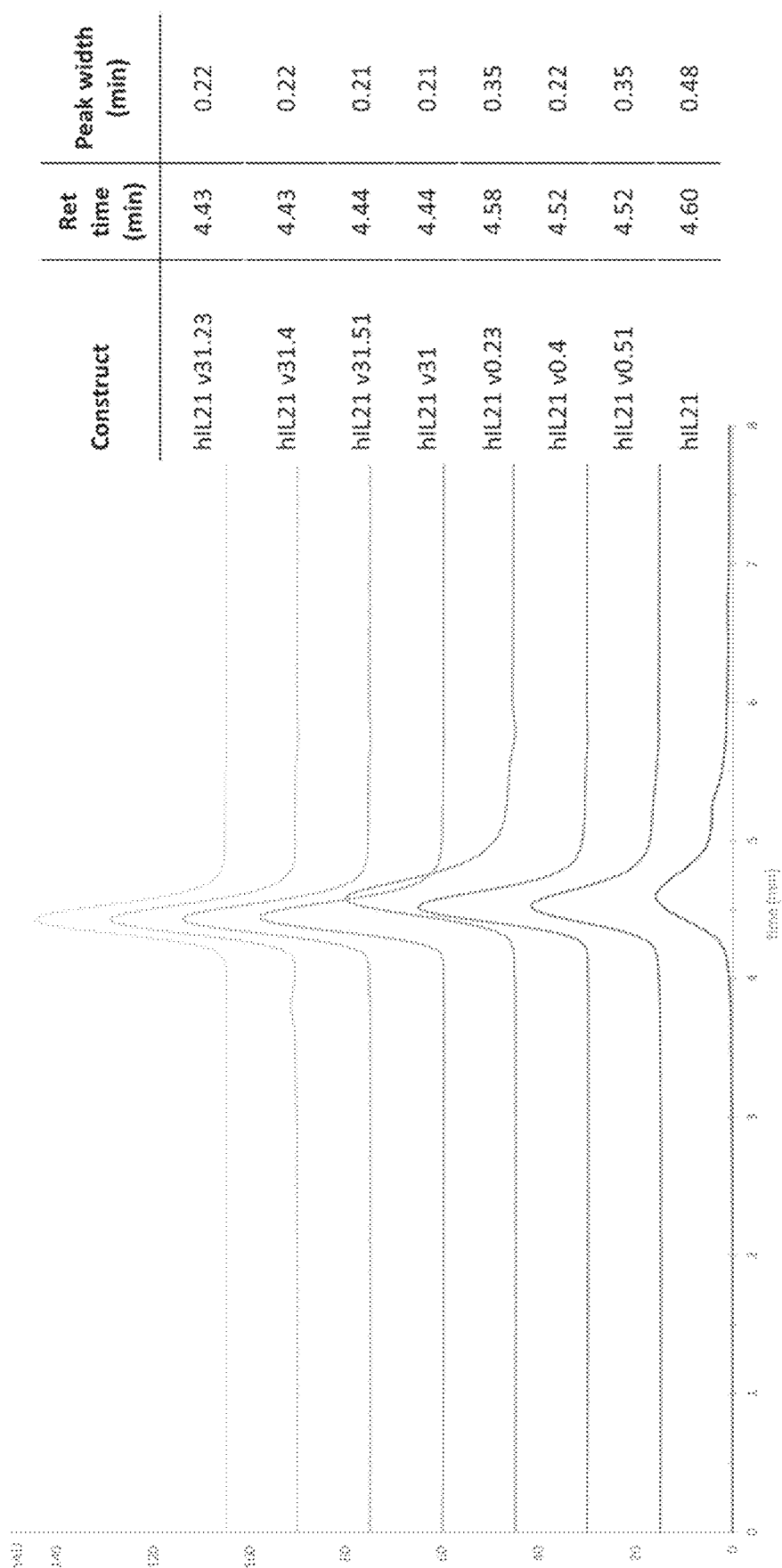
Figure 20:
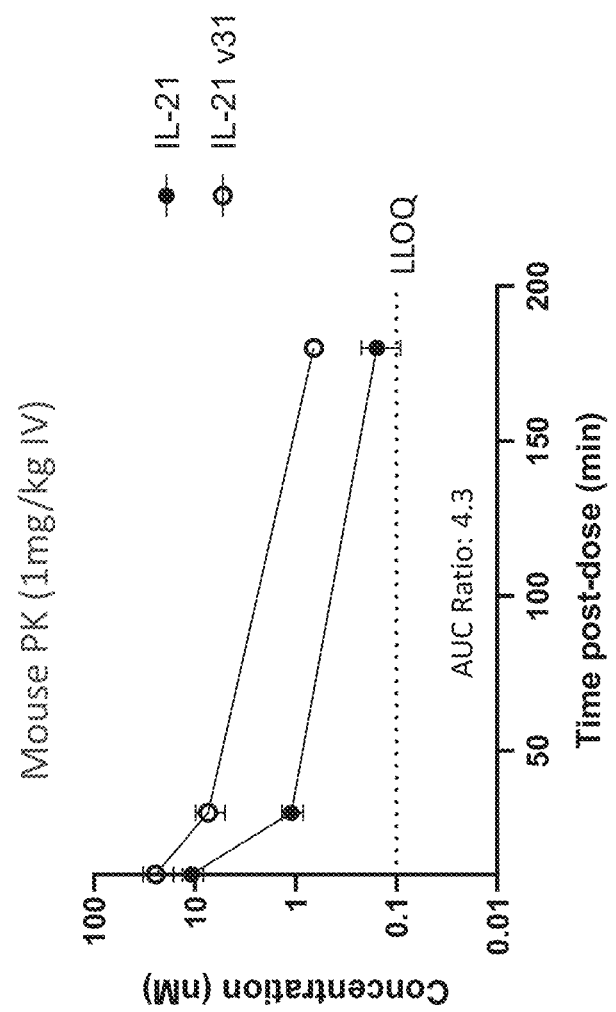
FIG. 20 shows the exposure of recombinant (non-fusion) wildtype human IL-21 and IL-21 v31 charge variant in mouse. IL-21 v31 shows increased in vivo exposure compared to wildtype IL-21.
Figure 23D:
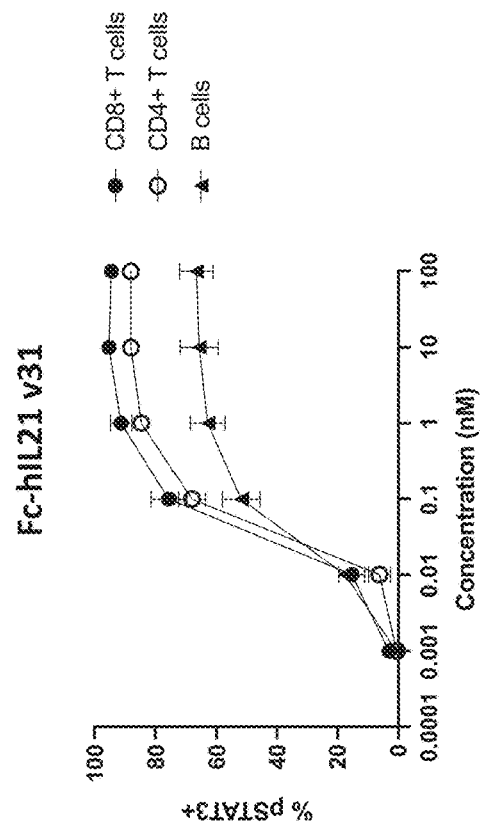
Figure 23C:
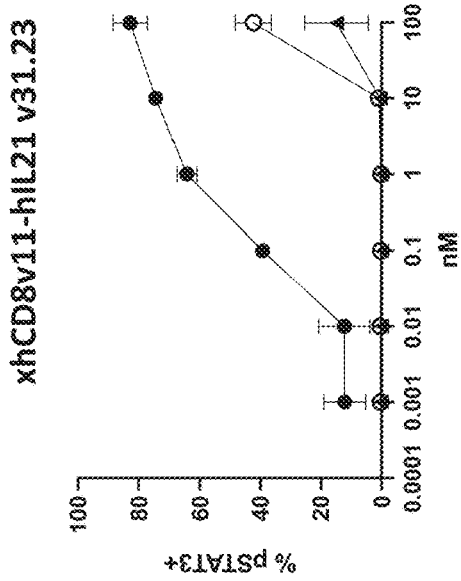

Cynomolgus monkey blood were stimulated with various IL-21 molecules in vitro and STAT3 activation in various blood cell types were determined. Similar to the preferential activities demonstrated on human CD8+ T cells (FIGS. 14 and 15), CD8+ T cell targeted IL-21 fusion proteins xhCD8.1-IL-21 v31.4 (FIG. 23A), xhCD8.1-IL-21 v31.23 (FIG. 23B) and xhCD8v11-IL-21 v31.23 (FIG. 23C) all show preferential STAT3 activation of CD8+ T cells over B cells and CD4+ T cells in cynomolgus monkey blood, as measured by $EC_{50}$. In contrast, untargeted, unattenuated Fc-hIL21 v31 (FIG. 23D) indiscriminately activates STAT3 in all cell types.

The in vivo selectivity of a CD8+ T cell targeted fusion, xhCD8.1-IL-21 v31.4, was assessed. Cynomolgus monkeys were dosed with xhCD8.1-IL-21 v31.4 and in vivo STAT3 activation in various blood cell types was determined by directly staining for the phosphorylated STAT3 levels in collected blood samples. Similar to observed in vitro selectivity, FIG. 24 shows that xhCD8.1-IL-21 v31.4 selectively and preferentially activate STAT3 in CD8+ T cells over NK cells, B cells and CD4+ T cells in vivo.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 1

IL-21 Sequences

| SEQ ID NO: | Name | Sequence |
|---|---|---|
| 1 | Wild-Type IL-21 | QGQDRHMIRMRQLIDIVDQLKNYVNDLVPEFLPAPEDVET NCEWSAFSCFQKAQLKSANTGNNERIINVSIKKLKRKPPS TNAGRRQKHRLTCPSCDSYEKKPPKEFLERFKSLLQKMIH QHLSSRTHGSEDS |
| 2 | Exemplary IL-21 polypeptide sequence | QGQDRHMIRMRQLIDIVDQLKNYVNDLVPEFLPAPEDVET NCEWSAFSCFQKAQLKSANTGNNERIINVSIKKLKRKPPS TNAGGGQGHELTCPSCDSYEKKPPKEFLERFKSLLQKMIH QHLSSRTHGSEDS |

TABLE 1-continued

IL-21 Sequences

| SEQ ID NO: | Name | Sequence |
|---|---|---|
| 3 | Exemplary IL-21 scaffold sequence | QGQDX$_1$HMX$_2$X$_3$MX$_4$X$_5$LX$_6$X$_7$IVX$_8$X$_9$LKNX$_{10}$VNDLVPEFLPAPED VETNCEWSAFSCFQKAQLX$_{11}$SANTGNNEX$_{12}$IINVX$_{13}$IX$_{14}$X$_{15}$LX$_{16}$X$_{17}$ X$_{18}$PPX$_{19}$X$_{20}$X$_{21}$X$_{22}$X$_{23}$X$_{24}$X$_{25}$X$_{26}$X$_{27}$X$_{28}$X$_{29}$X$_{30}$X$_{31}$CPSCDSYEKKP PKEFLERFKSLLX$_{32}$X$_{33}$MIHQHLSSRTHGSEDS |
| 22 | Exemplary IL-21 scaffold sequence | QGQDX$_1$HMX$_2$X$_3$MX$_4$X$_5$LX$_6$X$_7$IVX$_8$X$_9$LKNX$_{10}$VNDLVPEFLPAPED VETNCEWSAFSCFQKAQLKSANTGNNEX$_{11}$IINVX$_{12}$IX$_{13}$X$_{14}$LX$_{15}$X$_{16}$ X$_{17}$PPX$_{18}$TNAGRRQKHRLTCPSCDSYEKKPPKEFLERFKSLLX$_{19}$X$_{20}$ MIHQHLSSRTHGSEDS |

TABLE 2

IL-21 Charge Variants

| IL-21 Variant | Amino Acid Sequence | Theoretical pI | SEQ ID NO |
|---|---|---|---|
| Exemplary IL-21 polypeptide sequence 1 | QGQDRHMIRMRQLIDIVDQLKNYVNDLVPEFLPAP EDVETNCEWSAFSCFQKAQLKSANTGNNERIINVS IKKLKRKPPSTNAGGGQGHALTCPSCDSYEKKPPK EFLERFKSLLQKMIHQHLSSRTHGSEDS | 8.72 | 4 |
| Exemplary IL-21 polypeptide sequence 2 | QGQDRHMIRMRQLIDIVDQLKNYVNDLVPEFLPAP EDVETNCEWSAFSCFQKAQLKSANTGNNERIINVS IKKLKRKPPSTNAGGGQGHELTCPSCDSYEKKPPK EFLERFKSLLQ KMIHQHLSSRTHGSEDS | 8.39 | 2 |
| Exemplary IL-21 polypeptide sequence 3 | QGQDRHMIRMRQLIDIVDQLKNYVNDLVPEFLPAP EDVETNCEWSAFSCFQKAQLASANTGNNERIINVS IKKLARKPPSTNAGGGQGHALTCPSCDSYEKKPPK EFLERFKSLLQKMIHQHLSSRTHGSEDS | 7.87 | 5 |
| Exemplary IL-21 polypeptide sequence 4 | QGQDRHMIRMRQLIDIVDQLKNYVNDLVPEFLPAP EDVETNCEWSAFSCFQKAQLESANTGNNERIINVS IKKLARKPPSTNAGGGQGHALTCPSCDSYEKKPPK EFLERFKSLLQKMIHQHLSSRTHGSEDS | 7.12 | 6 |
| Exemplary IL-21 polypeptide sequence 5 | QGQDRHMIRMRQLIDIVDQLKNYVNDLVPEFLPAP EDVETNCEWSAFSCFQKAQLASANTGNNERIINVS IKKLERKPPSTNAGGGQGHALTCPSCDSYEKKPPK EFLERFKSLLQKMIHQHLSSRTHGSEDS | 7.12 | 7 |
| Exemplary IL-21 polypeptide sequence 6 | QGQDRHMIRMRQLIDIVDQLKNYVNDLVPEFLPAP EDVETNCEWSAFSCFQKAQLASANTGNNERIINVS IKKLARKPPSTNAGGGQGHELTCPSCDSYEKKPPK EFLERFKSLLQKMIHQHLSSRTHGSEDS | 7.12 | 8 |
| Exemplary IL-21 polypeptide sequence 7 | QGQDRHMIRMRQLIDIVDQLKNYVNDLVPEFLPAP EDVETNCEWSAFSCFQKAQLKSANTGNNERIINVS IKKLKRKPPGGGSGEGSGGSLTCPSCDSYEKKPPK EFLERFKSLLQKMIHQHLSSRTHGSEDS | 8.39 | 9 |
| Exemplary IL-21 polypeptide sequence 8 | QGQDRHMIRMRQLIDIVDQLKNYVNDLVPEFLPAP EDVETNCEWSAFSCFQKAQLKSANTGNNERIINVS IKKLKRKPPGGGSGGGSGGELTCPSCDSYEKKPPK EFLERFKSLLQKMIHQHLSSRTHGSEDS | 8.39 | 10 |
| Exemplary IL-21 polypeptide sequence 9 | QGQDRHMIRMRQLIDIVDQLKNYVNDLVPEFLPAP EDVETNCEWSAFSCFQKAQLKSANTGNNERIINVS IKKLKRKPPSTNAGGGSGGELTCPSCDSYEKKPPK EFLERFKSLLQKMIHQHLSSRTHGSEDS | 8.39 | 11 |
| Exemplary IL-21 polypeptide sequence 10 | QGQDRHMIRMRQLIDIVDQLKNYVNDLVPEFLPAP EDVETNCEWSAFSCFQKAQLKSANTGNNERIINVS IKKLKRKPPSTNAGGGSGGSLTCPSCDSYEKKPPK EFLERFKSLLQKMIHQHLSSRTHGSEDS | 8.72 | 12 |
| Exemplary IL-21 polypeptide sequence 11 | QGQDRHMIRMRQLIDIVDQLKNYVNDLVPEFLPAP EDVETNCEWSAFSCFQKAQLKSANTGNNERIINVS IKKLKRKPPSTNAGGGGGGELTCPSCDSYEKKPPK EFLERFKSLLQKMIHQHLSSRTHGSEDS | 8.39 | 13 |

TABLE 2-continued

IL-21 Charge Variants

| IL-21 Variant | Amino Acid Sequence | Theoretical pI | SEQ ID NO |
|---|---|---|---|
| Exemplary IL-21 polypeptide sequence 12 | QGQDRHMIRMRQLIDIVDQLKNYVNDLVPEFLPAP EDVETNCEWSAFSCFQKAQLKSANTGNNERIINVS IKKLKRKPPSTNAGGGGGGGLTCPSCDSYEKKPPK EFLERFKSLLQKMIHQHLSSRTHGSEDS | 8.72 | 14 |
| Exemplary IL-21 polypeptide sequence 13 | QGQDRHMIRMRQLIDIVDQLKNYVNDLVPEFLPAP EDVETNCEWSAFSCFQKAQLKSANTGNNERIINVS IKKLKRKPPSTNAGGGEGGGLTCPSCDSYEKKPPK EFLERFKSLLQKMIHQHLSSRTHGSEDS | 8.39 | 15 |
| Exemplary IL-21 polypeptide sequence 14 | QGQDRHMIRMRQLIDIVDQLKNYVNDLVPEFLPAP EDVETNCEWSAFSCFQKAQLKSANTGNNERIINVS IKKLKRKPPGGGSGGGSGGGSGCPSCDSYEKKPPK EFLERFKSLLQKMIHQHLSSRTHGSEDS | 8.72 | 23 |
| Exemplary IL-21 polypeptide sequence 15 | QGQDRHMIRMRQLIDIVDQLKNYVNDLVPEFLPAP EDVETNCEWSAFSCFQKAQLKSANTGNNERIINVS IKKLKRKPPGGGGGGGGGGGGGCPSCDSYEKKPPK EFLERFKSLLQKMIHQHLSSRTHGSEDS | 8.72 | 24 |
| Exemplary IL-21 polypeptide sequence 16 | QGQDRHMIRMRQLIDIVDQLKNYVNDLVPEFLPAP EDVETNCEWSAFSCFQKAQLKSANTGNNERIINVS IKKLKRKPPGGGSGGGEGGGSGCPSCDSYEKKPPK EFLERFKSLLQKMIHQHLSSRTHGSEDS | 8.39 | 25 |
| Exemplary IL-21 polypeptide sequence 17 | QGQDRHMIRMRQLIDIVDQLKNYVNDLVPEFLPAP EDVETNCEWSAFSCFQKAQLKSANTGNNERIINVS IKKLKRKPPGGGEGGGEGGGSGCPSCDSYEKKPPK EFLERFKSLLQKMIHQHLSSRTHGSEDS | 7.85 | 26 |
| Exemplary IL-21 polypeptide sequence 18 | QGQDRHMIRMRQLIDIVDQLKNYVNDLVPEFLPAP EDVETNCEWSAFSCFQKAQLKSANTGNNERIINVS IKKLKRKPPSTGGGSGGGSGGSCPSCDSYEKKPPK EFLERFKSLLQKMIHQHLSSRTHGSEDS | 8.72 | 27 |
| Exemplary IL-21 polypeptide sequence 19 | QGQDRHMIRMRQLIDIVDQLKNYVNDLVPEFLPAP EDVETNCEWSAFSCFQKAQLKSANTGNNERIINVS IKKLKRKPPSTGGGEGGGSGGSCPSCDSYEKKPPK EFLERFKSLLQKMIHQHLSSRTHGSEDS | 8.39 | 28 |
| Exemplary IL-21 polypeptide sequence 20 | QGQDRHMIRMRQLIDIVDQLKNYVNDLVPEFLPAP EDVETNCEWSAFSCFQKAQLKSANTGNNERIINVS IKKLKRKPPGGGGGEGGGGGGCPSCDSYEKKPPK EFLERFKSLLQKMIHQHLSSRTHGSEDS | 8.39 | 29 |
| Exemplary IL-21 polypeptide sequence 21 | QGQDRHMIRMRQLIDIVDQLKNYVNDLVPEFLPAP EDVETNCEWSAFSCFQKAQLKSANTGNNERIINVS IKKLKRKPPGGGSGGGSGGEGGCPSCDSYEKKPPK EFLERFKSLLQKMIHQHLSSRTHGSEDS | 8.39 | 30 |
| Exemplary IL-21 polypeptide sequence 22 | QGQDRHMIRMRQLIDIVDQLKNYVNDLVPEFLPAP EDVETNCEWSAFSCFQKAQLKSANTGNNERIINVS IKKLKRKPPGGGGGGGGGGEGGCPSCDSYEKKPPK EFLERFKSLLQKMIHQHLSSRTHGSEDS | 8.39 | 31 |
| Exemplary IL-21 polypeptide sequence 23 | QGQDRHMIRMRQLIDIVDQLKNYVNDLVPEFLPAP EDVETNCEWSAFSCFQKAQLKSANTGNNERIINVS IKKLKRKPPSTGGGSGGGSEGSCPSCDSYEKKPPK EFLERFKSLLQKMIHQHLSSRTHGSEDS | 8.39 | 32 |
| Exemplary IL-21 polypeptide sequence 24 | QGQDRHMIRMRQLIDIVDQLKNYVNDLVPEFLPAP EDVETNCEWSAFSCFQKAQLKSANTGNNERIINVS IKKLKRKPPSTGGGGGGGGEGGCPSCDSYEKKPPK EFLERFKSLLQKMIHQHLSSRTHGSEDS | 8.39 | 33 |
| Exemplary IL-21 polypeptide sequence 25 | QGQDRHMIRMRQLIDIVDQLKNYVNDLVPEFLPAP EDVETNCEWSAFSCFQKAQLKSANTGNNERIINVS IKKLKRKPPSTNAGGGGGGGEGTCPSCDSYEKKPPK EFLERFKSLLQKMIHQHLSSRTHGSEDS | 8.39 | 34 |
| Exemplary IL-21 polypeptide sequence 26 | QGQDRHMIRMRQLIDIVDQLKNYVNDLVPEFLPAP EDVETNCEWSAFSCFQKAQLKSANTGNNERIINVS IKKLKRKPPSTGGGGGGGGEGTCPSCDSYEKKPPK EFLERFKSLLQKMIHQHLSSRTHGSEDS | 8.39 | 35 |

TABLE 2-continued

IL-21 Charge Variants

| IL-21 Variant | Amino Acid Sequence | Theoretical pI | SEQ ID NO |
|---|---|---|---|
| Exemplary IL-21 polypeptide sequence 27 | QGQDRHMIRMRQLIDIVDQLKNYVNDLVPEFLPAPEDVETNCEWSAFSCFQKAQLKSANTGNNERIINVSIKKLKRKPPSTGGGGEGGGEGTCPSCDSYEKKPPKEFLERFKSLLQKMIHQHLSSRTHGSEDS | 7.85 | 36 |
| Exemplary IL-21 polypeptide sequence 28 | QGQDRHMIRMRQLIDIVDQLKNYVNDLVPEFLPAPEDVETNCEWSAFSCFQKAQLKSANTGNNERIINVSIKKLKRKPPSTGGGEGGGGEGTCPSCDSYEKKPPKEFLERFKSLLQKMIHQHLSSRTHGSEDS | 7.85 | 37 |
| Exemplary IL-21 polypeptide sequence 29 | QGQDRHMIRMRQLIDIVDQLKNYVNDLVPEFLPAPEDVETNCEWSAFSCFQKAQLKSANTGNNERIINVSIKKLKRKPPGGGGEGGGGGEGGCPSCDSYEKKPPKEFLERFKSLLQKMIHQHLSSRTHGSEDS | 7.85 | 38 |
| Exemplary IL-21 polypeptide sequence 30 | QGQDRHMIRMRQLIDIVDQLKNYVNDLVPEFLPAPEDVETNCEWSAFSCFQKAQLKSANTGNNERIINVSIKKLKRKPPGGGEGGGGGEGGCPSCDSYEKKPPKEFLERFKSLLQKMIHQHLSSRTHGSEDS | 7.85 | 39 |
| Exemplary IL-21 polypeptide sequence 31 | QGQDRHMIRMRQLIDIVDQLKNYVNDLVPEFLPAPEDVETNCEWSAFSCFQKAQLKSANTGNNERIINVSIKKLKRKPPGGEGGGGGGGEGGCPSCDSYEKKPPKEFLERFKSLLQKMIHQHLSSRTHGSEDS | 7.85 | 40 |

TABLE 3

Intermediate and final yields for fusion proteins of IL-21 charge variants

| IL-21 Mutein | Antibody fusion | Yield after Protein A (mg/L) | Yield after Protein A + IEX (mg/L) |
|---|---|---|---|
| WT | xhCD8 | 36 | 8 |
| v1 | xhCD8 | 61 | 21 |
| v2 | xhCD8 | 112 | 23 |
| v3 | xhCD8 | 35 | ND* |
| v4 | xhCD8 | 31 | ND |
| v5 | xhCD8 | 30 | ND |
| v6 | xhCD8 | 40 | 9 |
| WT | xhCD8.1 | 32 | 5 |
| v2 | xhCD8.1 | 129 | 69 |
| v7 | xhCD8.1 | 132 | 67 |
| v8 | xhCD8.1 | 114 | 46 |
| v9 | xhCD8.1 | 120 | 65 |
| v10 | xhCD8.1 | 111 | 46 |
| v11 | xhCD8.1 | 126 | 59 |
| v12 | xhCD8.1 | 117 | 63 |
| v13 | xhCD8.1 | 153 | 78 |
| v14 | xhCD8.1 | 78 | 29 |
| v15 | xhCD8.1 | 87 | 22 |
| v16 | xhCD8.1 | 111 | 46 |
| v17 | xhCD8.1 | 127 | 57 |
| v18 | xhCD8.1 | 81 | 26 |
| v19 | xhCD8.1 | 97 | 33 |
| v20 | xhCD8.1 | 99 | 32 |
| v21 | xhCD8.1 | 90 | 34 |
| v22 | xhCD8.1 | 97 | 34 |
| v23 | xhCD8.1 | 130 | 40 |
| v24 | xhCD8.1 | 110 | 49 |
| v25 | xhCD8.1 | 119 | 43 |
| v26 | xhCD8.1 | 99 | 37 |
| v27 | xhCD8.1 | 123 | 43 |
| v28 | xhCD8.1 | 107 | 36 |
| v29 | xhCD8.1 | 97 | 39 |
| v30 | xhCD8.1 | 136 | 59 |
| v31 | xhCD8.1 | 116 | 59 |

*ND indicates that the measurement was not determined

TABLE 4

IL-21R binding kinetics of IL-21 charge variants

| Construct | $k_a$ ($\times 10^6 M^{-1} s^{-1}$) | $k_d$ ($\times 10^{-4} s^{-1}$) | $K_D$ (pM) |
|---|---|---|---|
| Fc-hIL21 WT | 5.0 ± 0.1 | 7.6 ± 0.3 | 154 ± 7 |
| xhCD8-hIL21 v1 | 8.3 ± 0.5 | 9.7 ± 2.7 | 117 ± 33 |
| xhCD8-hIL21 v2 | 8.9 ± 0.4 | 11 ± 1 | 122 ± 14 |
| xhCD8-hIL21 v6 | 5.2 ± 0.2 | 25 ± 2 | 478 ± 53 |
| xhCD8.1-hIL21 v27 | 13.1 ± 0.5 | 13.9 ± 0.2 | 106 ± 4 |
| xhCD8.1-hIL21 v28 | 13.1 ± 0.6 | 13.9 ± 0.2 | 106 ± 5 |
| xhCD8.1-hIL21 v29 | 12.7 ± 0.2 | 11.9 ± 0.2 | 94 ± 2 |
| xhCD8.1-hIL21 v30 | 11.6 ± 0.2 | 10.7 ± 0.2 | 93 ± 2 |
| xhCD8.1-hIL21 v31 | 12.0 ± 0.3 | 11.3 ± 0.2 | 94 ± 3 |

TABLE 5

Polyreactivity ELISA of IL-21 fusion proteins

| Construct | Binding to KLH | Binding to heparin | Binding to hemoglobin |
|---|---|---|---|
| Bococizumab | 47.13 | 15.58 | 29.12 |
| xhCD8.1-hIL21 | 30.11 | 32.85 | 10.90 |
| xhCD8.1-hIL21 v2 | 9.68 | 11.75 | 4.95 |
| xhCD8.1-hIL21 v14 | 13.20 | 12.37 | 4.50 |
| xhCD8.1-hIL21 v15 | 12.01 | 11.28 | 5.36 |
| xhCD8.1-hIL21 v16 | 11.22 | 10.26 | 5.20 |
| xhCD8.1-hIL21 v17 | 9.90 | 9.47 | 5.02 |
| xhCD8.1-hIL21 v18 | 11.49 | 11.85 | 5.09 |
| xhCD8.1-hIL21 v19 | 10.47 | 12.34 | 5.13 |
| xhCD8.1-hIL21 v20 | 11.27 | 11.20 | 5.03 |

TABLE 5-continued

Polyreactivity ELISA of IL-21 fusion proteins

| Construct | Binding to KLH | Binding to heparin | Binding to hemoglobin |
|---|---|---|---|
| xhCD8.1-hIL21 v21 | 12.22 | 12.87 | 6.08 |
| xhCD8.1-hIL21 v22 | 11.28 | 12.72 | 5.37 |
| xhCD8.1-hIL21 v23 | 11.00 | 11.18 | 5.72 |
| xhCD8.1-hIL21 v24 | 9.24 | 9.49 | 5.05 |
| xhCD8.1-hIL21 v25 | 10.87 | 11.69 | 5.77 |
| xhCD8.1-hIL21 v26 | 9.89 | 11.14 | 4.85 |
| xhCD8.1-hIL21 v27 | 9.49 | 9.93 | 4.74 |
| xhCD8.1-hIL21 v28 | 9.76 | 9.13 | 4.26 |
| xhCD8.1-hIL21 v29 | 10.57 | 9.08 | 5.38 |
| xhCD8.1-hIL21 v30 | 11.36 | 10.46 | 5.69 |
| xhCD8.1-hIL21 v31 | 10.50 | 8.80 | 5.29 |

TABLE 6

IL-21 charge variants with reduced affinity to IL-21R

| IL-21 Mutein | Amino Acid Sequence | $K_D$ at 37° C. (nM) | SEQ ID NO |
|---|---|---|---|
| IL-21 v2.1 | QGQDRHMIRMDQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | ND | 16 |
| IL-21 v2.2 | QGQDRHMIRMEQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | ND | 17 |
| IL-21 v2.3 | QGQDRHMIRMRQLDDIVAQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQAMIHQHLSSRTHGSEDS | ND | 18 |
| IL-21 v2.4 | QGQDRHMIRMRQLIDIVDQLKNYVNDLVPEFLPAPEDVETNCEWSAFSCFQKAQLKSANTGNNERIINVSIKKLKEKPPSTNAGGGQGHELTCPSCDSYEKKPPKEFLERFKSLLQKMIHQHLSSRTHGSEDS | >5000 | 19 |
| IL-21 v2.5 | QGQDFHMIRMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | ND | 20 |
| IL-21 v2.6 | QGQDRHMIRMRQLIDIVDQLKNYVNDLVPEFLPAPEDVETNCEWSAFSCFQKAQLKSANTGNNERIINVSIKKLKFKPPSTNAGGGQGHELTCPSCDSYEKKPPKEFLERFKSLLQKMIHQHLSSRTHGSEDS | 1700 | 21 |
| IL-21 v2.7 | QGQDRHMERMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 156 | 41 |
| IL-21 v2.8 | QGQDAHMIRMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 18.9 | 42 |
| IL-21 v2.9 | QGQDEHMIRMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 420 | 43 |
| IL-21 v2.10 | QGQDSHMIRMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 24.4 | 44 |
| IL-21 v2.11 | QGQDTHMIRMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 9.4 | 45 |
| IL-21 v2.12 | QGQDNHMIRMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 54.6 | 46 |
| IL-21 v2.13 | QGQDQHMIRMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 15.2 | 47 |

TABLE 6-continued

IL-21 charge variants with reduced affinity to IL-21R

| IL-21 Mutein | Amino Acid Sequence | $K_D$ at 37° C. (nM) | SEQ ID NO |
|---|---|---|---|
| IL-21 v2.14 | QGQDVHMIRMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | 6.5 | 48 |
| IL-21 v2.15 | QGQDIHMIRMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | 6.2 | 49 |
| IL-21 v2.16 | QGQDLHMIRMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | 2.1 | 50 |
| IL-21 v2.17 | QGQDYHMIRMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | 9.8 | 51 |
| IL-21 v2.18 | QGQDRHMIRMRQLIDIVDQLKNYVNDLVPEFLPAPEDVETNCEWS AFSCFQKAQLKSANTGNNERIINVSIKKLKAKPPSTNAGGGQGHE LTCPSCDSYEKKPPKEFLERFKSLLQKMIHQHLSSRTHGSEDS | 3180 | 52 |
| IL-21 v2.19 | QGQDRHMIRMRQLIDIVDQLKNYVNDLVPEFLPAPEDVETNCEWS AFSCFQKAQLKSANTGNNERIINVSIKKLKNKPPSTNAGGGQGHE LTCPSCDSYEKKPPKEFLERFKSLLQKMIHQHLSSRTHGSEDS | 2310 | 53 |
| IL-21 v2.20 | QGQDRHMIRMRQLIDIVDQLKNYVNDLVPEFLPAPEDVETNCEWS AFSCFQKAQLKSANTGNNERIINVSIKKLKDKPPSTNAGGGQGHE LTCPSCDSYEKKPPKEFLERFKSLLQKMIHQHLSSRTHGSEDS | NB | 54 |
| IL-21 v2.21 | QGQDRHMIRMRQLIDIVDQLKNYVNDLVPEFLPAPEDVETNCEWS AFSCFQKAQLKSANTGNNERIINVSIKKLKSKPPSTNAGGGQGHE LTCPSCDSYEKKPPKEFLERFKSLLQKMIHQHLSSRTHGSEDS | 3800 | 55 |
| IL-21 v2.22 | QGQDRHMIRMRQLIDIVDQLKNYVNDLVPEFLPAPEDVETNCEWS AFSCFQKAQLKSANTGNNERIINVSIKKLKTKPPSTNAGGGQGHE LTCPSCDSYEKKPPKEFLERFKSLLQKMIHQHLSSRTHGSEDS | 3030 | 56 |
| IL-21 v2.23 | QGQDRHMIRMRQLIDIVDQLKNYVNDLVPEFLPAPEDVETNCEWS AFSCFQKAQLKSANTGNNERIINVSIKKLKQKPPSTNAGGGQGHE LTCPSCDSYEKKPPKEFLERFKSLLQKMIHQHLSSRTHGSEDS | 2410 | 57 |
| IL-21 v2.24 | QGQDRHMIRMRQLIDIVDQLKNYVNDLVPEFLPAPEDVETNCEWS AFSCFQKAQLKSANTGNNERIINVSIKKLKVKPPSTNAGGGQGHE LTCPSCDSYEKKPPKEFLERFKSLLQKMIHQHLSSRTHGSEDS | 5180 | 58 |
| IL-21 v2.25 | QGQDRHMIRMRQLIDIVDQLKNYVNDLVPEFLPAPEDVETNCEWS AFSCFQKAQLKSANTGNNERIINVSIKKLKIKPPSTNAGGGQGHE LTCPSCDSYEKKPPKEFLERFKSLLQKMIHQHLSSRTHGSEDS | 2990 | 59 |
| IL-21 v2.26 | QGQDRHMIRMRQLIDIVDQLKNYVNDLVPEFLPAPEDVETNCEWS AFSCFQKAQLKSANTGNNERIINVSIKKLKLKPPSTNAGGGQGHE LTCPSCDSYEKKPPKEFLERFKSLLQKMIHQHLSSRTHGSEDS | 651 | 60 |
| IL-21 v2.27 | QGQDRHMIRMRQLIDIVDQLKNYVNDLVPEFLPAPEDVETNCEWS AFSCFQKAQLKSANTGNNERIINVSIKKLKYKPPSTNAGGGQGHE LTCPSCDSYEKKPPKEFLERFKSLLQKMIHQHLSSRTHGSEDS | 2150 | 61 |
| IL-21 v2.28 | QGQDRHMIRMRQLIDIVDQLKNYVNDLVPEFLPAPEDVETNCEWS AFSCFQKAQLKSANTGNNERIINVSIKKLKRAPPSTNAGGGQGHE LTCPSCDSYEKKPPKEFLERFKSLLQKMIHQHLSSRTHGSEDS | 0.693 | 62 |
| IL-21 v2.29 | QGQDRHMIRMRQLIDIVDQLKNYVNDLVPEFLPAPEDVETNCEWS AFSCFQKAQLKSANTGNNERIINVSIKKLKREPPSTNAGGGQGHE LTCPSCDSYEKKPPKEFLERFKSLLQKMIHQHLSSRTHGSEDS | 2.8 | 63 |
| IL-21 v2.30 | QGQDRHMIRMRQLIDIVDQLKNYVNDLVPEFLPAPEDVETNCEWS AFSCFQKAQLKSANTGNNERIINVSIAKLKRKPPSTNAGGGQGHE LTCPSCDSYEKKPPKEFLERFKSLLQKMIHQHLSSRTHGSEDS | 0.419 | 64 |
| IL-21 v2.31 | QGQDRHMIRMRQLIDIVDQLKNYVNDLVPEFLPAPEDVETNCEWS AFSCFQKAQLKSANTGNNERIINVSIEKLKRKPPSTNAGGGQGHE LTCPSCDSYEKKPPKEFLERFKSLLQKMIHQHLSSRTHGSEDS | 3.4 | 65 |

TABLE 6-continued

IL-21 charge variants with reduced affinity to IL-21R

| IL-21 Mutein | Amino Acid Sequence | $K_D$ at 37° C. (nM) | SEQ ID NO |
|---|---|---|---|
| IL-21 v2.32 | QGQDRHMIRMRQLIDIVDQLKNYVNDLVPEFLPAPEDVETNCEWSAFSCFQKAQLKSANTGNNERIINVSIKKLARKPPSTNAGGGQGHELTCPSCDSYEKKPPKEFLERFKSLLQKMIHQHLSSRTHGSEDS | 0.236 | 66 |
| IL-21 v2.33 | QGQDRHMIRMRQLIDIVDQLKNYVNDLVPEFLPAPEDVETNCEWSAFSCFQKAQLKSANTGNNERIINVSIKKLERKPPSTNAGGGQGHELTCPSCDSYEKKPPKEFLERFKSLLQKMIHQHLSSRTHGSEDS | 1.3 | 67 |
| IL-21 v2.34 | QGQDRHMIRMRQLIDIVDQLKNYVNDLVPEFLPAPEDVETNCEWSAFSCFQKAQLKSANTGNNERIINVSIKALRKPPSTNAGGGQGHELTCPSCDSYEKKPPKEFLERFKSLLQKMIHQHLSSRTHGSEDS | 2.0 | 68 |
| IL-21 v2.35 | QGQDRHMIRMRQLIDIVDQLKNYVNDLVPEFLPAPEDVETNCEWSAFSCFQKAQLKSANTGNNERIINVSIKELRKPPSTNAGGGQGHELTCPSCDSYEKKPPKEFLERFKSLLQKMIHQHLSSRTHGSEDS | 449.0 | 69 |
| IL-21 v2.36 | QGQDFHMIRMRQLIDIVDQLKNYVNDLVPEFLPAPEDVETNCEWSAFSCFQKAQLKSANTGNNERIINVSIKKLKRAPPSTNAGGGQGHELTCPSCDSYEKKPPKEFLERFKSLLQKMIHQHLSSRTHGSEDS | 125.0 | 70 |
| IL-21 v2.37 | QGQDFHMIRMRQLIDIVDQLKNYVNDLVPEFLPAPEDVETNCEWSAFSCFQKAQLKSANTGNNERIINVSIKKLKREPPSTNAGGGQGHELTCPSCDSYEKKPPKEFLERFKSLLQKMIHQHLSSRTHGSEDS | 601.0 | 71 |
| IL-21 v2.38 | QGQDFHMIRMRQLIDIVDQLKNYVNDLVPEFLPAPEDVETNCEWSAFSCFQKAQLKSANTGNNERIINVSIAKLKRKPPSTNAGGGQGHELTCPSCDSYEKKPPKEFLERFKSLLQKMIHQHLSSRTHGSEDS | 66.9 | 72 |
| IL-21 v2.39 | QGQDFHMIRMRQLIDIVDQLKNYVNDLVPEFLPAPEDVETNCEWSAFSCFQKAQLKSANTGNNERIINVSIEKLKRKPPSTNAGGGQGHELTCPSCDSYEKKPPKEFLERFKSLLQKMIHQHLSSRTHGSEDS | 614.0 | 73 |
| IL-21 v2.40 | QGQDFHMIRMRQLIDIVDQLKNYVNDLVPEFLPAPEDVETNCEWSAFSCFQKAQLKSANTGNNERIINVSIKKLARKPPSTNAGGGQGHELTCPSCDSYEKKPPKEFLERFKSLLQKMIHQHLSSRTHGSEDS | 54.7 | 74 |
| IL-21 v2.41 | QGQDFHMIRMRQLIDIVDQLKNYVNDLVPEFLPAPEDVETNCEWSAFSCFQKAQLKSANTGNNERIINVSIKKLERKPPSTNAGGGQGHELTCPSCDSYEKKPPKEFLERFKSLLQKMIHQHLSSRTHGSEDS | 104.0 | 75 |
| IL-21 v2.42 | QGQDRHMIRMRQLIDIVDQLKNYVNDLVPEFLPAPEDVETNCEWSAFSCFQKAQLKSANTGNNERIINVSIKALKFKPPSTNAGGGQGHELTCPSCDSYEKKPPKEFLERFKSLLQKMIHQHLSSRTHGSEDS | NB | 76 |
| IL-21 v2.43 | QGQDRHMIRMRQLIDIVDQLKNYVNDLVPEFLPAPEDVETNCEWSAFSCFQKAQLKSANTGNNERIINVSIKELKFKPPSTNAGGGQGHELTCPSCDSYEKKPPKEFLERFKSLLQKMIHQHLSSRTHGSEDS | NB | 77 |
| IL-21 v2.44 | QGQDRHMIAMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 3250 | 78 |
| IL-21 v2.45 | QGQDRHMIDMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | NB | 79 |
| IL-21 v2.46 | QGQDRHMIEMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | NB | 80 |
| IL-21 v2.47 | QGQDRHMIHMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 16.5 | 81 |
| IL-21 v2.48 | QGQDRHMISMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | 4760 | 82 |
| IL-21 v2.49 | QGQDRHMITMRQLIDIVDQLKNYVNDLVPEFLPAPEDVETNCEWSAFSCFQKAQLKSANTGNNERIINVSIKKLKRKPPSTNAGGGQGHELTCPSCDSYEKKPPKEFLERFKSLLQKMIHQHLSSRTHGSEDS | >5000 | 83 |

TABLE 6-continued

IL-21 charge variants with reduced affinity to IL-21R

| IL-21 Mutein | Amino Acid Sequence | $K_D$ at 37° C. (nM) | SEQ ID NO |
|---|---|---|---|
| IL-21 v2.50 | QGQDRHMINMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | 2880 | 84 |
| IL-21 v2.51 | QGQDRHMIGMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | 4840 | 85 |
| IL-21 v2.52 | QGQDRHMIVMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | >5000 | 86 |
| IL-21 v2.53 | QGQDRHMIIMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | >5000 | 87 |
| IL-21 v2.54 | QGQDRHMILMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | 4690 | 88 |
| IL-21 v2.55 | QGQDRHMIYMRQLIDIVDQLKNYVNDLVPEFLPAPEDVETNCEWS AFSCFQKAQLKSANTGNNERIINVSIKKLKRKPPSTNAGGGQGHE LTCPSCDSYEKKPPKEFLERFKSLLQKMIHQHLSSRTHGSEDS | 394 | 89 |
| IL-21 v2.56 | QGQDRHMIRMRQLIDIVDQLKNYVNDLVPEFLPAPEDVETNCEWS AFSCFQKAQLKSANTGNNERIINVSIAKLKFKPPSTNAGGGQGHE LTCPSCDSYEKKPPKEFLERFKSLLQKMIHQHLSSRTHGSEDS | 156 | 90 |
| IL-21 v2.57 | QGQDRHMIRMRQLIDIVDQLKNYVNDLVPEFLPAPEDVETNCEWS AFSCFQKAQLKSANTGNNERIINVSIKKLAFKPPSTNAGGGQGHE LTCPSCDSYEKKPPKEFLERFKSLLQKMIHQHLSSRTHGSEDS | 18.9 | 91 |
| IL-21 v2.58 | QGQDRHMIRMRQLIDIVDQLKNYVNDLVPEFLPAPEDVETNCEWS AFSCFQKAQLKSANTGNNERIINVSIKKLKFAPPSTNAGGGQGHE LTCPSCDSYEKKPPKEFLERFKSLLQKMIHQHLSSRTHGSEDS | 420 | 92 |
| IL-21 v2.59 | QGQDRHMIRMRQLIDIVDQLKNYVNDLVPEFLPAPEDVETNCEWS AFSCFQKAQLKSANTGNNERIINVSIKKLEFKPPSTNAGGGQGHE LTCPSCDSYEKKPPKEFLERFKSLLQKMIHQHLSSRTHGSEDS | 24.4 | 93 |
| IL-21 v2.60 | QGQDRHMIRMRQLIDIIDQLKNYVNDLVPEFLPAPEDVETNCEWS AFSCFQKAQLKSANTGNNERIINVSIKKIKRKPPSTNAGGGQGHE LTCPSCDSYEKKPPKEFLERFKSLLQKMIHQHLSSRTHGSEDS | 0.15 | 374 |
| IL-21 v2.61 | QGQDRHMIRMRQLIDAVDQLKNYVNDLVPEFLPAPEDVETNCEWS AFSCFQKAQLKSANTGNNERIINVSIKKFKRKPPSTNAGGGQGHE LTCPSCDSYEKKPPKEFLERFKSLLQKMIHQHLSSRTHGSEDS | 11.9 | 375 |
| IL-21 v2.62 | QGQDRHMIRMRQLIDSIDQLKNYVNDLVPEFLPAPEDVETNCEWS AFSCFQKAQLKSANTGNNERIINVSIKKVKRKPPSTNAGGGQGHE LTCPSCDSYEKKPPKEFLERFKSLLQKMIHQHLSSRTHGSEDS | 13.6 | 376 |
| IL-21 v2.63 | QGQDRHMIRMRQLIDRIDQLKNYVNDLVPEFLPAPEDVETNCEWS AFSCFQKAQLKSANTGNNERIINVSIKKIKRKPPSTNAGGGQGHE LTCPSCDSYEKKPPKEFLERFKSLLQKMIHQHLSSRTHGSEDS | 1400 | 377 |
| IL-21 v2.64 | QGQDRHMIRMRQFIDAADQLKNYVNDLVPEFLPAPEDVETNCEWS AFSCFQKAQLKSANTGNNERIINVSIKKMKRKPPSTNAGGGQGHE LTCPSCDSYEKKPPKEFLERFKSLLQKMIHQHLSSRTHGSEDS | 1050 | 378 |
| IL-21 v2.65 | QGQDRHMIRMRQRIDAIDQLKNYVNDLVPEFLPAPEDVETNCEWS AFSCFQKAQLKSANTGNNERIINVSIKKIKRKPPSTNAGGGQGHE LTCPSCDSYEKKPPKEFLERFKSLLQKMIHQHLSSRTHGSEDS | 5910 | 379 |

ND indicates that the affinity was not determined
NB indicates no binding detected at highest concentration tested

TABLE 7

Additional IL-21 charge variants with reduced affinity to IL-21R

| IL-21 Mutein | Amino Acid Sequence | SEQ ID NO |
|---|---|---|
| IL-21 v31.4 | QGQDRHMIRMRQLIDIVDQLKNYVNDLVPEFLPAPEDVETNCEWSAFSCFQKAQLKSANTGNNERIINVSIKKLKEKPPGGEGGGGGGEGGCPSCDSYEKKPPKEFLERFKSLLQKMIHQHLSSRTHGSEDS | 94 |
| IL-21 v31.6 | QGQDRHMIRMRQLIDIVDQLKNYVNDLVPEFLPAPEDVETNCEWSAFSCFQKAQLKSANTGNNERIINVSIKKLKFKPPGGEGGGGGGEGGCPSCDSYEKKPPKEFLERFKSLLQKMIHQHLSSRTHGSEDS | 95 |
| IL-21 v31.23 | QGQDRHMIRMRQLIDIVDQLKNYVNDLVPEFLPAPEDVETNCEWSAFSCFQKAQLKSANTGNNERIINVSIKKLKQKPPGGEGGGGGGEGGCPSCDSYEKKPPKEFLERFKSLLQKMIHQHLSSRTHGSEDS | 96 |
| IL-21 v31.48 | QGQDRHMISMRQLIDIVDQLKNYVNDLVPEFLPAPEDVETNCEWSAFSCFQKAQLKSANTGNNERIINVSIKKLKRKPPGGEGGGGGGEGGCPSCDSYEKKPPKEFLERFKSLLQKMIHQHLSSRTHGSEDS | 97 |
| IL-21 v31.51 | QGQDRHMIGMRQLIDIVDQLKNYVNDLVPEFLPAPEDVETNCEWSAFSCFQKAQLKSANTGNNERIINVSIKKLKRKPPGGEGGGGGGEGGCPSCDSYEKKPPKEFLERFKSLLQKMIHQHLSSRTHGSEDS | 98 |

TABLE 8

Example antibody-cytokine fusion protein sequences

| Name | Light chain sequence | Heavy chain sequence (with IL-21 fusion) | Heavy chain sequence (without IL-21 fusion) | Heavy chain sequence (without IL-21 fusion) plus C-term lysine |
|---|---|---|---|---|
| xhCD8.1-v31.4 xhCD8.1-hIL21 v31.6 | DIQMTQSPSSLSASVGDRVTITCRASQSIYGALNWYQQKPGKAPKLLIYATANYAQKFQGRVTITAYGASNLQSGVPSRFSGSGSGTDFTLTISSLQPEDFATYYCQSTYTAPWTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO: 262) | QVQLVQSGAEVKKPGSSVKVSCKASGGTFSSYAISWVRQAPGQGLEWMGGIIPGYATANYAQKFQGRVTITADESTSTAYMELSSLRSEDTAVYYCARDAAGIRLFADWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCREEMTKNQVSLSCAVKGFYPSDIAVEWESNGQPENNYKTTPPVLDSDGSFFLVSKLTVDKSRWQQGNVFSCSVMHEALHNHYTQKSLSLSPGSGGGGSGGGGSGGGGSQGQDRHMIRMRQLIDIVDQLKNYVNDLVPEFLPAPEDVETNCEWSAFSCFQKAQLKSANTGNNERIINVSIKKLKEKPPGGEGGGGGGEGGCPSCDSYEKKPPKEFLERFKSLLQKMIHQHLSSRTHGSEDS (SEQ ID NO: 263) | QVQLVQSGAEVKKPGSSVKVSCKASGGTFSSYAISWVRQAPGQGLEWMGGIIPGYATANYAQKFQGRVTITADESTSTAYMELSSLRSEDTAVYYCARDAAGIRLFADWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG (SEQ ID NO: 264) | QVQLVQSGAEVKKPGSSVKVSCKASGGTFSSYAISWVRQAPGQGLEWMGGIIPGYATANYAQKFQGRVTITADESTSTAYMELSSLRSEDTAVYYCARDAAGIRLFADWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVCTLPPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK (SEQ ID NO: 265) |
| xhCD8.1-hIL21 v31.4 | DIQMTQSPSSLSASVGDRVTITCRASQSIYGALNWYQQKPGKAPKLLIYATANYAQKFQGRVTITAYGASNLQSGVPSDESTSTAYMELSSLRSED | QVQLVQSGAEVKKPGSSVKVSCKASGGTFSSYAISWVRQAPGQGLEWMGGIIPGYATANYAQKFQGRVTITADES | QVQLVQSGAEVKKPGSSVKVSCKASGGTFSSYAISWVRQAPGQGLEWMGGIIPGYATANYAQKFQGRVTITADES | |

TABLE 8-continued

Example antibody-cytokine fusion protein sequences

| Name | Light chain sequence | Heavy chain sequence (with IL-21 fusion) | Heavy chain sequence (without IL-21 fusion) | Heavy chain sequence (without IL-21 fusion) plus C-term lysine |
|---|---|---|---|---|
| | RFSGSGSGTDFT LTISSLQPEDFA TYYCQSTYTAPW TFGGGTKVEIKR TVAAPSVFIFPP SDEQLKSGTASV VCLLNNFYPREA KVQWKVDNALQS GNSQESVTEQDS KDSTYSLSSTLT LSKADYEKHKVY ACEVTHQGLSSP VTKSFNRGEC (SEQ ID NO: 266) | TAVYYCARDAAGIRLFAD WGQGTLVTVSSASTKGPS VFPLAPSSKSTSGGTAAL GCLVKDYFPEPVTVSWNS GALTSGVHTFPAVLQSSG LYSLSSVVTVPSSSLGTQ TYICNVNHKPSNTKVDKK VEPKSCDKTHTCPPCPAP EAAGAPSVFLFPPKPKDT LMISRTPEVTCVVVDVSH EDPEVKFNWYVDGVEVHN AKTKPREEQYNSTYRVVS VLTVLHQDWLNGKEYKCK VSNKALPAPIEKTISKAK GQPREPQVYTLPPCREEM TKNQVSLSCAVKGFYPSD IAVEWESNGQPENNYKTT PPVLDSDGSFFLVSKLTV DKSRWQQGNVFSCSVMHE ALHNHYTQKSLSLSPGSG GGGSGGGGSGGGGSQGQD RHMIRMRQLIDIVDQLKN YVNDLVPEFLPAPEDVET NCEWSAFSCFQKAQLKSA NTGNNERIINVSIKKLKF KPPGGEGGGGGGEGGCP SCDSYEKKPPKEFLERFK SLLQKMIHQHLSSRTHGS EDS (SEQ ID NO: 267) | TSTAYMELSSLRSED TAVYYCARDAAGIRL FADWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPEAAGAP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVCTLPPSREEM TKNQVSLWCLVKGFY PSDIAVEWESNGQPE NNYKTTPPVLDSDGS FFLYSKLTVDKSRWQ QGNVFSCSVMHEALH NHYTQKSLSLSPG (SEQ ID NO: 268) | TSTAYMELSSLRSED TAVYYCARDAAGIRL FADWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPEAAGAP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVCTLPPSREEM TKNQVSLWCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 269) |
| xhCD8. 1-hIL21 v31.23 | DIQMTQSPSSLS ASVGDRVTITCR ASQSIYGALNWY QQKPGKAPKLLI YGASNLQSGVPS RFSGSGSGTDFT LTISSLQPEDFA TYYCQSTYTAPW TFGGGTKVEIKR TVAAPSVFIFPP SDEQLKSGTASV VCLLNNFYPREA KVQWKVDNALQS GNSQESVTEQDS KDSTYSLSSTLT LSKADYEKHKVY ACEVTHQGLSSP VTKSFNRGEC (SEQ ID NO: 270) | QVQLVQSGAEVKKPGSSV KVSCKASGGTFSSYAISW VRQAPGQGLEWMGGIIPG YATANYAQKFQGRVTITA DESTSTAYMELSSLRSED TAVYYCARDAAGIRLFAD WGQGTLVTVSSASTKGPS VFPLAPSSKSTSGGTAAL GCLVKDYFPEPVTVSWNS GALTSGVHTFPAVLQSSG LYSLSSVVTVPSSSLGTQ TYICNVNHKPSNTKVDKK VEPKSCDKTHTCPPCPAP EAAGAPSVFLFPPKPKDT LMISRTPEVTCVVVDVSH EDPEVKFNWYVDGVEVHN AKTKPREEQYNSTYRVVS VLTVLHQDWLNGKEYKCK VSNKALPAPIEKTISKAK GQPREPQVYTLPPCREEM TKNQVSLSCAVKGFYPSD IAVEWESNGQPENNYKTT PPVLDSDGSFFLVSKLTV DKSRWQQGNVFSCSVMHE ALHNHYTQKSLSLSPGSG GGGSGGGGSGGGGSQGQD RHMIRMRQLIDIVDQLKN YVNDLVPEFLPAPEDVET NCEWSAFSCFQKAQLKSA NTGNNERIINVSIKKLKQ KPPGGEGGGGGGEGGCP SCDSYEKKPPKEFLERFK SLLQKMIHQHLSSRTHGS EDS (SEQ ID NO: 271) | QVQLVQSGAEVKKPG SSVKVSCKASGGTFS SYAISWVRQAPGQGL EWMGGIIPGYATANY AQKFQGRVTITADES TSTAYMELSSLRSED TAVYYCARDAAGIRL FADWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPEAAGAP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVCTLPPSREEM TKNQVSLWCLVKGFY PSDIAVEWESNGQPE NNYKTTPPVLDSDGS FFLYSKLTVDKSRWQ QGNVFSCSVMHEALH NHYTQKSLSLSPG (SEQ ID NO: 272) | QVQLVQSGAEVKKPG SSVKVSCKASGGTFS SYAISWVRQAPGQGL EWMGGIIPGYATANY AQKFQGRVTITADES TSTAYMELSSLRSED TAVYYCARDAAGIRL FADWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPEAAGAP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVCTLPPSREEM TKNQVSLWCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 273) |
| xhCD8.1- hIL21 v31.48 | DIQMTQSPSSLS ASVGDRVTITCR ASQSIYGALNWY QQKPGKAPKLLI YGASNLQSGVPS | QVQLVQSGAEVKKPGSSV KVSCKASGGTFSSYAISW VRQAPGQGLEWMGGIIPG YATANYAQKFQGRVTITA DESTSTAYMELSSLRSED | QVQLVQSGAEVKKPG SSVKVSCKASGGTFS SYAISWVRQAPGQGL EWMGGIIPGYATANY AQKFQGRVTITADES | QVQLVQSGAEVKKPG SSVKVSCKASGGTFS SYAISWVRQAPGQGL EWMGGIIPGYATANY AQKFQGRVTITADES |

TABLE 8-continued

Example antibody-cytokine fusion protein sequences

| Name | Light chain sequence | Heavy chain sequence (with IL-21 fusion) | Heavy chain sequence (without IL-21 fusion) | Heavy chain sequence (without IL-21 fusion) plus C-term lysine |
|---|---|---|---|---|
| | RFSGSGSGTDFT LTISSLQPEDFA TYYCQSTYTAPW TFGGGTKVEIKR TVAAPSVFIFPP SDEQLKSGTASV VCLLNNFYPREA KVQWKVDNALQS GNSQESVTEQDS KDSTYSLSSTLT LSKADYEKHKVY ACEVTHQGLSSP VTKSFNRGEC (SEQ ID NO: 274) | TAVYYCARDAAGIRLFAD WGQGTLVTVSSASTKGPS VFPLAPSSKSTSGGTAAL GCLVKDYFPEPVTVSWNS GALTSGVHTFPAVLQSSG LYSLSSVVTVPSSSLGTQ TYICNVNHKPSNTKVDKK VEPKSCDKTHTCPPCPAP EAAGAPSVFLFPPKPKDT LMISRTPEVTCVVVDVSH EDPEVKFNWYVDGVEVHN AKTKPREEQYNSTYRVVS VLTVLHQDWLNGKEYKCK VSNKALPAPIEKTISKAK GQPREPQVYTLPPCREEM TKNQVSLSCAVKGFYPSD IAVEWESNGQPENNYKTT PPVLDSDGSFFLVSKLTV DKSRWQQGNVFSCSVMHE ALHNHYTQKSLSLSPGSG GGGSGGGGSGGGGSQGQD RHMISMRQLIDIVDQLKN YVNDLVPEFLPAPEDVET NCEWSAFSCFQKAQLKSA NTGNNERIINVSIKKLKR KPPGGEGGGGGGEGGCP SCDSYEKKPPKEFLERFK SLLQKMIHQHLSSRTHGS EDS (SEQ ID NO: 275) | TSTAYMELSSLRSED TAVYYCARDAAGIRL FADWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPEAAGAP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVCTLPPSREEM TKNQVSLWCLVKGFY PSDIAVEWESNGQPE NNYKTTPPVLDSDGS FFLYSKLTVDKSRWQ QGNVFSCSVMHEALH NHYTQKSLSLSPG (SEQ ID NO: 276) | TSTAYMELSSLRSED TAVYYCARDAAGIRL FADWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPEAAGAP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVCTLPPSREEM TKNQVSLWCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 277) |
| xhCD8.1-hIL21 v31.51 | DIQMTQSPSSLS ASVGDRVTITCR ASQSIYGALNWY QQKPGKAPKLLI YGASNLQSGVPS RFSGSGSGTDFT LTISSLQPEDFA TYYCQSTYTAPW TFGGGTKVEIKR TVAAPSVFIFPP SDEQLKSGTASV VCLLNNFYPREA KVQWKVDNALQS GNSQESVTEQDS KDSTYSLSSTLT LSKADYEKHKVY ACEVTHQGLSSP VTKSFNRGEC (SEQ ID NO: 278) | QVQLVQSGAEVKKPGSSV KVSCKASGGTFSSYAISW VRQAPGQGLEWMGGIIPG YATANYAQKFQGRVTITA DESTSTAYMELSSLRSED TAVYYCARDAAGIRLFAD WGQGTLVTVSSASTKGPS VFPLAPSSKSTSGGTAAL GCLVKDYFPEPVTVSWNS GALTSGVHTFPAVLQSSG LYSLSSVVTVPSSSLGTQ TYICNVNHKPSNTKVDKK VEPKSCDKTHTCPPCPAP EAAGAPSVFLFPPKPKDT LMISRTPEVTCVVVDVSH EDPEVKFNWYVDGVEVHN AKTKPREEQYNSTYRVVS VLTVLHQDWLNGKEYKCK VSNKALPAPIEKTISKAK GQPREPQVYTLPPCREEM TKNQVSLSCAVKGFYPSD IAVEWESNGQPENNYKTT PPVLDSDGSFFLVSKLTV DKSRWQQGNVFSCSVMHE ALHNHYTQKSLSLSPGSG GGGSGGGGSGGGGSQGQD RHMIGMRQLIDIVDQLKN YVNDLVPEFLPAPEDVET NCEWSAFSCFQKAQLKSA NTGNNERIINVSIKKLKR KPPGGEGGGGGGEGGCP SCDSYEKKPPKEFLERFK SLLQKMIHQHLSSRTHGS EDS (SEQ ID NO: 279) | QVQLVQSGAEVKKPG SSVKVSCKASGGTFS SYAISWVRQAPGQGL EWMGGIIPGYATANY AQKFQGRVTITADES TSTAYMELSSLRSED TAVYYCARDAAGIRL FADWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPEAAGAP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVCTLPPSREEM TKNQVSLWCLVKGFY PSDIAVEWESNGQPE NNYKTTPPVLDSDGS FFLYSKLTVDKSRWQ QGNVFSCSVMHEALH NHYTQKSLSLSPG (SEQ ID NO: 280) | QVQLVQSGAEVKKPG SSVKVSCKASGGTFS SYAISWVRQAPGQGL EWMGGIIPGYATANY AQKFQGRVTITADES TSTAYMELSSLRSED TAVYYCARDAAGIRL FADWGQGTLVTVSSA STKGPSVFPLAPSSK STSGGTAALGCLVKD YFPEPVTVSWNSGAL TSGVHTFPAVLQSSG LYSLSSVVTVPSSSL GTQTYICNVNHKPSN TKVDKKVEPKSCDKT HTCPPCPAPEAAGAP SVFLFPPKPKDTLMI SRTPEVTCVVVDVSH EDPEVKFNWYVDGVE VHNAKTKPREEQYNS TYRVVSVLTVLHQDW LNGKEYKCKVSNKAL PAPIEKTISKAKGQP REPQVCTLPPSREEM TKNQVSLWCLVKGFY PSDIAVEWESNGQPE NNYKTTPPVLDSDGS FFLYSKLTVDKSRWQ QGNVFSCSVMHEALH NHYTQKSLSLSPGK (SEQ ID NO: 281) |
| xhCD8v11-hIL21 v31.4 | EIVLTQSPGTLS LSPGERATLSCR ASQSVSSNLAWY QQKPGQAPRLLI YGASSRATGIPD | EVQLVESGGGLVQPGGSL RLSCAASGFTFSSYAMSW VRQAPGKGLEWVSDITYA GGSTAYADSVKGRFTISR DNAKNSLYLQMNSLRAED | EVQLVESGGGLVQPG GSLRLSCAASGFTFS SYAMSWVRQAPGKGL EWVSDITYAGGSTAY ADSVKGRFTISRDNA | EVQLVESGGGLVQPG GSLRLSCAASGFTFS SYAMSWVRQAPGKGL EWVSDITYAGGSTAY ADSVKGRFTISRDNA |

TABLE 8-continued

Example antibody-cytokine fusion protein sequences

| Name | Light chain sequence | Heavy chain sequence (with IL-21 fusion) | Heavy chain sequence (without IL-21 fusion) | Heavy chain sequence (without IL-21 fusion) plus C-term lysine |
|---|---|---|---|---|
| | RFSGSGSGTDFT LTISRLEPEDFA VYYCQQYGSSPP VTFGQGTKVEIK RTVAAPSVFIFP PSDEQLKSGTAS VVCLLNNFYPRE AKVQWKVDNALQ SGNSQESVTEQD SKDSTYSLSSTL TLSKADYEKHKV YACEVTHQGLSS PVTKSFNRGEC (SEQ ID NO: 297) | TAVYYCARSNAYAWDDAL DIWGQGTLVTVSSASTKG PSVFPLAPSSKSTSGGTA ALGCLVKDYFPEPVTVSW NSGALTSGVHTFPAVLQS SGLYSLSSVVTVPSSSLG TQTYICNVNHKPSNTKVD KKVEPKSCDKTHTCPPCP APEAAGAPSVFLFPPKPK DTLMISRTPEVTCVVVDV SHEDPEVKFNWYVDGVEV HNAKTKPREEQYNSTYRV VSVLTVLHQDWLNGKEYK CKVSNKALPAPIEKTISK AKGQPREPQVYTLPPCRE EMTKNQVSLSCAVKGFYP SDIAVEWESNGQPENNYK TTPPVLDSDGSFFLVSKL TVDKSRWQQGNVFSCSVM HEALHNHYTQKSLSLSPG SGGGGSGGGGSGGGGSQG QDRHMIRMRQLIDIVDQL KNYVNDLVPEFLPAPEDV ETNCEWSAFSCFQKAQLK SANTGNNERIINVSIKKL KEKPPGGEGGGGGGEGG CPSCDSYEKKPPKEFLER FKSLLQKMIHQHLSSRTH GSEDS (SEQ ID NO: 298) | KNSLYLQMNSLRAED TAVYYCARSNAYAWD DALDIWGQGTLVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPEAAG APSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVCTLPPSRE EMTKNQVSLWCLVKG FYPSDIAVEWESNGQ PENNYKTTPPVLDSD GSFFLYSKLTVDKSR WQQGNVFSCSVMHEA LHNHYTQKSLSLSPG (SEQ ID NO: 299) | KNSLYLQMNSLRAED TAVYYCARSNAYAWD DALDIWGQGTLVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPEAAG APSVFLPPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVCTLPPSRE EMTKNQVSLWCLVKG FYPSDIAVEWESNGQ PENNYKTTPPVLDSD GSFFLYSKLTVDKSR WQQGNVFSCSVMHEA LHNHYTQKSLSLSPG K (SEQ ID NO: 300) |
| xhCD8v11-hIL21 v31.6 | EIVLTQSPGTLS LSPGERATLSCR ASQSVSSNLAWY QQKPGQAPRLLI YGASSRATGIPD RFSGSGSGTDFT LTISRLEPEDFA VYYCQQYGSSPP VTFGQGTKVEIK RTVAAPSVFIFP PSDEQLKSGTAS VVCLLNNFYPRE AKVQWKVDNALQ SGNSQESVTEQD SKDSTYSLSSTL TLSKADYEKHKV YACEVTHQGLSS PVTKSFNRGEC (SEQ ID NO: 301) | EVQLVESGGGLVQPGGSL RLSCAASGFTFSSYAMSW VRQAPGKGLEWVSDITYA GGSTAYADSVKGRFTISR DNAKNSLYLQMNSLRAED TAVYYCARSNAYAWDDAL DIWGQGTLVTVSSASTKG PSVFPLAPSSKSTSGGTA ALGCLVKDYFPEPVTVSW NSGALTSGVHTFPAVLQS SGLYSLSSVVTVPSSSLG TQTYICNVNHKPSNTKVD KKVEPKSCDKTHTCPPCP APEAAGAPSVFLFPPKPK DTLMISRTPEVTCVVVDV SHEDPEVKFNWYVDGVEV HNAKTKPREEQYNSTYRV VSVLTVLHQDWLNGKEYK CKVSNKALPAPIEKTISK AKGQPREPQVYTLPPCRE EMTKNQVSLSCAVKGFYP SDIAVEWESNGQPENNYK TTPPVLDSDGSFFLVSKL TVDKSRWQQGNVFSCSVM HEALHNHYTQKSLSLSPG SGGGGSGGGGSGGGGSQG QDRHMIRMRQLIDIVDQL KNYVNDLVPEFLPAPEDV ETNCEWSAFSCFQKAQLK SANTGNNERIINVSIKKL KFKPPGGEGGGGGGEGG CPSCDSYEKKPPKEFLER FKSLLQKMIHQHLSSRTH GSEDS (SEQ ID NO: 302) | EVQLVESGGGLVQPG GSLRLSCAASGFTFS SYAMSWVRQAPGKGL EWVSDITYAGGSTAY ADSVKGRFTISRDNA KNSLYLQMNSLRAED TAVYYCARSNAYAWD DALDIWGQGTLVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPEAAG APSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVCTLPPSRE EMTKNQVSLWCLVKG FYPSDIAVEWESNGQ PENNYKTTPPVLDSD GSFFLYSKLTVDKSR WQQGNVFSCSVMHEA LHNHYTQKSLSLSPG (SEQ ID NO: 303) | EVQLVESGGGLVQPG GSLRLSCAASGFTFS SYAMSWVRQAPGKGL EWVSDITYAGGSTAY ADSVKGRFTISRDNA KNSLYLQMNSLRAED TAVYYCARSNAYAWD DALDIWGQGTLVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPEAAG APSVFLPPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVCTLPPSRE EMTKNQVSLWCLVKG FYPSDIAVEWESNGQ PENNYKTTPPVLDSD GSFFLYSKLTVDKSR WQQGNVFSCSVMHEA LHNHYTQKSLSLSPG K (SEQ ID NO: 304) |
| xhCD8v11-hIL21 v31.23 | EIVLTQSPGTLS LSPGERATLSCR ASQSVSSNLAWY QQKPGQAPRLLI YGASSRATGIPD | EVQLVESGGGLVQPGGSL RLSCAASGFTFSSYAMSW VRQAPGKGLEWVSDITYA GGSTAYADSVKGRFTISR DNAKNSLYLQMNSLRAED | EVQLVESGGGLVQPG GSLRLSCAASGFTFS SYAMSWVRQAPGKGL EWVSDITYAGGSTAY ADSVKGRFTISRDNA | EVQLVESGGGLVQPG GSLRLSCAASGFTFS SYAMSWVRQAPGKGL EWVSDITYAGGSTAY ADSVKGRFTISRDNA |

TABLE 8-continued

Example antibody-cytokine fusion protein sequences

| Name | Light chain sequence | Heavy chain sequence (with IL-21 fusion) | Heavy chain sequence (without IL-21 fusion) | Heavy chain sequence (without IL-21 fusion) plus C-term lysine |
|---|---|---|---|---|
| | RFSGSGSGTDFT LTISRLEPEDFA VYYCQQYGSSPP VTFGQGTKVEIK RTVAAPSVFIFP PSDEQLKSGTAS VVCLLNNFYPRE AKVQWKVDNALQ SGNSQESVTEQD SKDSTYSLSSTL TLSKADYEKHKV YACEVTHQGLSS PVTKSFNRGEC (SEQ ID NO: 305) | TAVYYCARSNAYAWDDAL DIWGQGTLVTVSSASTKG PSVFPLAPSSKSTSGGTA ALGCLVKDYFPEPVTVSW NSGALTSGVHTFPAVLQS SGLYSLSSVVTVPSSSLG TQTYICNVNHKPSNTKVD KKVEPKSCDKTHTCPPCP APEAAGAPSVFLFPPKPK DTLMISRTPEVTCVVVDV SHEDPEVKFNWYVDGVEV HNAKTKPREEQYNSTYRV VSVLTVLHQDWLNGKEYK CKVSNKALPAPIEKTISK AKGQPREPQVYTLPPCRE EMTKNQVSLSCAVKGFYP SDIAVEWESNGQPENNYK TTPPVLDSDGSFFLVSKL TVDKSRWQQGNVFSCSVM HEALHNHYTQKSLSLSPG SGGGGSGGGGSGGGGSQG QDRHMIRMRQLIDIVDQL KNYVNDLVPEFLPAPEDV ETNCEWSAFSCFQKAQLK SANTGNNERIINVSIKKL KQKPPGGEGGGGGGEGG CPSCDSYEKKPPKEFLER FKSLLQKMIHQHLSSRTH GSEDS (SEQ ID NO: 306) | KNSLYLQMNSLRAED TAVYYCARSNAYAWD DALDIWGQGTLVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPEAAG APSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVCTLPPSRE EMTKNQVSLWCLVKG FYPSDIAVEWESNGQ PENNYKTTPPVLDSD GSFFLYSKLTVDKSR WQQGNVFSCSVMHEA LHNHYTQKSLSLSPG (SEQ ID NO: 307) | KNSLYLQMNSLRAED TAVYYCARSNAYAWD DALDIWGQGTLVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPEAAG APSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVCTLPPSRE EMTKNQVSLWCLVKG FYPSDIAVEWESNGQ PENNYKTTPPVLDSD GSFFLYSKLTVDKSR WQQGNVFSCSVMHEA LHNHYTQKSLSLSPG K (SEQ ID NO: 308) |
| xhCD8v11-hIL21 v31.51 | EIVLTQSPGTLS LSPGERATLSCR ASQSVSSNLAWY QQKPGQAPRLLI YGASSRATGIPD RFSGSGSGTDFT LTISRLEPEDFA VYYCQQYGSSPP VTFGQGTKVEIK RTVAAPSVFIFP PSDEQLKSGTAS VVCLLNNFYPRE AKVQWKVDNALQ SGNSQESVTEQD SKDSTYSLSSTL TLSKADYEKHKV YACEVTHQGLSS PVTKSFNRGEC (SEQ ID NO: 309) | EVQLVESGGGLVQPGGSL RLSCAASGFTFSSYAMSW VRQAPGKGLEWVSDITYA GGSTAYADSVKGRFTISR DNAKNSLYLQMNSLRAED TAVYYCARSNAYAWDDAL DIWGQGTLVTVSSASTKG PSVFPLAPSSKSTSGGTA ALGCLVKDYFPEPVTVSW NSGALTSGVHTFPAVLQS SGLYSLSSVVTVPSSSLG TQTYICNVNHKPSNTKVD KKVEPKSCDKTHTCPPCP APEAAGAPSVFLFPPKPK DTLMISRTPEVTCVVVDV SHEDPEVKFNWYVDGVEV HNAKTKPREEQYNSTYRV VSVLTVLHQDWLNGKEYK CKVSNKALPAPIEKTISK AKGQPREPQVYTLPPCRE EMTKNQVSLSCAVKGFYP SDIAVEWESNGQPENNYK TTPPVLDSDGSFFLVSKL TVDKSRWQQGNVFSCSVM HEALHNHYTQKSLSLSPG SGGGGSGGGGSGGGGSQG QDRHMIGMRQLIDIVDQL KNYVNDLVPEFLPAPEDV ETNCEWSAFSCFQKAQLK SANTGNNERIINVSIKKL KRKPPGGEGGGGGGEGG CPSCDSYEKKPPKEFLER FKSLLQKMIHQHLSSRTH GSEDS (SEQ ID NO: 310) | EVQLVESGGGLVQPG GSLRLSCAASGFTFS SYAMSWVRQAPGKGL EWVSDITYAGGSTAY ADSVKGRFTISRDNA KNSLYLQMNSLRAED TAVYYCARSNAYAWD DALDIWGQGTLVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPEAAG APSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVCTLPPSRE EMTKNQVSLWCLVKG FYPSDIAVEWESNGQ PENNYKTTPPVLDSD GSFFLYSKLTVDKSR WQQGNVFSCSVMHEA LHNHYTQKSLSLSPG (SEQ ID NO: 311) | EVQLVESGGGLVQPG GSLRLSCAASGFTFS SYAMSWVRQAPGKGL EWVSDITYAGGSTAY ADSVKGRFTISRDNA KNSLYLQMNSLRAED TAVYYCARSNAYAWD DALDIWGQGTLVTVS SASTKGPSVFPLAPS SKSTSGGTAALGCLV KDYFPEPVTVSWNSG ALTSGVHTFPAVLQS SGLYSLSSVVTVPSS SLGTQTYICNVNHKP SNTKVDKKVEPKSCD KTHTCPPCPAPEAAG APSVFLFPPKPKDTL MISRTPEVTCVVVDV SHEDPEVKFNWYVDG VEVHNAKTKPREEQY NSTYRVVSVLTVLHQ DWLNGKEYKCKVSNK ALPAPIEKTISKAKG QPREPQVCTLPPSRE EMTKNQVSLWCLVKG FYPSDIAVEWESNGQ PENNYKTTPPVLDSD GSFFLYSKLTVDKSR WQQGNVFSCSVMHEA LHNHYTQKSLSLSPG K (SEQ ID NO: 312) |

TABLE 9

Engineered mouse IL-21 muteins

| Mouse IL-21 Mutein | Amino Acid Sequence | SEQ ID NO |
|---|---|---|
| mIL-21 v1 | QGPDRLLIRLRHLIDIVEQLKIYENDLDPELLSAPQDVK GHCEHAAFACFQKAKLKPSNPGNNKTFIIDLVAQLERRL PAGEGGEGQEHIAKCPSCDSYEKRTPKEFLERLKWLLQK MIHQHLS | 282 |
| mIL-21 v1.1 | QGPDRLLIRLRHLIDIVEQLKIYENDLDPELLSAPQDVK GHCEHAAFACFQKAKLKPSNPGNNKTFIIDLVAQLEERL PAGEGGEGQEHIAKCPSCDSYEKRTPKEFLERLKWLLQK MIHQHLS | 283 |

TABLE 10

Anti-CD8 antibody CDRs (Kabat)

| Name | CDR-H1 | CDR-H2 | CDR-H3 | CDR-L1 | CDR-L2 | CDR-L3 |
|---|---|---|---|---|---|---|
| xhCD8 | KYTMH (SEQ ID NO: 137) | HFNPNNDET KYNQKFTG (SEQ ID NO: 138) | DGLGLRLFA D (SEQ ID NO: 139) | GASENIYGAL N (SEQ ID NO: 140) | GATNLAD (SEQ ID NO: 141) | QNILDTPWT (SEQ ID NO: 142) |
| xhCD8v1 | KYAIS (SEQ ID NO: 252) | HFNPNNDET KYNQKFQG (SEQ ID NO: 253) | DGLGLRLFA D (SEQ ID NO: 254) | RASENIYGAL N (SEQ ID NO: 255) | GATNLAD (SEQ ID NO: 256) | QNILDTPWT (SEQ ID NO: 257) |
| xhCD8v2 | NFAIS (SEQ ID NO: 149) | GIIPGHAKAN YAQKFQG (SEQ ID NO: 150) | DGLGIRLFAD (SEQ ID NO: 151) | RASQEIYGAL N (SEQ ID NO: 152) | GATNLQS (SEQ ID NO: 153) | QDIYDAPWT (SEQ ID NO: 154) |
| xhCD8v3 | KFAIS (SEQ ID NO: 155) | GIIPGHAKAN YAQKFQG (SEQ ID NO: 156) | DGLGIRLFAD (SEQ ID NO: 157) | RASQEIYGAL N (SEQ ID NO: 158) | GATNLQS (SEQ ID NO: 159) | QDIYDAPWT (SEQ ID NO: 160) |
| xhCD8v4 | KYAIS (SEQ ID NO: 161) | GIIPGHAKAN YAQKFQG (SEQ ID NO: 162) | DGLGIRLFAD (SEQ ID NO: 163) | RASQKIYGAL N (SEQ ID NO: 164) | GATNLQS (SEQ ID NO: 165) | QNTYDTPW T (SEQ ID NO: 166) |
| xhCD8v5 | GHAIS (SEQ ID NO: 167) | GIIPGHAKAN YAQKFQG (SEQ ID NO: 168) | DGLGIRLFAD (SEQ ID NO: 169) | RASQKIYGAL N (SEQ ID NO: 170) | GATNLQS (SEQ ID NO: 171) | QNTYDTPW T (SEQ ID NO: 172) |
| xhCD8v6 | DYGMS (SEQ ID NO: 173) | DINWSGEIT AYADSVKG (SEQ ID NO: 174) | SNSYRWDD ALDI (SEQ ID NO: 175) | RASQSVSSN LA (SEQ ID NO: 176) | GASSRAT (SEQ ID NO: 177) | QQYGSSPPV T (SEQ ID NO: 178) |
| xhCD8v7 | DYAMH (SEQ ID NO: 179) | VISYDGSNKY YADSVKG (SEQ ID NO: 180) | DRIGWYDYD AFDI (SEQ ID NO: 181) | RASHSVGSN LA (SEQ ID NO: 182) | DASNRAT (SEQ ID NO: 183) | QQRSNWPP T (SEQ ID NO: 184) |
| xhCD8v8 | SYWMN (SEQ ID NO: 143) | QIYPGDGDT NYNGKFKG (SEQ ID NO: 144) | SGAAFSSYYA MDY (SEQ ID NO: 145) | RASENIYSNL A (SEQ ID NO: 146) | AATNLAD (SEQ ID NO: 147) | QHFWGTPW T (SEQ ID NO: 148) |
| xhCD8v9 | SYAIS (SEQ ID NO: 199) | GIIPGAATAN YAQKFQG (SEQ ID NO: 200) | DAAGIRLFA D (SEQ ID NO: 201) | RASQEIYGAL N (SEQ ID NO: 152) | GATNLQS (SEQ ID NO: 153) | QSTYDAPWT (SEQ ID NO: 202) |
| xhCD8v10 | SYAMS (SEQ ID NO: 220) | DITYAGGSTA YADSVKG (SEQ ID NO: 221) | SNAYAWDD ALDI (SEQ ID NO: 222) | RASQSVSSN LA (SEQ ID NO: 176) | GASSRAT (SEQ ID NO: 177) | QQYGSSPPV T (SEQ ID NO: 178) |
| xhCD8v11 | SYAMS (SEQ ID NO: 220) | DITYAGGSTA YADSVKG (SEQ ID NO: 221) | SNAYAWDD ALDI (SEQ ID NO: 222) | RASQSVSSN LA (SEQ ID NO: 176) | GASSRAT (SEQ ID NO: 177) | QQYGSSPPV T (SEQ ID NO: 178) |

TABLE 10-continued

Anti-CD8 antibody CDRs (Kabat)

| Name | CDR-H1 | CDR-H2 | CDR-H3 | CDR-L1 | CDR-L2 | CDR-L3 |
|---|---|---|---|---|---|---|
| xhCD8v12 (xhCD8.1) | SYAIS (SEQ ID NO: 199) | GIIPGYATAN YAQKFQG (SEQ ID NO: 203) | DAAGIRLFA D (SEQ ID NO: 204) | RASQSIYGAL N (SEQ ID NO: 205) | GASNLQS (SEQ ID NO: 206) | QSTYTAPWT (SEQ ID NO: 207) |
| xhCD8v13 | SYAIS (SEQ ID NO: 199) | GIIPGYATAN YAQKFQG (SEQ ID NO: 203) | DAAGIRLFA D (SEQ ID NO: 204) | RASQEIYGAL N (SEQ ID NO: 152) | GATNLQS (SEQ ID NO: 153) | QSTYDAPWT (SEQ ID NO: 202) |
| xhCD8v14 | SYAMS (SEQ ID NO: 220) | DISYAGGSTA YADSVKG (SEQ ID NO: 260) | SNAYAWDD ALDI (SEQ ID NO: 222) | RASQSVSSN LA (SEQ ID NO: 176) | GASSRAT (SEQ ID NO: 177) | QQYGSSPPV T (SEQ ID NO: 178) |
| xhCD8v15 | SYAMS (SEQ ID NO: 220) | DISYAGGSTA YADSVKG (SEQ ID NO: 260) | SNAYAWDD ALDI (SEQ ID NO: 222) | RASQSVSSN LA (SEQ ID NO: 176) | GASSRAT (SEQ ID NO: 177) | QQYGSSPPV T (SEQ ID NO: 178) |
| V9 family | $X_1X_2$AIS $X_1$ is S, K, G, N, R, D, T, or G $X_2$ Is Y, L, H, or F (SEQ ID NO: 185) | $X_1X_2X_3PX_4X_5X_6$ $X_7X_8X_9YX_{10}Q$ $KFX_{11}G$ $X_1$ is G or H, $X_2$ is I or F, $X_3$ is I, N, or M, $X_4$ is G, N, H, S, R, I, or A, $X_5$ is A, N, H, S, T, F, or Y, $X_6$ is A, D, or G, $X_7$ is T, E, K, V, Q, or A, $X_8$ is A or T, $X_9$ is N or K, $X_{10}$ is A or N, $X_{11}$ is Q or T (SEQ ID NO: 186) | $X_1X_2X_3GX_4X_5$ $LFX_6X_7$ $X_1$ is D or A, $X_2$ is A, G, E, R, Y, K, N, Q, L, or F, $X_3$ is A, L, P, or Y, $X_4$ is I or L, $X_5$ is R, A, Q, or S $X_6$ is A or D, $X_7$ is D, E, A, or S (SEQ ID NO: 187) | $X_1X_2SX_3X_4X_5$ $GX_6LN$ $X_1$ is R or G, $X_2$ is A or T, $X_3$ is Q or E, $X_4$ is E, N, T, S, A, K, D, G, R, or Q, $X_5$ is Y or S, $X_6$ is A or V (SEQ ID NO: 188) | $GX_1X_2X_3LX_4X_5$ $X_1$ is T, S, E, Q, or D, $X_2$ is N, R, A, E, or H, $X_3$ is Q or A, $X_4$ is Q or A, $X_5$ is S or D (SEQ ID NO: 189) | $QX_1X_2X_3X_4X_5$ PWT $X_1$ is S, N, D, Q, A, or E, $X_2$ is T, I, or S, $X_3$ is Y, L, or F, $X_4$ is D, G, T, E, Q, A, or Y, $X_5$ is A, T, R, S, K, or Y (SEQ ID NO: 190) |
| V11 family | $X_1YX_2MS$ $X_1$ is S, D, E, A, or Q $X_2$ is A, G, or T (SEQ ID NO: 208) | $DIX_1X_2X_3GX_4$ $X_5TX_6YADSV$ KG $X_1$ is T, N, S, Q, E, H, R, or A, $X_2$ Is Y, W, F, or H, $X_3$ is A, S, Q, E, or T, $X_4$ is G or E, $X_5$ is S or I, $X_6$ is A or G (SEQ ID NO: 209) | $X_1X_2X_3YX_4W$ $X_5X_6AX_7DX_8$ $X_1$ is S or A, $X_2$ is N, H, A, D, L, Q, Y, or R, $X_3$ is A, N, S, or G, $X_4$ is A, V, R, E, or S, $X_5$ is D or S, $X_6$ is D, N, Q, E, S, T, or L, $X_7$ is L, F, or M, $X_8$ is I, Y, or V (SEQ ID NO: 210) | RASQSVSSN LA (SEQ ID NO: 176) | GASSRAT (SEQ ID NO: 177) | QQYGSSPPV T (SEQ ID NO: 178) |

TABLE 11

Anti-CD8 antibody CDRs (Chothia)

| Name | CDR-H1 | CDR-H2 | CDR-H3 | CDR-L1 | CDR-L2 | CDR-L3 |
|---|---|---|---|---|---|---|
| xhCD8 | GYTFTKY (SEQ ID NO: 223) | NPNNDE (SEQ ID NO: 224) | DGLGLRLFA D (SEQ ID NO: 225) | GASENIYGAL N (SEQ ID NO: 140) | GATNLAD (SEQ ID NO: 141) | QNILDTPWT (SEQ ID NO: 142) |

TABLE 11-continued

Anti-CD8 antibody CDRs (Chothia)

| Name | CDR-H1 | CDR-H2 | CDR-H3 | CDR-L1 | CDR-L2 | CDR-L3 |
|---|---|---|---|---|---|---|
| xhCD8v1 | GYTFTKY (SEQ ID NO: 223) | NPNNDE (SEQ ID NO: 224) | DGLGLRLFAD (SEQ ID NO: 284) | RASENIYGALN (SEQ ID NO: 285) | GATNLAD (SEQ ID NO: 286) | QNILDTPWT (SEQ ID NO: 287) |
| xhCD8v2 | GYRFHNF (SEQ ID NO: 226) | IPGHAK (SEQ ID NO: 227) | DGLGIRLFAD (SEQ ID NO: 151) | RASQEIYGALN (SEQ ID NO: 152) | GATNLQS (SEQ ID NO: 153) | QDIYDAPWT (SEQ ID NO: 154) |
| xhCD8v3 | GSRFYKF (SEQ ID NO: 228) | IPGHAK (SEQ ID NO: 227) | DGLGIRLFAD (SEQ ID NO: 157) | RASQEIYGALN (SEQ ID NO: 158) | GATNLQS (SEQ ID NO: 159) | QDIYDAPWT (SEQ ID NO: 160) |
| xhCD8v4 | GYTFTKY (SEQ ID NO: 223) | IPGHAK (SEQ ID NO: 227) | DGLGIRLFAD (SEQ ID NO: 163) | RASQKIYGALN (SEQ ID NO: 164) | GATNLQS (SEQ ID NO: 165) | QNTYDTPWT (SEQ ID NO: 166) |
| xhCD8v5 | GSGFRGH (SEQ ID NO: 229) | IPGHAK (SEQ ID NO: 227) | DGLGIRLFAD (SEQ ID NO: 169) | RASQKIYGALN (SEQ ID NO: 170) | GATNLQS (SEQ ID NO: 171) | QNTYDTPWT (SEQ ID NO: 172) |
| xhCD8v6 | GFTFDDY (SEQ ID NO: 230) | NWSGEI (SEQ ID NO: 231) | SNSYRWDDALDI (SEQ ID NO: 175) | RASQSVSSNLA (SEQ ID NO: 176) | GASSRAT (SEQ ID NO: 177) | QQYGSSPPVT (SEQ ID NO: 178) |
| xhCD8v7 | GFTFDDY (SEQ ID NO: 230) | SYDGSN (SEQ ID NO: 232) | DRIGWYDYDAFDI (SEQ ID NO: 181) | RASHSVGSNLA (SEQ ID NO: 182) | DASNRAT (SEQ ID NO: 183) | QQRSNWPPT (SEQ ID NO: 184) |
| xhCD8v8 | GYAFSSY (SEQ ID NO: 233) | YPGDGD (SEQ ID NO: 234) | SGAAFSSYYAMDY (SEQ ID NO: 145) | RASENIYSNLA (SEQ ID NO: 146) | AATNLAD (SEQ ID NO: 147) | QHFWGTPWT (SEQ ID NO: 148) |
| xhCD8v9 | GGTFSSY (SEQ ID NO: 241) | IPGAAT (SEQ ID NO: 242) | DAAGIRLFAD (SEQ ID NO: 204) | RASQEIYGALN (SEQ ID NO: 152) | GATNLQS (SEQ ID NO: 153) | QSTYDAPWT (SEQ ID NO: 202) |
| xhCD8v10 | GFTFSSY (SEQ ID NO: 250) | TYAGGS (SEQ ID NO: 251) | SNAYAWDDALDI (SEQ ID NO: 288) | RASQSVSSNLA (SEQ ID NO: 176) | GASSRAT (SEQ ID NO: 177) | QQYGSSPPVT (SEQ ID NO: 178) |
| xhCD8v11 | GFTFSSY (SEQ ID NO: 250) | TYAGGS (SEQ ID NO: 251) | SNAYAWDDALDI (SEQ ID NO: 288) | RASQSVSSNLA (SEQ ID NO: 176) | GASSRAT (SEQ ID NO: 177) | QQYGSSPPVT (SEQ ID NO: 178) |
| xhCD8v12 (xhCD8.1) | GGTFSSY (SEQ ID NO: 241) | IPGYAT (SEQ ID NO: 243) | DAAGIRLFAD (SEQ ID NO: 204) | RASQSIYGALN (SEQ ID NO: 205) | GASNLQS (SEQ ID NO: 206) | QSTYTAPWT (SEQ ID NO: 207) |
| xhCD8v13 | GGTFSSY (SEQ ID NO: 241) | IPGYAT (SEQ ID NO: 243) | DAAGIRLFAD (SEQ ID NO: 204) | RASQEIYGALN (SEQ ID NO: 152) | GATNLQS (SEQ ID NO: 153) | QSTYDAPWT (SEQ ID NO: 202) |
| xhCD8v14 | GFTFSSY (SEQ ID NO: 250) | SYAGGS (SEQ ID NO: 261) | SNAYAWDDALDI (SEQ ID NO: 288) | RASQSVSSNLA (SEQ ID NO: 176) | GASSRAT (SEQ ID NO: 177) | QQYGSSPPVT (SEQ ID NO: 178) |
| xhCD8v15 | GFTFSSY (SEQ ID NO: 250) | SYAGGS (SEQ ID NO: 261) | SNAYAWDDALDI (SEQ ID NO: 288) | RASQSVSSNLA (SEQ ID NO: 176) | GASSRAT (SEQ ID NO: 177) | QQYGSSPPVT (SEQ ID NO: 178) |

TABLE 11-continued

Anti-CD8 antibody CDRs (Chothia)

| Name | CDR-H1 | CDR-H2 | CDR-H3 | CDR-L1 | CDR-L2 | CDR-L3 |
|---|---|---|---|---|---|---|
| V9 family | $GX_1X_2FX_3X_4X_5$<br>$X_1$ is G, Y, S, or A,<br>$X_2$ is T, S, G, R, N, or H,<br>$X_3$ is S, T, R, H, Y, G, or P,<br>$X_4$ is S, K, G, N, R, D, T, or G,<br>$X_5$ is Y, L, H, or F (SEQ ID NO: 235) | $X_1PX_2X_3X_4X_5$<br>$X_1$ is I, N, or M,<br>$X_2$ is G, N, H, S, R, I, or A,<br>$X_3$ is A, N, H, S, T, F, or Y,<br>$X_4$ is A, D, or G,<br>$X_5$ is T, E, K, V, Q, or A (SEQ ID NO: 236) | $X_1X_2X_3GX_4X_5$<br>$LFX_6X_7$<br>$X_1$ is D or A,<br>$X_2$ is A, G, E, R, Y, K, N, Q, L, or F,<br>$X_3$ is A, L, P, or Y,<br>$X_4$ is I or L,<br>$X_5$ is R, A, Q, or S,<br>$X_6$ is A or D,<br>$X_7$ is D, E, A, or S (SEQ ID NO: 237) | $X_1X_2SX_3X_4IX_5$<br>$GX_6LN$<br>$X_1$ is R or G,<br>$X_2$ is A or T,<br>$X_3$ is Q or E,<br>$X_4$ is E, N, T, S, A, K, D, G, R, or Q,<br>$X_5$ is Y or S,<br>$X_6$ is A or V (SEQ ID NO: 188) | $GX_1X_2X_3LX_4X_5$<br>$X_1$ is A or S,<br>$X_2$ is T, S, E, Q, or D,<br>$X_3$ is N, R, A, E, or H,<br>$X_4$ is Q or A,<br>$X_5$ is S or D (SEQ ID NO: 189) | $QX_1X_2X_3X_4X_5$<br>PWT<br>$X_1$ is S, N, D, Q, A, or E,<br>$X_2$ is T, I, or S,<br>$X_3$ is Y, L, or F,<br>$X_4$ is D, G, T, E, Q, A, or Y,<br>$X_5$ is A, T, R, S, K, or Y (SEQ ID NO: 190) |
| V11 family | $GFTFX_1X_2Y$<br>$X_1$ is S, D, E, Q, S, or A,<br>$X_2$ is S, D, E, A, or Q (SEQ ID NO: 244) | $X_1X_2X_3GX_4X_5$<br>$X_1$ is T, N, S, Q, E, H, R or A,<br>$X_2$ is Y, W, F, or H,<br>$X_3$ is A, S, Q, E, or T,<br>$X_4$ is G or E,<br>$X_5$ is S or I (SEQ ID NO: 245) | $X_1X_2X_3YX_4W$<br>$X_5X_6AX_7DX_8$<br>$X_1$ is S or A,<br>$X_2$ is N, H, A, D, L, Q, Y, or R<br>$X_3$ is A, N, S, or G,<br>$X_4$ is A, V, R, E, or S,<br>$X_5$ is D or S,<br>$X_6$ is D, N, Q, E, S, T, or L,<br>$X_7$ is L, F, or M,<br>$X_8$ is I, Y, or V (SEQ ID NO: 246) | RASQSVSSN<br>LA<br>(SEQ ID NO: 176) | GASSRAT<br>(SEQ ID NO: 177) | QQYGSSPPV<br>T<br>(SEQ ID NO: 178) |

TABLE 12

Anti-CD8 antibody variable domain sequences

| Name | VH | VL |
|---|---|---|
| xhCD8 | QVHLQQSGPELVKPGASVKMSCKTSGYTFTKY<br>TMHWVKQGHEESLEWIGHFNPNNDETKYNQ<br>KFTGKATLTVDKSSTTAYMELRSLTSDDSALYY<br>CARDGLGLRLFADWGQGTLITVSA<br>(SEQ ID NO: 107) | DIQMTQSPASLSASVGETVTITCGASENIYGAL<br>NWYQRKQGKSPQLLIFGATNLADGVSSRFSGS<br>GSDRQYSLKISSLHPDDVATYYCQNILDTPWTF<br>GGGTKLEIK<br>(SEQ ID NO: 108) |
| xhCD8v1 | QVQLVQSGAEVKKPGSSVKVSCKASGYTFTKY<br>AISWVRQAPGQGLEWMGHFNPNNDETKYN<br>QKFQGRVTITADESTSTAYMELSSLRSEDTAVY<br>YCARDGLGLRLFADWGQGT LVTVSS<br>(SEQ ID NO: 258) | DIQMTQSPSSLSASVGDRVTITCRASENIYGAL<br>NWYQQKPGKAPKLLIYGATNLADGVPSRFSGS<br>GSGTDFTLTISSLQPEDFATYYCQNILDTPWTF<br>GGGTKLEIK<br>(SEQ ID NO: 259) |
| xhCD8v2 | QVQLVQSGAEVKKPGSSVKVSCKASGYRFHNF<br>AISWVRQAPGQGLEWMGGIIPGHAKANYAQ<br>KFQGRVTITADESTSTAYMELSSLRSEDTAVYY<br>CARDGLGIRLFADWGQGTLVTVSS<br>(SEQ ID NO: 109) | DIQMTQSPSSLSASVGDRVTITCRASQEIYGAL<br>NWYQQKPGKAPKLLIYGATNLQSGVPSRFSGS<br>GSGTDFTLTISSLQPEDFATYYCQDIYDAPWTF<br>GGGTKVEIK<br>(SEQ ID NO: 110) |
| xhCD8v3 | QVQLVQSGAEVKKPGSSVKVSCKASGSRFYKF<br>AISWVRQAPGQGLEWMGGIIPGHAKANYAQ<br>KFQGRVTITADESTSTAYMELSSLRSEDTAVYY<br>CARDGLGIRLFADWGQGTLVTVSS<br>(SEQ ID NO: 111) | DIQMTQSPSSLSASVGDRVTITCRASQEIYGAL<br>NWYQQKPGKAPKLLIYGATNLQSGVPSRFSGS<br>GSGTDFTLTISSLQPEDFATYYCQDIYDAPWTF<br>GGGTKVEIK<br>(SEQ ID NO: 112) |
| xhCD8v4 | QVQLVQSGAEVKKPGSSVKVSCKASGYTFTKY<br>AISWVRQAPGQGLEWMGGIIPGHAKANYAQ<br>KFQGRVTITADESTSTAYMELSSLRSEDTAVYY<br>CARDGLGIRLFADWGQGTLVTVSS<br>(SEQ ID NO: 113) | DIQMTQSPSSLSASVGDRVTITCRASQKIYGAL<br>NWYQQKPGKAPKLLIYGATNLQSGVPSRFSGS<br>GSGTDFTLTISSLQPEDFATYYCQNTYDTPWTF<br>GGGTKVEIK<br>(SEQ ID NO: 114) |

TABLE 12-continued

Anti-CD8 antibody variable domain sequences

| Name | VH | VL |
|---|---|---|
| xhCD8v5 | QVQLVQSGAEVKKPGSSVKVSCKASGSGFRG HAISWVRQAPGQGLEWMGGIIPGHAKANYA QKFQGRVTITADESTSTAYMELSSLRSEDTAVY YCARDGLGIRLFADWGQGTLVTVSS (SEQ ID NO: 115) | DIQMTQSPSSLSASVGDRVTITCRASQKIYGAL NWYQQKPGKAPKLLIYGATNLQSGVPSRFSGS GSGTDFTLTISSLQPEDFATYYCQNTYDTPWTF GGGTKVEIK (SEQ ID NO: 116) |
| xhCD8v6 | EVQLVESGGGAVRPGGSLRLSCAASGFTFDDY GMSWVRQAPGKGLEWVSDINWSGEITAYAD SVKGRFTISRDNAKNSLYLQMNSLRAEDTAVY YCARSNSYRWDDALDIWGQGTMVTVSS (SEQ ID NO: 117) | EIVLTQSPATLSVSPGERATLSCRASQSVSSNL AWYQQKPGQAPRLLIYGASSRATGIPDRFSGSG SGTDFTLTISRLEPEDFAVYYCQQYGSSPPVTF GQGTKVEIK (SEQ ID NO: 118) |
| xhCD8v7 | EVQLVESGGGLVQPGRSLRLSCAASGFTFDDY AMHWVRQAPGKGLEWVAVISYDGSNKYYAD SVKGRFTISRDNSKNTLYLQMNSLRAEDTAVY YCAKDRIGWYDYDAFDIWGQGTMVTVSS (SEQ ID NO: 119) | EIVLTQSPATLSVTPGEGATLSCRASHSVGSNL AWYQQKPGQAPRLLIYDASNRATGIPARFSGS GSGTDFTLTISSLEPEDLAVYYCQQRSNWPPTF GQGTRLEIK (SEQ ID NO: 120) |
| xhCD8v8 | QVQLQQSGAELVRPGSSVKISCKASGYAFSSY WMNWVKQRPGQGLEWIGQIYPGDGDTNYN GKFKGKATLTADKSSSTAYMQLSSLTSEDSAVY FCARSGAAFSSYYAMDYWGQGTSVTVSS (SEQ ID NO: 121) | DIQMTQSPASLSVSVGETVTITCRASENIYSNL AWYQQKQGKSPQLLVYAATNLADGVPSRFSG SGSGTQYSLKINSLQSEDFGSYYCQHFWGTPW TFGGGTKLEIK (SEQ ID NO: 122) |
| xhCD8v9 | QVQLVQSGAEVKKPGSSVKVSCKASGGTFSSY AISWVRQAPGQGLEWMGGIIPGAATANYAQ KFQGRVTITADESTSTAYMELSSLRSEDTAVYY CARDAAGIRLFADWGQGTLVTVSS (SEQ ID NO: 123) | DIQMTQSPSSLSASVGDRVTITCRASQEIYGAL NWYQQKPGKAPKLLIYGATNLQSGVPSRFSGS GSGTDFTLTISSLQPEDFATYYCQSTYDAPWTF GGGTKVEIK (SEQ ID NO: 124) |
| xhCD8v10 | EVQLVESGGGLVQPGGSLRLSCAASGFTFSSY AMSWVRQAPGKGLEWVSDITYAGGSTAYAD SVKGRFTISRDNAKNSLYLQMNSLRAEDTAVY YCARSNAYAWDDALDIWGQGTMVTVSS (SEQ ID NO: 125) | EIVLTQSPGTLSLSPGERATLSCRASQSVSSNL AWYQQKPGQAPRLLIYGASSRATGIPDRFSGSG SGTDFTLTISRLEPEDFAVYYCQQYGSSPPVTF GQGTKVEIK (SEQ ID NO: 126) |
| xhCD8v11 | EVQLVESGGGLVQPGGSLRLSCAASGFTFSSY AMSWVRQAPGKGLEWVSDITYAGGSTAYAD SVKGRFTISRDNAKNSLYLQMNSLRAEDTAVY YCARSNAYAWDDALDIWGQGTLVTVSS (SEQ ID NO: 127) | EIVLTQSPGTLSLSPGERATLSCRASQSVSSNL AWYQQKPGQAPRLLIYGASSRATGIPDRFSGSG SGTDFTLTISRLEPEDFAVYYCQQYGSSPPVTF GQGTKVEIK (SEQ ID NO: 128) |
| xhCD8v12 (xhCD8.1) | QVQLVQSGAEVKKPGSSVKVSCKASGGTFSSY AISWVRQAPGQGLEWMGGIIPGYATANYAQ KFQGRVTITADESTSTAYMELSSLRSEDTAVYY CARDAAGIRLFADWGQGTLVTVSS (SEQ ID NO: 129) | DIQMTQSPSSLSASVGDRVTITCRASQSIYGAL NWYQQKPGKAPKLLIYGASNLQSGVPSRFSGS GSGTDFTLTISSLQPEDFATYYCQSTYTAPWTF GGGTKVEIK (SEQ ID NO: 130) |
| xhCD8v13 | QVQLVQSGAEVKKPGSSVKVSCKASGGTFSSY AISWVRQAPGQGLEWMGGIIPGYATANYAQ KFQGRVTITADESTSTAYMELSSLRSEDTAVYY CARDAAGIRLFADWGQGTLVTVSS (SEQ ID NO: 131) | DIQMTQSPSSLSASVGDRVTITCRASQEIYGAL NWYQQKPGKAPKLLIYGATNLQSGVPSRFSGS GSGTDFTLTISSLQPEDFATYYCQSTYDAPWTF GGGTKVEIK (SEQ ID NO: 132) |
| xhCD8v14 | EVQLVESGGGLVQPGGSLRLSCAASGFTFSSY AMSWVRQAPGKGLEWVSDISYAGGSTAYAD SVKGRFTISRDNAKNSLYLQMNSLRAEDTAVY YCARSNAYAWDDALDIWGQGTMVTVSS (SEQ ID NO: 133) | EIVLTQSPGTLSLSPGERATLSCRASQSVSSNL AWYQQKPGQAPRLLIYGASSRATGIPDRFSGSG SGTDFTLTISRLEPEDFAVYYCQQYGSSPPVTF GQGTKVEIK (SEQ ID NO: 134) |
| xhCD8v15 | EVQLVESGGGLVQPGGSLRLSCAASGFTFSSY AMSWVRQAPGKGLEWVSDISYAGGSTAYAD SVKGRFTISRDNAKNSLYLQMNSLRAEDTAVY YCARSNAYAWDDALDIWGQGTLVTVSS (SEQ ID NO: 135) | EIVLTQSPGTLSLSPGERATLSCRASQSVSSNL AWYQQKPGQAPRLLIYGASSRATGIPDRFSGSG SGTDFTLTISRLEPEDFAVYYCQQYGSSPPVTF GQGTKVEIK (SEQ ID NO: 136) |

TABLE 13

Intermediate and final yields for fusion proteins of IL-21 charge variants

| Fusion protein | Yield after Protein A (mg/L) | Yield after Protein A + IEX (mg/L) |
|---|---|---|
| xhCD8.1-hIL21 v31.4 | 198 | 89 |
| xhCD8.1-hIL21 v31.23 | 170 | 83 |
| xhCD8v11-hIL21 v31.23 | 158 | 77 |

TABLE 14

Wild type IL-21 variants

| IL-21 Mutein | Amino Acid Sequence | $K_D$ at 25° C. (nM) | SEQ ID NO |
|---|---|---|---|
| IL-21 | QGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS | 0.25 | 1 |
| IL-21 v0.1 | QGQDRHMIRMDQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS | 0.54 | 313 |
| IL-21 v0.2 | QGQDRHMIRMEQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS | 0.37 | 314 |
| IL-21 v0.3 | QGQDRHMIRMRQLDDIVAQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQAMIHQHLSSRTHGSEDS | NB | 315 |
| IL-21 v0.4 | QGQDRHMIRMRQLIDIVDQLKNYVNDLVPEFLPAPEDVETNCEWSAFSCFQKAQLKSANTGNNERIINVSIKKLKEKPPSTNAGRRQKHRLTCPSCDSYEKKPPKEFLERFKSLLQKMIHQHLSSRTHGSEDS | >10000 | 316 |
| IL-21 v0.5 | QGQDFHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS | 5.5 | 317 |
| IL-21 v0.6 | QGQDRHMIRMRQLIDIVDQLKNYVNDLVPEFLPAPEDVETNCEWSAFSCFQKAQLKSANTGNNERIINVSIKKLKFKPPSTNAGRRQKHRLTCPSCDSYEKKPPKEFLERFKSLLQKMIHQHLSSRTHGSEDS | 2205 | 318 |
| IL-21 v0.7 | QGQDRHMERMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS | 171.9 | 319 |
| IL-21 v0.8 | QGQDAHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS | 12.4 | 320 |
| IL-21 v0.9 | QGQDEHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS | 184.6 | 321 |
| IL-21 v0.10 | QGQDSHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS | 20.8 | 322 |

TABLE 14-continued

Wild type IL-21 variants

| IL-21 Mutein | Amino Acid Sequence | $K_D$ at 25° C. (nM) | SEQ ID NO |
|---|---|---|---|
| IL-21 v0.11 | QGQDTHMIRMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 6.6 | 323 |
| IL-21 v0.12 | QGQDNHMIRMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 23.4 | 324 |
| IL-21 v0.13 | QGQDQHMIRMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 7.7 | 325 |
| IL-21 v0.14 | QGQDVHMIRMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 4.6 | 326 |
| IL-21 v0.15 | QGQDIHMIRMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 6.2 | 327 |
| IL-21 v0.16 | QGQDLHMIRMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 2.5 | 328 |
| IL-21 v0.17 | QGQDYHMIRMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 7.2 | 329 |
| IL-21 v0.18 | QGQDRHMIRMRQLIDIVDQLKNYVNDLVPEFLPAPEDVETNC EWSAFSCFQKAQLKSANTGNNERIINVSIKKLKAKPPSTNAG RRQKHRLTCPSCDSYEKKPPKEFLERFKSLLQKMIHQHLSSR THGSEDS | 2976 | 330 |
| IL-21 v0.19 | QGQDRHMIRMRQLIDIVDQLKNYVNDLVPEFLPAPEDVETNC EWSAFSCFQKAQLKSANTGNNERIINVSIKKLKNKPPSTNAG RRQKHRLTCPSCDSYEKKPPKEFLERFKSLLQKMIHQHLSSR THGSEDS | 3981 | 331 |
| IL-21 v0.20 | QGQDRHMIRMRQLIDIVDQLKNYVNDLVPEFLPAPEDVETNC EWSAFSCFQKAQLKSANTGNNERIINVSIKKLKDKPPSTNAG RRQKHRLTCPSCDSYEKKPPKEFLERFKSLLQKMIHQHLSSR THGSEDS | >10000 | 332 |
| IL-21 v0.21 | QGQDRHMIRMRQLIDIVDQLKNYVNDLVPEFLPAPEDVETNC EWSAFSCFQKAQLKSANTGNNERIINVSIKKLKSKPPSTNAG RRQKHRLTCPSCDSYEKKPPKEFLERFKSLLQKMIHQHLSSR THGSEDS | 3671 | 333 |
| IL-21 v0.22 | QGQDRHMIRMRQLIDIVDQLKNYVNDLVPEFLPAPEDVETNC EWSAFSCFQKAQLKSANTGNNERIINVSIKKLKTKPPSTNAG RRQKHRLTCPSCDSYEKKPPKEFLERFKSLLQKMIHQHLSSR THGSEDS | 4085 | 334 |
| IL-21 v0.23 | QGQDRHMIRMRQLIDIVDQLKNYVNDLVPEFLPAPEDVETNC EWSAFSCFQKAQLKSANTGNNERIINVSIKKLKQKPPSTNAG RRQKHRLTCPSCDSYEKKPPKEFLERFKSLLQKMIHQHLSSR THGSEDS | 3375 | 335 |
| IL-21 v0.24 | QGQDRHMIRMRQLIDIVDQLKNYVNDLVPEFLPAPEDVETNC EWSAFSCFQKAQLKSANTGNNERIINVSIKKLKVKPPSTNAG RRQKHRLTCPSCDSYEKKPPKEFLERFKSLLQKMIHQHLSSR THGSEDS | 4351 | 336 |

TABLE 14-continued

Wild type IL-21 variants

| IL-21 Mutein | Amino Acid Sequence | $K_D$ at 25° C. (nM) | SEQ ID NO |
|---|---|---|---|
| IL-21 v0.25 | QGQDRHMIRMRQLIDIVDQLKNYVNDLVPEFLPAPEDVETNC EWSAFSCFQKAQLKSANTGNNERIINVSIKKLKIKPPSTNAG RRQKHRLTCPSCDSYEKKPPKEFLERFKSLLQKMIHQHLSSR THGSEDS | 3639 | 337 |
| IL-21 v0.26 | QGQDRHMIRMRQLIDIVDQLKNYVNDLVPEFLPAPEDVETNC EWSAFSCFQKAQLKSANTGNNERIINVSIKKLKLKPPSTNAG RRQKHRLTCPSCDSYEKKPPKEFLERFKSLLQKMIHQHLSSR THGSEDS | 934.1 | 338 |
| IL-21 v0.27 | QGQDRHMIRMRQLIDIVDQLKNYVNDLVPEFLPAPEDVETNC EWSAFSCFQKAQLKSANTGNNERIINVSIKKLKYKPPSTNAG RRQKHRLTCPSCDSYEKKPPKEFLERFKSLLQKMIHQHLSSR THGSEDS | 1353 | 339 |
| IL-21 v0.28 | QGQDRHMIRMRQLIDIVDQLKNYVNDLVPEFLPAPEDVETNC EWSAFSCFQKAQLKSANTGNNERIINVSIKKLKRAPPSTNAG RRQKHRLTCPSCDSYEKKPPKEFLERFKSLLQKMIHQHLSSR THGSEDS | 0.77 | 340 |
| IL-21 v0.29 | QGQDRHMIRMRQLIDIVDQLKNYVNDLVPEFLPAPEDVETNC EWSAFSCFQKAQLKSANTGNNERIINVSIKKLKREPPSTNAG RRQKHRLTCPSCDSYEKKPPKEFLERFKSLLQKMIHQHLSSR THGSEDS | 0.69 | 341 |
| IL-21 v0.30 | QGQDRHMIRMRQLIDIVDQLKNYVNDLVPEFLPAPEDVETNC EWSAFSCFQKAQLKSANTGNNERIINVSIAKLKRKPPSTNAG RRQKHRLTCPSCDSYEKKPPKEFLERFKSLLQKMIHQHLSSR THGSEDS | 0.72 | 342 |
| IL-21 v0.31 | QGQDRHMIRMRQLIDIVDQLKNYVNDLVPEFLPAPEDVETNC EWSAFSCFQKAQLKSANTGNNERIINVSIEKLKRKPPSTNAG RRQKHRLTCPSCDSYEKKPPKEFLERFKSLLQKMIHQHLSSR THGSEDS | 2.3 | 343 |
| IL-21 v0.32 | QGQDRHMIRMRQLIDIVDQLKNYVNDLVPEFLPAPEDVETNC EWSAFSCFQKAQLKSANTGNNERIINVSIKKLARKPPSTNAG RRQKHRLTCPSCDSYEKKPPKEFLERFKSLLQKMIHQHLSSR THGSEDS | 0.78 | 344 |
| IL-21 v0.33 | QGQDRHMIRMRQLIDIVDQLKNYVNDLVPEFLPAPEDVETNC EWSAFSCFQKAQLKSANTGNNERIINVSIKKLERKPPSTNAG RRQKHRLTCPSCDSYEKKPPKEFLERFKSLLQKMIHQHLSSR THGSEDS | 1.2 | 345 |
| IL-21 v0.34 | QGQDRHMIRMRQLIDIVDQLKNYVNDLVPEFLPAPEDVETNC EWSAFSCFQKAQLKSANTGNNERIINVSIKALKRKPPSTNAG RRQKHRLTCPSCDSYEKKPPKEFLERFKSLLQKMIHQHLSSR THGSEDS | 1.81 | 346 |
| IL-21 v0.35 | QGQDRHMIRMRQLIDIVDQLKNYVNDLVPEFLPAPEDVETNC EWSAFSCFQKAQLKSANTGNNERIINVSIKELKRKPPSTNAG RRQKHRLTCPSCDSYEKKPPKEFLERFKSLLQKMIHQHLSSR THGSEDS | 511.4 | 347 |
| IL-21 v0.36 | QGQDFHMIRMRQLIDIVDQLKNYVNDLVPEFLPAPEDVETNC EWSAFSCFQKAQLKSANTGNNERIINVSIKKLKRAPPSTNAG RRQKHRLTCPSCDSYEKKPPKEFLERFKSLLQKMIHQHLSSR THGSEDS | 40.2 | 348 |
| IL-21 v0.37 | QGQDFHMIRMRQLIDIVDQLKNYVNDLVPEFLPAPEDVETNC EWSAFSCFQKAQLKSANTGNNERIINVSIKKLKREPPSTNAG RRQKHRLTCPSCDSYEKKPPKEFLERFKSLLQKMIHQHLSSR THGSEDS | 46.4 | 349 |
| IL-21 v0.38 | QGQDFHMIRMRQLIDIVDQLKNYVNDLVPEFLPAPEDVETNC EWSAFSCFQKAQLKSANTGNNERIINVSIAKLKRKPPSTNAG RRQKHRLTCPSCDSYEKKPPKEFLERFKSLLQKMIHQHLSSR THGSEDS | 35.0 | 350 |

TABLE 14-continued

Wild type IL-21 variants

| IL-21 Mutein | Amino Acid Sequence | $K_D$ at 25° C. (nM) | SEQ ID NO |
|---|---|---|---|
| IL-21 v0.39 | QGQDFHMIRMRQLIDIVDQLKNYVNDLVPEFLPAPEDVETNC EWSAFSCFQKAQLKSANTGNNERIINVSIEKLKRKPPSTNAG RRQKHRLTCPSCDSYEKKPPKEFLERFKSLLQKMIHQHLSSR THGSEDS | 265.1 | 351 |
| IL-21 v0.40 | QGQDFHMIRMRQLIDIVDQLKNYVNDLVPEFLPAPEDVETNC EWSAFSCFQKAQLKSANTGNNERIINVSIKKLARKPPSTNAG RRQKHRLTCPSCDSYEKKPPKEFLERFKSLLQKMIHQHLSSR THGSEDS | 31.9 | 352 |
| IL-21 v0.41 | QGQDFHMIRMRQLIDIVDQLKNYVNDLVPEFLPAPEDVETNC EWSAFSCFQKAQLKSANTGNNERIINVSIKKLERKPPSTNAG RRQKHRLTCPSCDSYEKKPPKEFLERFKSLLQKMIHQHLSSR THGSEDS | 86.9 | 353 |
| IL-21 v0.42 | QGQDRHMIRMRQLIDIVDQLKNYVNDLVPEFLPAPEDVETNC EWSAFSCFQKAQLKSANTGNNERIINVSIKALKFKPPSTNAG RRQKHRLTCPSCDSYEKKPPKEFLERFKSLLQKMIHQHLSSR THGSEDS | >10000 | 354 |
| IL-21 v0.43 | QGQDRHMIRMRQLIDIVDQLKNYVNDLVPEFLPAPEDVETNC EWSAFSCFQKAQLKSANTGNNERIINVSIKELKFKPPSTNAG RRQKHRLTCPSCDSYEKKPPKEFLERFKSLLQKMIHQHLSSR THGSEDS | NB | 355 |
| IL-21 v0.44 | QGQDRHMIAMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 4982 | 356 |
| IL-21 v0.45 | QGQDRHMIDMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | >10000 | 357 |
| IL-21 v0.46 | QGQDRHMIEMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | >10000 | 358 |
| IL-21 v0.47 | QGQDRHMIHMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 11.9 | 359 |
| IL-21 v0.48 | QGQDRHMISMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 3932 | 360 |
| IL-21 v0.49 | QGQDRHMITMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 11664 | 361 |
| IL-21 v0.50 | QGQDRHMINMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 4159 | 362 |
| IL-21 v0.51 | QGQDRHMIGMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 7677 | 363 |
| IL-21 v0.52 | QGQDRHMIVMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 11082 | 364 |
| IL-21 v0.53 | QGQDRHMIIMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | >10000 | 365 |

TABLE 14-continued

Wild type IL-21 variants

| IL-21 Mutein | Amino Acid Sequence | K_D at 25° C. (nM) | SEQ ID NO |
|---|---|---|---|
| IL-21 v0.54 | QGQDRHMILMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 7168 | 366 |
| IL-21 v0.55 | QGQDRHMIYMRQLIDIVDQLKNYVNDLVPEFLPAPEDVETNC EWSAFSCFQKAQLKSANTGNNERIINVSIKKLKRKPPSTNAG RRQKHRLTCPSCDSYEKKPPKEFLERFKSLLQKMIHQHLSSR THGSEDS | 675.7 | 367 |
| IL-21 v0.56 | QGQDRHMIRMRQLIDIVDQLKNYVNDLVPEFLPAPEDVETNC EWSAFSCFQKAQLKSANTGNNERIINVSIAKLKFKPPSTNAG RRQKHRLTCPSCDSYEKKPPKEFLERFKSLLQKMIHQHLSSR THGSEDS | 3431 | 368 |
| IL-21 v0.57 | QGQDRHMIRMRQLIDIVDQLKNYVNDLVPEFLPAPEDVETNC EWSAFSCFQKAQLKSANTGNNERIINVSIKKLAFKPPSTNAG RRQKHRLTCPSCDSYEKKPPKEFLERFKSLLQKMIHQHLSSR THGSEDS | 5041 | 369 |
| IL-21 v0.58 | QGQDRHMIRMRQLIDIVDQLKNYVNDLVPEFLPAPEDVETNC EWSAFSCFQKAQLKSANTGNNERIINVSIKKLKFAPPSTNAG RRQKHRLTCPSCDSYEKKPPKEFLERFKSLLQKMIHQHLSSR THGSEDS | 4760 | 370 |
| IL-21 v0.59 | QGQDRHMIRMRQLIDIVDQLKNYVNDLVPEFLPAPEDVETNC EWSAFSCFQKAQLKSANTGNNERIINVSIKKLEFKPPSTNAG RRQKHRLTCPSCDSYEKKPPKEFLERFKSLLQKMIHQHLSSR THGSEDS | NB | 371 |
| hIL21 v31 | QGQDRHMIRMRQLIDIVDQLKNYVNDLVPEFLPAPEDVETNC EWSAFSCFQKAQLKSANTGNNERIINVSIKKLKRKPPGGEGG GGGGGEGGCPSCDSYEKKPPKEFLERFKSLLQKMIHQHLSSR THGSEDS | 0.24 | 40 |
| hIL21 v31.4 | QGQDRHMIRMRQLIDIVDQLKNYVNDLVPEFLPAPEDVETNC EWSAFSCFQKAQLKSANTGNNERIINVSIKKLKEKPPGGEGG GGGGGEGGCPSCDSYEKKPPKEFLERFKSLLQKMIHQHLSSR THGSEDS | >10000 | 94 |
| hIL21 v31.23 | QGQDRHMIRMRQLIDIVDQLKNYVNDLVPEFLPAPEDVETNC EWSAFSCFQKAQLKSANTGNNERIINVSIKKLKQKPPGGEGG GGGGGEGGCPSCDSYEKKPPKEFLERFKSLLQKMIHQHLSSR THGSEDS | 6059 | 96 |
| hIL21 v31.51 | QGQDRHMIGMRQLIDIVDQLKNYVNDLVPEFLPAPEDVETNC EWSAFSCFQKAQLKSANTGNNERIINVSIKKLKRKPPGGEGG GGGGGEGGCPSCDSYEKKPPKEFLERFKSLLQKMIHQHLSSR THGSEDS | 7730 | 98 |
| IL-21 v2.63 | QGQDRHMIRMRQLIDRIDQLKNYVNDLVPEFLPAPEDVETNC EWSAFSCFQKAQLKSANTGNNERIINVSIKKIKRKPPSTNAG GGQGHELTCPSCDSYEKKPPKEFLERFKSLLQKMIHQHLSSR THGSEDS | 1186 | 377 |
| IL-21 v2.64 | QGQDRHMIRMRQFIDAADQLKNYVNDLVPEFLPAPEDVETNC EWSAFSCFQKAQLKSANTGNNERIINVSIKKMKRKPPSTNAG GGQGHELTCPSCDSYEKKPPKEFLERFKSLLQKMIHQHLSSR THGSEDS | 2823 | 378 |
| IL-21 v2.65 | QGQDRHMIRMRQRIDAIDQLKNYVNDLVPEFLPAPEDVETNC EWSAFSCFQKAQLKSANTGNNERIINVSIKKIKRKPPSTNAG GGQGHELTCPSCDSYEKKPPKEFLERFKSLLQKMIHQHLSSR THGSEDS | 10471 | 379 |

TABLE 15

Polyreactivity ELISA of IL-21R-attenuated fusion proteins

| Construct | Binding to KLH | Binding to heparin | Binding to hemoglobin |
| --- | --- | --- | --- |
| Bococizumab | 24.35 | 10.20 | 25.37 |
| xhCD8.1-hIL21 v0.4 | 5.67 | 7.39 | 6.59 |
| xhCD8.1-hIL21 v31.4 | 2.98 | 2.92 | 3.94 |
| xhCD8.1-hIL21 v31.23 | 4.66 | 3.61 | 5.45 |
| xhCD8v11-hIL21 v31.23 | 3.06 | 3.37 | 2.10 |

TABLE 16

Polyreactivity ELISA of non-fusion IL-21 and IL-21 variants

| Construct | Binding to KLH | Binding to heparin | Binding to hemoglobin |
| --- | --- | --- | --- |
| hIL21 | 24.06 | 51.09 | 31.42 |
| hIL21 v0.51 | 23.54 | 48.90 | 30.58 |
| hIL21 v0.4 | 22.93 | 44.65 | 28.60 |
| hIL21 v0.23 | 23.76 | 51.02 | 30.94 |
| hIL21 v31 | 20.97 | 44.73 | 19.99 |
| hIL21 v31.51 | 15.67 | 31.45 | 12.22 |
| hIL21 v31.4 | 6.44 | 12.22 | 3.40 |
| hIL21 v31.23 | 12.78 | 26.22 | 9.81 |

SEQUENCE LISTING

```
Sequence total quantity: 392
SEQ ID NO: 1              moltype = AA  length = 133
FEATURE                   Location/Qualifiers
source                    1..133
                          mol_type = protein
                          organism = Homo sapiens
SEQUENCE: 1
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDS                                                    133

SEQ ID NO: 2              moltype = AA  length = 133
FEATURE                   Location/Qualifiers
REGION                    1..133
                          note = Description of Artificial Sequence: Synthetic
                          polypeptide
source                    1..133
                          mol_type = protein
                          organism = synthetic construct
SEQUENCE: 2
QGQDRHMIRM RQLIDIVDQL KNYVNDLVPE FLPAPEDVET NCEWSAFSCF QKAQLKSANT  60
GNNERIINVS IKKLKRKPPS TNAGGGQGHE LTCPSCDSYE KKPPKEFLER FKSLLQKMIH  120
QHLSSRTHGS EDS                                                    133

SEQ ID NO: 3              moltype = AA  length = 133
FEATURE                   Location/Qualifiers
REGION                    1..133
                          note = Description of Artificial Sequence: Synthetic
                          polypeptide
VARIANT                   5
                          note = R, A, D, E, S, T, N, Q, V, I, L, Y, or F
VARIANT                   8
                          note = I, Q, H, or E
VARIANT                   9
                          note = R, A, D, E, S, T, N, Q, V, I, L, Y, or F
VARIANT                   11
                          note = R, D or E
VARIANT                   12
                          note = Q, L, I, or Y
VARIANT                   14
                          note = I or D or E
VARIANT                   15
                          note = D, R, K, H, L, Y, or F
VARIANT                   18
                          note = D, A, K, or R
VARIANT                   19
                          note = Q, L, or Y
VARIANT                   23
                          note = Y or E
VARIANT                   56
                          note = G, S, E, D, or A
VARIANT                   65
                          note = R, G, S, E, D, or A
VARIANT                   70
                          note = S, H, Y, L, V, or F
VARIANT                   72
                          note = K, G, S, E, D, or A
VARIANT                   73
```

```
                        note = K, A, Y, L, F, G, S, T, E, A, or D
VARIANT                 75
                        note = K, G, S, E, D, or A
VARIANT                 76
                        note = R, A, D, E, S, T, N, Q, V, I, L, Y, or F
VARIANT                 77
                        note = K, G, S, E, D, or A
VARIANT                 80
                        note = S, H, A, G, E, or D
VARIANT                 81
                        note = G, S, E, D, or A
VARIANT                 82
                        note = G, S, E, D, or A
VARIANT                 83
                        note = G, S, E, or D
VARIANT                 84
                        note = A, S, E, or D
VARIANT                 85
                        note = G, S, E, D, or A
VARIANT                 86
                        note = G, S, E, D, or A
VARIANT                 87
                        note = G, S, E, D, or A
VARIANT                 88
                        note = G, S, E, D, or A
VARIANT                 89
                        note = G, S, E, D, or A
VARIANT                 90
                        note = G, S, E, D, or A
VARIANT                 91
                        note = G, S, E, D, or A
VARIANT                 92
                        note = G, S, E, D, or A
VARIANT                 117
                        note = A, D, or E
source                  1..133
                        mol_type = protein
                        organism = synthetic construct
SEQUENCE: 3
QGQDXHMXXM XXLXXIV

```
GNNERIIINVS IKKLARKPPS TNAGGGQGHA LTCPSCDSYE KKPPKEFLER FKSLLQKMIH    120
QHLSSRTHGS EDS                                                       133

SEQ ID NO: 7              moltype = AA  length = 133
FEATURE                   Location/Qualifiers
REGION                    1..133
                          note = Description of Artificial Sequence: Synthetic
                            polypeptide
source                    1..133
                          mol_type = protein
                          organism = synthetic construct
SEQUENCE: 7
QGQDRHMIRM RQLIDIVDQL KNYVNDLVPE FLPAPEDVET NCEWSAFSCF QKAQLASANT     60
GNNERIIINVS IKKLERKPPS TNAGGGQGHA LTCPSCDSYE KKPPKEFLER FKSLLQKMIH   120
QHLSSRTHGS EDS                                                       133

SEQ ID NO: 8              moltype = AA  length = 133
FEATURE                   Location/Qualifiers
REGION                    1..133
                          note = Description of Artificial Sequence: Synthetic
                            polypeptide
source                    1..133
                          mol_type = protein
                          organism = synthetic construct
SEQUENCE: 8
QGQDRHMIRM RQLIDIVDQL KNYVNDLVPE FLPAPEDVET NCEWSAFSCF QKAQLASANT     60
GNNERIIINVS IKKLARKPPS TNAGGGQGHE LTCPSCDSYE KKPPKEFLER FKSLLQKMIH   120
QHLSSRTHGS EDS                                                       133

SEQ ID NO: 9              moltype = AA  length = 133
FEATURE                   Location/Qualifiers
REGION                    1..133
                          note = Description of Artificial Sequence: Synthetic
                            polypeptide
source                    1..133
                          mol_type = protein
                          organism = synthetic construct
SEQUENCE: 9
QGQDRHMIRM RQLIDIVDQL KNYVNDLVPE FLPAPEDVET NCEWSAFSCF QKAQLKSANT     60
GNNERIIINVS IKKLKRKPPG GGSGEGSGGS LTCPSCDSYE KKPPKEFLER FKSLLQKMIH   120
QHLSSRTHGS EDS                                                       133

SEQ ID NO: 10             moltype = AA  length = 133
FEATURE                   Location/Qualifiers
REGION                    1..133
                          note = Description of Artificial Sequence: Synthetic
                            polypeptide
source                    1..133
                          mol_type = protein
                          organism = synthetic construct
SEQUENCE: 10
QGQDRHMIRM RQLIDIVDQL KNYVNDLVPE FLPAPEDVET NCEWSAFSCF QKAQLKSANT     60
GNNERIIINVS IKKLKRKPPG GGSGGGSGGE LTCPSCDSYE KKPPKEFLER FKSLLQKMIH   120
QHLSSRTHGS EDS                                                       133

SEQ ID NO: 11             moltype = AA  length = 133
FEATURE                   Location/Qualifiers
REGION                    1..133
                          note = Description of Artificial Sequence: Synthetic
                            polypeptide
source                    1..133
                          mol_type = protein
                          organism = synthetic construct
SEQUENCE: 11
QGQDRHMIRM RQLIDIVDQL KNYVNDLVPE FLPAPEDVET NCEWSAFSCF QKAQLKSANT     60
GNNERIIINVS IKKLKRKPPS TNAGGGSGGE LTCPSCDSYE KKPPKEFLER FKSLLQKMIH   120
QHLSSRTHGS EDS                                                       133

SEQ ID NO: 12             moltype = AA  length = 133
FEATURE                   Location/Qualifiers
REGION                    1..133
                          note = Description of Artificial Sequence: Synthetic
                            polypeptide
source                    1..133
                          mol_type = protein
                          organism = synthetic construct
SEQUENCE: 12
QGQDRHMIRM RQLIDIVDQL KNYVNDLVPE FLPAPEDVET NCEWSAFSCF QKAQLKSANT     60
GNNERIIINVS IKKLKRKPPS TNAGGGSGGS LTCPSCDSYE KKPPKEFLER FKSLLQKMIH   120
```

```
QHLSSRTHGS EDS                                                                  133

SEQ ID NO: 13           moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 13
QGQDRHMIRM RQLIDIVDQL KNYVNDLVPE FLPAPEDVET NCEWSAFSCF QKAQLKSANT   60
GNNERIINVS IKKLKRKPPS TNAGGGGGGE LTCPSCDSYE KKPPKEFLER FKSLLQKMIH  120
QHLSSRTHGS EDS                                                    133

SEQ ID NO: 14           moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 14
QGQDRHMIRM RQLIDIVDQL KNYVNDLVPE FLPAPEDVET NCEWSAFSCF QKAQLKSANT   60
GNNERIINVS IKKLKRKPPS TNAGGGGGGG LTCPSCDSYE KKPPKEFLER FKSLLQKMIH  120
QHLSSRTHGS EDS                                                    133

SEQ ID NO: 15           moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 15
QGQDRHMIRM RQLIDIVDQL KNYVNDLVPE FLPAPEDVET NCEWSAFSCF QKAQLKSANT   60
GNNERIINVS IKKLKRKPPS TNAGGGEGGG LTCPSCDSYE KKPPKEFLER FKSLLQKMIH  120
QHLSSRTHGS EDS                                                    133

SEQ ID NO: 16           moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 16
QGQDRHMIRM DQLIDIVDQL KNYVNDLVPE FLPAPEDVET NCEWSAFSCF QKAQLKSANT   60
GNNERIINVS IKKLKRKPPS TNAGGGQGHE LTCPSCDSYE KKPPKEFLER FKSLLQKMIH  120
QHLSSRTHGS EDS                                                    133

SEQ ID NO: 17           moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 17
QGQDRHMIRM EQLIDIVDQL KNYVNDLVPE FLPAPEDVET NCEWSAFSCF QKAQLKSANT   60
GNNERIINVS IKKLKRKPPS TNAGGGQGHE LTCPSCDSYE KKPPKEFLER FKSLLQKMIH  120
QHLSSRTHGS EDS                                                    133

SEQ ID NO: 18           moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 18
QGQDRHMIRM RQLDDIVAQL KNYVNDLVPE FLPAPEDVET NCEWSAFSCF QKAQLKSANT   60
GNNERIINVS IKKLKRKPPS TNAGGGQGHE LTCPSCDSYE KKPPKEFLER FKSLLQAMIH  120
QHLSSRTHGS EDS                                                    133
```

```
SEQ ID NO: 19              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 19
QGQDRHMIRM RQLIDIVDQL KNYVNDLVPE FLPAPEDVET NCEWSAFSCF QKAQLKSANT    60
GNNERIINVS IKKLKEKPPS TNAGGGQGHE LTCPSCDSYE KKPPKEFLER FKSLLQKMIH   120
QHLSSRTHGS EDS                                                      133

SEQ ID NO: 20              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 20
QGQDFHMIRM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                      133

SEQ ID NO: 21              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 21
QGQDRHMIRM RQLIDIVDQL KNYVNDLVPE FLPAPEDVET NCEWSAFSCF QKAQLKSANT    60
GNNERIINVS IKKLKFKPPS TNAGGGQGHE LTCPSCDSYE KKPPKEFLER FKSLLQKMIH   120
QHLSSRTHGS EDS                                                      133

SEQ ID NO: 22              moltype = AA  length = 133
FEATURE                    Location/Qualifiers
REGION                     1..133
                           note = Description of Artificial Sequence: Synthetic
                            polypeptide
VARIANT                    5
                           note = R, A, D, E, S, T, N, Q, V, I, L, Y, or F
VARIANT                    8
                           note = I, Q, H, or E
VARIANT                    9
                           note = R, A, D, E, S, T, N, Q, V, I, L, Y, or F
VARIANT                    11
                           note = R, D or E
VARIANT                    12
                           note = Q, L, I, or Y
VARIANT                    14
                           note = I, D or E
VARIANT                    15
                           note = D, R, K, H, L, Y, or F
VARIANT                    18
                           note = D, A, K, or R
VARIANT                    19
                           note = Q, L, or Y
VARIANT                    23
                           note = Y or E
VARIANT                    65
                           note = R, G, S, E, D, or A
VARIANT                    70
                           note = S, H, Y, L, V, or F
VARIANT                    72
                           note = K, G, S, E, D, or A
VARIANT                    73
                           note = K, A, Y, L, F, G, S, T, E, A, or D
VARIANT                    75
                           note = K, G, S, E, D, or A
VARIANT                    76
                           note = R, A, D, E, S, T, N, Q, V, I, L, Y, or F
VARIANT                    77
                           note = K, G, S, E, D, or A
```

```
VARIANT                  80
                         note = S, H, A, G, E, or D
VARIANT                  116
                         note = Q or Y
VARIANT                  117
                         note = K, A, D, or E
source                   1..133
                         mol_type = protein
                         organism = synthetic construct
SEQUENCE: 22
QGQDXHMXXM XXLXXIVXXL KNXVNDLVPE FLPAPEDVET NCEWSAFSCF QKAQLKSANT   60
GNNEXIINVX IXXLXXXPPX TNAGRRQKHR LTCPSCDSYE KKPPKEFLER FKSLLXXMIH  120
QHLSSRTHGS EDS                                                    133

SEQ ID NO: 23            moltype = AA  length = 133
FEATURE                  Location/Qualifiers
REGION                   1..133
                         note = Description of Artificial Sequence: Synthetic
                          polypeptide
source                   1..133
                         mol_type = protein
                         organism = synthetic construct
SEQUENCE: 23
QGQDRHMIRM RQLIDIVDQL KNYVNDLVPE FLPAPEDVET NCEWSAFSCF QKAQLKSANT   60
GNNERIINVS IKKLKRKPPG GGSGGGSGGG SGCPSCDSYE KKPPKEFLER FKSLLQKMIH  120
QHLSSRTHGS EDS                                                    133

SEQ ID NO: 24            moltype = AA  length = 133
FEATURE                  Location/Qualifiers
REGION                   1..133
                         note = Description of Artificial Sequence: Synthetic
                          polypeptide
source                   1..133
                         mol_type = protein
                         organism = synthetic construct
SEQUENCE: 24
QGQDRHMIRM RQLIDIVDQL KNYVNDLVPE FLPAPEDVET NCEWSAFSCF QKAQLKSANT   60
GNNERIINVS IKKLKRKPPG GGGGGGGGGG GGCPSCDSYE KKPPKEFLER FKSLLQKMIH  120
QHLSSRTHGS EDS                                                    133

SEQ ID NO: 25            moltype = AA  length = 133
FEATURE                  Location/Qualifiers
REGION                   1..133
                         note = Description of Artificial Sequence: Synthetic
                          polypeptide
source                   1..133
                         mol_type = protein
                         organism = synthetic construct
SEQUENCE: 25
QGQDRHMIRM RQLIDIVDQL KNYVNDLVPE FLPAPEDVET NCEWSAFSCF QKAQLKSANT   60
GNNERIINVS IKKLKRKPPG GGSGGGEGGG SGCPSCDSYE KKPPKEFLER FKSLLQKMIH  120
QHLSSRTHGS EDS                                                    133

SEQ ID NO: 26            moltype = AA  length = 133
FEATURE                  Location/Qualifiers
REGION                   1..133
                         note = Description of Artificial Sequence: Synthetic
                          polypeptide
source                   1..133
                         mol_type = protein
                         organism = synthetic construct
SEQUENCE: 26
QGQDRHMIRM RQLIDIVDQL KNYVNDLVPE FLPAPEDVET NCEWSAFSCF QKAQLKSANT   60
GNNERIINVS IKKLKRKPPG GGEGGGEGGG SGCPSCDSYE KKPPKEFLER FKSLLQKMIH  120
QHLSSRTHGS EDS                                                    133

SEQ ID NO: 27            moltype = AA  length = 133
FEATURE                  Location/Qualifiers
REGION                   1..133
                         note = Description of Artificial Sequence: Synthetic
                          polypeptide
source                   1..133
                         mol_type = protein
                         organism = synthetic construct
SEQUENCE: 27
QGQDRHMIRM RQLIDIVDQL KNYVNDLVPE FLPAPEDVET NCEWSAFSCF QKAQLKSANT   60
GNNERIINVS IKKLKRKPPS TGGGSGGGSG GSCPSCDSYE KKPPKEFLER FKSLLQKMIH  120
QHLSSRTHGS EDS                                                    133
```

```
SEQ ID NO: 28              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 28
QGQDRHMIRM RQLIDIVDQL KNYVNDLVPE FLPAPEDVET NCEWSAFSCF QKAQLKSANT   60
GNNERIINVS IKKLKRKPPS TGGGEGGGSG GSCPSCDSYE KKPPKEFLER FKSLLQKMIH  120
QHLSSRTHGS EDS                                                    133

SEQ ID NO: 29              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 29
QGQDRHMIRM RQLIDIVDQL KNYVNDLVPE FLPAPEDVET NCEWSAFSCF QKAQLKSANT   60
GNNERIINVS IKKLKRKPPG GGGGEGGGGG GGCPSCDSYE KKPPKEFLER FKSLLQKMIH  120
QHLSSRTHGS EDS                                                    133

SEQ ID NO: 30              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 30
QGQDRHMIRM RQLIDIVDQL KNYVNDLVPE FLPAPEDVET NCEWSAFSCF QKAQLKSANT   60
GNNERIINVS IKKLKRKPPG GGSGGGSGGE GGCPSCDSYE KKPPKEFLER FKSLLQKMIH  120
QHLSSRTHGS EDS                                                    133

SEQ ID NO: 31              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 31
QGQDRHMIRM RQLIDIVDQL KNYVNDLVPE FLPAPEDVET NCEWSAFSCF QKAQLKSANT   60
GNNERIINVS IKKLKRKPPG GGGGGGGGGE GGCPSCDSYE KKPPKEFLER FKSLLQKMIH  120
QHLSSRTHGS EDS                                                    133

SEQ ID NO: 32              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 32
QGQDRHMIRM RQLIDIVDQL KNYVNDLVPE FLPAPEDVET NCEWSAFSCF QKAQLKSANT   60
GNNERIINVS IKKLKRKPPS TGGGSGGGSE GSCPSCDSYE KKPPKEFLER FKSLLQKMIH  120
QHLSSRTHGS EDS                                                    133

SEQ ID NO: 33              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 33
QGQDRHMIRM RQLIDIVDQL KNYVNDLVPE FLPAPEDVET NCEWSAFSCF QKAQLKSANT   60
GNNERIINVS IKKLKRKPPS TGGGGGGGGE GGCPSCDSYE KKPPKEFLER FKSLLQKMIH  120
QHLSSRTHGS EDS                                                    133

SEQ ID NO: 34              moltype = AA  length = 133
```

```
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 34
QGQDRHMIRM RQLIDIVDQL KNYVNDLVPE FLPAPEDVET NCEWSAFSCF QKAQLKSANT    60
GNNERIINVS IKKLKRKPPS TNAGGGGGGE GTCPSCDSYE KKPPKEFLER FKSLLQKMIH   120
QHLSSRTHGS EDS                                                     133

SEQ ID NO: 35           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 35
QGQDRHMIRM RQLIDIVDQL KNYVNDLVPE FLPAPEDVET NCEWSAFSCF QKAQLKSANT    60
GNNERIINVS IKKLKRKPPS TGGGGGGGGE GTCPSCDSYE KKPPKEFLER FKSLLQKMIH   120
QHLSSRTHGS EDS                                                     133

SEQ ID NO: 36           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 36
QGQDRHMIRM RQLIDIVDQL KNYVNDLVPE FLPAPEDVET NCEWSAFSCF QKAQLKSANT    60
GNNERIINVS IKKLKRKPPS TGGGGEGGGE GTCPSCDSYE KKPPKEFLER FKSLLQKMIH   120
QHLSSRTHGS EDS                                                     133

SEQ ID NO: 37           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 37
QGQDRHMIRM RQLIDIVDQL KNYVNDLVPE FLPAPEDVET NCEWSAFSCF QKAQLKSANT    60
GNNERIINVS IKKLKRKPPS TGGGEGGGGE GTCPSCDSYE KKPPKEFLER FKSLLQKMIH   120
QHLSSRTHGS EDS                                                     133

SEQ ID NO: 38           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 38
QGQDRHMIRM RQLIDIVDQL KNYVNDLVPE FLPAPEDVET NCEWSAFSCF QKAQLKSANT    60
GNNERIINVS IKKLKRKPPG GGGEGGGGGE GGCPSCDSYE KKPPKEFLER FKSLLQKMIH   120
QHLSSRTHGS EDS                                                     133

SEQ ID NO: 39           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 39
QGQDRHMIRM RQLIDIVDQL KNYVNDLVPE FLPAPEDVET NCEWSAFSCF QKAQLKSANT    60
GNNERIINVS IKKLKRKPPG GGEGGGGGGE GGCPSCDSYE KKPPKEFLER FKSLLQKMIH   120
QHLSSRTHGS EDS                                                     133

SEQ ID NO: 40           moltype = AA  length = 133
FEATURE                 Location/Qualifiers
```

```
REGION                  1..133
                        note = Description of Artificial Sequence: Synthetic
                         polypeptide
source                  1..133
                        mol_type = protein
                        organism = synthetic construct
SEQUENCE: 40
QGQDRHMIRM RQLIDIVDQL KNYVNDLVPE FLPAPEDVET NCEWSAFSCF QKAQLKSANT  60
GNNERIINVS IKKLKRKPPG GEGGGGGGGE GGCPSCDSYE KKPPKEFLER FKSLLQKMIH  120
QHLSSRTHGS EDS                                                    133

SEQ ID NO: 41           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 41
QGQDRHMERM RQLIDIVDQL KNYVNDLVPE FLPAPEDVET NCEWSAFSCF QKAQLKSANT  60
GNNERIINVS IKKLKRKPPS TNAGGGQGHE LTCPSCDSYE KKPPKEFLER FKSLLQKMIH  120
QHLSSRTHGS EDS                                                    133

SEQ ID NO: 42           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 42
QGQDAHMIRM RQLIDIVDQL KNYVNDLVPE FLPAPEDVET NCEWSAFSCF QKAQLKSANT  60
GNNERIINVS IKKLKRKPPS TNAGGGQGHE LTCPSCDSYE KKPPKEFLER FKSLLQKMIH  120
QHLSSRTHGS EDS                                                    133

SEQ ID NO: 43           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 43
QGQDEHMIRM RQLIDIVDQL KNYVNDLVPE FLPAPEDVET NCEWSAFSCF QKAQLKSANT  60
GNNERIINVS IKKLKRKPPS TNAGGGQGHE LTCPSCDSYE KKPPKEFLER FKSLLQKMIH  120
QHLSSRTHGS EDS                                                    133

SEQ ID NO: 44           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 44
QGQDSHMIRM RQLIDIVDQL KNYVNDLVPE FLPAPEDVET NCEWSAFSCF QKAQLKSANT  60
GNNERIINVS IKKLKRKPPS TNAGGGQGHE LTCPSCDSYE KKPPKEFLER FKSLLQKMIH  120
QHLSSRTHGS EDS                                                    133

SEQ ID NO: 45           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 45
QGQDTHMIRM RQLIDIVDQL KNYVNDLVPE FLPAPEDVET NCEWSAFSCF QKAQLKSANT  60
GNNERIINVS IKKLKRKPPS TNAGGGQGHE LTCPSCDSYE KKPPKEFLER FKSLLQKMIH  120
QHLSSRTHGS EDS                                                    133

SEQ ID NO: 46           moltype = AA  length = 133
FEATURE                 Location/Qualifiers
REGION                  1..133
```

```
                        note = Description of Artificial Sequence: Synthetic
                              polypeptide
source                  1..133
                        mol_type = protein
                        organism = synthetic construct
SEQUENCE: 46
QGQDNHMIRM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                      133

SEQ ID NO: 47           moltype = AA   length = 133
FEATURE                 Location/Qualifiers
REGION                  1..133
                        note = Description of Artificial Sequence: Synthetic
                              polypeptide
source                  1..133
                        mol_type = protein
                        organism = synthetic construct
SEQUENCE: 47
QGQDQHMIRM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                      133

SEQ ID NO: 48           moltype = AA   length = 133
FEATURE                 Location/Qualifiers
REGION                  1..133
                        note = Description of Artificial Sequence: Synthetic
                              polypeptide
source                  1..133
                        mol_type = protein
                        organism = synthetic construct
SEQUENCE: 48
QGQDVHMIRM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                      133

SEQ ID NO: 49           moltype = AA   length = 133
FEATURE                 Location/Qualifiers
REGION                  1..133
                        note = Description of Artificial Sequence: Synthetic
                              polypeptide
source                  1..133
                        mol_type = protein
                        organism = synthetic construct
SEQUENCE: 49
QGQDIHMIRM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                      133

SEQ ID NO: 50           moltype = AA   length = 133
FEATURE                 Location/Qualifiers
REGION                  1..133
                        note = Description of Artificial Sequence: Synthetic
                              polypeptide
source                  1..133
                        mol_type = protein
                        organism = synthetic construct
SEQUENCE: 50
QGQDLHMIRM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                      133

SEQ ID NO: 51           moltype = AA   length = 133
FEATURE                 Location/Qualifiers
REGION                  1..133
                        note = Description of Artificial Sequence: Synthetic
                              polypeptide
source                  1..133
                        mol_type = protein
                        organism = synthetic construct
SEQUENCE: 51
QGQDYHMIRM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                      133

SEQ ID NO: 52           moltype = AA   length = 133
FEATURE                 Location/Qualifiers
REGION                  1..133
                        note = Description of Artificial Sequence: Synthetic
```

```
                                    polypeptide
source                     1..133
                           mol_type = protein
                           organism = synthetic construct
SEQUENCE: 52
QGQDRHMIRM RQLIDIVDQL KNYVNDLVPE FLPAPEDVET NCEWSAFSCF QKAQLKSANT   60
GNNERIINVS IKKLKAKPPS TNAGGGQGHE LTCPSCDSYE KKPPKEFLER FKSLLQKMIH  120
QHLSSRTHGS EDS                                                    133

SEQ ID NO: 53              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 53
QGQDRHMIRM RQLIDIVDQL KNYVNDLVPE FLPAPEDVET NCEWSAFSCF QKAQLKSANT   60
GNNERIINVS IKKLKNKPPS TNAGGGQGHE LTCPSCDSYE KKPPKEFLER FKSLLQKMIH  120
QHLSSRTHGS EDS                                                    133

SEQ ID NO: 54              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 54
QGQDRHMIRM RQLIDIVDQL KNYVNDLVPE FLPAPEDVET NCEWSAFSCF QKAQLKSANT   60
GNNERIINVS IKKLKDKPPS TNAGGGQGHE LTCPSCDSYE KKPPKEFLER FKSLLQKMIH  120
QHLSSRTHGS EDS                                                    133

SEQ ID NO: 55              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 55
QGQDRHMIRM RQLIDIVDQL KNYVNDLVPE FLPAPEDVET NCEWSAFSCF QKAQLKSANT   60
GNNERIINVS IKKLKSKPPS TNAGGGQGHE LTCPSCDSYE KKPPKEFLER FKSLLQKMIH  120
QHLSSRTHGS EDS                                                    133

SEQ ID NO: 56              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 56
QGQDRHMIRM RQLIDIVDQL KNYVNDLVPE FLPAPEDVET NCEWSAFSCF QKAQLKSANT   60
GNNERIINVS IKKLKTKPPS TNAGGGQGHE LTCPSCDSYE KKPPKEFLER FKSLLQKMIH  120
QHLSSRTHGS EDS                                                    133

SEQ ID NO: 57              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 57
QGQDRHMIRM RQLIDIVDQL KNYVNDLVPE FLPAPEDVET NCEWSAFSCF QKAQLKSANT   60
GNNERIINVS IKKLKQKPPS TNAGGGQGHE LTCPSCDSYE KKPPKEFLER FKSLLQKMIH  120
QHLSSRTHGS EDS                                                    133

SEQ ID NO: 58              moltype = AA  length = 133
FEATURE                    Location/Qualifiers
REGION                     1..133
                           note = Description of Artificial Sequence: Synthetic
                            polypeptide
```

```
source                    1..133
                          mol_type = protein
                          organism = synthetic construct
SEQUENCE: 58
QGQDRHMIRM RQLIDIVDQL KNYVNDLVPE FLPAPEDVET NCEWSAFSCF QKAQLKSANT    60
GNNERIINVS IKKLKVKPPS TNAGGGQGHE LTCPSCDSYE KKPPKEFLER FKSLLQKMIH   120
QHLSSRTHGS EDS                                                      133

SEQ ID NO: 59             moltype = AA   length = 133
FEATURE                   Location/Qualifiers
REGION                    1..133
                          note = Description of Artificial Sequence: Synthetic
                           polypeptide
source                    1..133
                          mol_type = protein
                          organism = synthetic construct
SEQUENCE: 59
QGQDRHMIRM RQLIDIVDQL KNYVNDLVPE FLPAPEDVET NCEWSAFSCF QKAQLKSANT    60
GNNERIINVS IKKLKIKPPS TNAGGGQGHE LTCPSCDSYE KKPPKEFLER FKSLLQKMIH   120
QHLSSRTHGS EDS                                                      133

SEQ ID NO: 60             moltype = AA   length = 133
FEATURE                   Location/Qualifiers
REGION                    1..133
                          note = Description of Artificial Sequence: Synthetic
                           polypeptide
source                    1..133
                          mol_type = protein
                          organism = synthetic construct
SEQUENCE: 60
QGQDRHMIRM RQLIDIVDQL KNYVNDLVPE FLPAPEDVET NCEWSAFSCF QKAQLKSANT    60
GNNERIINVS IKKLKLKPPS TNAGGGQGHE LTCPSCDSYE KKPPKEFLER FKSLLQKMIH   120
QHLSSRTHGS EDS                                                      133

SEQ ID NO: 61             moltype = AA   length = 133
FEATURE                   Location/Qualifiers
REGION                    1..133
                          note = Description of Artificial Sequence: Synthetic
                           polypeptide
source                    1..133
                          mol_type = protein
                          organism = synthetic construct
SEQUENCE: 61
QGQDRHMIRM RQLIDIVDQL KNYVNDLVPE FLPAPEDVET NCEWSAFSCF QKAQLKSANT    60
GNNERIINVS IKKLKYKPPS TNAGGGQGHE LTCPSCDSYE KKPPKEFLER FKSLLQKMIH   120
QHLSSRTHGS EDS                                                      133

SEQ ID NO: 62             moltype = AA   length = 133
FEATURE                   Location/Qualifiers
REGION                    1..133
                          note = Description of Artificial Sequence: Synthetic
                           polypeptide
source                    1..133
                          mol_type = protein
                          organism = synthetic construct
SEQUENCE: 62
QGQDRHMIRM RQLIDIVDQL KNYVNDLVPE FLPAPEDVET NCEWSAFSCF QKAQLKSANT    60
GNNERIINVS IKKLKRAPPS TNAGGGQGHE LTCPSCDSYE KKPPKEFLER FKSLLQKMIH   120
QHLSSRTHGS EDS                                                      133

SEQ ID NO: 63             moltype = AA   length = 133
FEATURE                   Location/Qualifiers
REGION                    1..133
                          note = Description of Artificial Sequence: Synthetic
                           polypeptide
source                    1..133
                          mol_type = protein
                          organism = synthetic construct
SEQUENCE: 63
QGQDRHMIRM RQLIDIVDQL KNYVNDLVPE FLPAPEDVET NCEWSAFSCF QKAQLKSANT    60
GNNERIINVS IKKLKREPPS TNAGGGQGHE LTCPSCDSYE KKPPKEFLER FKSLLQKMIH   120
QHLSSRTHGS EDS                                                      133

SEQ ID NO: 64             moltype = AA   length = 133
FEATURE                   Location/Qualifiers
REGION                    1..133
                          note = Description of Artificial Sequence: Synthetic
                           polypeptide
source                    1..133
```

```
                        mol_type = protein
                        organism = synthetic construct
SEQUENCE: 64
QGQDRHMIRM RQLIDIVDQL KNYVNDLVPE FLPAPEDVET NCEWSAFSCF QKAQLKSANT    60
GNNERIINVS IAKLKRKPPS TNAGGGQGHE LTCPSCDSYE KKPPKEFLER FKSLLQKMIH   120
QHLSSRTHGS EDS                                                     133

SEQ ID NO: 65           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 65
QGQDRHMIRM RQLIDIVDQL KNYVNDLVPE FLPAPEDVET NCEWSAFSCF QKAQLKSANT    60
GNNERIINVS IEKLKRKPPS TNAGGGQGHE LTCPSCDSYE KKPPKEFLER FKSLLQKMIH   120
QHLSSRTHGS EDS                                                     133

SEQ ID NO: 66           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 66
QGQDRHMIRM RQLIDIVDQL KNYVNDLVPE FLPAPEDVET NCEWSAFSCF QKAQLKSANT    60
GNNERIINVS IKKLARKPPS TNAGGGQGHE LTCPSCDSYE KKPPKEFLER FKSLLQKMIH   120
QHLSSRTHGS EDS                                                     133

SEQ ID NO: 67           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 67
QGQDRHMIRM RQLIDIVDQL KNYVNDLVPE FLPAPEDVET NCEWSAFSCF QKAQLKSANT    60
GNNERIINVS IKKLERKPPS TNAGGGQGHE LTCPSCDSYE KKPPKEFLER FKSLLQKMIH   120
QHLSSRTHGS EDS                                                     133

SEQ ID NO: 68           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 68
QGQDRHMIRM RQLIDIVDQL KNYVNDLVPE FLPAPEDVET NCEWSAFSCF QKAQLKSANT    60
GNNERIINVS IKALKRKPPS TNAGGGQGHE LTCPSCDSYE KKPPKEFLER FKSLLQKMIH   120
QHLSSRTHGS EDS                                                     133

SEQ ID NO: 69           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 69
QGQDRHMIRM RQLIDIVDQL KNYVNDLVPE FLPAPEDVET NCEWSAFSCF QKAQLKSANT    60
GNNERIINVS IKELKRKPPS TNAGGGQGHE LTCPSCDSYE KKPPKEFLER FKSLLQKMIH   120
QHLSSRTHGS EDS                                                     133

SEQ ID NO: 70           moltype = AA  length = 133
FEATURE                 Location/Qualifiers
REGION                  1..133
                        note = Description of Artificial Sequence: Synthetic
                         polypeptide
source                  1..133
                        mol_type = protein
```

```
                        organism = synthetic construct
SEQUENCE: 70
QGQDFHMIRM RQLIDIVDQL KNYVNDLVPE FLPAPEDVET NCEWSAFSCF QKAQLKSANT    60
GNNERIINVS IKKLKRAPPS TNAGGGQGHE LTCPSCDSYE KKPPKEFLER FKSLLQKMIH   120
QHLSSRTHGS EDS                                                      133

SEQ ID NO: 71           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 71
QGQDFHMIRM RQLIDIVDQL KNYVNDLVPE FLPAPEDVET NCEWSAFSCF QKAQLKSANT    60
GNNERIINVS IKKLKREPPS TNAGGGQGHE LTCPSCDSYE KKPPKEFLER FKSLLQKMIH   120
QHLSSRTHGS EDS                                                      133

SEQ ID NO: 72           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 72
QGQDFHMIRM RQLIDIVDQL KNYVNDLVPE FLPAPEDVET NCEWSAFSCF QKAQLKSANT    60
GNNERIINVS IAKLKRKPPS TNAGGGQGHE LTCPSCDSYE KKPPKEFLER FKSLLQKMIH   120
QHLSSRTHGS EDS                                                      133

SEQ ID NO: 73           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 73
QGQDFHMIRM RQLIDIVDQL KNYVNDLVPE FLPAPEDVET NCEWSAFSCF QKAQLKSANT    60
GNNERIINVS IEKLKRKPPS TNAGGGQGHE LTCPSCDSYE KKPPKEFLER FKSLLQKMIH   120
QHLSSRTHGS EDS                                                      133

SEQ ID NO: 74           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 74
QGQDFHMIRM RQLIDIVDQL KNYVNDLVPE FLPAPEDVET NCEWSAFSCF QKAQLKSANT    60
GNNERIINVS IKKLARKPPS TNAGGGQGHE LTCPSCDSYE KKPPKEFLER FKSLLQKMIH   120
QHLSSRTHGS EDS                                                      133

SEQ ID NO: 75           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 75
QGQDFHMIRM RQLIDIVDQL KNYVNDLVPE FLPAPEDVET NCEWSAFSCF QKAQLKSANT    60
GNNERIINVS IKKLERKPPS TNAGGGQGHE LTCPSCDSYE KKPPKEFLER FKSLLQKMIH   120
QHLSSRTHGS EDS                                                      133

SEQ ID NO: 76           moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
```

```
SEQUENCE: 76
QGQDRHMIRM RQLIDIVDQL KNYVNDLVPE FLPAPEDVET NCEWSAFSCF QKAQLKSANT    60
GNNERIINVS IKALKFKPPS TNAGGGQGHE LTCPSCDSYE KKPPKEFLER FKSLLQKMIH   120
QHLSSRTHGS EDS                                                     133

SEQ ID NO: 77          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 77
QGQDRHMIRM RQLIDIVDQL KNYVNDLVPE FLPAPEDVET NCEWSAFSCF QKAQLKSANT    60
GNNERIINVS IKELKFKPPS TNAGGGQGHE LTCPSCDSYE KKPPKEFLER FKSLLQKMIH   120
QHLSSRTHGS EDS                                                     133

SEQ ID NO: 78          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 78
QGQDRHMIAM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 79          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 79
QGQDRHMIDM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 80          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 80
QGQDRHMIEM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 81          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 81
QGQDRHMIHM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 82          moltype = AA  length = 133
FEATURE                Location/Qualifiers
REGION                 1..133
                       note = Description of Artificial Sequence: Synthetic
                        polypeptide
source                 1..133
                       mol_type = protein
                       organism = synthetic construct
SEQUENCE: 82
```

```
QGQDRHMISM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 83              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 83
QGQDRHMITM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 84              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 84
QGQDRHMINM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 85              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 85
QGQDRHMIGM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 86              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 86
QGQDRHMIVM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 87              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 87
QGQDRHMIIM RQLIDIVDQL KNYVNDLVPE FLPAPEDVET NCEWSAFSCF QKAQLKSANT    60
GNNERIINVS IKKLKRKPPS TNAGGGQGHE LTCPSCDSYE KKPPKEFLER FKSLLQKMIH   120
QHLSSRTHGS EDS                                                     133

SEQ ID NO: 88              moltype = AA  length = 133
FEATURE                    Location/Qualifiers
REGION                     1..133
                           note = Description of Artificial Sequence: Synthetic
                            polypeptide
source                     1..133
                           mol_type = protein
                           organism = synthetic construct
SEQUENCE: 88
QGQDRHMILM RQLIDIVDQL KNYVNDLVPE FLPAPEDVET NCEWSAFSCF QKAQLKSANT    60
```

GNNERIIINVS IKKLKRKPPS TNAGGGQGHE LTCPSCDSYE KKPPKEFLER FKSLLQKMIH    120
QHLSSRTHGS EDS                                                      133

SEQ ID NO: 89           moltype = AA  length = 133
FEATURE                 Location/Qualifiers
REGION                  1..133
                        note = Description of Artificial Sequence: Synthetic
                        polypeptide
source                  1..133
                        mol_type = protein
                        organism = synthetic construct
SEQUENCE: 89
QGQDRHMIYM RQLIDIVDQL KNYVNDLVPE FLPAPEDVET NCEWSAFSCF QKAQLKSANT    60
GNNERIIINVS IKKLKRKPPS TNAGGGQGHE LTCPSCDSYE KKPPKEFLER FKSLLQKMIH   120
QHLSSRTHGS EDS                                                      133

SEQ ID NO: 90           moltype = AA  length = 133
FEATURE                 Location/Qualifiers
REGION                  1..133
                        note = Description of Artificial Sequence: Synthetic
                        polypeptide
source                  1..133
                        mol_type = protein
                        organism = synthetic construct
SEQUENCE: 90
QGQDRHMIRM RQLIDIVDQL KNYVNDLVPE FLPAPEDVET NCEWSAFSCF QKAQLKSANT    60
GNNERIIINVS IAKLKFKPPS TNAGGGQGHE LTCPSCDSYE KKPPKEFLER FKSLLQKMIH   120
QHLSSRTHGS EDS                                                      133

SEQ ID NO: 91           moltype = AA  length = 133
FEATURE                 Location/Qualifiers
REGION                  1..133
                        note = Description of Artificial Sequence: Synthetic
                        polypeptide
source                  1..133
                        mol_type = protein
                        organism = synthetic construct
SEQUENCE: 91
QGQDRHMIRM RQLIDIVDQL KNYVNDLVPE FLPAPEDVET NCEWSAFSCF QKAQLKSANT    60
GNNERIIINVS IKKLAFKPPS TNAGGGQGHE LTCPSCDSYE KKPPKEFLER FKSLLQKMIH   120
QHLSSRTHGS EDS                                                      133

SEQ ID NO: 92           moltype = AA  length = 133
FEATURE                 Location/Qualifiers
REGION                  1..133
                        note = Description of Artificial Sequence: Synthetic
                        polypeptide
source                  1..133
                        mol_type = protein
                        organism = synthetic construct
SEQUENCE: 92
QGQDRHMIRM RQLIDIVDQL KNYVNDLVPE FLPAPEDVET NCEWSAFSCF QKAQLKSANT    60
GNNERIIINVS IKKLKFAPPS TNAGGGQGHE LTCPSCDSYE KKPPKEFLER FKSLLQKMIH   120
QHLSSRTHGS EDS                                                      133

SEQ ID NO: 93           moltype = AA  length = 133
FEATURE                 Location/Qualifiers
REGION                  1..133
                        note = Description of Artificial Sequence: Synthetic
                        polypeptide
source                  1..133
                        mol_type = protein
                        organism = synthetic construct
SEQUENCE: 93
QGQDRHMIRM RQLIDIVDQL KNYVNDLVPE FLPAPEDVET NCEWSAFSCF QKAQLKSANT    60
GNNERIIINVS IKKLEFKPPS TNAGGGQGHE LTCPSCDSYE KKPPKEFLER FKSLLQKMIH   120
QHLSSRTHGS EDS                                                      133

SEQ ID NO: 94           moltype = AA  length = 133
FEATURE                 Location/Qualifiers
REGION                  1..133
                        note = Description of Artificial Sequence: Synthetic
                        polypeptide
source                  1..133
                        mol_type = protein
                        organism = synthetic construct
SEQUENCE: 94
QGQDRHMIRM RQLIDIVDQL KNYVNDLVPE FLPAPEDVET NCEWSAFSCF QKAQLKSANT    60
GNNERIIINVS IKKLKEKPPG GEGGGGGGGE GGCPSCDSYE KKPPKEFLER FKSLLQKMIH   120

```
QHLSSRTHGS EDS                                                                     133

SEQ ID NO: 95               moltype = AA  length = 133
FEATURE                     Location/Qualifiers
REGION                      1..133
                            note = Description of Artificial Sequence: Synthetic
                            polypeptide
source                      1..133
                            mol_type = protein
                            organism = synthetic construct
SEQUENCE: 95
QGQDRHMIRM RQLIDIVDQL KNYVNDLVPE FLPAPEDVET NCEWSAFSCF QKAQLKSANT   60
GNNERIINVS IKKLKFKPPG GEGGGGGGGE GGCPSCDSYE KKPPKEFLER FKSLLQKMIH  120
QHLSSRTHGS EDS                                                    133

SEQ ID NO: 96               moltype = AA  length = 133
FEATURE                     Location/Qualifiers
REGION                      1..133
                            note = Description of Artificial Sequence: Synthetic
                            polypeptide
source                      1..133
                            mol_type = protein
                            organism = synthetic construct
SEQUENCE: 96
QGQDRHMIRM RQLIDIVDQL KNYVNDLVPE FLPAPEDVET NCEWSAFSCF QKAQLKSANT   60
GNNERIINVS IKKLKQKPPG GEGGGGGGGE GGCPSCDSYE KKPPKEFLER FKSLLQKMIH  120
QHLSSRTHGS EDS                                                    133

SEQ ID NO: 97               moltype = AA  length = 133
FEATURE                     Location/Qualifiers
REGION                      1..133
                            note = Description of Artificial Sequence: Synthetic
                            polypeptide
source                      1..133
                            mol_type = protein
                            organism = synthetic construct
SEQUENCE: 97
QGQDRHMISM RQLIDIVDQL KNYVNDLVPE FLPAPEDVET NCEWSAFSCF QKAQLKSANT   60
GNNERIINVS IKKLKRKPPG GEGGGGGGGE GGCPSCDSYE KKPPKEFLER FKSLLQKMIH  120
QHLSSRTHGS EDS                                                    133

SEQ ID NO: 98               moltype = AA  length = 133
FEATURE                     Location/Qualifiers
REGION                      1..133
                            note = Description of Artificial Sequence: Synthetic
                            polypeptide
source                      1..133
                            mol_type = protein
                            organism = synthetic construct
SEQUENCE: 98
QGQDRHMIGM RQLIDIVDQL KNYVNDLVPE FLPAPEDVET NCEWSAFSCF QKAQLKSANT   60
GNNERIINVS IKKLKRKPPG GEGGGGGGGE GGCPSCDSYE KKPPKEFLER FKSLLQKMIH  120
QHLSSRTHGS EDS                                                    133

SEQ ID NO: 99               moltype = AA  length = 117
FEATURE                     Location/Qualifiers
REGION                      1..117
                            note = Description of Artificial Sequence: Synthetic
                            polypeptide
source                      1..117
                            mol_type = protein
                            organism = synthetic construct
SEQUENCE: 99
EVQLVESGGG LVQPGRSLKL SCAASGFTFS NYYMAWVRQA PTKGLEWVAY INTGGGTTYY   60
RDSVKGRFTI SRDDAKSTLY LQMDSLRSED TATYYCTTAI GYYFDYWGQG VMVTVSS    117

SEQ ID NO: 100              moltype = AA  length = 107
FEATURE                     Location/Qualifiers
REGION                      1..107
                            note = Description of Artificial Sequence: Synthetic
                            polypeptide
source                      1..107
                            mol_type = protein
                            organism = synthetic construct
SEQUENCE: 100
DIQLTQSPAS LSASLGETVS IECLASEDIY SYLAWYQQKP GKSPQVLIYA ANRLQDGVPS   60
RFSGSGSGTQ YSLKISGMQP EDEGDYFCLQ GSKFPYTFGA GTKLELK               107

SEQ ID NO: 101              moltype = AA  length = 117
```

```
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 101
EVKLQESGPS LVQPSQTLSL TCSVSGFSLI SDSVHWVRQP PGKGLEWMGG IWADGSTDYN    60
SALKSRLSIS RDTSKSQGFL KMNSLQTDDT AIYFCTSNRE SYYFDYWGQG TMVTVSS      117

SEQ ID NO: 102          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 102
DIQMTQSPAS LSASLGDKVT ITCQASQNID KYIAWYQQKP GKAPRQLIHY TSTLVSGTPS    60
RFSGSGSGRD YSFSISSVES EDIASYYCLQ YDTLYTFGAG TKLELK                  106

SEQ ID NO: 103          moltype = AA  length = 117
FEATURE                 Location/Qualifiers
REGION                  1..117
                        note = Description of Artificial Sequence: Synthetic
                         polypeptide
source                  1..117
                        mol_type = protein
                        organism = synthetic construct
SEQUENCE: 103
EVKLQESGPS LVQPSQTLSL TCSVSGFSLI SDSVHWVRQP PGKGLEWMGG IWADGSTDYN    60
SALKSRLSIS RDTSKSQGFL KMNSLQTDDT AIYFCTSARE SYYFDYWGQG TMVTVSS      117

SEQ ID NO: 104          moltype = AA  length = 106
FEATURE                 Location/Qualifiers
REGION                  1..106
                        note = Description of Artificial Sequence: Synthetic
                         polypeptide
source                  1..106
                        mol_type = protein
                        organism = synthetic construct
SEQUENCE: 104
DIQMTQSPAS LSASLGDKVT ITCQASQNID KYIAWYQQKP GKAPRQLIHY TSTLVSGTPS    60
RFSGSGSGRD YSFSISSVES EDIASYYCLQ YATLYTFGAG TKLELK                  106

SEQ ID NO: 105          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 105
EVQLVESGGA LVQPGRSLKL SCAASGLTFS DCYMAWVRQT PTKGLEWVSY ISSDGGSTYY    60
GDSVKGRFTI SRDNAKSTLY LQMNSLRSED MATYYCACAT DLSSYWSFDF WGPGTMVTVS   120
S                                                                  121

SEQ ID NO: 106          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 106
DIQMTQSPSS LPVSLGERVT ISCRASQGIS NNLNWYQQKP DGTIKPLIYH TSNLQSGVPS    60
RFSGSGSGTD YSLTISSLEP EDFAMYYCQQ DATFPLTFGS GTKLEIK                 107

SEQ ID NO: 107          moltype = AA  length = 119
FEATURE                 Location/Qualifiers
REGION                  1..119
                        note = Description of Artificial Sequence: Synthetic
                         polypeptide
source                  1..119
                        mol_type = protein
```

```
                       organism = synthetic construct
SEQUENCE: 107
QVHLQQSGPE LVKPGASVKM SCKTSGYTFT KYTMHWVKQG HEESLEWIGH FNPNNDETKY     60
NQKFTGKATL TVDKSSTTAY MELRSLTSDD SALYYCARDG LGLRLFADWG QGTLITVSA     119

SEQ ID NO: 108          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 108
DIQMTQSPAS LSASVGETVT ITCGASENIY GALNWYQRKQ GKSPQLLIFG ATNLADGVSS     60
RFSGSGSDRQ YSLKISSLHP DDVATYYCQN ILDTPWTFGG GTKLEIK                  107

SEQ ID NO: 109          moltype = AA   length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 109
QVQLVQSGAE VKKPGSSVKV SCKASGYRFH NFAISWVRQA PGQGLEWMGG IIPGHAKANY     60
AQKFQGRVTI TADESTSTAY MELSSLRSED TAVYYCARDG LGIRLFADWG QGTLVTVSS    119

SEQ ID NO: 110          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 110
DIQMTQSPSS LSASVGDRVT ITCRASQEIY GALNWYQQKP GKAPKLLIYG ATNLQSGVPS     60
RFSGSGSGTD FTLTISSLQP EDFATYYCQD IYDAPWTFGG GTKVEIK                  107

SEQ ID NO: 111          moltype = AA   length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 111
QVQLVQSGAE VKKPGSSVKV SCKASGSRFY KFAISWVRQA PGQGLEWMGG IIPGHAKANY     60
AQKFQGRVTI TADESTSTAY MELSSLRSED TAVYYCARDG LGIRLFADWG QGTLVTVSS    119

SEQ ID NO: 112          moltype = AA   length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 112
DIQMTQSPSS LSASVGDRVT ITCRASQEIY GALNWYQQKP GKAPKLLIYG ATNLQSGVPS     60
RFSGSGSGTD FTLTISSLQP EDFATYYCQD IYDAPWTFGG GTKVEIK                  107

SEQ ID NO: 113          moltype = AA   length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 113
QVQLVQSGAE VKKPGSSVKV SCKASGYTFT KYAISWVRQA PGQGLEWMGG IIPGHAKANY     60
AQKFQGRVTI TADESTSTAY MELSSLRSED TAVYYCARDG LGIRLFADWG QGTLVTVSS    119

SEQ ID NO: 114          moltype = AA   length = 107
FEATURE                 Location/Qualifiers
```

```
REGION                  1..107
                        note = Description of Artificial Sequence: Synthetic
                         polypeptide
source                  1..107
                        mol_type = protein
                        organism = synthetic construct
SEQUENCE: 114
DIQMTQSPSS LSASVGDRVT ITCRASQKIY GALNWYQQKP GKAPKLLIYG ATNLQSGVPS    60
RFSGSGSGTD FTLTISSLQP EDFATYYCQN TYDTPWTFGG GTKVEIK                 107

SEQ ID NO: 115          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 115
QVQLVQSGAE VKKPGSSVKV SCKASGSGFR GHAISWVRQA PGQGLEWMGG IIPGHAKANY    60
AQKFQGRVTI TADESTSTAY MELSSLRSED TAVYYCARDG LGIRLFADWG QGTLVTVSS    119

SEQ ID NO: 116          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 116
DIQMTQSPSS LSASVGDRVT ITCRASQKIY GALNWYQQKP GKAPKLLIYG ATNLQSGVPS    60
RFSGSGSGTD FTLTISSLQP EDFATYYCQN TYDTPWTFGG GTKVEIK                 107

SEQ ID NO: 117          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 117
EVQLVESGGG AVRPGGSLRL SCAASGFTFD DYGMSWVRQA PGKGLEWVSD INWSGEITAY    60
ADSVKGRFTI SRDNAKNSLY LQMNSLRAED TAVYYCARSN SYRWDDALDI WGQGTMVTVS   120
S                                                                  121

SEQ ID NO: 118          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 118
EIVLTQSPAT LSVSPGERAT LSCRASQSVS SNLAWYQQKP GQAPRLLIYG ASSRATGIPD    60
RFSGSGSGTD FTLTISRLEP EDFAVYYCQQ YGSSPPVTFG QGTKVEIK                108

SEQ ID NO: 119          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 119
EVQLVESGGG LVQPGRSLRL SCAASGFTFD DYAMHWVRQA PGKGLEWVAV ISYDGSNKYY    60
ADSVKGRFTI SRDNSKNTLY LQMNSLRAED TAVYYCAKDR IGWYDYDAFD IWGQGTMVTV   120
SS                                                                 122

SEQ ID NO: 120          moltype = AA  length = 107
FEATURE                 Location/Qualifiers
REGION                  1..107
                        note = Description of Artificial Sequence: Synthetic
                         polypeptide
source                  1..107
                        mol_type = protein
```

```
                               organism = synthetic construct
SEQUENCE: 120
EIVLTQSPAT LSVTPGEGAT LSCRASHSVG SNLAWYQQKP GQAPRLLIYD ASNRATGIPA         60
RFSGSGSGTD FTLTISSLEP EDLAVYYCQQ RSNWPPTFGQ GTRLEIK                      107

SEQ ID NO: 121             moltype = AA   length = 122
FEATURE                    Location/Qualifiers
REGION                     1..122
                           note = Description of Artificial Sequence: Synthetic
                            polypeptide
source                     1..122
                           mol_type = protein
                           organism = synthetic construct
SEQUENCE: 121
QVQLQQSGAE LVRPGSSVKI SCKASGYAFS SYWMNWVKQR PGQGLEWIGQ IYPGDGDTNY         60
NGKFKGKATL TADKSSSTAY MQLSSLTSED SAVYFCARSG AAFSSYYAMD YWGQGTSVTV        120
SS                                                                      122

SEQ ID NO: 122             moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 122
DIQMTQSPAS LSVSVGETVT ITCRASENIY SNLAWYQQKQ GKSPQLLVYA ATNLADGVPS         60
RFSGSGSGTQ YSLKINSLQS EDFGSYYCQH FWGTPWTFGG GTKLEIK                      107

SEQ ID NO: 123             moltype = AA   length = 119
FEATURE                    Location/Qualifiers
REGION                     1..119
                           note = Description of Artificial Sequence: Synthetic
                            polypeptide
source                     1..119
                           mol_type = protein
                           organism = synthetic construct
SEQUENCE: 123
QVQLVQSGAE VKKPGSSVKV SCKASGGTFS SYAISWVRQA PGQGLEWMGG IIPGAATANY         60
AQKFQGRVTI TADESTSTAY MELSSLRSED TAVYYCARDA AGIRLFADWG QGTLVTVSS         119

SEQ ID NO: 124             moltype = AA   length = 107
FEATURE                    Location/Qualifiers
REGION                     1..107
                           note = Description of Artificial Sequence: Synthetic
                            polypeptide
source                     1..107
                           mol_type = protein
                           organism = synthetic construct
SEQUENCE: 124
DIQMTQSPSS LSASVGDRVT ITCRASQEIY GALNWYQQKP GKAPKLLIYG ATNLQSGVPS         60
RFSGSGSGTD FTLTISSLQP EDFATYYCQS TYDAPWTFGG GTKVEIK                      107

SEQ ID NO: 125             moltype = AA   length = 121
FEATURE                    Location/Qualifiers
REGION                     1..121
                           note = Description of Artificial Sequence: Synthetic
                            polypeptide
source                     1..121
                           mol_type = protein
                           organism = synthetic construct
SEQUENCE: 125
EVQLVESGGG LVQPGGSLRL SCAASGFTFS SYAMSWVRQA PGKGLEWVSD ITYAGGSTAY         60
ADSVKGRFTI SRDNAKNSLY LQMNSLRAED TAVYYCARSN AYAWDDALDI WGQGTMVTVS        120
S                                                                       121

SEQ ID NO: 126             moltype = AA   length = 108
FEATURE                    Location/Qualifiers
REGION                     1..108
                           note = Description of Artificial Sequence: Synthetic
                            polypeptide
source                     1..108
                           mol_type = protein
                           organism = synthetic construct
SEQUENCE: 126
EIVLTQSPGT LSLSPGERAT LSCRASQSVS SNLAWYQQKP GQAPRLLIYG ASSRATGIPD         60
RFSGSGSGTD FTLTISRLEP EDFAVYYCQQ YGSSPPVTFG QGTKVEIK                     108
```

```
SEQ ID NO: 127           moltype = AA   length = 121
FEATURE                  Location/Qualifiers
REGION                   1..121
                         note = Description of Artificial Sequence: Synthetic
                         polypeptide
source                   1..121
                         mol_type = protein
                         organism = synthetic construct
SEQUENCE: 127
EVQLVESGGG LVQPGGSLRL SCAASGFTFS SYAMSWVRQA PGKGLEWVSD ITYAGGSTAY   60
ADSVKGRFTI SRDNAKNSLY LQMNSLRAED TAVYYCARSN AYAWDDALDI WGQGTLVTVS  120
S                                                                 121

SEQ ID NO: 128           moltype = AA   length = 108
FEATURE                  Location/Qualifiers
REGION                   1..108
                         note = Description of Artificial Sequence: Synthetic
                         polypeptide
source                   1..108
                         mol_type = protein
                         organism = synthetic construct
SEQUENCE: 128
EIVLTQSPGT LSLSPGERAT LSCRASQSVS SNLAWYQQKP GQAPRLLIYG ASSRATGIPD   60
RFSGSGSGTD FTLTISRLEP EDFAVYYCQQ YGSSPPVTFG QGTKVEIK              108

SEQ ID NO: 129           moltype = AA   length = 119
FEATURE                  Location/Qualifiers
REGION                   1..119
                         note = Description of Artificial Sequence: Synthetic
                         polypeptide
source                   1..119
                         mol_type = protein
                         organism = synthetic construct
SEQUENCE: 129
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSS  119

SEQ ID NO: 130           moltype = AA   length = 107
FEATURE                  Location/Qualifiers
REGION                   1..107
                         note = Description of Artificial Sequence: Synthetic
                         polypeptide
source                   1..107
                         mol_type = protein
                         organism = synthetic construct
SEQUENCE: 130
DIQMTQSPSS LSASVGDRVT ITCRASQSIY GALNWYQQKP GKAPKLLIYG ASNLQSGVPS   60
RFSGSGSGTD FTLTISSLQP EDFATYYCQS TYTAPWTFGG GTKVEIK               107

SEQ ID NO: 131           moltype = AA   length = 119
FEATURE                  Location/Qualifiers
REGION                   1..119
                         note = Description of Artificial Sequence: Synthetic
                         polypeptide
source                   1..119
                         mol_type = protein
                         organism = synthetic construct
SEQUENCE: 131
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSS  119

SEQ ID NO: 132           moltype = AA   length = 107
FEATURE                  Location/Qualifiers
REGION                   1..107
                         note = Description of Artificial Sequence: Synthetic
                         polypeptide
source                   1..107
                         mol_type = protein
                         organism = synthetic construct
SEQUENCE: 132
DIQMTQSPSS LSASVGDRVT ITCRASQEIY GALNWYQQKP GKAPKLLIYG ATNLQSGVPS   60
RFSGSGSGTD FTLTISSLQP EDFATYYCQS TYDAPWTFGG GTKVEIK               107

SEQ ID NO: 133           moltype = AA   length = 121
FEATURE                  Location/Qualifiers
REGION                   1..121
                         note = Description of Artificial Sequence: Synthetic
                         polypeptide
source                   1..121
```

```
                            mol_type = protein
                            organism = synthetic construct
SEQUENCE: 133
EVQLVESGGG LVQPGGSLRL SCAASGFTFS SYAMSWVRQA PGKGLEWVSD ISYAGGSTAY      60
ADSVKGRFTI SRDNAKNSLY LQMNSLRAED TAVYYCARSN AYAWDDALDI WGQGTMVTVS     120
S                                                                    121

SEQ ID NO: 134          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 134
EIVLTQSPGT LSLSPGERAT LSCRASQSVS SNLAWYQQKP GQAPRLLIYG ASSRATGIPD      60
RFSGSGSGTD FTLTISRLEP EDFAVYYCQQ YGSSPPVTFG QGTKVEIK                 108

SEQ ID NO: 135          moltype = AA  length = 121
FEATURE                 Location/Qualifiers
REGION                  1..121
                        note = Description of Artificial Sequence: Synthetic
                         polypeptide
source                  1..121
                        mol_type = protein
                        organism = synthetic construct
SEQUENCE: 135
EVQLVESGGG LVQPGGSLRL SCAASGFTFS SYAMSWVRQA PGKGLEWVSD ISYAGGSTAY      60
ADSVKGRFTI SRDNAKNSLY LQMNSLRAED TAVYYCARSN AYAWDDALDI WGQGTLVTVS     120
S                                                                    121

SEQ ID NO: 136          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 136
EIVLTQSPGT LSLSPGERAT LSCRASQSVS SNLAWYQQKP GQAPRLLIYG ASSRATGIPD      60
RFSGSGSGTD FTLTISRLEP EDFAVYYCQQ YGSSPPVTFG QGTKVEIK                 108

SEQ ID NO: 137          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 137
KYTMH                                                                  5

SEQ ID NO: 138          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 138
HFNPNNDETK YNQKFTG                                                    17

SEQ ID NO: 139          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 139
DGLGLRLFAD                                                            10

SEQ ID NO: 140          moltype = AA  length = 11
FEATURE                 Location/Qualifiers
REGION                  1..11
                        note = Description of Artificial Sequence: Synthetic peptide
source                  1..11
```

```
SEQ ID NO: 140        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 140
GASENIYGAL N                                                              11

SEQ ID NO: 141        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 141
GATNLAD                                                                    7

SEQ ID NO: 142        moltype = AA  length = 9
FEATURE               Location/Qualifiers
REGION                1..9
                      note = Description of Artificial Sequence: Synthetic peptide
source                1..9
                      mol_type = protein
                      organism = synthetic construct
SEQUENCE: 142
QNILDTPWT                                                                  9

SEQ ID NO: 143        moltype = AA  length = 5
FEATURE               Location/Qualifiers
REGION                1..5
                      note = Description of Artificial Sequence: Synthetic peptide
source                1..5
                      mol_type = protein
                      organism = synthetic construct
SEQUENCE: 143
SYWMN                                                                      5

SEQ ID NO: 144        moltype = AA  length = 17
FEATURE               Location/Qualifiers
REGION                1..17
                      note = Description of Artificial Sequence: Synthetic peptide
source                1..17
                      mol_type = protein
                      organism = synthetic construct
SEQUENCE: 144
QIYPGDGDTN YNGKFKG                                                        17

SEQ ID NO: 145        moltype = AA  length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 145
SGAAFSSYYA MDY                                                            13

SEQ ID NO: 146        moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 146
RASENIYSNL A                                                              11

SEQ ID NO: 147        moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 147
AATNLAD                                                                    7

SEQ ID NO: 148        moltype = AA  length = 9
FEATURE               Location/Qualifiers
REGION                1..9
                      note = Description of Artificial Sequence: Synthetic peptide
```

```
source                      1..9
                            mol_type = protein
                            organism = synthetic construct
SEQUENCE: 148
QHFWGTPWT                                                              9

SEQ ID NO: 149              moltype = AA  length = 5
FEATURE                     Location/Qualifiers
REGION                      1..5
                            note = Description of Artificial Sequence: Synthetic peptide
source                      1..5
                            mol_type = protein
                            organism = synthetic construct
SEQUENCE: 149
NFAIS                                                                  5

SEQ ID NO: 150              moltype = AA  length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 150
GIIPGHAKAN YAQKFQG                                                    17

SEQ ID NO: 151              moltype = AA  length = 10
FEATURE                     Location/Qualifiers
REGION                      1..10
                            note = Description of Artificial Sequence: Synthetic peptide
source                      1..10
                            mol_type = protein
                            organism = synthetic construct
SEQUENCE: 151
DGLGIRLFAD                                                            10

SEQ ID NO: 152              moltype = AA  length = 11
FEATURE                     Location/Qualifiers
REGION                      1..11
                            note = Description of Artificial Sequence: Synthetic peptide
source                      1..11
                            mol_type = protein
                            organism = synthetic construct
SEQUENCE: 152
RASQEIYGAL N                                                          11

SEQ ID NO: 153              moltype = AA  length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 153
GATNLQS                                                                7

SEQ ID NO: 154              moltype = AA  length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 154
QDIYDAPWT                                                              9

SEQ ID NO: 155              moltype = AA  length = 5
FEATURE                     Location/Qualifiers
REGION                      1..5
                            note = Description of Artificial Sequence: Synthetic peptide
source                      1..5
                            mol_type = protein
                            organism = synthetic construct
SEQUENCE: 155
KFAIS                                                                  5

SEQ ID NO: 156              moltype = AA  length = 17
FEATURE                     Location/Qualifiers
REGION                      1..17
```

|  |  |
|---|---|
| source | note = Description of Artificial Sequence: Synthetic peptide<br>1..17<br>mol_type = protein<br>organism = synthetic construct |

SEQUENCE: 156
GIIPGHAKAN YAQKFQG                                                17

| SEQ ID NO: 157 | moltype = AA   length = 10 |
|---|---|
| FEATURE | Location/Qualifiers |
| REGION | 1..10 |
|  | note = Description of Artificial Sequence: Synthetic peptide |
| source | 1..10 |
|  | mol_type = protein |
|  | organism = synthetic construct |

SEQUENCE: 157
DGLGIRLFAD                                                        10

| SEQ ID NO: 158 | moltype = AA   length = 11 |
|---|---|
| FEATURE | Location/Qualifiers |
| REGION | 1..11 |
|  | note = Description of Artificial Sequence: Synthetic peptide |
| source | 1..11 |
|  | mol_type = protein |
|  | organism = synthetic construct |

SEQUENCE: 158
RASQEIYGAL N                                                      11

| SEQ ID NO: 159 | moltype = AA   length = 7 |
|---|---|
| FEATURE | Location/Qualifiers |
| REGION | 1..7 |
|  | note = Description of Artificial Sequence: Synthetic peptide |
| source | 1..7 |
|  | mol_type = protein |
|  | organism = synthetic construct |

SEQUENCE: 159
GATNLQS                                                            7

| SEQ ID NO: 160 | moltype = AA   length = 9 |
|---|---|
| FEATURE | Location/Qualifiers |
| REGION | 1..9 |
|  | note = Description of Artificial Sequence: Synthetic peptide |
| source | 1..9 |
|  | mol_type = protein |
|  | organism = synthetic construct |

SEQUENCE: 160
QDIYDAPWT                                                          9

| SEQ ID NO: 161 | moltype = AA   length = 5 |
|---|---|
| FEATURE | Location/Qualifiers |
| REGION | 1..5 |
|  | note = Description of Artificial Sequence: Synthetic peptide |
| source | 1..5 |
|  | mol_type = protein |
|  | organism = synthetic construct |

SEQUENCE: 161
KYAIS                                                              5

| SEQ ID NO: 162 | moltype = AA   length = 17 |
|---|---|
| FEATURE | Location/Qualifiers |
| REGION | 1..17 |
|  | note = Description of Artificial Sequence: Synthetic peptide |
| source | 1..17 |
|  | mol_type = protein |
|  | organism = synthetic construct |

SEQUENCE: 162
GIIPGHAKAN YAQKFQG                                                17

| SEQ ID NO: 163 | moltype = AA   length = 10 |
|---|---|
| FEATURE | Location/Qualifiers |
| REGION | 1..10 |
|  | note = Description of Artificial Sequence: Synthetic peptide |
| source | 1..10 |
|  | mol_type = protein |
|  | organism = synthetic construct |

SEQUENCE: 163
DGLGIRLFAD                                                        10

| SEQ ID NO: 164 | moltype = AA   length = 11 |
|---|---|
| FEATURE | Location/Qualifiers |

```
REGION                    1..11
                          note = Description of Artificial Sequence: Synthetic peptide
source                    1..11
                          mol_type = protein
                          organism = synthetic construct
SEQUENCE: 164
RASQKIYGAL N                                                                    11

SEQ ID NO: 165            moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 165
GATNLQS                                                                          7

SEQ ID NO: 166            moltype = AA  length = 9
FEATURE                   Location/Qualifiers
REGION                    1..9
                          note = Description of Artificial Sequence: Synthetic peptide
source                    1..9
                          mol_type = protein
                          organism = synthetic construct
SEQUENCE: 166
QNTYDTPWT                                                                        9

SEQ ID NO: 167            moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 167
GHAIS                                                                            5

SEQ ID NO: 168            moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 168
GIIPGHAKAN YAQKFQG                                                              17

SEQ ID NO: 169            moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 169
DGLGIRLFAD                                                                      10

SEQ ID NO: 170            moltype = AA  length = 11
FEATURE                   Location/Qualifiers
REGION                    1..11
                          note = Description of Artificial Sequence: Synthetic peptide
source                    1..11
                          mol_type = protein
                          organism = synthetic construct
SEQUENCE: 170
RASQKIYGAL N                                                                    11

SEQ ID NO: 171            moltype = AA  length = 7
FEATURE                   Location/Qualifiers
REGION                    1..7
                          note = Description of Artificial Sequence: Synthetic peptide
source                    1..7
                          mol_type = protein
                          organism = synthetic construct
SEQUENCE: 171
GATNLQS                                                                          7

SEQ ID NO: 172            moltype = AA  length = 9
```

```
FEATURE              Location/Qualifiers
REGION               1..9
                     note = Description of Artificial Sequence: Synthetic peptide
source               1..9
                     mol_type = protein
                     organism = synthetic construct
SEQUENCE: 172
QNTYDTPWT                                                                        9

SEQ ID NO: 173       moltype = AA  length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 173
DYGMS                                                                            5

SEQ ID NO: 174       moltype = AA  length = 17
FEATURE              Location/Qualifiers
REGION               1..17
                     note = Description of Artificial Sequence: Synthetic peptide
source               1..17
                     mol_type = protein
                     organism = synthetic construct
SEQUENCE: 174
DINWSGEITA YADSVKG                                                              17

SEQ ID NO: 175       moltype = AA  length = 12
FEATURE              Location/Qualifiers
REGION               1..12
                     note = Description of Artificial Sequence: Synthetic peptide
source               1..12
                     mol_type = protein
                     organism = synthetic construct
SEQUENCE: 175
SNSYRWDDAL DI                                                                   12

SEQ ID NO: 176       moltype = AA  length = 11
FEATURE              Location/Qualifiers
REGION               1..11
                     note = Description of Artificial Sequence: Synthetic peptide
source               1..11
                     mol_type = protein
                     organism = synthetic construct
SEQUENCE: 176
RASQSVSSNL A                                                                    11

SEQ ID NO: 177       moltype = AA  length = 7
FEATURE              Location/Qualifiers
REGION               1..7
                     note = Description of Artificial Sequence: Synthetic peptide
source               1..7
                     mol_type = protein
                     organism = synthetic construct
SEQUENCE: 177
GASSRAT                                                                          7

SEQ ID NO: 178       moltype = AA  length = 10
FEATURE              Location/Qualifiers
REGION               1..10
                     note = Description of Artificial Sequence: Synthetic peptide
source               1..10
                     mol_type = protein
                     organism = synthetic construct
SEQUENCE: 178
QQYGSSPPVT                                                                      10

SEQ ID NO: 179       moltype = AA  length = 5
FEATURE              Location/Qualifiers
REGION               1..5
                     note = Description of Artificial Sequence: Synthetic peptide
source               1..5
                     mol_type = protein
                     organism = synthetic construct
SEQUENCE: 179
DYAMH                                                                            5
```

```
SEQ ID NO: 180              moltype = AA   length = 17
FEATURE                     Location/Qualifiers
REGION                      1..17
                            note = Description of Artificial Sequence: Synthetic peptide
source                      1..17
                            mol_type = protein
                            organism = synthetic construct
SEQUENCE: 180
VISYDGSNKY YADSVKG                                                          17

SEQ ID NO: 181              moltype = AA   length = 13
FEATURE                     Location/Qualifiers
REGION                      1..13
                            note = Description of Artificial Sequence: Synthetic peptide
source                      1..13
                            mol_type = protein
                            organism = synthetic construct
SEQUENCE: 181
DRIGWYDYDA FDI                                                              13

SEQ ID NO: 182              moltype = AA   length = 11
FEATURE                     Location/Qualifiers
REGION                      1..11
                            note = Description of Artificial Sequence: Synthetic peptide
source                      1..11
                            mol_type = protein
                            organism = synthetic construct
SEQUENCE: 182
RASHSVGSNL A                                                                11

SEQ ID NO: 183              moltype = AA   length = 7
FEATURE                     Location/Qualifiers
REGION                      1..7
                            note = Description of Artificial Sequence: Synthetic peptide
source                      1..7
                            mol_type = protein
                            organism = synthetic construct
SEQUENCE: 183
DASNRAT                                                                      7

SEQ ID NO: 184              moltype = AA   length = 9
FEATURE                     Location/Qualifiers
REGION                      1..9
                            note = Description of Artificial Sequence: Synthetic peptide
source                      1..9
                            mol_type = protein
                            organism = synthetic construct
SEQUENCE: 184
QQRSNWPPT                                                                    9

SEQ ID NO: 185              moltype =      length =
SEQUENCE: 185
000

SEQ ID NO: 186              moltype = AA   length = 17
FEATURE                     Location/Qualifiers
REGION                      1..17
                            note = Description of Artificial Sequence: Synthetic peptide
VARIANT                     1
                            note = G or H
VARIANT                     2
                            note = I or F
VARIANT                     3
                            note = I, N, or M
VARIANT                     5
                            note = G, N, H, S, R, I, or A
VARIANT                     6
                            note = A, N, H, S, T, F, or Y
VARIANT                     7
                            note = A, D, or G
VARIANT                     8
                            note = T, E, K, V, Q, or A
VARIANT                     9
                            note = A or T
VARIANT                     10
                            note = N or K
VARIANT                     12
                            note = A or N
VARIANT                     16
```

```
                        note = Q or T
source                  1..17
                        mol_type = protein
                        organism = synthetic construct
SEQUENCE: 186
XXXPXXXXXX YXQKFXG                                                          17

SEQ ID NO: 187          moltype =    length =
SEQUENCE: 187
000

SEQ ID NO: 188          moltype = AA   length = 11
FEATURE                 Location/Qualifiers
REGION                  1..11
                        note = Description of Artificial Sequence: Synthetic peptide
VARIANT                 1
                        note = R or G
VARIANT                 2
                        note = A or T
VARIANT                 4
                        note = Q or E
VARIANT                 5
                        note = E, N, T, S, A, K, D, G, R, or Q
VARIANT                 7
                        note = Y or S
VARIANT                 9
                        note = A or V
source                  1..11
                        mol_type = protein
                        organism = synthetic construct
SEQUENCE: 188
XXSXXIXGXL N                                                                11

SEQ ID NO: 189          moltype =    length =
SEQUENCE: 189
000

SEQ ID NO: 190          moltype = AA   length = 9
FEATURE                 Location/Qualifiers
REGION                  1..9
                        note = Description of Artificial Sequence: Synthetic peptide
VARIANT                 2
                        note = S, N, D, Q, A, or E
VARIANT                 3
                        note = T, I, or S
VARIANT                 4
                        note = Y, L, or F
VARIANT                 5
                        note = D, G, T, E, Q, A, or Y
VARIANT                 6
                        note = A, T, R, S, K, or Y
source                  1..9
                        mol_type = protein
                        organism = synthetic construct
SEQUENCE: 190
QXXXXXPWT                                                                   9

SEQ ID NO: 191          moltype = AA   length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 191
QVQLVQSGAE VKKPGSSVKV SCKASGGTFS                                            30

SEQ ID NO: 192          moltype = AA   length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 192
WVRQAPGQGL EWMG                                                             14

SEQ ID NO: 193          moltype = AA   length = 32
```

```
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 193
RVTITADEST STAYMELSSL RSEDTAVYYC AR                                        32

SEQ ID NO: 194          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 194
WGQGTLVTVS S                                                               11

SEQ ID NO: 195          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 195
DIQMTQSPSS LSASVGDRVT ITC                                                  23

SEQ ID NO: 196          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 196
WYQQKPGKAP KLLIY                                                           15

SEQ ID NO: 197          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 197
GVPSRFSGSG SGTDFTLTIS SLQPEDFATY YC                                        32

SEQ ID NO: 198          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 198
FGGGTKVEIK                                                                 10

SEQ ID NO: 199          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 199
SYAIS                                                                      5

SEQ ID NO: 200          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 200
```

```
GIIPGAATAN YAQKFQG                                                          17

SEQ ID NO: 201         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 201
DAAGIRLFAD                                                                  10

SEQ ID NO: 202         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 202
QSTYDAPWT                                                                   9

SEQ ID NO: 203         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 203
GIIPGYATAN YAQKFQG                                                          17

SEQ ID NO: 204         moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 204
DAAGIRLFAD                                                                  10

SEQ ID NO: 205         moltype = AA  length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 205
RASQSIYGAL N                                                                11

SEQ ID NO: 206         moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 206
GASNLQS                                                                     7

SEQ ID NO: 207         moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 207
QSTYTAPWT                                                                   9

SEQ ID NO: 208         moltype =    length =
SEQUENCE: 208
000

SEQ ID NO: 209         moltype = AA  length = 17
FEATURE                Location/Qualifiers
REGION                 1..17
```

```
                        note = Description of Artificial Sequence: Synthetic peptide
VARIANT                 3
                        note = T, N, S, Q, E, H, R, or A
VARIANT                 4
                        note = Y, W, F, or H
VARIANT                 5
                        note = A, S, Q, E, or T
VARIANT                 7
                        note = G or E
VARIANT                 8
                        note = S or I
VARIANT                 10
                        note = A or G
source                  1..17
                        mol_type = protein
                        organism = synthetic construct
SEQUENCE: 209
DIXXXGXXTX YADSVKG                                                              17

SEQ ID NO: 210          moltype = AA  length = 12
FEATURE                 Location/Qualifiers
REGION                  1..12
                        note = Description of Artificial Sequence: Synthetic peptide
VARIANT                 1
                        note = S or A
VARIANT                 2
                        note = N, H, A, D, L, Q, Y, or R
VARIANT                 3
                        note = A, N, S, or G
VARIANT                 5
                        note = A, V, R, E, or S
VARIANT                 7
                        note = D or S
VARIANT                 8
                        note = D, N, Q, E, S, T, or L
VARIANT                 10
                        note = L, F, or M
VARIANT                 12
                        note = I, Y, or V
source                  1..12
                        mol_type = protein
                        organism = synthetic construct
SEQUENCE: 210
XXXYXWXXAX DX                                                                   12

SEQ ID NO: 211          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 211
EVQLVESGGG LVQPGGSLRL SCAASGFTFS                                                30

SEQ ID NO: 212          moltype = AA  length = 14
FEATURE                 Location/Qualifiers
REGION                  1..14
                        note = Description of Artificial Sequence: Synthetic peptide
source                  1..14
                        mol_type = protein
                        organism = synthetic construct
SEQUENCE: 212
WVRQAPGKGL EWVS                                                                 14

SEQ ID NO: 213          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 213
RFTISRDNAK NSLYLQMNSL RAEDTAVYYC AR                                             32

SEQ ID NO: 214          moltype = AA  length = 11
FEATURE                 Location/Qualifiers
```

```
REGION                  1..11
                        note = Description of Artificial Sequence: Synthetic peptide
source                  1..11
                        mol_type = protein
                        organism = synthetic construct
SEQUENCE: 214
WGQGTMVTVS S                                                                      11

SEQ ID NO: 215          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 215
WGQGTLVTVS S                                                                      11

SEQ ID NO: 216          moltype = AA  length = 23
FEATURE                 Location/Qualifiers
REGION                  1..23
                        note = Description of Artificial Sequence: Synthetic peptide
source                  1..23
                        mol_type = protein
                        organism = synthetic construct
SEQUENCE: 216
EIVLTQSPGT LSLSPGERAT LSC                                                         23

SEQ ID NO: 217          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 217
WYQQKPGQAP RLLIY                                                                  15

SEQ ID NO: 218          moltype = AA  length = 32
FEATURE                 Location/Qualifiers
REGION                  1..32
                        note = Description of Artificial Sequence: Synthetic
                         polypeptide
source                  1..32
                        mol_type = protein
                        organism = synthetic construct
SEQUENCE: 218
GIPDRFSGSG SGTDFTLTIS RLEPEDFAVY YC                                                32

SEQ ID NO: 219          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 219
FGQGTKVEIK                                                                        10

SEQ ID NO: 220          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 220
SYAMS                                                                              5

SEQ ID NO: 221          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 221
DITYAGGSTA YADSVKG                                                                17
```

| | |
|---|---|
| SEQ ID NO: 222 | moltype = AA  length = 12 |
| FEATURE | Location/Qualifiers |
| REGION | 1..12 |
| | note = Description of Artificial Sequence: Synthetic peptide |
| source | 1..12 |
| | mol_type = protein |
| | organism = synthetic construct |
| SEQUENCE: 222 | |
| SNAYAWDDAL DI | 12 |
| SEQ ID NO: 223 | moltype = AA  length = 7 |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |
| SEQUENCE: 223 | |
| GYTFTKY | 7 |
| SEQ ID NO: 224 | moltype = AA  length = 6 |
| FEATURE | Location/Qualifiers |
| REGION | 1..6 |
| | note = Description of Artificial Sequence: Synthetic peptide |
| source | 1..6 |
| | mol_type = protein |
| | organism = synthetic construct |
| SEQUENCE: 224 | |
| NPNNDE | 6 |
| SEQ ID NO: 225 | moltype = AA  length = 10 |
| FEATURE | Location/Qualifiers |
| REGION | 1..10 |
| | note = Description of Artificial Sequence: Synthetic peptide |
| source | 1..10 |
| | mol_type = protein |
| | organism = synthetic construct |
| SEQUENCE: 225 | |
| DGLGLRLFAD | 10 |
| SEQ ID NO: 226 | moltype = AA  length = 7 |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |
| SEQUENCE: 226 | |
| GYRFHNF | 7 |
| SEQ ID NO: 227 | moltype = AA  length = 6 |
| FEATURE | Location/Qualifiers |
| REGION | 1..6 |
| | note = Description of Artificial Sequence: Synthetic peptide |
| source | 1..6 |
| | mol_type = protein |
| | organism = synthetic construct |
| SEQUENCE: 227 | |
| IPGHAK | 6 |
| SEQ ID NO: 228 | moltype = AA  length = 7 |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |
| SEQUENCE: 228 | |
| GSRFYKF | 7 |
| SEQ ID NO: 229 | moltype = AA  length = 7 |
| FEATURE | Location/Qualifiers |
| REGION | 1..7 |
| | note = Description of Artificial Sequence: Synthetic peptide |
| source | 1..7 |
| | mol_type = protein |
| | organism = synthetic construct |
| SEQUENCE: 229 | |
| GSGFRGH | 7 |

```
SEQ ID NO: 230         moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 230
GFTFDDY                                                                          7

SEQ ID NO: 231         moltype = AA   length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 231
NWSGEI                                                                           6

SEQ ID NO: 232         moltype = AA   length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 232
SYDGSN                                                                           6

SEQ ID NO: 233         moltype = AA   length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 233
GYAFSSY                                                                          7

SEQ ID NO: 234         moltype = AA   length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 234
YPGDGD                                                                           6

SEQ ID NO: 235         moltype =     length =
SEQUENCE: 235
000

SEQ ID NO: 236         moltype =     length =
SEQUENCE: 236
000

SEQ ID NO: 237         moltype =     length =
SEQUENCE: 237
000

SEQ ID NO: 238         moltype = AA   length = 25
FEATURE                Location/Qualifiers
REGION                 1..25
                       note = Description of Artificial Sequence: Synthetic peptide
source                 1..25
                       mol_type = protein
                       organism = synthetic construct
SEQUENCE: 238
QVQLVQSGAE VKKPGSSVKV SCKAS                                                      25

SEQ ID NO: 239         moltype = AA   length = 19
FEATURE                Location/Qualifiers
REGION                 1..19
                       note = Description of Artificial Sequence: Synthetic peptide
source                 1..19
                       mol_type = protein
```

```
                           organism = synthetic construct
SEQUENCE: 239
AISWVRQAPG QGLEWMGGI                                                19

SEQ ID NO: 240          moltype = AA   length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 240
ANYAQKFQGR VTITADESTS TAYMELSSLR SEDTAVYYCA R                       41

SEQ ID NO: 241          moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 241
GGTFSSY                                                             7

SEQ ID NO: 242          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 242
IPGAAT                                                              6

SEQ ID NO: 243          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 243
IPGYAT                                                              6

SEQ ID NO: 244          moltype = AA   length = 7
FEATURE                 Location/Qualifiers
REGION                  1..7
                        note = Description of Artificial Sequence: Synthetic peptide
VARIANT                 5
                        note = S, D, E, Q, S, or A
VARIANT                 6
                        note = S, D, E, A, or Q
source                  1..7
                        mol_type = protein
                        organism = synthetic construct
SEQUENCE: 244
GFTFXXY                                                             7

SEQ ID NO: 245          moltype =    length =
SEQUENCE: 245
000

SEQ ID NO: 246          moltype = AA   length = 12
FEATURE                 Location/Qualifiers
REGION                  1..12
                        note = Description of Artificial Sequence: Synthetic peptide
VARIANT                 1
                        note = S or A
VARIANT                 2
                        note = N, H, A, D, L, Q, Y, or R
VARIANT                 3
                        note = A, N, S, or G
VARIANT                 5
                        note = A, V, R, E, or S
VARIANT                 7
                        note = D or S
VARIANT                 8
                        note = D, N, Q, E, S, T, or L
```

```
VARIANT                 10
                        note = L, F, or M
VARIANT                 12
                        note = I, Y, or V
source                  1..12
                        mol_type = protein
                        organism = synthetic construct
SEQUENCE: 246
XXXYXWXXAX DX                                                          12

SEQ ID NO: 247          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 247
EVQLVESGGG LVQPGGSLRL SCAAS                                            25

SEQ ID NO: 248          moltype = AA  length = 19
FEATURE                 Location/Qualifiers
REGION                  1..19
                        note = Description of Artificial Sequence: Synthetic peptide
source                  1..19
                        mol_type = protein
                        organism = synthetic construct
SEQUENCE: 248
AMSWVRQAPG KGLEWVSDI                                                   19

SEQ ID NO: 249          moltype = AA  length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 249
TAYADSVKGR FTISRDNAKN SLYLQMNSLR AEDTAVYYCA R                           41

SEQ ID NO: 250          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 250
GFTFSSY                                                                7

SEQ ID NO: 251          moltype = AA  length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 251
TYAGGS                                                                 6

SEQ ID NO: 252          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 252
KYAIS                                                                  5

SEQ ID NO: 253          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 253
```

-continued

```
HFNPNNDETK YNQKFQG                                                       17

SEQ ID NO: 254          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 254
DGLGLRLFAD                                                               10

SEQ ID NO: 255          moltype = AA  length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 255
RASENIYGAL N                                                             11

SEQ ID NO: 256          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 256
GATNLAD                                                                  7

SEQ ID NO: 257          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 257
QNILDTPWT                                                                9

SEQ ID NO: 258          moltype = AA  length = 119
FEATURE                 Location/Qualifiers
REGION                  1..119
                        note = Description of Artificial Sequence: Synthetic
                         polypeptide
source                  1..119
                        mol_type = protein
                        organism = synthetic construct
SEQUENCE: 258
QVQLVQSGAE VKKPGSSVKV SCKASGYTFT KYAISWVRQA PGQGLEWMGH FNPNNDETKY    60
NQKFQGRVTI TADESTSTAY MELSSLRSED TAVYYCARDG LGLRLFADWG QGTLVTVSS    119

SEQ ID NO: 259          moltype = AA  length = 107
FEATURE                 Location/Qualifiers
REGION                  1..107
                        note = Description of Artificial Sequence: Synthetic
                         polypeptide
source                  1..107
                        mol_type = protein
                        organism = synthetic construct
SEQUENCE: 259
DIQMTQSPSS LSASVGDRVT ITCRASENIY GALNWYQQKP GKAPKLLIYG ATNLADGVPS    60
RFSGSGSGTD FTLTISSLQP EDFATYYCQN ILDTPWTFGG GTKLEIK                 107

SEQ ID NO: 260          moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 260
DISYAGGSTA YADSVKG                                                       17

SEQ ID NO: 261          moltype = AA  length = 6
FEATURE                 Location/Qualifiers
REGION                  1..6
```

```
                        note = Description of Artificial Sequence: Synthetic peptide
source                  1..6
                        mol_type = protein
                        organism = synthetic construct
SEQUENCE: 261
SYAGGS                                                                       6

SEQ ID NO: 262          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 262
DIQMTQSPSS LSASVGDRVT ITCRASQSIY GALNWYQQKP GKAPKLLIYG ASNLQSGVPS    60
RFSGSGSGTD FTLTISSLQP EDFATYYCQS TYTAPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 263          moltype = AA  length = 597
FEATURE                 Location/Qualifiers
REGION                  1..597
                        note = Description of Artificial Sequence: Synthetic
                         polypeptide
source                  1..597
                        mol_type = protein
                        organism = synthetic construct
SEQUENCE: 263
QVQLVQSGAE VKKPGSSVKV SCKASGGTFS SYAISWVRQA PGQGLEWMGG IIPGYATANY    60
AQKFQGRVTI TADESTSTAY MELSSLRSED TAVYYCARDA AGIRLFADWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPCREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPGSG GGGSGGGGS GGGSQGQDRH MIRMRQLIDI   480
VDQLKNYVND LVPEFLPAPE DVETNCEWSA FSCFQKAQLK SANTGNNERI INVSIKKLKE   540
KPPGGEGGGG GGGEGGCPSC DSYEKKPPKE FLERFKSLLQ KMIHQHLSSR THGSEDS     597

SEQ ID NO: 264          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 264
QVQLVQSGAE VKKPGSSVKV SCKASGGTFS SYAISWVRQA PGQGLEWMGG IIPGYATANY    60
AQKFQGRVTI TADESTSTAY MELSSLRSED TAVYYCARDA AGIRLFADWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV CTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 265          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 265
QVQLVQSGAE VKKPGSSVKV SCKASGGTFS SYAISWVRQA PGQGLEWMGG IIPGYATANY    60
AQKFQGRVTI TADESTSTAY MELSSLRSED TAVYYCARDA AGIRLFADWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV CTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 266          moltype = AA  length = 214
FEATURE                 Location/Qualifiers
```

```
REGION                  1..214
                        note = Description of Artificial Sequence: Synthetic
                         polypeptide
source                  1..214
                        mol_type = protein
                        organism = synthetic construct
SEQUENCE: 266
DIQMTQSPSS LSASVGDRVT ITCRASQSIY GALNWYQQKP GKAPKLLIYG ASNLQSGVPS    60
RFSGSGSGTD FTLTISSLQP EDFATYYCQS TYTAPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 267          moltype = AA  length = 597
FEATURE                 Location/Qualifiers
REGION                  1..597
                        note = Description of Artificial Sequence: Synthetic
                         polypeptide
source                  1..597
                        mol_type = protein
                        organism = synthetic construct
SEQUENCE: 267
QVQLVQSGAE VKKPGSSVKV SCKASGGTFS SYAISWVRQA PGQGLEWMGG IIPGYATANY    60
AQKFQGRVTI TADESTSTAY MELSSLRSED TAVYYCARDA AGIRLFADWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPCREEM   360
TKNQVSLSCA VKGFYPSDIA VEWESNGQPE NNYKTTPPVL DSDGSFFLVS KLTVDKSRWQ   420
QGNVFSCSVM HEALHNHYTQ KSLSLSPGSG GGGSGGGGSG GGGSQGQDRH MIRMRQLIDI   480
VDQLKNYVND LVPEFLPAPE DVETNCEWSA FSCFQKAQLK SANTGNNERI INVSIKKLKF   540
KPPGGEGGGG GGGEGGCPSC DSYEKKPPKE FLERFKSLLQ KMIHQHLSSR THGSEDS      597

SEQ ID NO: 268          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 268
QVQLVQSGAE VKKPGSSVKV SCKASGGTFS SYAISWVRQA PGQGLEWMGG IIPGYATANY    60
AQKFQGRVTI TADESTSTAY MELSSLRSED TAVYYCARDA AGIRLFADWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV CTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 269          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 269
QVQLVQSGAE VKKPGSSVKV SCKASGGTFS SYAISWVRQA PGQGLEWMGG IIPGYATANY    60
AQKFQGRVTI TADESTSTAY MELSSLRSED TAVYYCARDA AGIRLFADWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV CTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 270          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 270
DIQMTQSPSS LSASVGDRVT ITCRASQSIY GALNWYQQKP GKAPKLLIYG ASNLQSGVPS    60
RFSGSGSGTD FTLTISSLQP EDFATYYCQS TYTAPWTFGG GTKVEIKRTV AAPSVFIFPP   120
```

```
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 271           moltype = AA  length = 597
FEATURE                  Location/Qualifiers
REGION                   1..597
                         note = Description of Artificial Sequence: Synthetic
                         polypeptide
source                   1..597
                         mol_type = protein
                         organism = synthetic construct
SEQUENCE: 271
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPCREEM  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGSG GGGSGGGGSG GGGSQGQDRH MIRMRQLIDI  480
VDQLKNYVND LVPEFLPAPE DVETNCEWSA FSCFQKAQLK SANTGNNERI INVSIKKLKQ  540
KPPGEGGGG GGGEGGCPSC DSYEKKPPKE FLERFKSLLQ KMIHQHLSSR THGSEDS     597

SEQ ID NO: 272           moltype = AA  length = 448
FEATURE                  Location/Qualifiers
REGION                   1..448
                         note = Description of Artificial Sequence: Synthetic
                         polypeptide
source                   1..448
                         mol_type = protein
                         organism = synthetic construct
SEQUENCE: 272
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV CTLPPSREEM  360
TKNQVSLWCL VKGFYPSDIA VEWESNGQPE NNYKTTPPVL DSDGSFFLYS KLTVDKSRWQ  420
QGNVFSCSVM HEALHNHYTQ KSLSLSPG                                     448

SEQ ID NO: 273           moltype = AA  length = 449
FEATURE                  Location/Qualifiers
REGION                   1..449
                         note = Description of Artificial Sequence: Synthetic
                         polypeptide
source                   1..449
                         mol_type = protein
                         organism = synthetic construct
SEQUENCE: 273
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV CTLPPSREEM  360
TKNQVSLWCL VKGFYPSDIA VEWESNGQPE NNYKTTPPVL DSDGSFFLYS KLTVDKSRWQ  420
QGNVFSCSVM HEALHNHYTQ KSLSLSPGK                                    449

SEQ ID NO: 274           moltype = AA  length = 214
FEATURE                  Location/Qualifiers
REGION                   1..214
                         note = Description of Artificial Sequence: Synthetic
                         polypeptide
source                   1..214
                         mol_type = protein
                         organism = synthetic construct
SEQUENCE: 274
DIQMTQSPSS LSASVGDRVT ITCRASQSIY GALNWYQQKP GKAPKLLIYG ASNLQSGVPS   60
RFSGSGSGTD FTLTISSLQP EDFATYYCQS TYTAPWTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 275           moltype = AA  length = 597
FEATURE                  Location/Qualifiers
REGION                   1..597
                         note = Description of Artificial Sequence: Synthetic
                         polypeptide
source                   1..597
```

```
                        mol_type = protein
                        organism = synthetic construct
SEQUENCE: 275
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPCREEM  360
TKNQVSLSCA VKGFYPSDIA VEWESNGQPE NNYKTTPPVL DSDGSFFLVS KLTVDKSRWQ  420
QGNVFSCSVM HEALHNHYTQ KSLSLSPGSG GGGSGGGGSG GGGSQGQDRH MISMRQLIDI  480
VDQLKNYVND LVPEFLPAPE DVETNCEWSA FSCFQKAQLK SANTGNNERI INVSIKKLKR  540
KPPGEGGGG GGGEGGCPSC DSYEKKPPKE FLERFKSLLQ KMIHQHLSSR THGSEDS     597

SEQ ID NO: 276          moltype = AA  length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 276
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV CTLPPSREEM  360
TKNQVSLWCL VKGFYPSDIA VEWESNGQPE NNYKTTPPVL DSDGSFFLYS KLTVDKSRWQ  420
QGNVFSCSVM HEALHNHYTQ KSLSLSPG                                    448

SEQ ID NO: 277          moltype = AA  length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 277
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV CTLPPSREEM  360
TKNQVSLWCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 278          moltype = AA  length = 214
FEATURE                 Location/Qualifiers
REGION                  1..214
                        note = Description of Artificial Sequence: Synthetic
                         polypeptide
source                  1..214
                        mol_type = protein
                        organism = synthetic construct
SEQUENCE: 278
DIQMTQSPSS LSASVGDRVT ITCRASQSIY GALNWYQQKP GKAPKLLIYG ASNLQSGVPS   60
RFSGSGSGTD FTLTISSLQP EDFATYYCQS TYTAPWTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 279          moltype = AA  length = 597
FEATURE                 Location/Qualifiers
REGION                  1..597
                        note = Description of Artificial Sequence: Synthetic
                         polypeptide
source                  1..597
                        mol_type = protein
                        organism = synthetic construct
SEQUENCE: 279
QVQLVQSGAE VKKPGSSVKV SCKASGGTFS SYAISWVRQA PGQGLEWMGG IIPGYATANY   60
AQKFQGRVTI TADESTSTAY MELSSLRSED TAVYYCARDA AGIRLFADWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPCREEM  360
```

```
TKNQVSLSCA VKGFYPSDIA VEWESNGQPE NNYKTTPPVL DSDGSFFLVS KLTVDKSRWQ    420
QGNVFSCSVM HEALHNHYTQ KSLSLSPGSG GGGSGGGGSG GGGSQGQDRH MIGMRQLIDI    480
VDQLKNYVND LVPEFLPAPE DVETNCEWSA FSCFQKAQLK SANTGNNERI INVSIKKLKR    540
KPPGEGGGG GGGEGGCPSC DSYEKKPPKE FLERFKSLLQ KMIHQHLSSR THGSEDS        597

SEQ ID NO: 280          moltype = AA   length = 448
FEATURE                 Location/Qualifiers
REGION                  1..448
                        note = Description of Artificial Sequence: Synthetic
                         polypeptide
source                  1..448
                        mol_type = protein
                        organism = synthetic construct
SEQUENCE: 280
QVQLVQSGAE VKKPGSSVKV SCKASGGTFS SYAISWVRQA PGQGLEWMGG IIPGYATANY    60
AQKFQGRVTI TADESTSTAY MELSSLRSED TAVYYCARDA AGIRLFADWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV CTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 281          moltype = AA   length = 449
FEATURE                 Location/Qualifiers
REGION                  1..449
                        note = Description of Artificial Sequence: Synthetic
                         polypeptide
source                  1..449
                        mol_type = protein
                        organism = synthetic construct
SEQUENCE: 281
QVQLVQSGAE VKKPGSSVKV SCKASGGTFS SYAISWVRQA PGQGLEWMGG IIPGYATANY    60
AQKFQGRVTI TADESTSTAY MELSSLRSED TAVYYCARDA AGIRLFADWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPEAAGAP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV CTLPPSREEM   360
TKNQVSLWCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 282          moltype = AA   length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 282
QGPDRLLIRL RHLIDIVEQL KIYENDLDPE LLSAPQDVKG HCEHAAFACF QKAKLKPSNP    60
GNNKTFIIDL VAQLERRLPA GEGGEGQEHI AKCPSCDSYE KRTPKEFLER LKWLLQKMIH   120
QHLS                                                                124

SEQ ID NO: 283          moltype = AA   length = 124
FEATURE                 Location/Qualifiers
REGION                  1..124
                        note = Description of Artificial Sequence: Synthetic
                         polypeptide
source                  1..124
                        mol_type = protein
                        organism = synthetic construct
SEQUENCE: 283
QGPDRLLIRL RHLIDIVEQL KIYENDLDPE LLSAPQDVKG HCEHAAFACF QKAKLKPSNP    60
GNNKTFIIDL VAQLEERLPA GEGGEGQEHI AKCPSCDSYE KRTPKEFLER LKWLLQKMIH   120
QHLS                                                                124

SEQ ID NO: 284          moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 284
DGLGLRLFAD                                                          10

SEQ ID NO: 285          moltype = AA   length = 11
FEATURE                 Location/Qualifiers
```

```
REGION                  1..11
                        note = Description of Artificial Sequence: Synthetic peptide
source                  1..11
                        mol_type = protein
                        organism = synthetic construct
SEQUENCE: 285
RASENIYGAL N                                                                      11

SEQ ID NO: 286          moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 286
GATNLAD                                                                            7

SEQ ID NO: 287          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 287
QNILDTPWT                                                                          9

SEQ ID NO: 288          moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 288
SNAYAWDDAL DI                                                                     12

SEQ ID NO: 289          moltype = AA  length = 52
FEATURE                 Location/Qualifiers
REGION                  1..52
                        note = Description of Artificial Sequence: Synthetic
                         polypeptide
SITE                    2..49
                        note = This region may encompass 1-12 "Gly Gly Gly Ser"
                         repeating units
SITE                    50..52
                        note = This region may encompass 0-3 residues
source                  1..52
                        mol_type = protein
                        organism = synthetic construct
SEQUENCE: 289
SGGGSGGGSG GGSGGGSGGG SGGGSGGGSG GGSGGGSGGG SGGGSGGGSG GG                          52

SEQ ID NO: 290          moltype = AA  length = 64
FEATURE                 Location/Qualifiers
REGION                  1..64
                        note = Description of Artificial Sequence: Synthetic
                         polypeptide
SITE                    2..61
                        note = This region may encompass 1-12 "Gly Gly Gly Gly Ser"
                         repeating units
SITE                    62..64
                        note = This region may encompass 0-3 residues
source                  1..64
                        mol_type = protein
                        organism = synthetic construct
SEQUENCE: 290
SGGGGSGGGG SGGGGSGGGG SGGGGSGGGG SGGGGSGGGG SGGGGSGGGG SGGGGSGGGG                  60
SGGG                                                                              64

SEQ ID NO: 291          moltype = AA  length = 76
FEATURE                 Location/Qualifiers
REGION                  1..76
                        note = Description of Artificial Sequence: Synthetic
                         polypeptide
SITE                    2..73
                        note = This region may encompass 1-12 "Gly Gly Gly Gly Gly
                         Ser" repeating units
```

```
SITE                    74..76
                        note = This region may encompass 0-3 residues
source                  1..76
                        mol_type = protein
                        organism = synthetic construct
SEQUENCE: 291
SGGGGGSGGG GGSGGGGGSG GGGGSGGGG SGGGGGSGGG GGSGGGGGSG GGGGSGGGG       60
SGGGGGSGGG GGSGGG                                                      76

SEQ ID NO: 292          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 292
SGGGGSGGGG SGGGGS                                                      16

SEQ ID NO: 293          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 293
SGGGGSGGGG SGGGG                                                       15

SEQ ID NO: 294          moltype = AA  length = 51
FEATURE                 Location/Qualifiers
REGION                  1..51
                        note = Description of Artificial Sequence: Synthetic
                        polypeptide
SITE                    1..48
                        note = This region may encompass 1-12 "Gly Gly Gly Ser"
                        repeating units
SITE                    49..51
                        note = This region may encompass 0-3 residues
source                  1..51
                        mol_type = protein
                        organism = synthetic construct
SEQUENCE: 294
GGGSGGGSGG GSGGGSGGGS GGGSGGGSGG GSGGGSGGGS GGGSGGGSGG G               51

SEQ ID NO: 295          moltype = AA  length = 63
FEATURE                 Location/Qualifiers
REGION                  1..63
                        note = Description of Artificial Sequence: Synthetic
                        polypeptide
SITE                    1..60
                        note = This region may encompass 1-12 "Gly Gly Gly Gly Ser"
                        repeating units
SITE                    61..63
                        note = This region may encompass 0-3 residues
source                  1..63
                        mol_type = protein
                        organism = synthetic construct
SEQUENCE: 295
GGGGSGGGGS GGGGSGGGGS GGGGSGGGGS GGGGSGGGGS GGGGSGGGGS GGGGSGGGGS      60
GGG                                                                    63

SEQ ID NO: 296          moltype = AA  length = 75
FEATURE                 Location/Qualifiers
REGION                  1..75
                        note = Description of Artificial Sequence: Synthetic
                        polypeptide
SITE                    1..72
                        note = This region may encompass 1-12 "Gly Gly Gly Gly Gly
                        Ser" repeating units
SITE                    73..75
                        note = This region may encompass 0-3 residues
source                  1..75
                        mol_type = protein
                        organism = synthetic construct
SEQUENCE: 296
GGGGGSGGGG GSGGGGGSGG GGGSGGGGGS GGGGGSGGGG GSGGGGGSGG GGGSGGGGGS      60
GGGGGSGGGG GSGGG                                                       75
```

```
SEQ ID NO: 297              moltype = AA   length = 215
FEATURE                     Location/Qualifiers
REGION                      1..215
                            note = Description of Artificial Sequence: Synthetic
                            polypeptide
source                      1..215
                            mol_type = protein
                            organism = synthetic construct
SEQUENCE: 297
EIVLTQSPGT LSLSPGERAT LSCRASQSVS SNLAWYQQKP GQAPRLLIYG ASSRATGIPD    60
RFSGSGSGTD FTLTISRLEP EDFAVYYCQQ YGSSPPVTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 298              moltype = AA   length = 599
FEATURE                     Location/Qualifiers
REGION                      1..599
                            note = Description of Artificial Sequence: Synthetic
                            polypeptide
source                      1..599
                            mol_type = protein
                            organism = synthetic construct
SEQUENCE: 298
EVQLVESGGG LVQPGGSLRL SCAASGFTFS SYAMSWVRQA PGKGLEWVSD ITYAGGSTAY    60
ADSVKGRFTI SRDNAKNSLY LQMNSLRAED TAVYYCARSN AYAWDDALDI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
APSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPCRE   360
EMTKNQVSLS CAVKGFYPSD IAVEWESNGQ PENNYKTTPP VLDSDGSFFL VSKLTVDKSR   420
WQQGNVFSCS VMHEALHNHY TQKSLSLSPG SGGGGSGGGG SGGGGSQGQD RHMIRMRQLI   480
DIVDQLKNYV NDLVPEFLPA PEDVETNCEW SAFSCFQKAQ LKSANTGNNE RIINVSIKKL   540
KEKPPGGEGG GGGGGEGGCP SCDSYEKKPP KEFLERFKSL LQKMIHQHLS SRTHGSEDS    599

SEQ ID NO: 299              moltype = AA   length = 450
FEATURE                     Location/Qualifiers
REGION                      1..450
                            note = Description of Artificial Sequence: Synthetic
                            polypeptide
source                      1..450
                            mol_type = protein
                            organism = synthetic construct
SEQUENCE: 299
EVQLVESGGG LVQPGGSLRL SCAASGFTFS SYAMSWVRQA PGKGLEWVSD ITYAGGSTAY    60
ADSVKGRFTI SRDNAKNSLY LQMNSLRAED TAVYYCARSN AYAWDDALDI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
APSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVCTLPPSRE   360
EMTKNQVSLC LVKGFYPSD IAVEWESNGQ PENNYKTTPP VLDSDGSFFL YSKLTVDKSR    420
WQQGNVFSCS VMHEALHNHY TQKSLSLSPG                                    450

SEQ ID NO: 300              moltype = AA   length = 451
FEATURE                     Location/Qualifiers
REGION                      1..451
                            note = Description of Artificial Sequence: Synthetic
                            polypeptide
source                      1..451
                            mol_type = protein
                            organism = synthetic construct
SEQUENCE: 300
EVQLVESGGG LVQPGGSLRL SCAASGFTFS SYAMSWVRQA PGKGLEWVSD ITYAGGSTAY    60
ADSVKGRFTI SRDNAKNSLY LQMNSLRAED TAVYYCARSN AYAWDDALDI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
APSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVCTLPPSRE   360
EMTKNQVSLW CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 301              moltype = AA   length = 215
FEATURE                     Location/Qualifiers
REGION                      1..215
                            note = Description of Artificial Sequence: Synthetic
                            polypeptide
source                      1..215
                            mol_type = protein
                            organism = synthetic construct
SEQUENCE: 301
```

```
EIVLTQSPGT LSLSPGERAT LSCRASQSVS SNLAWYQQKP GQAPRLLIYG ASSRATGIPD    60
RFSGSGSGTD FTLTISRLEP EDFAVYYCQQ YGSSPPVTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 302          moltype = AA  length = 599
FEATURE                 Location/Qualifiers
REGION                  1..599
                        note = Description of Artificial Sequence: Synthetic
                         polypeptide
source                  1..599
                        mol_type = protein
                        organism = synthetic construct
SEQUENCE: 302
EVQLVESGGG LVQPGGSLRL SCAASGFTFS SYAMSWVRQA PGKGLEWVSD ITYAGGSTAY    60
ADSVKGRFTI SRDNAKNSLY LQMNSLRAED TAVYYCARSN AYAWDDALDI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
APSVFLPPKP KDTLMISRT  PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPCRE   360
EMTKNQVSLS CAVKGFYPSD IAVEWESNGQ PENNYKTTPP VLDSDGSFFL VSKLTVDKSR   420
WQQGNVFSCS VMHEALHNHY TQKSLSLSPG SGGGGSGGGG SGGGGSGQGD RHMIRMQLI    480
DIVDQLKNYV NDLVPEFLPA PEDVETNCEW SAFSCFGKAQ LKSANTGNNE RIINVSIKKL   540
KFKPPGEGG GGGGGEGGCP SCDSYEKKPP KEFLERFKSL LQKMIHQHLS SRTHGSEDS    599

SEQ ID NO: 303          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 303
EVQLVESGGG LVQPGGSLRL SCAASGFTFS SYAMSWVRQA PGKGLEWVSD ITYAGGSTAY    60
ADSVKGRFTI SRDNAKNSLY LQMNSLRAED TAVYYCARSN AYAWDDALDI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
APSVFLPPKP KDTLMISRT  PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVCTLPPSRE   360
EMTKNQVSLW CLVKGFYPSD IAVEWESNGQ PENNYKTTPP VLDSDGSFFL YSKLTVDKSR   420
WQQGNVFSCS VMHEALHNHY TQKSLSLSPG                                    450

SEQ ID NO: 304          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 304
EVQLVESGGG LVQPGGSLRL SCAASGFTFS SYAMSWVRQA PGKGLEWVSD ITYAGGSTAY    60
ADSVKGRFTI SRDNAKNSLY LQMNSLRAED TAVYYCARSN AYAWDDALDI WGQGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPEAAG   240
APSVFLPPKP KDTLMISRT  PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVCTLPPSRE   360
EMTKNQVSLW CLVKGFYPSD IAVEWESNGQ PENNYKTTPP VLDSDGSFFL YSKLTVDKSR   420
WQQGNVFSCS VMHEALHNHY TQKSLSLSPG K                                  451

SEQ ID NO: 305          moltype = AA  length = 215
FEATURE                 Location/Qualifiers
REGION                  1..215
                        note = Description of Artificial Sequence: Synthetic
                         polypeptide
source                  1..215
                        mol_type = protein
                        organism = synthetic construct
SEQUENCE: 305
EIVLTQSPGT LSLSPGERAT LSCRASQSVS SNLAWYQQKP GQAPRLLIYG ASSRATGIPD    60
RFSGSGSGTD FTLTISRLEP EDFAVYYCQQ YGSSPPVTFG QGTKVEIKRT VAAPSVFIFP   120
PSDEQLKSGT ASVVCLLNNF YPREAKVQWK VDNALQSGNS QESVTEQDSK DSTYSLSSTL   180
TLSKADYEKH KVYACEVTHQ GLSSPVTKSF NRGEC                              215

SEQ ID NO: 306          moltype = AA  length = 599
FEATURE                 Location/Qualifiers
REGION                  1..599
                        note = Description of Artificial Sequence: Synthetic
```

```
                            polypeptide
source                      1..599
                            mol_type = protein
                            organism = synthetic construct
SEQUENCE: 306
EVQLVESGGG LVQPGGSLRL SCAASGFTFS SYAMSWVRQA PGKGLEWVSD ITYAGGSTAY   60
ADSVKGRFTI SRDNAKNSLY LQMNSLRAED TAVYYCARSN AYAWDDALDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPCRE  360
EMTKNQVSLS CAVKGFYPSD IAVEWESNGQ PENNYKTTPP VLDSDGSFFL VSKLTVDKSR  420
WQQGNVFSCS VMHEALHNHY TQKSLSLSPG SGGGGSGGGG SGGGGSQGQD RHMIRMRQLI  480
DIVDQLKNYV NDLVPEFLPA PEDVETNCEW SAFSCFQKAQ LKSANTGNNE RIINVSIKKL  540
KQKPPGGEGG GGGGGEGGCP SCDSYEKKPP KEFLERFKSL LQKMIHQHLS SRTHGSEDS   599

SEQ ID NO: 307              moltype = AA  length = 450
FEATURE                     Location/Qualifiers
REGION                      1..450
                            note = Description of Artificial Sequence: Synthetic
                            polypeptide
source                      1..450
                            mol_type = protein
                            organism = synthetic construct
SEQUENCE: 307
EVQLVESGGG LVQPGGSLRL SCAASGFTFS SYAMSWVRQA PGKGLEWVSD ITYAGGSTAY   60
ADSVKGRFTI SRDNAKNSLY LQMNSLRAED TAVYYCARSN AYAWDDALDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVCTLPPSRE  360
EMTKNQVSLW CLVKGFYPSD IAVEWESNGQ PENNYKTTPP VLDSDGSFFL YSKLTVDKSR  420
WQQGNVFSCS VMHEALHNHY TQKSLSLSPG                                   450

SEQ ID NO: 308              moltype = AA  length = 451
FEATURE                     Location/Qualifiers
REGION                      1..451
                            note = Description of Artificial Sequence: Synthetic
                            polypeptide
source                      1..451
                            mol_type = protein
                            organism = synthetic construct
SEQUENCE: 308
EVQLVESGGG LVQPGGSLRL SCAASGFTFS SYAMSWVRQA PGKGLEWVSD ITYAGGSTAY   60
ADSVKGRFTI SRDNAKNSLY LQMNSLRAED TAVYYCARSN AYAWDDALDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVCTLPPSRE  360
EMTKNQVSLW CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 309              moltype = AA  length = 215
FEATURE                     Location/Qualifiers
REGION                      1..215
                            note = Description of Artificial Sequence: Synthetic
                            polypeptide
source                      1..215
                            mol_type = protein
                            organism = synthetic construct
SEQUENCE: 309
EIVLTQSPGT LSLSPGERAT LSCRASQSVS SNLAWYQQKP GQAPRLLIYG ASSRATGIPD   60
RFSGSGSGTD FTLTISRLEP EDFAVYYCQQ YGSSPPVTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 310              moltype = AA  length = 599
FEATURE                     Location/Qualifiers
REGION                      1..599
                            note = Description of Artificial Sequence: Synthetic
                            polypeptide
source                      1..599
                            mol_type = protein
                            organism = synthetic construct
SEQUENCE: 310
EVQLVESGGG LVQPGGSLRL SCAASGFTFS SYAMSWVRQA PGKGLEWVSD ITYAGGSTAY   60
ADSVKGRFTI SRDNAKNSLY LQMNSLRAED TAVYYCARSN AYAWDDALDI WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPEAAG  240
```

```
APSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPCRE    360
EMTKNQVSLS CAVKGFYPSD IAVEWESNGQ PENNYKTTPP VLDSDGSFFL VSKLTVDKSR    420
WQQGNVFSCS VMHEALHNHY TQKSLSLSPG SGGGGSGGGG SGGGGSQGQD RHMIGMRQLI    480
DIVDQLKNYV NDLVPEFLPA PEDVETNCEW SAFSCFQKAQ LKSANTGNNE RIINVSIKKL    540
KRKPPGGEGG GGGGGEGGCP SCDSYEKKPP KEFLERFKSL LQKMIHQHLS SRTHGSEDS     599

SEQ ID NO: 311          moltype = AA  length = 450
FEATURE                 Location/Qualifiers
REGION                  1..450
                        note = Description of Artificial Sequence: Synthetic
                         polypeptide
source                  1..450
                        mol_type = protein
                        organism = synthetic construct
SEQUENCE: 311
EVQLVESGGG LVQPGGSLRL SCAASGFTFS SYAMSWVRQA PGKGLEWVSD ITYAGGSTAY     60
ADSVKGRFTI SRDNAKNSLY LQMNSLRAED TAVYYCARSN AYAWDDALDI WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
APSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVCTLPPSRE    360
EMTKNQVSLW CLVKGFYPSD IAVEWESNGQ PENNYKTTPP VLDSDGSFFL YSKLTVDKSR    420
WQQGNVFSCS VMHEALHNHY TQKSLSLSPG                                    450

SEQ ID NO: 312          moltype = AA  length = 451
FEATURE                 Location/Qualifiers
REGION                  1..451
                        note = Description of Artificial Sequence: Synthetic
                         polypeptide
source                  1..451
                        mol_type = protein
                        organism = synthetic construct
SEQUENCE: 312
EVQLVESGGG LVQPGGSLRL SCAASGFTFS SYAMSWVRQA PGKGLEWVSD ITYAGGSTAY     60
ADSVKGRFTI SRDNAKNSLY LQMNSLRAED TAVYYCARSN AYAWDDALDI WGQGTLVTVS    120
SASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPEAAG    240
APSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVCTLPPSRE    360
EMTKNQVSLW CLVKGFYPSD IAVEWESNGQ PENNYKTTPP VLDSDGSFFL YSKLTVDKSR    420
WQQGNVFSCS VMHEALHNHY TQKSLSLSPG K                                  451

SEQ ID NO: 313          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 313
QGQDRHMIRM DQLIDIVDQL KNYVNDLVPE FLPAPEDVET NCEWSAFSCF QKAQLKSANT     60
GNNERIINVS IKKLKRKPPS TNAGRRQKHR LTCPSCDSYE KKPPKEFLER FKSLLQKMIH    120
QHLSSRTHGS EDS                                                     133

SEQ ID NO: 314          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 314
QGQDRHMIRM EQLIDIVDQL KNYVNDLVPE FLPAPEDVET NCEWSAFSCF QKAQLKSANT     60
GNNERIINVS IKKLKRKPPS TNAGRRQKHR LTCPSCDSYE KKPPKEFLER FKSLLQKMIH    120
QHLSSRTHGS EDS                                                     133

SEQ ID NO: 315          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 315
QGQDRHMIRM RQLDDIVAQL KNYVNDLVPE FLPAPEDVET NCEWSAFSCF QKAQLKSANT     60
```

```
GNNERIINVS IKKLKRKPPS TNAGRRQKHR LTCPSCDSYE KKPPKEFLER FKSLLQAMIH    120
QHLSSRTHGS EDS                                                      133

SEQ ID NO: 316          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 316
QGQDRHMIRM RQLIDIVDQL KNYVNDLVPE FLPAPEDVET NCEWSAFSCF QKAQLKSANT    60
GNNERIINVS IKKLKEKPPS TNAGRRQKHR LTCPSCDSYE KKPPKEFLER FKSLLQKMIH    120
QHLSSRTHGS EDS                                                      133

SEQ ID NO: 317          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 317
QGQDFHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH    120
QHLSSRTHGS EDS                                                      133

SEQ ID NO: 318          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 318
QGQDRHMIRM RQLIDIVDQL KNYVNDLVPE FLPAPEDVET NCEWSAFSCF QKAQLKSANT    60
GNNERIINVS IKKLKFKPPS TNAGRRQKHR LTCPSCDSYE KKPPKEFLER FKSLLQKMIH    120
QHLSSRTHGS EDS                                                      133

SEQ ID NO: 319          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 319
QGQDRHMERM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH    120
QHLSSRTHGS EDS                                                      133

SEQ ID NO: 320          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 320
QGQDAHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH    120
QHLSSRTHGS EDS                                                      133

SEQ ID NO: 321          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 321
QGQDEHMIRM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH    120
```

```
QHLSSRTHGS EDS                                                                   133

SEQ ID NO: 322              moltype = AA   length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 322
QGQDSHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH 120
QHLSSRTHGS EDS                                                   133

SEQ ID NO: 323              moltype = AA   length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 323
QGQDTHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH 120
QHLSSRTHGS EDS                                                   133

SEQ ID NO: 324              moltype = AA   length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 324
QGQDNHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH 120
QHLSSRTHGS EDS                                                   133

SEQ ID NO: 325              moltype = AA   length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 325
QGQDQHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH 120
QHLSSRTHGS EDS                                                   133

SEQ ID NO: 326              moltype = AA   length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 326
QGQDVHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH 120
QHLSSRTHGS EDS                                                   133

SEQ ID NO: 327              moltype = AA   length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 327
QGQDIHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH 120
QHLSSRTHGS EDS                                                   133
```

```
SEQ ID NO: 328          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 328
QGQDLHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDS                                                    133

SEQ ID NO: 329          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 329
QGQDYHMIRM RQLIDIVDQL KNYVNDLVPE FLPAPEDVET NCEWSAFSCF QKAQLKSANT   60
GNNERIINVS IKKLKRKPPS TNAGRRQKHR LTCPSCDSYE KKPPKEFLER FKSLLQKMIH  120
QHLSSRTHGS EDS                                                    133

SEQ ID NO: 330          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 330
QGQDRHMIRM RQLIDIVDQL KNYVNDLVPE FLPAPEDVET NCEWSAFSCF QKAQLKSANT   60
GNNERIINVS IKKLKAKPPS TNAGRRQKHR LTCPSCDSYE KKPPKEFLER FKSLLQKMIH  120
QHLSSRTHGS EDS                                                    133

SEQ ID NO: 331          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 331
QGQDRHMIRM RQLIDIVDQL KNYVNDLVPE FLPAPEDVET NCEWSAFSCF QKAQLKSANT   60
GNNERIINVS IKKLKNKPPS TNAGRRQKHR LTCPSCDSYE KKPPKEFLER FKSLLQKMIH  120
QHLSSRTHGS EDS                                                    133

SEQ ID NO: 332          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 332
QGQDRHMIRM RQLIDIVDQL KNYVNDLVPE FLPAPEDVET NCEWSAFSCF QKAQLKSANT   60
GNNERIINVS IKKLKDKPPS TNAGRRQKHR LTCPSCDSYE KKPPKEFLER FKSLLQKMIH  120
QHLSSRTHGS EDS                                                    133

SEQ ID NO: 333          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 333
QGQDRHMIRM RQLIDIVDQL KNYVNDLVPE FLPAPEDVET NCEWSAFSCF QKAQLKSANT   60
GNNERIINVS IKKLKSKPPS TNAGRRQKHR LTCPSCDSYE KKPPKEFLER FKSLLQKMIH  120
QHLSSRTHGS EDS                                                    133
```

```
SEQ ID NO: 334          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 334
QGQDRHMIRM RQLIDIVDQL KNYVNDLVPE FLPAPEDVET NCEWSAFSCF QKAQLKSANT  60
GNNERIINVS IKKLKTKPPS TNAGRRQKHR LTCPSCDSYE KKPPKEFLER FKSLLQKMIH 120
QHLSSRTHGS EDS                                                   133

SEQ ID NO: 335          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 335
QGQDRHMIRM RQLIDIVDQL KNYVNDLVPE FLPAPEDVET NCEWSAFSCF QKAQLKSANT  60
GNNERIINVS IKKLKQKPPS TNAGRRQKHR LTCPSCDSYE KKPPKEFLER FKSLLQKMIH 120
QHLSSRTHGS EDS                                                   133

SEQ ID NO: 336          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 336
QGQDRHMIRM RQLIDIVDQL KNYVNDLVPE FLPAPEDVET NCEWSAFSCF QKAQLKSANT  60
GNNERIINVS IKKLKVKPPS TNAGRRQKHR LTCPSCDSYE KKPPKEFLER FKSLLQKMIH 120
QHLSSRTHGS EDS                                                   133

SEQ ID NO: 337          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 337
QGQDRHMIRM RQLIDIVDQL KNYVNDLVPE FLPAPEDVET NCEWSAFSCF QKAQLKSANT  60
GNNERIINVS IKKLKIKPPS TNAGRRQKHR LTCPSCDSYE KKPPKEFLER FKSLLQKMIH 120
QHLSSRTHGS EDS                                                   133

SEQ ID NO: 338          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 338
QGQDRHMIRM RQLIDIVDQL KNYVNDLVPE FLPAPEDVET NCEWSAFSCF QKAQLKSANT  60
GNNERIINVS IKKLKLKPPS TNAGRRQKHR LTCPSCDSYE KKPPKEFLER FKSLLQKMIH 120
QHLSSRTHGS EDS                                                   133

SEQ ID NO: 339          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 339
QGQDRHMIRM RQLIDIVDQL KNYVNDLVPE FLPAPEDVET NCEWSAFSCF QKAQLKSANT  60
GNNERIINVS IKKLKYKPPS TNAGRRQKHR LTCPSCDSYE KKPPKEFLER FKSLLQKMIH 120
QHLSSRTHGS EDS                                                   133

SEQ ID NO: 340          moltype = AA   length = 133
```

```
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 340
QGQDRHMIRM RQLIDIVDQL KNYVNDLVPE FLPAPEDVET NCEWSAFSCF QKAQLKSANT    60
GNNERIINVS IKKLKRAPPS TNAGRRQKHR LTCPSCDSYE KKPPKEFLER FKSLLQKMIH   120
QHLSSRTHGS EDS                                                      133

SEQ ID NO: 341          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 341
QGQDRHMIRM RQLIDIVDQL KNYVNDLVPE FLPAPEDVET NCEWSAFSCF QKAQLKSANT    60
GNNERIINVS IKKLKREPPS TNAGRRQKHR LTCPSCDSYE KKPPKEFLER FKSLLQKMIH   120
QHLSSRTHGS EDS                                                      133

SEQ ID NO: 342          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 342
QGQDRHMIRM RQLIDIVDQL KNYVNDLVPE FLPAPEDVET NCEWSAFSCF QKAQLKSANT    60
GNNERIINVS IAKLKRKPPS TNAGRRQKHR LTCPSCDSYE KKPPKEFLER FKSLLQKMIH   120
QHLSSRTHGS EDS                                                      133

SEQ ID NO: 343          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 343
QGQDRHMIRM RQLIDIVDQL KNYVNDLVPE FLPAPEDVET NCEWSAFSCF QKAQLKSANT    60
GNNERIINVS IEKLKRKPPS TNAGRRQKHR LTCPSCDSYE KKPPKEFLER FKSLLQKMIH   120
QHLSSRTHGS EDS                                                      133

SEQ ID NO: 344          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 344
QGQDRHMIRM RQLIDIVDQL KNYVNDLVPE FLPAPEDVET NCEWSAFSCF QKAQLKSANT    60
GNNERIINVS IKKLARKPPS TNAGRRQKHR LTCPSCDSYE KKPPKEFLER FKSLLQKMIH   120
QHLSSRTHGS EDS                                                      133

SEQ ID NO: 345          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 345
QGQDRHMIRM RQLIDIVDQL KNYVNDLVPE FLPAPEDVET NCEWSAFSCF QKAQLKSANT    60
GNNERIINVS IKKLERKPPS TNAGRRQKHR LTCPSCDSYE KKPPKEFLER FKSLLQKMIH   120
QHLSSRTHGS EDS                                                      133

SEQ ID NO: 346          moltype = AA  length = 133
FEATURE                 Location/Qualifiers
```

```
REGION                  1..133
                        note = Description of Artificial Sequence: Synthetic
                         polypeptide
source                  1..133
                        mol_type = protein
                        organism = synthetic construct
SEQUENCE: 346
QGQDRHMIRM RQLIDIVDQL KNYVNDLVPE FLPAPEDVET NCEWSAFSCF QKAQLKSANT    60
GNNERIINVS IKALKRKPPS TNAGRRQKHR LTCPSCDSYE KKPPKEFLER FKSLLQKMIH   120
QHLSSRTHGS EDS                                                     133

SEQ ID NO: 347          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 347
QGQDRHMIRM RQLIDIVDQL KNYVNDLVPE FLPAPEDVET NCEWSAFSCF QKAQLKSANT    60
GNNERIINVS IKELKRKPPS TNAGRRQKHR LTCPSCDSYE KKPPKEFLER FKSLLQKMIH   120
QHLSSRTHGS EDS                                                     133

SEQ ID NO: 348          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 348
QGQDFHMIRM RQLIDIVDQL KNYVNDLVPE FLPAPEDVET NCEWSAFSCF QKAQLKSANT    60
GNNERIINVS IKKLKRAPPS TNAGRRQKHR LTCPSCDSYE KKPPKEFLER FKSLLQKMIH   120
QHLSSRTHGS EDS                                                     133

SEQ ID NO: 349          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 349
QGQDFHMIRM RQLIDIVDQL KNYVNDLVPE FLPAPEDVET NCEWSAFSCF QKAQLKSANT    60
GNNERIINVS IKKLKREPPS TNAGRRQKHR LTCPSCDSYE KKPPKEFLER FKSLLQKMIH   120
QHLSSRTHGS EDS                                                     133

SEQ ID NO: 350          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 350
QGQDFHMIRM RQLIDIVDQL KNYVNDLVPE FLPAPEDVET NCEWSAFSCF QKAQLKSANT    60
GNNERIINVS IAKLKRKPPS TNAGRRQKHR LTCPSCDSYE KKPPKEFLER FKSLLQKMIH   120
QHLSSRTHGS EDS                                                     133

SEQ ID NO: 351          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 351
QGQDFHMIRM RQLIDIVDQL KNYVNDLVPE FLPAPEDVET NCEWSAFSCF QKAQLKSANT    60
GNNERIINVS IEKLKRKPPS TNAGRRQKHR LTCPSCDSYE KKPPKEFLER FKSLLQKMIH   120
QHLSSRTHGS EDS                                                     133

SEQ ID NO: 352          moltype = AA  length = 133
FEATURE                 Location/Qualifiers
REGION                  1..133
```

```
                    note = Description of Artificial Sequence: Synthetic
                     polypeptide
source              1..133
                    mol_type = protein
                    organism = synthetic construct
SEQUENCE: 352
QGQDFHMIRM RQLIDIVDQL KNYVNDLVPE FLPAPEDVET NCEWSAFSCF QKAQLKSANT    60
GNNERIINVS IKKLARKPPS TNAGRRQKHR LTCPSCDSYE KKPPKEFLER FKSLLQKMIH   120
QHLSSRTHGS EDS                                                     133

SEQ ID NO: 353      moltype = AA   length = 133
FEATURE             Location/Qualifiers
REGION              1..133
                    note = Description of Artificial Sequence: Synthetic
                     polypeptide
source              1..133
                    mol_type = protein
                    organism = synthetic construct
SEQUENCE: 353
QGQDFHMIRM RQLIDIVDQL KNYVNDLVPE FLPAPEDVET NCEWSAFSCF QKAQLKSANT    60
GNNERIINVS IKKLERKPPS TNAGRRQKHR LTCPSCDSYE KKPPKEFLER FKSLLQKMIH   120
QHLSSRTHGS EDS                                                     133

SEQ ID NO: 354      moltype = AA   length = 133
FEATURE             Location/Qualifiers
REGION              1..133
                    note = Description of Artificial Sequence: Synthetic
                     polypeptide
source              1..133
                    mol_type = protein
                    organism = synthetic construct
SEQUENCE: 354
QGQDRHMIRM RQLIDIVDQL KNYVNDLVPE FLPAPEDVET NCEWSAFSCF QKAQLKSANT    60
GNNERIINVS IKALKFKPPS TNAGRRQKHR LTCPSCDSYE KKPPKEFLER FKSLLQKMIH   120
QHLSSRTHGS EDS                                                     133

SEQ ID NO: 355      moltype = AA   length = 133
FEATURE             Location/Qualifiers
REGION              1..133
                    note = Description of Artificial Sequence: Synthetic
                     polypeptide
source              1..133
                    mol_type = protein
                    organism = synthetic construct
SEQUENCE: 355
QGQDRHMIRM RQLIDIVDQL KNYVNDLVPE FLPAPEDVET NCEWSAFSCF QKAQLKSANT    60
GNNERIINVS IKELKFKPPS TNAGRRQKHR LTCPSCDSYE KKPPKEFLER FKSLLQKMIH   120
QHLSSRTHGS EDS                                                     133

SEQ ID NO: 356      moltype = AA   length = 133
FEATURE             Location/Qualifiers
REGION              1..133
                    note = Description of Artificial Sequence: Synthetic
                     polypeptide
source              1..133
                    mol_type = protein
                    organism = synthetic construct
SEQUENCE: 356
QGQDRHMIAM RQLIDIVDQL KNYVNDLVPE FLPAPEDVET NCEWSAFSCF QKAQLKSANT    60
GNNERIINVS IKKLRKPPS TNAGRRQKHR LTCPSCDSYE KKPPKEFLER FKSLLQKMIH    120
QHLSSRTHGS EDS                                                     133

SEQ ID NO: 357      moltype = AA   length = 133
FEATURE             Location/Qualifiers
REGION              1..133
                    note = Description of Artificial Sequence: Synthetic
                     polypeptide
source              1..133
                    mol_type = protein
                    organism = synthetic construct
SEQUENCE: 357
QGQDRHMIDM RQLIDIVDQL KNYVNDLVPE FLPAPEDVET NCEWSAFSCF QKAQLKSANT    60
GNNERIINVS IKKLRKPPS TNAGRRQKHR LTCPSCDSYE KKPPKEFLER FKSLLQKMIH    120
QHLSSRTHGS EDS                                                     133

SEQ ID NO: 358      moltype = AA   length = 133
FEATURE             Location/Qualifiers
REGION              1..133
                    note = Description of Artificial Sequence: Synthetic
```

```
                        polypeptide
source                  1..133
                        mol_type = protein
                        organism = synthetic construct
SEQUENCE: 358
QGQDRHMIEM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                      133

SEQ ID NO: 359          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 359
QGQDRHMIHM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                      133

SEQ ID NO: 360          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 360
QGQDRHMISM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                      133

SEQ ID NO: 361          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 361
QGQDRHMITM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                      133

SEQ ID NO: 362          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 362
QGQDRHMINM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                      133

SEQ ID NO: 363          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 363
QGQDRHMIGM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                      133

SEQ ID NO: 364          moltype = AA   length = 133
FEATURE                 Location/Qualifiers
REGION                  1..133
                        note = Description of Artificial Sequence: Synthetic
                         polypeptide
```

```
source                  1..133
                        mol_type = protein
                        organism = synthetic construct
SEQUENCE: 364
QGQDRHMIVM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                     133

SEQ ID NO: 365          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 365
QGQDRHMIIM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                     133

SEQ ID NO: 366          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 366
QGQDRHMILM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                     133

SEQ ID NO: 367          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 367
QGQDRHMIYM RQLIDIVDQL KNYVNDLVPE FLPAPEDVET NCEWSAFSCF QKAQLKSANT    60
GNNERIINVS IKKLKRKPPS TNAGRRQKHR LTCPSCDSYE KKPPKEFLER FKSLLQKMIH   120
QHLSSRTHGS EDS                                                     133

SEQ ID NO: 368          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 368
QGQDRHMIRM RQLIDIVDQL KNYVNDLVPE FLPAPEDVET NCEWSAFSCF QKAQLKSANT    60
GNNERIINVS IAKLKFKPPS TNAGRRQKHR LTCPSCDSYE KKPPKEFLER FKSLLQKMIH   120
QHLSSRTHGS EDS                                                     133

SEQ ID NO: 369          moltype = AA   length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 369
QGQDRHMIRM RQLIDIVDQL KNYVNDLVPE FLPAPEDVET NCEWSAFSCF QKAQLKSANT    60
GNNERIINVS IKKLAFKPPS TNAGRRQKHR LTCPSCDSYE KKPPKEFLER FKSLLQKMIH   120
QHLSSRTHGS EDS                                                     133

SEQ ID NO: 370          moltype = AA   length = 133
FEATURE                 Location/Qualifiers
REGION                  1..133
                        note = Description of Artificial Sequence: Synthetic
                         polypeptide
source                  1..133
```

```
                            mol_type = protein
                            organism = synthetic construct
SEQUENCE: 370
QGQDRHMIRM RQLIDIVDQL KNYVNDLVPE FLPAPEDVET NCEWSAFSCF QKAQLKSANT    60
GNNERIINVS IKKLKFAPPS TNAGRRQKHR LTCPSCDSYE KKPPKEFLER FKSLLQKMIH   120
QHLSSRTHGS EDS                                                      133

SEQ ID NO: 371              moltype = AA  length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 371
QGQDRHMIRM RQLIDIVDQL KNYVNDLVPE FLPAPEDVET NCEWSAFSCF QKAQLKSANT    60
GNNERIINVS IKKLEFKPPS TNAGRRQKHR LTCPSCDSYE KKPPKEFLER FKSLLQKMIH   120
QHLSSRTHGS EDS                                                      133

SEQ ID NO: 372              moltype = AA  length = 21
FEATURE                     Location/Qualifiers
REGION                      1..21
                            note = Description of Artificial Sequence: Synthetic peptide
SITE                        1..20
                            note = This region may encompass 2-4 "Gly Gly Gly Gly Ser"
                             repeating units
SITE                        21
                            note = This residue may be absent
source                      1..21
                            mol_type = protein
                            organism = synthetic construct
SEQUENCE: 372
GGGGSGGGGS GGGGSGGGGS G                                              21

SEQ ID NO: 373              moltype = AA  length = 16
FEATURE                     Location/Qualifiers
REGION                      1..16
                            note = Description of Artificial Sequence: Synthetic peptide
SITE                        16
                            note = This residue may be absent
source                      1..16
                            mol_type = protein
                            organism = synthetic construct
SEQUENCE: 373
GGGGSGGGGS GGGGSG                                                    16

SEQ ID NO: 374              moltype = AA  length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 374
QGQDRHMIRM RQLIDIIDQL KNYVNDLVPE FLPAPEDVET NCEWSAFSCF QKAQLKSANT    60
GNNERIINVS IKKIKRKPPS TNAGGGQGHE LTCPSCDSYE KKPPKEFLER FKSLLQKMIH   120
QHLSSRTHGS EDS                                                      133

SEQ ID NO: 375              moltype = AA  length = 133
FEATURE                     Location/Qualifiers
REGION                      1..133
                            note = Description of Artificial Sequence: Synthetic
                             polypeptide
source                      1..133
                            mol_type = protein
                            organism = synthetic construct
SEQUENCE: 375
QGQDRHMIRM RQLIDAVDQL KNYVNDLVPE FLPAPEDVET NCEWSAFSCF QKAQLKSANT    60
GNNERIINVS IKKFKRKPPS TNAGGGQGHE LTCPSCDSYE KKPPKEFLER FKSLLQKMIH   120
QHLSSRTHGS EDS                                                      133

SEQ ID NO: 376              moltype = AA  length = 133
FEATURE                     Location/Qualifiers
REGION                      1..133
                            note = Description of Artificial Sequence: Synthetic
                             polypeptide
source                      1..133
```

```
                        mol_type = protein
                        organism = synthetic construct
SEQUENCE: 376
QGQDRHMIRM RQLIDSIDQL KNYVNDLVPE FLPAPEDVET NCEWSAFSCF QKAQLKSANT    60
GNNERIINVS IKKVKRKPPS TNAGGGQGHE LTCPSCDSYE KKPPKEFLER FKSLLQKMIH   120
QHLSSRTHGS EDS                                                     133

SEQ ID NO: 377          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 377
QGQDRHMIRM RQLIDRIDQL KNYVNDLVPE FLPAPEDVET NCEWSAFSCF QKAQLKSANT    60
GNNERIINVS IKKIKRKPPS TNAGGGQGHE LTCPSCDSYE KKPPKEFLER FKSLLQKMIH   120
QHLSSRTHGS EDS                                                     133

SEQ ID NO: 378          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 378
QGQDRHMIRM RQFIDAADQL KNYVNDLVPE FLPAPEDVET NCEWSAFSCF QKAQLKSANT    60
GNNERIINVS IKKMKRKPPS TNAGGGQGHE LTCPSCDSYE KKPPKEFLER FKSLLQKMIH   120
QHLSSRTHGS EDS                                                     133

SEQ ID NO: 379          moltype = AA  length = 133
FEATURE                 Location/Qualifiers
REGION                  1..133
                        note = Description of Artificial Sequence: Synthetic
                         polypeptide
source                  1..133
                        mol_type = protein
                        organism = synthetic construct
SEQUENCE: 379
QGQDRHMIRM RQRIDAIDQL KNYVNDLVPE FLPAPEDVET NCEWSAFSCF QKAQLKSANT    60
GNNERIINVS IKKIKRKPPS TNAGGGQGHE LTCPSCDSYE KKPPKEFLER FKSLLQKMIH   120
QHLSSRTHGS EDS                                                     133

SEQ ID NO: 380          moltype = AA  length = 133
FEATURE                 Location/Qualifiers
REGION                  1..133
                        note = Description of Artificial Sequence: Synthetic
                         polypeptide
VARIANT                 80
                        note = G or S
VARIANT                 81
                        note = G or T
VARIANT                 82
                        note = G, E, or N
VARIANT                 83
                        note = G, S, E, or A
VARIANT                 85
                        note = G, E, S, or R
VARIANT                 86
                        note = G, E, or R
VARIANT                 87
                        note = S, G, E, or Q
VARIANT                 88
                        note = G or K
VARIANT                 89
                        note = G, S, or H
VARIANT                 90
                        note = A, E, S, G, or R
VARIANT                 91
                        note = S, G, or L
VARIANT                 92
                        note = G, S, or T
source                  1..133
                        mol_type = protein
                        organism = synthetic construct
SEQUENCE: 380
```

```
QGQDRHMIRM RQLIDIVDQL KNYVNDLVPE FLPAPEDVET NCEWSAFSCF QKAQLKSANT   60
GNNERIINVS IKKLKRKPPX XXXGXXXXXX XXCPSCDSYE KKPPKEFLER FKSLLQKMIH  120
QHLSSRTHGS EDS                                                    133

SEQ ID NO: 381            moltype = AA  length = 519
FEATURE                   Location/Qualifiers
source                    1..519
                          mol_type = protein
                          organism = Homo sapiens
SEQUENCE: 381
CPDLVCYTDY LQTVICILEM WNLHPSTLTL TWQDQYEELK DEATSCSLHR SAHNATHATY   60
TCHMDVFHFM ADDIFSVNIT DQSGNYSQEC GSFLLAESIK PAPPFNVTVT FSGQYNISWR  120
SDYEDPAFYM LKGKLQYELQ YRNRGDPWAV SPRRKLISVD SRSVSLLPLE FRKDSSYELQ  180
VRAGPMPGSS YQGTWSEWSD PVIFQTQSEE LKEGWNPHLL LLLLLVIVFI PAFWSLKTHP  240
LWRLWKKIWA VPSPERFFMP LYKGCSGDFK KWVGAPFTGS SLELGPWSPE VPSTLEVYSC  300
HPPRSPAKRL QLTELQEPAE LVESDGVPKP SFWPTAQNSG GSAYSEERDR PYGLVSIDTV  360
TVLDAEGPCT WPCSCEDDGY PALDLDAGLE PSPGLEDPLL DAGTTVLSCG CVSAGSPGLG  420
GPLGSLLDRL KPPLADGEDW AGGLPWGGRS PGGVSESEAG SPLAGLDMDT FDSGFVGSDC  480
SSPVECDFTS PGDEGPPRSY LRQWVVIPPP LSSPGPQAS                         519

SEQ ID NO: 382            moltype = AA  length = 347
FEATURE                   Location/Qualifiers
source                    1..347
                          mol_type = protein
                          organism = Homo sapiens
SEQUENCE: 382
LNTTILTPNG NEDTTADFFL TTMPTDSLSV STLPLPEVQC FVFNVEYMNC TWNSSSEPQP   60
TNLTLHYWYK NSDNDKVQKC SHYLFSEEIT SGCQLKKEI HLYQTFVVQL QDPREPRRQA  120
TQMLKLQNLV IPWAPENLTL HKLSESQLEL NWNNRFLNHC LEHLVQYRTD WDHSWTEQSV  180
DYRHKFSLPS VDGQKRYTFR VRSRFNPLCG SAQHWSEWSH PIHWGSNTSK ENPFLFALEA  240
VVISVGSMGL IISLLCVYFW LERTMPRIPT LKNLEDLVTE YHGNFSAWSG VSKGLAESLQ  300
PDYSERLCLV SEIPPKGGAL GEGPGASPCN QHSPYWAPPC YTLKPET               347

SEQ ID NO: 383            moltype = AA  length = 133
FEATURE                   Location/Qualifiers
REGION                    1..133
                          note = Description of Artificial Sequence: Synthetic
                          polypeptide
VARIANT                   56
                          note = A, E, or K
VARIANT                   75
                          note = A, E, or K
VARIANT                   80
                          note = G or S
VARIANT                   81
                          note = G or T
VARIANT                   82
                          note = G, E, or N
VARIANT                   83
                          note = G, S, E, or A
VARIANT                   84
                          note = E or G
VARIANT                   85
                          note = G, E, S, or R
VARIANT                   86
                          note = G, E, or R
VARIANT                   87
                          note = S, G, E, or Q
VARIANT                   88
                          note = G or K
VARIANT                   89
                          note = G, S, or H
VARIANT                   90
                          note = A, E, S, G, or R
VARIANT                   91
                          note = S, G, or L
VARIANT                   92
                          note = G, S, or T
source                    1..133
                          mol_type = protein
                          organism = synthetic construct
SEQUENCE: 383
QGQDRHMIRM RQLIDIVDQL KNYVNDLVPE FLPAPEDVET NCEWSAFSCF QKAQLXSANT   60
GNNERIINVS IKKLXRKPPX XXXXXXXXXX XXCPSCDSYE KKPPKEFLER FKSLLQKMIH  120
QHLSSRTHGS EDS                                                    133

SEQ ID NO: 384            moltype = AA  length = 133
FEATURE                   Location/Qualifiers
REGION                    1..133
```

```
                        note = Description of Artificial Sequence: Synthetic
                         polypeptide
VARIANT                 5
                        note = F, A, E, S, T, N, Q, V, I, L, Y, or R
VARIANT                 8
                        note = E or I
VARIANT                 9
                        note = A, D, E, H, S, T, N, G, V, I, L, Y, or R
VARIANT                 11
                        note = D, E, or R
VARIANT                 13
                        note = F, R, or L
VARIANT                 14
                        note = D or I
VARIANT                 16
                        note = A, S, R, or I
VARIANT                 17
                        note = I, A, or V
VARIANT                 18
                        note = A or D
VARIANT                 72
                        note = A, E, or K
VARIANT                 73
                        note = A, E, or K
VARIANT                 74
                        note = I, F, M, or L
VARIANT                 75
                        note = A, K, or E
VARIANT                 76
                        note = E, F, A, N, D, S, T, Q, V, I, L, Y, M, or R
VARIANT                 77
                        note = A, E, or K
VARIANT                 117
                        note = A or K
source                  1..133
                        mol_type = protein
                        organism = synthetic construct
SEQUENCE: 384
QGQDXHMXXM XQXXDXXXQL KNYVNDLVPE FLPAPEDVET NCEWSAFSCF QKAQLKSANT    60
GNNERIINVS IXXXXXXPPS TNAGRRQKHR LTCPSCDSYE KKPPKEFLER FKSLLQXMIH   120
QHLSSRTHGS EDS                                                     133

SEQ ID NO: 385          moltype = AA   length = 133
FEATURE                 Location/Qualifiers
REGION                  1..133
                        note = Description of Artificial Sequence: Synthetic
                         polypeptide
VARIANT                 5
                        note = F, A, E, S, T, N, Q, V, I, L, Y, or R
VARIANT                 8
                        note = E or I
VARIANT                 9
                        note = A, D, E, H, S, T, N, G, V, I, L, Y, or R
VARIANT                 11
                        note = D, E, or R
VARIANT                 13
                        note = F, R, or L
VARIANT                 14
                        note = D or I
VARIANT                 16
                        note = A, S, R, or I
VARIANT                 17
                        note = I, A, or V
VARIANT                 18
                        note = A or D
VARIANT                 56
                        note = A, E, or K
VARIANT                 72
                        note = A, E, or K
VARIANT                 73
                        note = A, E, or K
VARIANT                 74
                        note = I, F, M, or L
VARIANT                 75
                        note = A, K, or E
VARIANT                 76
                        note = E, F, A, N, D, S, T, Q, V, I, L, Y, M, or R
VARIANT                 77
                        note = A, E, or K
```

```
VARIANT                 80
                        note = G or S
VARIANT                 81
                        note = G or T
VARIANT                 82
                        note = G, E, or N
VARIANT                 83
                        note = G, S, E, or A
VARIANT                 84
                        note = E or G
VARIANT                 85
                        note = G, E, S, or R
VARIANT                 86
                        note = G, E, or R
VARIANT                 87
                        note = S, G, E, or Q
VARIANT                 88
                        note = G or K
VARIANT                 89
                        note = G, S, or H
VARIANT                 90
                        note = A, E, S, G, or R
VARIANT                 91
                        note = S, G, or L
VARIANT                 92
                        note = G, S, or T
VARIANT                 117
                        note = A or K
source                  1..133
                        mol_type = protein
                        organism = synthetic construct
SEQUENCE: 385
QGQDXHMXXM XQXXDXXXQL KNYVNDLVPE FLPAPEDVET NCEWSAFSCF QKAQLXSANT    60
GNNERIINVS IXXXXXXPPX XXXXXXXXXX XXCPSCDSYE KKPPKEFLER FKSLLQXMIH   120
QHLSSRTHGS EDS                                                     133

SEQ ID NO: 386          moltype = AA  length = 17
FEATURE                 Location/Qualifiers
REGION                  1..17
                        note = Description of Artificial Sequence: Synthetic peptide
VARIANT                 3
                        note = G or S
VARIANT                 4
                        note = G or T
VARIANT                 5
                        note = G, E, or N
VARIANT                 6
                        note = G, S, E, or A
VARIANT                 8
                        note = G, E, S, or R
VARIANT                 9
                        note = G, E, or R
VARIANT                 10
                        note = S, G, E, or Q
VARIANT                 11
                        note = G or K
VARIANT                 12
                        note = G, S, or H
VARIANT                 13
                        note = A, E, S, G, or R
VARIANT                 14
                        note = S, G, or L
VARIANT                 15
                        note = G, S, or T
source                  1..17
                        mol_type = protein
                        organism = synthetic construct
SEQUENCE: 386
PPXXXXGXXX XXXXXCP                                                  17

SEQ ID NO: 387          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 387
GGGGS                                                                5
```

| SEQ ID NO: 388 | moltype = AA length = 5 |
| --- | --- |
| FEATURE | Location/Qualifiers |
| REGION | 1..5 |
| | note = Description of Artificial Sequence: Synthetic peptide |
| source | 1..5 |
| | mol_type = protein |
| | organism = synthetic construct |
| SEQUENCE: 388 | |
| GGNGT | 5 |

| SEQ ID NO: 389 | moltype = AA length = 5 |
| --- | --- |
| FEATURE | Location/Qualifiers |
| REGION | 1..5 |
| | note = Description of Artificial Sequence: Synthetic peptide |
| source | 1..5 |
| | mol_type = protein |
| | organism = synthetic construct |
| SEQUENCE: 389 | |
| YGNGT | 5 |

| SEQ ID NO: 390 | moltype = AA length = 15 |
| --- | --- |
| FEATURE | Location/Qualifiers |
| REGION | 1..15 |
| | note = Description of Artificial Sequence: Synthetic peptide |
| source | 1..15 |
| | mol_type = protein |
| | organism = synthetic construct |
| SEQUENCE: 390 | |
| GGGGSGGGGS GGGGS | 15 |

| SEQ ID NO: 391 | moltype = AA length = 8 |
| --- | --- |
| FEATURE | Location/Qualifiers |
| REGION | 1..8 |
| | note = Description of Artificial Sequence: Synthetic 8xHis tag |
| source | 1..8 |
| | mol_type = protein |
| | organism = synthetic construct |
| SEQUENCE: 391 | |
| HHHHHHHH | 8 |

| SEQ ID NO: 392 | moltype = AA length = 4 |
| --- | --- |
| FEATURE | Location/Qualifiers |
| REGION | 1..4 |
| | note = Description of Artificial Sequence: Synthetic peptide |
| source | 1..4 |
| | mol_type = protein |
| | organism = synthetic construct |
| SEQUENCE: 392 | |
| GGAS | 4 |

The invention claimed is:

1. A fusion protein comprising:
(a) an IL-21 polypeptide,
  wherein the IL-21 polypeptide comprises a polypeptide sequence having at least 90% sequence identity to the sequence of SEQ ID NO: 1;
  wherein the IL-21 polypeptide comprises:
    (i) one or more amino acid substitutions in a region from position S80 to position T92 relative to the sequence of SEQ ID NO: 1, wherein the one or more amino acid substitutions provide an isoelectric point of the IL-21 polypeptide that is at least 0.6 units to 5 units lower compared to isoelectric point of a human IL-21 polypeptide comprising the sequence of SEQ ID NO: 1, and wherein the one or more amino acid substitutions comprise at least one amino acid substitution at position R85, R86, K88, H89, or R90 numbered according to the sequence of SEQ ID NO: 1; and
    (ii) at least one amino acid substitution relative to the sequence of SEQ ID NO: 1, which reduces binding to a human IL-21 receptor compared to binding by the human IL-21 polypeptide comprising the sequence of SEQ ID NO: 1; and
(b) an antibody or antigen-binding fragment thereof that specifically binds to CD8.

2. The fusion protein of claim 1, wherein the isoelectric point of the IL-21 polypeptide is 7.12 to 8.72.

3. The fusion protein of claim 1, wherein the IL-21 polypeptide does not comprise an amino acid substitution at position G84 numbered according to the sequence of SEQ ID NO: 1.

4. The fusion protein of claim 1, wherein the one or more amino acid substitutions comprise at least four amino acid substitutions at positions selected from the group consisting of: S80, T81, N82, A83, R85, R86, Q87, K88, H89, R90, L91, and T92 numbered according to the sequence of SEQ ID NO: 1.

5. The fusion protein of claim 1, wherein the at least one amino acid substitution is at one or more positions selected from the group consisting of: R5, I8, R9, R11, L13, I14, I16, V17, D18, K72, K73, L74, K75, R76, K77, and K117 numbered according to the sequence of SEQ ID NO: 1.

6. The fusion protein of claim 1, wherein the polypeptide sequence of the IL-21 polypeptide has at least 99% identity to the sequence set forth in any one of SEQ ID NOs: 16-21, 41-98, and 374-379.

7. The fusion protein of claim 1, wherein the one or more amino acid substitutions comprise at least four amino acid substitutions of (1)-(12):
   (1) S80G, relative to the sequence of SEQ ID NO: 1;
   (2) T81G, relative to the sequence of SEQ ID NO: 1;
   (3) N82G or N82E, relative to the sequence of SEQ ID NO: 1;
   (4) A83G, A83E, or A83S, relative to the sequence of SEQ ID NO: 1;
   (5) R85G, R85E, or R85S, relative to the sequence of SEQ ID NO: 1;
   (6) R86G or R86E, relative to the sequence of SEQ ID NO: 1;
   (7) Q87G, Q87E, or Q87S, relative to the sequence of SEQ ID NO: 1;
   (8) K88G, relative to the sequence of SEQ ID NO: 1;
   (9) H89G or H89S, relative to the sequence of SEQ ID NO: 1;
   (10) R90G, R90S, R90E, or R90A, relative to the sequence of SEQ ID NO: 1;
   (11) L91G or L91S, relative to the sequence of SEQ ID NO: 1; or
   (12) T92G or T92S, relative to the sequence of SEQ ID NO: 1.

8. The fusion protein of claim 1, wherein the one or more amino acid substitutions comprise amino acid substitutions of (1)-(12):
   (1) S80G, relative to the sequence of SEQ ID NO: 1;
   (2) T81G, relative to the sequence of SEQ ID NO: 1;
   (3) N82G or N82E, relative to the sequence of SEQ ID NO: 1;
   (4) A83G, A83E, or A83S, relative to the sequence of SEQ ID NO: 1;
   (5) R85G, R85E, or R85S, relative to the sequence of SEQ ID NO: 1;
   (6) R86G or R86E, relative to the sequence of SEQ ID NO: 1;
   (7) Q87G, Q87E, or Q87S, relative to the sequence of SEQ ID NO: 1;
   (8) K88G, relative to the sequence of SEQ ID NO: 1;
   (9) H89G or H89S, relative to the sequence of SEQ ID NO: 1;
   (10) R90G, R90S, R90E, or R90A, relative to the sequence of SEQ ID NO: 1;
   (11) L91G or L91S, relative to the sequence of SEQ ID NO: 1; and
   (12) T92G or T92S, relative to the sequence of SEQ ID NO: 1.

9. The fusion protein of claim 8, wherein the one or more amino acid substitutions comprise
   (1) S80G, relative to the sequence of SEQ ID NO: 1;
   (2) T81G, relative to the sequence of SEQ ID NO: 1;
   (3) N82E, relative to the sequence of SEQ ID NO: 1;
   (4) A83G, relative to the sequence of SEQ ID NO: 1;
   (5) R85G, relative to the sequence of SEQ ID NO: 1;
   (6) R86G, relative to the sequence of SEQ ID NO: 1;
   (7) Q87G, relative to the sequence of SEQ ID NO: 1;
   (8) K88G, relative to the sequence of SEQ ID NO: 1;
   (9) H89G, relative to the sequence of SEQ ID NO: 1;
   (10) R90E, relative to the sequence of SEQ ID NO: 1;
   (11) L91G, relative to the sequence of SEQ ID NO: 1; and
   (12) T92G, relative to the sequence of SEQ ID NO: 1.

10. The fusion protein of claim 1, wherein the one or more amino acid substitutions comprise substitutions at positions R85, R86, K88, and R90 numbered according to the sequence of SEQ ID NO: 1.

11. The fusion protein of claim 10, wherein the one or more amino acid substitutions comprise:
   (1) R85G, R85E, or R85S, relative to the sequence of SEQ ID NO: 1;
   (2) R86G or R86E, relative to the sequence of SEQ ID NO: 1;
   (3) K88G, relative to the sequence of SEQ ID NO: 1; and
   (4) R90G, R90S, R90E, or R90A, relative to the sequence of SEQ ID NO: 1.

12. The fusion protein of claim 10, wherein the one or more amino acid substitutions further comprise substitutions at positions S80, T81, N82, A83, Q87, H89, L91, and T92 numbered according to the sequence of SEQ ID NO: 1.

13. The fusion protein of claim 12, wherein the one or more amino acid substitutions comprise:
   (1) S80G, relative to the sequence of SEQ ID NO: 1;
   (2) T81G, relative to the sequence of SEQ ID NO: 1;
   (3) N82G or N82E, relative to the sequence of SEQ ID NO: 1;
   (4) A83G, A83E, or A83S, relative to the sequence of SEQ ID NO: 1;
   (5) Q87G, Q87E, or Q87S, relative to the sequence of SEQ ID NO: 1;
   (6) H89G or H89S, relative to the sequence of SEQ ID NO: 1;
   (7) L91G or L91S, relative to the sequence of SEQ ID NO: 1; and
   (8) T92G or T92S, relative to the sequence of SEQ ID NO: 1.

14. The fusion protein of claim 1, wherein the at least one amino acid substitution is selected from the group consisting of (1)-(17):
   (1) R5F, R5A, R5E, R5S, R5T, R5N, R5Q, R5V, R5I, R5L, or R5Y, relative to the sequence of SEQ ID NO: 1;
   (2) I8E, relative to the sequence of SEQ ID NO: 1;
   (3) R9A, R9D, R9E, R9H, R9S, R0T, R9N, R9G, R9V, R9I, R0L, or R9Y, relative to the sequence of SEQ ID NO: 1;
   (4) R11D or R11E, relative to the sequence of SEQ ID NO: 1;
   (5) L13F or L13R, relative to the sequence of SEQ ID NO: 1;
   (6) I14D, relative to the sequence of SEQ ID NO: 1;
   (7) I16A, I16S, or I16R, relative to the sequence of SEQ ID NO: 1;
   (8) V17I or V17A, relative to the sequence of SEQ ID NO: 1;
   (9) D18A, relative to the sequence of SEQ ID NO: 1;
   (10) K72A or K72E, relative to the sequence of SEQ ID NO: 1;
   (11) K73A or K73E, relative to the sequence of SEQ ID NO: 1;
   (12) K75A or K75E, relative to the sequence of SEQ ID NO: 1;
   (13) L74I, L74F, L74M, or L74V, relative to the sequence of SEQ ID NO: 1;
   (14) R76E, R76F, R76A, R76N, R76D, R76S, R76T, R76Q, R76V, R76I, R76L, R76Y, or R76M, relative to the sequence of SEQ ID NO: 1;
   (15) K77A or K77E, relative to the sequence of SEQ ID NO: 1;

(16) K117A, relative to the sequence of SEQ ID NO: 1; and

(17) any combination of up to 12 substitutions of (1)-(16).

15. The fusion protein of claim 14, wherein the at least one amino acid substitution is R76E or R76Q, relative to the sequence of SEQ ID NO: 1.

16. The fusion protein of claim 15, wherein the at least one amino acid substitution is R76E, relative to the sequence of SEQ ID NO: 1.

17. The fusion protein of claim 1, wherein the one or more amino acid substitutions comprise R85G, R85E, or R85S, relative to the sequence of SEQ ID NO: 1.

18. The fusion protein of claim 1, wherein the one or more amino acid substitutions comprise R86G or R86E, relative to the sequence of SEQ ID NO: 1.

19. The fusion protein of claim 1, wherein the one or more amino acid substitutions comprise K88G, relative to the sequence of SEQ ID NO: 1.

20. The fusion protein of claim 1, wherein the one or more amino acid substitutions comprise H89G or H89S, relative to the sequence of SEQ ID NO: 1.

21. The fusion protein of claim 1, wherein the one or more amino acid substitutions comprise R90G, R90S, R90E, or R90A, relative to the sequence of SEQ ID NO: 1.

22. The fusion protein of claim 11, wherein the one or more amino acid substitutions comprise:

(1) R85G, relative to the sequence of SEQ ID NO: 1;
(2) R86G, relative to the sequence of SEQ ID NO: 1;
(3) K88G, relative to the sequence of SEQ ID NO: 1; and
(4) R90E, relative to the sequence of SEQ ID NO: 1.

23. The fusion protein of claim 22, wherein the one or more amino acid substitutions further comprise S80G and T81G, relative to the sequence of SEQ ID NO: 1.

24. The fusion protein of claim 22, wherein the one or more amino acid substitutions further comprise N82E and A83G relative to the sequence of SEQ ID NO: 1.

25. The fusion protein of claim 22, wherein the one or more amino acid substitutions further comprise Q87G and H89G relative to the sequence of SEQ ID NO: 1.

26. The fusion protein of claim 22, wherein the one or more amino acid substitutions further comprise L91G and T92G relative to the sequence of SEQ ID NO: 1.

27. A pharmaceutical composition comprising the fusion protein of claim 1.

28. A kit comprising a container comprising the fusion protein of claim 1 and instructions for administering the fusion protein to a subject with a disease.

29. A fusion protein comprising:

(a) an IL-21 polypeptide comprising a polypeptide sequence set forth in any one of SEQ ID NOs: 16-21, 41-98, and 374-379; and (b) an antibody or antigen-binding fragment thereof that specifically binds to CD8.

30. The fusion protein of claim 29, wherein the IL-21 polypeptide comprises the sequence set forth in SEQ ID NO: 94.

* * * * *

UNITED STATES PATENT AND TRADEMARK OFFICE
CERTIFICATE OF CORRECTION

PATENT NO. : 12,122,827 B2
APPLICATION NO. : 18/307477
DATED : October 22, 2024
INVENTOR(S) : Yik Andy Yeung et al.

It is certified that error appears in the above-identified patent and that said Letters Patent is hereby corrected as shown below:

In the Claims

Claim 14, Column 408, Line 41:
18E

Should be corrected to:
I8E

Claim 14, Column 408, Line 42:
ROT

Should be corrected to:
R9T

Claim 14, Column 408, Line 43:
ROL

Should be corrected to:
R9L

Signed and Sealed this
Tenth Day of December, 2024

Katherine Kelly Vidal
*Director of the United States Patent and Trademark Office*